US 9,040,525 B2

(12) United States Patent
Okano et al.

(10) Patent No.: US 9,040,525 B2
(45) Date of Patent: May 26, 2015

(54) CYCLIC AMIDE DERIVATIVE

(75) Inventors: Akihiro Okano, Tokyo (JP); Munetaka Ohkouchi, Tokyo (JP); Muneyoshi Makabe, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 13/877,626

(22) PCT Filed: Oct. 11, 2011

(86) PCT No.: PCT/JP2011/073355
§ 371 (c)(1),
(2), (4) Date: Apr. 3, 2013

(87) PCT Pub. No.: WO2012/046869
PCT Pub. Date: Apr. 12, 2012

(65) Prior Publication Data
US 2013/0203739 A1    Aug. 8, 2013

(30) Foreign Application Priority Data

| Oct. 8, 2010 | (JP) | 2010-229151 |
| Apr. 28, 2011 | (JP) | 2011-102535 |
| Aug. 26, 2011 | (JP) | 2011-185340 |

(51) Int. Cl.
| C07D 279/02 | (2006.01) |
| A61K 31/541 | (2006.01) |
| C07D 277/04 | (2006.01) |
| C07D 275/02 | (2006.01) |
| C07D 285/10 | (2006.01) |
| C07D 285/16 | (2006.01) |
| C07D 417/12 | (2006.01) |
| A61K 31/425 | (2006.01) |
| A61K 31/433 | (2006.01) |
| A61K 31/4439 | (2006.01) |
| A61K 31/549 | (2006.01) |
| A61K 45/06 | (2006.01) |
| C07D 285/34 | (2006.01) |
| C07D 417/14 | (2006.01) |

(52) U.S. Cl.
CPC ............ *C07D 277/04* (2013.01); *C07D 275/02* (2013.01); *C07D 279/02* (2013.01); *C07D 285/10* (2013.01); *C07D 285/16* (2013.01); *C07D 417/12* (2013.01); *A61K 31/425* (2013.01); *A61K 31/433* (2013.01); *A61K 31/4439* (2013.01); *A61K 31/541* (2013.01); *A61K 31/549* (2013.01); *A61K 45/06* (2013.01); *C07D 285/34* (2013.01); *C07D 417/14* (2013.01)

(58) Field of Classification Search
USPC ......................... 544/56; 514/222.2
See application file for complete search history.

(56) References Cited

U.S. PATENT DOCUMENTS

2005/0090502 A1    4/2005 Coppola et al.
2006/0100261 A1    5/2006 Hamamura et al.
2006/0258722 A1    11/2006 Yasuma et al.
(Continued)

FOREIGN PATENT DOCUMENTS

| EP | 2 518 060 A1 | 10/2012 |
| JP | 2005-535568 A | 11/2005 |

(Continued)

OTHER PUBLICATIONS

PCT/ISA/210—International Search Report mailed on Dec. 20, 2011, issued in PCT/JP2011/073355.
Campbell, "Expedient Syntheses of Sulfonylhydantoins and Two Six-Membered Analogues," Letter, Synlett, No. 5, 2005, pp. 834-838.
Chiasson et al., "Acarbose Treatment and the Risk of Cardiovascular Disease and Hypertension in Patients With Impaired Glucose Tolerance: The STOP-NIDDM Trial," JAMA, Jul. 23/30, 2003, vol. 290, No. 4, pp. 486-494.
Itoh et al., "Free fatty acids regulate insulin secretion from pancreatic β cells through GPR40," Nature, vol. 422, Mar. 13, 2003, pp. 173-176.

(Continued)

*Primary Examiner* — Bruck Kifle
(74) *Attorney, Agent, or Firm* — Birch, Stewart, Kolasch & Birch, LLP

(57) ABSTRACT

[Problem]
To provide a GPR40 activating agent having, as an active ingredient, a novel compound having a GPR40 agonist action, a salt of the compound, a solvate of the salt or the compound, or the like, particularly, an insulin secretagogues and a prophylactic and/or therapeutic agent against diabetes, obesity, or other diseases.
[Means of Solving the Problem]
A compound of Formula (1):

(where n is 0 to 2; p is 0 to 4; h is 0 to 3; j is 0 to 3; k is 0 to 2; a ring B is an aryl group or a heteroaryl group; X is O, S, or —NR$^7$—; J$_1$ is —CR$^{11a}$R$^{11b}$— or —NR$^{11c}$—; J$_2$ is —CR$^{12a}$R$^{12b}$— or —NR$^{12c}$—; and R$^1$ to R$^{12c}$ are specific groups),
a salt of the compound, or a solvate of the salt or the compound.

18 Claims, No Drawings

(56) References Cited

U.S. PATENT DOCUMENTS

| | | |
|---|---|---|
| 2007/0142384 A1 | 6/2007 | Akerman et al. |
| 2009/0170908 A1 | 7/2009 | Shimada et al. |
| 2009/0186909 A1 | 7/2009 | Negoro et al. |
| 2010/0130599 A1 | 5/2010 | Coty et al. |
| 2010/0261645 A1 | 10/2010 | Defossa et al. |
| 2010/0267775 A1 | 10/2010 | Negoro et al. |
| 2011/0065739 A1 | 3/2011 | Ishikawa et al. |
| 2012/0157459 A1 | 6/2012 | Okano et al. |
| 2012/0220772 A1 | 8/2012 | Okano et al. |
| 2012/0277150 A1 | 11/2012 | Ohkouchi |
| 2014/0057871 A1 | 2/2014 | Okano et al. |

FOREIGN PATENT DOCUMENTS

| | | |
|---|---|---|
| JP | 2007-525516 A | 9/2007 |
| WO | WO 00/42029 A1 | 7/2000 |
| WO | WO 03/082841 A1 | 10/2003 |
| WO | WO 2004/011446 A1 | 2/2004 |
| WO | WO 2004/022551 A1 | 3/2004 |
| WO | WO 2004/041266 A1 | 5/2004 |
| WO | WO 2005/035551 A2 | 4/2005 |
| WO | WO 2005/051890 A1 | 6/2005 |
| WO | WO 2005/063729 A1 | 7/2005 |
| WO | WO 2005/086661 A2 | 9/2005 |
| WO | WO 2007/033002 A1 | 3/2007 |
| WO | WO 2007/067612 A1 | 6/2007 |
| WO | WO 2007/067613 A1 | 6/2007 |
| WO | WO 2007/067614 A1 | 6/2007 |
| WO | WO 2007/089857 A2 | 8/2007 |
| WO | WO 2007/115058 A2 | 10/2007 |
| WO | WO 2007/123225 A1 | 11/2007 |
| WO | WO 2008/001931 A2 | 1/2008 |
| WO | WO 2008/022771 A1 | 2/2008 |
| WO | WO 2008/030520 A1 | 3/2008 |
| WO | WO 2008/033931 A1 | 3/2008 |
| WO | WO 2008/066131 A1 | 6/2008 |
| WO | WO 2008/130514 A1 | 10/2008 |
| WO | WO 2009/039943 A1 | 4/2009 |
| WO | WO 2009/048527 A1 | 4/2009 |
| WO | WO 2009/054390 A1 | 4/2009 |
| WO | WO 2009/054423 A1 | 4/2009 |
| WO | WO 2009/054479 A1 | 4/2009 |
| WO | WO 2009/109999 A1 | 9/2009 |
| WO | WO 2009/111056 A1 | 9/2009 |
| WO | WO 2009/147990 A1 | 12/2009 |
| WO | WO 2010/085525 A1 | 7/2010 |
| WO | WO 2010/091176 A1 | 8/2010 |
| WO | WO 2010/143733 A1 | 12/2010 |
| WO | WO 2011/046851 A2 | 4/2011 |
| WO | WO 2011/052756 A1 | 5/2011 |
| WO | WO 2011/066183 A1 | 6/2011 |
| WO | WO 2011/078371 A1 | 6/2011 |
| WO | WO 2012/046869 A1 | 4/2012 |
| WO | WO 2012/147516 A1 | 11/2012 |
| WO | WO 2012/147518 A1 | 11/2012 |

OTHER PUBLICATIONS

Kotarsky, "A human cell surface receptor activated by free fatty acids and thiazolidinedione drugs," Biochemical and Biophysical Research Communications, vol. 301, 2003, pp. 406-410.

Extended European Search Report dated Aug. 25, 2014 for Application No. 11830798.2.

CYCLIC AMIDE DERIVATIVE

TECHNICAL FIELD

The present invention relates to a compound for modulationg the functions of G protein-coupled receptor 40 (GPR40). In particular, the present invention relates to a compound having a saturated cyclic amide structure having —S(O)$_n$—NH—CO— (n is an integer of 0 to 2) bonded to a ring B (hereinafter, referred to as the cyclic amide structure) of Formula (I), a salt of the compound, a solvate of the compound or the salt, a pharmaceutical composition containing the compound as an active ingredient, prophylactic and/or therapeutic agents against GPR40-involving diseases, especially diabetes, and an insulin secretagogues.

BACKGROUND ART

Diabetes is categorized into Type 1 diabetes (insulin-dependent diabetes) and Type 2 diabetes (non-insulin-dependent diabetes), and boederline type diabetes (glucose tolerance disorders) has also attracted attention as a pre-diabetic condition in recent years. Type 1 diabetes is characterized by a partial or complete inability to produce insulin, which is a blood glucose regulating hormone. Type 2 diabetes is characterized by induced peripheral insulin resistance and impaired insulin secretion. Borderline type diabetes is a pathological condition exhibiting impaired glucose tolerance (IGT) or impaired fasting glucose (IFG), associated with a risk of developing Type 2 diabetes or diabetes complications.

Diabetes is caused by several predisposing factors. It is a disease characterized by high glucose levels in blood plasma in fasting and postprandial states or during an oral glucose tolerance test or by chronic hyperglycemia, in general. Controlling chronic hyperglycemia is essential in clinical management and treatment of diabetes. In particular, reduced insulin secretion from beta cells of the pancreas can induce an abrupt increase in postprandial blood glucose levels in Type 2 diabetes or boederline type diabetes. An international large-scale clinical trial has revealed that it is essential to control postprandial hyperglycemia in impaired glucose tolerance for suppressing the development and progress of not only diabetes but also hypertension and cardiovascular diseases (JAMA, 290, 486-494 (2003) (Non-Patent Document 1)). On the basis of these findings, the International Diabetes Federation published new guidelines for diabetes treatment (postprandial blood glucose control guidelines) in 2007, which recommend control of postprandial blood glucose levels as essential for Type 1 and 2 diabetic patients to alleviate diabetes and reduce risk of complications. As a practical step, an increased administration of an alpha-glucosidase inhibitor (voglibose) that is a drug for alleviating excessive postprandial blood glucose levels associated with diabetes, has been approved in Japan as a prophylactic agent against diabetes, aiming to "inhibit the development of Type 2 diabetes from impaired glucose tolerance". As described above, there has been increasing awareness of the needs of nonpharmacological and pharmacological treatments against diabetes and boederline type diabetes, targeting the control of postprandial blood glucose levels in recent years.

Diabetes is treated mainly through diet regulation and exercise. When these fail to alleviate symptoms, pharmacological treatment is needed. Various types of drugs are available as prophylactic or therapeutic agents against diabetes. Among them, examples of insulin secretagogues include sulfonylurea agents (e.g., glibenclamide, glimepiride) and rapid-acting insulin secretagogues (e.g., mitiglinide), all of which stimulate beta cells of the pancreas so as to accelerate insulin secretion. These drugs are, however, known for their ineffectiveness (primary failure, secondary failure) and side effects such as induced hypoglycemic effects. Analogs (e.g., exenatide, liraglutide) of glucagon-like peptide-1 (GLP-1), which are hormones accelerating glucose-responsive insulin secretion in beta cells of the pancreas, have become available as novel insulin secretagogues, but they are administered by injection and known for their side effects of transient gastrointestinal tract disorders. Other examples of insulin secretagogues include dipeptidyl peptidase IV (DPP-IV) inhibitors (e.g., sitagliptin, vildagliptin), which inhibit the degradation of intrinsic GLP-1, but they are known for their side effects of epipharyngitis, headache, and infections. Alpha-glucosidase inhibitors (e.g., acarbose, voglibose) inhibit the degradation and digestion of carbohydrate and thus limit an abrupt increase in postprandial blood glucose levels, but they need to be taken immediately before meals and are known for their side effects such as distension and diarrhea and serious liver disorders. Biguanides (e.g., metformin, buformin) are insulin resistance improving agents enhancing insulin sensitivity and thereby alleviating hyperglycemia, but are known to potentially induce side effects such as lactic acidosis, nausea, and vomiting. Thiazolidinedione derivatives (e.g., pioglitazone, rosiglitazone) are peroxisome proliferator-activated receptor (PPAR) gamma agonists. The derivatives increase insulin sensitivity in adipose tissue, the liver, and skeletal muscles and thereby alleviate chronic hyperglycemia, but are known to cause edema, weight gain, and serious side effects of liver disorders. Side effects of these drugs do not always occur, but remain as a major obstacle to high satisfaction with treatment. Therefore, the demand has been increasing for insulin secretagogues, particularly orally administrable insulin secretagogues, entailing few problems and side effects caused by conventional prophylactic and therapeutic agents as described above and inhibiting postprandial hyperglycemia without inducing hypoglycemia.

Fatty acid plays an important role in insulin use in the liver and skeletal muscles, glucose-responsive insulin secretion from the pancreas, and inflammation associated with fat accumulation in adipose tissue. A strong correlation is known between increased levels of fatty acid in blood plasma and the development of diabetes, metabolic syndrome, obesity, and adiposity.

GPR40, one of the G-protein-coupled receptors, is categorized in the free fatty acid receptor (FFAR) family and activated by $C_{6-22}$ saturated or unsaturated fatty acid. It is reported that high expression of GPR40 is observed in beta cells of the pancreas where the receptor is involved in insulin secretion caused by fatty acid (Nature, 422, 173-176 (2003) (Non-Patent Document 2)). Non-fatty-acid low-molecular-weight compounds having a GPR40 agonist action have been found in recent years, and it is reported that thiazolidinediones, which are insulin sensitivity improving agents, and MEDICA 16, which is a hypolipidemic agent, also exhibit agonist actions (Biochem. Biophys. Res. Comm., 301, 406-410 (2003) (Non-Patent Document 3)).

In the pancreatic islets of Langerhans isolated from GPR40 knockout mice, the glucose-responsive insulin secretagogue action of fatty acid is lower than the case with normal mice. Accordingly, substances having a GPR40 agonist action like fatty acid are expected to have the effect of inhibiting postprandial hyperglycemia based on the glucose-responsive insulin secretagogue action in the pancreas. Therefore, substances having a GPR40 agonist action are considered to be effective as prophylactic and therapeutic agents against diabetes or boederline type diabetes.

Studies have been progressed on compounds having a GPR40 activating action as insulin secretagogues or therapeutic agents against diabetes. Technologies related to compounds having a GPR40 agonist action are disclosed, for example, in WO 2004/041266 pamphlet (Patent Document 1), WO 2005/086661 pamphlet (Patent Document 2), WO 2007/123225 pamphlet (Patent Document 3), WO 2008/001931 pamphlet (Patent Document 4), WO 2009/054390 pamphlet (Patent Document 5), WO 2009/054423 pamphlet (Patent Document 6), WO 2009/054479 pamphlet (Patent Document 7), WO 2011/046851 pamphlet (Patent Document 8), WO 2010/143733 pamphlet (Patent Document 9), WO 2007/033002 pamphlet (Patent Document 10), WO 2009/048527 pamphlet (Patent Document 11), WO 2009/111056 pamphlet (Patent Document 12), WO 2005/051890 pamphlet (Patent Document 13), WO 2004/022551 pamphlet (Patent Document 14), WO 2004/011446 pamphlet (Patent Document 15), WO 2008/030520 pamphlet (Patent Document 16), WO 2011/066183 pamphlet (Patent Document 17), WO 2010/091176 pamphlet (Patent Document 18), WO 2010/085525 pamphlet (Patent Document 19), WO 2009/039943 pamphlet (Patent Document 20), WO 2005/063729 pamphlet (Patent Document 21), and WO 2008/130514 pamphlet (Patent Document 22). These documents, however, do not disclose or suggest any compounds having a saturated cyclic amide structure bonded to a benzene ring or the like.

A technique related to a compound having a 5-aryl-3-isothiazolidinone ring is disclosed in WO 2005/035551 pamphlet (Patent Document 23). The compound disclosed in Patent Document 23, however, is a compound having an inhibitory effect on protein tyrosine phosphatase 1B (PTP1B), and its structure of a linker moiety is fundamentally different from that of the compounds according to the present invention.

Another compound group having a 5-aryl-3-isothiazolidinone ring is disclosed in WO 2008/033931 pamphlet (Patent Document 24) as a compound having an inhibitory effect on PTP1B. The compound disclosed in Patent Document 24, however, has a fundamental framework different from that of the compounds according to the present invention.

Techniques related to compounds having a 5-aryl-1,2,5-thiadiazolidin-3-one ring are disclosed in WO 2003/082841 pamphlet (Patent Document 25), WO 2005/035551 pamphlet (Patent Document 24), WO 2007/067612 pamphlet (Patent Document 26), WO 2007/067613 pamphlet (Patent Document 27), WO 2007/067614 pamphlet (Patent Document 28), WO 2007/089857 pamphlet (Patent Document 29), WO 2007/115058 pamphlet (Patent Document 30), and WO 2009/109999 pamphlet (Patent Document 31). The compounds disclosed in Patent Documents 24 to 31, however, are compounds having an inhibitory effect on PTP1B, and their fundamental structures of linker moieties are different from that of the compounds according to the present invention.

The compound having a 5-aryl-1,2,5-thiadiazolidin-3-one ring is also disclosed in WO 2008/022771 pamphlet (Patent Document 32). The compound disclosed in Patent Document 32, however, is a compound having an inhibitory effect on sphingomyelin and having an amide structure on its linker moiety, and is different from that of the compounds according to the present invention.

A technique related to the compound having a 5-aryl-1,2,6-thiadiazinan-3-one ring and a 5-aryl-1,2-thiazinan-3-one ring is disclosed in Synlett, 834-838 (2005) (Non-Patent Document 4). The compound disclosed in Non-Patent Document 4, however, has a fundamental framework different from that of the compounds according to the present invention and does not disclose or suggest any compounds having a GPR40 agonist action like the present invention.

WO 2008/066131 pamphlet (Patent Document 33) and WO 2009/147990 pamphlet (Patent Document 34) disclose compounds having a 3-hydroxy-5-arylisoxazolyl group as compounds having a G protein-coupled receptor 120 (GPR120) agonist action. These documents, however, do not disclose or suggest any compounds having a GPR40 agonist action or a saturated cyclic amide structure bonded to a benzene ring or the like as in the present invention.

WO 2011/052756 pamphlet (Patent Document 35) and WO 2011/078371 pamphlet (Patent Document 36) have recently disclosed compounds having a 3-hydroxy-5-arylisoxazole group or a 3-hydroxy-5-arylisothiazole group as compounds having a GPR40 activating action.

In the development of drugs, various strict criteria must be met in terms of absorption, distribution, metabolism, excretion, and other factors as well as targeted pharmacological actions. There are various things to consider, for example, interaction with other drugs, desensitization or durability, digestive tract absorption after oral administration, speed to reach the small intestine, absorption speed and first pass effect, organ barriers, protein binding, drug metabolizing enzyme induction or inhibition, excretion route and clearance in the body, and application methods (application sites, methods, purposes). It is difficult to find a drug that meets all the criteria.

Several compounds are reported to have a GPR40 agonist action, but none of them has been marketed so far. Such agonists could also involve the above-mentioned general issues in the development phase of drugs. More specifically, they have problems in usefulness and safety, such as low metabolism stability and difficulty in systemic exposure by oral administration, unfavorable pharmacokinetic effects including absorption and persistence properties, an activity of inhibiting the human ether-a-go-go related gene (hERG) channel, possibly resulting in arrhythmia, and an activity of inducing or inhibiting drug metabolizing enzymes (e.g., cytochrome P450). Therefore, required is a compound that solves these problems as much as possible and still has high efficacy.

In addition, required as a GPR40 agonist is a compound with fewer problems or side effects as described above than the aforementioned conventional drugs that have been used to prevent or treat diabetes (particularly Type 2 diabetes or boederline type diabetes).

RELATED-ART DOCUMENTS

Patent Documents

Patent Document 1: WO 2004/041266 pamphlet
Patent Document 2: WO 2005/086661 pamphlet
Patent Document 3: WO 2007/123225 pamphlet
Patent Document 4: WO 2008/001931 pamphlet
Patent Document 5: WO 2009/054390 pamphlet
Patent Document 6: WO 2009/054423 pamphlet
Patent Document 7: WO 2009/054479 pamphlet
Patent Document 8: WO 2011/046851 pamphlet
Patent Document 9: WO 2010/143733 pamphlet
Patent Document 10: WO 2007/033002 pamphlet
Patent Document 11: WO 2009/048527 pamphlet
Patent Document 12: WO 2009/111056 pamphlet
Patent Document 13: WO 2005/051890 pamphlet
Patent Document 14: WO 2004/022551 pamphlet
Patent Document 15: WO 2004/011446 pamphlet
Patent Document 16: WO 2008/030520 pamphlet
Patent Document 17: WO 2011/066183 pamphlet
Patent Document 18: WO 2010/091176 pamphlet
Patent Document 19: WO 2010/085525 pamphlet
Patent Document 20: WO 2009/039943 pamphlet
Patent Document 21: WO 2005/063729 pamphlet
Patent Document 22: WO 2008/130514 pamphlet
Patent Document 23: WO 2005/035551 pamphlet
Patent Document 24: WO 2008/033931 pamphlet Patent Document 25: WO 2003/082841 pamphlet
Patent Document 26: WO 2007/067612 pamphlet
Patent Document 27: WO 2007/067613 pamphlet
Patent Document 28: WO 2007/067614 pamphlet
Patent Document 29: WO 2007/089857 pamphlet
Patent Document 30: WO 2007/115058 pamphlet
Patent Document 31: WO 2009/109999 pamphlet
Patent Document 32: WO 2008/022771 pamphlet
Patent Document 33: WO 2008/066131 pamphlet
Patent Document 34: WO 2009/147990 pamphlet
Patent Document 35: WO 2011/052756 pamphlet
Patent Document 36: WO 2011/078371 pamphlet Non-Patent Documents Non-Patent Document 1: JAMA, 290, 486-494 (2003)
Non-Patent Document 2: Nature, 422, 173-176 (2003)
Non-Patent Document 3: Biochem. Biophys. Res. Comm., 301, 406-410 (2003)
Non-Patent Document 4: Synlett, 834-838 (2005)

SUMMARY OF THE INVENTION

Problem to be Solved by the Invention

In view of such medical circumstances related to diabetes, prophylactic and therapeutic drugs are required that accelerate insulin secretion, particularly glucose-responsive insulin secretion, through activation of GPR40, and thus exhibit the action of lowering blood glucose levels, particularly inhibiting postprandial hyperglycemia.

Particularly required are orally administrable GPR40 activating agents, insulin secretagogues, prophylactic and/or therapeutic agents against GPR40-involving diseases (particularly prophylactic and/or therapeutic agents against diabetes or obesity) all of which have high safety, excellent efficacy, and high selectivity with respect to other members of the FFAR family or similar receptors.

In particular, there are issues to be addressed as problems with the conventional techniques described above. More specifically, there are the following issues to be addressed with prophylactic and therapeutic agents against diabetes: ineffectiveness (primary failure, secondary failure) and side effects such as induced hypoglycemic effects caused by sulfonylurea agents and rapid-acting insulin secretagogues; transient gastrointestinal tract disorders caused by GLP-1 analogs; side effects of epipharyngitis, headache, and infections caused by DPP-IV inhibitors; side effects such as distension and diarrhea and serious liver disorders caused by alpha-glucosidase inhibitors; side effects such as lactic acidosis, nausea, and vomiting caused by biguanides; edema, weight gain, and serious liver disorders caused by thiazolidinedione derivatives; and so on. Other issues to be addressed include solubility, improvement in metabolism stability, enhancement of absorption properties, improvement in pharmacokinetic effects, reduction in the activity of inhibiting hERG, and reduction in the activity of inducing or inhibiting drug metabolizing enzymes (e.g., cytochrome P450). Consequently, there are needs for insulin secretagogues and prophylactic and/or therapeutic agents against GPR40-involving diseases (particularly prophylactic and/or therapeutic agents against diabetes or obesity) all of which solve at least one of the issues, to be orally administrable to mammals including human beings, and clinically usable in particular.

Means for Solving the Problem

As a result of assiduous research for solving the above problems by obtaining a compound having high safety and/or excellent efficacy and modulationg the functions of GPR40, the inventors of the present invention have found that a derivative having a cyclic amide structure of Formula (I) has a GPR40 agonist action. The compound of the present invention has an excellent glucose-responsive insulin secretagogue action and has a strong hyperglycemia-inhibiting action during glucose load.

Effects of Invention

The present invention provides: a compound characterized by having a cyclic amide structure of Formula (I), a salt of the compound, or a solvate of the compound or the salt; and a pharmaceutical composition characterized by containing as an active ingredient, the compound, a pharmaceutically acceptable salt of the compound, or a solvate of the compound or the pharmaceutically acceptable salt.

The compound of the present invention is a compound having a GPR40 agonist action, or a compound having an action of lowering a blood glucose level, particularly an action of inhibiting postprandial hyperglycemia, by activating GPR40 to accelerate an insulin secretion, particularly a glucose-responsive insulin secretion. The pharmaceutical composition containing the compound of the present invention as an active ingredient can be orally administrated and is expected as an insulin secretagogue or a prophylactic agent and/or a therapeutic agent for a GPR40-involving disease, particularly diabetes (particularly Type 2 diabetes or boederline type diabetes) or obesity and adiposity.

The group of the compounds of the present invention has at least one of characteristics such as having advantageous solubility, having high metabolism stability, having excellent oral absorption properties, and having a small activity of inhibiting the hERG channel, and thus is highly useful.

MODES FOR CARRYING OUT THE INVENTION

The present invention provides: a compound of Formula (I), characterized by having the cyclic amide structure shown in the following aspects, a salt of the compound, or a solvate of the compound or the salt; and a pharmaceutical composition or GPR40 activating agent, characterized by containing the compound, the salt, or the solvate as an active ingredient.

[Aspects of the Present Invention]

[1] Aspect [1] of the present invention

A first aspect of the present invention is a compound of Formula (I):

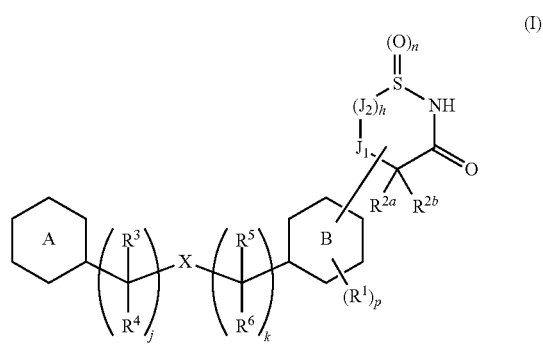

(where n is an integer of 0 to 2; p is an integer of 0 to 4; h is an integer of 0 to 3; j is an integer of 0 to 3; k is an integer of 0 to 2;

a ring A is a $C_{6-14}$ aryl group which is optionally substituted with 1 to 5 L(s), a 3- to 14-membered heterocyclic group which is optionally substituted with 1 to 5 L(s), a $C_{5-7}$ cycloalkyl group which is optionally substituted with 1 to 5 L(s), a $C_{5-7}$ cycloalkenyl group which is optionally substituted with 1 to 5 L(s), a 6- to 14-membered spiro ring group which is optionally substituted with 1 to 5 L(s), or a 2-phenylamino-2-oxoacetyl group which is optionally substituted with 1 to 5 L(s);

a ring B is a $C_{6-14}$ aryl group or a 5- to 14-membered heteroaryl group;

X is an oxygen atom, a sulfur atom, or $-NR^7-$;

$J_1$ is $-CR^{11a}R^{11b}-$ or $-NR^{11c}-$; $J_2$ is $-CR^{12a}R^{12b}-$ or $-NR^{12c}-$ (with the proviso that when $J_1$ is $-NR^{11c}-$, h is 0);

$R^1$s are independently a group optionally selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group;

$R^{2a}$ and $R^{2b}$ are independently a group optionally selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, and a cyano group;

$R^3$, $R^4$, $R^5$, $R^6$, and $R^7$ are independently a group optionally selected from a hydrogen atom, a $C_{1-6}$ alkyl group, a halogenated $C_{1-6}$ alkyl group, a $C_{2-6}$ alkenyl group, and a $C_{2-6}$ alkynyl group;

$R^{11a}$ and $R^{11b}$ are independently a group optionally selected from a hydrogen atom, a halogen atom, a $C_{1-6}$ alkyl group, a halogenated $C_{1-6}$ alkyl group, a $C_{2-6}$ alkenyl group, a $C_{2-6}$ alkynyl group, a $C_{1-6}$ alkoxy group, a halogenated $C_{1-6}$ alkoxy group, a $C_{2-7}$ alkanoyl group, and a carboxy group which is optionally protected;

$R^{12a}$ and $R^{12b}$ are independently a group optionally selected from a hydrogen atom, a halogen atom, a $C_{1-6}$ alkyl group, a halogenated $C_{1-6}$ alkyl group, a $C_{2-6}$ alkenyl group, a $C_{2-6}$ alkynyl group, a $C_{1-6}$ alkoxy group, a halogenated $C_{1-6}$ alkoxy group, and a cyano group;

$R^{11c}$ and $R^{12c}$ are independently a group optionally selected from a hydrogen atom, a $C_{1-6}$ alkyl group, and a halogenated $C_{1-6}$ alkyl group;

with the proviso that in the cyclic amide structure moiety, there is not one of the substituents ($R^{2b}$, $R^{11b}$, $R^{11c}$, $R^{12b}$, or $R^{12c}$) on an atom to which the ring B is bonded;

Ls are independently a group optionally selected from a halogen atom, $-OH$, an oxo group, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, a $C_{2-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, $-SH$, $-SF_5$, a $-S(O)_iR^a$ (i is an integer of 0 to 2) group, a $-NR^bR^c$ group, and a substituted spiropiperidinylmethyl group;

$R^a$ is a $C_{1-6}$ alkyl group or a halogenated $C_{1-6}$ alkyl group;

$R^b$ and $R^c$ are independently a group optionally selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with $-OH$ or a $C_{1-6}$ alkoxy group), a $C_{1-6}$ alkylsulfonyl group, an arylcarbonyl group, and a heterocyclic carbonyl group, where $R^b$ and $R^c$ optionally form together with a nitrogen atom to which they are bonded, a 3- to 8-membered cyclic group, where in the cyclic group, one or two carbon atom(s) is(are) optionally substituted with an atom optionally selected from an oxygen atom, a sulfur atom, and a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

where the substituents RI may be the same as or different from each other and be each a group optionally selected from a halogen atom, $-OH$, a cyano group, a $C_{1-6}$ alkoxy group (the $C_{1-6}$ alkoxy group is optionally substituted with 1 to 5 halogen atom(s), 1 to 5 $-OH$, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 $-S(O)_iR^a$ (i is an integer of 0 to 2) group(s), 1 to 5 $-SO_2NR^dR^e$ group(s), 1 to 5 $-CONR^dR^e$ group(s), or 1 to 5 $-NR^{b1}R^{c1}$ group(s)), a $-NR^{b1}R^{c1}$ group, and a heterocyclic oxy group (the heterocyclic oxy group is optionally substituted with 1 to 3 $C_{1-6}$ alkyl group(s) or 1 to 3 oxo group(s));

the substituents RII may be the same as or different from each other and be each a group optionally selected from the substituents RI, a $C_{1-6}$ alkyl group (the $C_{1-6}$ alkyl group is optionally substituted with 1 to 5 halogen atom(s), 1 to 5 $-OH$, 1 to 5 $C_{1-6}$ alkoxy group(s), 1 to 5 $-S(O)_iR^a$ (i is an integer of 0 to 2) group(s), 1 to 5 $-NR^{b1}R^{c1}$ group(s), 1 to 5 $-SO_2NR^dR^e$ group(s), or 1 to 5 $-CONR^dR^e$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a $-S(O)_iR^a$ (i is an integer of 0 to 2) group, a $-CONR^dR^e$ group, and a $-CONR^dR^{e1}$ group;

$R^d$ and $R^e$ are independently a hydrogen atom or a $C_{1-6}$ alkyl group (the $C_{1-6}$ alkyl group is optionally substituted with 1 to 5 halogen atom(s), 1 to 5 $-OH$, or 1 to 5 $C_{1-6}$ alkoxy group(s));

$R^{e1}$ is a $C_{1-6}$ alkyl group (the $C_{1-6}$ alkyl group is substituted with 1 to 5 $-OH$, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 $-S(O)_iR^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s));

R$^{b1}$ and R$^{c1}$ are independently a group optionally selected from a hydrogen atom, a C$_{1-6}$ alkyl group, a C$_{2-7}$ alkanoyl group, and a C$_{1-6}$ alkylsulfonyl group, where R$^{b1}$ and R$^{c1}$ optionally form together with a nitrogen atom to which they are bonded, a 3- to 8-membered cyclic group, wherein the cyclic group, one or two carbon atom(s) is(are) optionally substituted with an atom optionally selected from an oxygen atom, a sulfur atom, and a nitrogen atom (the nitrogen atom is optionally substituted with a C$_{1-6}$ alkyl group) or with a carbonyl group (with the proviso that there are excluded a compound which is 5-[4-[2-(2-phenyl-4-oxazolyl)ethoxy]phenyl]-1,1-dioxo-1,2,5-thiadiazolidin-3-one; a compound in which a saturated cyclic amide structure having —S(O)$_n$—NH—CO— is 1,1-dioxo-1,2-thiazolidin-3-one, the ring B is a benzene ring, the ring B is bonded to J$_1$, k is 1, and in the ring B, a linker moiety containing X and the cyclic amide structure are positioned at a p-position; and a compound in which the cyclic amide structure is 1,1-dioxo-1,2,5-thiadiazolidin-3-one, the ring B is bonded to J$_1$, and in the ring B, the cyclic amide structure is bonded to an atom adjacent to an atom to which a linker containing X is bonded)), a salt of the compound, or a solvate of the compound or the salt.

Each group in Formula (I) according to Aspect [1] is specifically described below.

In the explanation of the compound according to the present invention, for example, "C$_{1-6}$" indicates that the number of constituent carbon atoms, which is the number of carbon atoms in a linear, branched, or cyclic group unless otherwise indicated, is 1 to 6. The number of constituent carbon atoms includes the total number of carbon atoms in a group having a linear or branched group substituted with a cyclic group or a cyclic group substituted with a linear or branched group. Therefore, as for an acyclic group, "C$_{1-6}$" means a "linear or branched chain with the number of constituent carbon atoms of 1 to 6". As for a cyclic group, "C$_{1-6}$" means a "cyclic group with the number of ring-constituting carbon atoms of 1 to 6". As for a group having an acyclic group and a cyclic group, "C$_{1-6}$" means a "group with the total number of carbon atoms of 1 to 6".

The "alkyl group" is a linear, branched, or cyclic alkyl group. For example, examples of the "C$_{1-6}$ alkyl group" include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclobutylmethyl, cyclopentylmethyl, 1-cyclopropylethyl, 2-cyclopropylethyl, 2-cyclobutylethyl, and 2-methylcyclopropyl. Examples of the "C$_{1-10}$ alkyl group" include, in addition to the groups mentioned as the "C$_{1-6}$ alkyl group", heptyl, 1-methylhexyl, octyl, 2-ethylhexyl, 1,1-dimethylhexyl, nonyl, decyl, cycloheptyl, cyclohexylmethyl, 2-cyclohexylethyl, 4-methylcyclohexyl, 4,4-dimethylcyclohexyl, and 3,3,5,5-tetramethylcyclohexyl. The cyclic alkyl group is also expressed as "cycloalkyl group". Examples of the "C$_{5-7}$ cycloalkyl group" include cyclopentyl, cyclohexyl, and cycloheptyl.

The "alkenyl group" is a linear, branched, or cyclic alkenyl group. For example, examples of the "C$_{2-6}$ alkenyl group" include vinyl, allyl, isopropenyl, 2-methylallyl, butenyl, pentenyl, isopentenyl, hexenyl, 1-cyclopropen-1-yl, 2-cyclopropen-1-yl, 1-cyclobuten-1-yl, 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, 2,4-cyclopentadien-1-yl, and 2,5-cyclohexadien-1-yl. Examples of the "C$_{2-10}$ alkenyl group" include, in addition to the groups mentioned as the "C$_{2-6}$ alkenyl group", heptenyl, octenyl, nonenyl, decenyl, 1-cyclohepten-1-yl, 1-cyclohexen-1-ylmethyl, 4-methyl-1-cyclohexen-1-yl, 4,4-dimethyl-1-cyclohexen-1-yl, and 3,3,5,5-tetramethyl-1-cyclohexen-1-yl. The cyclic alkenyl group is also expressed as "cycloalkenyl group". Examples of the "C$_{5-7}$ cycloalkenyl group" include 1-cyclopenten-1-yl, 2-cyclopenten-1-yl, 3-cyclopenten-1-yl, 1-cyclohexen-1-yl, 2-cyclohexen-1-yl, 3-cyclohexen-1-yl, and 1-cyclohepten-1-yl.

The "alkynyl group" is a linear, branched, or cyclic alkynyl group. For example, examples of the "C$_{2-6}$ alkynyl group" include ethynyl, 1-propynyl, 2-propynyl, butynyl, pentynyl, and hexynyl. Examples of the "C$_{2-10}$ alkynyl group" include, in addition to the groups mentioned as the "C$_{2-6}$ alkynyl group", heptynyl, octynyl, nonynyl, and decynyl.

The "alkoxy group" is a linear, branched, or cyclic alkoxy group and comprehensively a group of RO— (as for the C$_{1-6}$ alkoxy group, R is the C$_{1-6}$ alkyl group listed above). For example, examples of the "C$_{1-6}$ alkoxy group" include methoxy, ethoxy, propoxy, isopropoxy, butoxy, isobutoxy, sec-butoxy, tert-butoxy, pentyloxy, isopentyloxy, neopentyloxy, tert-pentyloxy, 1-methylbutoxy, 2-methylbutoxy, 1,2-dimethylpropoxy, 1-ethylpropoxy, hexyloxy, isohexyloxy, 1-methylpentyloxy, 2-methylpentyloxy, 3-methylpentyloxy, 1,1-dimethylbutyloxy, 1,2-dimethylbutyloxy, 2,2-dimethylbutyloxy, 1,3-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy, 1-ethyl-2-methylpropyloxy, cyclopropyloxy, cyclobutyloxy, cyclopentyloxy, cyclohexyloxy, cyclopropylmethoxy, cyclobutylmethoxy, cyclopentylmethoxy, 1-cyclopropylethoxy, 2-cyclopropylethoxy, 2-cyclobutylethoxy, and 2-methylcyclopropyloxy. Examples of the "C$_{1-10}$ alkoxy group" include, in addition to the groups mentioned as the "C$_{1-6}$ alkoxy group", heptyloxy, octyloxy, 2-ethylhexyloxy, nonyloxy, decyloxy, cyclohepty-loxy, cyclohexylmethoxy, 2-cyclohexylethoxy, 4-methylcyclohexyloxy, 4,4-dimethylcyclohexyloxy, and 3,3,5,5-tetramethylcyclohexyloxy.

The "alkenyloxy group" is the "alkenyl group" which is substituted with an oxygen atom, denoting a linear, branched, or cyclic alkenyloxy group. For example, examples of the "C$_{2-6}$ alkenyloxy group" include vinyloxy, allyloxy, isopropenyloxy, 2-methylallyloxy, butenyloxy, pentenyloxy, isopentenyloxy, hexenyloxy, 1-cyclopropen-1-yloxy, 2-cyclopropen-1-yloxy, 1-cyclobuten-1-yloxy, 1-cyclopenten-1-yloxy, 2-cyclopenten-1-yloxy, 3-cyclopenten-1-yloxy, 1-cyclohexen-1-yloxy, 2-cyclohexen-1-yloxy, 3-cyclohexen-1-yloxy, 2,4-cyclopentadien-1-yloxy, and 2,5-cyclohexadien-1-yloxy. Examples of the "C$_{2-10}$ alkenyloxy group" include, in addition to the groups mentioned as the "C$_{2-6}$ alkenyloxy group", heptenyloxy, octenyloxy, nonenyloxy, decenyloxy, 1-cyclohepten-1-yloxy, 1-cyclohexen-1-ylmethoxy, 4-methyl-1-cyclohexen-1-yloxy, 4,4-dimethyl-1-cyclohexen-1-yloxy, and 3,3,5,5-tetramethyl-1-cyclohexen-1-yloxy.

The "alkynyloxy group" is the "alkynyl group" which is substituted with an oxygen atom, denoting a linear, branched, or cyclic alkynyloxy group. For example, examples of the "$C_{2-6}$ alkynyloxy group" include ethynyloxy, 1-propynyloxy, 2-propynyloxy, butynyloxy, pentynyloxy, and hexynyloxy. Examples of the "$C_{2-10}$ alkynyloxy group" include, in addition to the groups mentioned as the "$C_{2-6}$ alkynyloxy group", heptynyloxy, octynyloxy, nonynyloxy, and decynyloxy.

Examples of the "aryl group" include a monocyclic or ring-fused $C_{6-14}$ aryl groups, for example, phenyl, 1-naphthyl, 2-naphthyl, anthryl, phenanthryl, and acenaphthyl, or a fused aryl group which is partly hydrogenated such as (1-, 2-, 4-, or 5-)indanyl, indenyl, and tetrahydronaphthyl. The fused aryl group which is partly hydrogenated means a monovalent group obtained by removing any hydrogen atom from a fused ring which is partly hydrogenated, and the hydrogen atom to be removed is optionally a hydrogen atom in an aromatic ring moiety or a hydrogen atom in a hydrogenated moiety of the fused ring. For example, tetrahydronaphthyl includes 1,2,3,4-tetrahydronaphthalene (-1-yl, -2-yl, -3-yl, -4-yl, -5-yl, -6-yl, -7-yl, -8-yl), and the like.

Examples of the "heterocyclic group" include a "heteroaryl group" and a saturated or unsaturated "non-aromatic heterocyclic group". The term "cyclic" used for these groups means a monovalent group obtained by removing any hydrogen atom from a ring having a 3- to 14-membered, preferably a 3- to 12-membered, monocyclic ring or fused ring containing, in addition to carbon atoms, at least one (preferably 1 to 4) heteroatom(s) optionally selected from N, O, and S.

The "heteroaryl group" can be monocyclic or ring-fused, and the monocyclic heteroaryl group preferably has 5 to 7 ring members and examples of the "heteroaryl group" include pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, and 1,4-oxazepinyl.

The ring-fused heteroaryl group preferably has 8 to 14 ring members and includes a monovalent group obtained by removing any hydrogen atom from a fused ring formed by fusing the 5- to 7-membered heterocyclic ring and a monocyclic aryl group or a monocyclic heteroaryl group, and the like. The hydrogen atom is optionally removed from any of the fused rings.

Specifically, indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, dibenzofuranyl, and the like are mentioned.

In addition, a ring-fused heteroaryl group, etc. which is partly hydrogenated, such as indolinyl, dihydrobenzofuranyl, dihydroisobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,3-benzodioxanyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl is mentioned. The ring-fused heteroaryl group, etc. which is partly hydrogenated is preferably one having 8 to 14 ring members, namely a monovalent group obtained by removing any hydrogen atom from a ring which is partly hydrogenated in the fused ring formed by fusing the 5- to 7-membered heterocyclic ring and a monocyclic aryl group or a monocyclic heteroaryl group. The hydrogen atom to be removed is optionally a hydrogen atom in the aryl group or in the heterocyclic moiety or a hydrogen atom in the hydrogenated moiety. In the case of tetrahydroquinolyl, examples of the partly hydrogenated ring-fused heteroaryl group include 5,6,7,8-tetrahydroquinolyl and 1,2,3,4-tetrahydroquinolyl. Depending on the position in these groups from which the hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" include a 3- to 8-membered saturated or unsaturated non-aromatic heterocyclic group, for example, aziridinyl, azetidinyl, oxiranyl, oxetanyl, thietanyl, pyrrolidinyl, tetrahydrofuryl, thiolanyl, pyrazolinyl, pyrazolidinyl, piperidinyl, dihydropyranyl, tetrahydropyranyl (oxanyl), tetrahydrothiopyranyl, piperazinyl, dioxanyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, and oxepanyl, and the "non-aromatic heterocyclic group" means a monovalent group obtained by removing any hydrogen atom from the ring.

Examples of the "heterocyclic group (the heterocyclic group is optionally substituted with 1 to 3 $C_{1-6}$ alkyl group(s) or 1 to 3 oxo group(s))" include, in addition to the groups mentioned as the "heterocyclic group", a group in which the cyclic group is substituted with 1 to 3 "$C_{1-6}$ alkyl group(s)" or 1 to 3 oxo group(s) at any position. For example, methylpyrrolyl, methylfuryl, methylthienyl, methylimidazolyl, methylpyrazolyl, methyloxazolyl, methylisoxazolyl, methylthiazolyl, methylisothiazolyl, methylpyridyl, methylpyrimidinyl, methylaziridinyl, methylazetidinyl, methyloxiranyl, methyloxetanyl, methylthietanyl, methylpyrrolidinyl, methyltetrahydrofuryl, methylthiolanyl, methylpyrazolinyl, methylpyrazolidinyl, methylpiperidinyl, methyltetrahydropyranyl, methylpiperazinyl, methyloxazolinyl, methylisoxazolinyl, methyloxazolidinyl, methylisoxazolidinyl, methylthiazolinyl, methylisothiazolinyl, methylthiazolidinyl, methylisothiazolidinyl, methyloxadiazolinyl, methyloxadiazolidinyl, methylmorpholinyl, methylthiomorpholinyl, methylquinuclidinyl, methyloxepanyl, oxopyrrolidinyl, 1,1-dioxidetetrahydrothiopyranyl, and the like are mentioned.

The "aralkyl group" is a group in which a linear or branched alkyl group of the "$C_{1-6}$ alkyl group" is substituted with the "aryl group", and examples of the "aralkyl group" include benzyl, phenethyl, 3-phenylpropyl, 1-naphthylmethyl, 2-naphthylmethyl, 2-(1-naphthyl)ethyl, 2-(2-naphthyl)ethyl, 1-indanylmethyl, 2-indanylmethyl, 1,2,3,4-tetrahydronaphthalen-1-ylmethyl, and 1,2,3,4-tetrahydronaphthalen-2-ylmethyl.

The "heteroarylalkyl group" is a group in which a linear or branched alkyl group of the "$C_{1-6}$ alkyl group" is substituted with the "heteroaryl group", and examples of the "heteroarylalkyl group" include those substituted with the "monocyclic heteroaryl group", such as pyrrolylmethyl, furylmethyl, thienylmethyl, imidazolylmethyl, pyrazolylmethyl, oxazolylmethyl, isoxazolylmethyl, thiazolylmethyl, isothiazolylmethyl, 1,2,3-triazolylmethyl, 1,2,4-triazolylmethyl, 1,2,3-oxadiazolylmethyl, 1,2,4-oxadiazolylmethyl, 1,3,4-oxadiazolylmethyl, furazanylmethyl, 1,2,3-thiadiazolylmethyl, 1,2,4-thiadiazolylmethyl, 1,3,4-thiadiazolylmethyl, tetrazolylmethyl, pyridylmethyl, pyridazinylmethyl, pyrimidinylmethyl, pyrazinylmethyl, 1,2,3-triazinylmethyl, 1,2,4-triazinylmethyl, 1,3,5-triazinylmethyl, 2H-1,2,3-thiadiazinylmethyl, 4H-1,2,4-thiadiazinylmethyl, 6H-1,3,4-thiadiazinylmethyl, 1,4-diazepinylmethyl, and 1,4-oxazepinylmethyl, and those substituted with the "ring-fused heteroaryl group", such as indolylmethyl, isoindolylmethyl, benzofuranylmethyl, isobenzofuranylmethyl, benzothienylmethyl, isobenzothienylmethyl, benzoxazolylmethyl, 1,2-benzisoxazolylmethyl, benzothiazolylmethyl, 1,2-benzisothiazolylmethyl, 1H-benzimidazolylmethyl, 1H-indazolylmethyl, 1H-benzotriazolylmethyl, 2,1,3-benzothiadiazinylmethyl, chromenylmethyl, isochromenylmethyl, 4H-1,4-benzoxazinylmethyl, 4H-1,4-benzothiazinylmethyl, quinolylmethyl, isoquinolylmethyl, cinnolinylmethyl, quinazolinylmethyl, quinoxalinylmethyl, phthalazinylmethyl, benzoxazepinylmethyl, benzoazepinylmethyl, benzodiazepinylmethyl, naphthyridinylmethyl, purinylmethyl, pteridinylmethyl, carbazolylmethyl, carbolinylmethyl, acridinylmethyl, phenoxazinylmethyl, phenothiazinylmethyl, phenazinylmethyl, phenoxathiinylmethyl, thianthrenylmethyl, phenanthridinylmethyl, phenanthrolinylmethyl, indolizinylmethyl, thieno[3,2-c]pyridylmethyl, thiazolo[5,4-c]pyridylmethyl, pyrrolo[1,2-b]pyridazinylmethyl, pyrazolo[1,5-a]pyridylmethyl, imidazo[1,2-a]pyridylmethyl, imidazo[1,5-a]pyridylmethyl, imidazo[1,2-b]pyridazinylmethyl, imidazo[1,5-a]pyrimidinylmethyl, 1,2,4-triazolo[4,3-a]pyridylmethyl, 1,2,4-triazolo[4,3-b]pyridazinylmethyl, 1H-pyrazolo[3,4-b]pyridylmethyl, 1,2,4-triazolo[1,5-a]pyrimidinylmethyl, indolinylmethyl, dihydrobenzofuranylmethyl, chromanylmethyl, tetrahydroquinolylmethyl, tetrahydroisoquinolylmethyl, 1,4-benzodioxanylmethyl, and 1,3-benzodioxolylmethyl.

The "non-aromatic heterocyclic alkyl group" is a group in which a linear or branched alkyl group of the "$C_{1-6}$ alkyl group" is substituted with the "non-aromatic heterocyclic group", and examples of the "non-aromatic heterocyclic alkyl group" include aziridinylmethyl, azetidinylmethyl, oxiranylmethyl, oxetanylmethyl, thietanylmethyl, pyrrolidinylmethyl, tetrahydrofurylmethyl, thiolanylmethyl, pyrazolinylmethyl, pyrazolidinylmethyl, piperidinylmethyl, dihydropyranylmethyl, tetrahydropyranylmethyl, tetrahydrothiopyranylmethyl, piperazinylmethyl, dioxanylmethyl, oxazolinylmethyl, isoxazolinylmethyl, oxazolidinylmethyl, isoxazolidinylmethyl, thiazolinylmethyl, isothiazolinylmethyl, thiazolidinylmethyl, isothiazolidinylmethyl, oxadiazolinylmethyl, oxadiazolidinylmethyl, morpholinylmethyl, thiomorpholinylmethyl, quinuclidinylmethyl, and oxepanylmethyl.

The "aryloxy group" is the "aryl group" which is substituted with an oxygen atom, and specifically, a group in which the group mentioned as the "aryl group" is substituted with an oxygen atom is mentioned. For example, examples of the "aryloxy group" include phenoxy, 1-naphthyloxy, 2-naphthyloxy, 2-anthryloxy, phenanthryloxy, 1-indanyloxy, 2-indanyloxy, 1,2,3,4-tetrahydronaphthalen-1-yloxy, 1,2,3,4-tetrahydronaphthalen-2-yloxy, and 1,2,3,4-tetrahydronaphthalen-8-yloxy.

The "heterocyclic oxy group" is the "heterocyclic group" which is substituted with an oxygen atom, and a "heteroaryloxy group" or a "non-aromatic heterocyclic oxy group" is mentioned. Specifically, a group in which the group mentioned as the "heterocyclic group" is substituted with an oxygen atom is mentioned.

The "heteroaryloxy group" is the "heteroaryl group" which is substituted with an oxygen atom, and specifically, a group in which the group mentioned as the "heteroaryl group" is substituted with an oxygen atom is mentioned. For example, examples of the "heteroaryloxy group" include pyrrolyloxy, furyloxy, thienyloxy, imidazolyloxy, pyrazolyloxy, oxazolyloxy, isoxazolyloxy, thiazolyloxy, isothiazolyloxy, (2-, 3-, or 4-)pyridyloxy, pyridazinyloxy, pyrimidinyloxy, pyrazinyloxy, indolyloxy, quinolyloxy, isoquinolyloxy, indolinyloxy, dihydrobenzofuranyloxy, chromanyloxy, tetrahydroquinolyloxy, tetrahydroisoquinolyloxy, 1,4-benzodioxanyloxy, and 1,3-benzodioxolyloxy.

The "non-aromatic heterocyclic oxy group" is the "non-aromatic heterocyclic group" which is substituted with an oxygen atom, and specifically, a group in which the group mentioned as the "non-aromatic heterocyclic group" is substituted with an oxygen atom is mentioned. Examples of the "non-aromatic heterocyclic oxy group" include 3- to 8-membered saturated or unsaturated non-aromatic heterocyclic oxy groups such as aziridinyloxy, azetidinyloxy, oxiranyloxy, oxetanyloxy, thietanyloxy, pyrrolidinyloxy, tetrahydrofuryloxy, thiolanyloxy, pyrazolinyloxy, pyrazolidinyloxy, (1-, 2-, 3-, or 4-)piperidinyloxy, dihydropyranyloxy, (2-, 3-, or 4-)tetrahydropyranyloxy ((2-, 3-, or 4-)oxanyloxy), tetrahydrothiopyranyloxy, piperazinyloxy, dioxanyloxy, oxazolinyloxy, isoxazolinyloxy, oxazolidinyloxy, isoxazolidinyloxy, thiazolinyloxy, isothiazolinyloxy, thiazolidinyloxy, isothiazolidinyloxy, oxadiazolinyloxy, oxadiazolidinyloxy, morpholinyloxy, thiomorpholinyloxy, quinuclidinyloxy, and oxepanyloxy.

Examples of the "heterocyclic oxy group (the heterocyclic oxy group is optionally substituted with 1 to 3 $C_{1-6}$ alkyl group(s) or 1 to 3 oxo group(s))" include, in addition to the groups mentioned as the "heterocyclic oxy group", a group in which the cyclic group is substituted with 1 to 3 "$C_{1-6}$ alkyl group(s)" or 1 to 3 oxo group(s) at any position. The "heterocyclic oxy group" can also be expressed as a group in which the "heterocyclic group (the heterocyclic group is optionally substituted with 1 to 3 $C_{1-6}$ alkyl group(s) or 1 to 3 oxo group(s))" is substituted with an oxygen atom, and specifically, a group in which the groups mentioned as the "heterocyclic group (the heterocyclic group is optionally substituted with 1 to 3 $C_{1-6}$ alkyl group(s) or 1 to 3 oxo group(s))" are substituted with an oxygen atom, is mentioned.

The "aralkyloxy group" is the "aralkyl group" which is substituted with an oxygen atom, and specifically, a group in which the groups mentioned as the "aralkyl group" are substituted with an oxygen atom is mentioned. For example, examples of the "aralkyloxy group" include benzyloxy, phenethyloxy, 3-phenylpropoxy, 1-naphthylmethoxy, 2-naphthylmethoxy, 2-(1-naphthyl)ethoxy, 2-(2-naphthyl)ethoxy, 1-indanylmethoxy, 2-indanylmethoxy, 1,2,3,4-tetrahydronaphthalene-1-ylmethoxy, and 1,2,3,4-tetrahydronaphthalene-2-ylmethoxy.

The "heteroarylalkyloxy group" is the "heteroarylalkyl group" which is substituted with an oxygen atom, and specifically, a group in which the groups mentioned as the "heteroarylalkyl group" are substituted with an oxygen atom is mentioned. For example, a "monocyclic heteroarylalkyl group" substituted with an oxygen atom, such as pyrrolylmethoxy, furylmethoxy, thienylmethoxy, imidazolyl-methoxy, pyrazolylmethoxy, oxazolylmethoxy, isoxazolylmethoxy, thiazolylmethoxy, isothiazolylmethoxy, 1,2,3-triazolylmethoxy, 1,2,4-triazolylmethoxy, 1,2,3-oxadiazolylmethoxy, 1,2,4-oxadiazolylmethoxy, 1,3,4-oxadiazolylmethoxy, furazanylmethoxy, 1,2,3-thiadiazolylmethoxy, 1,2,4-thiadiazolylmethoxy, 1,3,4-thiadiazolylmethoxy, tetrazolylmethoxy, pyridylmethoxy, pyridazinylmethoxy, pyrimidinylmethoxy, pyrazinylmethoxy, 1,2,3-triazinylmethoxy, 1,2,4-triazinylmethoxy, 1,3,5-triazinylmethoxy, 2H-1,2,3-thiadiazinylmethoxy, 4H-1,2,4-thiadiazinylmethoxy, 6H-1,3,4-thiadiazinylmethoxy, 1,4-diazepinylmethoxy, 1,4-oxazepinylmethoxy, and the like, and a "ring-fused heteroarylalkyl group" which is optionally partly hydrogenated and is substituted with an oxygen atom, such as indolylmethoxy, isoindolylmethoxy, benzofuranylmethoxy, isobenzofuranylmethoxy, benzothienylmethoxy, isobenzothienylmethoxy, benzoxazolylmethoxy, 1,2-benzisoxazolylmethoxy, benzothiazolylmethoxy, 1,2-benzisothiazolylmethoxy, 1H-benzimidazolylmethoxy, 1H-indazolylmethoxy, 1H-benzotriazolylmethoxy, 2,1,3-benzothiadiazinylmethoxy, chromenylmethoxy, isochromenylmethoxy, 4H-1,4-benzoxazinylmethoxy, 4H-1,4-benzothiazinylmethoxy, quinolylmethoxy, isoquinolylmethoxy, cinnolinylmethoxy, quinazolinylmethoxy, quinoxalinylmethoxy, phthalazinylmethoxy, benzoxazepinylmethoxy, benzoazepinylmethoxy, benzodiazepinylmethoxy, naphthyridinylmethoxy, purinylmethoxy, pteridinylmethoxy, carbazolylmethoxy, carbolinylmethoxy, acridinylmethoxy, phenoxazinylmethoxy, phenothiazinylmethoxy, phenazinylmethoxy, phenoxathiinylmethoxy, thianthrenylmethoxy, phenanthridinylmethoxy, phenanthrolinylmethoxy, indolizinylmethoxy, thieno[3,2-c]pyridylmethoxy, thiazolo[5,4-c]pyridylmethoxy, pyrrolo[1,2-b]pyridazinylmethoxy, pyrazolo[1,5-a]pyridylmethoxy, imidazo[1,2-a]pyridylmethoxy, imidazo[1,5-a]pyridylmethoxy, imidazo[1,2-b]pyridazinylmethoxy, imidazo[1,5-a]pyrimidinylmethoxy, 1,2,4-triazolo[4,3-a]pyridylmethoxy, 1,2,4-triazolo[4,3-b]pyridazinylmethoxy, 1H-pyrazolo[3,4-b]pyridylmethoxy, 1,2,4-triazolo[1,5-a]pyrimidinylmethoxy, indolinylmethoxy, dihydrobenzofuranylmethoxy, chromanylmethoxy, tetrahydroquinolylmethoxy, tetrahydroisoquinolylmethoxy, 1,4-benzodioxanylmethoxy, 1,3-benzodioxolylmethoxy, and the like, are mentioned.

The "spiro ring group" is a 6- to 18-membered mono spirocyclic group in which two cyclic groups share one atom as a spiro atom to be spiro-fused. Each cyclic group forming a Spiro ring is a carbon ring group (such as a cyclic alkyl group and a partly hydrogenated fused aryl group) or a heterocyclic group (such as a non-aromatic heterocyclic group and a partly hydrogenated ring-fused heteroaryl group) and may be a monocyclic ring or a fused ring. The number of members of the spiro ring group is preferably 6 to 14, and when each cyclic group forming the spiro ring is monocyclic, the cyclic groups are independently preferably a 3- to 7-membered cyclic group. Each cyclic group forming the spiro ring may independently have, in the ring, 1 to 3 double bond(s), preferably 1 double bond. Examples of the "spiro ring group" include spiro[4,4]nona-(1- or 2-)ene-2-yl, spiro[4,5]dec-(1- or 2-)ene-2-yl, spiro[4,5]dec-(6- or 7-)ene-7-yl, spiro[5,5]undec-2-yl, spiro[5,5]undec-(1- or 2-)ene-2-yl, spiro[inden-1,4'-piperidin]-1'-yl, spiro[indolin-3,4'-piperidin]-1'-yl, and spiro[isobenzofuran-1(3H),4'-piperidin]-1'-yl. These spiro rings are optionally substituted with, for example, 1 to 5 halogen atom(s), 1 to 5 —OH group(s), 1 to 5 $C_{1-6}$ alkyl group(s), 1 to 5 halogenated $C_{1-6}$ alkyl group(s), 1 to 5 $C_{1-6}$ alkoxy group(s), or 1 to 5 oxo group(s) which may be the same as or different from each other.

The "substituted spiropiperidinylmethyl group" is a methyl group to which a substituted spiropiperidinyl group defined by Formula (SP):

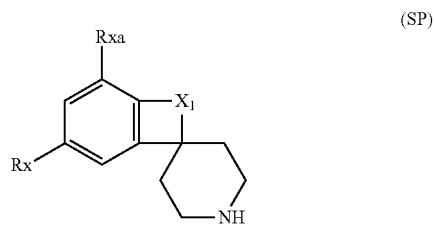

(where Rx and Rxa are independently a group selected from a hydrogen atom, a fluorine atom, a chlorine atom, a $C_{1-3}$ alkyl group, a trifluoromethyl group, and a methoxy group;
$X_1$ is —CH(Ry)CH$_2$—, —C(Ry)=CH—, —N(Rz)CH$_2$—, or —C(O)CH$_2$—;
Ry is a hydrogen atom or a $C_{1-3}$ alkyl group; and
Rz is a hydrogen atom, a $C_{1-3}$ alkyl group, or a phenyl group) is bonded,
or a methyl group to which Formula (SP'):

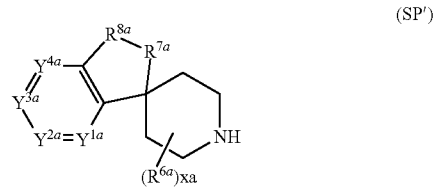

(where $R^{6a}$s are independently a halogen atom or a $C_{1-3}$ alkyl group; xa is an integer of 0 to 8; $R^{7a}$ is an oxygen atom or —CH$_2$—, $R^{8a}$ is an oxygen atom, —CH$_2$—, or —C(O)—, or $R^{7a}$ and $R^{8a}$ together optionally form —CH=CH— (with the proviso that $R^{7a}$ and $R^{8a}$ are not simultaneously an oxygen atom); $Y^{1a}$ is =CR$^{9a}$— or a nitrogen atom, $Y^{2a}$ is =CR$^{9b}$— or a nitrogen atom, $Y^{3a}$ is =CR$^{9c}$— or a nitrogen atom, and $Y^{4a}$ is =CR$^{9d}$— or a nitrogen atom; and $R^{9a}$, $R^{9b}$, $R^{9c}$, and $R^{9d}$ are independently a hydrogen atom, a halogen atom, or a $C_{1-6}$ alkyl group (with the proviso that 2 or more of $Y^{1a}$ to $Y^{4a}$ are not simultaneously a nitrogen atom))
is bonded.

Specifically, the "substituted spiropiperidinylmethyl group" is Formula (SP)—CH$_2$—:

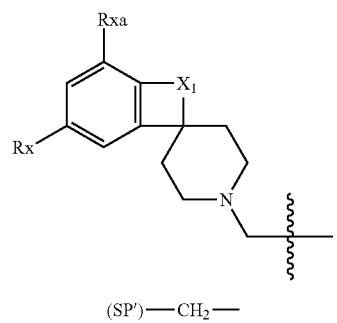

(SP')—CH$_2$—

(where each definition is the same as defined in Formula (SP)), or Formula (SP')—CH$_2$—:

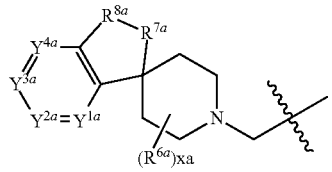

(SP')—CH$_2$—

(where each definition is the same as defined in Formula (SP')).

More specific examples of the "substituted spiropiperidinylmethyl group" as Formula (SP)—CH$_2$— include spiro[indan-1,4'-piperidin]-1'-ylmethyl, (1'H-spiro[inden-1,4'-piperidin]-1'-yl)methyl, 1,2-dihydro-1'H-spiro[indol-3,4'-piperidin]-1'-ylmethyl, (1-methyl-1,2-dihydro-1'H-spiro[indol-3,4'-piperidin]-1'-yl)methyl, {1-(1-methylethyl)-1,2-dihydro-1'H-spiro[indol-3,4'-piperidin]-1'-yl}methyl, (1-phenyl-1,2-dihydro-1'H-spiro[indol-3,4'-piperidin]-1'-yl)methyl, (2,3-dihydro-1'H-spiro[inden-1,4'-piperidin]-1'-yl)methyl, (7-chloro-1-methyl-1,2-dihydro-1'H-spiro[indol-3,4'-piperidin]-1'-yl)methyl, (5-fluoro-1-methyl-1,2-dihydro-1'H-spiro[indol-3,4'-piperidin]-1'-yl)methyl, (5-methoxy-1-methyl-1,2-dihydro-1'H-spiro[indol-3,4'-piperidin]-1'-yl)methyl, (1,5-dimethyl-1,2-dihydro-1'H-spiro[indol-3,4'-piperidin]-1'-yl)methyl, [1-methyl-5-(trifluoromethyl)-1,2-dihydro-1'H-spiro[indol-3,4'-piperidin]-1'-yl]methyl, and (3-oxo-2,3-dihydro-1'H-spiro[inden-1,4'-piperidin]-1'-yl)methyl.

As the explanation for the substituted spiropiperidinyl group or the examples for the substituent in Formula (SP)—CH$_2$—, the description in WO 2011/046851 pamphlet, particularly Formula (3) in p.8 or the structural formulae and the chemical names in Example 1 to Example 39, and the like can be referred to.

Specific examples of the "substituted spiropiperidinylmethyl group" as Formula (SP')—CH$_2$— include (spiro[isobenzofuran-1(3H),4'-piperidin]-1-yl)methyl, (spiro[benzofuran-3(2H),4'-piperidin]-1-yl)methyl, (3-oxospiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, (spiro[6-azaisobenzofuran-1(3H),4'-piperidin]-1-yl)methyl, (spiro[5-fluoroisobenzofuran-1(3H),4'-piperidin]-1-yl)methyl, (spiro[6-fluoroisobenzofuran-1(3H),4'-piperidin]-1-yl)methyl, (spiro[5-fluoro-6-azaisobenzofuran-1(3H),4'-piperidin]-1-yl)methyl, and (7-fluoro-1H-spiro[fluoro[3,4-c]pyridin-3,4'-piperidin]-1-yl)methyl.

As the explanation for the substituted spiropiperidinyl group or the examples for the substituent in Formula (SP')—CH$_2$—, each definition, explanation, and Example for a spiropiperidine ring below disclosed as Formula [II] (for the definition for the substituent and the like, each definition in Formula [I] in p.4-5 is to be referred to) in p.9 of WO 2002/088989 pamphlet, can be referred to.

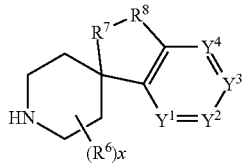

($R^6$s are the same as or different from each other and are a halogen atom or a $C_{1-3}$ alkyl group;

x is an integer of 0 or 1 to 8; $R^7$ is an oxygen atom or —CH$_2$—, or $R^7$ and $R^8$ together form —CH=CH—; $R^8$ is an oxygen atom, —CH$_2$—, or —C(O)—, or $R^7$ and $R^8$ together form —CH=CH—, with the proviso that $R^7$ and $R^8$ are not simultaneously an oxygen atom; $Y^1$ is =CR$^{9a}$— or a nitrogen atom, $Y^2$ is =CR$^{9b}$— or a nitrogen atom, $Y^3$ is =CR$^{9c}$— or a nitrogen atom, and $Y^4$ is =CR$^{9d}$— or a nitrogen atom; and $R^{9a}$, $R^{9b}$, $R^{9c}$, and $R^{9d}$ are the same as or different from each other and are a hydrogen atom, a halogen atom, or a $C_{1-6}$ alkyl group, with the proviso that 2 or more of $Y^1$ to $Y^4$ are not simultaneously a nitrogen atom).

Specific examples of the substituted spiropiperidinyl group include spiropiperidines used in Examples of WO 2002/088989 pamphlet and more specific examples thereof include spiro[isobenzofuran-1(3H),4'-piperidine], spiro[benzofuran-3(2H),4'-piperidine], spiro[6-azaisobenzofuran-1(3H),4'-piperidine], 3-oxospiro[4-azaisobenzofuran-1(3H),4'-piperidine], and 3-oxospiro[6-azaisobenzofuran-1(3H),4'-piperidine].

As the subordinate concept of the spiropiperidines disclosed in WO 2002/088989 pamphlet and as specific examples for the halogenated spiropiperidine ring, further, Examples in EP 1595867 and WO 2011/037771 pamphlet can be referred to. More specific examples of the substituted spiropiperidinyl group include spiro[5-fluoroisobenzofuran-1(3H),4'-piperidine], spiro[6-fluoroisobenzofuran-1(3H),4'-piperidine], spiro[5-fluoro-6-azaisobenzofuran-1(3H),4'-piperidine], spiro[6-fluoro-5-azaisobenzofuran-1(3H),4'-piperidine], and 7-fluoro-1H-spiro[fluoro[3,4-c]pyridin-3,4'-piperidine].

In the present invention, as a preferred aspect of various compounds having a substituted spiropiperidinyl group of Formula (SP') as a substructure: xa is preferably 0; $R^{7a}$ and $R^{8a}$ together form —$R^{7a}$—$R^{8a}$— which is any one of —OCH$_2$—, —CH$_2$O—, —CH$_2$—CH$_2$—, —CH=CH—, and —OC(O)—, more preferably —OCH$_2$— or —CH$_2$—CH$_2$—; $Y^{1a}$ is =CR$^{9a}$— or a nitrogen atom, $Y^{2a}$ is =CR$^{9b}$— or a nitrogen atom, $Y^{3a}$ is =CR$^{9c}$— or a nitrogen atom, and $Y^{4a}$ is =CR$^{9d}$— or a nitrogen atom; and $R^{9a}$, $R^{9b}$, $R^{9c}$, and $R^{9d}$ are independently a hydrogen atom, a halogen atom, or a $C_{1-6}$ alkyl group (with the proviso that 2 or more of $Y^{1a}$ to $Y^{4a}$ are not simultaneously a nitrogen atom).

Examples of the "halogen atom" include a fluorine atom, a chlorine atom, a bromine atom, and an iodine atom.

The "halogenated $C_{1-6}$ alkyl group" is a group in which the "$C_{1-6}$ alkyl group" is optionally substituted with 1 to 5 halogen atom(s). For example, trifluoromethyl, trifluoroethyl, tetrafluoroethyl, pentafluoroethyl, and the like are mentioned.

The "halogenated $C_{1-6}$ alkoxy" is a group in which the "$C_{1-6}$ alkoxy" is optionally substituted with 1 to 5 halogen atom(s). For example, trifluoromethoxy, trifluoroethoxy, tetrafluoroethoxy, pentafluoroethoxy, and the like are mentioned.

Examples of the protective group for the "carboxy which is optionally protected" include: an alkyl ester-based protective group such as methyl, ethyl, tert-butyl, benzyl, diphenylmethyl, and trityl; and a silyl ester-based protective group such as trimethylsilyl and tert-butyldimethylsilyl.

The "$C_{2-7}$ alkanoyl group" means a "linear, branched, or cyclic $C_{2-7}$ alkylcarbonyl group" and is expressed as R—CO— (R is the "$C_{1-6}$ alkyl group"). Examples thereof include acetyl, propionyl, butyryl, isobutyryl, valeryl, isovaleryl, pivaloyl, hexanoyl, heptanoyl, cyclopropylcarbonyl, cyclobutylcarbonyl, cyclopentylcarbonyl, cyclohexylcarbonyl, cyclopropylmethylcarbonyl, and 2-methylcyclopropylcarbonyl.

Examples of the "C$_{2-7}$ alkanoyl group (the alkanoyl group is optionally substituted with —OH or a C$_{1-6}$ alkoxy group)" include, in addition to the groups mentioned as the "C$_{2-7}$ alkanoyl group", a group in which the alkanoyl group is substituted with —OH or a C$_{1-6}$ alkoxy group at any position and specific examples thereof include hydroxyacetyl and methoxyacetyl.

The "arylcarbonyl group" is a group in which a carbonyl group is bonded to the "aryl group", and examples thereof include C$_{6-14}$ arylcarbonyl such as benzoyl and naphthylcarbonyl.

The "heterocyclic carbonyl group" means a "heterocyclic carbonyl group", and examples thereof include the "heterocyclic group" (for example, a heteroaryl group, a saturated or unsaturated non-aromatic heterocyclic group, and the like) to which a carbonyl group is bonded, including a carbonyl group to which the "monocyclic heteroaryl group" is bonded, such as pyrrolylcarbonyl, furylcarbonyl, thienylcarbonyl, imidazolylcarbonyl, pyrazolylcarbonyl, oxazolylcarbonyl, isoxazolylcarbonyl, thiazolylcarbonyl, isothiazolylcarbonyl, 1,2,3-triazolylcarbonyl, 1,2,4-triazolylcarbonyl, 1,2,3-oxadiazolylcarbonyl, 1,2,4-oxadiazolylcarbonyl, 1,3,4-oxadiazolylcarbonyl, furazanylcarbonyl, 1,2,3-thiadiazolylcarbonyl, 1,2,4-thiadiazolylcarbonyl, 1,3,4-thiadiazolylcarbonyl, tetrazolylcarbonyl, pyridylcarbonyl, pyridazinylcarbonyl, pyrimidinylcarbonyl, pyrazinylcarbonyl, 1,2,3-triazinylcarbonyl, 1,2,4-triazinylcarbonyl, 1,3,5-triazinylcarbonyl, 2H-1,2,3-thiadiazinylcarbonyl, 4H-1,2,4-thiadiazinylcarbonyl, 6H-1,3,4-thiadiazinylcarbonyl, 1,4-diazepinylcarbonyl, and 1,4-oxazepinylcarbonyl; a carbonyl group to which the "ring-fused heteroaryl group" which is optionally partly hydrogenated is bonded, such as indolylcarbonyl, isoindolylcarbonyl, benzofuranylcarbonyl, isobenzofuranylcarbonyl, benzothienylcarbonyl, isobenzothienylcarbonyl, benzoxazolylcarbonyl, 1,2-benzisoxazolylcarbonyl, benzothiazolylcarbonyl, 1,2-benzisothiazolylcarbonyl, 1H-benzimidazolylcarbonyl, 1H-indazolylcarbonyl, 1H-benzotriazolylcarbonyl, 2,1,3-benzothiadiazinylcarbonyl, chromenylcarbonyl, isochromenylcarbonyl, 4H-1,4-benzoxazinylcarbonyl, 4H-1,4-benzothiazinylcarbonyl, quinolylcarbonyl, isoquinolylcarbonyl, cinnolinylcarbonyl, quinazolinylcarbonyl, quinoxalinylcarbonyl, phthalazinylcarbonyl, benzoxazepinylcarbonyl, benzoazepinylcarbonyl, benzodiazepinylcarbonyl, naphthyridinylcarbonyl, purinylcarbonyl, pteridinylcarbonyl, carbazolylcarbonyl, carbolinylcarbonyl, acridinylcarbonyl, phenoxazinylcarbonyl, phenothiazinylcarbonyl, phenazinylcarbonyl, phenoxathiinylcarbonyl, thianthrenylcarbonyl, phenanthridinylcarbonyl, phenanthrolinylcarbonyl, indolizinylcarbonyl, thieno[3,2-c]pyridylcarbonyl, thiazolo[5,4-c]pyridylcarbonyl, pyrrolo[1,2-b]pyridazinylcarbonyl, pyrazolo[1,5-a]pyridylcarbonyl, imidazo[1,2-a]pyridylcarbonyl, imidazo[1,5-a]pyridylcarbonyl, imidazo[1,2-b]pyridazinylcarbonyl, imidazo[1,5-a]pyrimidinylcarbonyl, 1,2,4-triazolo[4,3-a]pyridylcarbonyl, 1,2,4-triazolo[4,3-b]pyridazinylcarbonyl, 1H-pyrazolo[3,4-b]pyridylcarbonyl, 1,2,4-triazolo[1,5-a]pyrimidinylcarbonyl, indolinylcarbonyl, dihydrobenzofuranylcarbonyl, chromanylcarbonyl, tetrahydroquinolylcarbonyl, tetrahydroisoquinolylcarbonyl, 1,4-benzodioxanylcarbonyl, and 1,3-benzodioxolylcarbonyl, and a carbonyl group to which the "saturated or unsaturated non-aromatic heterocyclic group" is bonded, such as aziridinylcarbonyl, azetidinylcarbonyl, pyrrolidinylcarbonyl, tetrahydrofurylcarbonyl, piperidinylcarbonyl, tetrahydropyranylcarbonyl, piperazinylcarbonyl, and morpholinylcarbonyl.

The "non-aromatic heterocyclic carbonyl group" is the "heterocyclic carbonyl group" in which the "heterocyclic group" is a "non-aromatic heterocyclic group", that is, a group in which a carbonyl group is bonded to the "non-aromatic heterocyclic group". Specifically, a carbonyl group to which the "saturated or unsaturated non-aromatic heterocyclic group" mentioned as the "heterocyclic group" is bonded is mentioned.

In the "—COOR$^f$ group", R$^f$ is a hydrogen atom or a C$_{1-6}$ alkyl group and means a carboxy group or an alkoxycarbonyl group. Specifically, for example, carboxy, methoxycarbonyl, ethoxycarbonyl, and the like are mentioned.

In the "—S(O)$_i$R$^a$ group", i is an integer of 0 to 2, and R$^a$ is a group optionally selected from a C$_{1-6}$ alkyl group and a halogenated C$_{1-6}$ alkyl group. When i is 0, examples of the "—S(O)$_i$R$^a$ group" include a "C$_{1-6}$ alkylthio group" and a "halogenated C$_{1-6}$ alkylthio group", when i is 1, examples of the "—S(O)$_i$R$^a$ group" include a "C$_{1-6}$ alkylsulfinyl group" and a "halogenated C$_{1-6}$ alkylsulfinyl group", and when i is 2, examples of the "—S(O)$_i$R$^a$ group" include a "C$_{1-6}$ alkylsulfonyl group" and a "halogenated C$_{1-6}$ alkylsulfonyl group".

The "C$_{1-6}$ alkylthio group" means a linear, branched, or cyclic C$_{1-6}$ alkylthio group, and examples thereof include methylthio, ethylthio, propylthio, isopropylthio, butylthio, isobutylthio, sec-butylthio, tert-butylthio, pentylthio, isopentylthio, neopentylthio, tert-pentylthio, 1-methylbutylthio, 2-methylbutylthio, 1,2-dimethylpropylthio, 1-ethylpropylthio, hexylthio, isohexylthio, 1-methylpentylthio, 2-methylpentylthio, 3-methylpentylthio, 1,1-dimethylbutylthio, 1,2-dimethylbutylthio, 2,2-dimethylbutylthio, 1,3-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, 1-ethyl-2-methylpropylthio, cyclopropylthio, cyclobutylthio, cyclopentylthio, cyclohexylthio, cyclopropylmethylthio, cyclobutylmethylthio, cyclopentylmethylthio, 1-cyclopropylethylthio, 2-cyclopropylethylthio, 2-cyclobutylethylthio, and 2-methylcyclopropylthio. The "halogenated C$_{1-6}$ alkylthio group" is a group in which the "C$_{1-6}$ alkylthio group" is optionally substituted with 1 to 5 halogen atom(s), and examples thereof include trifluoromethylthio.

The "C$_{1-6}$ alkylsulfinyl group" means a linear, branched, or cyclic C$_{1-6}$ alkylsulfinyl group, and examples thereof include methylsulfinyl, ethylsulfinyl, propylsulfinyl, isopropylsulfinyl, cyclopropylsulfinyl, cyclopropylmethylsulfinyl, and 2-methylcyclopropylsulfinyl. The "halogenated C$_{1-6}$ alkylsulfinyl group" is a group in which the "C$_{1-6}$ alkylsulfinyl group" is optionally substituted with 1 to 5 halogen atom(s), and examples thereof include trifluoromethylsulfinyl.

The "C$_{1-6}$ alkylsulfonyl group" means a linear, branched, or cyclic C$_{1-6}$ alkylsulfonyl group, and examples thereof include methylsulfonyl, ethylsulfonyl, propylsulfonyl, isopropylsulfonyl, cyclopropylsulfonyl, cyclopropylmethylsulfonyl, and 2-methylcyclopropylsulfonyl. The "halogenated C$_{1-6}$ alkylsulfonyl group" is a group in which the "C$_{1-6}$ alkylsulfonyl group" is optionally substituted with 1 to 5 halogen atom(s), and examples thereof include trifluoromethylsulfonyl.

The "—SO$_2$NR$^d$R$^e$ group", in which R$^d$ and R$^e$ are independently a hydrogen atom or a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group(s)), means, in addition to a sulfamoyl group in which 1 or 2 hydrogen atom(s) on a nitrogen atom of the sulfamoyl group is(are) optionally substituted with the "C$_{1-6}$ alkyl group", a sulfamoyl group substituted with a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group(s)). Specifically, example, a sulfamoyl group, a methylsulfamoyl group, an ethylsulfamoyl group, a propylsulfamoyl group, an isopropylsulfamoyl group, a cyclopropylsulfamoyl group, a butylsulfamoyl group, an isobutylsulfamoyl group, a pentylsulfamoyl group, an isopentylsulfamoyl group, a hexylsulfamoyl group, an isohexylsulfamoyl group, a dimethylsulfamoyl group, a diethylsulfamoyl group, a dipropylsulfamoyl group, a di-isopropylsulfamoyl group, a dibutylsulfamoyl group, a dipentylsulfamoyl group, an ethylmethylsulfamoyl group, a methylpropylsulfamoyl group, an ethylpropylsulfamoyl group, a butylmethylsulfamoyl group, a butylethylsulfamoyl group, a butylpropylsulfamoyl group, a trifluoromethylsulfamoyl group, a hydroxymethylsulfamoyl group, a 2-hydroxyethylsulfamoyl group, a 3-hydroxypropylsulfamoyl group, a 3-hydroxybutylsulfamoyl group, a 3-hydroxy-3-methylbutylsulfamoyl group, a 2,3-dihydroxypropylsulfamoyl group, a 3-hydroxy-2-hydroxymethylpropylsulfamoyl group, a 3-hydroxy-2-hydroxymethyl-2 methylpropylsulfamoyl group, a 2-methoxyethylsulfamoyl group, a 2-ethoxyethylsulfamoyl group, a 2-methoxy-3-hydroxypropylsulfamoyl group, and the like are mentioned.

The "—CONR$^d$R$^e$ group", in which R$^d$ and R$^e$ are independently a hydrogen atom or a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group(s)), means, in addition to a carbamoyl group in which 1 or 2 hydrogen atom(s) on a nitrogen atom of the carbamoyl group is(are) optionally substituted with the "C$_{1-6}$ alkyl group", a carbamoyl group substituted with a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group(s)). Specifically, for example, a carbamoyl group, a methylcarbamoyl group, an ethylcarbamoyl group, a propylcarbamoyl group, an isopropylcarbamoyl group, a cyclopropylcarbamoyl group, a butylcarbamoyl group, an isobutylcarbamoyl group, a pentylcarbamoyl group, an isopentylcarbamoyl group, a hexylcarbamoyl group, an isohexylcarbamoyl group, a dimethylcarbamoyl group, a diethylcarbamoyl group, a dipropylcarbamoyl group, a di-isopropylcarbamoyl group, a dibutylcarbamoyl group, a dipentylcarbamoyl group, an ethylmethylcarbamoyl group, a methylpropylcarbamoyl group, an ethylpropylcarbamoyl group, a butylmethylcarbamoyl group, a butylethylcarbamoyl group, a butylpropylcarbamoyl group, a trifluoromethylcarbamoyl group, a hydroxymethylcarbamoyl group, a 2-hydroxyethylcarbamoyl group, a 3-hydroxypropylcarbamoyl group, a 3-hydroxybutylcarbamoyl group, a 3-hydroxy-3-methylbutylcarbamoyl group, a 2,3-dihydroxypropylcarbamoyl group, a 3-hydroxy-2-hydroxymethylpropylcarbamoyl group, a 3-hydroxy-2-hydroxymethyl-2 methylpropylcarbamoyl group, a 2-methoxyethylcarbamoyl group, a 2-ethoxyethylcarbamoyl group, a 2-methoxy-3-hydroxypropylcarbamoyl group, and the like are mentioned.

In the "—CONR$^d$R$^{e1}$ group", R$^d$ is a hydrogen atom or a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group(s)), and R$^{e1}$ is a C$_{1-6}$ alkyl group (the C$_{1-6}$ alkyl group is substituted with 1 to 5 —OH, 1 to 5 C$_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 C$_{1-6}$ alkyl groups) or 1 to 3 oxo group(s)), 1 to 5—S(O)$_i$R$^a$ group(s) (i is an integer of 0 to 2), 1 to 5 —SO$_2$NR$^d$R$^e$ group(s), 1 to 5 —CONR$^d$R$^e$ group(s), or 1 to 5 —NR$^{b1}$R$^{e1}$ group(s)). That is to say, the "—CONR$^d$R$^{e1}$ group" means, in addition to a carbamoyl group in which one hydrogen atom on a nitrogen atom of the carbamoyl group is substituted with R$^{e1}$, a carbamoyl group in which another hydrogen atom on the nitrogen atom of the carbamoyl group is substituted with a C$_{1-6}$ alkyl group (the C$_{1-6}$ alkyl group is optionally substituted with 1 to 5 halogen atom(s), 1 to 5 —OH, or 1 to 5 C$_{1-6}$ alkoxy group(s)). Specifically, for example, a hydroxymethylcarbamoyl group, a 2-hydroxyethylcarbamoyl group, a 3-hydroxypropylcarbamoyl group, a 3-hydroxybutylcarbamoyl group, a 3-hydroxy-3-methylbutylcarbamoyl group, a 2,3-dihydroxypropylcarbamoyl group, a 3-hydroxy-2-hydroxymethylpropylcarbamoyl group, a 3-hydroxy-2-hydroxymethyl-2 methylpropylcarbamoyl group, a 2-methoxyethylcarbamoyl group, a 2-ethoxyethylcarbamoyl group, a 2-methoxy-3-hydroxypropylcarbamoyl group, a 3-methylsulfonyl-propylcarbamoyl group, a 2-(morpholin-4-yl)ethylcarbamoyl group, a 2-(4-methylpiperazin-1-yl)ethylcarbamoyl group, a 2-(2-oxopyrrolidin-1-yl)ethylcarbamoyl group, a 3-(2-oxopyrrolidin-1-yl)propylcarbamoyl group, a (5-oxopyrrolidin-2-yl)methylcarbamoyl group, a 3-(2-oxooxazolidin-3-yl)propylcarbamoyl group, a (3-methyloxetan-3-yl) methylcarbamoyl group, a 3-(methylsulfonylamino) propylcarbamoyl group, and the like are mentioned.

In the "—NR$^b$R$^c$ group", R$^b$ and R$^c$ are independently a group optionally selected from a hydrogen atom, a C$_{1-6}$ alkyl group, a halogenated C$_{1-6}$ alkyl group, a C$_{2-6}$ alkenyl group, a C$_{2-6}$ alkynyl group, a C$_{2-7}$ alkanoyl group (the alkanoyl group is optionally substituted with —OH or a C$_{1-6}$ alkoxy group), a C$_{1-6}$ alkylsulfonyl group, an arylcarbonyl group, and a heterocyclic carbonyl group. R$^b$ and R$^c$ optionally form, together with a nitrogen atom to which they are bonded, a 3- to 8-membered cyclic group, where in the cyclic group, one or two carbon atom(s) is(are) optionally substituted with an atom optionally selected from an oxygen atom, a sulfur atom, and a nitrogen atom (the nitrogen atom is optionally substituted with a C$_{1-6}$ alkyl group which is optionally substituted with 1 to 5 substituent(s) RI) or with a carbonyl group, and the cyclic group is optionally further substituted with 1 to 5 substituent(s) RII. Examples of the "—NR$^b$R$^c$ group" include amino, "mono/di C$_{1-6}$ alkylamino", "halogenated mono/di C$_{1-6}$ alkylamino", "mono/di C$_{2-6}$ alkenylamino", "mono/di C$_{2-6}$ alkynylamino", "C$_{2-7}$ alkanoylamino which is optionally substituted with —OH or C$_{1-6}$ alkoxy", "C$_{1-6}$ alkylsulfonylamino", "arylcarbonylamino", and "heterocyclic carbonylamino".

In the "—NR$^{b1}$R$^{c1}$ group", R$^{b1}$ and R$^{c1}$ are independently a group optionally selected from a hydrogen atom, a C$_{1-6}$ alkyl group, a C$_{2-7}$ alkanoyl group, and a C$_{1-6}$ alkylsulfonyl group. R$^{b1}$ and R$^{c1}$ optionally form, together with a nitrogen atom to which they are bonded, a 3- to 8-membered cyclic group, where in the cyclic group, one carbon atom is optionally substituted with an atom optionally selected from an oxygen atom, a sulfur atom, and a nitrogen atom (the nitrogen atom is optionally substituted with a C$_{1-6}$ alkyl group) or with a carbonyl group. Examples of the "—NR$^{b1}$R$^{c1}$ group" include amino, "mono/di C$_{1-6}$ alkylamino", "C$_{2-7}$ alkanoylamino", and "C$_{1-6}$ alkylsulfonylamino".

The "mono/di C$_{1-6}$ alkylamino" means an amino group, 1 or 2 hydrogen atom(s) of which is(are) substituted with a linear, branched, or cyclic "C$_{1-6}$ alkyl group". Specifically, methylamino, ethylamino, propylamino, isopropylamino, butylamino, isobutylamino, pentylamino, isopentylamino, hexylamino, isohexylamino, cyclopropylamino, cyclobutylamino, cyclopentylamino, cyclohexylamino, 1-cyclopropylmethylamino, 1-cyclobutylmethylamino, 1-cyclopentylmethylamino, 1-cyclohexylmethylamino, dimethylamino, diethylamino, dipropylamino, diisopropylamino, dibutylamino, dipentylamino, ethylmethylamino, propylmethylamino, propylethylamino, butylmethylamino, butylethylamino, butylpropylamino, N-cyclopropyl-N-methylamino, N-cyclobutyl-N-methylamino, N-cyclopentyl-N-methylamino, N-cyclohexyl-N-methylamino, and the like are mentioned.

The "halogenated mono/di $C_{1-6}$ alkylamino" is a group in which the "mono/di $C_{1-6}$ alkylamino" is substituted with 1 to 5 halogen atom(s). For example, trifluoromethylamino and the like are mentioned.

The "mono/di $C_{2-6}$ alkenylamino" means an amino group, 1 or 2 hydrogen atom(s) of which is(are) substituted with a linear, branched, or cyclic "$C_{2-6}$ alkenyl group". Specifically, vinylamino, allylamino, isopropenylamino, 2-methylallylamino, butenylamino, pentenylamino, hexenylamino, 1-cyclopropen-1-ylamino, 2-cyclopropen-1-ylamino, 1-cyclobuten-1-ylamino, 1-cyclopenten-1-ylamino, 2-cyclopenten-1-ylamino, 3-cyclopenten-1-ylamino, 1-cyclohexen-1-ylamino, 2-cyclohexen-1-ylamino, 3-cyclohexen-1-ylamino, 2,4-cyclopentadien-1-ylamino, 2,5-cyclohexadien-1-ylamino, divinylamino, diallylamino, diisopropenylamino, di(2-methylallyl)amino, dibutenylamino, dipentenylamino, dihexenylamino, di(1-cyclopropen-1-yl)amino, di(2-cyclopropen-1-yl)amino, di(1-cyclobuten-1-yl)amino, di(1-cyclopenten-1-yl)amino, di(2-cyclopenten-1-yl)amino, di(3-cyclopenten-1-yl)amino, di(1-cyclohexen-1-yl)amino, di(2-cyclohexen-1-yl)amino, di(3-cyclohexen-1-yl)amino, di(2,4-cyclopentadien-1-yl)amino, di(2,5-cyclohexadien-1-yl)amino, and the like are mentioned.

The "mono/di $C_{2-6}$ alkynylamino" means an amino group, 1 or 2 hydrogen atom(s) of which is(are) substituted with a linear, branched, or cyclic "$C_{2-6}$ alkynyl group". Specifically, ethynylamino, 1-propynylamino, 2-propynylamino, butynylamino, pentynylamino, hexynylamino, diethynylamino, di(1-propynyl)amino, di(2-propynyl)amino, dibutynylamino, dipentynylamino, dihexynylamino, and the like are mentioned.

The "$C_{2-7}$ alkanoylamino which is optionally substituted with —OH or $C_{1-6}$ alkoxy" means an amino group, a hydrogen atom of which is substituted with a linear, branched, or cyclic "$C_{2-7}$ alkanoyl group (the alkanoyl group is optionally substituted with —OH or a $C_{1-6}$ alkoxy group)". Specifically, acetamide, propionamide, butylamide, isobutylamide, valeramide, isovaleramide, pivalamide, hexanamide, heptanamide, cyclopropanecarboxamide, cyclobutanecarboxamide, cyclopentanecarboxamide, cyclohexanecarboxamide, 2-methylcyclopropanecarboxamide, hydroxyacetylamino, methoxyacetylamino, and the like are mentioned.

The "$C_{1-6}$ alkylsulfonylamino" means an amino group, a hydrogen atom of which is substituted with a linear, branched, or cyclic $C_{1-6}$ alkylsulfonyl group. Specifically, methylsulfonylamino, ethylsulfonylamino, propylsulfonylamino, isopropylsulfonylamino, cyclopropylsulfonylamino, cyclopropylmethylsulfonylamino, 2-methylcyclopropylsulfonylamino, and the like are mentioned.

The "arylcarbonylamino" means an amino group, a hydrogen atom of which is substituted with the "arylcarbonyl group". Specifically, $C_{6-14}$ arylcarbonylamino such as benzamide and naphthamide is mentioned.

The "heterocyclic carbonylamino" means an amino group, a hydrogen atom of which is substituted with the "heterocyclic carbonyl group". Specifically, pyrrolecarboxamide, furancarboxamide, thiophenecarboxamide, imidazolecarboxamide, pyrazolecarboxamide, pyridinecarboxamide, indolecarboxamide, quinolinecarboxamide, piperidinecarboxamide, and the like are mentioned.

With regard to "$R^b$ and $R^c$ optionally form, together with a nitrogen atom to which they are bonded, a 3- to 8-membered cyclic group" and "$R^{b1}$ and $R^{c1}$ optionally form, together with a nitrogen atom to which they are bonded, a 3- to 8-membered cyclic group", the 3- to 8-membered cyclic group specifically means, for example, a monovalent cyclic group obtained by removing a hydrogen atom which is bonded to a nitrogen atom from a ring that has a nitrogen atom in addition to carbon atoms in a 3- to 8-membered saturated or unsaturated non-aromatic heterocyclic group that is one of the "non-aromatic heterocyclic groups". For example, aziridinyl, azetidinyl, pyrrolidinyl, pyrazolinyl, pyrazolidinyl, piperidinyl, piperazinyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, 2-oxopyrrolidinyl, and the like are mentioned. As for $R^b$ and $R^c$, and $R^{b1}$ and $R^{c1}$, with regard to "where in the cyclic group, one carbon atom is substituted with an oxygen atom, a sulfur atom, or a carbonyl group", examples of the cyclic group include, among the above-mentioned cyclic groups, oxazolinyl, isoxazolinyl, oxazolidinyl, isoxazolidinyl, thiazolinyl, isothiazolinyl, thiazolidinyl, isothiazolidinyl, morpholinyl, thiomorpholinyl, and 2-oxopyrrolidinyl.

As for $R^b$ and $R^c$, with regard to "where the nitrogen atom is substituted with a $C_{1-6}$ alkyl group which is optionally substituted with 1 to 5 substituent(s) RI", examples of the cyclic group include 4-methylpiperazin-1-yl, 4-ethylpiperazin-1-yl, 4-propylpiperazin-1-yl, and 4-trifluoromethylpiperazin-1-yl.

As for $R^{b1}$ and $R^{c1}$, with regard to "where the nitrogen atom is substituted with a $C_{1-6}$ alkyl group", examples of the cyclic group include 4-methylpiperazin-1-yl, 4-ethylpiperazin-1-yl, and 4-propylpiperazin-1-yl.

As for $R^b$ and $R^c$, with regard to "where the cyclic group is further substituted with 1 to 5 substituent(s) RII", examples of the cyclic group include 4,4-difluoropiperidin-1-yl.

The "substituent RI" is a group optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5—SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)).

The "substituent RII" is a group optionally selected from the same groups as in the case of the "substituent RI", a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5—S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group.

Here, $R^a$, $R^d$, $R^e$, $R^{b1}$, $R^{c1}$, and $R^{e1}$ are the same as defined above as $R^a$, $R^d$, $R^e$, $R^{b1}$, $R^{c1}$, and $R^{e1}$ respectively in the "—S(O)$_i$R$^a$ group", the "—SO$_2$NR$^d$R$^e$ group", the "—CONR$^d$R$^e$ group", the "—CONR$^d$R$^{e1}$ group", and the "—NR$^{b1}$R$^{c1}$ group".

The "$C_{1-6}$ alkyl group which is optionally substituted with 1 to 5 substituent(s) RI" is a "$C_{1-6}$ alkyl group which is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)), and specific examples thereof include the following.

For example, a "$C_{1-6}$ alkyl group which is optionally substituted with 1 to 5 halogen atom(s)" includes, in addition to the "$C_{1-6}$ alkyl group", a group in which the alkyl group is optionally substituted with 1 to 5 halogen atom(s). Specifically, in addition to methyl, ethyl, propyl, isopropyl, butyl, isobutyl, sec-butyl, and tert-butyl, for example, trifluoromethyl, trifluoroethyl, tetrafluoroethyl, pentafluoroethyl, and the like are mentioned.

For example, a "$C_{1-6}$ alkyl group which is optionally substituted with 1 to 5 —OH" includes, in addition to the "$C_{1-6}$ alkyl group", a group in which the alkyl group is optionally substituted with 1 to 5 hydroxy, and there are many regioisomers depending on a substitution position. Specifically, in addition to methyl, ethyl, propyl, isopropyl, butyl, isobutyl, sec-butyl, and tert-butyl, for example, hydroxymethyl, 2-hydroxyethyl, 1-hydroxyethyl, 3-hydroxy-1-propyl, 2-hydroxy-1-propyl, 1-hydroxy-1-propyl, 2,3-dihydroxy-1-propyl, 1-hydroxy-1-methyl-1-ethyl, 2-hydroxy-1-methyl-1-ethyl, 4-hydroxy-1-butyl, 3-hydroxy-1-butyl, 2-hydroxy-1-butyl, 1-hydroxy-1-butyl, 3-hydroxy-2-methylpropyl, 2-hydroxy-2-methylpropyl, 3-hydroxy-2-hydroxymethylpropyl, 2-hydroxy-1,1-dimethyl-1-ethyl, 1-hydroxy-2-methylpropyl, 5-hydroxy-1-pentyl, 4-hydroxy-1-pentyl, 3-hydroxy-1-pentyl, 2-hydroxy-1-pentyl, 1-hydroxy-1-pentyl, 4-hydroxy-3-methylbutyl, 4-hydroxy-2-methylbutyl, 4-hydroxy-1-methylbutyl, 3-hydroxy-3-methylbutyl, 3-hydroxy-2-methylbutyl, 3-hydroxy-1-methylbutyl, 2-hydroxy-3-methylbutyl, 2-hydroxy-2-methylbutyl, 2-hydroxy-1-methylbutyl, 3-hydroxy-2,2-dimethylpropyl, 3-hydroxy-1,1-dimethylpropyl, 3-hydroxy-2-hydroxymethyl-2-methylpropyl, 6-hydroxy-1-hexyl, 4-hydroxy-1,1-dimethyl-1-butyl, 4-hydroxy-3,3-dimethyl-1-butyl, 2-hydroxycyclopropyl, 4-hydroxycyclohexyl, and the like are mentioned.

For example, a "$C_{1-6}$ alkyl group which is optionally substituted with 1 to 5 $C_{1-6}$ alkoxy group(s)" includes, in addition to the "$C_{1-6}$ alkyl group", a group in which the alkyl group is optionally substituted with 1 to 5 of the "$C_{1-6}$ alkoxy groups".

Specifically, in addition to methyl, ethyl, propyl, isopropyl, butyl, isobutyl, sec-butyl, and tert-butyl, for example, methoxymethyl, methoxyethyl, methoxypropyl, ethoxyethyl, and the like are mentioned.

For example, a "$C_{1-6}$ alkyl group which is optionally substituted with 1 to 5 $C_{1-6}$ alkoxy group(s) which is optionally substituted with 1 to 5 halogen atom(s)" includes, in addition to the "$C_{1-6}$ alkyl group" and the "$C_{1-6}$ alkyl group which is optionally substituted with 1 to 5 $C_{1-6}$ alkoxy group(s)", a group in which the alkyl group is optionally substituted with 1 to 5 of the "$C_{1-6}$ alkoxy groups" which is optionally substituted with 1 to 5 halogen atom(s). Specifically, in addition to methyl, ethyl, propyl, isopropyl, butyl, isobutyl, sec-butyl, tert-butyl, methoxymethyl, methoxyethyl, and methoxypropyl, for example, trifluoromethoxymethyl, trifluoromethoxyethyl, trifluoromethoxypropyl, and the like are mentioned.

The alkyl group is optionally substituted with 2 to 5 groups optionally selected from two or more kinds of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)). For example, a $C_{1-6}$ alkyl group which is substituted with one —OH and one $C_{1-6}$ alkoxy group, such as 2-hydroxy-3-methoxypropyl and 3-hydroxy-2-methoxypropyl, and the like are mentioned.

Similarly, the "$C_{2-6}$ alkenyl group which is optionally substituted with 1 to 5 substituent(s) RI" includes, in addition to the "$C_{2-6}$ alkenyl group", a group in which the alkenyl group is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)). Specifically, in addition to vinyl, allyl, isopropenyl, 2-methylallyl, butenyl, pentenyl, and hexenyl, for example, trifluorovinyl, 2-hydroxyvinyl, 2-methoxyvinyl, 2-trifluoromethoxyvinyl, and the like are mentioned.

The "$C_{2-6}$ alkynyl group which is optionally substituted with 1 to 5 substituent(s) RI" includes, in addition to the "$C_{2-6}$ alkynyl group", a group in which the alkynyl group is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)). Specifically, in addition to ethynyl, 1-propynyl, 2-propynyl, butynyl, pentynyl, and hexynyl, for example, fluoroethynyl, 2-hydroxyethynyl, 2-methoxyethynyl, 2-trifluoromethoxyethynyl, and the like are mentioned.

The "$C_{1-6}$ alkoxy group which is optionally substituted with 1 to 5 substituent(s) RI" includes, in addition to the "$C_{1-6}$ alkoxy group", a group in which the alkoxy group is optionally substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a —NR$^{b1}$R$^{c1}$ group, and a heterocyclic oxy group (the heterocyclic oxy group is optionally substituted with 1 to 3 $C_{1-6}$ alkyl group(s) or 1 to 3 oxo group(s)). Specifically, in addition to methoxy, ethoxy, propoxy, isopropoxy, butoxy, isobutoxy, sec-butoxy, and tert-butoxy, for example, trifluoromethoxy, hydroxymethoxy, 2-hydroxyethoxy, 3-hydroxypropoxy, 3-hydroxybutoxy, 3-hydroxy-3-methylbutoxy, 2,3-dihydroxypropoxy, 3-hydroxy-2-hydroxymethylpropoxy, 3-hydroxy-2-hydroxymethyl-2 methylpropoxy, 2-methoxyethoxy, 2-ethoxyethoxy, 2-trifluoromethoxyethoxy, 2-methoxy-3-hydroxypropoxy, 2-hydroxy-3-methoxypropoxy, and the like are mentioned.

The "aryl group which is optionally substituted with 1 to 5 substituent(s) RII" is a group in which any hydrogen atom in the "aryl group" is optionally substituted with 1 to 5 substituent(s) RII. That is to say, the "aryl group which is optionally substituted with 1 to 5 substituent(s) RII" includes, in addition to the "aryl group", an "aryl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group".

Specifically, in addition to the "aryl group", for example, an "aryl group which is optionally substituted with 1 to 5 halogen atom(s)", an "aryl group which is substituted with 1 to 5 group(s) optionally selected from the "$C_{1-6}$ alkoxy group" (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))", an "aryl group which is substituted with 1 to 5 group(s) optionally selected from the "$C_{1-6}$ alkyl group" (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))", and the like are mentioned.

The aryl group is optionally substituted with 2 to 5 groups optionally selected from two or more kinds of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group. Specifically, for example, an "aryl group which is optionally substituted with 1 or 2 of the "$C_{1-6}$ alkyl groups" and 1 or 2 of the "$C_{1-6}$ alkoxy groups" (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s))" and the like are mentioned. More preferably, for example, an "aryl group which is optionally substituted with 1 or 2 of the "$C_{1-6}$ alkyl groups" and one of the "$C_{1-6}$ alkoxy group" (the $C_{1-6}$ alkoxy group is optionally substituted with 1 or 2 —OH, 1 or 2 $C_{1-6}$ alkoxy group(s), 1 or 2 non-aromatic heterocyclic group(s) (the heterocyclic group is optionally substituted with a $C_{1-6}$ alkyl group), 1 or 2—S(O)$_i$R$^a$ (i is an integer of 0 to 2) group(s), or 1 or 2 —NR$^{b1}$R$^{c1}$ group(s))", and the like are mentioned.

Examples of the "aryl group which is optionally substituted with 1 to 5 substituent(s) RII" more specifically include, in addition to phenyl, (1- or 2-)naphthyl, indanyl, and tetrahydronaphthyl, (2-, 3-, or 4-)fluorophenyl, (2-, 3-, or 4-)chlorophenyl, (2,6-, 2,5-, 2,4-, 2,3-, or 3,5-)difluorophenyl, 4-chloro-2-fluorophenyl, (2-, 3-, or 4-)hydroxyphenyl, (2-, 3-, or 4-)cyanophenyl, (2,6-, 2,5-, 2,4-, 2,3-, 3,4-, or 3,5-)dicyanophenyl, (2-, 3-, or 4-)methoxyphenyl, (2-, 3-, or 4-)ethoxyphenyl, (2-, 3-, or 4-)propoxyphenyl, (2-, 3-, or 4-)isopropoxyphenyl, (2-, 3-, or 4-)trifluoromethoxyphenyl, (2-, 3-, or 4-)methylphenyl, (2-, 3-, or 4-)ethylphenyl, (2-, 3-, or 4-)propylphenyl, (2-, 3-, or 4-)isopropylphenyl, (2-, 3-, or 4-)isobutylphenyl, (2-, 3-, or 4-)tert-butylphenyl, (2-, 3-, or 4-)trifluoromethylphenyl, (2,6-, 2,5-, 2,4-, 2,3-, or 3,5-)dimethoxyphenyl, (2,6-, 2,5-, 2,4-, or 2,3-) dimethylphenyl, 3,5-ditrifluoromethylphenyl, (4- or 5-)fluoro-(2- or 3-)methylphenyl, 3-fluoro-4-methylphenyl, 2-chloro-(4- or 5-)methylphenyl, (4- or 5-)fluoro-2-trifluoromethylphenyl, (4- or 5-)chloro-2-trifluoromethylphenyl, 2-(fluoro- or chloro-)$_5$-trifluoromethylphenyl, (4- or 5-)fluoro-(2- or 3-)methoxyphenyl, 2-fluoro-(3-, 4-, or 5-)methoxyphenyl, (4- or 5-)chloro-(2- or 3-)methoxyphenyl, 2-chloro-(3-, 4-, or 5-)methoxyphenyl, (4- or 5-)fluoro-2-ethoxyphenyl, (4- or 5-)chloro-2-ethoxyphenyl, 3-(fluoro- or chloro-)4-ethoxyphenyl, 2-methoxy-5-methylphenyl, 4-methoxy-2-methylphenyl, 4-methoxy-(2,6-, 2,5-, or 2,3-)dimethylphenyl, (2-, 3-, or 4-)hydroxymethylphenyl, 4-cyano-3-hydroxymethylphenyl, (3- or 4-)(2-hydroxyethyl)phenyl, (3- or 4-)(3-hydroxy-3-methylbutoxy)phenyl, 4-(2-hydroxyethoxy)-2-methylphenyl, 4-(2,3-dihydroxypropoxy)-2-methylphenyl, 4-(3-hydroxy-3-methylbutoxy)-2-methylphenyl, 3-(3-hydroxy-3-methylbutoxy)-2-methylphenyl, 4-(2-hydroxyethoxy)-(2,6-, 2,5-, or 2,3-)dimethylphenyl, 4-(3-hydroxypropoxy)-2-methylphenyl, 4-(3-hydroxypropoxy)-(2,6-, 2,5-, or 2,3-)dimethylphenyl, 4-(2,3-dihydroxypropoxy)-(2,6-, 2,5-, or 2,3-)dimethylphenyl, 4-((2R)-2,3-dihydroxypropoxy)-(2,6-, 2,5-, or 2,3-)dimethylphenyl, 4-((2S)-2,3-dihydroxypropoxy)-(2,6-, 2,5-, or 2,3-)dimethylphenyl, 4-(3-hydroxy-2-hydroxymethylpropoxy)-2-methylphenyl, 4-(3-hydroxy-2-hydroxymethyl-2-methylpropoxy)-2-methylphenyl, 4-(3-hydroxybutoxy)-2-methylphenyl, 4-((3S)-3-hydroxybutoxy)-2-methylphenyl, 4-((3R)-3-hydroxybutoxy)-2-methylphenyl, 4-(3-hydroxy-2-hydroxymethylpropoxy)-(2,6-, 2,5-, or 2,3-)dimethylphenyl, 4-(3-hydroxy-2-hydroxymethyl-2-methylpropoxy)-(2,6-, 2,5-, or 2,3-)dimethylphenyl, 4-(3-hydroxybutoxy)-(2,6-, 2,5-, or 2,3-)dimethylphenyl, 4-((3S)-3-hydroxybutoxy)-(2,6-, 2,5-, or 2,3-)dimethylphenyl, 4-((3R)-3-hydroxybutoxy)-(2,6-, 2,5-, or 2,3-)dimethylphenyl, 4-(3-hydroxy-3-methylbutoxy)-(2,6-, 2,5-, or 2,3-)dimethylphenyl, 4-(3-aminopropoxy)-2-methylphenyl, 4-(3-aminopropoxy)-(2,6-, 2,5-, or 2,3-)dimethylphenyl, 4-(2-(2-oxo-1-pyrrolidinyl)ethoxy)-2-methylphenyl, 4-(2-(2-oxo-1-pyrrolidinyl)ethoxy)-(2,6-, 2,5-, or 2,3-)dimethylphenyl, 4-(3-(2-oxo-1-pyrrolidinyl)propoxy)-2-methylphenyl, 4-(3-(2-oxo-1-pyrrolidinyl)propoxy)-(2,6-, 2,5-, or 2,3-)dimethylphenyl, 4-(5-oxo-2-pyrrolidinyl)methoxy-2-methylphenyl, 4-(5-oxo-2-pyrrolidinyl)methoxy-(2,6-, 2,5-, or 2,3-)dimethylphenyl, 4-(2-ethoxy-ethoxy)-2-methylphenyl, 4-(2-ethoxy-ethoxy)-(2,6-, 2,5-, or 2,3-)dimethylphenyl, 4-(2-methylsulfonyl-ethoxy)-2-methylphenyl, 4-(2-methylsulfonyl-ethoxy)-(2,6-, 2,5-, or 2,3-)dimethylphenyl, 4-(3-methylsulfonyl-propoxy)phenyl, 4-(3-methylsulfonyl-propoxy)-2-methylphenyl, 4-(3-methylsulfonyl-propoxy)-(2,6-, 2,5-, or 2,3-)dimethylphenyl, 4-((1,1-dioxidetetrahydro-2H-thiopyran-4-yl)oxy)-2-methylphenyl, 4((1,1-dioxidetetrahydro-2H-thiopyran-4-yl)oxy)-(2,6-, 2,5-, or 2,3-)dimethylphenyl, 4-((4-hydroxy-1,1-dioxidetetrahydro-2H-thiopyran-4-yl)methoxy)-2-methylphenyl, 4-((4-hydroxy-1,1-dioxidetetrahydro-2H-thiopyran-4-yl)methoxy)-(2,6-, 2,5-, or 2,3-)dimethylphenyl, 4-((3-methyloxetan-3-yl)methoxy)-2-methylphenyl, 4-((3-methyloxetan-3-yl)methoxy)-(2,6-, 2,5-, or 2,3-)dimethylphenyl, 4-(2-acetylamino-ethoxy)-2-methylphenyl, 4-(2-acetylamino-ethoxy)-(2,6-, 2,5-, or 2,3-)dimethylphenyl, 4-(3-acetylamino-propoxy)-2-methylphenyl, 4-(3-acetylamino-propoxy)-(2,6-, 2,5-, or 2,3-)dimethylphenyl, 4-(2-methylsulfonylamino-ethoxy)-2-methylphenyl, 4-(2-methylsulfonylamino-ethoxy)-(2,6-, 2,5-, or 2,3-)dimethylphenyl, 4-(3-methylsulfonylamino-propoxy)-2-methylphenyl, 4-(3-methylsulfonylamino-propoxy)-(2,6-, 2,5-, or 2,3-)dimethylphenyl, 4-(2-carbamoyl-ethoxy)-2-methylphenyl, 4-(2-carbamoyl-ethoxy)-(2,6-, 2,5-, or 2,3-)dimethylphenyl, 4-(3-carbamoyl-propoxy)-2-methylphenyl, 4-(3-carbamoyl-propoxy)-(2,6-, 2,5-, or 2,3-)dimethylphenyl, 4-(2-methylcarbamoyl-ethoxy)-2-methylphenyl, 4-(2-methylcarbamoyl-ethoxy)-(2,6-, 2,5-, or 2,3-)dimethylphenyl, 4-(3-methylcarbamoyl-propoxy)-2-methylphenyl, 4-(3-methylcarbamoyl-propoxy)-(2,6-, 2,5-, or 2,3-)dimethylphenyl, 4-(2-dimethylcarbamoyl-ethoxy)-2-methylphenyl, 4-(2-dimethylcarbamoyl-ethoxy)-(2,6-, 2,5-, or 2,3-)dimethylphenyl, 4-(3-dimethylcarbamoyl-propoxy)-2-methylphenyl, 4-(3-dimethylcarbamoyl-propoxy)-(2,6-, 2,5-, or 2,3-)dimethylphenyl, 4-(2-sulfamoyl-ethoxy)-2-methylphenyl, 4-(2-sulfamoyl-ethoxy)-(2,6-, 2,5-, or 2,3-)dimethylphenyl, 4-(3-sulfamoyl-propoxy)-2-methylphenyl, 4-(3-sulfamoyl-propoxy)-(2,6-, 2,5-, or 2,3-)dimethylphenyl, 4-(2-methylsulfamoyl-ethoxy)-2-methylphenyl, 4-(2-methylsulfamoyl-ethoxy)-(2,6-, 2,5-, or 2,3-)dimethylphenyl, 4-(3-methylsulfamoyl-propoxy)-2-methylphenyl, 4-(3-methylsulfamoyl-propoxy)-(2,6-, 2,5-, or 2,3-)dimethylphenyl, 4-(2-dimethylsulfamoyl-ethoxy)-2-methylphenyl, 4-(2-dimethylsulfamoyl-ethoxy)-(2,6-, 2,5-, or 2,3-)dimethylphenyl, 4-(3-dimethylsulfamoyl-propoxy)-2-methylphenyl, 4-(3-dimethylsulfamoyl-propoxy)-(2,6-, 2,5-, or 2,3-)dimethylphenyl, 3-fluoro-4-(3-hydroxy-3-methylbutoxy)-2-methylphenyl, 3-fluoro-4-(3-hydroxy-3-methylbutoxy)-(2,6- or 2,5-)dimethylphenyl, 3-fluoro-4-(3-methylsulfonyl-propoxy)-2-methylphenyl, 3-fluoro-4-(3-methylsulfonyl-propoxy)-(2,6- or 2,5-)dimethylphenyl, 4-(3-hydroxy-3-methylbutoxy)-2-hydroxymethylphenyl, 4-(3-hydroxy-3-methylbutoxy)-6-methyl-2-hydroxymethylphenyl, 4-(3-methylsulfonyl-propoxy)-2-hydroxymethylphenyl, 4-(3-methylsulfonyl-propoxy)-6-methyl-2-hydroxymethylphenyl, (2-, 3-, or 4-)vinylphenyl, (2-, 3-, or 4-)acetylphenyl, (2-, 3-, or 4-)benzyloxyphenyl, 2-benzyloxy-(3-, 4-, 5-, or 6-)fluorophenyl, 4-benzyloxy-(2- or 3-)fluorophenyl, 4-benzyloxy-(2- or 3-)methylphenyl, (2-, 3-, or 4-)methylsulfonylphenyl, (2-, 3-, or 4-)carbamoylphenyl, (2-, 3-, or 4-)N-methylcarbamoylphenyl, (2-, 3-, or 4-)N,N-dimethylcarbamoylphenyl, (2-, 3-, or 4-)(N-(2-hydroxyethyl)carbamoyl)phenyl, (2-, 3-, or 4-)(N-(2-methoxyethyl)carbamoyl)phenyl, (2-, 3-, or 4-)(N-(2-hydroxyethyl)-N-methylcarbamoyl)phenyl, (2-, 3-, or 4-)(N-(2-methoxyethyl)-N-methylcarbamoyl)phenyl, (2-, 3-, or 4-)(N-(2-methylsulfonyl-ethyl)carbamoyl)phenyl, (2-, 3-, or 4-)(N-(2-methylsulfonyl-ethyl)-N-methylcarbamoyl)phenyl, 4-cyano-3-carbamoylphenyl, 3-cyano-4-carbamoylphenyl, (2-, 3-, or 4-)(pyrrolidine-1-yl)carbonylphenyl, (2-, 3-, or 4-)morpholinophenyl, 4-cyano-3-morpholinophenyl, (2-, 3-, or 4-)(2-oxooxazolidin-3-yl)phenyl, 4-cyano-3-(2-oxooxazolidin-3-yl)phenyl, (4-, 5-, 6-, or 7-)fluoro-1-indanyl, (4-, 5-, 6-, or 7-)chloro-1-indanyl, (4-, 5-, 6-, or 7-)bromo-1-indanyl, (4-, 5-, 6-, or 7-)trifluoromethyl-1-indanyl, (4-, 5-, 6-, or 7-)fluoro-2-indanyl, (4-, 5-, 6-, or 7-)chloro-2-indanyl, (4-, 5-, 6-, or 7-)bromo-2-indanyl, (4-, 5-, 6-, or 7-)trifluoromethyl-2-indanyl, (2-, 3-, 4-, 5-, 6-, 7-, or 8-)fluoro-naphthalene-1-yl, (2-, 3-, 4-, 5-, 6-, 7-, or 8-)chloro-naphthalene-1-yl, and (2-, 3-, 4-, 5-, 6-, 7-, or 8-)methyl-naphthalene-1-yl.

The "heterocyclic group which is optionally substituted with 1 to 5 substituent(s) RII" is a group in which any hydrogen atom in the "heterocyclic group" is optionally substituted with 1 to 5 substituent(s) RII. Namely, the "heterocyclic group which is optionally substituted with 1 to 5 substituent(s) RII" is, in addition to the unsubstituted "heteroaryl group" and the "non-aromatic heterocyclic group" both exemplified above as a "heterocyclic group" (these rings are each a monovalent group obtained by removing any hydrogen atom from a ring having a monocyclic ring or a fused ring that is a 3- to 14-membered ring, or preferably a 3- to 12-membered ring, containing, in addition to carbon atoms, at least one hetero atom (preferably 1 to 4 atom(s)) optionally selected from N, O, and S): a "heterocyclic group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a —$NR^{b1}R^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —$S(O)_iR^a$ (i is an integer of 0 to 2) group, a —$CONR^dR^e$ group, and a —$CONR^dR^{e1}$ group".

Specific examples of the "heterocyclic group which is optionally substituted with 1 to 5 substituent(s) RII" include, in addition to the "heterocyclic group", a "heterocyclic group optionally substituted with 1 to 5 halogen atom(s)", a "heterocyclic group substituted with 1 to 5 group(s) optionally selected from the "$C_{1-6}$ alkoxy group" (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s))", and a "heterocyclic group substituted with 1 to 5 group(s) optionally selected from the "$C_{1-6}$ alkyl group" (the $C_{1-6}$ alkyl group is optionally substituted with 1 to 5 halogen atom(s), 1 to 5 —OH, 1 to 5 $C_{1-6}$ alkoxy group(s), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s))". More specific examples thereof include a "heteroaryl group substituted with 1 to 5 group(s) optionally selected from the "$C_{1-6}$ alkyl group" (the $C_{1-6}$ alkyl group is optionally substituted with 1 to 5 halogen atom(s), 1 to 5—OH, 1 to 5 $C_{1-6}$ alkoxy group(s), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s))" and a "heteroaryl group substituted with 1 to 5 groups(s) optionally selected from the "$C_{1-6}$ alkoxy group" (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s))".

Furthermore, the heterocyclic group is optionally substituted with 2 to 5 groups optionally selected from 2 or more kinds of a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a —$NR^{b1}R^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5—$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —$S(O)_iR^a$ (i is an integer of 0 to 2) group, a —$CONR^dR^e$ group, and a —$CONR^dR^{e1}$ group. Specific examples thereof include a "heterocyclic group optionally substituted with 1 or 2 "$C_{1-6}$ alkyl group(s)" and 1 or 2 "$C_{1-6}$ alkoxy group(s)" (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s))". More preferred examples thereof include a "heteroaryl group optionally substituted with 1 or 2 "$C_{1-6}$ alkyl group(s)" and one "$C_{1-6}$ alkoxy group" (the $C_{1-6}$ alkoxy group is optionally substituted with 1 or 2 —OH, 1 or 2 $C_{1-6}$ alkoxy group(s), 1 or 2 non-aromatic heterocyclic group(s) (the heterocyclic group is optionally substituted with a $C_{1-6}$ alkyl group), 1 or 2—$S(O)_iR^a$ (i is an integer of 0 to 2) group(s), or 1 or 2 —$NR^{b1}R^{c1}$ group(s))".

The "heteroaryl group" in the "heterocyclic group which is optionally substituted with 1 to 5 substituent(s) RII" may be monocyclic or ring-fused. The monocyclic heteroaryl group preferably has a 5- to 7-membered ring, and examples thereof include those groups described in the definition of the "heteroaryl group", such as pyrrolyl, furyl, thienyl, imidazolyl, pyrazolyl, oxazolyl, isoxazolyl, thiazolyl, isothiazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,3,5-triazinyl, 2H-1,2,3-thiadiazinyl, 4H-1,2,4-thiadiazinyl, 6H-1,3,4-thiadiazinyl, 1,4-diazepinyl, and 1,4-oxazepinyl. The ring-fused heteroaryl group preferably has an 8- to 14-membered ring, and examples thereof include a monovalent group obtained by removing any hydrogen atom from a fused ring formed by fusing the 5- to 7-membered heterocyclic ring and a monocyclic aryl group (such as a benzene ring) or a monocyclic heteroaryl group. The hydrogen atom is optionally removed from any of the fused rings. Specific examples include those groups described in the definition of the "heteroaryl group", such as indolyl, isoindolyl, benzofuranyl, isobenzofuranyl, benzothienyl, isobenzothienyl, benzoxazolyl, 1,2-benzisoxazolyl, benzothiazolyl, 1,2-benzisothiazolyl, 1H-benzimidazolyl, 1H-indazolyl, 1H-benzotriazolyl, 2,1,3-benzothiadiazinyl, chromenyl, isochromenyl, 4H-1,4-benzoxazinyl, 4H-1,4-benzothiazinyl, quinolyl, isoquinolyl, cinnolinyl, quinazolinyl, quinoxalinyl, phthalazinyl, benzoxazepinyl, benzoazepinyl, benzodiazepinyl, naphthyridinyl, purinyl, pteridinyl, carbazolyl, carbolinyl, acridinyl, phenoxazinyl, phenothiazinyl, phenazinyl, phenoxathiinyl, thianthrenyl, phenanthridinyl, phenanthrolinyl, indolizinyl, thieno[3,2-c]pyridyl, thiazolo[5,4-c]pyridyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, 1H-pyrazolo[3,4-b]pyridyl, 1,2,4-triazolo[1,5-a]pyrimidinyl, and dibenzofuranyl. Specific examples thereof also include a ring-fused heteroaryl group which is partly hydrogenated, such as indolinyl, dihydrobenzofuranyl, dihydroisobenzofuranyl, dihydrobenzoxazolyl, dihydrobenzothiazolyl, chromanyl, isochromanyl, 3,4-dihydro-2H-1,4-benzoxazinyl, 3,4-dihydro-2H-1,4-benzothiazinyl, tetrahydroquinolyl, tetrahydroisoquinolyl, tetrahydroquinoxalinyl, 1,4-benzodioxanyl, 1,3-benzodioxolyl, tetrahydrobenzoxazepinyl, tetrahydrobenzoazepinyl, and 6,7,8,9-tetrahydro-5H-cyclohepta[b]pyridyl. The ring-fused heteroaryl group which is partly hydrogenated preferably has an 8- to 12-membered ring, namely a monovalent group obtained by removing any hydrogen atom from a fused ring which is partly hydrogenated and formed by fusing the 5- to 7-membered heterocyclic ring and a monocyclic aryl group (such as a benzene ring) or a monocyclic heteroaryl group. Any of the hydrogen atom in the aryl group or in the heterocyclic moiety and of the hydrogen atom in the hydrogenated moiety is optionally removed. In the case of tetrahydroquinolyl, examples of the partly hydrogenated ring-fused heteroaryl group include 5,6,7,8-tetrahydroquinolyl and 1,2,3,4-tetrahydroquinolyl. Depending on the position in these groups from which any hydrogen atom is removed, -2-yl, -3-yl, -4-yl, -5-yl, -6-yl, -7-yl, and -8-yl are exemplified in the case of 5,6,7,8-tetrahydroquinolyl, and in the case of 1,2,3,4-tetrahydroquinolyl, -1-yl, -2-yl, -3-yl, -4-yl, -5-yl, -6-yl, -7-yl, and -8-yl are exemplified.

Examples of the "non-aromatic heterocyclic group" in the "heterocyclic group which is optionally substituted with 1 to 5 substituent(s) RII" include a 3- to 8-membered saturated or unsaturated non-aromatic heterocyclic group. Specific examples thereof include aziridinyl, azetidinyl, oxiranyl, oxetanyl, thietanyl, pyrrolidinyl, tetrahydrofuryl, thiolanyl, pyrazolinyl, pyrazolidinyl, piperidinyl, dihydropyranyl, tetrahydropyranyl (oxanyl), tetrahydrothiopyranyl, piperazinyl, dioxanyl, oxazolinyl, isoxazolinyl, oxazolidinyl, isoxazolidinyl, thiazolinyl, isothiazolinyl, thiazolidinyl, isothiazolidinyl, oxadiazolinyl, oxadiazolidinyl, morpholinyl, thiomorpholinyl, quinuclidinyl, and oxepanyl. The "non-aromatic heterocyclic group" means a monovalent group obtained by removing any hydrogen atom from the ring.

Specific examples of the "heterocyclic group which is optionally substituted with 1 to 5 substituent(s) RII" include pyrrolyl, furyl, thienyl, pyrazolyl, isoxazolyl, pyridyl, pyrimidinyl, indolyl, 1H-benzimidazolyl, quinolyl, dibenzofuranyl, dihydrobenzofuranyl, dihydroisobenzofuranyl, chromanyl, 1,3-benzodioxanyl, 1,4-benzodioxanyl, piperidinyl, dihydropyranyl, and tetrahydropyranyl (oxanyl). Further specific examples thereof include 2-pyrrolyl, 3-pyrrolyl, 2-furyl, 3-furyl, 2-thienyl, 3-thienyl, 1-pyrazolyl, 3-pyrazolyl, 4-pyrazolyl, 5-pyrazolyl, 3-isoxazolyl, 4-isoxazolyl, 5-isoxazolyl, 2-pyridyl, 3-pyridyl, 4-pyridyl, 2-pyrimidinyl, 4-pyrimidinyl, 5-pyrimidinyl, 1-indolyl, 2-indolyl, 3-indolyl, 4-indolyl, 5-indolyl, 6-indolyl, 7-indolyl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 2-quinolyl, 3-quinolyl, 4-quinolyl, 5-quinolyl, 6-quinolyl, 7-quinolyl, 8-quinolyl, 1-dibenzofuranyl, 2-dibenzofuranyl, 3-dibenzofuranyl, 4-dibenzofuranyl, 1,4-benzodioxazine-2-yl, 1,4-benzodioxazine-3-yl, 1,4-benzodioxazine-5-yl, 1,4-benzodioxazine-6-yl, piperidin-1-yl, piperidin-2-yl, piperidin-3-yl, piperidin-4-yl, 3,6-dihydro-2H-pyran-4-yl, and 4-tetrahydropyranyl (4-oxanyl). Any hydrogen atom of the groups is optionally substituted with 1 to 5 substituent(s) RII. Specific examples thereof include (3-, 4-, or 5-)chlorothiophen-2-yl, (2-, 4-, or 5-)chlorothiophen-3-yl, (3-, 4-, or 5-)acetylthiophen-2-yl, 1-methylpyrazol-4-yl, 3,5-dimethylisoxazol-4-yl, (2-, 4-, 5-, or 6-)fluoropyridin-3-yl, (2-, 4-, 5-, or 6-)chloropyridin-3-yl, (2-, 4-, 5-, or 6-)hydroxypyridin-3-yl, (3-, 4-, 5-, or 6-)cyanopyridin-2-yl, (2-, 4-, 5-, or 6-)cyanopyridin-3-yl, (2- or 3-)cyanopyridin-4-yl, (3-, 4-, 5-, or 6-)methoxypyridin-2-yl, (2-, 4-, 5-, or 6-)methoxypyridin-3-yl, (2- or 3-)methoxypyridin-4-yl, (2-, 4-, 5-, or 6-)ethoxypyridin-3-yl, (2-, 4-, 5-, or 6-)cyclopropylmethoxypyridin-3-yl, (3-, 4-, 5-, or 6-)methylpyridin-2-yl, (2-, 4-, 5-, or 6-)methylpyridin-3-yl, (2- or 3-)methylpyridin-4-yl, (2-, 4-, 5-, or 6-)trifluoromethylpyridin-3-yl, 6-(3-hydroxybutoxy)pyridin-3-yl, 6-(3-hydroxy-3-methylbutoxy)pyridin-3-yl, 6-(2-ethoxyethoxy)pyridin-3-yl, 6-(3-methylsulfonyl-propoxy)pyridin-3-yl, (2,4-, 2,5-, 2,6-, 4,5-, 4,6-, or 5,6-)dimethylpyridin-3-yl, (2,4-, 2,5-, 2,6-, 4,5-, 4,6-, or 5,6-)dimethoxypyridin-3-yl, 6-isopropyl-(2-, 4-, or 5-)chloropyridin-3-yl, 6-methoxy-(2-, 4-, or 5-)methylpyridin-3-yl, 6-(2-hydroxyethoxy)-(2- or 4-)methylpyridin-3-yl, 6-(3-hydroxypropoxy)-(2- or 4-)methylpyridin-3-yl, 6-(2,3-dihydroxypropoxy)-(2- or 4-)methylpyridin-3-yl, 6-((2R)-2,3-dihydroxypropoxy)-(2- or 4-)methylpyridin-3-yl, 6-((2S)-2,3-dihydroxypropoxy)-(2- or 4-)methylpyridyl-3-yl, 6-((3S)-3-hydroxybutoxy)-(2- or 4-)methylpyridyl-3-yl, 6-((3R)-3-hydroxybutoxy)-(2- or 4-)methylpyridyl-3-yl, 6-(3-hydroxy-3-methylbutoxy)-(2- or 4-)methylpyridin-3-yl, 6-(3-hydroxy-2-hydroxymethylpropoxy)-(2- or 4-)methylpyridin-3-yl, 6-(3-hydroxy-2-hydroxymethyl-2-methylpropoxy)-(2- or 4-)methylpyridin-3-yl, 6-(3-hydroxybutoxy)-(2- or 4-)methylpyridin-3-yl, 6-(2-ethoxyethoxy)-(2- or 4-)methylpyridin-3-yl, 6-(2-methylsulfonylethoxy)-(2- or 4-)methylpyridin-3-yl, 6-(3-methylsulfonyl-propoxy)-(2- or 4-)methylpyridin-3-yl, 6-((1,1-dioxidetetrahydro-2H-thiopyran-4-yl)oxy)-(2- or 4-)methylpyridin-3-yl, 6-((4-hydroxy-1,1-dioxidetetrahydro-2H-thiopyran-4-yl)methoxy)-(2- or 4-)methylpyridin-3-yl, 6-((3-methyloxetane-3-yl)methoxy)-(2- or 4-)methylpyridin-3-yl, 6-(2-hydroxyethoxy)-(2,4-, 2,5-, or 4,5-)dimethylpyridin-3-yl, 6-(3-hydroxypropoxy)-(2,4-, 2,5-, or 4,5-)dimethylpyridin-3-yl, 6-(2,3-dihydroxypropoxy)-(2,4-, 2,5-, or 4,5-)dimethylpyridin-3-yl, 6-(3-hydroxy-2-hydroxymethylpropoxy)-(2,4-, 2,5-, or 4,5-)dimethylpyridin-3-yl, 6-(3-hydroxy-2-hydroxymethyl-2-methylpropoxy)-(2,4-, 2,5-, or 4,5-)dimethylpyridin-3-yl, 6-(3-hydroxybutoxy)-(2,4-, 2,5-, or 4,5-)dimethylpyridin-3-yl, 6-(3-hydroxy-3-methylbutoxy)-(2,4-, 2,5-, or 4,5-)dimethylpyridin-3-yl, 6-(2-ethoxyethoxy)-(2,4-, 2,5-, or 4,5-)dimethylpyridin-3-yl, 6-(2-methylsulfonylethoxy)-(2,4-, 2,5-, or 4,5-)dimethylpyridin-3-yl, 6-(3-methylsulfonyl-propoxy)-(2,4-, 2,5-, or 4,5-)dimethylpyridin-3-yl, 6-((1,1-dioxidetetrahydro-2H-thiopyran-4-yl)oxy)-(2,4-, 2,5-, or 4,5-)dimethylpyridin-3-yl, 6-((4-hydroxy-1,1-dioxidetetrahydro-2H-thiopyran-4-yl)methoxy)-(2,4-, 2,5-, or 4,5-)dimethylpyridin-3-yl, 6-((3-methyloxetane-3-yl)methoxy)-(2,4-, 2,5-, or 4,5-)dimethylpyridin-3-yl, 6-(3-hydroxy-3-methylbutoxy)-(2- or 4-)methoxypyridin-3-yl, 6-(2-aminoethoxy)-(2- or 4-)methylpyridin-3-yl, 6-(2-aminoethoxy)-(2,4-, 2,5-, or 4,5-)dimethylpyridin-3-yl, 6-(3-aminopropoxy)-(2- or 4-)methylpyridin-3-yl, 6-(3-aminopropoxy)-(2,4-, 2,5-, or 4,5-)dimethylpyridin-3-yl, 6-(2-acetylamino-ethoxy)-(2- or 4-)methylpyridin-3-yl, 6-(2-acetylamino-ethoxy)-(2,4-, 2,5-, or 4,5-)dimethylpyridin-3-yl, 6-(3-acetylamino-propoxy)-(2- or 4-)methylpyridin-3-yl, 6-(3-acetylamino-propoxy)-(2,4-, 2,5-, or 4,5-)dimethylpyridin-3-yl, 6-(2-methylsulfonylamino-ethoxy)-(2- or 4-)methylpyridin-3-yl, 6-(2-methylsulfonylamino-ethoxy)-(2,4-, 2,5-, or 4,5-)dimethylpyridin-3-yl, 6-(3-methylsulfonylamino-propoxy)-(2- or 4-)methylpyridin-3-yl, 6-(3-methylsulfonylamino-propoxy)-(2,4-, 2,5-, or 4,5-)dimethylpyridin-3-yl, 6-(2-carbamoyl-ethoxy)-(2- or 4-)methylpyridin-3-yl, 6-(2-carbamoyl-ethoxy)-(2,4-, 2,5-, or 4,5-)dimethylpyridin-3-yl, 6-(3-carbamoyl-propoxy)-(2- or 4-)methylpyridin-3-yl, 6-(3-carbamoyl-propoxy)-(2,4-, 2,5-, or 4,5-)dimethylpyridin-3-yl, 6-(2-methylcarbamoyl-ethoxy)-(2- or 4-)methylpyridin-3-yl, 6-(2-methylcarbamoyl-ethoxy)-(2,4-, 2,5-, or 4,5-)dimethylpyridin-3-yl, 6-(3-methylcarbamoyl-propoxy)-(2- or 4-)methylpyridin-3-yl, 6-(3-methylcarbamoyl-propoxy)-(2,4-, 2,5-, or 4,5-)dimethylpyridin-3-yl, 6-(2-dimethylcarbamoyl-ethoxy)-(2- or 4-)methylpyridin-3-yl, 6-(2-dimethylcarbamoyl-ethoxy)-(2,4-, 2,5-, or 4,5-)dimethylpyridin-3-yl, 6-(3-dimethylcarbamoyl-propoxy)-(2- or 4-)methylpyridin-3-yl, 6-(3-dimethylcarbamoyl-propoxy)-(2,4-, 2,5-, or 4,5-)dimethylpyridin-3-yl, 6-(2-sulfamoyl-ethoxy)-(2- or 4-)methylpyridin-3-yl, 6-(2-sulfamoyl-ethoxy)-(2,4-, 2,5-, or 4,5-)dimethylpyridin-3-yl, 6-(3-sulfamoyl-propoxy)-(2- or 4-)methylpyridin-3-yl, 6-(3-sulfamoyl-propoxy)-(2,4-, 2,5-, or 4,5-)dimethylpyridin-3-yl, 6-(2-methylsulfamoyl-ethoxy)-(2- or 4-)methylpyridin-3-yl, 6-(2-methylsulfamoyl-ethoxy)-(2,4-, 2,5-, or 4,5-)dimethylpyridin-3-yl, 6-(3-methylsulfamoyl-propoxy)-(2- or 4-)methylpyridin-3-yl, 6-(3-methylsulfamoyl-propoxy)-(2,4-, 2,5-, or 4,5-)dimethylpyridin-3-yl, 6-(2-dimethylsulfamoyl-ethoxy)-(2- or 4-)methylpyridin-3-yl, 6-(2-dimethylsulfamoyl-ethoxy)-(2,4-, 2,5-, or 4,5-)dimethylpyridin-3-yl, 6-(3-dimethylsulfamoyl-propoxy)-(2- or 4-)methylpyridin-3-yl, 6-(3-dimethylsulfamoyl-propoxy)-(2,4-, 2,5-, or 4,5-)dimethylpyridin-3-yl, 6-(2-(2-oxo-1-pyrrolidinyl)ethoxy)-(2- or 4-)methylpyridin-3-yl, 6-(2-(2-oxo-1-pyrrolidinyl)ethoxy)-(2,4-, 2,5-, or 4,5-)dimethylpyridin-3-yl, 6-(3-(2-oxo-1-pyrrolidinyl)propoxy)-(2- or 4-)methylpyridin-3-yl, 6-(3-(2-oxo-1-pyrrolidinyl)propoxy)-(2,4-, 2,5-, or 4,5-)dimethylpyridin-3-yl, 6-(1-piperidinyl)pyridin-3-yl, 6-(4-morpholino)pyridin-3-yl, 6-(4-morpholino)-(2,4-, 2,5-, or 4,5-)dimethylpyridin-3-yl, 6-acetylpyridin-3-yl, 6-benzyloxypyridin-3-yl, 6-methylsulfonylpyridin-3-yl, 6-carbamoylpyridin-3-yl, (2- or 4-)methoxypyrimidin-5-yl, 2-(3-hydroxy-3-methylbutoxy)-4-methylpyrimidin-5-yl, 2-(3-methylsulfonyl-propoxy)-4-methylpyrimidin-5-yl, 2-(3-hydroxy-3-methylbutoxy)-4,6-dimethylpyrimidin-5-yl, 2-(3-methylsulfonyl-propoxy)-4,6-dimethylpyrimidin-5-yl, 2-(4-morpholino)-4,6-dimethylpyrimidin-5-yl, 2-ethyl-6,7-difluoro-1H-benzimidazol-1-yl, 2-ethoxy-6,7-difluoro-1H-benzimidazol-1-yl, (2-, 4-, 5-, 6-, 7-, or 8-) methylquinoline-3-yl, 6-(1-piperidinyl)pyridin-3-yl, 1-methylpiperidin-4-yl, and 4,4-difluoropiperidin-1-yl.

The "aralkyl group which is optionally substituted with 1 to 5 substituent(s) RII" is the "aralkyl group" in which any hydrogen atom is optionally substituted with 1 to 5 substituent(s) RII. That is to say, the "aralkyl group which is optionally substituted with 1 to 5 substituent(s) RII" includes, in addition to the unsubstituted groups exemplified as the "aralkyl group": "an aralkyl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5—CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the aralkyl group may be substituted with either the aryl moiety or the alkyl moiety. Specific examples thereof include, in addition to unsubstituted benzyl, phenethyl, 1-naphthylmethyl, or 2-naphthylmethyl: (2-, 3-, or 4-)fluorobenzyl, (2-, 3-, or 4-)chlorobenzyl, (2-, 3-, or 4-)hydroxybenzyl, (2-, 3-, or 4-)methoxybenzyl, (2-, 3-, or 4-)trifluoromethoxybenzyl, (2-, 3-, or 4-)methylbenzyl, (2-, 3-, or 4-)trifluoromethylbenzyl, (2,6-, 2,5-, 2,4-, or 2,3-)dimethylbenzyl, 3,5-ditrifluoromethylbenzyl, 4-(2-hydroxyethoxy)-2,6-dimethylbenzyl, 4-(2,3-dihydroxypropoxy)-2,6-dimethylbenzyl, and 4-(3-hydroxy-3-methylbutoxy)-2,6-dimethylbenzyl.

The "heteroarylalkyl group which is optionally substituted with 1 to 5 substituent(s) RII" is the "heteroarylalkyl group" in which any hydrogen atom is optionally substituted with 1 to 5 substituent(s) RII. That is to say, the "heteroarylalkyl group which is optionally substituted with 1 to 5 substituent(s) RII" includes, in addition to the unsubstituted groups exemplified as the "heteroarylalkyl group": "a heteroarylalkyl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the heteroarylalkyl group may be substituted with either the heteroaryl moiety or the alkyl moiety. Specific examples thereof include, in addition to unsubstituted pyrrolylmethyl, furylmethyl, pyridylmethyl, or quinolylmethyl:

(2-, 4-, 5-, or 6-)chloropyridin-3-ylmethyl, (2-, 4-, 5-, or 6-)hydroxypyridin-3-ylmethyl, (2-, 4-, 5-, or 6-)methoxypyridin-3-ylmethyl, (2-, 4-, 5-, or 6-)methylpyridin-3-ylmethyl, (2,4-, 2,5-, 2,6-, 4,5-, or 4,6-)dimethylpyridin-3-ylmethyl, 6-(2-hydroxyethoxy)-2,4-dimethylpyridin-3-ylmethyl, 6-(2,3-dihydroxypropoxy)-2,4-dimethylpyridin-3-ylmethyl, and 6-(3-hydroxy-3-methylbutoxy)-2,4-dimethylpyridin-3-ylmethyl.

The "non-aromatic heterocyclic alkyl group which is optionally substituted with 1 to 5 substituent(s) RII" is the "non-aromatic heterocyclic alkyl group" in which any hydrogen atom is optionally substituted with 1 to 5 substituent(s) RII. That is to say, the "non-aromatic heterocyclic alkyl group which is optionally substituted with 1 to 5 substituent(s) RII" includes, in addition to the unsubstituted groups exemplified as the "non-aromatic heterocyclic alkyl group": "a non-aromatic heterocyclic alkyl group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the non-aromatic heterocyclic alkyl group may be substituted with either the non-aromatic heterocyclic moiety or the alkyl moiety. Specific examples thereof include, in addition to unsubstituted pyrrolidinylmethyl, tetrahydrofurylmethyl, piperidinylmethyl, or tetrahydropyranylmethyl: (2-, 3-, or 4-)chloropiperidin-1-ylmethyl, (2-, 3-, or 4-)hydroxypiperidin-1-ylmethyl, (2-, 3-, or 4-)cyanopiperidin-1-ylmethyl, (2-, 3-, or 4-)methoxypiperidin-1-ylmethyl, (2-, 3-, or 4-)methylpiperidin-1-ylmethyl, (2,3-, 2,4-, 2,5-, 2,6-, 3,4-, or 3,5-)dimethylpiperidin-1-ylmethyl, 4-(2-hydroxyethoxy)-2,6-dimethylpiperidin-1-ylmethyl, 4-(2,3-dihydroxypropoxy)-2,6-dimethylpiperidin-1-ylmethyl, and 4-(3-hydroxy-3-methylbutoxy)-2,6-dimethylpiperidin-1-ylmethyl.

The "aryloxy group which is optionally substituted with 1 to 5 substituent(s) RII" is the "aryloxy group" in which any hydrogen atom is optionally substituted with 1 to 5 substituent(s) RII. The "aryloxy group which is optionally substituted with 1 to 5 substituent(s) RII" is also the "aryl group which is optionally substituted with 1 to 5 substituent(s) RII" which is substituted with an oxygen atom. That is to say, the "aryloxy group which is optionally substituted with 1 to 5 substituent(s) RII" includes, in addition to the unsubstituted groups exemplified as the "aryloxy group": "an aryloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5—OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". Specific examples thereof include a group in which the group exemplified specifically as the "aryl group which is optionally substituted with 1 to 5 substituent(s) RII" is substituted with an oxygen atom, such as, in addition to unsubstituted phenoxy, 1-naphthyloxy, 2-naphthyloxy, 1-indanyloxy, or 2-indanyloxy: (2-, 3-, or 4-)fluorophenoxy, (2-, 3-, or 4-)chlorophenoxy, (2-, 3-, or 4-)hydroxyphenoxy, (2-, 3-, or 4-)cyanophenoxy, (2-, 3-, or 4-)methoxyphenoxy, (2-, 3-, or 4-)trifluoromethoxyphenoxy, (2-, 3-, or 4-)methylphenoxy, (2-, 3-, or 4-)trifluoromethylphenoxy, (2,6-, 2,5-, 2,4-, or 2,3-)dimethylphenoxy, (3- or 4-)(2-hydroxyethyl)phenoxy, 4-(2-hydroxyethoxy)phenoxy, 4-(2,3-dihydroxypropoxy)phenoxy, (3- or 4-)(3-hydroxy-3-methylbutoxy)phenoxy, (3- or 4-)(2-ethoxy-ethoxy)phenoxy, (3- or 4-)(3-methylsulfonyl-propoxy)phenoxy, 4-(3-hydroxy-3-methylbutoxy)-2-methylphenoxy, 4-(2-ethoxy-ethoxy)-2-methylphenoxy, 4-(3-methylsulfonyl-propoxy)-2-methylphenoxy, 4-(2-hydroxyethoxy)-2,6-dimethylphenoxy, 4-(2,3-dihydroxypropoxy)-2,6-dimethylphenoxy, 4-(3-hydroxy-3-methylbutoxy)-2,6-dimethylphenoxy, 4-(2-ethoxy-ethoxy)-2,6-dimethylphenoxy, 4-(3-methylsulfonyl-propoxy)-2,6-dimethylphenoxy, 4-methylsulfonylphenoxy, and 4-(4-morpholino)phenoxy.

The "heteroaryloxy group which is optionally substituted with 1 to 5 substituent(s) RII" is the "heteroaryloxy group" in which any hydrogen atom is optionally substituted with 1 to 5 substituent(s) RII. The "heteroaryloxy group which is optionally substituted with 1 to 5 substituent(s) RII" is also a group in which a group having the "heteroaryl group" in the "heterocyclic group which is optionally substituted with 1 to 5 substituent(s) RII" is substituted with an oxygen atom. That is to say, the "heteroaryloxy group which is optionally substituted with 1 to 5 substituent(s) RII" includes, in addition to the unsubstituted groups exemplified as the "heteroaryloxy group": "a heteroaryloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 C$_{1-6}$ alkyl group(s) or 1 to 3 oxo group(s)), a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a C$_{2-6}$ alkenyl group, a C$_{2-7}$ alkanoyl group, an aralkyloxy group, a heterocyclic group (the heterocyclic group is optionally substituted with 1 to 3 C$_{1-6}$ alkyl group(s) or 1 to 3 oxo group(s)), a heterocyclic carbonyl group (the heterocyclic carbonyl group is optionally substituted with 1 to 3 C$_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". Specific examples thereof include a group in which a group having the "heteroaryl group" among the groups exemplified specifically as the "heterocyclic group which is optionally substituted with 1 to 5 substituent(s) RII" is substituted with an oxygen atom, such as, in addition to pyrroly-loxy, furyloxy, thienyloxy, (2-, 3-, or 4-)pyridyloxy, pyrimidinyloxy, or quinolyloxy: (2-, 4-, 5-, or 6-)chloropyridin-3-yloxy, (2- or 3-)chloropyridin-4-yloxy, (2-, 4-, 5-, or 6-)hydroxypyridin-3-yloxy, (2- or 3-)hydroxypyridin-4-yloxy, (3-, 4-, 5-, or 6-)cyanopyridin-2-yloxy, (2-, 4-, 5-, or 6-)cyanopyridin-3-yloxy, (2- or 3-)cyanopyridin-4-yloxy, (2-, 4-, 5-, or 6-)methoxypyridin-3-yloxy, (2- or 3-)methoxypyridin-4-yloxy, (2-, 4-, 5-, or 6-)methylpyridin-3-yloxy, (2- or 3-)methylpyridin-4-yloxy, (2,4-, 2,5-, 2,6-, 4,5-, or 4,6-)dimethylpyridin-3-yloxy, (2,3-, 2,5-, 2,6-, or 3,5-)dimethylpyridin-4-yloxy, 6-methoxy-(2-, 4-, or 5-)methylpyridin-3-yloxy, 6-(2-hydroxyethoxy)pyridin-3-yloxy, 6-(2,3-dihydroxypropoxy)pyridin-3-yloxy, 6-(3-hydroxy-3-methylbutoxy)pyridin-3-yloxy, 6-(2-ethoxyethoxy)pyridin-3-yloxy, 6-(3-methylsulfonyl-propoxy)pyridin-3-yloxy, 6-(3-hydroxy-3-methylbutoxy)-(2- or 4-)methylpyridin-3-yloxy, 6-(2-ethoxyethoxy)-(2- or 4-)methylpyridin-3-yloxy, 6-(3-methylsulfonyl-propoxy)-(2- or 4-)methylpyridin-3-yloxy, 6-(2-hydroxyethoxy)-2,4-dimethylpyridin-3-yloxy, 6-(2,3-dihydroxypropoxy)-2,4-dimethylpyridin-3-yloxy, 6-(3-hydroxy-3-methylbutoxy)-2,4-dimethylpyridin-3-yloxy, 6-(2-ethoxyethoxy)-2,4-dimethylpyridin-3-yloxy, 6-(3-methylsulfonyl-propoxy)-2,4-dimethylpyridin-3-yloxy, and 6-(4-morpholino)-pyridin-3-yloxy.

The "non-aromatic heterocyclic oxy group which is optionally substituted with 1 to 5 substituent(s) RII" is the "non-aromatic heterocyclic oxy group" in which any hydrogen atom is optionally substituted with 1 to 5 substituent(s) RII. That is to say, the "non-aromatic heterocyclic oxy group which is optionally substituted with 1 to 5 substituent(s) RII" includes, in addition to the unsubstituted groups exemplified as the "non-aromatic heterocyclic oxy group": "a non-aromatic heterocyclic oxy group which is substituted with 1 to 5 group(s) optionally selected from a halogen atom, —OH, a cyano group, a C$_{1-6}$ alkoxy group (the C$_{1-6}$ alkoxy group is optionally substituted with 1 to 5 halogen atom(s)), 1 to 5 —OH, 1 to 5 C$_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 C$_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 C$_{1-6}$ alkyl group(s) or 1 to 3 oxo group(s)), a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a C$_{2-6}$ alkenyl group, a C$_{2-7}$ alkanoyl group, an aralkyloxy group, a heterocyclic group (the heterocyclic group is optionally substituted with 1 to 3 C$_{1-6}$ alkyl group(s) or 1 to 3 oxo group(s)), a heterocyclic carbonyl group (the heterocyclic carbonyl group is optionally substituted with 1 to 3 C$_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". For example, a 3- to 8-membered saturated or unsaturated non-aromatic heterocyclic oxy group optionally substituted with 1 to 5 substituent(s) RII is included. Examples thereof include, in addition to pyrrolidinyloxy, tetrahydrofuryloxy, piperidinyloxy, dihydropyranyloxy, or tetrahydropyranyloxy(oxanyloxy): (2- or 3-)fluorooxane-4-yloxy, (2- or 3-)chlorooxane-4-yloxy, (2- or 3-)hydroxyoxane-4-yloxy, (2- or 3-)methoxyoxane-4-yloxy, (2- or 3-)trifluoromethoxyoxane-4-yloxy, (2- or 3-)methyloxane-4-yloxy, (2- or 3-)trifluoromethyloxane-4-yloxy, (2,3-, 2,5-, 2,6-, or 3,5-)dimethyloxane-4-yloxy, 1-methylpiperidin-4-yloxy, and (1,2- or 1,3-)dimethylpiperidin-4-yloxy.

The "aralkyloxy group which is optionally substituted with 1 to 5 substituent(s) RII" is the "aralkyloxy group" in which any hydrogen atom is optionally substituted with 1 to 5 substituent(s) RII. That is to say, the "aralkyloxy group which is optionally substituted with 1 to 5 substituent(s) RII" includes, in addition to the unsubstituted groups exemplified as the "aralkyloxy group": "an aralkyloxy group which is substituted with 1 to 5 group(s) optionally selected from a halogen atom, —OH, a cyano group, a C$_{1-6}$ alkoxy group (the C$_{1-6}$ alkoxy group is optionally substituted with 1 to 5 halogen atom(s), 1 to 5 —OH, 1 to 5 C$_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 C$_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 C$_{1-6}$ alkyl group(s) or 1 to 3 oxo group(s)), a C$_{1-6}$ alkyl group (the C$_{1-6}$ alkyl group is optionally substituted with 1 to 5 halogen atom(s), 1 to 5 —OH, 1 to 5 C$_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a C$_{2-6}$ alkenyl group, a C$_{2-7}$ alkanoyl group, an aralkyloxy group, a heterocyclic group (the heterocyclic group is optionally substituted with 1 to 3 C$_{1-6}$ alkyl group(s) or 1 to 3 oxo group(s)), a heterocyclic carbonyl group (the heterocyclic carbonyl group is optionally substituted with 1 to 3 C$_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the aralkyloxy group may be substituted with the aryl moiety or the alkyl moiety. Specific examples thereof include, in addition to benzyloxy, phenethyloxy, 1-naphthylmethoxy, or 2-naphthylmethoxy: (2-, 3-, or 4-)fluorobenzyloxy, (2-, 3-, or 4-)chlorobenzyloxy, (2-, 3-, or 4-)hydroxybenzyloxy, (2-, 3-, or 4-)methoxybenzyloxy, (2-, 3-, or 4-)trifluoromethoxybenzyloxy, (2-, 3-, or 4-)methylbenzyloxy, (2-, 3-, or 4-)trifluoromethylbenzyloxy, (2-, 3-, or 4-)methoxyphenethyloxy, (2,6-, 2,5-, 2,4-, or 2,3-)dimethylbenzyloxy, 4-(2-hydroxyethoxy)-2,6-dimethylbenzyloxy, 4-(2,3-dihydroxypropoxy)-2,6-dimethylbenzyloxy, and 4-(3-hydroxy-3-methylbutoxy)-2,6-dimethylbenzyloxy.

The "heteroarylalkyloxy group which is optionally substituted with 1 to 5 substituent(s) RII" is the "heteroarylalkyloxy group" in which any hydrogen atom is optionally substituted with 1 to 5 substituent(s) RII. That is to say, the "heteroarylalkyloxy group which is optionally substituted with 1 to 5 substituent(s) RII" includes, in addition to the unsubstituted groups exemplified as the "heteroarylalkyloxy group": "a heteroarylalkyloxy group which is substituted with 1 to 5 group(s) optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a —NR$^{b1}$R$^{c1}$ group, a heterocyclic oxy group (the heterocyclic oxy group is optionally substituted with 1 to 3 $C_{1-6}$ alkyl group(s) or 1 to 3 oxo group(s)), a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group". The substituent(s) of the heteroarylalkyloxy group may be substituted with either the heteroaryl moiety or the alkyl moiety. Specific examples thereof include, in addition to pyrrolylmethoxy, furylmethoxy, pyridylmethoxy, or quinolylmethoxy: (2-, 4-, 5-, or 6-)chloropyridin-3-yl-methoxy, (2-, 4-, 5-, or 6-)hydroxypyridin-3-ylmethoxy, (2-, 4-, 5-, or 6-)methoxypyridin-3-ylmethoxy, (2-, 4-, 5-, or 6-)methylpyridin-3-ylmethoxy, (2,4-, 2,5-, 2,6-, 4,5-, or 4,6-)dimethylpyridin-3-ylmethoxy, 6-(2-hydroxyethoxy)-2,4-dimethylpyridin-3-ylmethoxy, 6-(2,3-dihydroxypropoxy)-2,4-dimethylpyridin-3-ylmethoxy, and 6-(3-hydroxy-3-methylbutoxy)-2,4-dimethylpyridin-3-ylmethoxy.

In the compound of Formula (I), in the cyclic amide structure moiety, proton tautomerism shown by the formula below can be generated. The abundance ratio of this structure can vary depending on whether the compound of Formula (I) is in the solid state or in the dissolved state in a liquid. The tautomer generated by the cyclic amide moiety is included in Formula (I).

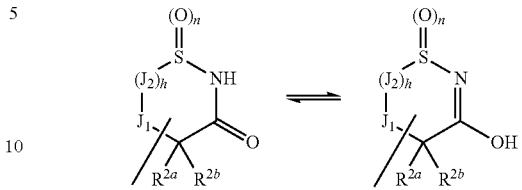

Namely, in Formula (I), for example, a proton tautomer as shown below is supposed and such a tautomer is also included in the range of the present compound.

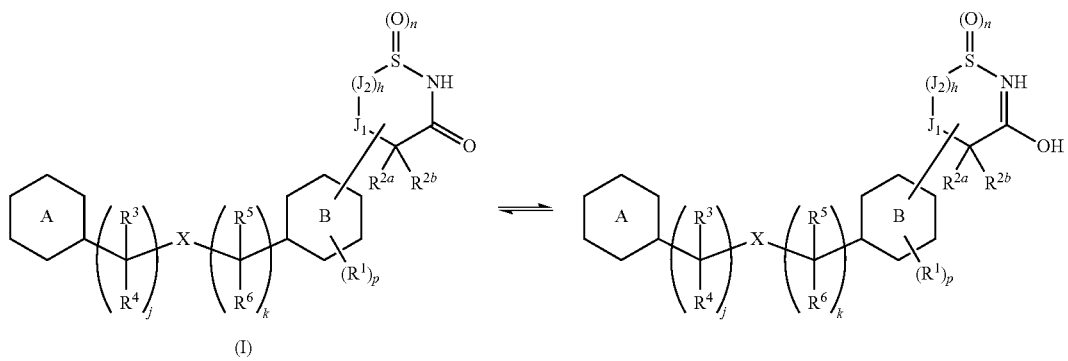

For example, when in the cyclic amide structure of Formula (I), n is 1, h is 0, $J_1$ is $CR^{11a}$, $R^{2a}$, $R^{2b}$, and $R^{11a}$ are a hydrogen atom, and the ring B is bonded to $J_1$, the tautomerism as shown below is supposed and such a tautomer is also included in the range of the present compound.

The description of any specific types of tautomers in any structural formulae of the present specification is not intended to limit the present invention, but is intended to represent the whole set of tautomers that are applicable.

Specifically, for example, a tautomer, namely, 5-[4-[[3-[4-(2-ethoxyethoxy)-2,6-dimethylphenyl]phenyl]methoxy]phenyl]-1-oxo-2-isothiazoline-3-ol, of the compounds described as 5-[4-[[3-[4-(2-ethoxyethoxy)-2,6-dimethylphenyl]phenyl]methoxy]phenyl]-1-oxo-1,2-thiazolidin-3-one among compounds of Example 1 is also categorized as a compound of Example 1. In addition, a tautomer, namely, 5-(4-((3-(2,6-dimethyl-4-(2-ethoxyethoxy)phenyl)phenyl)methoxy)phenyl)-4-isothiazolin e-3-one 1-oxide, of the compounds described as 5-(4-((3-(2,6-dimethyl-4-(2-ethoxyethoxy)phenyl)phenyl)methoxy)phenyl)isothiazol-3-ol 1-oxide among compounds of Step 6 of Example 1, which are a reaction intermediate, is also categorized as a compound of Step 6 of Example 1.

[1-1] In the compound of Formula (I) according to Aspect [1], Ls are independently a group optionally selected from a halogen atom, —OH, an oxo group, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, a $C_{2-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, —SF$_5$, a —S(O)$_i$R$^a$ (i is an integer of 0 to 2) group, a —NR$^b$R$^c$ group, and a substituted spiropiperidinylmethyl group; and
the substituent(s) RI, the substituent(s) RII, i, R$^a$, R$^b$, and R$^c$ are the same as defined in Aspect [1].

[1-1-a] Preferable examples of Ls include a group optionally selected from a halogen atom, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, a $C_{2-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, a —NR$^b$R$^c$ group, and a substituted spiropiperidinylmethyl group (the substituent(s) RI and the substituent(s) RII are the same as defined in Aspect [1]).

[1-1-b] More preferable examples of Ls include a group optionally selected from a halogen atom, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, a —NR$^b$R$^c$ group, and a substituted spiropiperidinylmethyl group (the substituent(s) RI and the substituent(s) RII are the same as defined in Aspect [1]).

[1-1-c] Further preferable examples of Ls include a group optionally selected from a halogen atom, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, and a substituted spiropiperidinylmethyl group (the substituent(s) RI and the substituent(s) RII are the same as defined in Aspect [1]).

[1-1-d] Most preferable examples of Ls include a group optionally selected from a halogen atom, a cyano group, a $C_{1-10}$ alkyl group (the $C_{1-10}$ alkyl group is optionally substituted with 1 to 5 halogen atom(s), 1 to 5 —OH, or 1 to 5 $C_{1-4}$ alkoxy group(s)), a $C_{2-10}$ alkenyl group (the $C_{2-10}$ alkenyl group is optionally substituted with 1 to 5 halogen atom(s), 1 to 5 —OH, or 1 to 5 $C_{1-4}$ alkoxy group(s)), a $C_{1-10}$ alkoxy group (the $C_{1-10}$ alkoxy group is optionally substituted with 1 to 5 halogen atom(s), 1 to 5 —OH, or 1 to 5 $C_{1-4}$ alkoxy group(s)), a $C_{2-10}$ alkenyloxy group (the $C_{2-10}$ alkenyloxy group is optionally substituted with 1 to 5 halogen atom(s), 1 to 5 —OH, or 1 to 5 $C_{1-4}$ alkoxy group(s)), an aryl group which is optionally substituted with 1 to 5 substituent(s) RIIa, a heterocyclic group which is optionally substituted with 1 to 5 substituent(s) RIIa, an aralkyl group which is optionally substituted with 1 to 5 substituent(s) RIIa, a non-aromatic heterocyclic alkyl group which is optionally substituted with 1 to 5 substituent(s) RII, an aryloxy group which is optionally substituted with 1 to 5 substituent(s) RIIa, a heteroaryloxy group which is optionally substituted with 1 to 5 substituent(s) RIIa, a non-aromatic heterocyclic oxy group which is optionally substituted with 1 to 5 substituent(s) RIIa, an aralkyloxy group which is optionally substituted with 1 to 5 substituent(s) RIIa, and a substituted spiropiperidinylmethyl group (the substituent(s) RIIa are the same as or different from each other and are each a group optionally selected from a halogen atom, a cyano group, a $C_{1-6}$ alkoxy group (the $C_{1-6}$ alkoxy group is optionally substituted with 1 to 5 halogen atom(s), 1 to 5 —OH, or 1 to 5 $C_{1-4}$ alkoxy group(s), 1 to 5 non-aromatic heterocyclic group(s) (the heterocyclic group is optionally substituted with 1 or 2 $C_{1-4}$ alkyl group(s) or 1 or 2 oxo group(s)), or 1 to 5 —S(O)$_i$R$^a$ (i is an integer of 0 to 2) group(s)), a —NR$^{b1}$R$^{c1}$ group, a non-aromatic heterocyclic oxy group (the heterocyclic oxy group is optionally substituted with 1 or 2 oxo group(s)), a $C_{1-6}$ alkyl group (the $C_{1-6}$ alkyl group is optionally substituted with 1 to 5 halogen atom(s), 1 to 5 —OH, or 1 to 5 $C_{1-4}$ alkoxy group(s)), a $C_{2-6}$ alkenyl group, a $C_{2-7}$ alkanoyl group, an aralkyloxy group, a non-aromatic heterocyclic carbonyl group (the heterocyclic carbonyl group is optionally substituted with 1 to 2 oxo group(s)), a —S(O)$_i$R$^a$ (i is an integer of 0 to 2) group, a —CONR$^d$R$^e$ group, and a —CONR$^{d3}$R$^{e3}$ group (R$^{d3}$ is a hydrogen atom or a $C_{1-4}$ alkyl group; and R$^{e3}$ is a $C_{1-6}$ alkyl group (the $C_{1-6}$ alkyl group is substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group))). Substitution with one to three substituent(s) RIIa is preferable.

More specific examples of Ls include the groups specifically exemplified above as the "halogen atom", the "$C_{1-6}$ alkyl group which is optionally substituted with 1 to 5 substituent(s) RI", the "$C_{1-6}$ alkoxy group which is optionally substituted with 1 to 5 substituent(s) RI", the "aryl group which is optionally substituted with 1 to 5 substituent(s) RII", the "heterocyclic group which is optionally substituted with 1 to 5 substituent(s) RII", the "aralkyl group which is optionally substituted with 1 to 5 substituent(s) RII", the "heteroarylalkyl group which is optionally substituted with 1 to 5 substituent(s) RII", the "non-aromatic heterocyclic alkyl group which is optionally substituted with 1 to 5 substituent(s) RII", the "aryloxy group which is optionally substituted with 1 to 5 substituent(s) RII", the "heteroaryloxy group which is optionally substituted with 1 to 5 substituent(s) RII", the "non-aromatic heterocyclic oxy group which is optionally substituted with 1 to 5 substituent(s) RII", the "aralkyloxy group which is optionally substituted with 1 to 5 substituent(s) RII", the "heteroarylalkyloxy group which is optionally substituted with 1 to 5 substituent(s) RII", the substituted spiropiperidinylmethyl group", and the like.

[1-2] In the compound of Formula (I) according to Aspect [1], R$^1$s are independently a group optionally selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI (the substituents RI are the same as or different from each other and are the same as defined as the substituent(s) RI above), and a cyano group.

[1-2-a] Preferable examples of R$^1$s include a halogen atom, a $C_{1-4}$ alkyl group which is optionally substituted with 1 to 5 substituent(s) RI, a $C_{1-4}$ alkoxy group which is optionally substituted with 1 to 5 substituent(s) RI (the substituents RI are the same as or different from each other and are the same as defined as the substituent(s) RI above), and a cyano group.

[1-2-b] More preferable examples of R$^1$s include a halogen atom, a $C_{1-4}$ alkyl group which is optionally substituted with 1 to 5 halogen atom(s), a $C_{1-4}$ alkoxy group which is optionally substituted with 1 to 5 halogen atom(s), and a cyano group. Specific examples of R$^1$ include a fluorine atom, a chlorine atom, a bromine atom, methyl, ethyl, propyl, isopropyl, butyl, isobutyl, sec-butyl, tert-butyl, trifluoromethyl, methoxy, ethoxy, propoxy, isopropoxy, butoxy, isobutoxy, sec-butoxy, tert-butoxy, trifluoromethoxy, and cyano.

[1-3] In the compound of Formula (I) according to Aspect [1], R$^{2a}$ and R$^{2b}$ are independently a group optionally selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, and a cyano group.

[1-3-a] Preferable examples of R$^{2a}$ and R$^{2b}$ independently include a hydrogen atom, a halogen atom, and a $C_{1-4}$ alkyl group, and specific examples thereof include a hydrogen atom, a fluorine atom, a chlorine atom, a bromine atom, and methyl.

[1-3-b] More preferably, any one of R$^{2a}$ and R$^{2b}$ is a hydrogen atom, and further preferably, both of R$^{2a}$ and R$^{2b}$ are a hydrogen atom.

[1-4] In the compound of Formula (I) according to Aspect [1], R$^3$, R$^4$, R$^5$, R$^6$, and R$^7$ are independently a group optionally selected from a hydrogen atom, a $C_{1-6}$ alkyl group, a halogenated $C_{1-6}$ alkyl group, a $C_{2-6}$ alkenyl group, and a $C_{2-6}$ alkynyl group.

[1-4-a] R$^3$, R$^4$, R$^5$, R$^6$, and R$^7$ are preferably a hydrogen atom.

[1-5] In the compound of Formula (I) according to Aspect [1], R$^{11a}$ and R$^{11b}$ are independently a group optionally selected from a hydrogen atom, a halogen atom, a $C_{1-6}$ alkyl group, a halogenated $C_{1-6}$ alkyl group, a $C_{2-6}$ alkenyl group, a $C_{2-6}$ alkynyl group, a $C_{1-6}$ alkoxy group, a halogenated $C_{1-6}$ alkoxy group, a $C_{2-7}$ alkanoyl group, and a carboxy group which is optionally protected.

[1-5-a] Preferable examples of R$^{11a}$ and R$^{11b}$ independently include a hydrogen atom, a halogen atom, a $C_{1-4}$ alkyl group, a halogenated $C_{1-4}$ alkyl group, a $C_{2-5}$ alkanoyl group, and a carboxy group. More specifically, R$^{11a}$ and R$^{11b}$ are independently a hydrogen atom, a fluorine atom, a chlorine atom, a bromine atom, methyl, ethyl, propyl, isopropyl, butyl, isobutyl, sec-butyl, tert-butyl, trifluoromethyl, acetyl, carboxy, or the like, more preferably a hydrogen atom.

[1-6] In the compound of Formula (I) according to Aspect [1], R$^{12a}$ and R$^{12b}$ are independently a group optionally selected from a hydrogen atom, a halogen atom, a $C_{1-6}$ alkyl group, a halogenated $C_{1-6}$ alkyl group, a $C_{2-6}$ alkenyl group, a $C_{2-6}$ alkynyl group, a $C_{1-6}$ alkoxy group, a halogenated $C_{1-6}$ alkoxy group, and a cyano group.

[1-6-a] Preferable examples of R$^{12a}$ and R$^{12b}$ independently include a hydrogen atom, a halogen atom, a $C_{1-4}$ alkyl group, a halogenated $C_{1-4}$ alkyl group, and a cyano group. Specifically, R$^{12a}$ and R$^{12b}$ are a hydrogen atom, a fluorine atom, a chlorine atom, a bromine atom, methyl, ethyl, propyl, isopropyl, butyl, isobutyl, sec-butyl, tert-butyl, trifluoromethyl, cyano, or the like.

[1-6-b] More preferably, any one of R$^{12a}$ and R$^{12b}$ is a hydrogen atom, and further preferably, both of R$^{12a}$ and R$^{12b}$ are a hydrogen atom.

[1-7] In the compound of Formula (I) according to Aspect [1], R$^{11c}$ and R$^{12c}$ are independently a group optionally selected from a hydrogen atom, a $C_{1-6}$ alkyl group, and a halogenated $C_{1-6}$ alkyl group.

[1-7-a] Preferable examples of R$^{11c}$ and R$^{12c}$ independently include a hydrogen atom and a $C_{1-4}$ alkyl group. More specifically, R$^{11c}$ and R$^{12c}$ are independently a hydrogen atom, a fluorine atom, a chlorine atom, a bromine atom, methyl, ethyl, propyl, isopropyl, butyl, isobutyl, sec-butyl, tert-butyl, or the like. More preferably, R$^{11c}$ and R$^{12c}$ are a hydrogen atom.

[1-8] In the compound of Formula (I) according to Aspect [1], X is an oxygen atom, a sulfur atom, or —NR$^7$— (R$^7$ is the same as defined as R$^7$ above).

[1-8-a] Preferably, X is an oxygen atom or —NH—.

[1-8-b] More preferably, X is an oxygen atom.

[1-9] In the compound of Formula (I) according to Aspect [1], j is an integer of 0 to 3, while k is an integer of 0 to 2. Preferably, j is 0 or 1, while k is 0. When the ring A is a monocyclic ring or a spiro ring, more preferably, j is 1, while k is 0. When the ring A is a fused ring, more preferably, j is 0, while k is 0.

[1-10] In the compound of Formula (I) according to Aspect [1], the ring B is a $C_{6-14}$ aryl group or a 5- to 14-membered heteroaryl group, preferably a benzene ring, a pyridine ring, a pyrimidine ring, or Formula (BB1) or Formula (BB2):

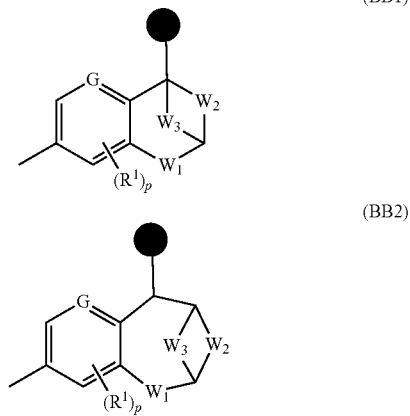

(where p and $R^1$ are the same as defined in Formula (I); G is a carbon atom or a nitrogen atom; $W_1$ is a single bond, an oxygen atom, a sulfur atom, —$CH_2$—, —$CF_2$—, —CO—, —SO—, or —$SO_2$—; $W_2$ is a single bond or —$CH_2$—; $W_3$ is none or —$CH_2$—; and ● is a single bond with a cyclic amide structure moiety). The ring B is more preferably a benzene ring, a pyridine ring, Formula (BB1), or Formula (BB2), further preferably a benzene ring.

Preferable aspects of p and $R^1$ in Formula (BB1) and Formula (BB2) are the same as the preferable aspects described in the below Aspect [1-11] and the above Aspects [1-2-a] to [1-2-b].

[1-10-a] In Formula (BB1) or Formula (BB2), G is preferably a carbon atom.

[1-10-b] In Formula (BB1), $W_1$ is preferably an oxygen atom, a sulfur atom, or —$CH_2$—. When $W_3$ is —$CH_2$—, $W_2$ is preferably —$CH_2$—.

[1-10-c] In Formula (BB2), $W_1$ is preferably a single bond, an oxygen atom, a sulfur atom, or —$CH_2$—. When $W_3$ is —$CH_2$—, $W_2$ is preferably —$CH_2$—.

[1-11] In the compound of Formula (I) according to Aspect [1], p is an integer of 0 to 4. p is preferably 0 or 1.

[1-12] In the compound of Formula (I) according to Aspect [1], n is an integer of 0 to 2; h is an integer of 0 to 3; $J_1$ is —$CR^{11a}R^{11b}$— or —$NR^{11c}$—; and $J_2$ is —$CR^{12a}R^{12b}$— or $NR^{12c}$— (with the proviso that when $J_1$ is —$NR^{11c}$—, h is 0). n is preferably 1 or 2. When $J_1$ is —$CR^{11a}R^{11b}$— and h is 0, n is more preferably 1. When $J_1$ is —$NR^{11c}$— and h is 0, n is more preferably 2. When h is an integer of 1 to 3, n is more preferably 2.

[1-13] In the compound of Formula (I) according to Aspect [1], the ring A is a $C_{6-14}$ aryl group which is optionally substituted with 1 to 5 L(s), a 3- to 14-membered heterocyclic group which is optionally substituted with 1 to 5 L(s), a $C_{5-7}$ cycloalkyl group which is optionally substituted with 1 to 5 L(s), a $C_{5-7}$ cycloalkenyl group which is optionally substituted with 1 to 5 L(s), a 6- to 14-membered spiro ring group which is optionally substituted with 1 to 5 L(s), or a 2-phenylamino-2-oxoacetyl group which is optionally substituted with 1 to 5 L(s).

[1-13-a] Preferably, the ring A is phenyl which is optionally substituted with 1 to 5 L(s), a $C_{6-14}$ fused aryl group which is optionally substituted with 1 to 5 L(s) and partly hydrogenated, a 5- to 7-membered monocyclic heteroaryl group which is optionally substituted with 1 to 5 L(s), an 8- to 14-membered ring-fused heteroaryl group which is optionally substituted with 1 to 5 L(s), an 8- to 14-membered ring-fused heteroaryl group which is optionally substituted with 1 to 5 L(s) and partly hydrogenated, a 3- to 8-membered non-aromatic heterocyclic group which is optionally substituted with 1 to 5 L(s), a $C_{5-7}$ cycloalkenyl group which is optionally substituted with 1 to 5 L(s), or a 7- to 13-membered spiro ring group which is optionally substituted with 1 to 5 L(s).

[1-13-b] More preferably, the ring A is phenyl which is optionally substituted with 1 to 5 L(s), indanyl which is optionally substituted with 1 to 5 L(s), 1,2,3,4-tetrahydronaphthyl which is optionally substituted with 1 to 5 L(s), thienyl which is optionally substituted with 1 to 5 L(s), thiazolyl which is optionally substituted with 1 to 5 L(s), phthalazinyl which is optionally substituted with 1 to 5 L(s), 1,2,3,4-tetrahydro-4-isoquinolyl which is optionally substituted with 1 to 5 L(s), 1,2,3,4-tetrahydro-4-quinolyl which is optionally substituted with 1 to 5 L(s), dihydrobenzofuranyl which is optionally substituted with 1 to 5 L(s), chromanyl which is optionally substituted with 1 to 5 L(s), pyrrolidinyl which is optionally substituted with 1 to 5 L(s), piperidinyl which is optionally substituted with 1 to 5 L(s), a cyclohexenyl group which is optionally substituted with 1 to 5 L(s), or a 7- to 13-membered spiro ring group which is optionally substituted with 1 to 5 L(s).

[1-13-b-1] Further preferably, the ring A is phenyl which is optionally substituted with 1 to 5 L(s), thienyl which is optionally substituted with 1 to 5 L(s), thiazolyl which is optionally substituted with 1 to 5 L(s), phthalazinyl which is optionally substituted with 1 to 5 L(s), 1,2,3,4-tetrahydro-4-isoquinolyl which is optionally substituted with 1 to 5 L(s), 1,2,3,4-tetrahydro-4-quinolyl which is optionally substituted with 1 to 5 L(s), pyrrolidinyl which is optionally substituted with 1 to 5 L(s), piperidinyl which is optionally substituted with 1 to 5 L(s), a cyclohexenyl group which is optionally substituted with 1 to 5 L(s), or a 7- to 13-membered spiro ring group which is optionally substituted with 1 to 5 L(s).

[1-13-b-2] Most preferably, the ring A is phenyl which is optionally substituted with 1 to 5 L(s), thienyl which is optionally substituted with 1 to 5 L(s), thiazolyl which is optionally substituted with 1 to 5 L(s), pyrrolidinyl which is optionally substituted with 1 to 5 L(s), piperidinyl which is optionally substituted with 1 to 5 L(s), a cyclohexenyl group which is optionally substituted with 1 to 5 L(s), or a 7- to 13-membered spiro ring group which is optionally substituted with 1 to 5 L(s).

[1-13-c] The ring A in Formula (I) according to Aspect [1] is preferably phenyl which is optionally substituted with 1 to 5 L(s). More preferable examples of the ring A include Partial Structural Formula (A):

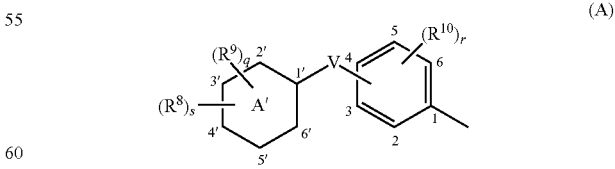

(where q and r are independently an integer of 0 to 4; s is an integer of 0 to 2 (with the proviso that q+s is an integer of 0 to 5);
the ring A' is an aryl group or a heteroaryl group;
V is a single bond or an oxygen atom;

$R^8$s are independently a group optionally selected from a $C_{1-6}$ alkoxy group which is substituted with 1 to 5 substituent(s) M, a $C_{2-6}$ alkenyloxy group which is substituted with 1 to 5 substituent(s) M, a $C_{2-6}$ alkynyloxy group which is substituted with 1 to 5 substituent(s) M, a —$CONR^dR^{e1}$ group, an aralkyloxy group, a heterocyclic oxy group (the heterocyclic oxy group is optionally substituted with 1 to 3 $C_{1-6}$ alkyl group(s) or 1 to 3 oxo group(s)), a heterocyclic group (the heterocyclic group is optionally substituted with 1 to 3 $C_{1-6}$ alkyl group(s) or 1 to 3 oxo group(s)), and a heterocyclic carbonyl group (the heterocyclic carbonyl group is optionally substituted with 1 to 3 $C_{1-6}$ alkyl group(s) or 1 to 3 oxo group(s));

the substituents M are independently a group optionally selected from a halogen atom, —OH, a $C_{1-6}$ alkoxy group, an aryl group (the aryl group is optionally substituted with 1 to 3 halogen atom(s)), a heterocyclic group (the heterocyclic group is optionally substituted with 1 to 3 —OH, 1 to 3 $C_{1-6}$ alkyl group(s), or 1 to 3 oxo group(s)), a —$S(O)_iR^a$ (i is an integer of 0 to 2) group, a —$NR^{b1}R^{c1}$ group, a —$SO_2NR^dR^e$ group, and a —$CONR^dR^e$ group;

$R^9$s and $R^{10}$s are independently a group optionally selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, a $C_{2-7}$ alkanoyl group, —SH, a —$S(O)_iR^a$ (i is an integer of 0 to 2) group, a —$NR^{b1}R^{c1}$ group, and a —$CONR^dR^e$ group;

the figures of 1 to 6 or 1' to 6' indicate where the ring A'-V— or each substituent is bonded; and $R^a$, $R^d$, $R^e$, $R^{b1}$, $R^{c1}$, and $R^{e1}$ are the same as defined in Formula (I)).

In Formula (A), the binding positions of the ring A'-V— and $R^{10}$s are any positions at which they can be optionally bonded in the benzene ring, and the binding positions of $R^8$s and $R^9$s are any positions at which they can be optionally bonded in the ring A'.

In Formula (A), preferably, the ring A' is a benzene ring, a pyridine ring, or a pyrimidine ring. Namely, preferable examples of Formula (A) include Formula (A)-1:

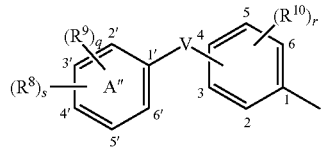

(A)-1

(where q, r, s, V, $R^8$s, $R^9$s, and $R^{10}$s are the same as defined in Formula (A); and the ring A" is a benzene ring, a pyridine ring, or a pyrimidine ring).

[1-13-c-1] Preferable examples of Formula (A) include Formula (A1) or Formula (A2):

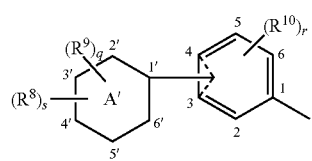

(A1)

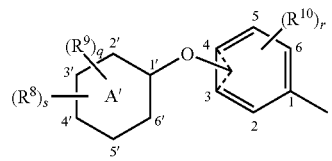

(A2)

(where q, r, s, the ring A', $R^8$s, $R^9$s, and $R^{10}$s are the same as defined in Formula (A) described in Aspect [1-13-c]; and the broken lines and the Figures 3 and 4 or the Figures 3' and 4' indicate where the ring A', the ring A'-O—, or $R^8$s are bonded).

Here, when the position of the single bond of the phenyl group (the binding position with the linker moiety containing X) is determined as 1-position, the binding position of the ring A' in Formula (A1) is 3-position or 4-position, preferably 3-position. In the case that the ring A' is a 6-membered ring, when the binding position with the phenyl group of the ring A' is determined as 1'-position, the binding position of $R^8$ in Formula (A1) is preferably 3'-position or 4'-position.

When the position of the single bond of the phenyl group (the binding position with the linker moiety containing X) is determined as 1-position, the binding position of the ring A'-O— in Formula (A2) is 3-position or 4-position, preferably 3-position. In the case that the ring A' is a 6-membered ring, when the binding position with the phenyl group-O— of the ring A' is determined as 1'-position, the binding position of $R^8$ in Formula (A2) is preferably 3'-position or 4'-position.

In Formula (A1) or Formula (A2), preferably, the ring A' is a benzene ring, a pyridine ring, or a pyrimidine ring. Namely, preferable examples of Formula (A1) or Formula (A2) include Formula (A1)-1 or Formula (A2)-1:

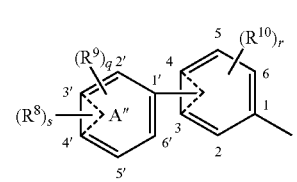

(A1)-1

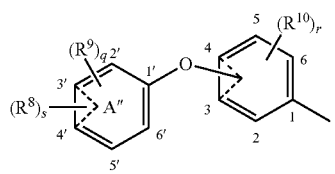

(A2)-1

(where q, r, s, $R^8$s, $R^9$s, and $R^{10}$s are the same as defined in Formula (A) described in Aspect [1-13-c]; the ring A" is the same as defined in Formula (A)-1 described in Aspect [1-13-c]; and the broken lines and the Figures 3 and 4 or the Figures 3 ' and 4 ' indicate where the ring A", the ring A"-O—, or $R^8$s are bonded).

Here, when the position of the single bond of the phenyl group (the binding position with the linker moiety containing X) is determined as 1-position, the binding position of the ring A" or the ring A"-O— in Formula (A1)-1 or Formula (A2)-1 is preferably 3-position. When the binding position with the phenyl group or the phenyl group-O— of the ring A" is determined as 1'-position, the binding position of $R^8$ in Formula (A1)-1 or Formula (A2)-1 is preferably 4'-position.

[1-13-c-1-1] More specifically, Formula (A) is preferably the above Partial Structural Formula (A1) or Formula (A1)-1.

[1-13-c-2] In Formula (A), Formula (A1), or Formula (A2), more specifically, the ring A' is preferably benzene, naphthalene, pyridine, pyrimidine, thiophene, quinoline, benzimidazole, or dibenzofuran, more preferably benzene, pyridine, pyrimidine, thiophene, or quinoline. Further preferably, the ring A' is benzene, pyridine, or pyrimidine, that is, the ring A" (Formula (A)-1, Formula (A1)-1, or Formula (A2)-1). Most preferably, the ring A' and the ring A" are benzene or pyridine.

[1-13-c-3] More specifically, Formula (A) is more preferably the above Partial Structural Formula (A), Formula (A)-1, Formula (A1), Formula (A2), Formula (A1)-1, or Formula (A2)-1 in which s is 0 or 1. In addition, preferably, any one of q and s is 1 or more.

[1-13-c-3-1] More preferably, Formula (A) is Formula (A1a) or Formula (A1b) when s is 1 in Formula (A1)-1, and Formula (A) is Formula (A1c) when s is 0 in Formula (A1)-1:

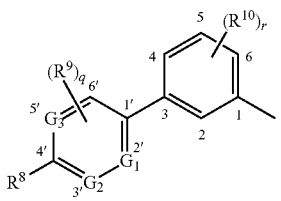

(A1a)

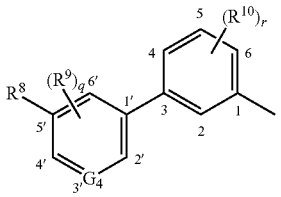

(A1b)

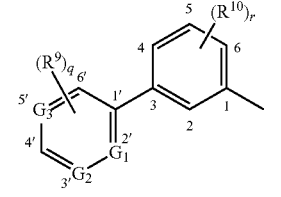

(A1c)

(where q, r, $R^8$, $R^9$ and $R^{10}$ are the same as defined in the above Formula (A) described in Aspect [1-13-c]; and $G_1$, $G_2$, $G_3$, and $G_4$ are a =CH— group, a =$CR^9$— group, or a nitrogen atom (with the proviso that when $G_1$ is a nitrogen atom, $G_2$ and $G_3$ are a =CH— group or a =$CR^9$— group)).

In Formula (A1a), Formula (A1b), or Formula (A1c), when the position of the single bond of the phenyl group (the binding position with the linker moiety containing X) is determined as 1-position, $R^{10}$ can be bonded at 2-position, 4-position, 5-position, or 6-position. The binding position of $R^9$ is any positions at which it can be optionally bonded in the ring including $G_1$ or $G_4$.

Formula (A) is more preferably Formula (A1a) or Formula (A1c).

[1-13-c-3-2] In Formula (A1a), preferably, $G_1$ is a =CH— group or a =$CR^9$— group; and $G_2$ and $G_3$ are independently a =CH— group, a =$CR^9$— group, or a nitrogen atom. More preferably, $G_1$ and $G_3$ are independently a =CH— group or a =$CR^9$— group; and $G_2$ is a =CH— group, a =$CR^9$— group, or a nitrogen atom.

In Formula (A1c), preferably, $G_1$ is a =CH— group or a =$CR^9$— group; and $G_2$ and $G_3$ are independently a =CH— group, a =$CR^9$— group or a nitrogen atom. More preferably, $G_1$ and $G_3$ are independently a =CH— group or a =$CR^9$— group; and $G_2$ is a =CH— group, a =$CR^9$— group, or a nitrogen atom.

[1-13-c-4] More specifically, Formula (A) is preferably Formula (A), Formula (A)-1, Formula (A1), Formula (A2), Formula (A1)-1, Formula (A2)-1, Formula (A1a), Formula (A1b), or Formula (A1c) in which r is 0 or 1. When r is not 0, at least one of the binding positions of $R^{10}$ is preferably 2-position, and when r is 1, the binding position of $R^{10}$ is preferably 2-position.

[1-13-c-5] More specifically, Formula (A) is preferably Formula (A), Formula (A)-1, Formula (A1), Formula (A2), Formula (A1)-1, Formula (A2)-1, Formula (A1a), Formula (A1b), or Formula (A1c) in which q is an integer of 0 to 3, more preferably Formula (A), Formula (A)-1, Formula (A1), Formula (A2), Formula (A1)-1, Formula (A2)-1, Formula (A1a), Formula (A1b), or Formula (A1c) in which q is an integer of 1 to 3. Preferably, any one of q and s is 1 or more.

[1-13-c-5-1] In Formula (A1a), when the binding position of the ring containing $G_1$ with 3-position of the phenyl group is determined as 1'-position, the binding position of $R^9$ when q is 1 is preferably 2'-position (with the proviso that the case where $G_1$ is a nitrogen atom is excluded) or 6'-position. The binding positions of $R^{9s}$ when q is 2 are preferably 2'-position and 6'-position, 2'-position and 5'-position, or 5'-position and 6'-position (with the proviso that the case where the binding position is a nitrogen atom is excluded), and more preferably, 2'-position and 6'-position or 2'-position and 5'-position. The binding positions of $R^9$ when q is 3 are preferably 2'-position, 5'-position, and 6'-position (with the proviso that the case where the binding position is a nitrogen atom is excluded).

In Formula (A1c), when the binding position of the ring containing $G_1$ with 3-position of the phenyl group is determined as 1'-position, the binding position of $R^9$ when q is 1 is preferably 2'-position (with the proviso that the case where $G_1$ is a nitrogen atom is excluded) or 6'-position. The binding positions of $R^9$s when q is 2 are preferably 2'-position and 6'-position, 2'-position and 5'-position, 2'-position and 4'-position, 4'-position and 6'-position, or 5'-position and 6'-position (with the proviso that the case where the binding position is a nitrogen atom is excluded), and more preferably, 2'-position and 6'-position, 2'-position and 5'-position, or 2'-position and 4'-position. The binding positions of $R^9$s when q is 3 are preferably 2'-position, 5'-position and 6'-position, or 2'-position, 4'-position and 6'-position, or 2'-position, 4'-position and 5'-position (with the proviso that the case where the binding position is a nitrogen atom is excluded).

[1-13-c-6] In Formula (A1a), r is preferably 0 or 1. When r is 1, the binding position of $R^{10}$ is preferably 2-position. When $G_1$ is a =CH— group or a =$CR^9$— group, $G_2$ is a =CH— group or a nitrogen atom, $G_3$ is a =CH— group, and q is 1 or 2, the binding position(s) of $R^9$(s) is more preferably 2'-position and/or 6'-position.

In Formula (A1c), r is preferably 0 or 1. When r is 1, the binding position of $R^{10}$ is preferably 2-position. When $G_1$ is a =CH— group or a =$CR^9$— group, $G_2$ is a =CH— group or a nitrogen atom, $G_3$ is a =CH— group, and q is 1 or 2, the binding position(s) of $R^9$(s) is more preferably 2'-position and/or 6'-position.

[1-13-c-7] In Formula (A), Formula (A)-1, Formula (A1), Formula (A2), Formula (A1)-1, Formula (A2)-1, Formula (A1a), or Formula (A1b), $R^8$s are independently a $C_{1-6}$ alkoxy group which is substituted with 1 to 5 substituent(s) Ma, a $C_{2-6}$ alkenyloxy group which is substituted with 1 to 5 substituent(s) Ma, a $C_{2-6}$ alkynyloxy group which is substituted with 1 to 5 substituent(s) Ma, a —CONR$^d$R$^{e2}$ group, an aralkyloxy group, a non-aromatic heterocyclic oxy group (the heterocyclic oxy group is optionally substituted with 1 to 2 oxo group(s)), or a non-aromatic heterocyclic carbonyl group (the heterocyclic carbonyl group is optionally substituted with 1 to 2 oxo group(s)); the substituents Ma are independently a halogen atom, —OH, a $C_{1-6}$ alkoxy group, a non-aromatic heterocyclic group (the heterocyclic group is optionally substituted with 1 to 3 —OH, 1 to 3 $C_{1-6}$ alkyl group(s), or 1 to 3 oxo group(s)), a —S(O)$_i$R$^a$ (i is an integer of 0 to 2) group, a —NR$^{b1}$R$^{c1}$ group, a —SO$_2$NR$^d$R$^e$ group, and a —CONR$^d$R$^e$ group; and R$^{e2}$ is a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 non-aromatic heterocyclic group(s) (the heterocyclic group is optionally substituted with 1 to 3 —OH, 1 to 3 $C_{1-6}$ alkyl group(s), or 1 to 3 oxo group(s)), 1 to 5 —S(O)$_i$R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s)).

[1-13-c-7-1] More preferable examples of R$^8$ include a $C_{1-6}$ alkoxy group (the alkoxy group is substituted with 1 to 5 group(s) optionally selected from —OH, a $C_{1-6}$ alkoxy group, a non-aromatic heterocyclic group (the heterocyclic group is optionally substituted with 1 to 2 —OH, 1 to 2 $C_{1-4}$ alkyl group(s), or 1 to 2 oxo group(s)), a —S(O)$_i$R$^a$ (i is an integer of 0 to 2) group, a —NR$^{b2}$R$^{c2}$ group, a —SO$_2$NR$^d$R$^e$ group, and a —CONR$^d$R$^e$ group), a —CONR$^{d3}$R$^{e3}$ group, an aralkyloxy group, a non-aromatic heterocyclic oxy group (the heterocyclic oxy group is optionally substituted with 1 to 2 oxo group(s)), and a non-aromatic heterocyclic carbonyl group (the heterocyclic carbonyl group is optionally substituted with 1 to 2 oxo group(s)); R$^{b2}$ and R$^{c2}$ are independently a group optionally selected from a hydrogen atom, a $C_{1-6}$ alkyl group, a $C_{2-7}$ alkanoyl group (the alkanoyl group is optionally substituted with —OH or a $C_{1-6}$ alkoxy group), and a $C_{1-6}$ alkylsulfonyl group, where R$^{b2}$ and R$^{c2}$ optionally form, together with a nitrogen atom to which they are bonded, a 3- to 8-membered cyclic group, and in the cyclic group, one carbon atom is optionally substituted with a carbonyl group; and R$^{d3}$ is a hydrogen atom or a $C_{1-4}$ alkyl group, and R$^{e3}$ is a $C_{1-6}$ alkyl group (the $C_{1-6}$ alkyl group is substituted with 1 to 5 group(s) optionally selected from —OH, a $C_{1-6}$ alkoxy group, a non-aromatic heterocyclic group (the heterocyclic group is optionally substituted with 1 to 2 —OH, 1 to 2 $C_{1-4}$ alkyl group(s), or 1 to 2 oxo group(s)), and a —S(O)$_i$R$^a$ (i is an integer of 0 to 2).

[1-13-c-7-2] Further preferable examples of R$^8$ include a $C_{1-6}$ alkoxy group (the alkoxy group is substituted with 1 to 5 —OH, 1 to 5 methoxy, 1 to 5 ethoxy, 1 to 5 4-hydroxy-1,1-dioxidotetrahydro-2H-thiopyran-4-yl, 1 to 5 3-methyloxetane-3-yl, 1 to 5 methylsulfonyl, 1 to 5 ethylsulfonyl, 1 to 5 —NH$_2$, 1 to 5 acetylamino, 1 to 5 methylsulfonylamino, 1 to 5 2-oxo-1-pyrrolidinyl, 1 to 5 5-oxo-2-pyrrolidinyl, 1 to 5 sulfamoyl, 1 to 5 methylsulfamoyl, 1 to 5 dimethylsulfamoyl, 1 to 5 carbamoyl, 1 to 5 methylcarbamoyl, or 1 to 5 dimethylcarbamoyl), a —CONR$^{d4}$R$^{e4}$ group (R$^{d4}$ is a hydrogen atom or a $C_{1-4}$ alkyl group; and R$^{e4}$ is a $C_{1-6}$ alkyl group (the $C_{1-6}$ alkyl group is substituted with 1 to 5 —OH, 1 to 5 methoxy, 1 to 5 ethoxy, 1 to 5 4-hydroxy-1,1-dioxidotetrahydro-2H-thiopyran-4-yl, 1 to 5 3-methyloxetane-3-yl, 1 to 5 methylsulfonyl, 1 to 5 ethylsulfonyl, 1 to 5 —NH$_2$, 1 to 5 acetylamino, 1 to 5 methylsulfonylamino, 1 to 5 2-oxo-1-pyrrolidinyl, 1 to 5 5-oxo-2-pyrrolidinyl, 1 to 5 sulfamoyl, 1 to 5 methylsulfamoyl, 1 to 5 dimethylsulfamoyl, 1 to 5 carbamoyl, 1 to 5 methylcarbamoyl, or 1 to 5 dimethylcarbamoyl), benzyloxy, (1,1-dioxidotetrahydro-2H-thiopyran-4-yl)oxy, and (pyrrolidine-1-yl)carbonyl. The substitution number of —OH, methoxy, ethoxy, 4-hydroxy-1,1-dioxidotetrahydro-2H-thiopyran-4-yl, 3-methyloxetane-3-yl, methylsulfonyl, ethylsulfonyl, —NH$_2$, acetylamino, methylsulfonylamino, 2-oxo-1-pyrrolidinyl, 5-oxo-2-pyrrolidinyl, sulfamoyl, methylsulfamoyl, dimethylsulfamoyl, carbamoyl, methylcarbamoyl, or dimethylcarbamoyl in the $C_{1-6}$ alkoxy group as R$^8$ or the $C_{1-6}$ alkyl group as R$^{e4}$ is particularly preferably 1 to 2.

More specifically, R$^8$ is 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-ethoxyethoxy, (4-hydroxy-1,1-dioxidotetrahydro-2H-thiopyran-4-yl)methoxy, (3-methyloxetane-3-yl)methoxy, 2-methylsulfonyl-ethoxy, 3-methylsulfonyl-propoxy, 2-ethylsulfonyl-ethoxy, 3-ethylsulfonyl-propoxy, 2-aminoethoxy, 3-aminopropoxy, 2-acetylamino-ethoxy, 3-acetylamino-propoxy, 2-methylsulfonylamino-ethoxy, 3-methylsulfonylamino-propoxy, 2-(2-oxo-1-pyrrolidinyl)ethoxy, 3-(2-oxo-1-pyrrolidinyl)propoxy, (5-oxo-2-pyrrolidinyl)methoxy, 2-sulfamoyl-ethoxy, 3-sulfamoyl-propoxy, 2-methylsulfamoyl-ethoxy, 3-methylsulfamoyl-propoxy, 2-dimethylsulfamoyl-ethoxy, 3-dimethylsulfamoyl-propoxy, 2-carbamoyl-ethoxy, 3-carbamoyl-propoxy, 2-methylcarbamoyl-ethoxy, 3-methylcarbamoyl-propoxy, 2-dimethylcarbamoyl-ethoxy, 3-dimethylcarbamoyl-propoxy, N-(2-hydroxyethyl)carbamoyl, N-(2-methoxyethyl)carbamoyl, N-(2-hydroxyethyl)-N-methylcarbamoyl, N-(2-methoxyethyl)-N-methylcarbamoyl, N-(2-methylsulfonyl-ethyl)carbamoyl, N-(2-methylsulfonyl-ethyl)-N-methylcarbamoyl, (1,1-dioxidotetrahydro-2H-thiopyran-4-yl)oxy, benzyloxy, (pyrrolidine-1-yl)carbonyl, or the like.

The $C_{1-6}$ alkoxy group or the heterocyclic oxy group which are substituted with a group of A in Formula (I) or the like in WO 2010/143733 pamphlet, particularly the $C_{1-6}$ alkoxy groups substituted with (2) to (8) which are shown in [9] (c) in p. 25 to 26 or the heterocyclic oxy group shown in [9] (e), and these groups shown in Examples can also be referred to as specific examples of R$^8$ of the present specification. Similarly, formulae and the corresponding groups shown in Examples in the pamphlets below can also be referred to as specific examples of R$^8$ of the present specification.
WO 2008/001931 pamphlet, a group of R$^1$—X—O— in Formula (I);
WO 2010/123017 pamphlet, a group of R$^7$ in Formula (I);
WO 2010/123016 pamphlet, a group of R$^{10}$ in Formula (I);
WO 2009/054423 pamphlet, groups of A and B in Formula (II).

[1-13-c-8] In Formula (A), Formula (A)-1, Formula (A1), Formula (A2), Formula (A1)-1, Formula (A2)-1, Formula (A1a), Formula (A1b), or Formula (A1c), preferable examples of R$^9$s independently include a halogen atom, a cyano group, a $C_{1-4}$ alkyl group (the $C_{1-4}$ alkyl group is optionally substituted with 1 to 5 halogen atom(s) or 1 to 5 —OH), a $C_{2-4}$ alkenyl group, a $C_{1-4}$ alkoxy group (the $C_{1-4}$ alkoxy group is optionally substituted with 1 to 5 halogen atom(s)), a $C_{2-5}$ alkanoyl group, a —S(O)$_i$R$^a$ (R$^a$ is a $C_{1-4}$ alkyl group) group, a —CONR$^d$R$^e$ (R$^d$ and R$^e$ are independently a hydrogen atom or a $C_{1-4}$ alkyl group) group, and a —NR$^{b1}$R$^{c1}$ group (R$^{b1}$ and R$^{c1}$ form, together with a nitrogen atom to which they are bonded, a 3- to 8-membered cyclic group; and in the cyclic group, one or two carbon atom(s)

is(are) optionally substituted with an atom optionally selected from an oxygen atom, a sulfur atom, and a nitrogen atom or with a carbonyl group).

More preferably, $R^9$s are independently a halogen atom, a cyano group, a $C_{1-4}$ alkyl group (the $C_{1-4}$ alkyl group is optionally substituted with 1 to 5 halogen atom(s) or 1 to 5—OH), a $C_{2-3}$ alkenyl group, a $C_{1-4}$ alkoxy group (the $C_{1-4}$ alkoxy group is optionally substituted with 1 to 5 halogen atom(s)), a $C_{2-3}$ alkanoyl group, a —S(O)$_t$R$^a$ (R$^a$ is a $C_{1-2}$ alkyl group) group, a —CONR$^d$R$^e$ (R$^d$ and R$^e$ are independently a hydrogen atom or a $C_{1-2}$ alkyl group) group, or a —NR$^{b1}$R$^{c1}$ group (R$^{b1}$ and R$^{c1}$ form, together with a nitrogen atom to which they are bonded, a 3- to 6-membered cyclic group; and in the cyclic group, one or two carbon atom(s) is(are) optionally substituted with an oxygen atom, a nitrogen atom, or a carbonyl group). Further preferably, $R^9$s are independently a halogen atom, a cyano group, a $C_{1-4}$ alkyl group which is optionally substituted with 1 to 5 halogen atom(s), or a $C_{1-4}$ alkoxy group which is optionally substituted with 1 to 5 halogen atom(s).

More specific examples of $R^9$ include a fluorine atom, a chlorine atom, a bromine atom, cyano, methyl, ethyl, propyl, isopropyl, butyl, isobutyl, sec-butyl, tert-butyl, trifluoromethyl, hydroxymethyl, 2-hydroxyethyl, methoxy, ethoxy, propoxy, isopropoxy, butoxy, isobutoxy, sec-butoxy, tert-butoxy, cyclopropylmethoxy, trifluoromethoxy, trifluoroethoxy, vinyl, acetyl, methylsulfonyl, carbamoyl, methylcarbamoyl, dimethylcarbamoyl, 1-piperidinyl, 4-morpholinyl, and 2-oxooxazolidin-3-yl. More preferable examples of $R^9$ include a fluorine atom, cyano, methyl, ethyl, methoxy, and ethoxy.

The amino group, the $C_{1-6}$ alkylthio group, the $C_{1-6}$ alkyl group, the $C_{3-10}$ cycloalkyl group, or the $C_{1-6}$ alkoxy group which are substituted with a group of A in Formula (I) or the like in WO 2010/143733 pamphlet, particularly the $C_{1-6}$ alkyl group and the halogenated $C_{1-6}$ alkyl group which are shown in [9] (b) in p. 25 to 26 or the $C_{1-6}$ alkoxy group which is optionally substituted with (1) shown in [9] (c), and the corresponding groups shown in Examples can also be referred to as specific examples of $R^9$ of the present specification. Similarly, formulae and the corresponding groups shown in Examples in the pamphlets below can also be referred to as specific examples of $R^9$ of the present specification.

WO 2008/001931 pamphlet, groups of $R^2$, $R^3$, $R^4$, and $R^5$ in Formula (I);

WO 2010/123017 pamphlet, groups of $R^5$, $R^6$, $R^7$, and $R^Y$ in Formula (I);

WO 2010/123016 pamphlet, groups of $R^8$, $R^9$, $R^{10}$, and $R^Y$ in Formula (I);

WO 2009/054423 pamphlet, groups of $R^3$, $R^4$, A, and B in Formula (II) and Formula (III).

[1-13-c-9] In Formula (A), Formula (A)-1, Formula (A1), Formula (A2), Formula (A1)-1, Formula (A2)-1, Formula (A1a), Formula (A1b), or Formula (A1e), preferable examples of $R^{10}$s independently include a halogen atom, a $C_{1-4}$ alkyl group which is optionally substituted with 1 to 5 halogen atom(s), and a $C_{1-4}$ alkoxy group which is optionally substituted with 1 to 5 halogen atom(s). More specific examples of $R^{10}$ include a fluorine atom, a chlorine atom, a bromine atom, methyl, ethyl, propyl, isopropyl, butyl, isobutyl, sec-butyl, tert-butyl, trifluoromethyl, methoxy, ethoxy, propoxy, isopropoxy, butoxy, isobutoxy, sec-butoxy, tert-butoxy, and trifluoromethoxy. More preferable examples of $R^{10}$ include a fluorine atom, methyl, ethyl, methoxy, and ethoxy.

[1-13-c-10] The preferable aspects of q, s, the ring A', $R^8$, and $R^9$ of the Partial Structural Formula (A'):

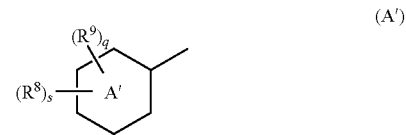

(where q, s, the ring A', $R^8$, and $R^9$ are the same as defined in Formula (A) in Aspect [1-13-c]) in Formula (A), Formula (A1), and Formula (A2) are the same as the preferable aspects described in Aspects [1-13-c-2], [1-13-c-3], [1-13-c-5], [1-13-c-7], [1-13-c-7-1], [1-13-c-7-2], or [1-13-c-8]. Examples of the preferable aspect of Formula (A') include the same groups as the groups having an aryl group or a heteroaryl group among the preferable aspects of L described in Aspect [1-1-d]. Specific examples of Formula (A') include specific examples of the "aryl group which is optionally substituted with 1 to 5 substituent(s) RII" or the same groups as the groups having a heteroaryl group among specific examples of the "heterocyclic group which is optionally substituted with 1 to 5 substituent(s) RII" that are described in Aspect [1]. More specific examples of Formula (A') include the same groups as the groups having benzene, naphthalene, pyridine, pyrimidine, thiophene, quinoline, benzimidazole, or dibenzofuran.

Specific examples of the ring A" moiety having $(R^8)_s$ and $(R^9)_q$ in Formula (A)-1, Formula (A1)-1, and Formula (A2)-1 include the same groups as the groups having a benzene ring, a pyridine ring, or a pyrimidine ring among specific examples of the "aryl group which is optionally substituted with 1 to 5 substituent(s) RII" and specific examples of the "heterocyclic group which is optionally substituted with 1 to 5 substituent(s) RII" that are described in Aspect [1].

Specific examples of the ring moiety having $R^8$ and $(R^9)_q$ in Formula (A1a), Formula (A1b), and Formula (A1c) include the groups having a benzene ring, a pyridine ring, or a pyrimidine ring and having any group of $R^8$ at the p-position or the m-position or not having any group of $R^8$ among specific examples of the "aryl group which is optionally substituted with 1 to 5 substituent(s) RII" and specific examples of the "heterocyclic group which is optionally substituted with 1 to 5 substituent(s) RII" that are described in Aspect [1]. For example in Formula (A1a), specific examples of the ring moiety having $R^8$ and $(R^9)_q$ include a phenyl group having any group of $R^8$ at 4-position (such as 4-(3-hydroxy-3-methylbutoxy)phenyl) and a 3-pyridinyl group having any group of $R^8$ at 6-position (such as 6-(3-methylsulfonyl-propoxy) pyridin-3-yl) and further include also a group having simultaneously any groups of $R^9$ (such as 4-(2-ethoxy-ethoxy)-2, 6-dimethylphenyl and 6-((1,1-dioxidetetrahydro-2H-thiopyran-4-yl)oxy)-2-methylpyridin-3-yl).

Specific examples of the ring A' moiety having $(R^8)_s$ and $(R^9)_q$ of the present specification also include the groups of A in Formula (I) or the like in WO 2010/143733 pamphlet and the groups of Q in Formula (V) in WO 2007/033002 pamphlet, particularly the groups having a cyclic group among the corresponding groups shown in Examples of these pamphlets. Similarly, also the corresponding groups shown in formulae and Examples in the pamphlets below can be referred to as the specific examples of the ring A' moiety having $(R^8)_s$ and $(R^9)_q$ of the present specification.

WO 2008/001931 pamphlet, phenyl groups having $R^1$—X—O—, $R^2$, $R^3$, $R^4$, and $R^5$ in Formula (I);

WO 2010/123017 pamphlet, 6-membered cyclic groups having $R^5$, $R^6$, and $R^7$ in Formula (I);
WO 2010/123016 pamphlet, 6-membered cyclic groups having $R^8$, $R^9$, and $R^{10}$ in Formula (I);
WO 2009/054423 pamphlet, groups of Formula (II) and Formula (III).

That is, 4-(3-methylsulfonyl-propoxy)-2,6-dimethylphenyl, 4((1,1-dioxidetetrahydro-2H-thiopyran-4-yl)oxy)-2,6-dimethylphenyl, 2-(4-morpholino)-4,6-dimethylpyrimidin-5-yl, 2-ethyl-6,7-difluoro-1H-benzimidazol-1-yl, 2-ethoxy-6,7-difluoro-1H-benzimidazol-1-yl, and the like are mentioned.

[1-13-c-11] Preferable examples of the ring A in Formula (I), Formula (A), Formula (A)-1, Formula (A1), Formula (A1)-1, or Formula (A1c) include Formula (A1)-1-1:

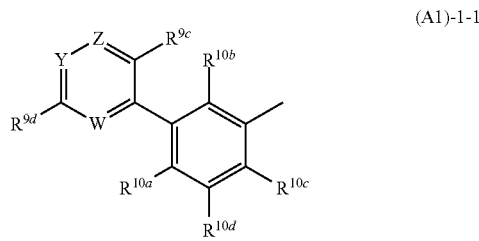

(A1)-1-1

(where W, Y, and Z are =CH— or a nitrogen atom (with the proviso that 0 or 1 of W, Y, and Z is a nitrogen atom, and when $R^{9c}$ is a fluorine atom, Z is =CH—);
$R^{9c}$ is a hydrogen atom, a fluorine atom, a chlorine atom, a trifluoromethyl group, or a $C_{1-6}$ alkoxy group; $R^{9d}$ is a hydrogen atom, a fluorine atom, a chlorine atom, —OH, a $C_{1-4}$ alkyl group, a $C_{1-3}$ alkoxy group, or a $C_{1-2}$ alkylthio group;
$R^{10a}$ is a $C_{1-10}$ alkyl group (the $C_{1-10}$ alkyl group is optionally substituted with 1 to 4 halogen atom(s), 1 to 4 —OH, or 1 to 4 $C_{1-4}$ alkoxy group (the $C_{1-4}$ alkoxy group is optionally substituted with 1 to 4 halogen atom(s), 1 to 4 —OH, or 1 to 4 $C_{1-2}$ alkoxy group)), a $C_{2-10}$ alkenyl group (the $C_{2-10}$ alkenyl group is optionally substituted with 1 to 4 halogen atom(s), 1 to 4 —OH, or 1 to 4 $C_{1-4}$ alkoxy group(s) (the $C_{1-4}$ alkoxy group is optionally substituted with 1 to 4 halogen atom(s), 1 to 4 —OH, or 1 to 4 $C_{1-2}$ alkoxy group(s))), a $C_{1-10}$ alkoxy group (the $C_{1-10}$ alkoxy group is optionally substituted with 1 to 4 halogen atom(s), 1 to 4 —OH, or 1 to 4 $C_{1-2}$ alkoxy group(s)), or a $C_{2-10}$ alkenyloxy group (the $C_{2-10}$ alkenyloxy group is optionally substituted with 1 to 4 halogen atom(s), 1 to 4 —OH, or 1 to 4 $C_{1-2}$ alkoxy group(s)); and
$R^{10b}$, $R^{10c}$, and $R^{10d}$ are independently a hydrogen atom, a fluorine atom, a chlorine atom, a $C_{1-4}$ alkyl group, or a $C_{1-4}$ alkoxy group).

In Formula (A1)-1-1, preferable examples of $R^{10a}$ include Formula ($R^{10a'}$):

($R^{10a'}$)

(where $R^{10a1}$, $R^{10a2}$, and $R^{10a3}$ are independently a hydrogen atom, a fluorine atom, or a $C_{1-4}$ alkyl group; at least two of $R^{10a1}$, $R^{10a2}$, and $R^{10a3}$ are other than a hydrogen atom; and $R^{10a1}$, $R^{10a2}$, and $R^{10a3}$ optionally form, together with a carbon atom to which they are bonded, a 3- to 8-membered cyclic group). Preferably, all of $R^{10a1}$, $R^{10a2}$, and $R^{10a3}$ are a methyl group, or $R^{10a1}$, $R^{10a2}$, and $R^{10a3}$ form a cyclopropyl group.

In Formula (A1)-1-1, W, Y, and Z are preferably =CH—, $R^{9c}$ is preferably a fluorine atom or a butoxy group, $R^{9d}$ is preferably a methoxy group, and $R^{10b}$, $R^{10c}$, and $R^{10d}$ are preferably a hydrogen atom.

Specific examples of Formula (A1)-1-1 include 6-(1,1-dimethylethyl)-2'-fluoro-5'-methoxy-1,1'-biphenyl-3-yl and 2'-butoxy-6-(1,1-dimethylethyl)-5'-methoxy-1,1'-biphenyl-3-yl.

[1-13-c-12] Preferable examples of the ring A in Formula (I), Formula (A), Formula (A)-1, Formula (A1), or Formula (A1)-1 include Formula (A1)-1-2:

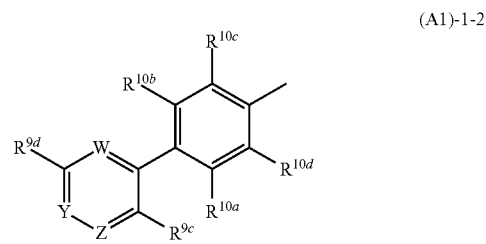

(A1)-1-2

(where W, Y, Z, $R^{9c}$, $R^{9d}$, $R^{10a}$, $R^{10b}$, $R^{10c}$, and $R^{10d}$ are the same as defined in Formula (A1)-1-1 described in Aspect [1-13-c-11]).

In Formula (A1)-1-2, an alkyl chain or an alkenyl chain of $R^{10a}$ is a linear, branched, or cyclic chain and also includes a linear chain or branched chain group substituted with a cyclic group and a cyclic group substituted with a linear chain or branched chain group. When $R^{10a}$ is a $C_{1-10}$ alkyl group, specific examples of $R^{10a}$ include Formula ($R^{10a1}$) described in Aspect [1-13-c-11]. More specific examples of $R^{10a}$ include 1,1-dimethylethyl(tert-butyl), 2,2-dimethylcyclopentyl, 5,5-dimethylcyclopent-1-enyl, 2,2-dimethyl-1-hydroxypropyl, and 2,2-dimethyl-1-methoxypropyl. Specific examples of $R^{10a}$ of the present specification also include a group of A in Formula I in WO 2009/048527 pamphlet, a group of A in Formula I and Formula III in WO 2009/111056 pamphlet, and a group of A in Formula I'A in WO 2010/045258 pamphlet, particularly the corresponding groups shown in Examples.

In Formula (A1)-1-2, W and Z are preferably =CH—, $R^{9c}$ is preferably a fluorine atom, $R^{9d}$ is preferably a methoxy group, $R^{10b}$ and $R^{10d}$ are preferably a hydrogen atom, and $R^{10c}$ is preferably a hydrogen atom or a fluorine atom.

Specific examples of Formula (A1)-1-2 include 2-(1,1-dimethylethyl)-2'-fluoro-5'-methoxy-1,1'-biphenyl-4-yl, 2-(2,2-dimethylcyclopentyl)-2'-fluoro-5'-methoxy-1,1'-biphenyl-4-yl, and 2-(2,2-dimethyl-1-methoxypropyl)-2'-fluoro-5'-methoxy-1,1'-biphenyl-4-yl.

[1-13-d] The ring A in Formula (I) according to Aspect [I] is preferably Partial Structural Formula (AA):

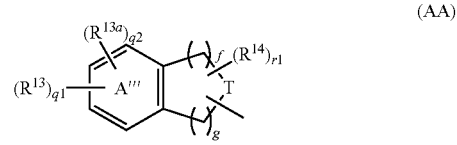

(AA)

(where f is an integer of 0 to 2; g is an integer of 1 to 4; q1 is an integer of 0 to 3; q2 is 0 or 1; r1 is an integer of 0 to 2 (with the proviso that q1+q2+r1 is an integer of 0 to 5); the ring A''' is a benzene ring or a pyridine ring;

T is —$CH_2$—, an oxygen atom, —$S(O)_i$— (i is an integer of 0 to 2), or —$NR^7$— ($R^7$ is the same as $R^7$ defined in Formula (I));

$R^{13}$s are independently a group optionally selected from a halogen atom, —OH, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, a $C_{2-10}$ alkynyloxy group which is optionally substituted with 1 to 5 substituent(s) RI, —SH, a —$S(O)_iR^a$ (i is an integer of 0 to 2) group, and a —$NR^bR^c$ group;

$R^{13a}$ is a group optionally selected from an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, and a substituted spiropiperidinylmethyl group;

$R^{14}$s are independently a group optionally selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a —$S(O)_iR^a$ (i is an integer of 0 to 2) group, and a —$NR^bR^c$ group; and $R^a$, $R^b$, $R^c$, the substituent RI, and the substituent RII are the same as defined in Formula (I)). In Formula (AA), the binding positions of the linker moiety containing X and $R^{14}$s are any positions at which they can be optionally bonded in the ring containing T, and the binding positions of $R^{13}$ and $R^{13a}$ are any positions at which they can be optionally bonded in the ring A'''.

[1-13-d-1] Specific examples of Formula (AA) include Formula (AA)-1:

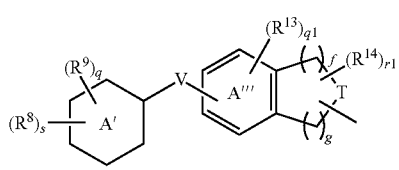

(AA)-1

(where f, g, q1, r1, the ring A''', T, $R^{13}$, and $R^{14}$ are the same as defined in Formula (AA) described in Aspect [1-13-d]; and q, s, the ring A', V, $R^8$, and $R^9$ are the same as defined in Formula (A) described in Aspect [1-13-c]). In Formula (AA)-1, the binding positions of the linker moiety containing X and $R^{14}$s are any positions at which they can be optionally bonded in the ring containing T; the binding positions of the ring A'-V— and $R^{13}$ are any positions at which they can be optionally bonded in the ring A'''; and the binding positions of $R^8$ and $R^9$ are any positions at which they can be optionally bonded in the ring A'.

The Formula (AA)-1 is preferably a Formula (AA)-1 in which the ring A' is a benzene ring, a pyridine ring, or a pyrimidine ring. That is, preferable examples of Formula (AA)-1 include Formula (AA)-1-1:

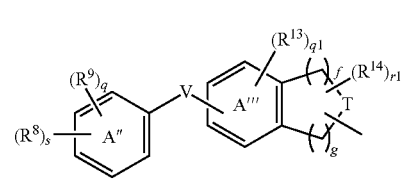

(AA)-1-1

(where f, g, q1, r1, the ring A''', T, $R^{13}$, and $R^{14}$ are the same as defined in Formula (AA) described in Aspect [1-13-d]; q, s, V, $R^8$, and $R^9$ are the same as defined in Formula (A) described in Aspect [1-13-c]; and the ring A'' is the same as defined in Formula (A)-1 described in Aspect [1-13-c]).

[1-13-d-2] In Formula (AA), Formula (AA)-1, or Formula (AA)-1-1, the ring A''' is preferably a benzene ring.

[1-13-d-3] In Formula (AA), Formula (AA)-1, or Formula (AA)-1-1, f is preferably 0 or 1, more preferably 0. g is preferably 2 or 3, more preferably 2. Preferably, f is 0 and g is 2 or 3, and more preferably, f is 0 and g is 2.

[1-13-d-4] Specific examples of Formula (AA) include Formula (AA1):

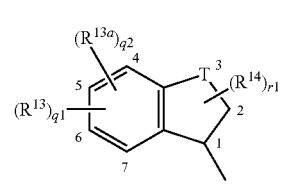

(AA1)

(where q1, q2, r1, T, $R^{13}$, $R^{13a}$, and $R^{14}$ are the same as defined in Formula (AA) described in Aspect [1-13-d]; and the Figures 1 to 7 indicate the binding position of a substituent in the ring).

[1-13-d-4-1] In Formula (AA1), when the binding position of the linker moiety containing X is determined as 1-position, the substitution position of $R^{13a}$ is preferably 4-position or 5-position, more preferably 4-position.

[1-13-d-5] More specifically, Formula (AA), Formula (AA)-1, Formula (AA)-1-1, or Formula (AA1) is preferably Formula (AA1)-1:

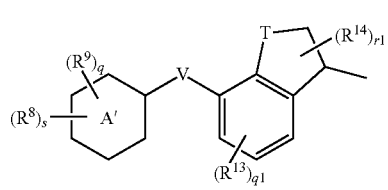

(AA1)-1

(where q1, r1, T, $R^{13}$, and $R^{14}$ are the same as defined in Formula (AA) described in Aspect [1-13-d]; and q, s, the ring A', V, $R^8$, and $R^9$ are the same as defined in Formula (A) described in Aspect [1-13-c]).

[1-13-d-5-1] Specific examples of Formula (AA1)-1 include Formula (AA1a)-1:

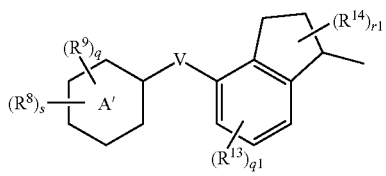

(AA1a)-1

(where q1, r1, $R^{13}$, and $R^{14}$ are the same as defined in Formula (AA) described in Aspect [1-13-d]; and q, s, the ring A', V, $R^8$, and $R^9$ are the same as defined in Formula (A) described in Aspect [1-13-c]).

The Formula (AA1a)-1 is preferably a Formula (AA1a)-1 in which the ring A' is a benzene ring, a pyridine ring, or a pyrimidine ring. That is, preferable examples of Formula (AA1a)-1 include Formula (AA1a)-1-1:

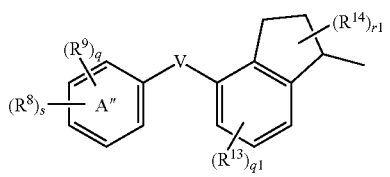

(AA1a)-1-1

(where q1, r1, $R^{13}$, and $R^{14}$ are the same as defined in Formula (AA) described in Aspect [1-13-d]; q, s, V, $R^8$, and $R^9$ are the same as defined in Formula (A) described in Aspect [1-13-c]; and the ring A" is the same as defined in Formula (A)-1 described in Aspect [1-13-c]).

[1-13-d-6] In Formula (AA), Formula (AA)-1, Formula (AA)-1-1, Formula (AA1), or Formula (AA1)-1, T is preferably —$CH_2$— or an oxygen atom.

[1-13-d-7] More specific examples of Formula (AA) or Formula (AA 1) include Formula (AA1b):

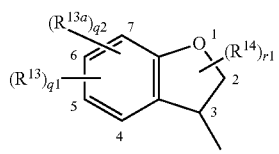

(AA1b)

(where q1, q2, r1, $R^{13}$, $R^{13a}$, and $R^{14}$ are the same as defined in Formula (AA) described in Aspect [1-13-d]; and the Figures 1 to 7 indicate the binding position of a substituent in the ring).

[1-13-d-7-1] More specific examples of Formula (AA1)-1 or Formula (AA1b) include Formula (AA1b)-1:

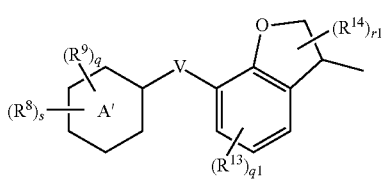

(AA1b)-1

(where q1, r1, $R^{13}$, and $R^{14}$ are the same as defined in Formula (AA) described in Aspect [1-13-d]; and q, s, the ring A', V, $R^8$, and $R^9$ are the same as defined in Formula (A) described in Aspect [1-13-c]).

[1-13-d-8] In Formula (AA), Formula (AA)-1, Formula (AA)-1-1, Formula (AA1), Formula (AA1)-1, Formula (AA1a)-1, Formula (AA1a)-1-1, Formula (AA1b), or Formula (AA1b)-1, q1 is preferably 0 or 1, more preferably 0.

[1-13-d-9] In Formula (AA), Formula (AA1), or Formula (AA1b), q2 is preferably 1.

[1-13-d-10] In Formula (AA), Formula (AA)-1, Formula (AA)-1-1, Formula (AA1), Formula (AA1)-1, Formula (AA1a)-1, Formula (AA1a)-1-1, Formula (AA1b), or Formula (AA1b)-1, r1 is preferably 0 or 1, more preferably 0.

[1-13-d-11] In Formula (AA), Formula (AA1), or Formula (AA1b), preferable examples of $R^{13a}$ include a group optionally selected from an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, and a substituted spiropiperidinylmethyl group (the substituent RII is the same as defined in Aspect [1]).

[1-13-d-11-1] In Formula (AA), Formula (AA1), or Formula (AA1b), more preferable examples of $R^{13a}$ include a group optionally selected from an aryl group which is optionally substituted with 1 to 5 substituent(s) $R^{11a}$, a heterocyclic group which is optionally substituted with 1 to 5 substituent(s) $R^{11a}$, an aralkyl group which is optionally substituted with 1 to 5 substituent(s) RIIa, a non-aromatic heterocyclic alkyl group which is optionally substituted with 1 to 5 substituent(s) RIIa, an aryloxy group which is optionally substituted with 1 to 5 substituent(s) RIIa, a heteroaryloxy group which is optionally substituted with 1 to 5 substituent(s) RIIa, a non-aromatic heterocyclic oxy group which is optionally substituted with 1 to 5 substituent(s) RIM, an aralkyloxy group which is optionally substituted with 1 to 5 substituent(s) RIIa, and a substituted spiropiperidinylmethyl group (the substituent RIM is the same as defined in Aspect [1-1-d]). The number of substitutions by the substituent RIIa is preferably 1 to 3.

[1-13-d-11-2] In Formula (AA), Formula (AA1), or Formula (AA1b), more specific examples of $R^{13a}$ include the groups specifically exemplified as the "aryl group which is optionally substituted with 1 to 5 substituent(s) RII", the "heterocyclic group which is optionally substituted with 1 to 5 substituent(s) RII", the "aralkyl group which is optionally substituted with 1 to 5 substituent(s) RII", the "heteroarylalkyl group which is optionally substituted with 1 to 5 substituent(s) RII", the "non-aromatic heterocyclic alkyl group which is optionally substituted with 1 to 5 substituent(s) RII", the "aryloxy group which is optionally substituted with 1 to 5 substituent(s) RII", the "heteroaryloxy group which is optionally substituted with 1 to 5 substituent(s) RII", the "non-aromatic heterocyclic oxy group which is optionally substituted with 1 to 5 substituent(s) RII", the "aralkyloxy group which is optionally substituted with 1 to 5 substituent(s) RII", the "heteroarylalkyloxy group which is optionally substituted with 1 to 5 substituent(s) RII", the "substituted spiropiperidinylmethyl group", and the like.

Specific examples of $R^{13a}$ of the present specification also include the groups of A in Formula (II) in WO 2010/143733 pamphlet and the groups of Q in Formula (V) in WO 2007/

033002 pamphlet, particularly the groups having a cyclic group among the corresponding groups shown in Examples of these pamphlets.

[1-13-d-11-3] Specific examples of $R^{13a}$ include, in addition to the Partial Structural Formula (A') described in Aspect [1-13-c-10], a group in which Formula (A') is substituted with an oxygen atom, a $C_{1-6}$ alkyl group, or a $C_{1-6}$ alkoxy group. Particularly, when $R^{13a}$ is a group of Formula (A') or a group in which Formula (A') is substituted with an oxygen atom (Formula (A')—O—), $R^{13a}$ can be Formula (A')-V—. For example, a Formula (AA) in which $R^{13a}$ is Formula (A') can be a Formula (AA)-1 in which V is a single bond. A Formula (AA) in which $R^{13a}$ is Formula (A')—O— can be a Formula (AA)-1 in which V is an oxygen atom.

In Formula (AA)-1, Formula (AA1)-1, Formula (AA1a)-1, or Formula (AA1b)-1, more specific examples of the Formula (A')-V-moiety when V is a single bond include the specific groups of the Partial Structural Formula (A') described in Aspect [1-13-c-10], that is, the same groups as specific examples of the "aryl group which is optionally substituted with 1 to 5 substituent(s) RII", or the groups having a heteroaryl group among specific examples of the "heterocyclic group which is optionally substituted with 1 to 5 substituent(s) RII" that are described in Aspect [1]. More specific examples of the Formula (A')-V— moiety when V is an oxygen atom include the groups in which the specific groups of the Partial Structural Formula (A') described in Aspect [1-13-c-10] are substituted with an oxygen atom, that is, the groups in which the same groups as specific examples of the "aryl group which is optionally substituted with 1 to 5 substituent(s) RII", or the groups having a heteroaryl group among specific examples of the "heterocyclic group which is optionally substituted with 1 to 5 substituent(s) RII", are substituted with an oxygen atom.

[1-13-d-12] In Formula (AA), Formula (AA)-1, Formula (AA)-1-1, Formula (AA1), Formula (AA1)-1, Formula (AA1a)-1, Formula (AA1a)-1-1, Formula (AA1b), or Formula (AA1b)-1, preferable examples of $R^{13}$ include a group optionally selected from a halogen atom, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, a $C_{2-6}$ alkenyloxy group which is optionally substituted with 1 to 5 substituent(s) RI, a $C_{2-6}$ alkynyloxy group which is optionally substituted with 1 to 5 substituent (s) RI, and a —$NR^bR^c$ group (the substituent RI is the same as defined in Aspect [1]).

[1-13-d-12-1] In Formula (AA), Formula (AA)-1, Formula (AA)-1-1, Formula (AA1), Formula (AA1)-1, Formula (AA1a)-1, Formula (AA1a)-1-1, Formula (AA1b), or Formula (AA1b)-1, more preferable examples of $R^{13}$ include a group optionally selected from a halogen atom, a cyano group, a $C_{1-6}$ alkyl group (the $C_{1-6}$ alkyl group is optionally substituted with 1 to 5 halogen atom(s), 1 to 5 —OH, or 1 to 5 $C_{1-4}$ alkoxy group(s)), a $C_{2-6}$ alkenyl group (the $C_{2-6}$ alkenyl group is optionally substituted with 1 to 5 halogen atom(s), 1 to 5 —OH, or 1 to 5 $C_{1-4}$ alkoxy group(s)), a $C_{1-6}$ alkoxy group (the $C_{1-6}$ alkoxy group is optionally substituted with 1 to 5 halogen atom(s), 1 to 5 —OH, or 1 to 5 $C_{1-4}$ alkoxy group(s)), and a $C_{2-6}$ alkenyloxy group (the $C_{2-6}$ alkenyloxy group is optionally substituted with 1 to 5 halogen atom(s), 1 to 5 —OH, or 1 to 5 $C_{1-4}$ alkoxy group(s)).

[1-13-d-12-2] In Formula (AA), Formula (AA)-1, Formula (AA)-1-1, Formula (AA1), Formula (AA1)-1, Formula (AA1a)-1, Formula (AA1a)-1-1, Formula (AA1b), or Formula (AA1b)-1, specific examples of $R^{13}$ include the groups specifically exemplified as the cyano group, the "halogen atom", the "$C_{1-6}$ alkyl group which is optionally substituted with 1 to 5 substituent(s) RI", the "$C_{1-6}$ alkoxy group which is optionally substituted with 1 to 5 substituent(s) RI", and the like. More specific examples of $R^{13}$ include a fluorine atom, a chlorine atom, a bromine atom, cyano, methyl, ethyl, trifluoromethyl, methoxy, ethoxy, and trifluoromethoxy.

[1-13-d-13] In Formula (AA), Formula (AA)-1, Formula (AA)-1-1, Formula (AA1), Formula (AA1)-1, Formula (AA1a)-1, Formula (AA1a)-1-1, Formula (AA1b), or Formula (AA1b)-1, preferable examples of $R^{14}$ include a halogen atom and a $C_{1-4}$ alkyl group which is optionally substituted with 1 to 5 halogen atom(s). More specific examples of $R^{14}$ include a fluorine atom, a chlorine atom, a bromine atom, methyl, ethyl, propyl, isopropyl, butyl, isobutyl, sec-butyl, tert-butyl, and trifluoromethyl.

[1-13-d-14] In Formula (AA)-1, Formula (AA)-1-1, Formula (AA1)-1, Formula (AA1a)-1, Formula (AA1a)-1-1, or Formula (AA1b)-1, preferable aspects of the ring A', the ring A", $R^8$, and $R^9$ are the same as the preferable aspects described in Aspects [1-13-c-2], [1-13-c-7], [1-13-c-7-1] [1-13-c-7-2], or [1-13-c-8]. The ring A' moiety having $(R^8)_s$, and $(R^9)_q$ can be Formula (N) described in Aspect [1-13-c-10] and the preferable aspects of the ring A' moiety having $(R^8)_s$, and $(R^9)_q$ are the same as the preferable aspects described in Aspect [1-13-c-10].

[1-13-d-15] In Formula (AA)-1, Formula (AA)-1-1, Formula (AA1)-1, Formula (AA1a)-1, Formula (AA1a)-1-1, or Formula (AA1b)-1, s is preferably 0 or 1. q is preferably an integer of 0 to 3, more preferably an integer of 0 to 2, further preferably 1 or 2. Preferably, any one of q and s is 1 or more.

[1-13-d-15-1] In Formula (AA)-1, Formula (AA)-1-1, Formula (AA1)-1, Formula (AA1a)-1, Formula (AA1a)-1-1, or Formula (AA1b)-1, when s is 1, the binding position of $R^8$ in the ring A' is preferably the m-position or the p-position, more preferably the p-position, relative to the binding position of V.

[1-13-e] Preferable examples of the ring A in Formula (I) include the Partial Structural Formula (A)-IV:

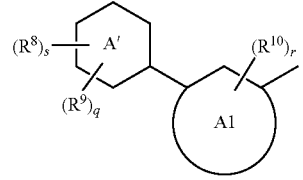

(A)-IV (where q, r, s, the ring A', $R^8$, $R^9$, and $R^{10}$ are the same as defined in Formula (A) described in Aspect [1-13-c]; and the ring A1 is a 5- or 6-membered heterocyclic group). In Formula (A)-IV, the binding positions of $R^{10s}$ are any positions at which they can be optionally bonded in the ring A1, and the binding positions of $R^8$s and $R^{9a}$ are any positions at which they can be optionally bonded in the ring A'.

[1-13-e-1] In Formula (A)-IV, the ring A1 is a 5- or 6-membered non-aromatic heterocyclic group or a 5- or 6-membered heteroaryl group, and specifically, the ring A1 is preferably pyrrolidine, piperidine, furan, thiophene, imidazole, oxazole, thiazole, pyrazole, isoxazole, 1,2,3-triazole, or 1,2,4-oxadiazole. More preferably, the ring A1 is pyrrolidine, piperidine, furan, thiophene, oxazole, or thiazole, further preferably pyrrolidine, piperidine, thiophene, or thiazole.

[1-13-e-2] The ring A in Formula (I), or Formula (A)-IV is preferably the Partial Structural Formula (A1)-IV:

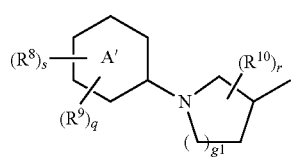
(A1)-IV (where q, r, s, the ring A', $R^8$, $R^9$, and $R^{10}$ are the same as defined in Formula (A) described in Aspect [1-13-c]; and g1 is 1 or 2). In Formula (A1)-IV, the binding positions of $R^{10}$s are any positions at which they can be optionally bonded in the pyrrolidine or piperidine ring, and the binding positions of $R^8$s and $R^9$s are any positions at which they can be optionally bonded in the ring A'.

[1-13-e-3] Preferable examples of the ring A in Formula (I), or Formula (A)-IV include the Partial Structural Formula (A2)-IV:

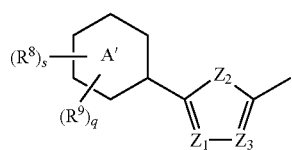
(A2)-IV (where q, s, the ring A', $R^8$, and $R^9$ are the same as defined in Formula (A) described in Aspect [1-13-c]; $Z_1$ is —$CR^{10e}$— or a nitrogen atom; $Z_2$ is a sulfur atom or an oxygen atom; $Z_3$ is —$CR^{10f}$- or a nitrogen atom; $R^{10e}$ and $R^{10f}$ are independently a hydrogen atom, a $C_{1-6}$ alkyl group, or a methoxy group (with the proviso that at least one of $Z_1$ and $Z_3$ is —$CR^{10e}$— or —$CR^{10f}$—)). In Formula (A2)-IV, the binding positions of $R^8$s and $R^9$s are any positions at which they can be optionally bonded in the ring A'. Here, in Formula (A2)-IV, the ring A' may be a substituted spiropiperidinylmethyl group in addition to the above description.

Specific examples of Formula (A2)-IV include Formula (A3)-IV described in Aspect [1-13-e-7] below and Formula (A4)-IV described in Aspect [1-13-e-8] below. Specific examples of Formula (A2)-IV of the present specification also include groups corresponding to Formula (A2)-IV of the present specification in WO 2005/086661 pamphlet, WO 2005/051890 pamphlet, WO 2004/022551 pamphlet, and WO 2004/011446 pamphlet (such as a 5-membered ring group and the like as examples of W in [0195] in p. 25 of WO 2005/086661 pamphlet), particularly the corresponding groups shown in Examples of these pamphlets.

[1-13-e-4] In Formula (A)-IV, Formula (A1)-IV, or Formula (A2)-IV, more specifically, the ring A' is preferably benzene, pyridine, or pyrimidine. More preferably, the ring A' is benzene or pyridine, further preferably benzene.

[1-13-e-5] In Formula (A)-IV, Formula (A1)-IV, or Formula (A2)-IV, more specifically, s is preferably 0 or 1, and when s is 1 and the ring A' is a 6-membered ring, the substitution position of $R^8$ is preferably p-position. q is more preferably an integer of 0 to 2, further preferably 1 or 2. Most preferably, s is 0 or 1 and q is 2.

[1-13-e-6] In Formula (A)-IV or Formula (A1)-IV, more specifically, r is preferably 0.

[1-13-e-7] The ring A in Formula (I), Formula (A)-IV, or Formula (A2)-IV is preferably the Partial Structural Formula (A3)-IV:

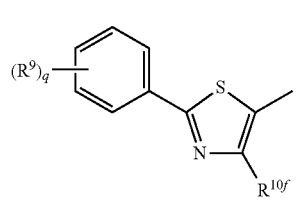
(A3)-IV (where q and $R^9$ are the same as defined in Formula (A) described in Aspect [1-13-c]; and $R^{10f}$ is the same as defined in Formula (A2)-IV described in Aspect [1-13-e-3]).

In Formula (A3)-IV, preferably, $R^9$ is a group optionally selected from a halogen atom, a cyano group, a $C_{1-6}$ alkyl group (the $C_{1-6}$ alkyl group is optionally substituted with 1 to 5 halogen atom(s)), and a $C_{1-6}$ alkoxy group (the $C_{1-6}$ alkoxy group is optionally substituted with 1 to 5 halogen atom(s)). q is preferably an integer of 0 to 2. $R^{10f}$ is preferably a hydrogen atom or a $C_{1-6}$ alkyl group, more preferably a hydrogen atom or a methyl group.

Specific examples of Formula (A3)-IV include 4-methyl-2-(4-trifluoromethylphenyl)thiazol-5-yl and 4-methyl-2-(4-butoxy-3-chlorophenyl)thiazol-5-yl. Specific examples of Formula (A3)-IV of the present specification also include groups of the same formula as Formula (A3)-IV of the present specification in WO 2008/030520 pamphlet, that is, the corresponding groups in groups of Formula VIIC in p. 8, particularly the corresponding groups shown in Examples.

[1-13-e-8] The ring A in Formula (I), Formula (A)-IV, or Formula (A2)-IV is preferably the Partial Structural Formula (A4)-IV:

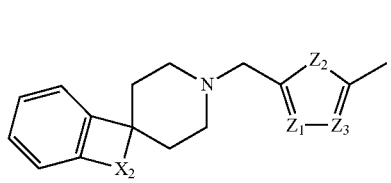
(A4)-IV (where $Z_1$, $Z_2$, and $Z_3$ are the same as defined in Formula (A2)-IV described in Aspect [1-13-e-3] (with the proviso that $R^{10e}$ and $R^{10f}$ are independently a hydrogen atom, a methyl group, or a methoxy group); $X_2$ is —$CH_2CH_2$—, —CH=CH—, or —N($R_{z1}$)$CH_2$—; and $R_{z1}$ is a hydrogen atom or a $C_{1-3}$ alkyl group).

In Formula (A4)-IV, preferably, $Z_1$ is —$CR^{10e}$—, $R^{10e}$ is a hydrogen atom or a methyl group, $Z_2$ is a sulfur atom, $Z_3$ is —$CR^{10f}$—, and $R^{10f}$ is a hydrogen atom. $X_2$ is —CH=CH— or —N($R_{z1}$) $CH_2$— and $R_{z1}$ is a methyl group.

Specific examples of Formula (A4)-IV include 5-(spiro[inden-1,4'-piperidin]-1'-ylmethyl)-2-thienyl, 4-methyl-5-(spiro[inden-1,4'-piperidin]-1'-ylmethyl)-2-thienyl, and 5-(1-methylspiro[indolin-3,4'-piperidin]-1'-ylmethyl)-2-thienyl. Specific examples of Formula (A4)-IV of the present specification also include groups of the same formula as Formula (A4)-IV of the present specification in WO 2011/066183 pamphlet, particularly the corresponding groups shown in Examples.

[1-13-e-9] In Formula (A)-IV, Formula (A1)-IV, or Formula (A2)-IV, more preferable examples of $R^8$ include a $C_{1-6}$ alkoxy group (the $C_{1-6}$ alkoxy group is substituted with 1 to 5 —OH, 1 to 5 methoxy, 1 to 5 ethoxy, 1 to 5 methysulfonyl, 1 to 5 sulfamoyl, 1 to 5 methysulfamoyl, 1 to 5 dimethysulfamoyl, 1 to 5 carbamoyl, 1 to 5 methylcarbamoyl, 1 to 5 dimethylcarbamoyl, 1 to 5 —NH$_2$, 1 to 5 acetylamino, 1 to 5 methysulfonylamino, 1 to 5 2-oxo-1-pyrrolidinyl, 1 to 5 5-oxo-2-pyrrolidinyl, or 1 to 5 3-methyloxetane-3-yl), a —CONR$^{d4}$R$^{e4}$ group (R$^{d4}$ is a hydrogen atom or a $C_{1-4}$ alkyl group; and R$^{e4}$ is a $C_{1-6}$ alkyl group (the $C_{1-6}$ alkyl group is substituted with 1 to 5 —OH, 1 to 5 methoxy, 1 to 5 ethoxy, 1 to 5 methysulfonyl, 1 to 5 sulfamoyl, 1 to 5 methylsulfamoyl, 1 to 5 dimethylsulfamoyl, 1 to 5 carbamoyl, 1 to 5 methylcarbamoyl, 1 to 5 dimethylcarbamoyl, 1 to 5 —NH$_2$, 1 to 5 acetylamino, 1 to 5 methylsulfonylamino, 1 to 5 2-oxo-1-pyrrolidinyl, 1 to 5 5-oxo-2-pyrrolidinyl, or 1 to 5 3-methyloxetane-3-yl), (1,1-dioxidetetrahydro-2H-thiopyran-4-yl)oxy, and (pyrrolidine-1-yl)carbonyl. The substitution number of —OH, methoxy, ethoxy, methylsulfonyl, sulfamoyl, methylsulfamoyl, dimethylsulfamoyl, carbamoyl, methylcarbamoyl, dimethylcarbamoyl, —NH$_2$, acetylamino, methylsulfonylamino, 2-oxo-1-pyrrolidinyl, 5-oxo-2-pyrrolidinyl, or 3-methyloxetane-3-yl is preferably 1 to 2.

More specific examples of R$^8$ include 2-hydroxyethoxy, 3-hydroxypropoxy, 3-hydroxybutoxy, 3-hydroxy-3-methylbutoxy, 2,3-dihydroxypropoxy, (2R)-2,3-dihydroxypropoxy, (2S)-2,3-dihydroxypropoxy, (3S)-3-hydroxybutoxy, (3R)-3-hydroxybutoxy, 3-hydroxy-2-hydroxymethylpropoxy, 3-hydroxy-2-hydroxymethyl-2-methylpropoxy, 2-aminoethoxy, 3-aminopropoxy, 2-(2-oxo-1-pyrrolidinyl)ethoxy, 3-(2-oxo-1-pyrrolidinyl)propoxy, (5-oxo-2-pyrrolidinyl)methoxy, 2-ethoxyethoxy, 2-methylsulfonylethoxy, 3-methylsulfonylpropoxy, (1,1-dioxidetetrahydro-2H-thiopyran-4-yl)oxy, (4-hydroxy-1,1-dioxidetetrahydro-2H-thiopyran-4-yl)methoxy, (3-methyloxetane-3-yl)methoxy, 2-acetylamino-ethoxy, 2-acetylamino-ethoxy, 3-acetylamino-propoxy, 2-methylsulfonylamino-ethoxy, 3-methylsulfonylamino-propoxy, 2-carbamoyl-ethoxy, 3-carbamoyl-propoxy, 2-methylcarbamoyl-ethoxy, 3-methylcarbamoyl-propoxy, 2-dimethylcarbamoyl-ethoxy, 3-dimethylcarbamoyl-propoxy, 2-sulfamoyl-ethoxy, 3-sulfamoyl-propoxy, 2-methylsulfamoyl-ethoxy, 3-methylsulfamoyl-propoxy, 2-dimethylsulfamoyl-ethoxy, 3-dimethylsulfamoyl-propoxy, N-(2-hydroxyethyl)carbamoyl, N-(2-methoxyethyl)carbamoyl, N-(2-hydroxyethyl)-N-methylcarbamoyl, N-(2-methoxyethyl)-N-methylcarbamoyl, N-(2-methylsulfonyl-ethyl)carbamoyl, N-(2-methylsulfonyl-ethyl)-N-methylcarbamoyl, and (pyrrolidine-1-yl)carbonyl.

[1-13-e-10] In Formula (A)-IV, Formula (A1)-IV, Formula (A2)-IV, or Formula (A3)-IV, preferable examples of R$^9$ and R$^{10}$ independently include a halogen atom, a cyano group, a $C_{1-4}$ alkyl group (the $C_{1-4}$ alkyl group is optionally substituted with 1 to 5 halogen atom(s) or 1 to 5 —OH), a $C_{1-4}$ alkoxy group which is optionally substituted with 1 to 5 halogen atom(s), a $C_{2-4}$ alkenyl group, a $C_{2-5}$ alkanoyl group, a —S(O)$_i$R$^a$ (i is 2; and R$^a$ is a $C_{1-4}$ alkyl group) group, a —CON-R$^d$R$^e$ (R$^d$ and R$^e$ are independently a hydrogen atom or a $C_{1-4}$ alkyl group) group, and a —NR$^{b1}$R$^{c1}$ group (R$^{b1}$ and R$^{c1}$ form, together with a nitrogen atom to which they are bonded, a 3- to 8-membered cyclic group; and in the cyclic group, one or two carbon atom(s) is(are) optionally substituted with an oxygen atom, a nitrogen atom, or a carbonyl group). More specific examples of R$^9$ and R$^{10}$ include a fluorine atom, a chlorine atom, a bromine atom, cyano, methyl, ethyl, propyl, isopropyl, butyl, isobutyl, sec-butyl, tert-butyl, trifluoromethyl, hydroxymethyl, 2-hydroxyethyl, methoxy, ethoxy, trifluoromethoxy, trifluoroethoxy, vinyl, acetyl, methylsulfonyl, carbamoyl, methylcarbamoyl, dimethylcarbamoyl, 1-piperidinyl, 4-morpholinyl, and 2-oxooxazolidin-3-yl. More preferable examples of R$^9$, R$^{9a}$, and R$^{9b}$ include a fluorine atom, methyl, and methoxy, and more preferable examples of R$^{10}$ include methyl.

[1-13-e-11] In Formula (A)-IV, Formula (A1)-IV, or Formula (A2)-IV, preferable aspects of the ring A' moiety having (R$^8$)$_s$, and (R$^9$)$_q$ are the same groups as the groups having an aryl group or a heteroaryl group among the preferable aspects of L described in Aspect [1-1-d]. Specific examples of the ring A' moiety having (R$^8$)$_s$ and (R$^9$)$_q$ include the same groups as specific examples of the "aryl group which is optionally substituted with 1 to 5 substituent(s) RII" or the groups having a heteroaryl group among specific examples of the "heterocyclic group which is optionally substituted with 1 to 5 substituent(s) RII" that are described in Aspect [1]. More specific examples thereof include the same groups as the groups having benzene, naphthalene, pyridine, pyrimidine, thiophene, quinoline, or dibenzofuran.

[1-13-f] The ring A in Formula (I) is preferably Partial Structural Formula (A)-V:

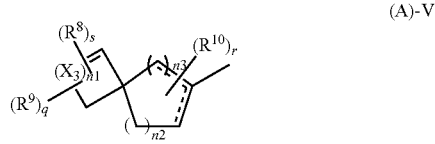

(A)-V (where q, r, s, R$^8$, R$^9$, and R$^{10}$ are the same as defined in Formula (A) described in Aspect [1-13-c]; n1 is an integer of 0 to 4; n2 is an integer of 1 to 4, n3 is an integer of 0 to 2 (with the proviso that n2+n3 is an integer of 2 to 4); X$_3$s are independently —CR$^{v1}$R$_{v2}$— or —NR$_{v3}$—; R$_{v1}$, R$_{v2}$, and R$_o$ are independently a hydrogen atom, R$^8$, or R$^9$; and the broken lines in the ring are a single bond or a double bond). In Formula (A)-V, the binding positions of R$^8$, R$^9$, and R$^{10}$ are any positions at which they can be optionally bonded in the ring. Here, in Formula (A)-V, R$^9$ and R$^{10}$ may be, in addition to the above description, —OH or an oxo group, and R$^8$ may be, in addition to the above description, —NHR$_{v4}$ (R$_{v4}$ is a $C_{1-6}$ alkyl group (the $C_{1-6}$ alkyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group) or a $C_{2-7}$ alkanoyl group (the $C_{2-7}$ alkanoyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group)). These substituents are the same as or different from each other and are optionally substituted with 1 to 5 group(s) in the spiro ring.

[1-13-f-1] In Formula (A)-V, X$_3$ is preferably —CR$_{v1}$R$_{v2}$— (R$_{v1}$ and R$_{v2}$ are the same as defined in Formula (A)-V).

[1-13-f-2] In Formula (A)-V, preferably, n1 is an integer of 0 to 4, n2 is an integer of 1 to 3, and n3 is 1 or 2. More preferably, n1 is 2 or 3, n2 is 1 or 2, and n3 is 1.

[1-13-f-3] In Formula (A)-V, preferably, q is an integer of 0 to 2 and r is an integer of 0 to 2. More preferably, q and r are 0.

[1-13-f-4] In Formula (A)-V, s is preferably 0 or 1. More preferably, s is 0.

[1-13-f-5] More preferable examples of Formula (A)-V include Formula (A1)-V:

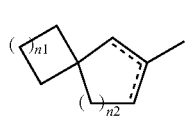

(A1)-V (where n1, n2, and the broken lines are the same as defined in Formula (A)-V). In Formula (A1)-V, most preferably, n1 is 2 or 3 and n2 is 1 or 2.

Specific examples of Formula (A)-V or Formula (A1)-V include spiro[4,5] dec-6-ene-7-yl, spiro[5,5]undec-2-yl, spiro[5,5]undec-1-ene-2-yl, and spiro[5,5]undec-2-ene-2-yl.

Specific examples of Formula (A)-V or Formula (A1)-V of the present specification also include groups of the same formula as Formula (A)-V or Formula (A1)-V of the present specification in WO 2009/054479 pamphlet, that is, the groups of the Spiro ring AB in the item 2 in p. 4 to 5, particularly the corresponding groups shown in Examples.

[1-13-f-6] In Formula (A)-V, preferable examples of $R^9$ and $R^{10}$ independently include a halogen atom, a $C_{1-4}$ alkyl group which is optionally substituted with 1 to 5 halogen atom(s), a $C_{1-4}$ alkoxy group which is optionally substituted with 1 to 5 halogen atom(s), an —OH group, and an oxo group. More specific examples of $R^9$ and $R^{10}$ include a fluorine atom, a chlorine atom, a bromine atom, methyl, ethyl, propyl, isopropyl, butyl, isobutyl, sec-butyl, tert-butyl, trifluoromethyl, methoxy, ethoxy, trifluoromethoxy, trifluoroethoxy, and —OH. More preferable examples of $R^9$ include a fluorine atom, methyl, methoxy, and —OH, and more preferable examples of $R^{10}$ include methyl and —OH.

Specific examples of Formula (A)-V of the present specification also include the corresponding groups of the spiro ring AB substituted with a substituent (an —OH group, a $C_{1-6}$ alkyl group, a $C_{1-6}$ alkoxy group, or an oxo group) in a formula of Formula [Ia.] of WO 2009/054479 pamphlet) as a group substituted with $R^9$ or $R^{10}$ in Formula (A)-V, particularly the corresponding groups shown in Examples.

[1-13-f-7] In Formula (A)-V, preferable examples of $R^8$s independently include a $C_{1-6}$ alkoxy group (the $C_{1-6}$ alkoxy group is substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group), a —CONR$^{d3}$R$^{e3}$ group (R$^{d3}$ is a hydrogen atom or a $C_{1-4}$ alkyl group; and R$^{e3}$ is a $C_{1-6}$ alkyl group (the $C_{1-6}$ alkyl group is substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group)), an aralkyloxy group, a non-aromatic heterocyclic oxy group (the heterocyclic oxy group is optionally substituted with 1 to 2 oxo group(s)), a non-aromatic heterocyclic carbonyl group (the heterocyclic carbonyl group is optionally substituted with 1 to 2 oxo group(s)), and —NHR$_{v4}$ (R$_{v4}$ is a $C_{1-6}$ alkyl group (the $C_{1-6}$ alkyl group is optionally substituted with 1 to 5 group(s) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group)) optionally selected from —OH, a $C_{1-6}$ alkoxy group, a non-aromatic heterocyclic group (the heterocyclic group is optionally substituted with 1 to 2 $C_{1-4}$ alkyl group(s) or 1 to 2 oxo group(s)), and a —S(O)$_i$R$^a$ (i is an integer of 0 to 2) group)). More specific examples of $R^8$ include a $C_{1-6}$ alkoxy group which is substituted with 1 to 2 —OH, 1 to 2 methoxy, 1 to 2 ethoxy, 1 to 2 2-oxo-1-pyrrolidinyl, 1 to 2 5-oxo-2-pyrrolidinyl, 1 to 2 3-methyloxetane-3-yl, or 1 to 2 methylsulfonyl; a —CONR$^{d4}$R$^{e4}$ group (R$^{d4}$ is a hydrogen atom or a $C_{1-4}$ alkyl group; and R$^{e4}$ is a $C_{1-6}$ alkyl group (the $C_{1-6}$ alkyl group is substituted with 1 to 5 —OH, 1 to 5 methoxy, 1 to 5 ethoxy, 1 to 5 2-oxo-1-pyrrolidinyl, 1 to 5 5-oxo-2-pyrrolidinyl, 1 to 5 3-methyloxetane-3-yl, or 1 to 5 methylsulfonyl)), an aralkyloxy group, (1,1-dioxidetetrahydro-2H-thiopyran-4-yl)oxy, (pyrrolidine-1-yl)carbonyl, and —NHR$_{v4}$ (R$_{v4}$ is a $C_{1-6}$ alkyl group (the $C_{1-6}$ alkyl group is optionally substituted with 1 to 2 —OH, 1 to 2 ethoxy, 1 to 2 2-oxo-1-pyrrolidinyl, 1 to 2 5-oxo-2-pyrrolidinyl, 1 to 2 3-methyloxetane-3-yl, or 1 to 2 methylsulfonyl) or a $C_{2-7}$ alkanoyl group (the $C_{2-7}$ alkanoyl group is optionally substituted with 1 to 2 —OH, 1 to 2 ethoxy, 1 to 2 2-oxo-1-pyrrolidinyl, 1 to 2 5-oxo-2-pyrrolidinyl, 1 to 2 3-methyloxetane-3-yl, or 1 to 2 methylsulfonyl)).

[1-13-f-8] The ring A in Formula (I) is preferably Partial Structural Formula (AA)-V:

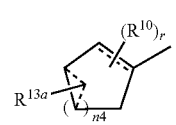

(AA)-V (where $R^{13a}$ is the same as defined in Formula (AA) described in Aspect [1-13-d]; r is the same as defined in Formula (A) described in Aspect [1-13-c]; $R^{10}$ is the same as defined in Formula (A)-V described in Aspect [1-13-f]; n4 is an integer of 1 to 3; and the broken lines are a single bond, a double bond, or the binding position of $R^{13a}$).

[1-13-f-9] The preferable aspects of $R^{13a}$ in Formula (AA)-V are the same as the preferable aspects described in Aspects [1-13-d-11] to [1-13-d-11-3]. More preferably, $R^{13a}$ is a group of Formula (A')-V—.

[1-13-f-10] Preferable examples of the ring A in Formula (I) or Formula (AA)-V include Formula (AA1)-V:

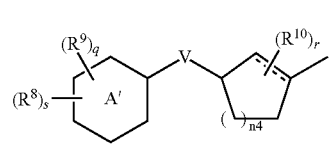

(AA1)-V (where q, r, s, the ring A', V, $R^8$, and $R^9$ are the same as defined in Formula (A) described in Aspect [1-13-c]; $R^{10}$ and the broken line are the same as defined in Formula (A)-V described in Aspect [1-13-f]; and n4 is the same as defined in Formula (AA)-V).

[1-13-f-11] In Formula (AA)-V or Formula (AA1)-V, n4 is preferably 1 or 2, more preferably 2.

[1-134-12] In Formula (AA)-V or Formula (AA1)-V, r is preferably an integer of 0 to 2. In Formula (AA1)-V, q is preferably an integer of 0 to 3, more preferably an integer of 0 to 2. s is preferably 0 or 1. More preferably, any one of q and s is 1 or more.

[1-13-f-13] In Formula (AA1)-V, the preferable aspects of the ring A', R⁸, and R⁹ are the same as the preferable aspects described in Aspects [1-13-c-2], [1-13-c-7] to [1-13-c-7-2], and [1-13-c-8]. The preferable aspects of the ring A' moiety having $(R^8)_s$ and $(R^9)_q$ are the same as the preferable aspects described in Aspect [1-13-c-10].

In Formula (AA)-V or Formula (AA1)-V, the preferable aspects of R¹⁰ are the same as the preferable aspects described in Aspect [1-13-f-6].

[1-13-g] The ring A in Formula (I) is preferably Partial Structural Formula (A)-VI:

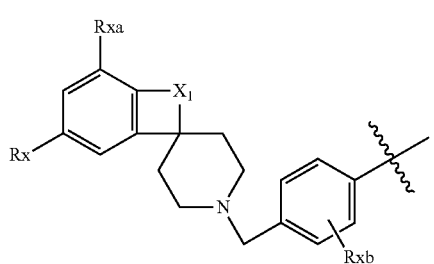

(A)-VI (where $R^x$, $R^{xa}$, and $X_1$ are the same as defined in Formula (SP) described as the "substituted spiropiperidinyl group" in Aspect [1]; and $R_{xb}$ is a group selected from a hydrogen atom, a fluorine atom, a chlorine atom, $C_{1-3}$ alkyl, trifluoromethyl, and methoxy).

[1-13-g-1] In Formula (A)-VI, preferably, at least any one of $R_x$ and $R_{xa}$ is a hydrogen atom. More preferably, $R_{xa}$ is a hydrogen atom and $R_x$ is a group selected from a hydrogen atom, a fluorine atom, methyl, trifluoromethyl, and methoxy, or $R_{xa}$ is a hydrogen atom or a chlorine atom and $R_x$ is a hydrogen atom, or both of $R_x$ and $R_{xa}$ are a hydrogen atom.

In Formula (A)-VI, $R_{xb}$ is preferably a group selected from a hydrogen atom, methyl, trifluoromethyl, and methoxy, more preferably a hydrogen atom.

In Formula (A)-VI, $X_1$ is preferably —CH($R_y$)CH₂—, —C($R_y$)=CH—, or —N($R_z$)CH₂, more preferably —C($R_y$)=CH— or —N($R_z$)CH₂.

In Formula (A)-VI, $R_y$ is preferably a hydrogen atom or methyl, more preferably a hydrogen atom.

In Formula (A)-VI, $R_z$ is preferably a hydrogen atom or $C_{1-3}$ alkyl, more preferably methyl.

Specifically, in Aspect [1-13-g], examples of Partial Structural Formula (SP)—CH₂—:

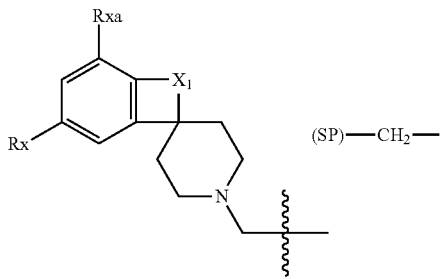

(SP)—CH₂— in Formula (A)-VI include a group selected from any of spiro[indan-1,4'-piperidin]-1'-ylmethyl, (1'H-spiro[inden-1,4'-piperidin]-1'-yl)methyl, 1,2-dihydro-1'H-spiro[indol-3,4'-piperidin]-1'-ylmethyl, (1-methyl-1,2-dihydro-1'H-spiro [indol-3,4'-piperidin]-1'-yl)methyl, {1-(1-methylethyl)-1,2-dihydro-1'H-spiro[indol-3,4'-piperidin]-1'-yl}methyl, (1-phenyl-1,2-dihydro-1'H-spiro[indol-3,4'-piperidin]-1'-yl) methyl, (2,3-dihydro-1'H-spiro[inden-1,4'-piperidin]-1'-yl-methyl, (7-chloro-1-methyl-1,2-dihydro-1'H-spiro[indol-3,4'-piperidin]-1'-yl)methyl, (5-fluoro-1-methyl-1,2-dihydro-1'H-spiro[indol-3,4'-piperidin]-1'-yl)methyl, (5-methoxy-1-methyl-1,2-dihydro-1'H-spiro[indol-3,4'-piperidin]-1'-yl) methyl, (1,5-dimethyl-1,2-dihydro-1'H-spiro[indol-3,4'-piperidin]-1'-yl)methyl, [1-methyl-5-(trifluoromethyl)-1,2-dihydro-1'H-spiro[indol-3,4'-piperidin]-1'-yl)methyl, and (3-oxo-2,3-dihydro-1'H-spiro[inden-1,4'-piperidin]-1'-yl) methyl.

[1-13-g-2] Preferable examples of the ring A in Formula (I) include Partial Structural Formula (AA)-VI:

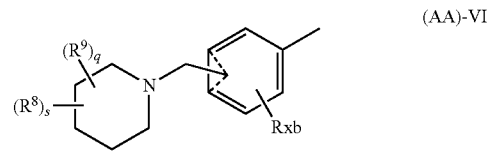

(AA)-VI (where q, s, R⁸, and R⁹ are the same as defined in Formula (A) described in Aspect [1-13-c]; $R_{xb}$ is the same as defined in Formula (A)-VI described in Aspect [1-13-g]; and the broken lines indicate the binding position of a piperidinylmethyl group).

The preferable aspects of q, s, R⁸, and R⁹ in Formula (AA)-VI are the same as the preferable aspects described in Aspects [1-13-c-3], [1-13-c-5], [1-13-c-7] to [1-13-c-7-2], or [1-13-c-8].

[1-13-h] The ring A in Formula (I) is preferably Partial Structural Formula (A)-VII:

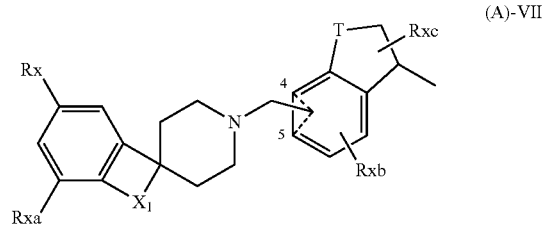

(A)-VII (where T is the same as defined in Formula (AA) described in Aspect [1-13-d]; $R_x$, $R_{xa}$, and $X_1$ are the same as defined in Formula (SP) described as the "substituted spiropiperidinyl group" in Aspect [1]; $R_{xb}$ is the same as defined in Formula (A)-VI described in Aspect [1-13-g]; $R_{xc}$ is a group selected from a hydrogen atom, a fluorine atom, a chlorine atom, $C_{1-3}$ alkyl, trifluoromethyl, and methoxy; and the broken lines and the Figures 4 and 5 indicate the binding position of the substituted spiropiperidinylmethyl group).

[1-13-h-1] Preferable examples of the ring A in Formula (I) include Partial Structural Formula (AA)-VII:

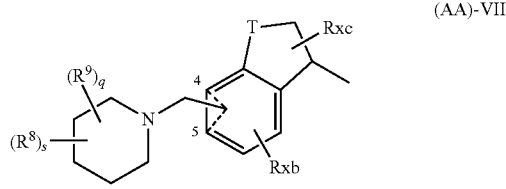

(AA)-VII (where T is the same as defined in Formula (AA) described in Aspect [1-13-d]; q, s, R⁸, and R⁹ are the same as defined in Formula (A) described in Aspect [1-13-c]; $R_{xb}$ is the same as defined in Formula (A)-VI described in Aspect [1-13-g]; $R_{xc}$ is the same as defined in Formula (A)-VII described in Aspect [1-13-h]; and the broken lines indicate the binding position of the piperidinylmethyl group).

The preferable aspects of q, s, $R^8$, and $R^9$ in Formula (AA)-VII are the same as the preferable aspects described in Aspects [1-13-c-3], [1-13-c-5], [1-13-c-7] to [1-13-c-7-2], or [1-13-c-8].

[1-13-i] Preferable examples of the ring A in Formula (I) include phthalazinyl which is optionally substituted with 1 to 5 L(s).

Specific examples of phthalazinyl which is optionally substituted with 1 to 5 L(s) include 4-chloro-1-phthalazinyl, 4-trifluoromethyl-1-phthalazinyl, 4-cyano-1-phthalazinyl, and 4-cyclopropylmethoxy-1-phthalazinyl.

Specific examples of the ring A of the present specification also include the groups of G in Formula (I) and the like in WO 2010/091176 pamphlet, particularly the corresponding groups shown in Examples.

[1-13-j] Preferable examples of the ring A in Formula (I) include Partial Structural Formula (A)-VIII:

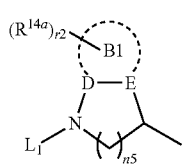

(A)-VIII (where r2 is an integer of 0 to 4; n5 is 1 or 2;
D is —CO—$CR^{14b}R^{14c}$— or —$(CR^{14b}R^{14c})_m$ (m is 1 or 2)-; E is —$CR^{14d}R^{14e}$—;
$L_1$ is a group optionally selected from a $C_{1-10}$ alkyl group (the $C_{1-10}$ alkyl group is optionally substituted with 1 to 5 halogen atom(s)), an aryl group (the aryl group is optionally substituted with 1 to 5 halogen atom(s), 1 to 5 $C_{1-6}$ alkyl group(s), or 1 to 5 halogenated $C_{1-6}$ alkyl group(s)), a heterocyclic group (the heterocyclic group is optionally substituted with 1 to 5 halogen atom(s), 1 to 5 $C_{1-6}$ alkyl group(s), or 1 to 5 halogenated $C_{1-6}$ alkyl group(s)), an aralkyl group (the aralkyl group is optionally substituted with 1 to 5 halogen atom(s), 1 to 5 $C_{1-6}$ alkyl group(s), or 1 to 5 halogenated $C_{1-6}$ alkyl group(s)), a heteroarylalkyl group (the heteroarylalkyl group is optionally substituted with 1 to 5 halogen atom(s), 1 to 5 $C_{1-6}$ alkyl group(s), or 1 to 5 halogenated $C_{1-6}$ alkyl group(s)), a $C_{2-7}$ alkanoyl group, and a —$S(O)_iR^a$ (i is an integer of 0 to 2; and $R^a$ is the same as defined in Formula (I)) group;
$R^{14a}$s are independently a halogen atom, a $C_{1-6}$ alkyl group (the $C_{1-6}$ alkyl group is optionally substituted with 1 to 5 halogen atom(s)), or a $C_{1-6}$ alkoxy group (the $C_{1-6}$ alkoxy group is optionally substituted with 1 to 5 halogen atom(s)); and $R^{14b}$, $R^{14c}$, $R^{14d}$, and $R^{14e}$, are independently a hydrogen atom, a halogen atom, or a $C_{1-6}$ alkyl group (the $C_{1-6}$ alkyl group is optionally substituted with 1 to 5 halogen atom(s)); and $R^{14c}$ and $R^{14e}$ optionally form, together with a carbon atom to which they are bonded, a 5- to 6-membered aryl group or heteroaryl group (ring B1)).

In Formula (A)-VIII, $L_1$ is preferably a group optionally selected from a $C_{1-4}$ alkyl group (the $C_{1-4}$ alkyl group is optionally substituted with 1 to 5 halogen atom(s)), a heteroaryl group (the heteroaryl group is optionally substituted with 1 to 5 halogen atom(s), 1 to 5 $C_{1-4}$ alkyl group(s), or 1 to 5 halogenated $C_{1-4}$ alkyl group(s)), and a —$S(O)_iR^a$ (i is an integer of 0 to 2; and $R^a$ is the same as defined in Formula (I)) group.

Specific examples of Formula (A)-VIII include 1,2,3,4-tetrahydro-1-oxo-2-(2,2,2-trifluoroethyl)-4-isoquinolyl, 2-cycloprop-ylmethyl-1,2,3,4-tetrahydro-1-oxo-4-isoquinolyl, 1,2,3,4-tetrahydro-2-(2-methylpropyl)-1-oxo-4-isoquinolyl, 1-(5-fluoro-2-pyridinyl)-3-piperidinyl, 1-(5-trifluoromethyl-2-pyridinyl)-3-piperidinyl, 1,2,3,4-tetrahydro-1-methylsulfonyl-4-quinolyl, 8-fluoro-1,2,3,4-tetrahydro-1-methylsulfonyl-4-quinolyl, 1,2,3,4-tetrahydro-1-(2,2,2-trifluoroethyl)-4-quinolyl, and 8-fluoro-1,2,3,4-tetrahydro-1-(2,2,2-trifluoroethyl)-4-quinolyl.

Specific examples of the ring A and Formula (A)-VIII of the present specification also include the cyclic group containing D and E in Formula (I) and the like in WO 2010/085525 pamphlet, particularly the corresponding groups shown in Examples.

[1-13-k] Preferable examples of the ring A in Formula (I) include a 2-phenylamino-2-oxoacetyl group which is optionally substituted with 1 to 5 L(s) and more preferable examples thereof include Partial Structural Formula (A)-IX:

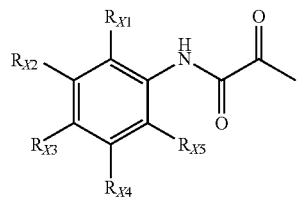

(A)-IX (where $R_{x3}$ is a group optionally selected from a hydrogen atom, a halogen atom, a $C_{1-8}$ alkyl group (the $C_{1-8}$ alkyl group is optionally substituted with 1 to 5 halogen atom(s)), a trifluoromethoxy group, a phenyl group, and a —$COOR^f$ group;
$R_{x1}$ and $R_{x5}$ are independently a group optionally selected from a hydrogen atom, a halogen atom, a $C_{1-6}$ alkyl group (the $C_{1-6}$ alkyl group is optionally substituted with 1 to 5 halogen atom(s)), a phenyl group, and a —$COOR^f$ group;
$R_{x2}$ and $R_{x4}$ are independently a group optionally selected from a hydrogen atom, a halogen atom, a $C_{1-6}$ alkyl group (the $C_{1-6}$ alkyl group is optionally substituted with 1 to 5 halogen atom(s)), and a —$COOR^f$ group; and
$R^f$ is a hydrogen atom or a $C_{1-6}$ alkyl group).

In Formula (A)-IX, $R_{x3}$ is preferably a hydrogen atom, a halogen atom, a $C_{1-6}$ alkyl group, a trifluoromethyl group, a methoxycarbonyl group, or a phenyl group. $R_{x1}$ and $R_{x5}$ are preferably independently a hydrogen atom, a halogen atom, a methyl group, a trifluoromethyl group, a methoxycarbonyl group, or a phenyl group. $R_{x2}$ and $R_{x4}$ are preferably independently a hydrogen atom, a halogen atom, or a trifluoromethyl group.

Specific examples of Formula (A)-IX include 2-((2-bromo-4-isopropylphenyl)amino)-2-oxoacetyl, 2((4-isopropyl-2-(trifluoromethyl)phenyl)amino)-2-oxoacetyl, 2-((2,4-bis(trifluoromethyl)phenyl)amino)-2-oxoacetyl, and 2-((4-bromo-3-chlorophenyl)amino)-2-oxoacetyl.

Specific examples of the ring A and Formula (A)-IX of the present specification also include the groups of the same formula as Formula (A)-IX of the present specification in Formula (I) in WO 2009/039943 pamphlet, particularly the corresponding groups shown in Examples.

[1-13-l] In the preferable Aspects [1-13-e-8], [1-13-g], and [1-13-h] of the ring A in Formula (I), an aspect in which each spiropiperidine ring (SP) is replaced with the above-described another spiropiperidine ring (SP') is also a preferable aspect.

Accordingly, it can be understood that examples of the preferable aspect of the ring A in Formula (I) of the present invention include, in addition to Aspects [1-13-e-8], [1-13-g], and [1-13-h], [1-13-e-8a], [1-13-ga], and [1-13-ha] below.

[1-13-e-8a] The ring A in Formula (I) is preferably Partial Structural Formula (A5)-IVa:

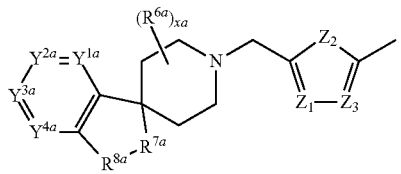

(where $Z_1$, $Z_2$, and $Z_3$ are the same as defined in Formula (A2)-IV described in Aspect [1-13-e-3]; and $R^{6a}$, $R^{7a}$, $R^{8a}$, xa, and $Y^{1a}$ to $Y^{4a}$ are the same as defined in the above Formula (SP')).

In Formula (A5)-IVa, preferably, $Z_1$ is —$CR^{10e}$—, $R^{10e}$ is a hydrogen atom or a methyl group, $Z_2$ is a sulfur atom, $Z_3$ is —$CR^{10f}$—, and $R^{10f}$ is a hydrogen atom. $X_2$ is —CH=CH— or —N($R_{z1}$)CH$_2$—, and $R_{z1}$ is a methyl group.

Specific examples of Formula (A5)-IVa include 5-(spiro [isobenzofuran-1(3H),4'-piperidin]-1'-ylmethyl)-2-thienyl, 5-(spiro[benzofuran-3(2H),4'-piperidin]-1'-ylmethyl)-2-thienyl, 5-(spiro[6-azaisobenzofuran-1(3H),4'-piperidin]-1'-ylmethyl)-2-thienyl, 5-(3-oxospiro[4-azaisobenzofuran-1(3H),4'-piperidin]-1'-ylmethyl)-2-thienyl, 5-(3-oxospiro[6-azaisobenzofuran-1(3H),4'-piperidin]-1'-ylmethyl)-2-thienyl, 5-(spiro[5-fluoroisobenzofuran-1(3H),4'-piperidin]-1'-ylmethyl)-2-thienyl, 5-(spiro[6-fluoroisobenzofuran-1(3H),4'-piperidin]-1'-ylmethyl)-2-thienyl, 5-(spiro[5-fluoro-6-azaisobenzofuran-1(3H),4'-piperidin]-1'-ylmethyl)-2-thienyl, 5-(spiro[6-fluoro-5-azaisobenzofuran-1(3H),4'-piperidin]-1'-ylmethyl)-2-thienyl, and 5-(7-fluoro-1H-spiro[fluoro[3,4-c]pyridin-3,4'-piperidin]-1'-ylmethyl)-2-thienyl.

[1-13-ga] The ring A in Formula (I) is preferably Formula (A)-VIa:

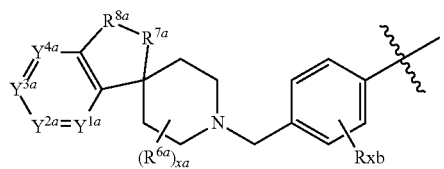

(where $R_{xb}$ is a group selected from a hydrogen atom, a fluorine atom, a chlorine atom, $C_{1-3}$ alkyl, trifluoromethyl, and methoxy, more preferably, a hydrogen atom; and $R^{6a}$, $R^{7a}$, $R^{8a}$, xa, and $Y^{1a}$ to $Y^{4a}$ are the same as defined in Formula (SP')).

Specific examples of the ring A include rings in which Partial Structural Formula (SP')—CH$_2$—:

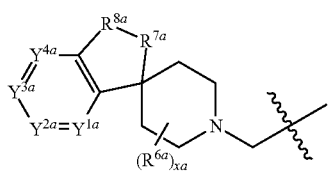

in Formula (A)-VIa is (spiro[isobenzofuran-1(3H), 4'-piperidin]-1-yl)methyl, (spiro[benzofuran-3(2H), 4'-piperidin]-1-yl)methyl, (3-oxospiro[6-azaisobenzofuran-1(3H), 4'-piperidin]-1-yl)methyl, (spiro[5-fluoroisobenzofuran-1(3H), 4'-piperidin]-1-yl)methyl, (spiro[6-fluoroisobenzofuran-1(3H), 4'-piperidin]-1-yl)methyl, (spiro[5-fluoro-6-azaisobenzofuran-1(3H), 4'-piperidin]-1-yl)methyl, (spiro[6-azaisobenzofuran-1(3H), 4'-piperidin]-1-yl)methyl, (spiro[5-fluoroisobenzofuran-1(3H), 4'-piperidin]-1-yl)methyl, (spiro[6-fluoroisobenzofuran-1(3H), 4'-piperidin]-1-yl)methyl, (spiro[5-fluoro-6-azaisobenzofuran-1(3H), 4'-piperidin]-1-yl)methyl, or (7-fluoro-1H-spiro[fluoro[3, 4-c]pyridin-3,4'-piperidin]-1-yl)methyl.

[1-13-ha] The ring A in Formula (I) is preferably Partial Structural Formula (A)-VIIa:

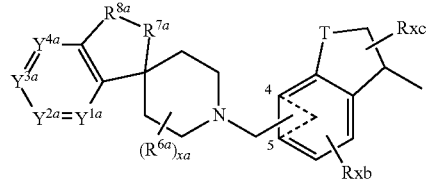

(where T is the same as defined in Formula (AA) described in Aspect [1-13-d]; the definitions of $R^{6a}$, $R^{7a}$, $R^{8a}$, xa, and $Y^{1a}$ to $Y^{4a}$ correspond to the definitions of $R^6$, $R^7$, $R^8$, x, and $Y^1$ to $Y^4$ respectively in Formula [II] in WO 2002/088989 pamphlet; $R_{xb}$ is a group selected from a hydrogen atom, a fluorine atom, a chlorine atom, $C_{1-3}$ alkyl, trifluoromethyl, and methoxy, preferably a hydrogen atom; $R_{xc}$ is a group selected from a hydrogen atom, a fluorine atom, a chlorine atom, $C_{1-3}$ alkyl, trifluoromethyl, and methoxy, preferably a hydrogen atom; and the broken lines and the Figures 4 and 5 indicate the binding position of the substituted spiropiperidinylmethyl group).

Specific examples of the ring A include rings in which Partial Structural Formula (SP')—CH$_2$—:

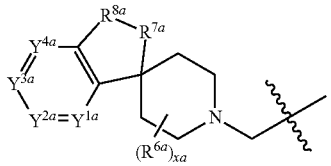

in Formula (A)-VIIa is (spiro[isobenzofuran-1(3H), 4'-piperidin]-1-yl)methyl, (spiro[benzofuran-3(2H), 4'-piperidin]-1-yl)methyl, (3-oxospiro[6-azaisobenzofuran-1(3H), 4'-piperidin]-1-yl)methyl, (spiro[5-fluoroisobenzofuran-1(3H), 4'-piperidin]-1-yl)methyl, (spiro[6-fluoroisobenzofuran-1(3H), 4'-piperidin]-1-yl)methyl, (spiro[5-fluoro-6-azaisobenzofuran-1(3H), 4'-piperidin]-1-yl)methyl, (spiro[6-azaisobenzofuran-1(3H), 4'-piperidin]-1-yl)methyl, (spiro[5-fluoroisobenzofuran-1(3H), 4'-piperidin]-1-yl)methyl, (spiro[6-fluoroisobenzofuran-1(3H), 4'-piperidin]-1-yl)methyl, (spiro[5-fluoro-6-azaisobenzofuran-1(3H), 4'-piperidin]-1-yl)methyl, or (7-fluoro-1H-spiro[fluoro[3, 4-c]pyridin-3,4'-piperidin]-1-yl)methyl.

[1-14] The group having the ring B and the cyclic amide structure of Formula (I) according to Aspect [1] is Partial Structural Formula (B):

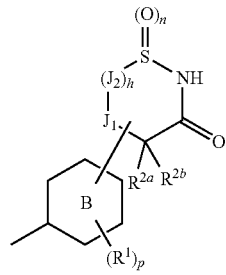
(B)

(where n, p, h, the ring B, $J_1$, $J_2$, $R^1$, $R^{2a}$, and $R^{2b}$ are the same as defined in Formula (I) described in Aspect [1]).

[1-14-a] In Formula (B), when the ring B is a monocyclic ring, the ring B is preferably bonded to $J_1$.

[1-14-a-1] In Formula (B), when the ring B is a benzene ring, a pyridine ring, or a pyrimidine ring, Formula (B) is preferably Formula (B)-1:

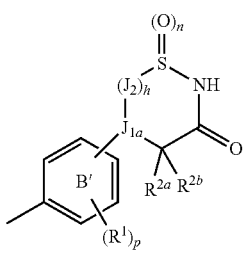
(B)-1

(where n, p, h, $J_2$, $R^1$, $R^{2a}$, and $R^{2b}$ are the same as defined in Formula (I) described in Aspect [1]; the ring B' is a benzene ring, a pyridine ring, or a pyrimidine ring; and $J_{1a}$ is $CR^{11a}$ or a nitrogen atom).

[1-14-a-2] More preferable examples of Formula (B) include Formula (B 1) and Formula (B2):

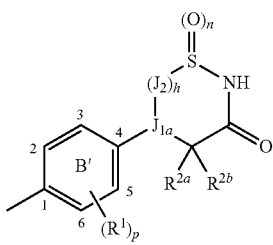
(B1)

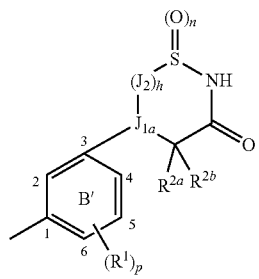
(B2)

(where n, p, h, $J_2$, $R^1$, $R^{2a}$, and $R^{2b}$ are the same as defined in Formula (I); and the ring B' and $J_{1a}$ are the same as defined in Formula (B)-1). When the binding position with the linker moiety containing X is determined as 1-position, in Formula (B1), $R^1$ can be bonded at 2-position, 3-position, 5-position, and 6-position, and in Formula (B2), $R^1$ can be bonded at 2-position, 4-position, 5-position, and 6-position.

[1-14-a-3] Formula (B) or Formula (B)-1 is preferably Formula (B1).

[1-14-a-4] More preferable examples of Formula (B) or Formula (B)-1 include Formula (B1a) and Formula (B 1b):

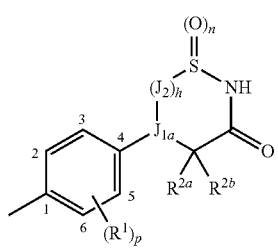
(B1a)

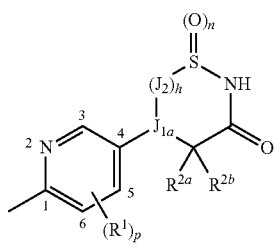
(B1b)

(where n, p, h, $J_2$, $R^1$, $R^{2a}$, and $R^{2b}$ are the same as defined in Formula (I); and $J_{1a}$ is the same as defined in Formula (B)-1).

[1-14-a-5] Further preferable examples of Formula (B) or Formula (B)-1 include Formula (B1a).

[1-14-b] When in Formula (B), the ring B is Formula (BB1) or Formula (BB2), Formula (B) is Formula (BB1)-1 or Formula (BB2)-1:

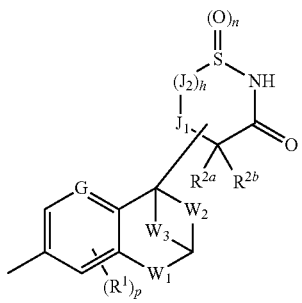
(BB1)-1

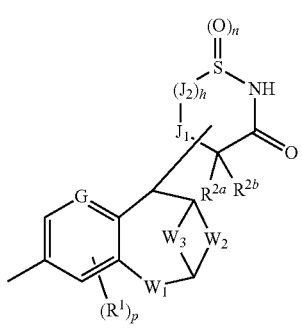
(BB2)-1

(where n, p, h, $J_1$, $J_2$, $R^1$, $R^{2a}$, and $R^{2b}$ are the same as defined in Formula (I) described in Aspect [1]; and G, $W_1$, $W_2$, and $W_3$ are the same as in Formula (BB1) and Formula (BB2) described in Aspect [1-10]). Specifically, Formula (B) is preferably Formula (BB1)-1a, Formula (BB1)-1b, Formula (BB2)-1a, or Formula (BB2)-1b:

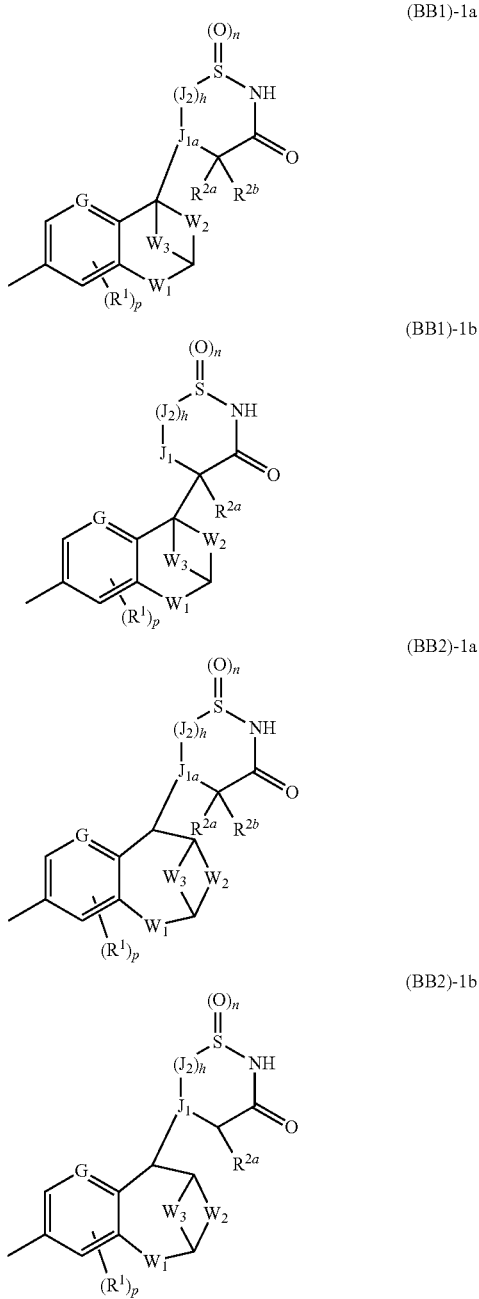

(where n, p, h, $J_1$, $J_2$, $R^1$, $R^{2a}$, and $R^{2b}$ are the same as defined in Formula (I) described in Aspect [1]; $J_{1a}$ is the same as defined in Formula (B)-1; and G, $W_1$, $W_2$, and $W_3$ are the same as in Formula (BB1) and Formula (BB2) described in Aspect [1-10]). When $J_2$ is —$CR^{12a}R^{12b}$—, a structure in which Formula (BB1) or Formula (BB2) is bonded to $J_2$ adjacent to S in the cyclic amide structure, is also preferred.

[1-14-c] When the ring A is Formula (A) described in Aspect [1-13-c] and the ring A'-V— is bonded at the m-position relative to the binding position with the linker moiety containing X, specifically when the ring A is Formula (A1a), Formula (A1b), Formula (A1c), or Formula (A1)-1-1 described in Aspect [1-13-c-3-1] or Aspect [1-13-c-11], in Formula (B)-1, an isothiazolyl group is preferably bonded at the p-position relative to the binding position with the linker moiety containing X. In addition, when the ring A is Formula (AA1) described in Aspect [1-13-d-4] and $R^{13a}$ is bonded at 4-position, or the ring A is Formula (AA1b) described in Aspect [1-13-d-7] and $R^{13a}$ is bonded at 7-position, specifically also when the ring A is Formula (AA1)-1, Formula (AA1a)-1, Formula (AA1a)-1-1, or Formula (AA1b)-1 described in Aspects [1-13-d-5] to [1-13-d-7-1], in Formula (B)-1, an isothiazolyl group is preferably bonded at the p-position relative to the binding position with the linker moiety containing X. Further, also when the ring A is Formula (A)-IV, Formula (A1)-IV, Formula (A2)-IV, Formula (A3)-IV, or Formula (A4)-IV described in Aspects [1-13-e] to [1-13-e-8], Formula (A)-V, Formula (A1)-V, Formula (AA)-V, or Formula (AA1)-V described in Aspects [1-13-f] to [1-13-f-10], or Formula (A)-VI or Formula (AA)-VI described in Aspects [1-13-g] to [1-13-g-2], in Formula (B)-1, an isothiazolyl group is preferably bonded at the p-position relative to the binding position with the linker moiety containing X.

[1-14-c-1] When the ring A is Formula (A) described in Aspect [1-13-c] and the ring A'-V— is bonded at the p-position relative to the binding position with the linker moiety containing X, specifically when the ring A is Formula (A1)-1-2 described in Aspect [1-13-c-12], in Formula (B)-1, an isothiazolyl group is preferably bonded at the m-position relative to the binding position with the linker moiety containing X.

[1-14-d] In Formula (B), Formula (B)-1, Formula (B1), Formula (B2), Formula (B1a), Formula (Bib), Formula (BB1)-1, Formula (BB2)-1, Formula (BB1)-1a, Formula (BB1)-1b, Formula (BB2)-1a, or Formula (BB2)-1b, $R^1$ is preferably a halogen atom, a $C_{1-4}$ alkyl group which is optionally substituted with 1 to 5 halogen atom(s), a $C_{1-4}$ alkoxy group which is optionally substituted with 1 to 5 halogen atom(s), or a cyano group, and more specifically, $R^1$ is preferably a fluorine atom, a chlorine atom, a bromine atom, methyl, ethyl, propyl, isopropyl, butyl, isobutyl, sec-butyl, tert-butyl, trifluoromethyl, methoxy, ethoxy, propoxy, isopropoxy, butoxy, isobutoxy, sec-butoxy, tert-butoxy, trifluoromethoxy, or cyano. p is preferably 0 or 1, more preferably 0.

In Formula (B), Formula (B)-1, Formula (B 1), Formula (B2), Formula (B1a), Formula (Bib), Formula (BB1)-1, Formula (BB2)-1, Formula (BB1)-1a, Formula (BB1)-1b, Formula (BB2)-1a, or Formula (BB2)-1b, $R^{2a}$ and $R^{2b}$ are preferably a hydrogen atom, a halogen atom, or a $C_{1-4}$ alkyl group. More specifically, $R^{2a}$ and $R^{2b}$ are preferably a hydrogen atom, a fluorine atom, a chlorine atom, a bromine atom, or methyl, and more preferably, any one of $R^{2a}$ and $R^{2b}$ is a hydrogen atom. Further preferably, both of $R^{2a}$ and $R^{2b}$ are a hydrogen atom.

In Formula (B), Formula (B)-1, Formula (B1), Formula (B2), Formula (B1a), Formula (B1b), Formula (BB1)-1, Formula (BB2)-1, Formula (BB1)-1a, Formula (BB1)-1b, Formula (BB2)-1a, or Formula (BB2)-1b, h is preferably 0 or 1 and n is preferably 1 or 2. When $J_{1a}$ is $CR^{11a}$ and h is 0, n is more preferably 1. When $J_{1a}$ is a nitrogen atom and h is 0, n is more preferably 2. When h is an integer of 1 to 3, n is more preferably 2.

[1-14-e] The cyclic amide structure bonded to the ring B in Formula (I), Formula (B), Formula (BB1)-1, or Formula (BB2)-1 is Partial Structural Formula (B-Het):

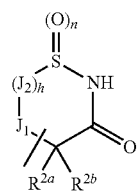
(B-Het)

(where n, h, $J_1$, $J_2$, $R^{2a}$, and $R^{2b}$ are the same as defined in Formula (I) described in Aspect [1]). In Formula (B-Het), the ring B can be bonded at any position in the ring, specifically to a carbon atom to which $R^{2a}$ and $R^{2b}$ are bonded, $J_1$, or $J_2$.

In Formula (I) or Formula (B), Formula (B-Het) is preferably Formula (B-Het)-1 or (B-Het)-2:

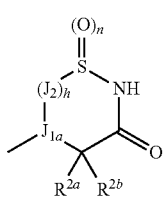
(B-Het)-1

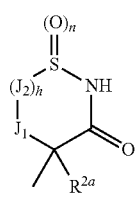
(B-Het)-2

(where n, h, $J_1$, $J_2$, $R^{2a}$, and $R^{2b}$ are the same as defined in Formula (I) described in Aspect [1]; and $J_{1a}$ is the same as defined in Formula (B)-1).

[1-14-e-1] More preferable examples of Formula (B-Het) or Formula (B-Het)-1 include Formula (B-Het)-1a, Formula (B-Het)-1b, Formula (B-Het)-1c, Formula (B-Het)-1d, Formula (B-Het)-1e, and Formula (B-Het)-1f:

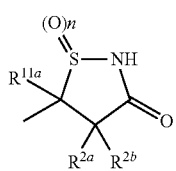
(B-Het)-1a

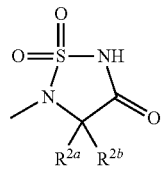
(B-Het)-1b

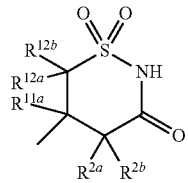
(B-Het)-1c

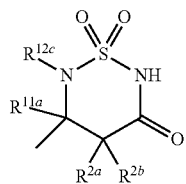
(B-Het)-1d

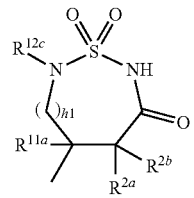
(B-Het)-1e

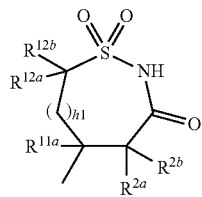
(B-Het)-1f where n, $R^{2a}$, $R^{2b}$, $R^{11a}$, $R^{12a}$, $R^{12b}$, and $R^{12c}$ are the same as defined in Formula (I) described in Aspect [1]; and h1 is 1 or 2).

More preferable examples of Formula (B-Het) or Formula (B-Het)-2 include Formula (B-Het)-2a, Formula (B-Het)-2b, Formula (B-Het)-2c, Formula (B-Het)-2d, Formula (B-Het)-2e, Formula (B-Het)-2f, Formula (B-Het)-3c, and Formula (B-Het)-3f:

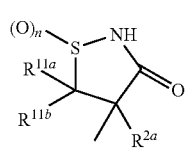
(B-Het)-2a

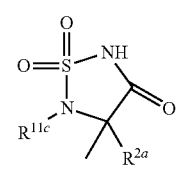
(B-Het)-2b

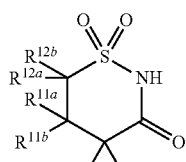
(B-Het)-2c

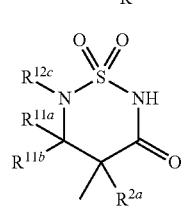
(B-Het)-2d

-continued

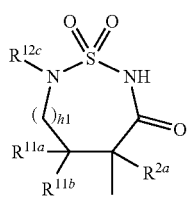
(B-Het)-2e

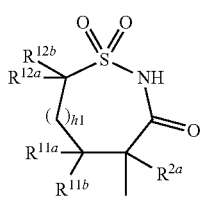
(B-Het)-2f

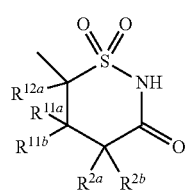
(B-Het)-3c

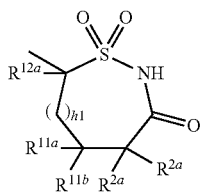
(B-Het)-3f (wherein, $R^{2a}$, $R^{2b}$, $R^{11a}$, $R^{11b}$, $R^{12a}$, $R^{12b}$, $R^{11c}$, and $R^{12c}$ are the same as defined in Formula (I) described in Aspect [1]; and h1 is 1 or 2).

In Formula (I) according to Aspect [1], a compound in which the cyclic amide structure bonded to the ring B (that is, Formula (B-Het)) is Formula (B-Het)-1a is Formula (I)-1a. Similarly, the compound having Formula (B-Het)-1b is Formula (I)-1b; the compound having Formula (B-Het)-1c is Formula (I)-1c; the compound having Formula (B-Het)-1d is Formula (I)-1d; the compound having Formula (B-Het)-1e is Formula (I)-1e; the compound having Formula (B-Het)-1f is Formula (I)-1f; the compound having Formula (B-Het)-2a is Formula (I)-2a; the compound having Formula (B-Het)-2b is Formula (I)-2b; the compound having Formula (B-Het)-2c is Formula (I)-2c; the compound having Formula (B-Het)-2d is Formula (I)-2d; the compound having Formula (B-Het)-2e is Formula (I)-2e; the compound having Formula (B-Het)-2f is Formula (I)-2f; the compound having Formula (B-Het)-3c is Formula (I)-3c; and the compound having Formula (B-Het)-3f is Formula (I)-3f.

In Formula (B-Het)-1a, n is preferably 1 or 2, and specifically, Formula (B-Het)-1a is Formula (B-Het)-1a1 or Formula (B-Het)-1a2:

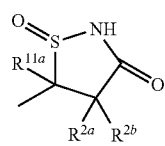
(B-Het)-1a1

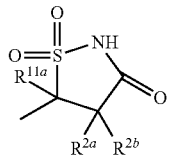
(B-Het)-1a2

(where $R^{2a}$, $R^{2b}$, and $R^{11a}$ are the same as defined in Formula (I)).

[1-14-e-2] In each formula used for a compound in each aspect of Aspect [1], the Formula (B-Het) moiety can be accordingly selected from, for example, Formulae (het1) to (het9):

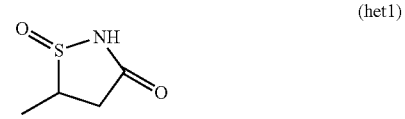
(het1)

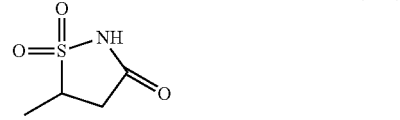
(het2)

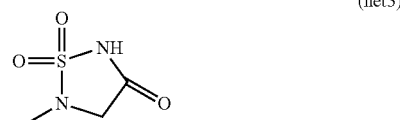
(het3)

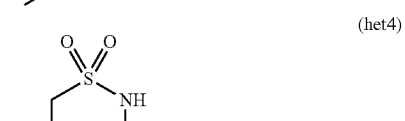
(het4)

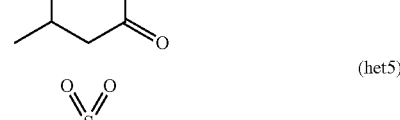
(het5)

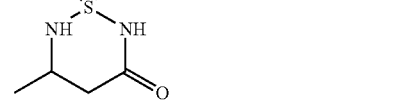
(het6)

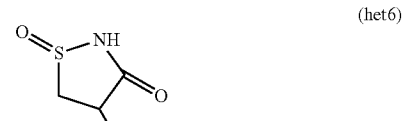
(het7)

(het8)

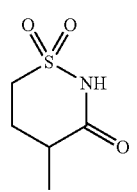

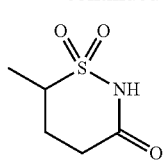
(het9)

The Formula (B-Het) moiety is particularly preferably Formulae (het1) to (het5) above.

[1-15] In a combination of j, k, X, $R^3$, $R^4$, $R^5$, and $R^6$, in Formula (I), the linker moiety containing X bonded to the ring A and the ring B is Partial Structural Formula (C):

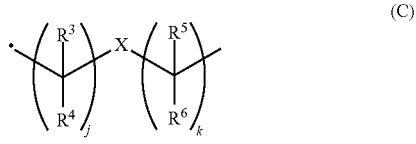
(C)

(where j, k, X, $R^3$, $R^4$, $R^5$, and $R^6$ are the same as defined in Formula (I) described in Aspect [1]; and ● is a single bond with the ring A).

Preferable specific examples of Formula (C) include Formula (c1) to Formula (c6):

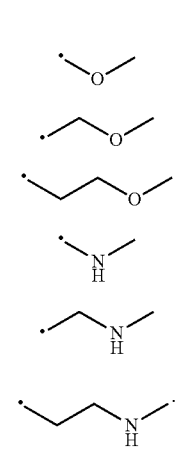

[1-15-a] More preferably, Formula (C) is Formula (c1), Formula (c2), Formula (c4), or Formula (c5).

[1-15-b] When the ring A is a monocyclic ring or a spiro ring, that is, when the ring A is a phenyl group, a monocyclic heterocyclic group, a cycloalkyl group, a cycloalkenyl group, or a spiro ring group, specifically, when the ring A is Formula (A), Formula (A)-1, Formula (A1), Formula (A2), Formula (A1)-1, Formula (A2)-1, Formula (A1a), Formula (A1b), Formula (A1c), Formula (A1)-1-1, or Formula (A1)-1-2 described in Aspects [1-13-c] to [1-13-c-12], Formula (A)-IV, Formula (A1)-IV, Formula (A2)-IV, Formula (A3)-IV, or Formula (A4)-IV described in Aspects [1-13-e] to [1-13-e-8], Formula (A)-V, Formula (A1)-V, Formula (AA)-V, or Formula (AA1)-V described in Aspects [1-13-f] to [1-13-f-10], Formula (A)-VI or Formula (AA)-VI described in Aspects [1-13-g] to [1-13-g-2], or Formula (A5)-IVa or Formula (A)-VIa described in Aspect [1-13-e-8a] or [1-13-ga], Formula (C) is further preferably Formula (c2) or Formula (c5), most preferably Formula (c2).

[1-15-c] When the ring A is a fused ring, that is, when the ring A is a ring-fused aryl group, a partly hydrogenated ring-fused aryl group, a ring-fused heteroaryl group, a partly hydrogenated ring-fused heteroaryl group, or a ring-fused non-aromatic heterocyclic group, specifically when the ring A is Formula (AA), Formula (AA)-1, Formula (AA)-1-1, Formula (AA1), Formula (AA1)-1, Formula (AA1a)-1, Formula (AA1a)-1-1, Formula (AA 1b), or Formula (AA1b)-1 described in Aspects [1-13-d] to [1-13-d-7-1], Formula (A)-VII or Formula (AA)-VII described in Aspect [1-13-h] or [1-13-h-1], a phthalazinyl group described in Aspect [1-13-i], Formula (A)-VIII described in Aspect [1-13-j], or Formula (A)-VIIa described in Aspect [1-13-ha], Formula (C) is further preferably Formula (c1) or Formula (c4), most preferably Formula (c1).

[1-15-d] When the ring A is a 2-phenylamino-2-oxoacetyl group, specifically when the ring A is Formula (A)-IX described in Aspect [1-13-k], the linker moiety is preferably —$NR^7$—, more preferably Formula (c4).

[1-16] The compound of Formula (I) according to Aspect [1] is preferably a compound of Formula (I)-1:

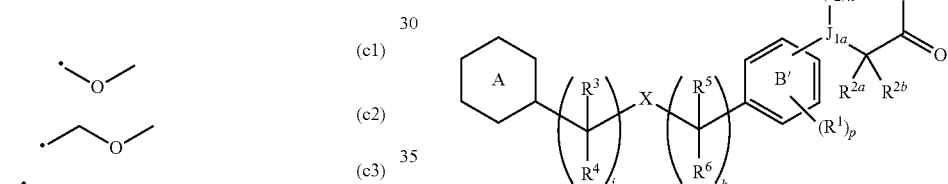
(I)-1

(where n, p, h, j, k, the ring A, X, $J_2$, $R^1$, $R^{2a}$, $R^{2b}$, $R^3$, $R^4$, $R^5$, and $R^6$ are the same as defined in Formula (I) described in Aspect [1]; and the ring B' and $J_{1a}$ are the same as defined in Formula (B)-1 described in Aspect [1-14-a-1] (with the proviso that a compound that is 5-[4-[2-(2-phenyl-4-oxazolyl) ethoxy]phenyl]-1,1-dioxo-1,2,5-thiadiazolidin-3-one; a compound in which a saturated cyclic amide structure having —S(O)$_n$—NH—CO— is 1,1-dioxo-1,2-thiazolidin-3-one, the ring B' is a benzene ring, k is 1, and in the ring B', the linker moiety containing X and the cyclic amide structure are at the p-position; and a compound in which the cyclic amide structure is 1,1-dioxo-1,2,5-thiadiazolidin-3-one, and in the ring B', the cyclic amide structure is bonded to an atom adjacent to an atom to which the linker containing X is bonded, are excluded)).

More specifically, the preferable aspects of n, p, h, j, k, the ring A, the ring B', X, $J_{1a}$, $J_2$, $R^1$, $R^{2a}$, $R^{2b}$, $R^3$, $R^4$, $R^5$, and $R^6$ are the same as the preferable aspects described in any one of Aspects [1-1] to [1-15] and subordinate Aspects thereof. The preferable aspects of the partial structure of Formula (I)-1 corresponding to the ring A, Partial Structural Formula (B)-1, Partial Structural Formula (B-Het)-1, or Partial Structural Formula (C) that are described in any one of Aspects [1-13], [1-14], and [1-15], and subordinate Aspects thereof are the same as described in any one of Aspects [1-13], [1-14], and [1-15], and subordinate Aspects thereof.

[1-16-1] The compound of Formula (I)-1 according to Aspect [1-16] is preferably a compound in which the ring A is Formula (A), that is, a compound of Formula (II):

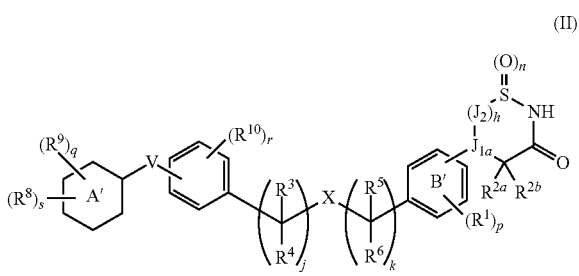
(II)

(where n, p, h, j, k, X, $J_2$, $R^1$, $R^{2a}$, $R^{2b}$, $R^3$, $R^4$, $R^5$, $R^6$ are the same as defined in Formula (I) described in Aspect [1]; the ring B' and $J_{1a}$ are the same as defined in Formula (B)-1 described in Aspect [1-14-a-1]; q, r, s, the ring A', V, $R^8$, $R^9$, and $R^{10}$ are the same as defined in Formula (A) described in Aspect [1-13-c] (with the proviso that a compound in which the saturated cyclic amide structure having —S(O)$_n$—NH—CO— is 1,1-dioxo-1,2-thiazolidin-3-one, the ring B' is a benzene ring, k is 1, and in the ring B', the linker moiety containing X and the cyclic amide structure are at the p-position is excluded)).

More specifically, the preferable aspects of n, p, q, r, s, h, j, k, the ring A', the ring B', X, V, $J_{1a}$, $J_2$, $R^1$, $R^{2a}$, $R^{2b}$, $R^3$, $R^4$, $R^5$, $R^6$, $R^8$, $R^9$, and $R^{10}$ are the same as the preferable aspects described in any one of Aspects [1-1] to [1-15] and subordinate Aspects thereof. The preferable aspects of the partial structure of Formula (II) corresponding to Partial Structural Formula (A), Partial Structural Formula (B)-1, Partial Structural Formula (B-Het)-1, or Partial Structural Formula (C) described in any one of Aspects [1-13-c], [1-14], and [1-15], and subordinate Aspects thereof are the same as described in any one of Aspects [1-13-c], [1-14], and [1-15], and subordinate Aspects thereof.

The compound of Formula (II) is preferably a compound of Formula (II) in which the ring A' is a benzene ring, a pyridine ring, or a pyrimidine ring, that is, a compound in which the ring A is Formula (A)-1 in Formula (I), which is a compound of Formula (II)1:

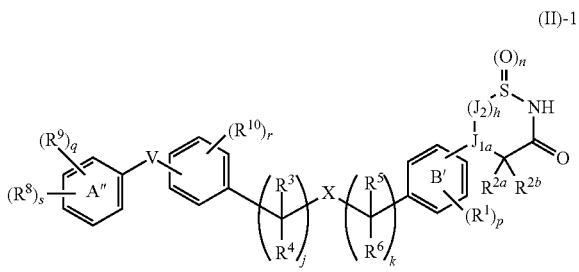
(II)-1

(where n, p, h, j, k, X, $J_2$, $R^1$, $R^{2a}$, $R^{2b}$, $R^3$, $R^4$, $R^5$, and $R^6$ are the same as defined in Formula (I) described in Aspect [1]; the ring B' and $J_{1a}$ are the same as defined in Formula (B)-1 described in Aspect [1-14-a-1]; q, r, s, the ring A", V, $R^8$, $R^9$, and $R^{10}$ are the same as defined in Formula (A) or Formula (A)-1 described in Aspect [1-13-c] (with the proviso that a compound in which the saturated cyclic amide structure having —S(O)$_n$—NH—CO— is 1,1-dioxo-1,2-thiazolidin-3-one, the ring B' is a benzene ring, k is 1, and in the ring B', the linker moiety containing X and the cyclic amide structure are at the p-position is excluded)).

More specifically, the preferable aspects of n, p, q, r, s, h, j, k, the ring A", the ring B', X, V, $J_{1a}$, $J_2$, $R^1$, $R^{2a}$, $R^{2b}$, $R^3$, $R^4$, $R^5$, $R^6$, $R^8$, $R^9$, and $R^{10}$ are the same as the preferable aspects described in any one of Aspects [1-1] to [1-15] and the subordinate Aspects thereof. The preferable aspects of the partial structure of Formula (II)-1 corresponding to Partial Structural Formula (A)-1, Partial Structural Formula (B)-1, Partial Structural Formula (B-Het)-1, or Partial Structural Formula (C) described in any one of Aspects [1-13-c], [1-14], and [1-15], and the subordinate Aspects thereof are the same as described in any one of Aspects [1-13-c], [1-14], and [1-15], and subordinate Aspects thereof.

In Formula (II) or Formula (II)-1, X is preferably an oxygen atom or —NH—, more preferably an oxygen atom. In Formula (II) or Formula (II)-1, j is preferably 1. k is preferably 0. In Formula (II) or Formula (II)-1, more preferably, X is an oxygen atom and k is 0. Further preferably, X is an oxygen atom, j is 1, and k is 0.

In Formula (II) or Formula (II)-1, in the ring B', the linker moiety containing X and the cyclic amide structure are preferably at the p-position, that is, the partial structure has preferably Formula (B1). The ring B' is preferably a benzene ring.

In Formula (II) or Formula (II)-1, preferably, any one of q and s is 1 or more, more preferably, s is 1.

In Formula (II) or Formula (II)-1, preferably, X is an oxygen atom, k is 0, and any one of q and s is 1 or more, more preferably, X is an oxygen atom, k is 0, and s is 1.

[1-16-1a] In the compound of Formula (II), compounds produced by optionally combining the groups of Partial Structural Formula (A) (on the left of the left wavy line), Partial Structural Formula (B) (on the right of the right wavy line), Partial Structural Formula (C) (between the two wavy lines) in Formula (II) can be produced optionally:

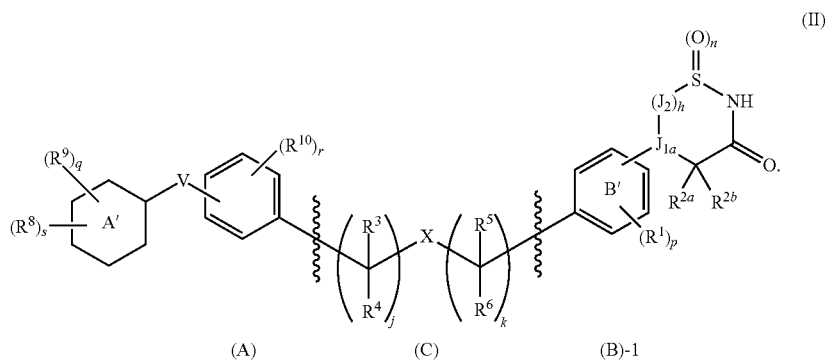

More specifically, Partial Structural Formula (A) is a group optionally selected from Formula (A)-1, Formula (A1), Formula (A2), Formula (A1)-1, Formula (A2)-1, Formula (A1a), Formula (A1b), Formula (A1c), Formula (A1)-1-1, and Formula (A1)-1-2 described in Aspects [1-13-c] to [1-13-c-12]. Partial Structural Formula (B)-1 is a group optionally selected from Formula (B 1), Formula (B2), Formula (B1a), and Formula (B1b) described in Aspects [1-14-a-2] and [1-14-a-4], and Partial Structural Formula (C) can be a group optionally selected from Formula (c1) to Formula (c6) described in Aspect [1-15]. An optional combination of each formula forms part of the compound of Formula (I) according to the present invention.

In the compound of Formula (II), preferably, Partial Structural Formula (A) is Formula (A2)-1 in which the ring A"-O— is bonded at 3-position, Formula (A1a), Formula (A1b), or Formula (A1c), Partial Structural Formula (B)-1 is Formula (B1a) or Formula (Bib), and Partial Structural Formula (C) is Formula (c2) or Formula (c5). More preferably, Partial Structural Formula (A) is Formula (A2)-1 in which the ring A"-O— is bonded at 3-position, Formula (A1a), or Formula (A1c), Partial Structural Formula (B)-1 is Formula (B1a), and Partial Structural Formula (C) is Formula (c2). Further preferably, Partial Structural Formula (B-Het)-1 in Partial Structural Formula (B)-1 is Formula (B-Het)-1a, Formula (B-Het)-1b, Formula (B-Het)-1c, Formula (B-Het)-1d, Formula (B-Het)-1e, or Formula (B-Het)-1f described in Aspect [1-14-e-1]. An optional combination of each formula forms part of the preferable compound of Formula (I) according to the present invention.

[1-16-1-a] The compound of Formula (II) or Formula (II)-1 according to Aspect [1-16-1] is preferably a compound of Formula (II)-1a:

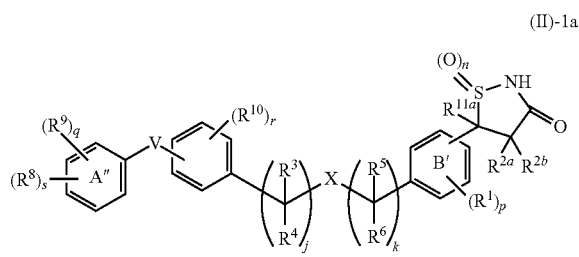

(II)-1a (where n, p, j, k, X, $R^1$, $R^{2a}$, $R^{2b}$, $R^3$, $R^4$, $R^5$, $R^6$, and $R^{11}$ are the same as defined in Formula (I); the ring B' is the same as defined in Formula (B)-1 described in Aspect [1-14-a-1]; and q, r, s, the ring A", V, $R^8$, $R^9$, and $R^{10}$ are the same as defined in Formula (A) or Formula (A)-1 described in Aspect [1-13-c] (with the proviso that a compound in which the saturated cyclic amide structure having —S(O)$_n$—NH—CO— is 1,1-dioxo-1,2-thiazolidin-3-one, the ring B' is a benzene ring, k is 1, and in the ring B', the linker moiety containing X and the cyclic amide structure are at the p-position is excluded)), a salt of the compound, or a solvate of the compound or the salt.

More specifically, the preferable aspects of n, p, q, r, s, j, k, the ring A", the ring B', X, V, $R_1$, $R^{2a}$, $R^{2b}$, $R^3$, $R^4$, $R^5$, $R^6$, $R^8$, $R^9$, $R^{10}$, and $R^{11a}$ are the same as preferable aspects described in any one of Aspects [1-1] to [1-15] and subordinate Aspects thereof. The preferable aspects of the partial structure of Formula (II)-1a corresponding to Partial Structural Formula (A)-1, Partial Structural Formula (B)-1, Partial Structural Formula (B-Het)-1a, or Partial Structural Formula (C) described in any one of Aspects [1-13-c], [1-14], and [1-15], and subordinate Aspects thereof are the same as described in any one of Aspects [1-13-c], [1-14], and [1-15], and subordinate Aspects thereof.

In Formula (II)-1a, X is preferably an oxygen atom or —NH—, more preferably an oxygen atom. In Formula (II)-1a, j is preferably 1. k is preferably 0. In Formula (II)-1a, more preferably, x is an oxygen atom and k is 0. Further preferably, X is an oxygen atom, j is 1, and k is 0.

In Formula (II)-1a, in the ring B', the linker moiety containing X and the cyclic amide structure are preferably at the p-position. The ring B' is preferably a benzene ring.

In Formula (II)-1a, preferably, any one of q and s is 1 or more, and more preferably, s is 1.

In Formula (II)-1a, preferably, X is an oxygen atom, k is 0, and any one of q and s is 1 or more, and more preferably, X is an oxygen atom, k is 0, and s is 1.

[1-16-1-b] The compound of Formula (II) or Formula (II)-1 according to Aspect [1-16-1] is preferably a compound of Formula (II)-1b:

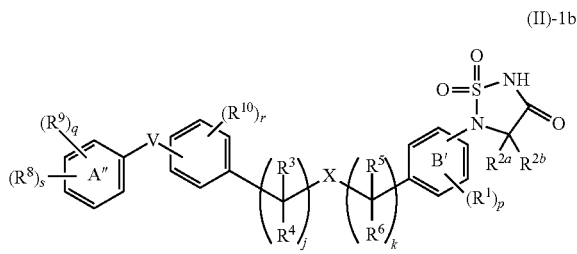

(II)-1b (where p, j, k, X, $R^1$, $R^{2a}$, $R^{2b}$, $R^3$, $R^4$, $R^5$, and $R^6$ are the same as defined in Formula (I) described in Aspect [1]; the ring B' is the same as defined in Formula (B)-1 described in Aspect [1-14-a-1]; and q, r, s, the ring A", V, $R^8$, $R^9$, and $R^{10}$ are the same as defined in Formula (A) or Formula (A)-1 described in Aspect [1-13-c]), or a salt of the compound, or a solvate of the compound or the salt.

More specifically, the preferable aspects of p, q, r, s, j, k, the ring A", the ring B', X, V, $R^1$, $R^{2a}$, $R^{2b}$, $R^3$, $R^4$, $R^5$, $R^6$, $R^8$, $R^9$, and $R^{10}$ are the same as the preferable aspects described in any one of Aspects [1-1] to [1-15] and subordinate Aspects thereof. The preferable aspects of the partial structure of Formula (II)-1b corresponding to Partial Structural Formula (A)-1, Partial Structural Formula (B)-1, Partial Structural Formula (B-Het)-1b, or Partial Structural Formula (C) described in any one of Aspects [1-13-c], [1-14], and [1-15], and subordinate Aspects thereof are the same as described in any one of Aspects [1-13-c], [1-14], and [1-15], and subordinate Aspects thereof.

In Formula (II)-1b, X is preferably an oxygen atom or —NH—, more preferably an oxygen atom. In Formula (II)-1b, j is preferably 1. k is preferably 0. In Formula (II)-1b, more preferably, X is an oxygen atom and k is 0. Further preferably, X is an oxygen atom, j is 1, and k is 0.

In Formula (II)-1b, in the ring B', the linker moiety containing X and the cyclic amide structure are preferably at the p-position. The ring B' is preferably a benzene ring.

In Formula (II)-1b, preferably, any one of q and s is 1 or more, and more preferably, is 1.

In Formula (II)-1b, preferably, X is an oxygen atom, k is 0, and any one of q and s is 1 or more, and more preferably, X is an oxygen atom, k is 0, and s is 1.

[1-16-1-c] The compound of Formula (II) or Formula (II)-1 according to Aspect [1-16-1] is preferably a compound of Formula (II)-1c:

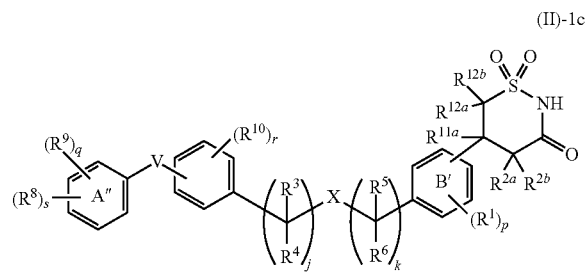

(II)-1c (where p, j, k, X, $R^1$, $R^{2a}$, $R^{2b}$, $R^3$, $R^4$, $R^5$, $R^6$, $R^{11a}$, $R^{12a}$, and $R^{12b}$ are the same as defined in Formula (I); the ring B' is the same as defined in Formula (B)-1 described in Aspect [1-14-a-1]; and q, r, s, the ring A", V, $R^8$, $R^9$, and $R^{10}$ are the same as defined in Formula (A) or Formula (A)-1 described in Aspect [1-13-c]), a salt of the compound, or a solvate of the compound or the salt.

More specifically, the preferable aspects of p, q, r, s, j, k, the ring A", the ring B', X, V, $R^1$, $R^{2a}$, $R^{2b}$, $R^3$, $R^4$, $R^5$, $R^6$, $R^8$, $R^9$, $R^{10}$, $R^{11a}$, $R^{12a}$, and $R^{12b}$ are the same as the preferable aspects described in any one of Aspects [1-1] to [1-15] and subordinate Aspects thereof. The preferable aspects of the partial structure of Formula (II)-1c corresponding to Partial Structural Formula (A)-1, Partial Structural Formula (B)-1, Partial Structural Formula (B-Het)-1c, or Partial Structural Formula (C) described in any one of Aspects [1-13-c], [1-14], and [1-15], and subordinate Aspects thereof are the same as described in any one of Aspects [1-13-c], [1-14], and [1-15], and subordinate Aspects thereof.

In Formula (II)-1c, X is preferably an oxygen atom or —NH—, more preferably an oxygen atom. In Formula (II)-1c, j is preferably 1. k is preferably 0. In Formula (II)-1c, more preferably, x is an oxygen atom and k is 0. Further preferably, X is an oxygen atom, j is 1, and k is 0.

In Formula (II)-1c, in the ring B', the linker moiety containing X and the cyclic amide structure are preferably at the p-position. The ring B' is preferably a benzene ring.

In Formula (II)-1c, preferably, any one of q and s is 1 or more, and more preferably, is 1.

In Formula (II)-1c, preferably, X is an oxygen atom, k is 0, and any one of q and s is 1 or more, and more preferably, X is an oxygen atom, k is 0, and s is 1.

[1-16-1-d] The compound of Formula (II) or Formula (II)-1 according to Aspect [1-16-1] is preferably a compound of Formula (II)-1d:

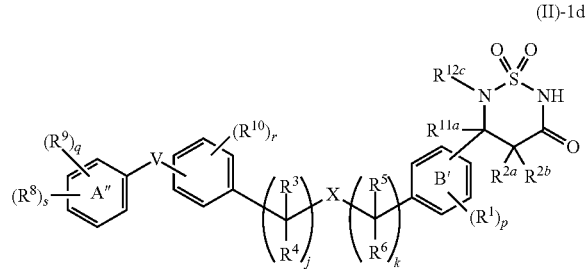

(II)-1d (where p, j, k, X, $R^1$, $R^{2a}$, $R^{2b}$, $R^3$, $R^4$, $R^5$, $R^6$, $R^{11a}$, and $R^{12c}$ are the same as defined in Formula (I); the ring B' is the same as defined in Formula (B)-1 described in Aspect [1-14-a-1]; and q, r, s, the ring A", V, $R^8$, $R^9$, and $R^{10}$ are the same as defined in Formula (A) or Formula (A)-1 described in Aspect [1-13-c]), a salt of the compound, or a solvate of the compound or the salt.

More specifically, the preferable aspects of p, q, r, s, j, k, the ring A", the ring B', X, V, $R^1$, $R^{2a}$, $R^{2b}$, $R^3$, $R^4$, $R^5$, $R^6$, $R^7$, $R^8$, $R^9$, $R^{10}$, $R^{11a}$, and $R^{12c}$ are the same as the preferable aspects described in any one of Aspects [1-1] to [1-15] and subordinate Aspects thereof. The preferable aspects of the partial structure of Formula (II)-1d corresponding to Partial Structural Formula (A)-1, Partial Structural Formula (B)-1, Partial Structural Formula (B-Het)-1d, or Partial Structural Formula (C) described in any one of Aspects [1-13-c], [1-14], and [1-15], and subordinate Aspects thereof are the same as described in any one of Aspects [1-13-c], [1-14], and [1-15], and subordinate Aspects thereof.

In Formula (II)-1d, X is preferably an oxygen atom or —NH—, more preferably an oxygen atom. In Formula (II)-1d, j is preferably 1. k is preferably 0. In Formula (II)-1d, more preferably, x is an oxygen atom and k is 0. Further preferably, X is an oxygen atom, j is 1, and k is 0.

In Formula (II)-1d, in the ring B', the linker moiety containing X and the cyclic amide structure are preferably at the p-position. The ring B' is preferably a benzene ring.

In Formula (II)-1d, preferably, any one of q and s is 1 or more, and more preferably, s is 1.

In Formula (II)-1d, preferably, x is an oxygen atom, k is 0, and any one of q and s is 1 or more, and more preferably, X is an oxygen atom, k is 0, and s is 1.

[1-16-1-e] The compound of Formula (II) or Formula (II)-1 according to Aspect [1-16-1] is preferably a compound of Formula (II)-1e:

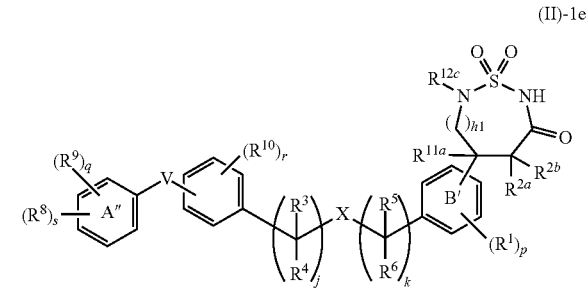

(II)-1e (where p, j, k, X, $R^1$, $R^{2a}$, $R^{2b}$, $R^3$, $R^4$, $R^5$, $R^6$, $R^{11a}$, and $R^{12c}$ are the same as defined in Formula (I); the ring B' is the same as defined in Formula (B)-1 described in Aspect [1-14-a-1]; q, r, s, the ring A", V, $R^8$, $R^9$, and $R^{10}$ are the same as defined in Formula (A) or Formula (A)-1 described in Aspect [1-13-c]; and h1 is the same as defined in Formula (B-Het)-1e described in Aspect [1-14-d]), a salt of the compound, or a solvate of the compound or the salt.

More specifically, the preferable aspects of p, q, r, s, j, k, the ring A", the ring B', X, V, $R^1$, $R^{2a}$, $R^{2b}$, $R^3$, $R^4$, $R^5$, $R^6$, $R^8$, $R^9$, $R^{10}$, $R^{11a}$, $R^{12c}$, and h1 are the same as the preferable aspects described in any one of Aspects [1-1] to [1-15] and subordinate Aspects thereof. The preferable aspects of the partial structure of Formula (II)-1e corresponding to Partial Structural Formula (A)-1, Partial Structural Formula (B)-1, Partial Structural Formula (B-Het)-1e, or Partial Structural Formula (C) described in any one of Aspects [1-13-c], [1-14], and

[1-15], and subordinate Aspects thereof are the same as described in any one of Aspects [1-13-c], [1-14], and [1-15], and subordinate Aspects thereof.

[1-16-1-f] The compound of Formula (II) or Formula (II)-1 according to Aspect [1-16-1] is preferably a compound of Formula (II)-1f:

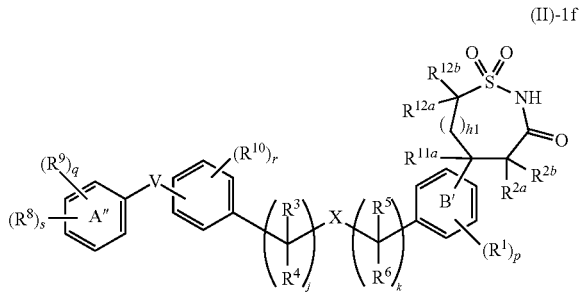

(II)-1f (where p, j, k, X, $R^1$, $R^{2a}$, $R^{2b}$, $R^3$, $R^4$, $R^5$, $R^6$, $R^{11a}$, $R^{12a}$, and $R^{12b}$ are the same as defined in Formula (I); the ring B' is the same as defined in Formula (B)-1 described in Aspect [1-14-a-1]; q, r, s, the ring A", V, $R^8$, $R^9$, and $R^{10}$ are the same as defined in Formula (A) or Formula (A)-1 described in Aspect [1-13-c]; and h1 is the same as defined in Formula (B-Het)-1f described in Aspect [1-14-d]), a salt of the compound, or a solvate of the compound or the salt.

More specifically, the preferable aspects of p, q, r, s, j, k, the ring A", the ring B', X, V, $R^1$, $R^{2a}$, $R^{2b}$, $R^3$, $R^4$, $R^5$, $R^6$, $R^8$, $R^9$, $R^{10}$, $R^{11a}$, $R^{12a}$, $R^{12b}$, and h1 are the same as the preferable aspects described in any one of Aspects [1-1] to [1-15] and subordinate Aspects thereof. The preferable aspects of the partial structure of Formula (II)-1f corresponding to Partial Structural Formula (A)-1, Partial Structural Formula (B)-1, Partial Structural Formula (B-Het)-1f, or Partial Structural Formula (C) described in any one of Aspects [1-13-c], [1-14], and [1-15], and subordinate Aspects thereof are the same as described in any one of Aspects [1-13-c], [1-14], and [1-15], and subordinate Aspects thereof.

[1-16-1-1] The compound of Formula (II) or Formula (II)-1 according to Aspect [1-16-1] is preferably Formula (II-1)-1:

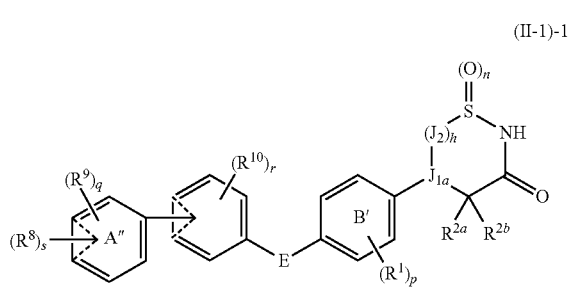

(II-1)-1

(where n, p, h, $J_2$, $R^1$, $R^{2a}$, and $R^{2b}$ are the same as defined in Formula (I); the ring B' and $J_{1a}$ are the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; the broken lines are the same as defined in Formula (A1)-1 described in Aspect [1-13-c-1]; and E is a group optionally selected from Formula (c1) to Formula (c6) shown as specific examples of Formula (C) described in Aspect [1-15]).

More specifically, the preferable aspects of n, p, q, r, s, h, the ring A", the ring B', $J_{1a}$, $J_2$, $R^1$, $R^{2a}$, $R^{2b}$, $R^8$, $R^9$, $R^{10}$, the broken lines, and E are the same as the preferable aspects described in any one of Aspects [1-1] to [1-15] and subordinate Aspects thereof. The preferable aspects of the partial structure of Formula (II-1)-1 corresponding to Partial Structural Formula (A1)-1 or Partial Structural Formula (B1) described in any one of Aspects [1-13-c-1] and [1-14-a-2] are the same as described in any one of Aspects [1-13-c] and [1-14], and subordinate Aspects thereof.

In Formula (II-1)-1, E is preferably Formula (c2) or Formula (c5), more preferably Formula (c2).

In Formula (II-1)-1, the ring B' is preferably a benzene ring.

In Formula (II-1)-1, E and the ring A" are preferably at the m-position.

In Formula (II-1)-1, preferably, any one of q and s is 1 or more, and more preferably, is 1.

In Formula (II-1)-1, preferably, E is Formula (c2), any one of q and s is 1 or more, and more preferably, E is Formula (c2) and s is 1.

[1-16-1-1-a] The compound of Formula (II-1)-1 is more preferably

Formula (II-1)-1a:

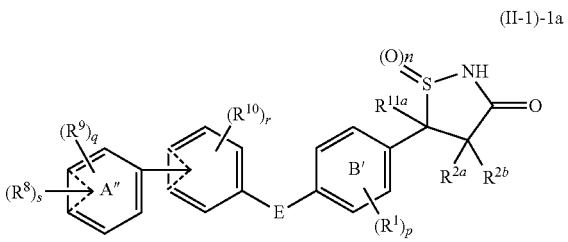

(II-1)-1a (where n, p, $R^1$, $R^{2a}$, $R^{2b}$, and $R^{11a}$ are the same as defined in Formula (I); the ring B' is the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; the broken lines are the same as defined in Formula (A1)-1 described in Aspect [1-13-c-1]; and E is a group optionally selected from Formula (c1) to Formula (c6) shown as specific examples of Formula (C) described in Aspect [1-15]).

More specifically, the preferable aspects of n, p, q, r, s, the ring A", the ring B', $R^1$, $R^{2a}$, $R^{2b}$, $R^8$, $R^9$, $R^{10}$, $R^{11a}$, the broken lines, and E are the same as the preferable aspects described in any one of Aspects [1-1] to [1-15] and subordinate Aspects thereof. The preferable aspects of the partial structure of Formula (II-1)-1a corresponding to Partial Structural Formula (A1)-1, Partial Structural Formula (B1), or Partial Structural Formula (B-Het)-1a described in any one of Aspects [1-13-c-1] and [1-14], and subordinate Aspects thereof are the same as described in any one of Aspects [1-13-c] and [1-14], and subordinate Aspects thereof.

In Formula (II-1)-1a, E is preferably Formula (c2) or Formula (c5), more preferably Formula (c2).

In Formula (II-1)-1a, the ring B' is preferably a benzene ring.

In Formula (II-1)-1a, E and the ring A" are preferably at the m-position.

In Formula (II-1)-1a, preferably, any one of q and s is 1 or more, and more preferably, s is 1.

In Formula (II-1)-1a, preferably, E is Formula (c2), any one of q and s is 1 or more, and more preferably, E is Formula (c2) and s is 1.

[1-16-1-1-b] The compound of Formula (II-1)-1 is more preferably Formula (II-1)-1b:

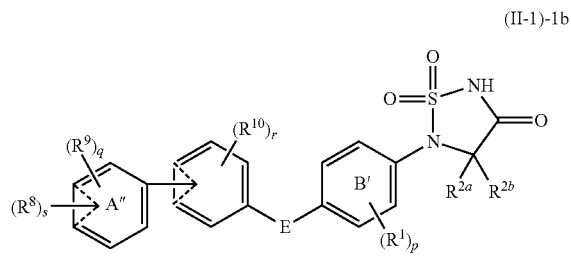

(II-1)-1b (where p, $R^1$, $R^{2a}$, and $R^{2b}$ are the same as defined in Formula (I); the ring B' is the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; the broken lines are the same as defined in Formula (A1)-1 described in Aspect [1-13-c-1]; and E is a group optionally selected from Formula (c 1) to Formula (c6) shown as specific examples of Formula (C) described in Aspect [1-15]).

More specifically, the preferable aspects of p, q, r, s, the ring A", the ring B', $R^1$, $R^{2a}$, $R^{2b}$, $R^8$, $R^9$, $R^{10}$, the broken lines, and E are the same as the preferable aspects described in any one of Aspects [1-1] to [1-15] and subordinate Aspects thereof. The preferable aspects of the partial structure of Formula (II-1)-1b corresponding to Partial Structural Formula (A1)-1, Partial Structural Formula (B1), or Partial Structural Formula (B-Het)-1b described in any one of Aspects [1-13-c-1] and [1-14], and subordinate Aspects thereof are the same as described in any one of Aspects [1-13-c] and [1-14], and subordinate Aspects thereof.

In Formula (II-1)-1b, E is preferably Formula (c2) or Formula (c5), more preferably Formula (c2).

In Formula (II-1)-1b, the ring B' is preferably a benzene ring.

In Formula (II-1)-1b, E and the ring A" are preferably at the m-position.

In Formula (II-1)-1b, preferably, any one of q and s is 1 or more, and more preferably, s is 1.

In Formula (II-1)-1b, preferably, E is Formula (c2), any one of q and s is 1 or more, and more preferably, E is Formula (c2) and s is 1.

[1-16-1-1-c] The compound of Formula (II-1)-1 is more preferably Formula (II-1)-1c:

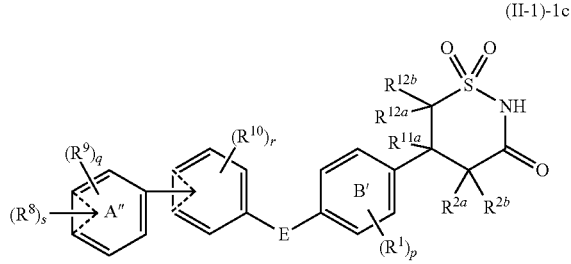

(II-1)-1c (where p, $R^1$, $R^{2a}$, $R^{2b}$, $R^{11a}$, $R^{12a}$, $R^{12b}$ are the same as defined in Formula (I); the ring B' is the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; the broken lines are the same as defined in Formula (A1)-1 described in Aspect [1-13-c-1]; and E is a group optionally selected from Formula (c1) to Formula (c6) shown as specific examples of Formula (C) described in Aspect [1-15]).

More specifically, the preferable aspects of p, q, r, s, the ring A", the ring B', $R^1$, $R^{2a}$, $R^{2b}$, $R^8$, $R^9$, $R^{10}$, $R^{11a}$, $R^{12a}$, $R^{12b}$, the broken lines, and E are the same as the preferable aspects described in any one of Aspects [1-1] to [1-15] and subordinate Aspects thereof.

The preferable aspects of the partial structure of Formula (II-1)-1c corresponding to Partial Structural Formula (A1)-1, Partial Structural Formula (B 1), or Partial Structural Formula (B-Het)-1c described in any one of Aspects [1-13-c-1] and [1-14], and subordinate Aspects thereof are the same as described in any one of Aspects [1-13-c] and [1-14], and subordinate Aspects thereof.

In Formula (II-1)-1c, E is preferably Formula (c2) or Formula (c5), more preferably Formula (c2).

In Formula (II-1)-1c, the ring B' is preferably a benzene ring.

In Formula (II-1)-1c, E and the ring A" are preferably at the m-position.

In Formula (II-1)-1c, preferably, any one of q and s is 1 or more, and more preferably, s is 1.

In Formula (II-1)-1c, preferably, E is Formula (c2), any one of q and s is 1 or more, and more preferably, E is Formula (c2) and s is 1.

[1-16-1-1-d] The compound of Formula (II-1)-1 is more preferably Formula (II-1)-1d:

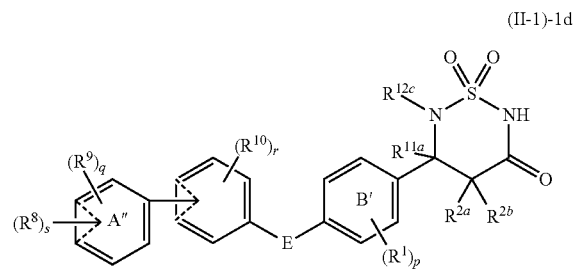

(II-1)-1d (where p, $R^1$, $R^{2a}$, $R^{2b}$, $R^{11a}$, and $R^{12c}$ are the same as defined in Formula (I); the ring B' is the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; the broken lines are the same as defined in Formula (A1)-1 described in Aspect [1-13-c-1]; and E is a group optionally selected from Formula (c1) to Formula (c6) shown as specific examples of Formula (C) described in Aspect [1-15]).

More specifically, the preferable aspects of p, q, r, s, the ring A", the ring B', $R^1$, $R^{2a}$, $R^{2b}$, $R^8$, $R^9$, $R^{10}$, $R^{11a}$, $R^{12c}$, the broken lines, and E are the same as the preferable aspects described in any one of Aspects [1-1] to [1-15] and subordinate Aspects thereof. The preferable aspects of the partial structure of Formula (II-1)-1d corresponding to Partial Structural Formula (A1)-1, Partial Structural Formula (B 1), or Partial Structural Formula (B-Het)-1d described in any one of Aspects [1-13-c-1] and [1-14], and subordinate Aspects thereof are the same as described in any one of Aspects [1-13-c] and [1-14], and subordinate Aspects thereof.

In Formula (II-1)-1d, E is preferably Formula (c2) or Formula (c5), more preferably Formula (c2).

In Formula (II-1)-1d, the ring B' is preferably a benzene ring.

In Formula (II-1)-1d, E and the ring A" are preferably at the m-position.

In Formula (II-1)-1d, preferably, any one of q and s is 1 or more, and more preferably, s is 1.

In Formula (II-1)-1d, preferably, E is Formula (c2), any one of q and s is 1 or more, and more preferably, E is Formula (c2) and s is 1.

[1-16-1-1-e] The compound of Formula (II-1)-1 is more preferably Formula (II-1)-1e:

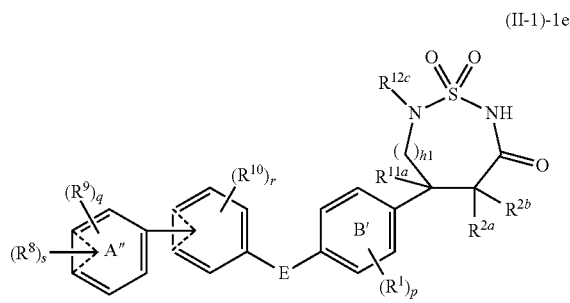

(II-1)-1e (where p, $R^1$, $R^{2a}$, $R^{2b}$, $R^{11a}$, and $R^{12c}$ are the same as defined in Formula (I); the ring B' is the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; h1 is the same as defined in Formula (B-Het)-1e described in Aspect [1-14-d]; the broken lines are the same as defined in Formula (A1)-1 described in Aspect [1-13-c-1]; and E is a group optionally selected from Formula (c1) to Formula (c6) shown as specific examples of Formula (C) described in Aspect [1-15]).

More specifically, preferable aspects of p, q, r, s, the ring A", the ring B', $R^1$, $R^{2a}$, $R^{2b}$, $R^8$, $R^9$, $R^{10}$, $R^{11a}$, $R^{12c}$, h1, the broken lines, and E are the same as the preferable aspects described in any one of Aspects [1-1] to [1-15] and subordinate Aspects thereof. Preferable aspects of the partial structure of Formula (II-1)-1e corresponding to Partial Structural Formula (A1)-1, Partial Structural Formula (B1), or Partial Structural Formula (B-Het)-1e described in any one of Aspects [1-13-c-1] and [1-14], and subordinate Aspects thereof are the same as described in any one of Aspects [1-13-c] and [1-14], and subordinate Aspects thereof.

[1-16-1-1-f] The compound of Formula (II-1)-1 is more preferably Formula (II-1)-1f:

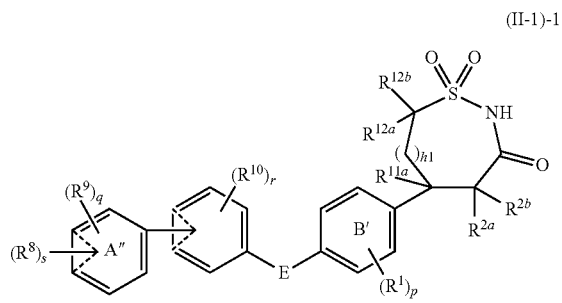

(II-1)-1f (where p, $R^1$, $R^{2a}$, $R^{2b}$, $R^{11a}$, $R^{12a}$, and $R^{12b}$ are the same as defined in Formula (I); the ring B' is the same as defined in Formula (B)-1 described in Aspect [1-14-a-1]; q, r, s, the ring A", $R^8$, $R^9$, and $R^{10}$ are the same as defined in Formula (A) or Formula (A)-1 described in Aspect [1-13-c]; h1 is the same as defined in Formula (B-Het)-1f described in Aspect [1-14-d]; the broken lines are the same as defined in Formula (A1)-1 described in Aspect [1-13-c-1]; and E is a group optionally selected from Formula (c1) to Formula (c6) shown as specific examples of Formula (C) described in Aspect [1-15]).

More specifically, preferable aspects of p, q, r, s, the ring A", the ring B', $R^1$, $R^{2a}$, $R^{2b}$, $R^8$, $R^9$, $R^{10}$, $R^{11a}$, $R^{12a}$, $R^{12b}$, h1, the broken lines, and E are the same as the preferable aspects described in any one of Aspects [1-1] to [1-15] and subordinate Aspects thereof. Preferable aspects of the partial structure of Formula (II-1)-1f corresponding to Partial Structural Formula (A1)-1, Partial Structural Formula (B1), or Partial Structural Formula (B-Het)-1f described in any one of Aspects [1-13-c-1] and [1-14], and subordinate Aspects thereof are the same as described in any one of Aspects [1-13-c] and [1-14], and subordinate Aspects thereof.

[1-16-1-2] The compound of Formula (II-1)-1 according to Aspect [1-16-1-1] is more preferably Formula (II-1-A):

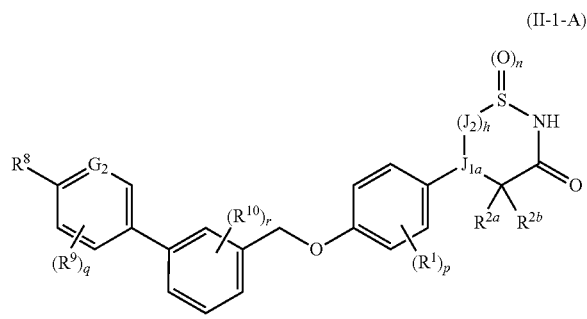

(II-1-A)

(where n, p, h, $J_2$, $R^1$, $R^{2a}$, and $R^{2b}$ are the same as defined in Formula (I); $J_{1a}$ is the same as defined in Formula (B)-1 described in Aspect [1-14-a-1]; q, r, $R^8$, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of n, p, q, r, h, $J_{1a}$, $R^1$, $R^{2a}$, $R^{2b}$, $R^8$, $R^9$, $R^{10}$, and $G_2$ are the same as the preferable aspects described in any one of Aspects [1-1] to [1-15] and subordinate Aspects thereof. Preferable aspects of the partial structure of Formula (II-1-A) corresponding to Partial Structural Formula (A1a) or Partial Structural Formula (B1a) described in Aspect [1-13-c-3-1] or [1-14-a-4] are the same as described in any one of Aspects [1-13-c] and [1-14], and subordinate Aspects thereof.

[1-16-1-2a] In Formula (II-1-A), preferably, r is 0 or 1 and $R^{10}$ is a $C_{1-4}$ alkyl group. Preferably, q is an integer of 1 to 3 and $R^9$ is a halogen atom or a $C_{1-4}$ alkyl group. $R^8$ is preferably a $C_{1-6}$ alkoxy group (the alkoxy group is substituted with 1 to 5—OH, 1 to 5 ethoxy, 1 to 5 methylsulfonyl, 1 to 5 sulfamoyl, 1 to 5 methylsulfamoyl, 1 to 5 dimethylsulfamoyl, 1 to 5 carbamoyl, 1 to 5 methylcarbamoyl, 1 to 5 dimethylcarbamoyl, 1 to 5—$NH_2$, 1 to 5 acetylamino, 1 to 5 methylsulfonylamino, 1 to 5 2-oxo-1-pyrrolidinyl, or 1 to 5 3-methyloxetane-3-yl) or (1,1-dioxidetetrahydro-2H-thiopyran-4-yl)oxy. More preferably, $R^8$ is a $C_{1-6}$ alkoxy group (the alkoxy group is substituted with 1 to 5 —OH, 1 to 5 ethoxy, 1 to 5 methylsulfonyl, 1 to 5—$NH_2$, 1 to 5 acetylamino, 1 to 5 methylsulfonylamino, 1 to 5 2-oxo-1-pyrrolidinyl, or 1 to 5 3-methyloxetane-3-yl) or (1,1-dioxidetetrahydro-2H-thiopyran-4-yl)oxy. Further preferably, $R^8$ is a $C_{1-6}$ alkoxy group (the alkoxy group is substituted with 1 to 2 —OH, 1 to 2 ethoxy, 1 to 2 methylsulfonyl, or 1 to 2 —NH$_2$).

[1-16-1-2-a] The compound of Formula (II-1-A) according to Aspect [1-16-1-2] is more preferably Formula (II-1-A)-a:

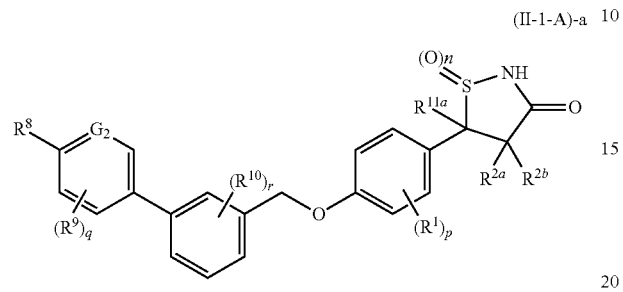

(II-1-A)-a (where n, p, $R^1$, $R^{2a}$, $R^{2b}$, and $R^{11a}$ are the same as defined in Formula (I); q, r, $R^8$, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of n, p, q, r, $R^1$, $R^{2a}$, $R^{2b}$, $R^8$, $R^9$, $R^{10}$, $R^{11}$, $R^{11a}$ and $G_2$ are the same as the preferable aspects described in any one of Aspects [1-1] to [1-15] and subordinate Aspects thereof. Preferable aspects of the partial structure of Formula (II-1-A)-a corresponding to Partial Structural Formula (A1a), Partial Structural Formula (B1a), or Partial Structural Formula (B-Het)-1a described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^8$, $R^9$, and $R^{10}$ are the same as described in Aspect [1-16-1-2a].

[1-16-1-2-b] The compound of Formula (II-1-A) according to Aspect [1-16-1-2] is more preferably Formula (II-1-A)-b:

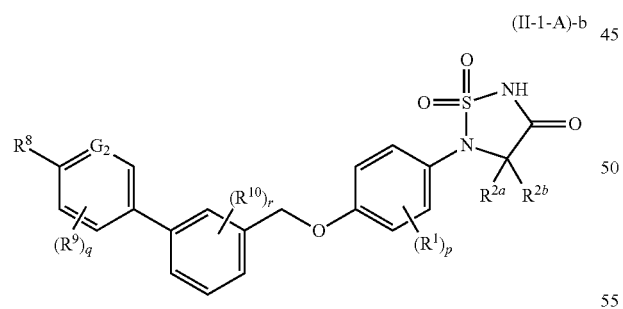

(II-1-A)-b (where p, $R^1$, $R^{2a}$, and $R^{2b}$ are the same as defined in Formula (I); q, r, $R^8$, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of p, q, r, $R^1$, $R^{2a}$, $R^{2b}$, $R^8$, $R^9$, $R^{10}$, and $G_2$ are the same as the preferable aspects described in any one of Aspects [1-1] to [1-15] and subordinate Aspects thereof. Preferable aspects of the partial structure of Formula (II-1-A)-b corresponding to Partial Structural Formula (A1a), Partial Structural Formula (B1a), or Partial Structural Formula (B-Het)-1b described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^8$, $R^9$, and $R^{10}$ are the same as described in Aspect [1-16-1-2a].

[1-16-1-2-c] The compound of Formula (II-1-A) according to Aspect [1-16-1-2] is more preferably Formula (II-1-A)-c:

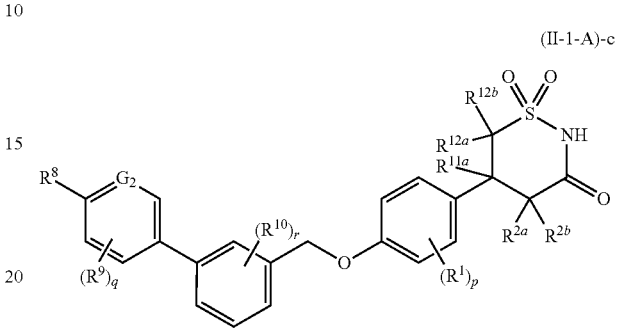

(II-1-A)-c (where p, $R^1$, $R^{2a}$, $R^{2b}$, $R^{11a}$, $R^{12a}$, and $R^{12b}$ are the same as defined in Formula (I); q, r, $R^8$, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of p, q, r, $R^1$, $R^{2a}$, $R^{2b}$, $R^8$, $R^9$, $R^{10}$, $R^{11a}$, $R^{12a}$, $R^{12b}$, and $G_2$ are the same as the preferable aspects described in any one of Aspects [1-1] to [1-15] and subordinate Aspects thereof. Preferable aspects of the partial structure of Formula (II-1-A)-c corresponding to Partial Structural Formula (A1a), Partial Structural Formula (B1a), or Partial Structural Formula (B-Het)-1c described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^8$, $R^9$, and $R^{10}$ are the same as described in Aspect [1-16-1-2a].

[1-16-1-2-d] The compound of Formula (II-1-A) according to Aspect [1-16-1-2] is more preferably Formula (II-1-A)-d:

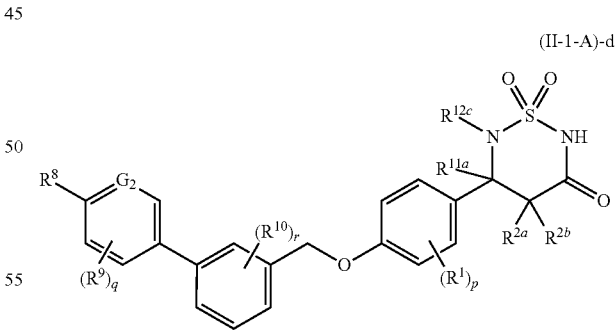

(II-1-A)-d (where p, $R^1$, $R^{2a}$, $R^{2b}$, $R^{11a}$, and $R^{12c}$ are the same as defined in Formula (I); q, r, $R^8$, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of p, q, r, $R^1$, $R^{2a}$, $R^{2b}$, $R^8$, $R^9$, $R^{10}$, $R^{11}$, $R^{12c}$, and $G_2$ are the same as the preferable aspects described in any one of Aspects [1-1] to [1-15] and subordinate Aspects thereof. Preferable aspects of the partial structure of Formula (II-A-1)-d corresponding to Partial Structural Formula (A1a), Partial Structural Formula (B1a), or Partial Structural Formula (B-Het)-1d described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^8$, $R^9$, and $R^{10}$ are the same as described in Aspect [1-16-1-2a].

[1-16-1-2-e] The compound of Formula (II-1-A) according to Aspect [1-16-1-2] is more preferably Formula (II-1-A)-e:

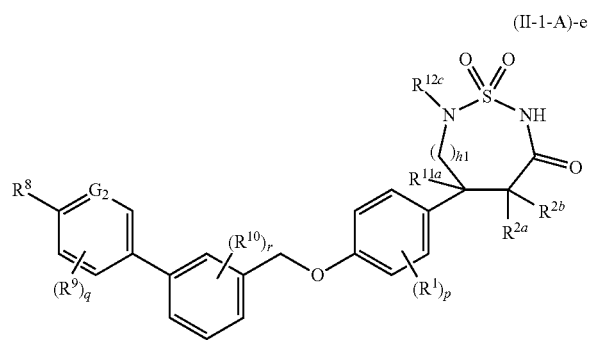

(II-1-A)-e (where p, $R^1$, $R^{2a}$, $R^{2b}$, $R^{11a}$, and $R^{12c}$ are the same as defined in Formula (I); q, r, $R^8$, $R^9$, and $R^{10}$ are the same as defined in Formula (A) described in Aspect [1-13-c]; h1 is the same as defined in Formula (B-Het)-1e described in Aspect [1-14-d]; and $G_2$ is the same as defined in Formula (A1a) described in Aspect [1-13-c-3-1]).

More specifically, preferable aspects of p, q, r, $R^1$, $R^{2a}$, $R^{2b}$, $R^8$, $R^9$, $R^{10}$, $R^{11a}$, $R^{12c}$, h1, and $G_2$ are the same as the preferable aspects described in any one of Aspects [1-1] to [1-15] and subordinate Aspects thereof. Preferable aspects of the partial structure of Formula (II-1-A)-e corresponding to Partial Structural Formula (A1a), Partial Structural Formula (B1a), or Partial Structural Formula (B-Het)-1e described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^8$, $R^9$, and $R^{10}$ are the same as described in Aspect [1-16-1-2a].

[1-16-1-2-f] The compound of Formula (II-1-A) according to Aspect [1-16-1-2] is more preferably Formula (II-1-A)-f:

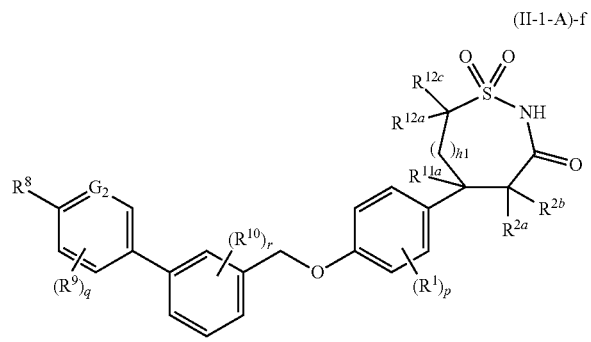

(II-1-A)-f (where p, $R^1$, $R^{2a}$, $R^{2b}$, $R^{11a}$, $R^{12a}$, and $R^{12b}$ are the same as defined in Formula (I); q, r, $R^8$, $R^9$, and $R^{10}$ are the same as defined in Formula (A) described in Aspect [1-13-c]; h1 is the same as defined in Formula (B-Het)-1f described in Aspect [1-14-d]; and $G_2$ is the same as defined in Formula (A1a) described in Aspect [1-13-c-3-1]).

More specifically, preferable aspects of p, q, r, $R^1$, $R^{2a}$, $R^{2b}$, $R^8$, $R^9$, $R^{10}$, $R^{11a}$, $R^{12a}$, $R^{12b}$, h1, and $G_2$ are the same as the preferable aspects described in any one of Aspects [1-1] to [1-15] and subordinate Aspects thereof. Preferable aspects of the partial structure of Formula (II-1-A)-f corresponding to Partial Structural Formula (A1a), Partial Structural Formula (B1a), or Partial Structural Formula (B-Het)-1f described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^8$, $R^9$, and $R^{10}$ are the same as described in Aspect [1-16-1-2a].

[1-16-1-3] The compound of Formula (II-1)-1 according to Aspect [1-16-1-1] is more preferably Formula (II-1-B):

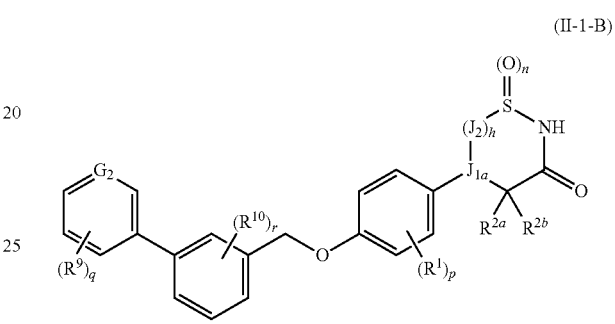

(II-1-B)

(where n, p, h, $J_2$, $R^1$, $R^{2a}$, and $R^{2b}$ are the same as defined in Formula (I); $J_{1a}$ is the same as defined in Formula (B)-1 described in Aspect [1-14-a-1]; q, r, $R^9$, and $R^{10}$ are the same as defined in Formula (A) described in Aspect [1-13-c]; and $G_2$ is the same as defined in Formula (A1a) described in Aspect [1-13-c-3-1]).

Specifically, preferable aspects of n, p, q, r, h, $J_{1a}$, $J_2$, $R^1$, $R^{2a}$, $R^{2b}$, $R^9$, $R^{10}$, and $G_2$ are the same as the preferable aspects described in any one of Aspects [1-1] to [1-15] and subordinate Aspects thereof. Preferable aspects of the partial structure of Formula (II-1-B) corresponding to Partial Structural Formula (A1c) or Partial Structural Formula (B1a) described in Aspect [1-13-c-3-1] or [1-14-a-4] are the same as described in any one of Aspects [1-13-c] and [1-14], and subordinate Aspects thereof.

[1-16-1-3a] In Formula (II-1-B), preferably, r is 0 or 1 and $R^{10}$ is a $C_{1-4}$ alkyl group. Preferably, q is an integer of 1 to 3 and $R^9$ is a halogen atom or a $C_{1-4}$ alkyl group.

[1-16-1-3-a] The compound of Formula (II-1-B) according to Aspect [1-16-1-3] is more preferably Formula (II-1-B)-a:

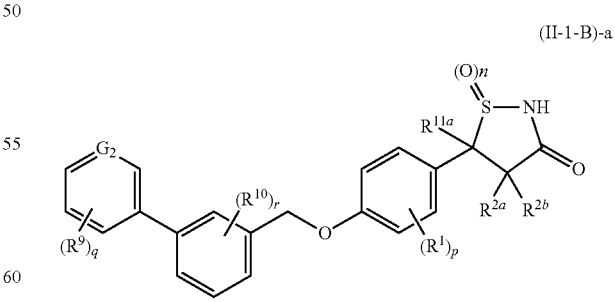

(II-1-B)-a (where n, p, $R^1$, $R^{2a}$, $R^{2b}$, and $R^{11a}$ are the same as defined in Formula (I); q, r, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of n, p, q, r, $R^1$, $R^{2a}$, $R^{2b}$, $R^9$, $R^{10}$, $R^{11a}$, and $G_2$ are the same as the preferable aspects described in any one of Aspects [1-1] to [1-15] and subordinate Aspects thereof. Preferable aspects of the partial structure of Formula (II-1-B)-a corresponding to Partial Structural Formula (A1c), Partial Structural Formula (B1a), or Partial Structural Formula (B-Het)-1a described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^9$, and $R^{10}$ are the same as described in Aspect [1-16-1-3a].

[1-16-1-3-b] The compound of Formula (II-1-B) according to Aspect [1-16-1-3] is more preferably Formula (II-1-B)-b:

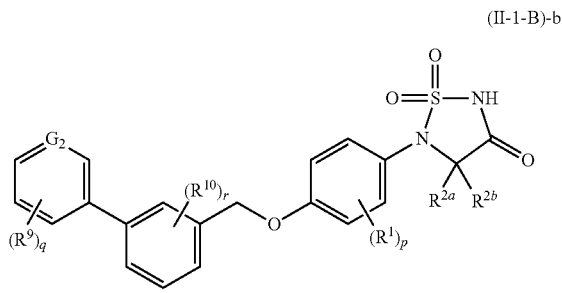

(II-1-B)-b (where p, $R^1$, $R^{2a}$, and $R^{2b}$ are the same as defined in Formula (I); q, r, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of p, q, r, $R^1$, $R^{2a}$, $R^{2b}$, $R^9$, $R^{10}$ and $G_2$ are the same as the preferable aspects described in any one of Aspects [1-1] to [1-15] and subordinate Aspects thereof. Preferable aspects of the partial structure of Formula (II-1-B)-b corresponding to Partial Structural Formula (A1c), Partial Structural Formula (B1a), or Partial Structural Formula (B-Het)-1b described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^9$, and $R^{10}$ are the same as described in Aspect [1-16-1-3a].

[1-16-1-3-c] The compound of Formula (II-1-B) according to Aspect [1-16-1-3] is more preferably Formula (II-1-B)-c:

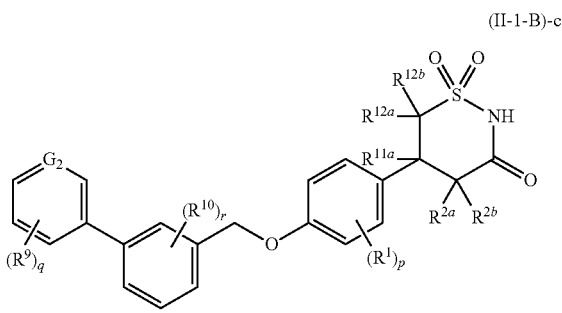

(II-1-B)-c (where p, $R^1$, $R^{2a}$, $R^{2b}$, $R^{11a}$, $R^{12a}$, and $R^{12b}$ are the same as defined in Formula (I); q, r, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of p, q, r, $R^1$, $R^{2a}$, $R^{2b}$, $R^9$, $R^{10}$, $R^{11a}$, $R^{12a}$, $R^{12b}$, and $G_2$ are the same as the preferable aspects described in any one of Aspects [1-1] to [1-15] and subordinate Aspects thereof. Preferable aspects of the partial structure of Formula (II-1-B)-c corresponding to Partial Structural Formula (A1c), Partial Structural Formula (B1a), or Partial Structural Formula (B-Het)-1c described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^9$, and $R^{10}$ are the same as described in Aspect [1-16-1-3a].

[1-16-1-3-d] The compound of Formula (II-1-B) according to Aspect [1-16-1-3] is more preferably Formula (II-1-B)-d:

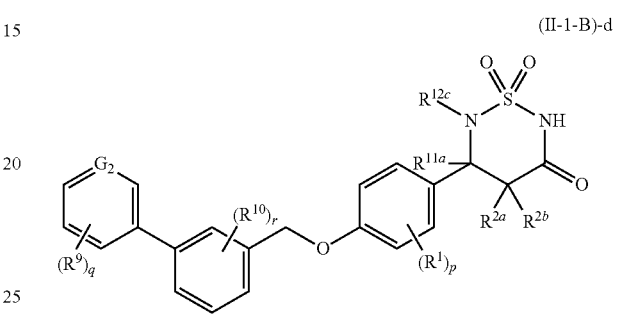

(II-1-B)-d (where p, $R^1$, $R^{2a}$, $R^{11a}$, and $R^{12c}$ are the same as defined in Formula (I); q, r, $R^9$, and $R^{10}$ are the same as defined in Formula (A) described in Aspect [1-13-c]; and $G_2$ is the same as defined in Formula (A1a) described in Aspect [1-13-c-3-1]).

More specifically, preferable aspects of p, q, r, $R^1$, $R^{2a}$, $R^{2b}$, $R^9$, $R^{10}$, $R^{11a}$, $R^{12c}$, and $G_2$ are the same as the preferable aspects described in any one of Aspects [1-1] to [1-15] and subordinate Aspects thereof. Preferable aspects of the partial structure of Formula (II-1-B)-d corresponding to Partial Structural Formula (A1c), Partial Structural Formula (B1a), or Partial Structural Formula (B-Het)-1d described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^9$, and $R^{10}$ are the same as described in Aspect [1-16-1-3a].

[1-16-1-3-e] The compound of Formula (II-1-B) according to Aspect [1-16-1-3] is more preferably Formula (II-1-B)-e:

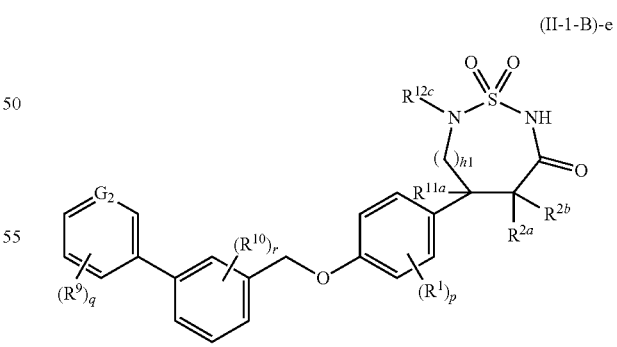

(II-1-B)-e (where p, $R^1$, $R^{2a}$, $R^{2b}$, R11a, and $R^{12c}$ are the same as defined in Formula (I); q, r, $R^9$, and $R^{10}$ are the same as defined in Formula (A) described in Aspect [1-13-c]; h1 is the same as defined in Formula (B-Het)-1e described in Aspect [1-14-d]; and $G_2$ is the same as defined in Formula (A1a) described in Aspect [1-13-c-3-1]).

More specifically, preferable aspects of p, q, r, $R^1$, $R^{2a}$, $R^{2b}$, $R^9$, $R^{10}$, $R^{11a}$, $R^{12c}$, h1, and $G_2$ are the same as the preferable aspects described in any one of Aspects [1-1] to [1-15] and subordinate Aspects thereof. Preferable aspects of the partial structure of Formula (II-1-B)-e corresponding to Partial Structural Formula (A1c), Partial Structural Formula (B1a), or Partial Structural Formula (B-Het)-1e described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^9$, and $R^{10}$ are the same as described in Aspect [1-16-1-3a].

[1-16-1-34] The compound of Formula (II-1-B) according to Aspect [1-16-1-3] is more preferably Formula (II-1-B)-f:

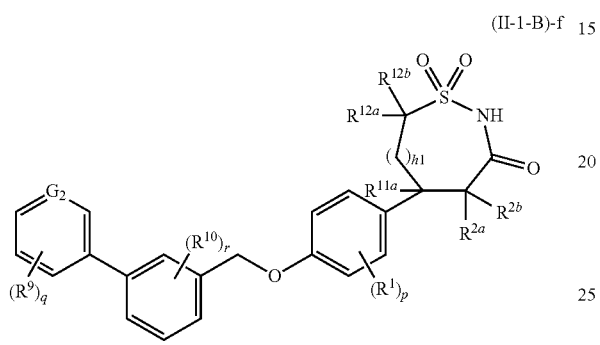

(II-1-B)-f (where p, $R^1$, $R^{2a}$, $R^{2b}$, $R^{11a}$, $R^{12a}$, and $R^{12b}$ are the same as defined in Formula (I); q, r, $R^9$, and $R^{10}$ are the same as defined in Formula (A) described in Aspect [1-13-c]; h1 is the same as defined in Formula (B-Het)-1f described in Aspect [1-14-d]; and $G_2$ is the same as defined in Formula (A1a) described in Aspect [1-13-c-3-1]).

More specifically, preferable aspects of p, q, r, $R^1$, $R^{2a}$, $R^{2b}$, $R^9$, $R^{10}$, $R^{11a}$, $R^{12a}$, $R^{12b}$, h1, and $G_2$ are the same as the preferable aspects described in any one of Aspects [1-1] to [1-15] and subordinate Aspects thereof. Preferable aspects of the partial structure of Formula (II-1-B)-f corresponding to Partial Structural Formula (A1c), Partial Structural Formula (B1a), or Partial Structural Formula (B-Het)-1f described in any one of Aspects [1-13-c-3-1] and [1-14], and subordinate Aspects thereof are the same as described in any one of Aspects [1-13-c] and [1-14], and subordinate Aspects thereof. Preferable aspects of q, r, $R^9$, and $R^{10}$ are the same as described in Aspect [1-16-1-3a].

[1-16-1-4] As the compound of Formula (I) according to Aspect [1] or of Formula (II) or Formula (II)-1 according to Aspect [1-16-1], a preferable compound is Formula (II-B):

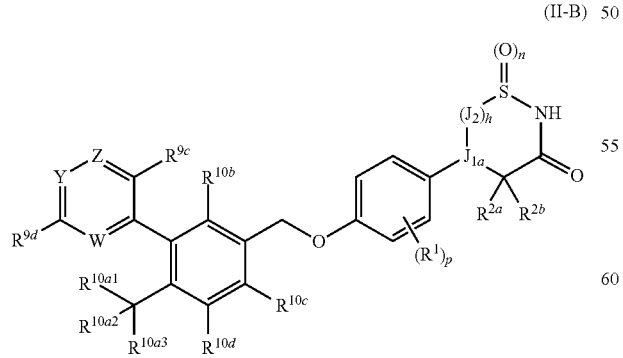

(II-B)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; and W, Y, Z, $R^{9c}$, $R^{9d}$, $R^{10a1}$, $R^{10a2}$, $R^{10a3}$, $R^{10b}$, $R^{10c}$, and $R^{10d}$, are the same as defined in Formula (A1)-1-1 or Formula ($R^{10a\prime}$) described in Aspect [1-13-c-11]).

More specifically, preferable aspects of n, p, h, $J_{1a}$, $J_2$, $R^1$, $R^{2a}$, $R^{2b}$, W, Y, Z, $R^{9c}$, $R^{9d}$, $R^{10a1}$, $R^{10a2}$, $R^{10a3}$, $R^{10b}$, $R^{10c}$, and $R^{10d}$ are the same as the preferable aspects described in any one of Aspects [1-1] to [1-15] and subordinate Aspects thereof.

[1-16-1-5] As the compound of Formula (I) according to Aspect [1] or of Formula (II) or Formula (II)-1 according to Aspect [1-16-1], a preferable compound is Formula (II-C):

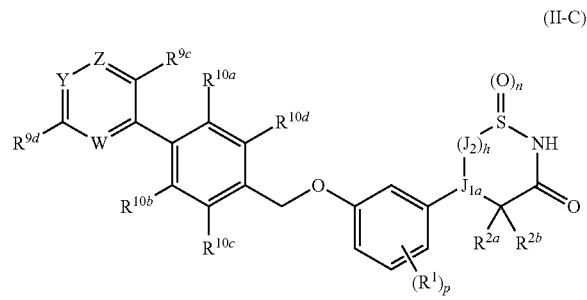

(II-C)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; and W, Y, Z, $R^{9c}$, $R^{9d}$, $R^{10a}$, $R^{10b}$, $R^{10c}$, and $R^{10d}$ are the same as defined in Formula (A1)-1-1 described in Aspect [1-13-c-11]).

More specifically, preferable aspects of n, p, h, $J_{1a}$, $J_2$, $R^1$, $R^{2a}$, $R^{2b}$, W, Y, Z, $R^{9c}$, $R^{9d}$, $R^{10a}$, $R^{10b}$, $R^{10c}$, and $R^{10d}$ are the same as the preferable aspects described in any one of Aspects [1-1] to [1-15] and subordinate Aspects thereof.

[1-16-2] As the compound of Formula (I) according to Aspect [1], a preferable compound is a compound in which the ring A is Formula (AA), that is, a compound of Formula (III):

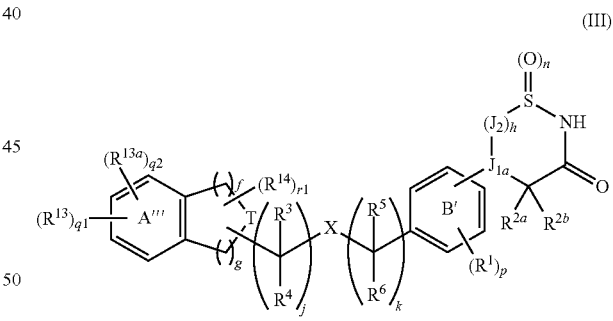

(III)

(where n, p, h, j, k, $J_2$, X, $R^1$, $R^{2a}$, $R^{2b}$, $R^3$, $R^4$, $R^5$, and $R^6$ are the same as defined in Formula (I); the ring B' and $J_{1a}$ are the same as defined in Formula (B)-1 described in Aspect [1-14-a-1]; and f, g, q1, q2, r1, the ring A''', T, $R^{13}$, $R^{13a}$, and $R^{14}$ are the same as defined in Formula (AA) described in Aspect [1-13-d]), a salt of the compound, or a solvate of the compound or the salt.

More specifically, preferable aspects of n, p, h, j, k, f, g, q1, q2, r1, the ring A''', the ring B', $J_{1a}$, $J_2$, T, X, $R^1$, $R^{2a}$, $R^{2b}$, $R^3$, $R^4$, $R^5$, $R^6$, $R^{13}$, $R^{13a}$, and $R^{14}$ are the same as described in any one of Aspects [1-1] to [1-15] and the subordinate Aspects thereof.

In Formula (III), X is preferably an oxygen atom or —NH—, more preferably an oxygen atom. In Formula (III), j is preferably 0 and k is preferably 0. In Formula (III), more preferably, X is an oxygen atom, j is 0, and k is 0.

In Formula (III), the ring B' is preferably a benzene ring.

In Formula (III), preferably, any one of q1 and q2 is 1 or more, more preferably, q2 is 1.

In Formula (III), preferably, X is an oxygen atom, j is 0, k is 0, and any one of q1 and q2 is 1 or more, more preferably, X is an oxygen atom, j is 0, k is 0, and q2 is 1.

[1-16-2a] In the compound of Formula (III) according to Aspect [1-16-2], compounds produced by optionally combining the groups of Partial Structural Formula (AA) (on the left of the left wavy line), Partial Structural Formula (B)-1 (on the right of the right wavy line), and Partial Structural Formula (C) (between the two wavy lines) in Formula (III) can be produced optionally:

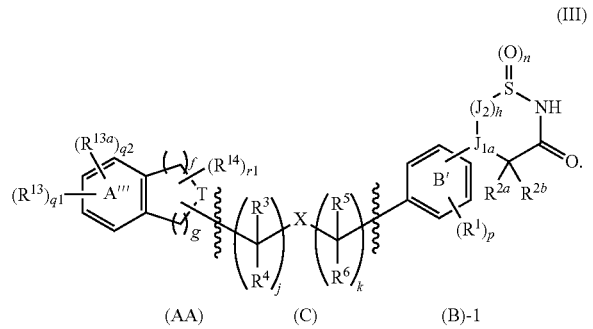

(AA)   (C)   (B)-1   (III)

More specifically, Partial Structural Formula (AA) is a group optionally selected from Formula (AA)-1, For (AA)-1-1, Formula (AA1), Formula (AA1)-1, Formula (AA1a)-1, Formula (AA1a)-1-1, Formula (AA1b), and Formula (AA1b)-1 described in Aspects [1-13-d-1] to [1-13-d-7-1]. Partial Structural Formula (B) is a group optionally selected from Formula (B 1), Formula (B2), Formula (B1a), and Formula (Bib) described in Aspects [1-14-a-2] and [1-14-a-4], and Partial Structural Formula (C) can be a group optionally selected from Formula (c1) to Formula (c6) described in Aspect [1-15]. An optional combination of each formula forms part of the compound of Formula (I) according to the present invention.

The cyclic amide structure bonded to the ring B' of Formula (III) is Partial Structural Formula (B-Het)-1 described in Aspect [1-14-e], and preferable examples of the cyclic amide structure include Formula (B-Het)-1a, (B-Het)-1b, Formula (B-Het)-1c, Formula (B-Het)-1d, Formula (B-Het)-1e, and Formula (B-Het)-1f described in Aspect [1-14-e-1]. In Formula (III), a compound having Formula (B-Het)-1a is Formula (III)-1a, a compound having Formula (B-Het)-1b is Formula (III)-1b, a compound having Formula (B-Het)-1c is Formula (III)-1c, a compound having Formula (B-Het)-1d is Formula (III)-1d, a compound having Formula (B-Het)-1e is Formula (III)-1e, and a compound having Formula (B-Het)-1f is Formula (III)-1f.

[1-16-2-1] The compound of Formula (III) according to Aspect [1-16-2] is preferably Formula (III-1):

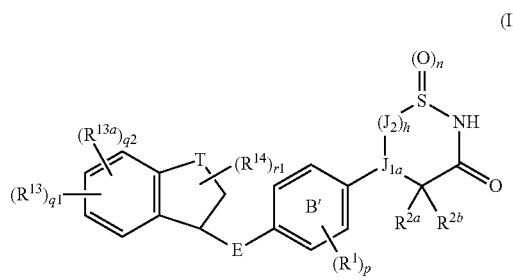

(III-1)

(where n, p, h, $J_2$, $R^1$, $R^{2a}$, and $R^{2b}$ are the same as defined in Formula (I); the ring B' and $J_{1a}$ are the same as defined in Formula (B)-1 described in Aspect [1-14-a-1]; q1, q2, r1, T, $R^{13}$, $R^{13a}$, and $R^{14}$ are the same as defined in Formula (AA) described in Aspect [1-13-d]; and E is a group optionally selected from Formula (c1) to Formula (c6) shown as specific examples of Formula (C) described in Aspect [1-15]).

More specifically, preferable aspects of n, p, h, q1, q2, r1, the ring B', T, $J_{1a}$, $J_2$, $R^1$, $R^{2a}$, $R^{2b}$, $R^{13}$, $R^{13a}$, $R^{14}$, and E are the same as the preferable aspects described in any one of Aspects [1-1] to [1-15] and subordinate Aspects thereof.

In Formula (III-1), E is preferably Formula (c1) or Formula (c4), more preferably Formula (c1).

In Formula (III-1), the ring B' is preferably a benzene ring.

In Formula (III-1), preferably, any one of q1 and q2 is 1 or more, and more preferably, q2 is 1.

In Formula (III-1), preferably, E is Formula (c1) and any one of q1 and q2 is 1 or more, more preferably, E is Formula (c1) and q2 is 1.

The cyclic amide structure bonded to the ring B' of Formula (III-1) is Partial Structural Formula (B-Het)-1 described in Aspect [1-14-e], and preferable examples of the cyclic amide structure include Formula (B-Het)-1a, (B-Het)-1b, Formula (B-Het)-1c, Formula (B-Het)-1d, Formula (B-Het)-1e, and Formula (B-Het)-1f described in Aspect [1-14-e-1]. In Formula (III-1), a compound having Formula (B-Het)-1a is Formula (III-1)-1a, a compound having Formula (B-Het)-1b is Formula (III-1)-1b, a compound having Formula (B-Het)-1c is Formula (III-1)-1c, a compound having Formula (B-Het)-1d is Formula (III-1)-1d, a compound having Formula (B-Het)-1e is Formula (III-1)-1e, and a compound having Formula (B-Het)-1f is Formula (III-1)-1f.

[1-16-2-2] The compound of Formula (III) according to Aspect [1-16-2] or of Formula (III-1) according to Aspect [16-2-1] is preferably Formula (III-1)-1:

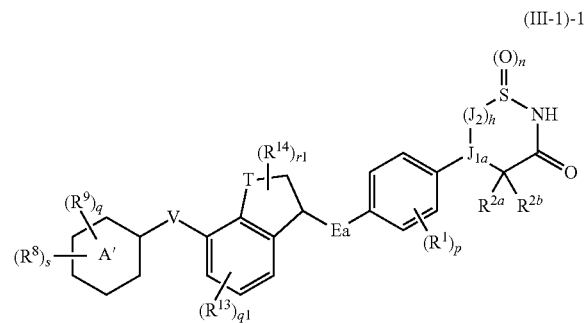

(III-1)-1

(where n, p, h, $J_2$, $R^1$, $R^{2a}$, and $R^{2b}$ are the same as defined in Formula (I); $J_{1a}$ is the same as defined in Formula (B)-1 described in Aspect [1-14-a-1]; q, s, the ring A', V, $R^8$, and $R^9$ are the same as defined in Formula (A) described in Aspect [1-13-c]; q1, r1, T, $R^{13}$, and $R^{14}$ are the same as defined in Formula (AA) described in Aspect [1-13-d]; and Ea is Formula (c1) or Formula (c4) shown as specific examples of Formula (C) described in Aspect [1-15]).

More specifically, preferable aspects of n, p, h, q, q1, r1, s, the ring A', V, T, $J_{1a}$, $J_2$, $R^1$, $R^{2a}$, $R^{2b}$, $R^8$, $R^9$, $R^{13}$, $R^{14}$, and Ea are the same as the preferable aspects described in any one of Aspects [1-1] to [1-15] and subordinate Aspects thereof.

In Formula (III-1)-1, Ea is preferably Formula (c1).

In Formula (III-1)-1, any one of q and s is preferably 1 or more.

In Formula (III-1)-1, more preferably, Ea is Formula (c1) and any one of q and s is 1 or more.

The cyclic amide structure bonded to the ring B of Formula (III-1)-1 is Partial Structural Formula (B-Het)-1 described in Aspect [1-14-e], and preferable examples of the cyclic amide structure include Formula (B-Het)-1a, (B-Het)-1b, Formula (B-Het)-1c, Formula (B-Het)-1d, Formula (B-Het)-1e, and Formula (B-Het)-1f described in Aspect [1-14-e-1]. In Formula (III-1)-1, a compound having Formula (B-Het)-1a is Formula (III-1)-1-1a, a compound having Formula (B-Het)-1b is Formula (III-1)-1-1b, a compound having Formula (B-Het)-1c is Formula (III-1)-1-1c, a compound having Formula (B-Het)-1d is Formula (III-1)-1-1d, a compound having Formula (B-Het)-1e is Formula (III-1)-1-1e, and a compound having Formula (B-Het)-1f is Formula (III-1)-1-1f.

[1-16-2-3] The compound of Formula (III-1)-1 according to Aspect [1-16-2-2] is preferably Formula (III-1-A)-1:

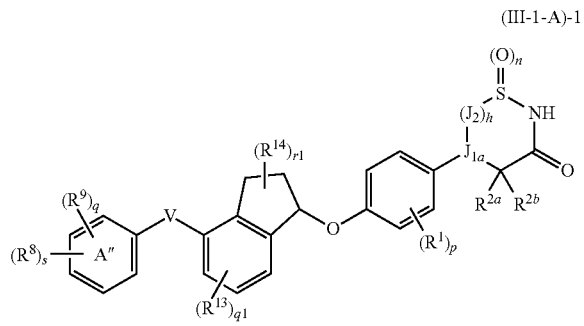

(III-1-A)-1

(where n, p, h, $J_2$, $R^1$, $R^{2a}$, and $R^{2b}$ are the same as defined in Formula (I); $J_{1a}$ is the same as defined in Formula (B)-1 described in Aspect [1-14-a-1]; q, s, the ring A", V, $R^8$, and $R^9$ are the same as defined in Formula (A) or Formula (A)-1 described in Aspect [1-13-c]; and q1, r1, $R^{13}$, and $R^{14}$ are the same as defined in Formula (AA) described in Aspect [1-13-d]).

More specifically, preferable aspects of n, p, h, q, q1, r1, s, the ring A", V, $J_{1a}$, $J_2$, $R^1$, $R^{2a}$, $R^{2b}$, $R^8$, $R^9$, $R^{13}$, and $R^{14}$ are the same as the preferable aspects described in any one of Aspects [1-1] to [1-15] and subordinate Aspects thereof.

In Formula (II-1-A)-1, any one of q and s is preferably 1 or more.

The cyclic amide structure bonded to the ring B of Formula (III-1-A)-1 is Partial Structural Formula (B-Het)-1 described in Aspect [1-14-e], and preferable examples of the cyclic amide structure include Formula (B-Het)-1a, (B-Het)-1b, Formula (B-Het)-1c, Formula (B-Het)-1d, Formula (B-Het)-1e, and Formula (B-Het)-1 f described in Aspect [1-14-e-1]. In Formula (II-1-A)-1, a compound having Formula (B-Het)-1a is Formula (II-1-A)-1-1a, a compound having Formula (B-Het)-1b is Formula (II-1-A)-1-1b, a compound having Formula (B-Het)-1c is Formula (III-1-A)-1-1c, a compound having Formula (B-Het)-1d is Formula (III-1-A)-1-1d, a compound having Formula (B-Het)-1e is Formula (III-1-A)-1-1e, and a compound having Formula (B-Het)-1f is Formula (III-1-A)-1-1f.

[1-16-2-4] The compound of Formula (III-1)-1 according to Aspect [1-16-2-2] is preferably Formula (III-1-B)-1:

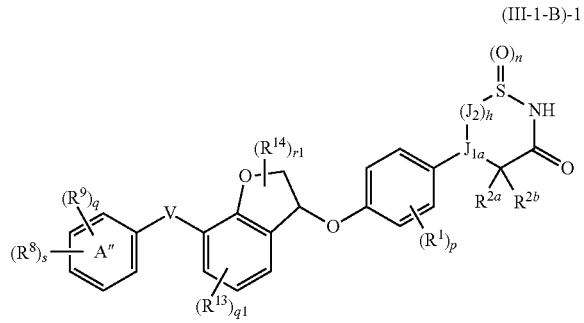

(III-1-B)-1

(where n, p, h, $J_2$, $R^1$, $R^{2a}$, and $R^{2b}$ are the same as defined in Formula (I); $J_{1a}$ is the same as defined in Formula (B)-1 described in Aspect [1-14-a-1]; q, s, the ring A", V, $R^8$, and $R^9$ are the same as defined in Formula (A) or Formula (A)-1 described in Aspect [1-13-c]; and q1, r1, $R^{13}$, and $R^{14}$ are the same as defined in Formula (AA) described in Aspect [1-13-d]).

More specifically, preferable aspects of n, p, h, q, q1, r1, s, the ring A", V, $J_{1a}$, $J_2$, $R^1$, $R^{2a}$, $R^{2b}$, $R^8$, $R^9$, $R^{13}$, and $R^{14}$ are the same as the preferable aspects described in any one of Aspects [1-1] to [1-15] and subordinate Aspects thereof.

In Formula (III-1-B)-1, any one of q and s is preferably 1 or more.

The cyclic amide structure bonded to the ring B of Formula (III-1-B)-1 is Partial Structural Formula (B-Het)-1 described in Aspect [1-14-e], and preferable examples of the cyclic amide structure include Formula (B-Het)-1a, (B-Het)-1b, Formula (B-Het)-1c, Formula (B-Het)-1d, Formula (B-Het)-1e, and Formula (B-Het)-1f described in Aspect [1-14-e-1]. In Formula (III-1-B)-1, a compound having Formula (B-Het)-1a is Formula (III-1-B)-1-1a, a compound having Formula (B-Het)-1b is Formula (III-1-B)-1-1b, a compound having Formula (B-Het)-1c is Formula (III-1-B)-1-1c, a compound having Formula (B-Het)-1d is Formula (III-1-B)-1-1d, a compound having Formula (B-Het)-1e is Formula (III-1-B)-1-1e, and a compound having Formula (B-Het)-1f is Formula (III-1-A)-1-1f.

[1-16-3] As the compound of Formula (I) according to Aspect [1], a preferable compound is a compound in which the ring A is Formula (A1)-IV and Formula (C) is Formula (c2), that is, Formula (IV-1):

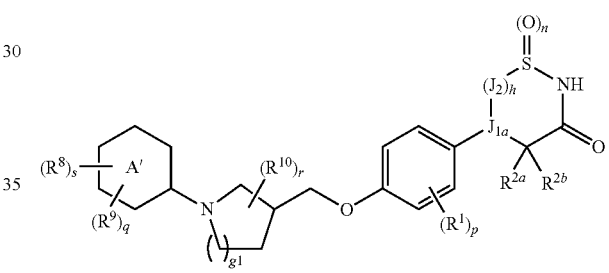

(IV-1)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; q, r, s, the ring A', $R^8$, $R^9$, and $R^{10}$ are the same as defined in Formula (A) described in Aspect [1-13-c]; and g1 is the same as defined in Formula (A1)-IV described in Aspect [1-13-e-2]).

More specifically, preferable aspects of n, p, h, q, r, s, the ring A', $J_{1a}$, $J_2$, $R^1$, $R^{2a}$, $R^{2b}$ $R^8$, $R^9$, $R^{10}$, and g1 are the same as the preferable aspects described in any one of Aspects [1-1] to [1-15] and subordinate Aspects thereof.

[1-16-3-1] As the compound of Formula (I) according to Aspect [1], a preferable compound is a compound in which the ring A is Formula (A3)-IV and Formula (C) is Formula (c2), that is, Formula (IV-3):

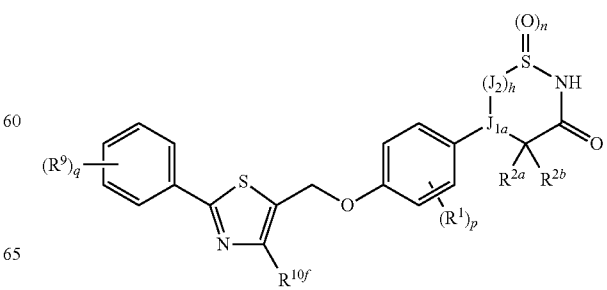

(IV-3)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; q and $R^9$ are the same as defined in Formula (A) described in Aspect [1-13-c]; and $R^{10f}$ is the same as defined in Formula (A2)-IV described in Aspect [1-13-e-3]).

More specifically, preferable aspects of n, p, h, q, $J_{1a}$, $J_2$, $R^1$, $R^{2a}$, $R^{2b}$, $R^9$, and $R^{10f}$ are the same as the preferable aspects described in any one of Aspects [1-1] to [1-15] and subordinate Aspects thereof.

[1-16-3-2] As the compound of Formula (I) according to Aspect [1], a preferable compound is a compound in which the ring A is Formula (A4)-IV and Formula (C) is Formula (c2), that is, Formula (IV-4):

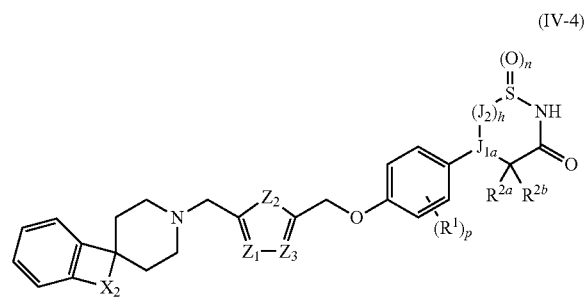

(IV-4)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; and $Z_1$, $Z_2$, $Z_3$, and $X_2$ are the same as defined in Formula (A4)-IV described in Aspect [1-13-e-8]).

More specifically, preferable aspects of n, p, h, $J_{1a}$, $J_2$, $R^1$, $R^{2a}$, $R^{2b}$, $Z_1$, $Z_2$, $Z_3$, and $X_2$ are the same as the preferable aspects described in any one of Aspects [1-1] to [1-15] and subordinate Aspects thereof.

[1-16-4] As the compound of Formula (I) according to Aspect [1], a preferable compound is a compound in which the ring A is Formula (A)-V and Formula (C) is Formula (c2), that is, Formula (V):

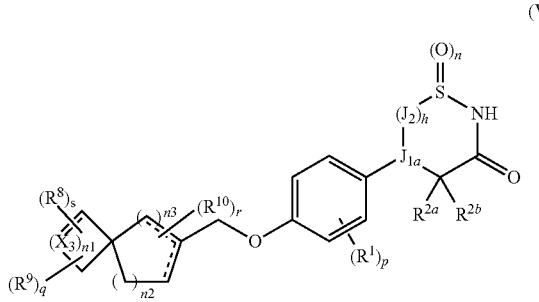

(V)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; q and s are the same as defined in Formula (A) described in Aspect [1-13-c]); r is the same as defined in Formula (AA) described in Aspect [1-13-d]; and $R^8$, $R^9$, $R^{10}$, n1, n2, n3, $X_3$, and the broken lines are the same as defined in Formula (A)-V described in Aspect [1-13-f]).

More specifically, preferable aspects of n, p, h, q, r, s, $J_{1a}$, $J_2$, $R^1$, $R^{2a}$, $R^{2b}$, $R^8$, $R^9$, $R^{10}$, n1, n2, n3, and $X_3$ are the same as the preferable aspects described in any one of Aspects [1-1] to [1-15] and subordinate Aspects thereof.

[1-16-4-1] The compound of Formula (V) according to Aspect [1-16-4] is further preferably Formula (V)-1:

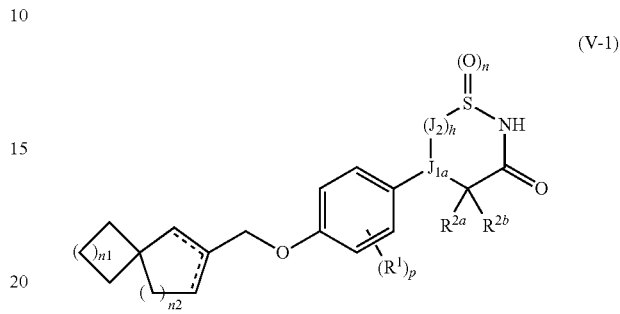

(V-1)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; and n1 and n2 are the same as defined in Formula (A)-V described in Aspect [1-13-f]).

More specifically, preferable aspects of n, p, h, $J_{1a}$, $J_2$, n1, n2, $R^1$, $R^{2a}$, and $R^{2b}$ are the same as the preferable aspects described in any one of Aspects [1-1] to [1-15] and subordinate Aspects thereof.

[1-16-4-2] As the compound of Formula (I) according to Aspect [1], a preferable compound is a compound in which the ring A is Formula (AA1)-V and Formula (C) is Formula (c2), that is, Formula (V-A):

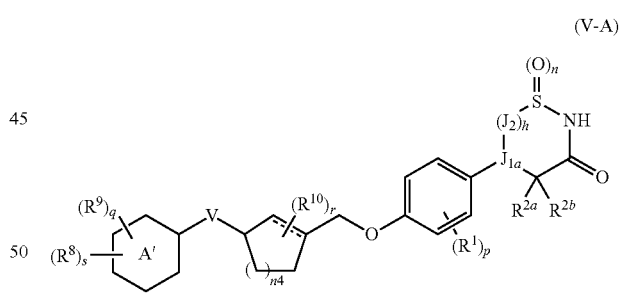

(V-A)

(where n, p, h, $J_2$, $R^1$, $R^{2a}$, and $R^{2b}$ are the same as defined in Formula (I) described in Aspect [1]; $J_{1a}$ is the same as defined in Formula (B)-1 described in Aspect [1-14-a-1]; q, s, the ring A', V, $R^8$, and $R^9$ are the same as defined in Formula (A) described in Aspect [1-13-c]); r is the same as defined in Formula (AA) described in Aspect [1-13-d]; $R^{10}$ and the broken lines are the same as defined in Formula (A)-V described in Aspect [1-13-f]; and n4 is the same as defined in Formula (AA)-V described in Aspect [1-13-f-8]).

More specifically, preferable aspects of n, p, h, q, r, s, the ring A', V, $J_{1a}$, $J_2$, $R^1$, $R^{2a}$, $R^{2b}$, $R^8$, $R^9$, $R^{10}$, and n4 are the same as the preferable aspects described in any one of Aspects [1-1] to [1-15] and subordinate Aspects thereof.

[1-16-5] As the compound of Formula (I) according to Aspect [1], a preferable compound is a compound in which the ring A is Formula (A)-VI, that is, Formula (VI):

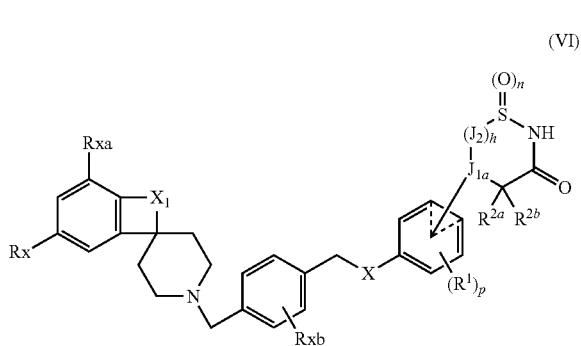

(where X, n, p, h, $J_2$, $R^1$, $R^{2a}$, $R^{2b}$, and the broken lines are the same as defined in Formula (I) described in Aspect [1]; $J_{1a}$ is the same as defined in Formula (B)-1 described in Aspect [1-14-a-1]; and Rx, Rxa, Rxb, and $X_1$ (including Ry and Rz) are the same as defined in Formula (A)-VI described in Aspect [1-13-g]). Preferable aspects of X, n, p, h, $J_{1a}$, $J_2$, $R^1$, $R^{2a}$, $R^{2b}$, Rx, Rxa, Rxb, and $X_1$ are the same as the preferable aspects described in any one of Aspects [1-1] to [1-15] and subordinate Aspects thereof.

Here, as preferable aspects and specific examples of the Partial Structural Formula (A)-VI moiety having a substituted spiropiperidinylmethyl group described in Aspect [1-13-g], the same as the preferable aspects and specific examples described in Aspects [1-13-g] and [1-13-g-1] can be mentioned.

[1-16-5-1] As the compound of Formula (I) according to Aspect [1], a preferable compound is a compound in which the ring A is Formula (AA)-VI, that is, Formula (VI-A):

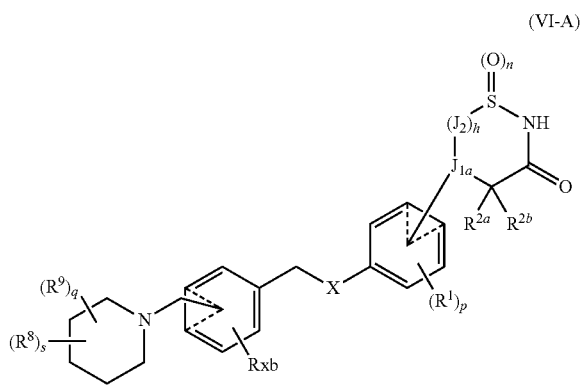

(where X, n, p, h, $J_2$, $R^1$, $R^{ea}$, and $R^{2b}$ are the same as defined in Formula (I) described in Aspect [1]; $J_{1a}$ is the same as defined in Formula (B)-1 described in Aspect [1-14-a-1]; q, s, $R^8$, and $R^9$ are the same as defined in Formula (A) described in Aspect [1-13-c]; Rxb is the same as defined in Formula (A)-VI described in Aspect [1-13-g]; and the broken lines are the binding position of an isothiazolyl group or a piperidinylmethyl group).

More specifically, preferable aspects of X, n, p, h, q, s, $J_{1a}$, $J_2$, $R^1$, $R^{2a}$, $R^{2b}$, $R^8$, $R^9$, and Rxb are the same as the preferable aspects described in any one of Aspects [1-1] to [1-15] and subordinate Aspects thereof.

[1-17] As the compound of Formula (I) according to Aspect [1], a preferable compound is Formula (I)-B1 or Formula (I)-B2:

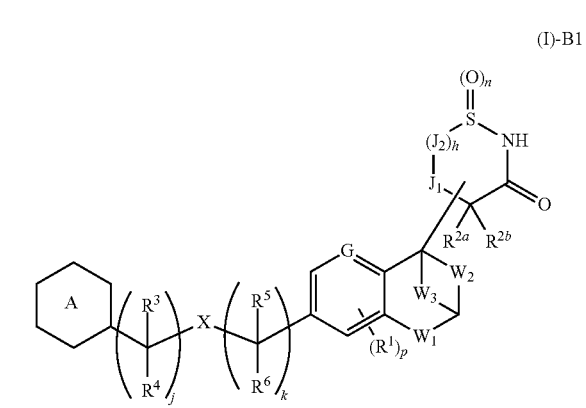

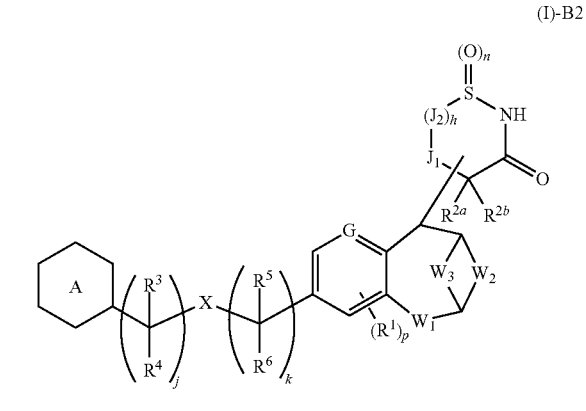

(where n, p, h, j, k, the ring A, X, $J_1$, $J_2$, $R^1$, $R^{2a}$, $R^{2b}$, $R^3$, $R^4$, $R^5$, and $R^6$ are the same as defined in Formula (I) described in Aspect [1]; and $W_1$, $W_2$, and $W_3$ are the same as in Formula (BB1) or Formula (BB2) described in Aspect [1-10]). $R^{2a}$, $R^{2b}$, More specifically, preferable aspects of n, p, h, j, k, the ring A, X, $J_1$, $J_2$, $R^1$, $R^{2a}$, $R^{2b}$, $R^3$, $R^4$, $R^5$, and $R^6$ are the same as the preferable aspects described in any one of Aspects [1-1] to [1-15] and subordinate Aspects thereof. Preferable aspects of G, $W_1$, $W_2$, and $W_3$ are the same as the preferable aspects described in Aspect [1-10] and subordinate Aspects thereof.

[1-17-a] As the compound of Formula (I)-B1 or Formula (I)-B2, a preferable compound is a compound in which the ring A is a $C_{6-14}$ aryl group which is optionally substituted with 1 to 5 L(s) or a 3- to 14-membered heterocyclic group which is optionally substituted with 1 to 5 L(s) and the linker moiety containing X is Formula (c1) or Formula (c4) described in Aspect [1-15].

A more preferable compound thereof is a compound in which the ring A is a phenyl group which is optionally substituted with 1 to 5 L(s), a phthalazinyl group which is optionally substituted with 1 to 5 L(s), or Formula (A)-VIII described in Aspect [1-13-j] and the linker moiety containing X is Formula (c1).

A further preferable compound thereof is a compound in which the ring A is a phenyl group (the phenyl group is optionally substituted with 1 to 3 halogen atom(s), 1 to 3 cyano group(s), 1 to 3 $C_{1-6}$ alkyl group(s), 1 to 3 halogenated $C_{1-6}$ alkyl group(s), 1 to 3 $C_{1-6}$ alkoxy group(s), or 1 to 3 —$SF_5$), a phthalazinyl group (the phthalazinyl group is optionally substituted with 1 to 3 halogen atom(s), 1 to 3 cyano group(s), 1 to 3 $C_{1-6}$ alkyl group(s), 1 to 3 halogenated $C_{1-6}$ alkyl group(s), 1 to 3 $C_{1-6}$ alkoxy group(s), or 1 to 3 —$SF_5$), or Formula (A)-VIII and the linker moiety containing X is Formula (c1).

[1-18] As described above, Aspects [1-1] to [1-17] and subordinate Aspects thereof of the present invention, respective preferable aspects described above, and the definitions of the substituents can be optionally combined, so that the preferable aspects of the compound of Formula (I) according to Aspect [1] can be optionally provided.

[1-19] Examples of preferable compounds as the compound of Formula (I) according to Aspect [1] include the following:

5-[4-[[3-[4-(2-ethoxyethoxy)-2,6-dimethylphenyl]phenyl]methoxy]phenyl]-1-oxo-1, 2-thiazolidin-3-one (Example 1);

5-[4-[[3-[4-(2-ethoxyethoxy)-3-fluoro-2,6-dimethylphenyl]phenyl]methoxy]phenyl]-1-oxo-1,2-thiazolidin-3-one (Example 2);

5-[4-[[3-[3-fluoro-4-(3-hydroxy-3-methylbutoxy)-2,6-dimethylphenyl]phenyl]methoxy]phenyl]-1-oxo-1,2-thiazolidin-3-one (Example 3);

5-[4-[[3-[4-(3-hydroxy-3-methylbutoxy)-2,6-dimethylphenyl]phenyl]methoxy]phenyl]-1-oxo-1,2-thiazolidin-3-one (Example 4);

5-[4-[[3-[2,4-dimethyl-6-(3-methylsulfonylpropoxy)pyridin-3-yl]phenyl]methoxy]phenyl]-1-oxo-1,2-thiazolidin-3-one (Example 5);

5-[4-[[3-[6-(3-hydroxy-3-methylbutoxy)-2,4-dimethylpyridin-3 yl]phenyl]methoxy]phenyl]-1-oxo-1,2-thiazolidin-3-one trifluoro acetic acid salt (Example 6);

5-[4-[[3-[4-(3-hydroxy-3-methylbutoxy)-2,5-dimethylphenyl]phenyl]methoxy]phenyl]-1-oxo-1,2-thiazolidin-3-one (Example 7);

5-[4-[[3-[4-(3-hydroxypropoxy)-2,6-dimethylphenyl]phenyl]methoxy]phenyl]-1-oxo -1,2-thiazolidin-3-one (Example 8);

5-[4-[[3-[4-[(2R)-2,3-dihydroxypropoxy]-2,6-dimethylphenyl]phenyl]methoxy]phenyl]-1-oxo-1,2-thiazolidin-3-one (Example 9);

5-[4-[[3-[4-[3-hydroxy-2-(hydroxymethyl)propoxy]-2,6-dimethylphenyl]phenyl] methoxy]phenyl]-1-oxo-1,2-thiazolidin-3-one (Example 10);

5-[4-[[3-[4-(3-aminopropoxy)-2,6-dimethylphenyl]phenyl]methoxy]phenyl]-1-oxo-1,2-thiazolidin-3-one trifluoro acetic acid salt (Example 11);

5-[4-[[3-[4-[(3R)-3-hydroxybutoxy]-2,6-dimethylphenyl]phenyl]methoxy]phenyl]-1-oxo-1,2-thiazolidin-3-one (Example 12);

5-[4-[[3-[2,6-dimethyl-4-(3-methylsulfonylpropoxy)phenyl]phenyl]methoxy]phenyl]-1-oxo-1,2-thiazolidin-3-one (Example 13);

5-[4-[[3-(2,6-dimethylphenyl)phenyl]methoxy]phenyl]-1,1-dioxo-1,2,5-thiadiazolidin-3-one (Example 14);

5-[4-[[3-[2,6-dimethyl-4-(3-methylsulfonylpropoxy)phenyl]phenyl]methoxy]phenyl]-1,1-dioxo-1,2,5-thiadiazolidin-3-one (Example 15);

5-[2-chloro-4-[[3-(2,6-dimethylphenyl)phenyl]methoxy]phenyl]-1,1-dioxo-1,2,5-thiadiazolidin-3-one (Example 16);

5-[4-[[3-(2,6-dimethylphenyl)phenyl]methoxy]-2-methylphenyl]-1,1-dioxo-1,2,5-thiadiazolidin-3-one (Example 17);

5-[4-[[3-(2,6-dimethylphenyl)phenyl]methoxy]phenyl]-4-methyl-1,1-dioxo-1,2,5-thiadiazolidin-3-one (Example 18);

5-[4-[[3-(2,6-dimethyl-4-(3-methylsulfonylpropoxy)phenyl]phenyl]methoxy]phenyl]-1,1-dioxo-1,2-thiazolidin-3-one (Example 19);

5-[4-[[346-(3-hydroxy-3-methylbutoxy)-2,4-dimethylpyridin-3-yl]phenyl]methoxy]phenyl]-1,1-dioxo-1,2-thiazolidin-3-one (Example 20);

5-[4-[[3-(2,6-dimethylphenyl)phenyl]methoxy]phenyl]-1,1-dioxo-1,2,6-thiadiazinane-3-one (Example 21);

5-[4-[[3-(2,6-dimethylphenyl)phenyl]methoxy]phenyl]-1,1-dioxo-1,2-thiazinan-3-one (Example 22);

5-(4-(((R)-4-(6-(3-hydroxy-3-methylbutoxy)-2-methylpyridin-3-yl)-2,3-dihydro-1H-inden-1-yl)oxy)phenyl)-1-oxo-1,2-thiazolidin-3-one (A) (Example 23);

5-[4-[[(1R)-4-[6-(3-hydroxy-3-methylbutoxy)-2,6-dimethylphenyl]-2,3-dihydro-1H-inden-1-yl]oxy]phenyl]-1-oxo-1,2-thiazolidin-3-one (A) (Example 24);

4-(((1R)-1-(4-(1-oxo-1,2-thiazolidin-3-one-5-yl)phenoxy)-2,3-dihydro-1H-inden-4-yl)oxy)benzonitrile (A) (Example 25);

4-(((1R)-1-(4-(1,1-dioxo-1,2,6-thiadiazinan-3-one-5-yl)phenoxy)-2,3-dihydro-1H-inden-4-yl)oxy)benzonitrile (Example 26);

5-(4-(((R)-4-phenoxy-2,3-dihydro-1H-inden-1-yl)oxy)phenyl)-1-oxo-1,2-thiazolidin-3-one (Example 27);

5-(4-((7-(trifluoromethyl)-2,3-dihydrobenzofuran-3-yl)oxy)phenyl)-1-oxo-1,2-thiazolidin-3-one (Example 28);

5-(4-(((R)-4-bromo-2,3-dihydro-1H-inden-1-yl)oxy)phenyl)-1-oxo-1,2-thiazolidin-3-one (Example 29);

5-(4-(((R)-4-(2,6-dimethyl-4-(3-(methylsulfonyl)propoxy)phenyl)-2,3-dihydro-1H-inden-1-yl)oxy)phenyl)-1-oxo-1,2-thiazolidin-3-one (Example 30);

5-[4-[[3-[2,6-dimethyl-4-(3-methylsulfonylpropoxy)phenyl]phenyl]methoxy]phenyl]-1,1-dioxo-1,2-thiazinan-3-one (Example 31);

4-(((1R)-1-(4-(1,1-dioxo-3-oxo-1,2-thiazinan-5-yl)phenoxy)-2,3-dihydro-1H-inden-4-yl)oxy)benzonitrile (Example 32);

5-(4-(((R)-4-bromo-2,3-dihydro-1H-inden-1-yl)oxy)phenyl)-1,1-dioxo-1,2-thiazinane-3-one (Example 33);

5-(4-(((R)-4-(4-(3-hydroxy-3-methylbutoxy)-2,6-dimethylphenyl)-2,3-dihydro-1H-inden-1-yl)oxy)phenyl)-1,1-dioxo-1,2-thiazinan-3-one (Example 34); and 5-[4-[[3-[6-(3-hydroxy-3-methylbutoxy)-2,4-dimethylpyridin-3-yl]phenyl]methoxy]phenyl]-1,1-dioxo-1,2-thiazinan-3-one (Example 35), a salt of the compound, a solvate of the compound or the salt, and an optical isomer thereof. Examples of the above preferable compounds also include the compounds of Structural Formulae 3 to 12 below in (Example 1P) to (Example 157P), a salt of the compound, a solvate of the compound or the salt, and an optical isomer thereof.

[1-19-1] In the compound of Formula (I) according to Aspect [1] or of Formula (I)-1 according to Aspect [1-16], compounds produced by optionally combining the groups of Partial Structural Formula (A)-(C) (on the left of the wavy line) and Partial Structural Formula (B)-1 (on the right of the wavy line) in Formula (I)-1 can be produced optionally:

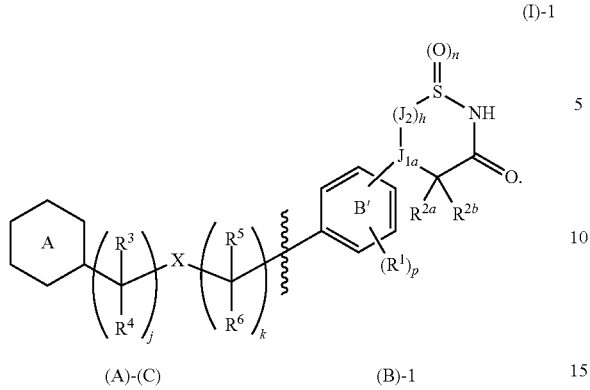
(I)-1
More specifically, Partial Structural Formula (B)-1 is a group optionally selected from Formula (B1a-het1) to Formula (B1a-het5) or Formula (B2a-het1) to Formula (B2a-het5) described below, and Partial Structural Formula (A)-(C) is a group optionally selected from Formula (a-1) to Formula (a-109) described below.
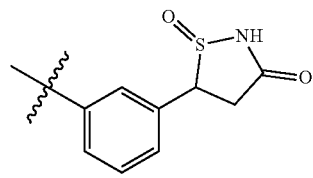
(B1a-het1)
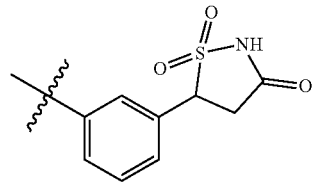
(B1a-het2)
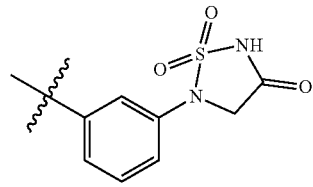
(B1a-het3)
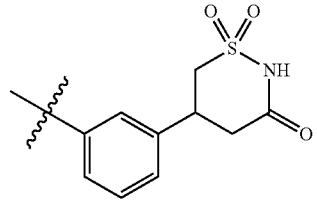
(B1a-het4)
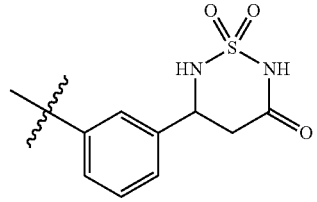
(B1a-het5)
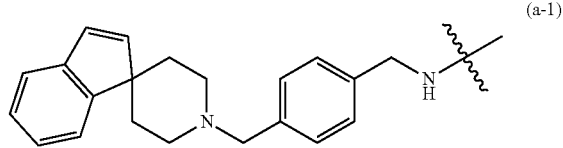
(B2a-het1), (B2a-het2), (B2a-het3), (B2a-het4), (B2a-het5)
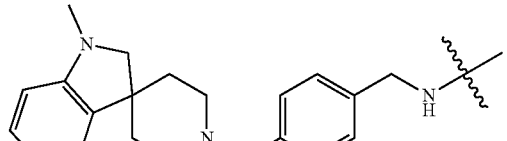
(a-1), (a-2)
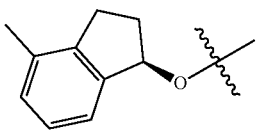
(a-3)

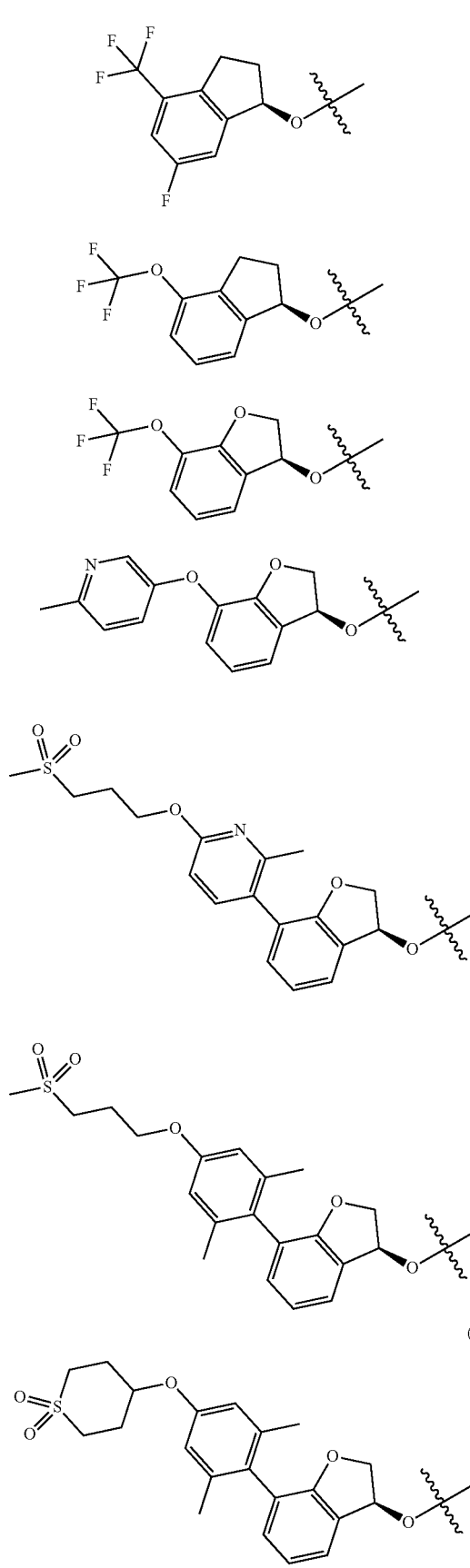
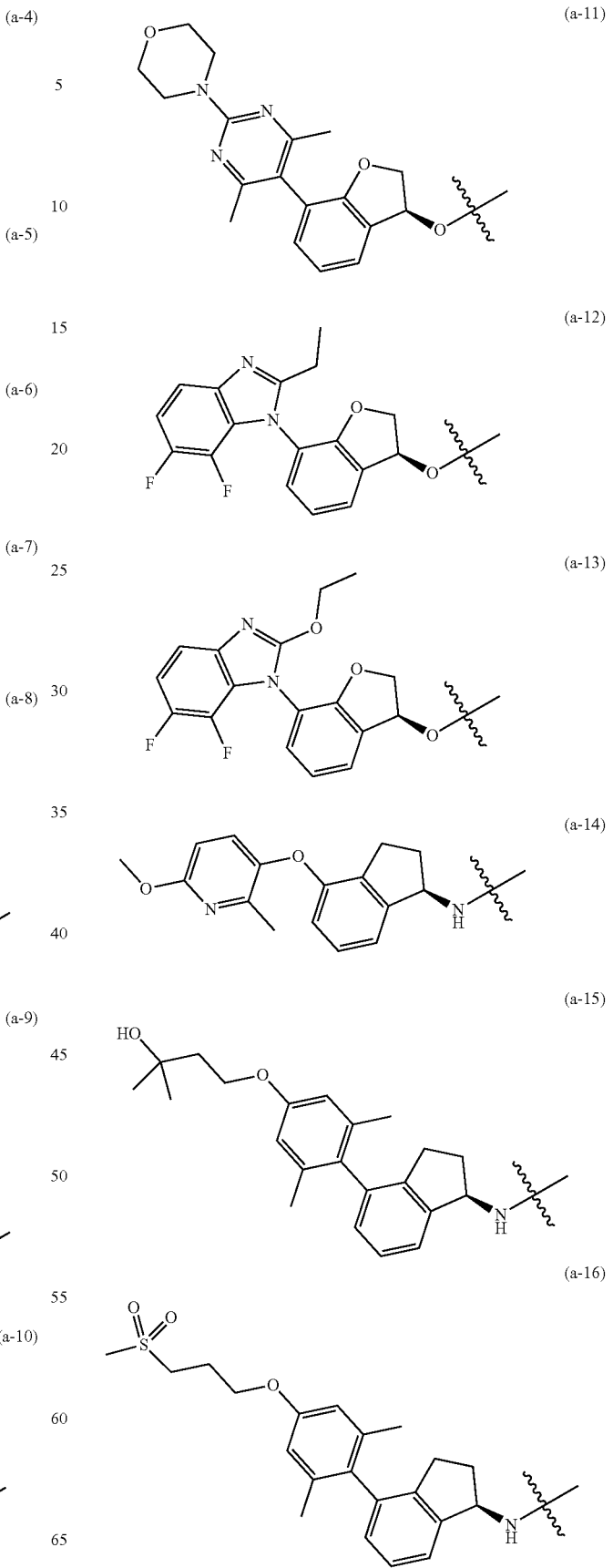

(a-17)
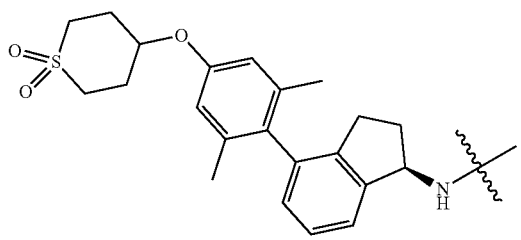
(a-18)
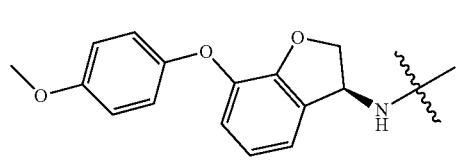
(a-19)
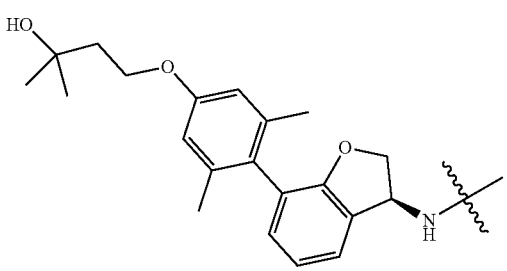
(a-20)
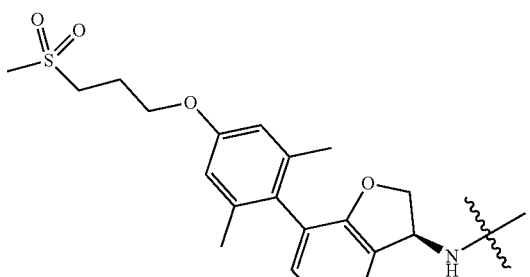
(a-21)
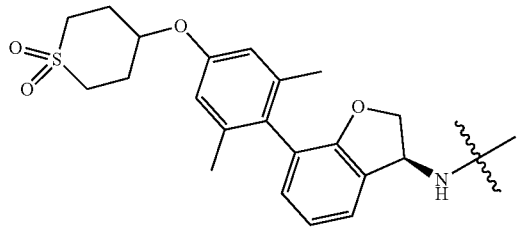
(a-22)
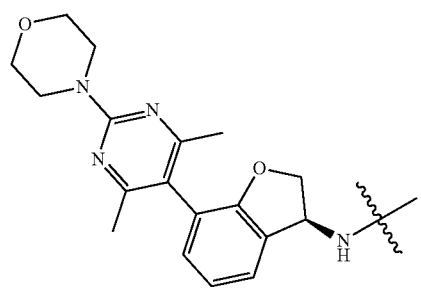
(a-23)
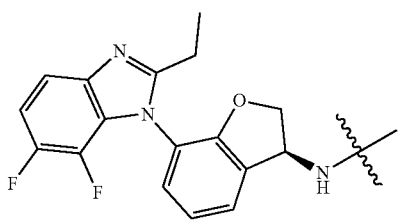
(a-24)
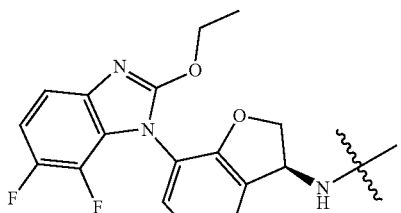
(a-25)
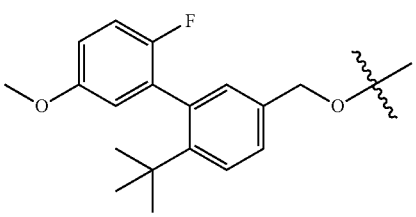
(a-26)
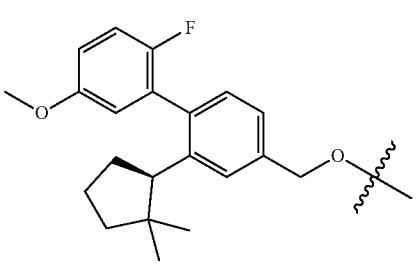
(a-27)
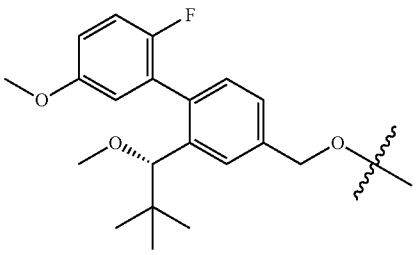
(a-28)
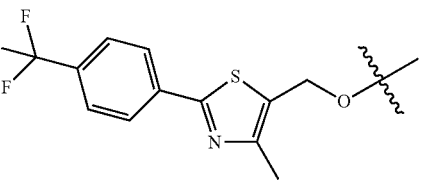
(a-29)
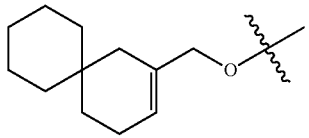

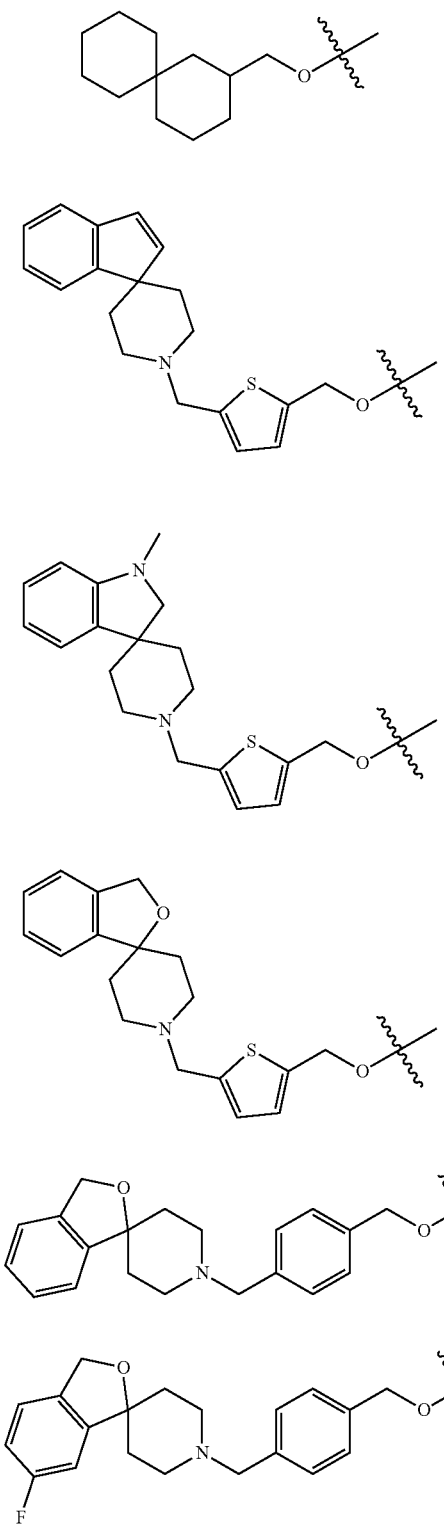
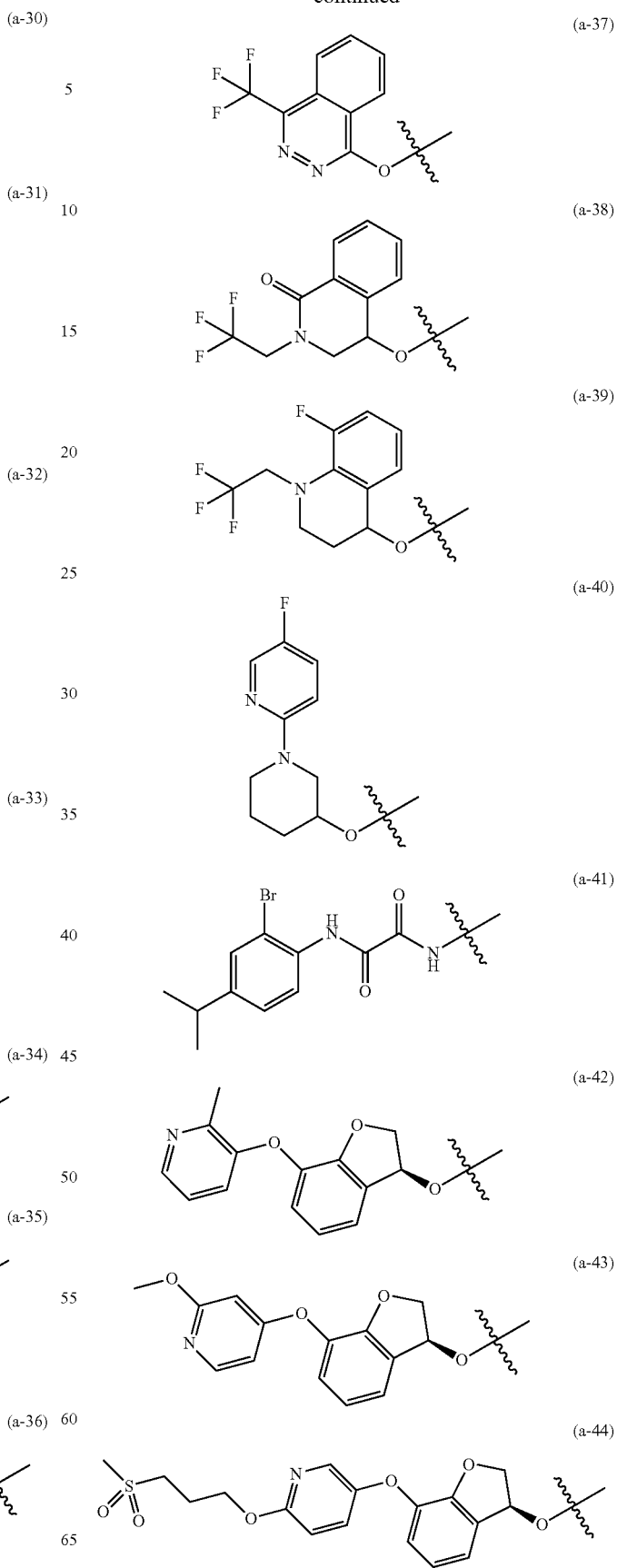

(a-45) 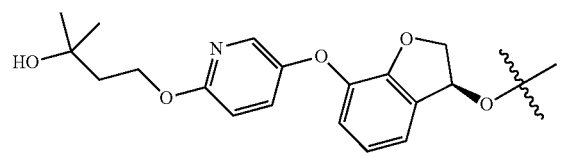
(a-46) 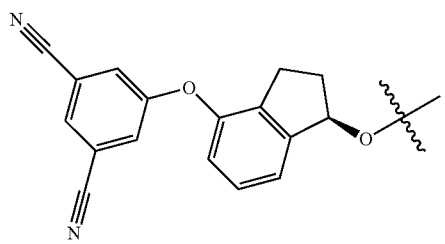
(a-47) 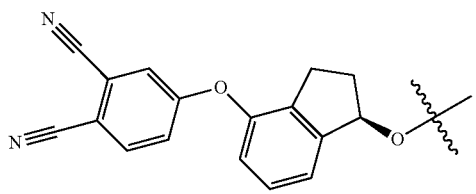
(a-48) 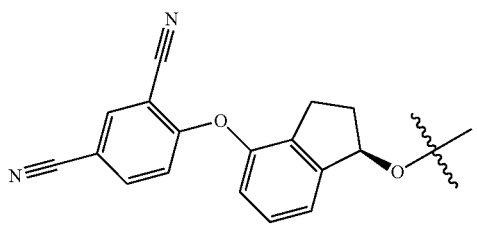
(a-49) 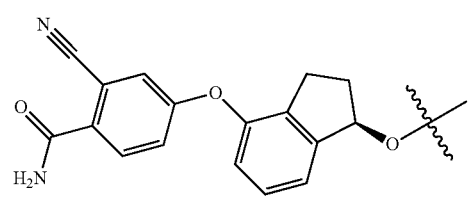
(a-50) 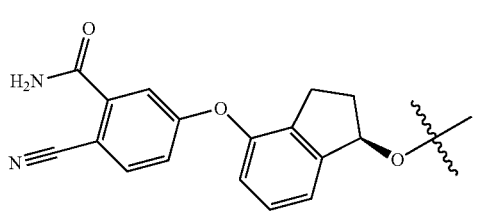
(a-51) 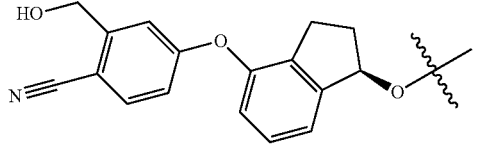
(a-52) 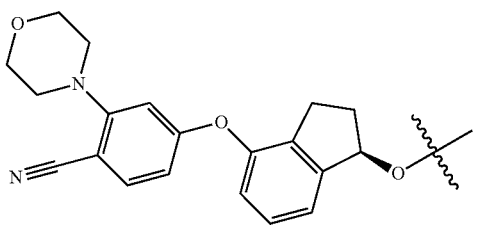
(a-53) 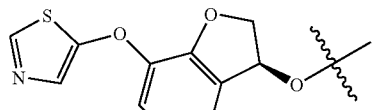
(a-54) 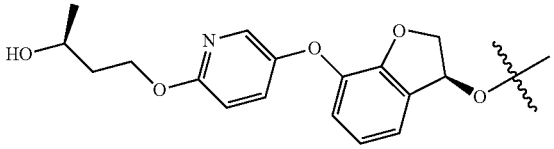
(a-55) 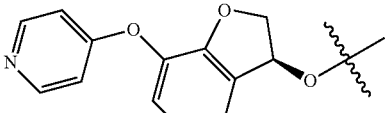
(a-56) 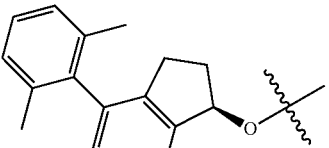
(a-57) 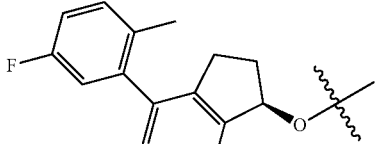
(a-58) 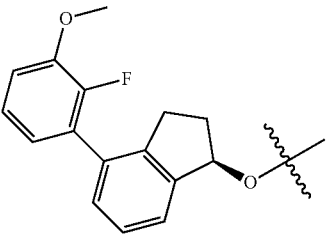
(a-59) 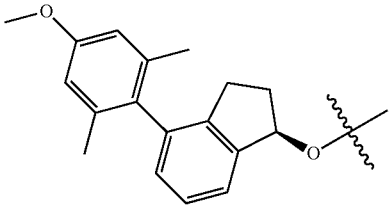

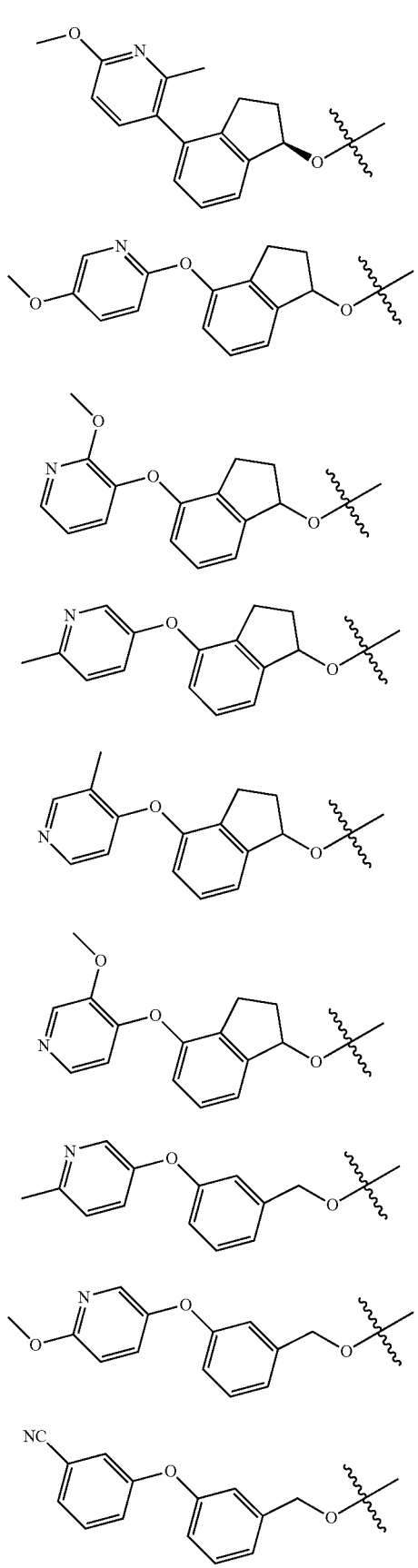
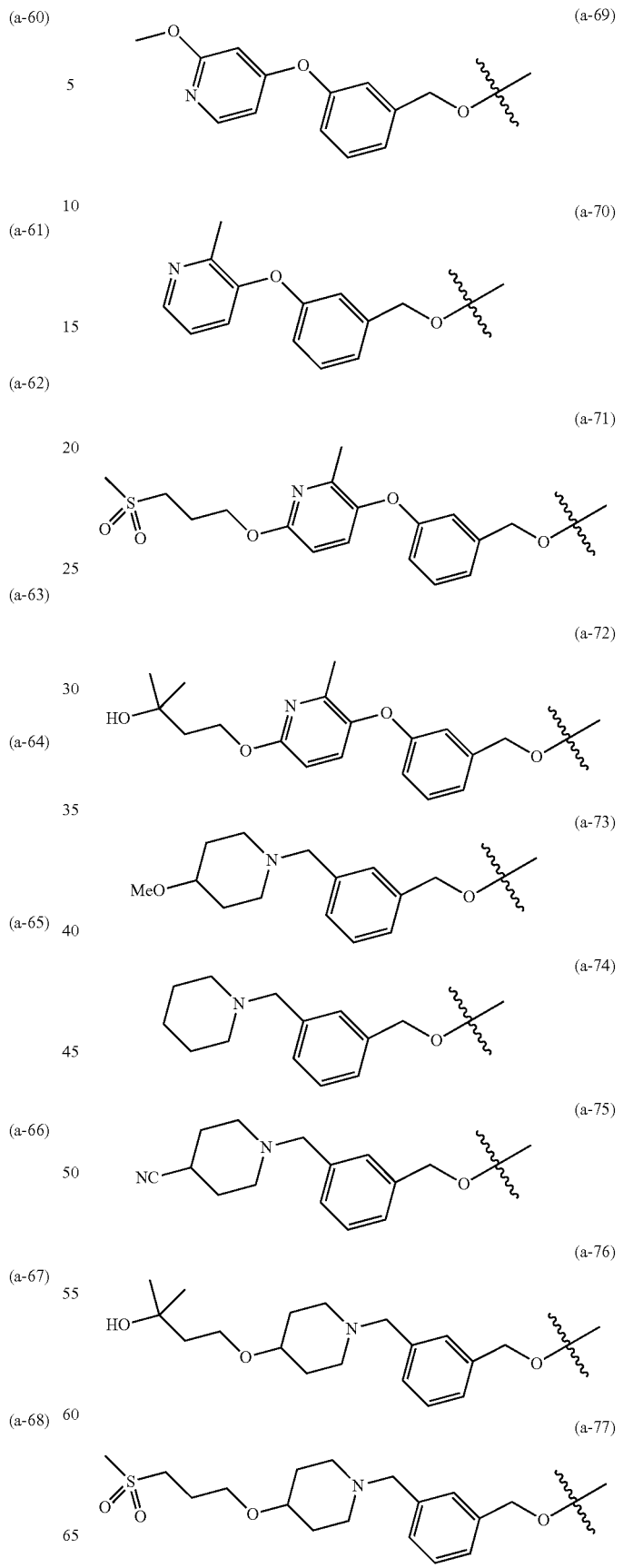

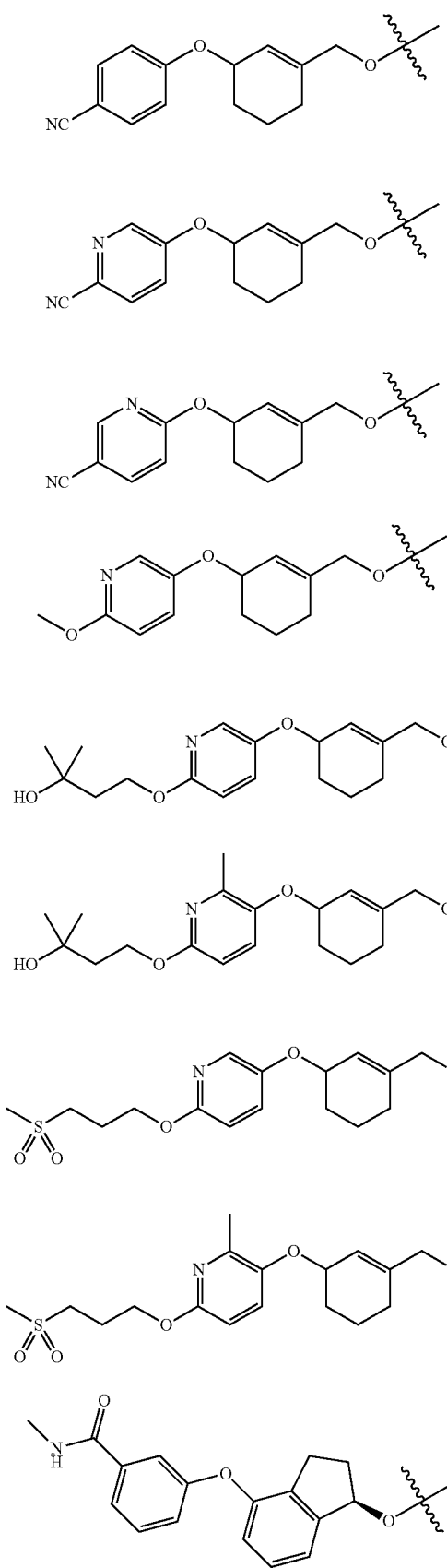
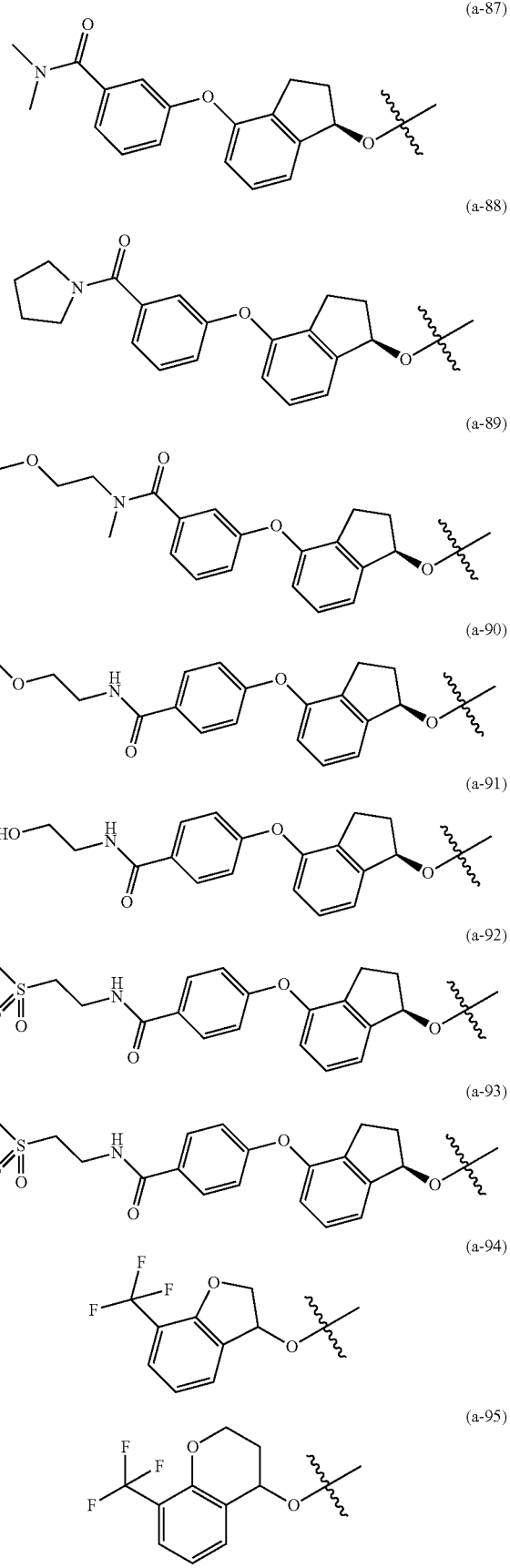

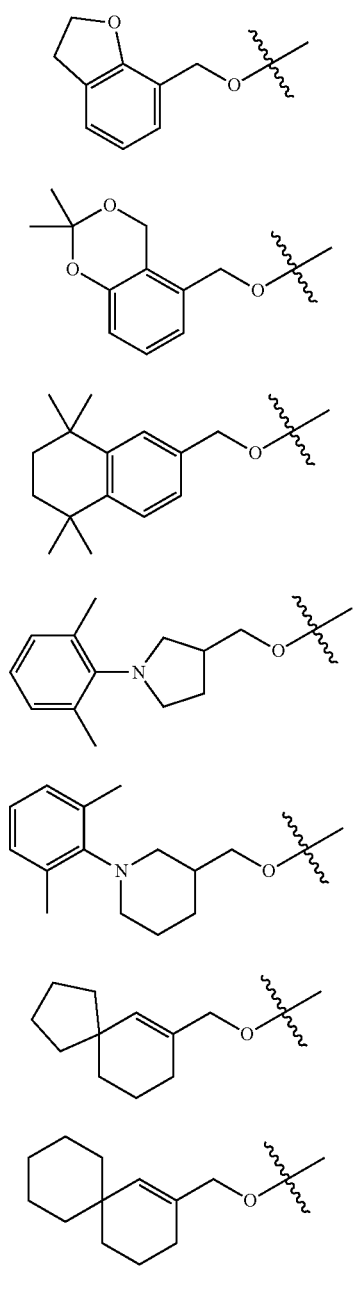
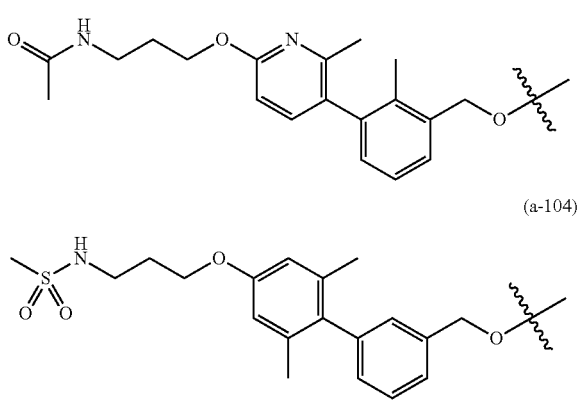
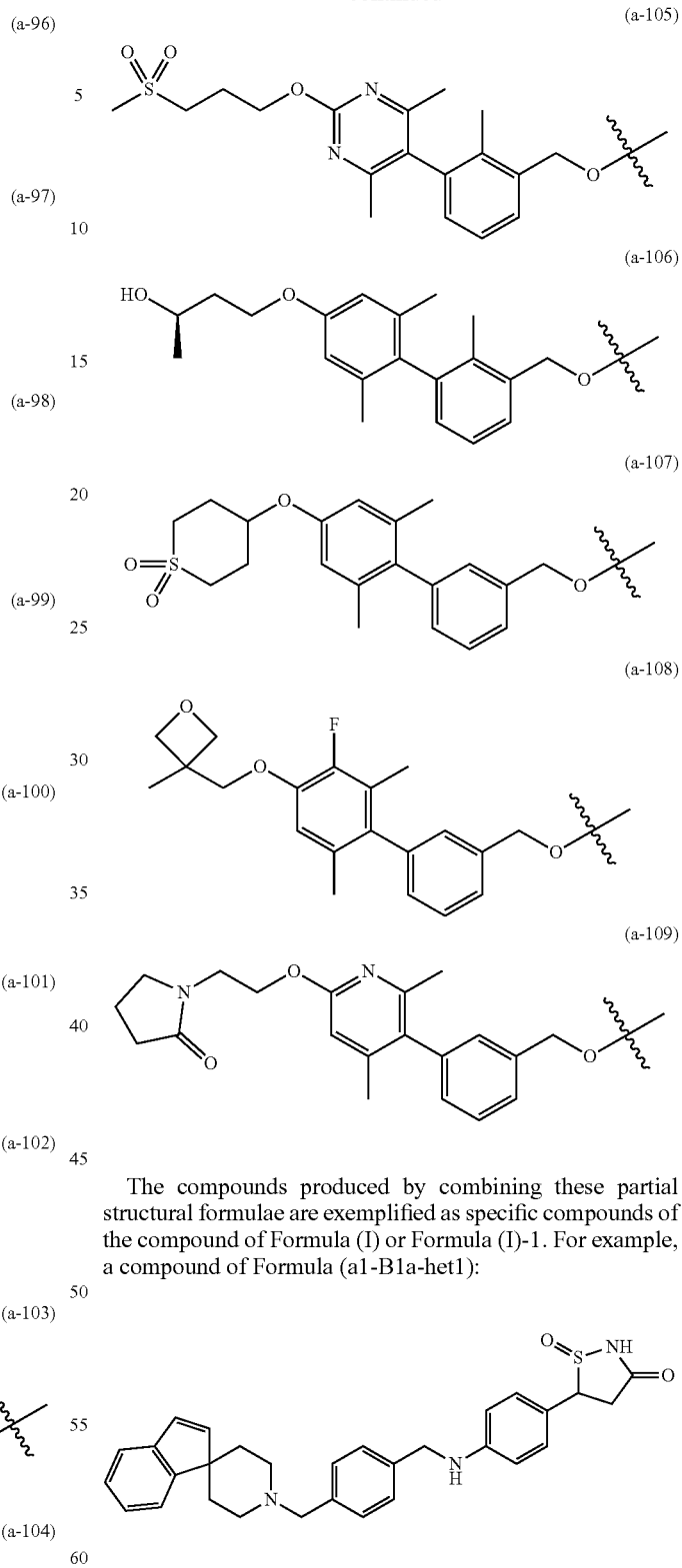

The compounds produced by combining these partial structural formulae are exemplified as specific compounds of the compound of Formula (I) or Formula (I)-1. For example, a compound of Formula (a1-B1a-het1):

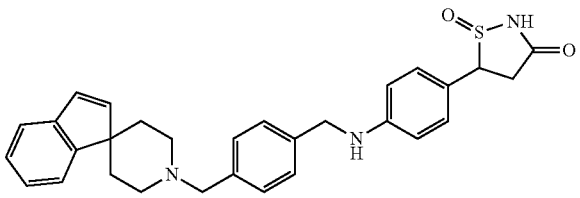 [SMILES: O=C1CC(c2ccc(NCc3ccc(CN4CCC5(C=Cc6ccccc65)CC4)cc3)cc2)S(=O)N1]

produced by combining Formula (B1a-het1) with Formula (a-1) is exemplified as the specific compound. In such a specific compound, a compound in which the moiety corresponding to X is exchanged from an oxygen atom to —NH— or from —NH— to an oxygen atom can also be optionally produced, and the thus produced compound is also exemplified as the specific compound.

[1-19-2] In the compound of Formula (I) according to Aspect [1] or of Formula (I)-B1 or Formula (I)-B2 according to Aspect [1-17], compounds produced by optionally combining the groups of Partial Structural Formula (A)-(C) (on the left of the left wavy line), Partial Structural Formula (BB1) or Formula (BB2) (between the two wavy lines), Partial Structural Formula (B-Het) (on the right of the right wavy line) in Formula (I)-B1 or Formula (I)-B2 can also be produced optionally:

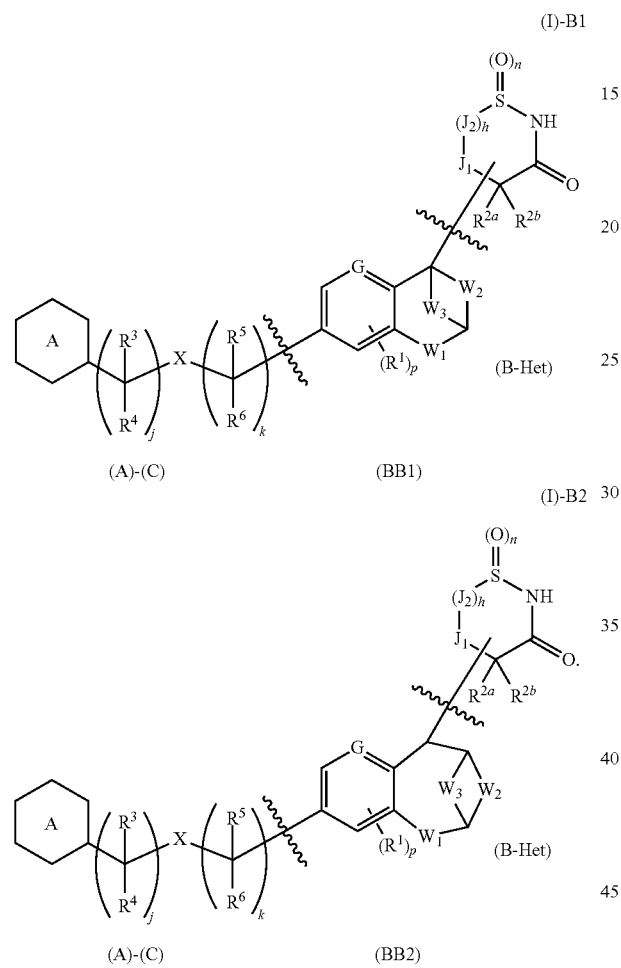

More specifically, Partial Structural Formula (B-Het) is a group optionally selected from Formula (het1) to Formula (het9). Partial Structural Formula (BB1) or Formula (BB2) is a group optionally selected from Formula (b-1) to Formula (b-5), and Partial Structural Formula (A)-(C) is a group optionally selected from Formula (a-37) to Formula (a-40) exemplified in Aspect [1-19-1] or Formula (a-94) to Formula (a-99) below.

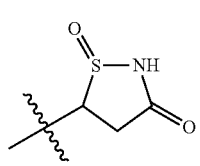
(het 1)

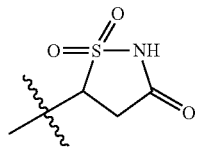
(het 2)

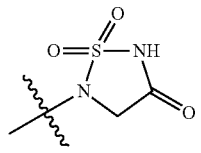
(het 3)

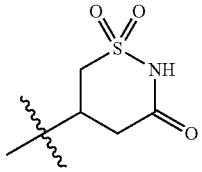
(het 4)

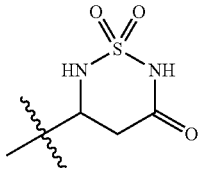
(het 5)

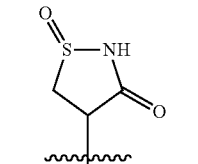
(het 6)

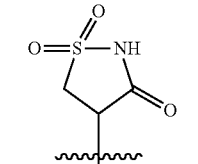
(het 7)

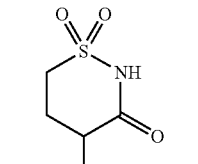
(het 8)

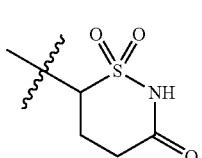
(het 9)

(b-1) 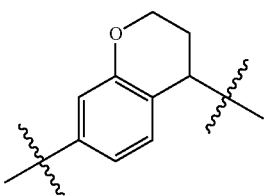

(b-2) 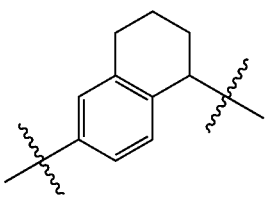

(b-3) 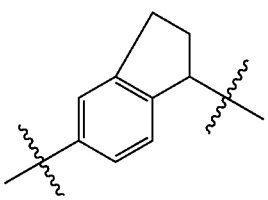

(b-4) 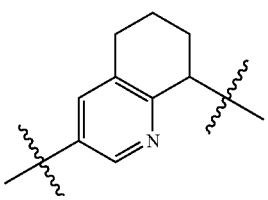

(b-5) 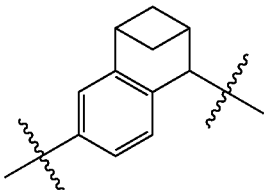

(a-94) 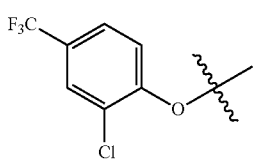

(a-95) 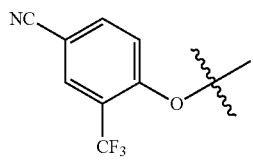

(a-96) 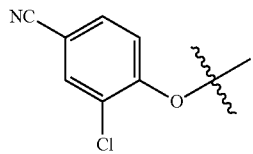

(a-97) 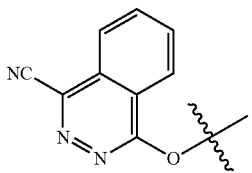

(a-98) 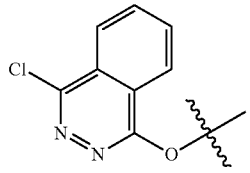

(a-99) 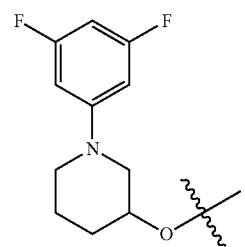

The compounds produced by combining these partial structural formulae are exemplified as specific compounds of the compound of Formula (I), Formula (I)-B1, or Formula (I)-B2. For example, a compound of Formula (a94-b1-het6):

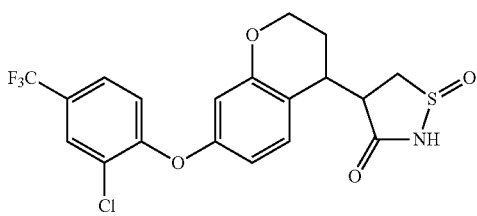 [SMILES: O=C1NS(=O)CC1C1CCOc2cc(Oc3ccc(C(F)(F)F)cc3Cl)ccc21]

produced by combining Formula (het6), Formula (b-1), and Formula (a-94) is exemplified as the specific compound.

[2] A second aspect of the present invention is a pharmaceutical composition, characterized by containing, as an active ingredient, at least one of the compound of Formula (I), a pharmaceutically acceptable salt of the compound, and a pharmaceutically acceptable solvate of the compound or the salt.

[3] A third aspect of the present invention is a prophylactic agent and/or a therapeutic agent for a GPR40-involving disease, characterized by containing, as an active ingredient, at least one of the compound of Formula (I), a pharmaceutically acceptable salt of the compound, and a pharmaceutically acceptable solvate of the compound or the salt.

[3-1] Specifically, a prophylactic agent and/or a therapeutic agent for each disease of diabetes [more specifically, any one of or all of Type 1 diabetes (insulin-dependent diabetes), Type 2 diabetes (non-insulin-dependent diabetes), and boederline type diabetes (impaired glucose tolerance (IGT) and/or impaired fasting glycemia (IFG))], obesity, and adiposity, characterized by containing, as an active ingredient, at least one of the compound of Formula (I), a pharmaceutically acceptable salt of the compound, and a pharmaceutically acceptable solvate of the compound or the salt. An inhibitor of Type 2 diabetes in the impaired glucose tolerance is also included in examples of the above prophylactic agent and therapeutic agent. A therapeutic agent for sulfonylurea secondary failure diabetes is also included in the examples thereof, and by the therapeutic agent, also in (administration-ineffective) diabetic patients who cannot obtain a satisfactory hypoglycemic effect even by being administrated with a sulfonylurea agent (such as glibenclamide and glimepiride) or a rapid-acting insulin secretagogues (such as mitiglinide), insulin secretion effect or hypoglycemic effect can be obtained.

Here, in relationship between the blood glucose level and the disease, the diabetes is characterized by exhibiting a fasting blood glucose level of 126 mg/dL or more, or a casual blood glucose level or a 2 hours value of the 75 g oral glucose tolerance test (OGTT) of 200 mg/dL or more. The boederline type diabetes (also called glucose tolerance disorders) refers to an impaired fasting glycemia (IFG) in which the fasting blood glucose level is 110 mg/dL or more and less than 126 mg/dL and/or an impaired glucose tolerance (IGT) in which a 2 hours value of the 75 g OGTT is 140 mg/dL or more and less than 200 mg/dL.

The insulin resistance refers to a pathological condition in which insulin becomes unable to lower the blood glucose level in the organism and is evaluated by a quantitative glucose clamp technique or HOMA-IR in clinical practice. It is known that the insulin resistance causes a hyperinsulinemia and becomes a risk of a hypertension and a coronary artery disease.

The "adiposity" is defined by the Japan Society for the Study of Obesity as "a pathological condition requiring medically a weight reduction in the case where an obesity-derived or -related health impairment is combined or such a combination is expected". The "obesity" defined here is evaluated by measuring BMI (body mass index, kg/m$^2$). Generally, a body having a BMI of 25 or more is diagnosed as obesity. Examples of the result of the therapy include the reduction of BMI.

[4] A fourth aspect of the present invention is an insulin secretagogues, characterized by containing, as an active ingredient, at least one of the compound of Formula (I), a pharmaceutically acceptable salt of the compound, and a pharmaceutically acceptable solvate of the compound or the salt.

[5] A fifth aspect of the present invention is a GPR40 activating agent containing one or more of the compound of Formula (I), a pharmaceutically acceptable salt of the compound, and a pharmaceutically acceptable solvate of the compound or the salt.

In the second to fifth aspects and preferable aspects thereof, more preferable substituents and a combination thereof in Formula (I) are according to descriptions described in the first aspect.

In each aspect as described in [1] to [5] of the present invention, it is preferable to use a compound having a $EC_{50}$ value of preferably, 3 µM or less, more preferably, 1 µM or less, further preferably, 300 nM or less, and most preferably, 100 nM or less, when the GPR40 agonist action is measured by a method accordingly selected (for example, the below described pharmacological test example 1 (an agonist action on GPR40 of human origin)).

In the above aspects of the present invention, the "therapeutic agent" is not only for treating diseases or symptoms, but also for improving diseases or symptoms.

In all of the above aspects, when the term "compound" is used, the compound refers also to a "pharmaceutically acceptable salt of the compound". In addition, there is the case where the compound of the present invention has an asymmetric carbon, and thus, the compound of the present invention includes a mixture of various stereoisomers such as a geometric isomer, a tautomer, and an optical isomer, and an isolated stereoisomer. The compound of Formula (I) may have an axial asymmetry due to a steric hindrance and an isomer caused by the axial asymmetry (axial chirality) is also included in the compound of the Formula (I). The isolation and the purification of such stereoisomers can be performed by a person skilled in the art by an ordinary technique through an optical resolution or an asymmetric synthesis using a preferential crystallization or a column chromatography.

The compound of Formula (I) of the present invention may form an acid addition salt or a salt with a base depending on the type of the substituent. Such salt is not particularly limited so long as the salt is a pharmaceutically acceptable salt. Specific examples thereof include acid addition salts with: mineral acids such as hydrochloric acid, hydrobromic acid, hydriodic acid, sulfuric acid, nitric acid, and phosphoric acid; organic carboxylic acids, for example, an aliphatic monocarboxylic acid such as formic acid, acetic acid, propionic acid, butyric acid, valeric acid, enanthic acid, capric acid, myristic acid, palmitic acid, stearic acid, lactic acid, sorbic acid, and mandelic acid, an aromatic monocarboxylic acid such as benzoic acid and salicylic acid, an aliphatic dicarboxylic acid such as oxalic acid, malonic acid, succinic acid, fumaric acid, maleic acid, malic acid, and tartaric acid, an aliphatic tricarboxylic acid such as citric acid, cinnamic acid, glycolic acid, pyruvic acid, oxylic acid, salicylic acid, and N-acetylcysteine; organic sulfonic acids, for example, an aliphatic sulfonic acid such as methanesulfonic acid, ethanesulfonic acid, and 2-hydroxyethanesulfonic acid, and an aromatic sulfonic acid such as benzenesulfonic acid and p-toluenesulfonic acid; and acidic amino acids such as aspartic acid and glutamic acid, salts (including, besides mono salts, disodium salts and dipotassium salts) with a metal, for example, alkali metals such as lithium, sodium, potassium, and cesium, and alkaline earth metals such as magnesium, calcium, and barium, salts with a metal such as aluminum, iron, copper, nickel, cobalt, and zinc, salts with an organic base such as methylamine, ethylamine, tert-butylamine, tert-octylamine, diethylamine, triethylamine, cyclohexylamine, dibenzylamine, ethanolamine, diethanolamine, triethanolamine, piperidine, morpholine, pyridine, lysine, arginine, ornithine, ethylenediamine, N-methylglucamine, glucosamine, a phenylglycine alkyl ester, and guanidine, and salts with glycine, histidine, choline, and ammonium.

These salts can be obtained by an ordinary method including, for example, mixing an equivalent of the compound of the present invention with a solution containing a desired acid, base, or the like, and collecting a desired salt by filtration or distillation-off of a solvent. The compound of the present invention or a salt of the compound can form a solvate with a solvent such as water, ethanol, and glycerol.

The salt of the compound of the present invention includes a mono-salt and a di-salt. The compound of the present invention can form both of an acid addition salt and a salt with a base simultaneously depending on the type of the substituent in the side chains. Further, the present invention encompasses also hydrates, various pharmaceutically acceptable solvates, and crystal polymorphs of the compound of Formula (I) of the present invention. Here, needless to say, the present invention is not limited to the compounds described in Examples below and encompasses all of the compounds of Formula (I) of the present invention and pharmaceutically acceptable salts of the compounds.

The compound of the present invention may be labeled with an isotope (such as $^3$H, $^{14}$C, and $^{35}$S).

[Method for producing the compound of the present invention]

Methods for producing the compound of Formula (I) of the present invention will be described below.

The compound of Formula (I) of the present invention, a salt of the compound, and a solvate of the compound or the salt can be produced by a combination of commonly known chemical production methods. Typical production methods will be described below.

In each Formula in the production methods below, each definition of ring A, ring B, ring A', ring A", ring A''', ring B', X, V, T, $J_1$, $J_{1a}$, $J_2$, $R^1$, $R^{2a}$, $R^{2b}$, $R^3$, $R^4$, $R^5$, $R^6$, $R^7$, $R^8$, $R^9$, $R^{10}$, $R^{11a}$, $R^{11b}$, $R^{11c}$, $R^{12a}$, $R^{12b}$, $R^{12c}$, $R^{13}$, $R^{13a}$, $R^{14}$, n, p, q, q1, q2, r, r1, s, h, j, k, f, g, g1, $X_3$, n1, n2, n3, n4, $Z_1$, $Z_2$, $Z_3$, Rx, Rxa, Rxb, $X_1$, and the like is the same as each definition in Formula (I), Formula (A), Formula (A)-1, Formula (AA), Formula (A1)-IV, Formula (A2)-IV, Formula (A)-V, Formula (AA)-V, Formula (A)-VI, and Formula (B)-I described in the first aspect above unless otherwise specified.

In the production methods, the definition of m is an integer of 1 or 2.

In the production methods, the definition of h2 is an integer of 0 to 2.

In the production methods, the definition of g-1 is an integer of 0 to 3.

In the production methods, the definition of R' is a $C_{1-6}$ alkyl group such as a methyl group, an ethyl group, and a t-butyl group unless otherwise specified.

In the production methods, the definition of R" is a hydrogen atom, a hydroxy group, or a $C_{1-6}$ alkoxy group such as a methoxy group and an ethoxy group unless otherwise specified.

In the production methods, each definition of Y, $Y_1$, and $Y_2$ is a halogen atom, a nitro group, a protected imino group ($-NP^1_2$), a formyl group, or an ester group unless otherwise specified.

In the production methods, the definition of Z is a leaving group including a hydroxy group, a halogen atom, and a sulfonyloxy group such as a methanesulfonyloxy group, a p-toluenesulfonyloxy group, and a trifluoromethanesulfonyloxy group unless otherwise specified.

In the production methods, the definition of W is boronic acid, a boronic ester, or a trifluoroborate salt unless otherwise specified.

In the production methods, for the definitions of $W^1$ and $W^2$, $W^2$ is boronic acid, a boronic ester, or a trifluoroborate salt when $W^1$ is a hydroxy group, a halogen atom, or a trifluoromethanesulfonyloxy group, and $W^2$ is a hydroxy group, a halogen atom, or a trifluoromethanesulfonyloxy group when $W^1$ is boronic acid, a boronic ester, or a trifluoroborate salt unless otherwise specified.

In the production methods, the definition of * is a chiral center.

In the production methods, each definition of $P^1$, $P^2$, $P^3$, $P^4$, and $P^5$ is a protective group for a hydroxy group (—OH), a thiol group (—SH), or an imino group (—NH—) unless otherwise specified. Examples of the protective group for a hydroxy group include an alkyl group such as a methyl group; an alkoxyalkyl group such as a methoxymethyl group, a methoxyethoxymethyl group, and a tetrahydropyranyl group; an arylmethyl group such as a benzyl group and a triphenylmethyl group; a silyl group such as a trimethylsilyl group, a triethylsilyl group, and a t-butyldimethylsilyl group; an alkanoyl group such as an acetyl group and a pivaloyl group; an aroyl group such as a benzoyl group; an alkoxycarbonyl group such as a t-butoxycarbonyl group; and an arylmethoxycarbonyl group such as a benzyloxycarbonyl group. Examples of the protective group for a thiol group include an alkyl group such as a methyl group; an arylmethyl group such as a benzyl group and a triphenylmethyl group; an alkanoyl group such as an acetyl group and a pivaloyl group; and an aroyl group such as a benzoyl group. Examples of the protective group for an imino group include an alkanoyl group such as an acetyl group; an alkoxycarbonyl group such as a methoxycarbonyl group, an ethoxycarbonyl group, and a t-butoxycarbonyl group; an arylmethoxycarbonyl group such as a benzyloxycarbonyl group, a para-methoxybenzyloxycarbonyl group, and a para-nitrobenzyloxycarbonyl group; an arylmethyl group such as a benzyl group, a para-methoxybenzyl group, a dimethoxybenzyl group, and a triphenylmethyl group; and an aroyl group such as a benzoyl group.

Deprotection methods of such protective groups are different depending on the chemical properties of a protected reactive group (a hydroxy group, a thiol group, or an imino group) and an employed protective group. For example, an acyl-type protective group such as an alkanoyl group, an alkoxycarbonyl group, and an aroyl group can be hydrolyzed using a suitable base such as an alkali metal hydroxide including lithium hydroxide, sodium hydroxide, and potassium hydroxide for the deprotection. An alkoxyalkyl-type protective group such as a methoxymethyl group, a methoxyethoxymethyl group, and a tetrahydropyranyl group, a substituted methoxycarbonyl-type protective group such as a t-butoxycarbonyl group and a para-methoxybenzyloxycarbonyl group, and a silyl-type protective group such as a triethylsilyl group and a t-butyldimethylsilyl group can be removed using a suitable acid such as acetic acid, hydrochloric acid, hydrobromic acid, sulfuric acid, phosphoric acid, trifluoroacetic acid, and trifluoromethanesulfonic acid or a combination of them. The silyl-type protective group can also be removed using a suitable fluorine ion (F$^-$) generating reagent such as tetrabutylammonium fluoride and hydrogen fluoride. An arylmethoxycarbonyl group such as a benzyloxycarbonyl group, a para-methoxybenzyloxycarbonyl group, and a para-nitrobenzyloxycarbonyl group and an arylmethyl group such as a benzyl group can be removed by hydrogenolysis using a palladium carbon catalyst. A benzyl group can be removed by Birch reduction using metallic sodium in liquid ammonia. A triphenylmethyl group can be removed using a suitable acid such as acetic acid, hydrochloric acid, hydrobromic acid, sulfuric acid, phosphoric acid, trifluoroacetic acid, and trifluoromethanesulfonic acid or a combination of them. It can also be removed by Birch reduction using metallic sodium in liquid ammonia and removed by hydrogenolysis using a palladium carbon catalyst.

During the production of the compound of Formula (I) of the present invention, when it has a reactive group such as a hydroxy group, an amino group, and a carboxy group, such a group may be properly protected in any reaction step, and the protective group may be removed in a suitable step.

Methods for introducing and removing such protective groups are properly performed depending on the type of a group to be protected or a protective group. For example, such introduction and removal can be performed by methods described in [Protective Groups in Organic Synthesis, edited by Greene et al., the fourth edition (2007), John Wiley & Sons].

Required starting materials are commercially available or can be easily obtained from commercial products by usual production methods in organic chemistry.

Reaction conditions in the production methods are as follows unless otherwise specified. The reaction temperature is in a range from −78° C. to the reflux temperature of a solvent, and the reaction time is a time sufficient for a reaction. Examples of the reaction inert solvent include, but are not limited to, an aromatic hydrocarbon solvent such as toluene, benzene, and xylene; an alcoholic solvent such as methanol, ethanol, and 2-propanol; a polar solvent such as water, acetonitrile, N,N-dimethylformamide, dimethyl sulfoxide, and 1,3-dimethyl-2-imidazolidinone; a basic solvent such as triethylamine and pyridine; a halogenated solvent such as chloroform, methylene chloride, and 1,2-dichloroethane; an ether solvent such as 1,2-dimethoxyethane, cyclopentyl methyl ether, diethyl ether, tetrahydrofuran, and dioxane; and a mixed solvent of them. Such solvents are properly selected depending on reaction conditions. Examples of the base include, but are not limited to, an inorganic base such as sodium carbonate, potassium carbonate, cesium carbonate, sodium hydroxide, potassium hydroxide, and sodium hydride; and an organic base such as triethylamine, N,N-diisopropylethylamine, pyridine, N,N-dialkylaniline, lithium diisopropylamide, and lithium bistrimethylsilylamide. Examples of the acid include, but are not limited to, a mineral acid such as hydrochloric acid, sulfuric acid, and nitric acid; and an organic acid such as methanesulfonic acid and p-toluenesulfonic acid.

Hereinafter, production methods will be described, but the present invention is not limited to these methods.

The compound of Formula (I) of the present invention can be obtained by a production method suitable for the type of the ring including a saturated amide structure having —S(O)n-NH—CO—. A material compound for the compound is typically shown as Formula (IX).

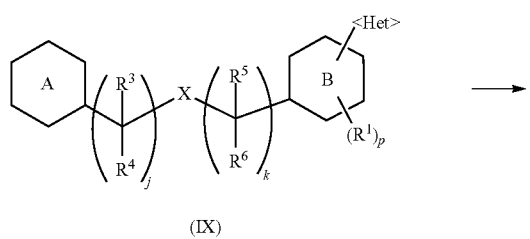

(IX)

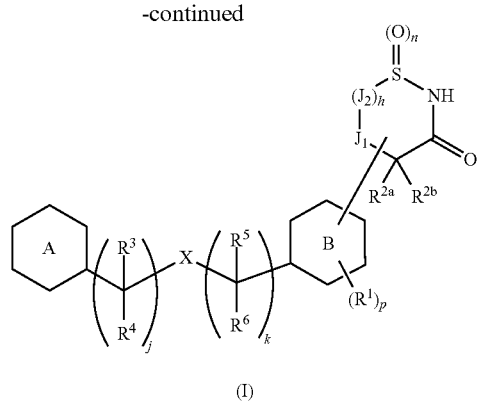

(I)

In the formulae in the production method, <Het> generally means a conversion part into the ring structure of a saturated cyclic amide structure that is bonded to the ring B and has —S(O)n-NH—CO— (n is an integer of 0 to 2), examples of which include W (for example, boronic acid, a boronic ester, and a trifluoroborate salt) and Y (for example, a halogen atom, a nitro group, a protected imino group (—NP$^1{}_2$), a formyl group, and an ester group) in the production method, and a molecular chain to form the saturated cyclic amide structure.

(1) Methods for producing the compound of Formula (I)-1a or Formula (I)-2a of the present invention will be described below.

<Production Method A>
<When $R^{2a}=R^{2b}=H$ and $R^{11a}=H$ in Formula (I)-1a above>

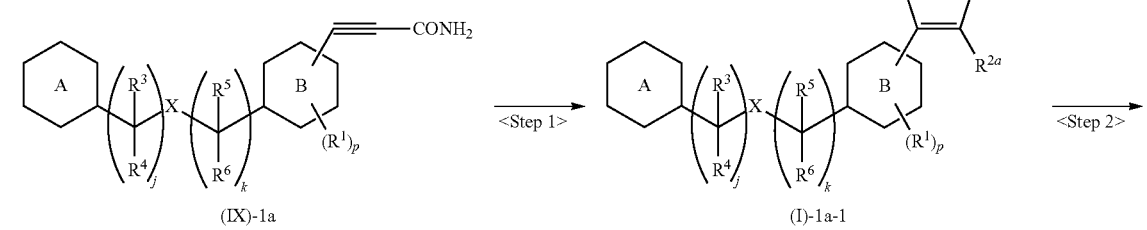

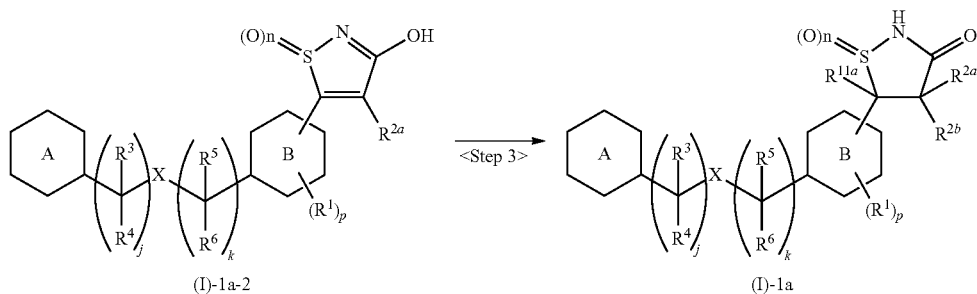

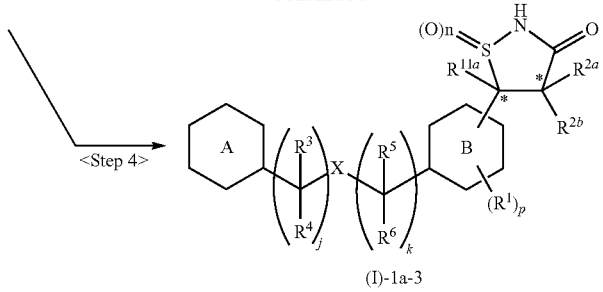

(I)-1a-3

<Step 1>

The compound of Formula (IX)-1a obtained in (Production Method E) or (Production Method F) described later is subjected to isothiazole ring formation reaction. In accordance with methods known in literatures, for example, the methods described in [Heterocyclic Compounds, New Edition, Applications, pp. 41-57 (2004), Kodansha Ltd.], [Chemische Berichte, vol. 94, p. 2950 (1961)], and [Chemische Berichte, vol. 96, p. 944 (1963)], a compound of (I)-1a-1 can be produced by reacting the compound of Formula (IX)-1a with a thiol (SH) source such as sodium hydrosulfide and hydrogen sulfide gas in a reaction inert solvent such as methanol, ethanol, and water or a mixed solvent of them at a temperature from 0° C. to a reflux temperature of the solvent, and then by reacting the obtained thiol adduct in the presence of a halogen such as iodine and bromine and in the presence or absence of a base such as pyridine and potassium carbonate in a reaction inert solvent such as methanol, ethanol, ethyl acetate, and water or a mixed solvent of them at a temperature from 0° C. to a reflux temperature of the solvent.

<Step 2>

The sulfur atom in the compound of Formula (I)-1a-1 is oxidized. In accordance with methods known in literatures, for example, the method described in [Jikken Kagaku Koza (Experimental Chemistry Course), the fourth edition, vol. 20, Organic Synthesis V, Oxidation Reaction, pp. 276-280 (1992), Maruzen Co., Ltd.], a compound of Formula (I)-1a-2 can be produced by reacting the compound of Formula (I)-1a-1 in the presence of a peracid or a peroxide such as hydrogen peroxide water, m-chloroperbenzoic acid (MCPBA), peracetic acid, trifluoroperacetic acid, Oxone (registered trademark) (DuPont), and tert-butylhydroperoxide (TBHP) in a reaction inert solvent including a halogenated solvent such as dichloromethane and chloroform, an aromatic hydrocarbon solvent such as toluene and benzene, and a polar solvent such as acetonitrile, methanol, acetone, and water or in a mixed solvent of them at a temperature from 0° C. to a reflux temperature of the solvent. In the oxidation reaction, selection of an oxidizing agent and suitable selection of equivalent weight of a reagent, a reaction temperature, a reaction time, a solvent, and the like can produce a sulfoxide (n=1) and a sulfone (n=2) separately. Such sulfoxide and sulfone can be separated by common techniques such as column chromatography.

<Step 3>

The compound of Formula (I)-1a-2 is subjected to reduction. In accordance with methods known in literatures, for example, the method described in [Japan Institute of Heterocyclic Chemistry, vol. 64, pp. 101-120 (2004)], the compound of Formula (I)-1a can be produced by reacting the compound of Formula (I)-1a-2 in the presence of a reducing agent such as lithium tri(sec-butyl)borohydride (L-selectride), potassium tri(sec-butyl)borohydride, lithium borohydride, and Raney nickel (Raney-Ni)-formic acid or a reducing agent such as a hydride of a metal or a metalloid and a complex compound of them in a reaction inert solvent including an ether solvent such as tetrahydrofuran, diethyl ether, and dioxane, an aromatic hydrocarbon solvent such as toluene and benzene, and a polar solvent such as acetonitrile and methanol or in a mixed solvent of them at a temperature from −78° C. to a reflux temperature of the solvent.

<Step 4>

In accordance with methods known in literatures, for example, the method described in [Jikken Kagaku Koza (Experimental Chemistry Course), the fourth edition, vol. 26, Organic Synthesis VIII, Asymmetric Synthesis, Reduction, Sugar, and Labelled Compound, pp. 23-68 (1992), Maruzen Co., Ltd.], the compound of Formula (I)-1a-3 as an optically active compound of Formula (I)-1a can be produced by reaction in the presence of the compound of Formula (I)-1a-2 in the presence of, for example, optically active dichloro[bis (diphenylphosphino)binaphthyl][diphenylethylenediamine] ruthenium and a basic reagent such as potassium hydroxide and potassium t-butoxide in a hydrogen gas atmosphere using 2-propanol as a solvent at a temperature from room temperature to a reflux temperature of the solvent. Alternatively, the compound of Formula (I)-1a-3 as an optically active compound can be produced by reaction in the presence of a transition-metal complex such as chlorotris(triphenylphosphine)rhodium(I), a reagent such as optically active 2,2'-bis (diphenylphosphino)-1,1'-binaphthyl, and a hydrogen source such as hydrogen and formic acid-triethylamine using a solvent such as ethanol at a temperature from room temperature to a reflux temperature of the solvent.

In the production methods below, when an isothiazole ring is subjected to reduction, a corresponding optically active compound can be obtained by the reduction in accordance with <Step 4> in <Production Method A>.

The compounds of Formula (II)-1a and Formula (III)-1a above are included in the compound of Formula (I)-1a in (Production Method A) and can be produced by a similar production method. In Formula (II-B), Formula (II-C), Formula (IV-1), Formula (IV-3), Formula (IV-4), Formula (V), Formula (V-A), Formula (VI), Formula (VI-A), Formula (1)-B 1, and Formula (I)-B2 above, the compound having Formula (B-Het)-1a is also included in the compound of Formula (I)-1a and can be produced by a similar production method to (Production Method A). These compounds of Formula (I)-1a are included in the compound of Formula (I).

Similarly, in the production methods in (Production Method B) or later, the compounds of Formula (II)-1a and Formula (III)-1a above and the compounds having Formula (B-Het)-1a in Formula (II-B), Formula (II-C), Formula (IV-1), Formula (IV-3), Formula (IV-4), Formula (V), Formula (V-A), Formula (VI), Formula (VI-A), Formula (I)-B1, and Formula (I)-B2 above are included in the compound of Formula (I)-1a and can be produced by a similar production method, and these compounds of Formula (I)-1a are included in the compound of Formula (I).

When n=0 in (Production Method A), a compound can be produced without the oxidation step in <Step 2>.

Similarly, in the production methods in (Production Method B) or later, it should be understood that when n is not specified to 0, 1, or 2, an oxide (a sulfoxide or a sulfone derivative) in which n=1 or 2 can be produced in accordance with the oxidation reaction in <Step 2> in (Production Method A) in the oxidation step shown in each reaction scheme or a compound (a sulfenamide derivative) in which n=0 can be produced without the oxidation step.

<Production Method B>

<When $R^{2a}=R^{2b}$=H and $R^{11a}$=H in Formula (I)-1a Above>

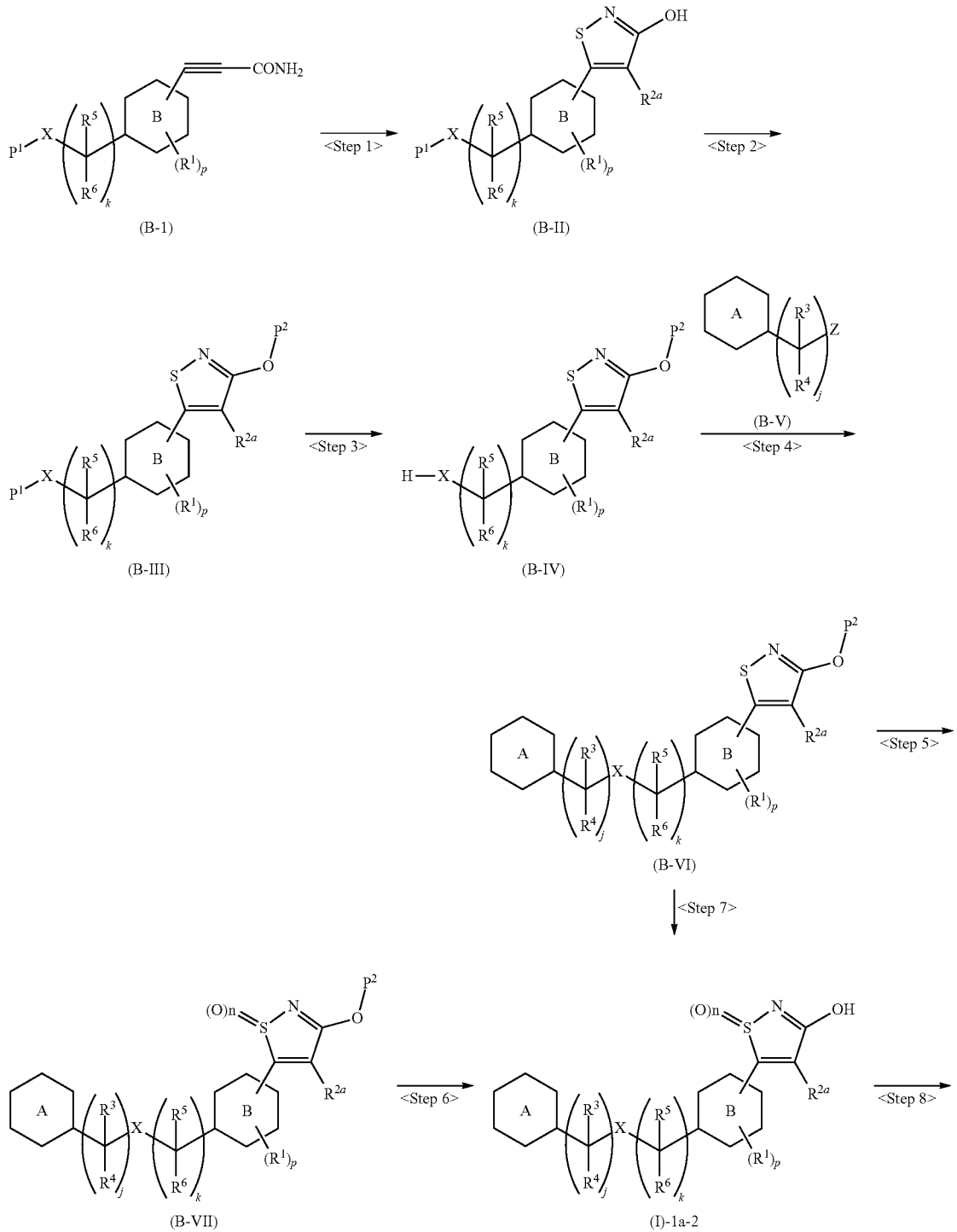

-continued

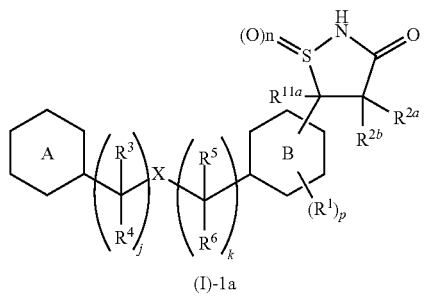

(I)-1a

<Step 1>

A compound of Formula (B-I) is subjected to isothiazole ring formation reaction. A compound of Formula (B-II) can be produced by reacting the compound of Formula (B-I) (it is known in the art or can be easily produced from a known compound as described later in (Production Method E) and is a properly protected compound) in a similar manner to that in <Step 1> in (Production Method A).

<Step 2>

The compound of Formula (B-II) is protected with a protective group $P^2$. A compound of Formula (B-III) can be produced by reacting the compound of Formula (B-II) with the protective group $P^2$ by a method suitable for the type of the protective group.

<Step 3>

The protective group $P^1$ in the compound of Formula (B-III) is deprotected. A compound of Formula (B-IV) can be produced by deprotecting the protective group $P^1$ in the compound of Formula (B-III) by a method suitable for the type of the protective group.

<Step 4>

The compound of Formula (B-IV) is subjected to substitution reaction with a compound of Formula (B-V).

<When Z=Halogen, Methanesulfonyloxy Group, or p-Toluenesulfonyloxy Group>

In accordance with methods known in literatures, for example, the methods described in [Jikken Kagaku Koza (Experimental Chemistry Course), the fourth edition, vol. 20, Organic Synthesis II, Alcohol and Amine, pp. 187-200 and 284-292 (1992), Maruzen Co., Ltd.] and [Jikken Kagaku Koza (Experimental Chemistry Course), the fourth edition, vol. 20, Organic Synthesis VI, Hetero Element- or Main Group Metal Element-Containing Compound, pp. 319-350 (1992), Maruzen Co., Ltd.], a compound of Formula (B-VI) can be produced by substitution reaction of the compound of Formula (B-IV) in the presence of the compound of Formula (B-V) in the presence or absence of a base such as triethylamine, pyridine, sodium hydride, sodium hydroxide, and potassium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<When Z=Hydroxy Group, X≠—NR$^7$—, and k=0>

In accordance with methods known in literatures, for example, the method described in [Tetrahedron, vol. 67 (10), pp. 3140-3149 (2011)], a compound of Formula (B-VI) can be produced by reacting the compound of Formula (B-IV) in the presence of the compound of Formula (B-V) in the presence of a base such as potassium tert-butoxide and a catalyst such as copper acetate in a reaction inert solvent including an ether solvent such as diethyl ether, tetrahydrofuran, and 1,4-dioxane and an aromatic hydrocarbon solvent such as toluene and benzene or in a mixed solvent of them at a temperature from 0° C. to a reflux temperature of the solvent.

<When Z=Hydroxy Group, X=Nitrogen Atom, and k=0>

In accordance with methods known in literatures, for example, the methods described in [WO 2010/143733 pamphlet, p. 71, [0179]: Step 2 in Reaction scheme 1], [Tetrahedron Letters, vol. 36, pp. 63733-6374 (1995)], and [Tetrahedron Letters, vol. 38, pp. 5831-5834 (1997)], a compound of Formula (B-VI) can be produced by Mitsunobu reaction of the compound of Formula (B-IV) in the presence of the compound of Formula (B-V) in the presence of an organophosphorus compound such as triphenylphosphine and an azo compound such as an azodicarboxylic acid ester and azodicarboxylic amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

The compound of Formula (B-V) used in the step is known in the art or can be produced from a corresponding known compound in accordance with methods known in literatures as described later in (Production Method J), (Production Method J-1), (Production Method J-2), (Production Method J-3), (Production Method J-4), (Production Method J-5), and (Production Method J-6). For example, it can be produced from a corresponding compound in accordance with the methods described in [WO 2005/063729 pamphlet, Reference Examples 2 and 3 and the like], [WO 2005/086661 pamphlet, Example 18 and the like], [WO 2008/001931 pamphlet, Reaction Scheme 2, Reference Examples 15-19, and the like], [WO 2009/039943 pamphlet, pp. 51-52], [WO 2009/054423 pamphlet, Production Examples 12, 24, 37, and the like], [WO 2010/085525 pamphlet, Examples 2-5,3-3,4-4, and the like], and [WO 2010/091176 pamphlet, Examples 1-3 and the like]. Examples of the compound include compounds that are obtained by properly protecting the compounds in Example 25-5 and the like.

The compound that is shown as Formula (I) in WO 2009/039943 pamphlet and that has a similar formula to Formula (A)-IX in the present application is represented by Formula III described in WO 2009/039943 pamphlet, p. 52 as Formula (B-V), and the compound is reacted under the condition of <When Z≠hydroxy group> above to produce the compound of Formula (B-VI) (X=nitrogen atom).

<Step 5>

The sulfur atom in the compound of Formula (B-VI) is oxidized. A compound of Formula (B-VII) can be produced by reacting the compound of Formula (B-VI) in a similar manner to that in <Step 2> in (Production Method A).

<Step 6>

The protective group $P^2$ in the compound of Formula (B-VII) is deprotected. A compound of Formula (I)-1a-2 can be produced by deprotecting the protective group $P^2$ in the compound of Formula (B-VII) by a method suitable for the type of the protective group.

<Step 7>

The compound of Formula (B-VI) is simultaneously subjected to oxidization of the sulfur atom and deprotection. When the protective group of $P^2$ is a protective group capable of being deprotected by a common oxidation method, a compound of Formula (I)-1a-2 can be produced by reacting the compound of Formula (B-VI) in a similar manner to that in <Step 2> in (Production Method A).

<Step 8>

The compound of Formula (I)-1a-2 is subjected to reduction. The compound of Formula (I)-1a can be produced by reacting the compound of Formula (I)-1a-2 in a similar manner to that in <Step 3> in (Production Method A).

<Production Method C>

<When $R^{2b}$=H and $R^{11b}$=H in Formula (I)-1a or Formula (I)-2a Above>

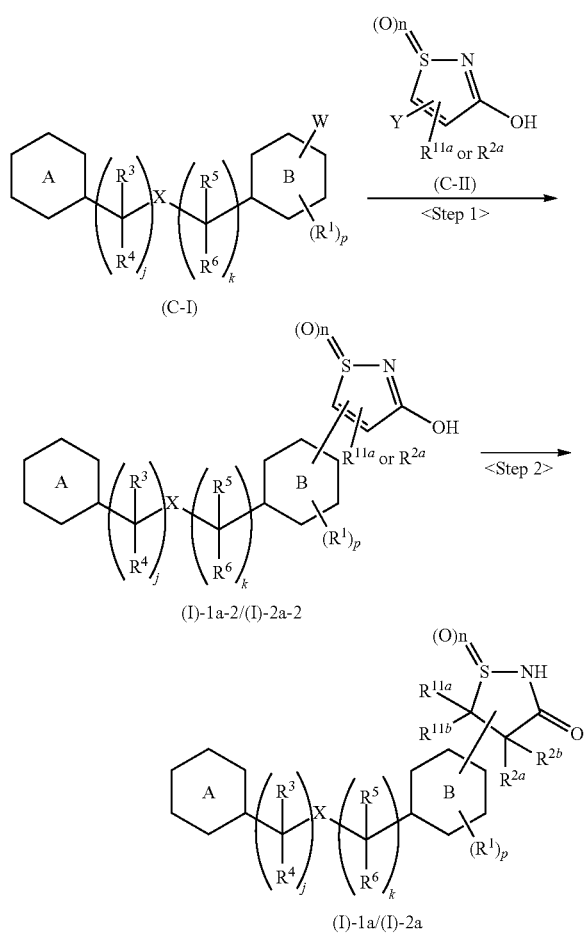

<Step 1>

A compound of Formula (C-I) obtained in (Production Method H), (Production Method H-1), (Production Method H-2), or (Production Method H-3) described later is subjected to substitution reaction with a compound of Formula (C-II) (Formula (G-III)a or Formula (I-I)) obtained in (Production Method I) described later. In accordance with methods known in literatures, for example, the methods described in [Jikken Kagaku Koza (Experimental Chemistry Course), the fifth edition, vol. 18, Synthesis of Organic Compound VI, Organic Synthesis Using Metal, pp. 327-352 (2004), Maruzen Co., Ltd.] and [Journal of Medicinal Chemistry, vol. 48 (20), pp. 6326-6339 (2005)], a compound of Formula (I)-1a-2/Formula (I)-2a-2 can be produced by reacting the compounds of Formula (C-I) and Formula (C-II) in the presence of three reagents of a palladium catalyst, a phosphine reagent or an alkylammonium halide reagent, and a base reagent using a reaction inert solvent such as toluene, xylene, N,N-dimethylformamide, and N,N-dimethylacetamide or a mixed solvent of them at a temperature from 0° C. to a reflux temperature of the solvent. Examples of the palladium catalyst include palladium(II) acetate, tetrakis triphenylphosphine palladium, tris(dibenzylideneacetone)dipalladium, bis(dibenzylideneacetone)palladium, and [1,1'-bis(diphenylphosphino)ferrocene]dichloropalladium(II). Examples of the phosphine reagent include triphenylphosphine, tris(tert-butyl)phosphine, tris(o-tolyl)phosphine, 2-dicyclohexylphosphino-2', 6'-dimethoxybiphenyl, 2-dicyclohexylphosphino-2',4',6'-triisopropylbiphenyl, and dicyclohexylphosphino-2',4',6'-trisisopropylbiphenyl (Xphos). Examples of the base reagent include sodium carbonate, cesium carbonate, potassium carbonate, triethylamine, N,N-diisopropylethylamine, and potassium phosphate. In the reaction above, in place of the phosphine reagent, an alkylammonium halide reagent such as tetramethylammonium chloride and tetrabutylammonium chloride may be used.

Formula (C-II) used in this step is a compound of Formula (G-III)a described later when n=0 and is a compound of Formula (I-I) described later when n≠0.

<Step 2>

The compound of Formula (I)-1a-2/Formula (I)-2a-2 is subjected to reduction.

The compound of Formula (I)-1a/Formula (I)-2a can be produced by reacting the compound of Formula (I)-1a-2/Formula (I)-2a-2 in a similar manner to that in <Step 3> in (Production Method A).

In the present specification, when n=1 in Formula (I)-1a-2/Formula (I)-2a-2 and Formula (I)-1a/Formula (I)-2a above, Formula (I)-1a-2/Formula (I)-2a-2 and Formula (1)-1a/Formula (I)-2a include optical isomers. A compound derived from an enantiomer A (I-I-A) that has a shorter column elution time when optically active Formula (I-I) obtained in (Production Method I) described later is separated by a chiral column is represented by Formula (I)-1a-2 (A)/Formula (I)-2a-2 (A).

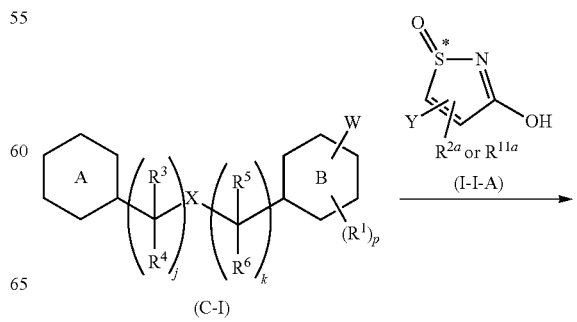

-continued

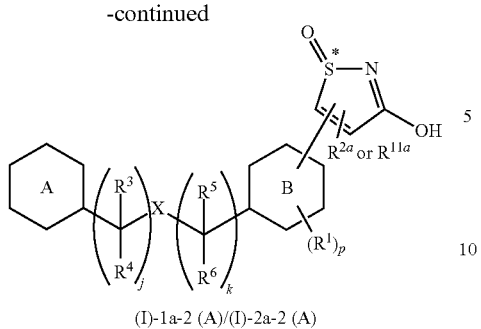

(I)-1a-2 (A)/(I)-2a-2 (A)

Isomers (diastereomers) of Formula (I)-1a (A)/Formula (I)-2a (A) that are obtained by reduction of the compound in a similar manner to that in <Step 3> in (Production Method A) can be separated through optical resolution using chiral column chromatography or asymmetric synthesis by a person skilled in the art based on conventional techniques.

<Column resolution>

(I)-1a (A)/(I)-2a (A)

+

(I)-1a (A)-a/(I)-2a (A)-a
<Shorter elution time>

-continued

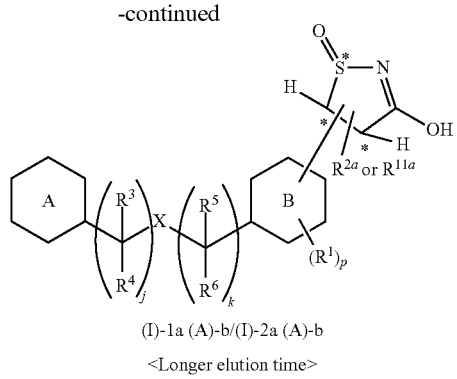

(I)-1a (A)-b/(I)-2a (A)-b
<Longer elution time>

For example, each diastereomer can be obtained using preparative chromatography as in Step 2 in Example 7 described later. In the present invention, in the preparative chromatography of a mixture of the diastereoisomers, a diastereomer having a shorter elution time is represented as a, while a diastereomer having a longer elution time is represented as b, and the diastereomers are correspondingly represented by Formula (I)-1a (A)-a/Formula (I)-2a (A)-a and Formula (I)-1a (A)-b/Formula (I)-2a (A)-b. In the present specification, the diastereomers are expressed as a compound name (A)-a and a compound name (A)-b for a compound name.

A compound obtained from an enantiomer (B) (I-I-B) having a longer elution time when Formula (I-I) is separated by chiral column resolution is represented as Formula (I)-1a-2 (B)/Formula (I)-2a-2 (B). A compound of Formula (I)-1a (B)/Formula (I)-2a (B) that is obtained by reduction using the compound also includes isomers (diastereomers), which are similarly represented by Formula (I)-1a (B)-a/Formula (I)-2a (B)-a and Formula (I)-1a (B)-b/Formula (I)-2a (B)-b. The diastereomers are expressed as a compound name (B)-a and a compound name (B)-b for a compound name.

In the present specification, when n=2 in Formula (I)-1a/Formula (I)-2a above, Formula (I)-1a/Formula (I)-2a includes optical isomers. The isomers can be separated through optical resolution using chiral column chromatography or asymmetric synthesis by a person skilled in the art based on conventional techniques.

<Production Method D>

<When $R^{2a} \neq H$, $R^{2b}=H$, and $R^{11a}=H$ in Formula (I)-1a Above>

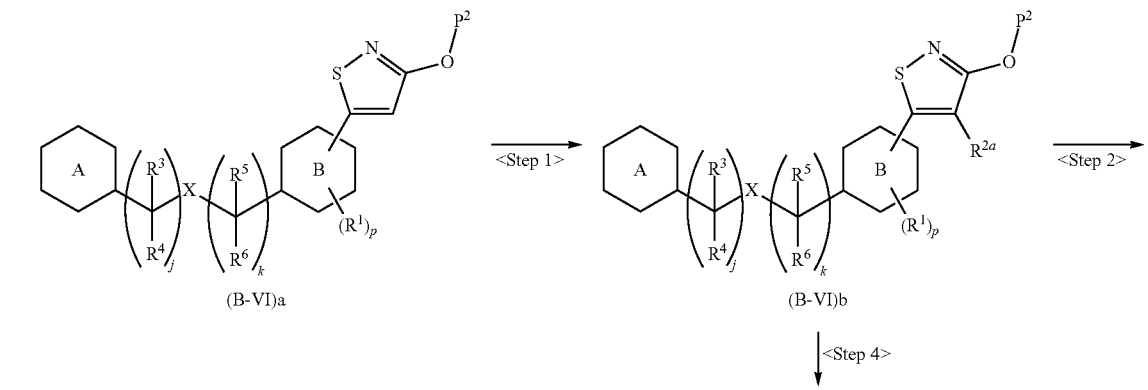

(B-VI)a    <Step 1>    (B-VI)b    <Step 2>

<Step 4>

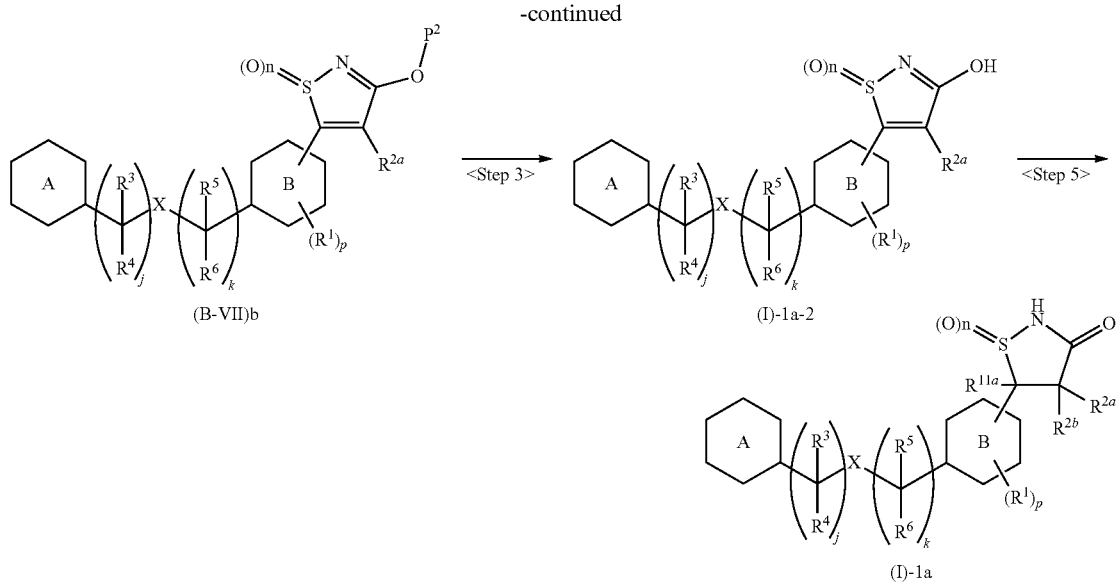

(B-VII)b     (I)-1a-2     (I)-1a

<Step 1>

The compound of Formula (B-VI)a obtained in <Step 4> in (Production Method B) above is subjected to substitution reaction on the isothiazole ring.

<When $R^{2a}$=Halogen Atom>

In accordance with methods known in literatures, for example, the method described in [Organic And Biomolecular Chemistry, vol. 5 (3), pp. 643-471 (2007)], a compound of Formula (B-VI)b can be produced by halogenation reaction of the compound of Formula (B-VI)a in the presence of a corresponding halogenating agent such as N-fluorodibenzenesulfonimide, N-chlorosuccinimide, N-bromosuccinimide, and N-iodosuccinimide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from −78° C. to a reflux temperature of the solvent.

<When $R^{2a}$=Cyano Group>

In accordance with methods known in literatures, for example, the method described in [Tetrahedron Letters, vol. 40 (47), pp. 8193-8195 (1999)], a compound of Formula (B-VI)b can be produced by reacting the compound of Formula (B-VI)b ($R^{2a}$=I, Br) obtained in <When $R^{2a}$=halogen atom> in <Step 1> in (Production Method D) in the presence of a corresponding cyanating agent such as zinc cyanide and potassium ferrocyanide in the presence of a palladium catalyst such as palladium(II) acetate, tetrakis triphenylphosphine palladium, tris(dibenzylideneacetone)dipalladium, and [1,1'-bis(diphenylphosphino)ferrocene]dichloropalladium (II), a phosphine reagent such as triphenylphosphine, tris(tert-butyl)phosphine, and tris(o-tolyl)phosphine, and an organic or inorganic base such as triethylamine, N,N-diisopropylethylamine, and potassium phosphate using a reaction inert solvent such as toluene, xylene, N,N-dimethylformamide, and N,N-dimethylacetamide or a mixed solvent of them at a temperature from 0° C. to a reflux temperature of the solvent. It can also be produced in a similar method using tetramethylammonium chloride, tetrabutylammonium chloride, or the like in place of the phosphine reagent.

<Step 2>

The sulfur atom in the compound of Formula (B-VI)b is oxidized. A compound of Formula (B-VII)b can be produced by reacting the compound of Formula (B-VI)b in a similar manner to that in <Step 2> in (Production Method A).

<Step 3>

The protective group $P^2$ in the compound of Formula (B-VII)b is deprotected. A compound of Formula (I)-1a-2 can be produced by reacting the compound of Formula (B-VII)b in a similar manner to that in <Step 6> in (Production Method B).

<Step 4>

The compound of Formula (B-VI)b is simultaneously subjected to oxidation and deprotection of the protective group $P^2$. A compound of Formula (I)-1a-2 can be produced by reacting the compound of Formula (B-VI)b in a similar manner to that in <Step 7> in (Production Method B).

<Step 5>

The compound of Formula (I)-1a-2 is subjected to reduction. The compound of Formula (I)-1a can be produced by reacting the compound of Formula (I)-1a-2 in a similar manner to that in <Step 3> in (Production Method A).

(2) Next, methods for producing the compounds of Formula (IX)-1a, Formula (B-I), and Formula (B-II) will be described.

The compounds of Formula (IX)-1a and Formula (B-I) can be produced by the methods below.

<Production Method E>

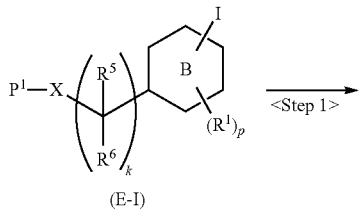

(E-I)

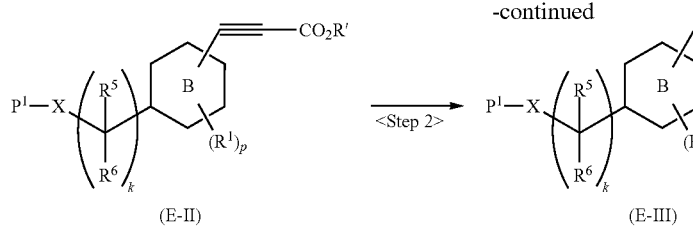

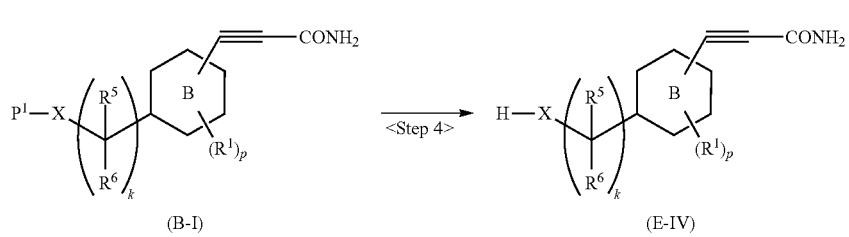

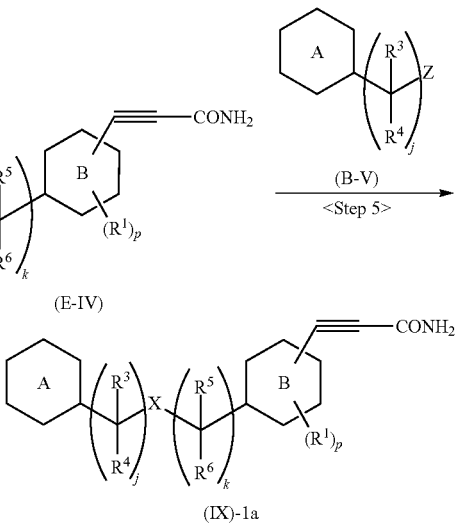

<Step 1>
A compound of Formula (E-I) is subjected to alkynylation. In accordance with methods known in literatures, for example, the methods described in [*Jikken Kagaku Koza* (Experimental Chemistry Course), the fourth edition, vol. 19, Organic Synthesis I, Hydrocarbon and Halogenated Compounds, pp. 318-335 (1992), Maruzen Co., Ltd.] and [WO 2008/066131 pamphlet, Reference Example 1], a compound of Formula (E-II) can be produced by reacting the compound of Formula (E-I), which is known in the art or can be easily produced from a known compound, in the presence of a corresponding propiolic acid ester such as methyl propiolate and ethyl propiolate and copper(II) oxide using a reaction inert solvent such as toluene, xylene, N,N-dimethylformamide, and N,N-dimethylacetamide or a mixed solvent of them at a temperature from 0° C. to a reflux temperature of the solvent.

The compound of Formula (E-II) can also be produced by reaction in the presence of an ortho ester of a corresponding propiolic acid such as 3,3,3-triethoxypropyne or a corresponding propiolic acid ester such as methyl propiolate and ethyl propiolate in the presence of copper(I) iodide or zinc bromide in the presence of a palladium catalyst such as palladium(II) acetate, tetrakis triphenylphosphine palladium, tris(dibenzylideneacetone)dipalladium, and [1,1'-bis(diphenylphosphino)ferrocene]dichloropalladium(II), a phosphine reagent such as triphenylphosphine, tris(tert-butyl)phosphine, and tris(o-tolyl)phosphine, and an organic or inorganic base such as triethylamine, N,N-diisopropylethylamine, potassium phosphate, and potassium carbonate using a reaction inert solvent such as toluene, xylene, N,N-dimethylformamide, and N,N-dimethylacetamide or a mixed solvent of them at a temperature from 0° C. to a reflux temperature of the solvent.

<Step 2>
The compound of Formula (E-II) is hydrolyzed. In accordance with methods known in literatures, for example, the method described in [*Jikken Kagaku Koza* (Experimental Chemistry Course), the fourth edition, vol. 22, Organic Synthesis IV, Acid, Amino Acid, and Peptide, pp. 1-43 (1992), Maruzen Co., Ltd.], a compound of Formula (E-III) can be produced by reacting the compound of Formula (E-II) in the presence of a base such as lithium hydroxide, sodium hydroxide, potassium hydroxide, lithium carbonate, sodium carbonate, and potassium carbonate using a reaction inert solvent such as water, methanol, ethanol, 2-propanol, N,N-dimethylformamide, 1,4-dioxane, and tetrahydrofuran or a mixed solvent of them at a temperature from 0° C. to a reflux temperature of the solvent.

<Step 3>
The compound of Formula (E-III) is subjected to amidation reaction. In accordance with methods known in literatures, for example, the method described in [*Jikken Kagaku Koza* (Experimental Chemistry Course), the fourth edition, vol. 22, Organic Synthesis IV, Acid, Amino Acid, and Peptide, pp. 191-309 (1992), Maruzen Co., Ltd.], a compound of Formula (B-I) can be produced by reacting the compound of Formula (E-III) with aqueous ammonia or ammonia gas in the presence of a condensing agent such as 1,3-dicyclohexylcarbodiimide (DCC), 1-ethyl-3-(3'-dimethylaminopropyl)carbodiimide hydrochloride (WSC—HCl), benzotriazol-1-yloxytris(dimethylamino)phosphonium hexafluorophosphate (BOP reagent), bis(2-oxo-3-oxazolidinyl)phosphinic chloride (BOP—Cl), 2-chloro-1,3-dimethylimidazolinium hexafluorophosphate (CIP), and 4-(4,6-dimethoxy-1,3,5-triazin-2-yl)-4-methylmorpholinium chloride (DMTMM) in a reaction inert solvent including a halogenated solvent such as dichloromethane and chloroform, an ether solvent such as diethyl ether and tetrahydrofuran, an aromatic hydrocarbon solvent such as toluene and benzene, a polar solvent such as N,N-dimethylformamide, or an alcoholic solvent such as methanol, ethanol, and 2-propanol or in a mixed solvent of them in the presence or absence of a base such as triethylamine and pyridine at a temperature from 0° C. to a reflux temperature of the solvent. When the compound of Formula (E-III) is converted into an acid chloride, in accordance with the methods described in [*Jikken Kagaku Koza* (Experimental Chemistry Course), the fourth edition, vol. 22, Organic Synthesis IV, Acid, Amino Acid, and Peptide, pp. 144-146 (1992), Maruzen Co., Ltd.] and the like, the compound of Formula (B-I) can be produced by reacting the acid chloride in the presence of a base such as triethylamine and pyridine in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<Step 4>
The protective group $P^1$ in the compound of Formula (B-I) is deprotected. A compound of Formula (E-IV) can be produced by reacting the compound of Formula (B-I) in a similar manner to that in <Step 3> in (Production Method B).

<Step 5>
The compound of Formula (E-IV) is subjected to substitution reaction with a compound of Formula (B-V). A compound of Formula (IX)-1a can be produced by reacting the compound of Formula (E-IV) with the compound of Formula (B-V) in a similar manner to that in <Step 4> in (Production Method B).

<Step 6>
The compound of Formula (B-I) can also be produced from the compound of Formula (E-II). Namely, in accordance with methods known in literatures, for example, the method described in [Tetrahedron, vol. 61 (48), pp. 11333-11344 (2001)], the compound of Formula (E-II) can be produced by reaction in the presence of ammonia using a reaction inert solvent such as water, methanol, ethanol, 2-propanol, N,N-dimethylformamide, 1,4-dioxane, and tetrahydrofuran or in a mixed solvent of them at a temperature from −78° C. to a reflux temperature of the solvent.

The compound of Formula (IX)-1a can also be produced by the following method.

<Production Method F>

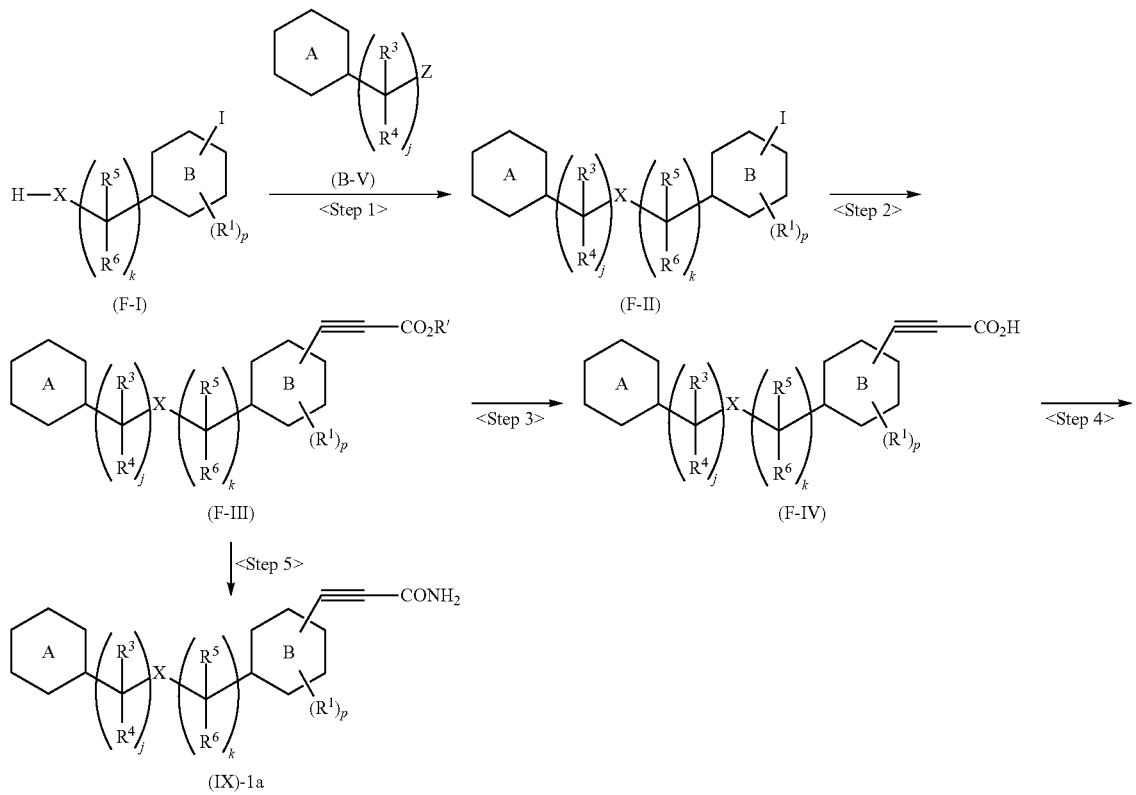

<Step 1>
A compound of Formula (F-I) is subjected to substitution reaction with a compound of Formula (B-V). A compound of Formula (F-II) can be produced by reacting the compound of Formula (F-I), which is known in the art or can be easily produced from a known compound, with the compound of Formula (B-V) in a similar manner to that in <Step 4> in (Production Method B).

<Step 2>
The compound of Formula (F-II) is subjected to alkynylation. A compound of Formula (F-III) can be produced by reacting the compound of Formula (F-II) in a similar manner to that in <Step 1> in (Production Method E).

<Step 3>
The compound of Formula (F-III) is hydrolyzed. A compound of Formula (F-IV) can be produced by reacting the compound of Formula (F-III) in a similar manner to that in <Step 2> in (Production Method E).

<Step 4>
The compound of Formula (F-IV) is subjected to amidation reaction. The compound of Formula (IX)-1a can be produced by reacting the compound of Formula (F-IV) in a similar manner to that in <Step 3> in (Production Method E).

<Step 5>
The compound of Formula (IX-Ia) can also be produced from the compound of Formula (F-III) in a similar manner to that in <Step 6> in <Production Method E>.

The compound of Formula (B-II) can also be produced by the method below.

<Production Method G>

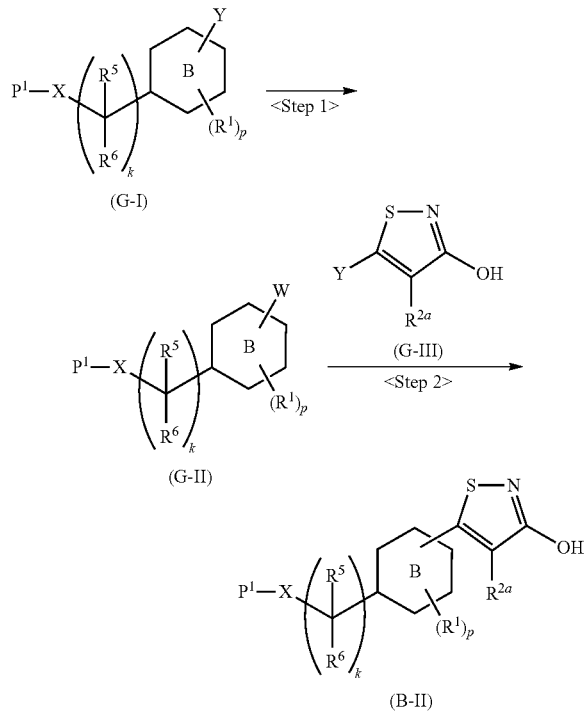

<Step 1>

A compound of Formula (G-I) is subjected to boration reaction.

<When W=Boronic Ester>

In accordance with methods known in literatures, for example, the method described in [The Journal of Organic Chemistry, vol. 60, pp. 7508-2665 (1995)], a boronic ester of Formula (G-II) can be produced by reacting the compound of Formula (G-I), which is known in the art or can be easily produced from a known compound, in the presence of a diboronic ester such as bis(pinacolato)diboron and bis(neopentylglycolato)diboron in the presence of a palladium catalyst such as palladium(II) acetate, tetrakis triphenylphosphine palladium, tris(dibenzylideneacetone)dipalladium, and [1,1'-bis(diphenylphosphino)ferrocene]dichloropalladium (II) in the presence or absence of a phosphine reagent such as triphenylphosphine, tris(tert-butyl)phosphine, tris(o-tolyl)phosphine, and 2-dicyclohexylphosphino-2',6'-dimethoxybiphenyl and an organic or inorganic base such as triethylamine, N,N-diisopropylethylamine, and potassium acetate using a reaction inert solvent such as toluene, N,N-dimethylformamide, dimethyl sulfoxide, and 1,4-dioxane or a mixed solvent of them at a temperature from 0° C. to a reflux temperature of the solvent. It can also be produced in a similar method using tetramethylammonium chloride, tetrabutylammonium chloride, or the like in place of the phosphine reagent.

<When W=Boronic Acid>

In accordance with methods known in literatures, for example, the method described in [Chemische Berichte, vol. 42, p. 3090 (1909)], a boronic acid of Formula (G-II) can be produced by reacting the compound of Formula (G-I) using a reaction inert solvent such as toluene, tetrahydrofuran, and 1,4-dioxane or a mixed solvent of them in the presence of an alkyllithium such as n-butyllithium and sec-butyllithium, a Grignard reagent such as isopropyl magnesium chloride, or metal magnesium, with a trialkyl borate such as trimethyl borate and triisopropyl borate at a temperature from −78° C. to room temperature, followed by reaction with an acid such as hydrochloric acid and sulfuric acid at a temperature from 0° C. to a reflux temperature of the solvent.

<When W=trifluoroborate salt>

In accordance with methods known in literatures, for example, the method described in [Chemical Reviews, vol. 108, pp. 288-325 (2008)], a trifluoroborate salt of Formula (G-II) can be produced by reacting the compound of Formula (G-II) (W=boronic ester or boronic acid) obtained in <When W=boronic ester or boronic acid> in <Step 1> in (Production Method G) in the presence of potassium hydrogen difluoride ($KHF_2$) using a reaction inert solvent such as methanol, ethanol, and water or a mixed solvent of them at a temperature from 0° C. to a reflux temperature of the solvent.

<When W=Boronic Acid N-Methylimino Diacetic Acid (MIDA) Ester>

In accordance with methods known in literatures, for example, the method described in [Journal of Organometallic Chemistry, vol. 307 (1), pp. 1-6 (1986)], a boronic acid N-methylimino diacetic acid (MIDA) ester of Formula (G-II) can be produced by reacting the compound of Formula (G-II) (W=boronic acid) obtained in <When W=boronic acid> in <Step 1> in (Production Method G) in the presence of N-methyliminodiacetic acid (MIDA) using a reaction inert solvent such as benzene, toluene, xylene, and dimethyl sulfoxide or a mixed solvent of them at a temperature from 0° C. to a reflux temperature of the solvent.

<Step 2>

The compound of Formula (G-II) is subjected to substitution reaction with a compound of Formula (G-III). The compound of Formula (B-II) can be produced by reacting the compound of Formula (G-II) with the compound of Formula (G-III), which is known in the art or can be easily produced from a known compound, in a similar manner to that in <Step 1> in (Production Method C).

(3) Next, a method for producing the compound of Formula (C-I) will be described.

<Production Method H>

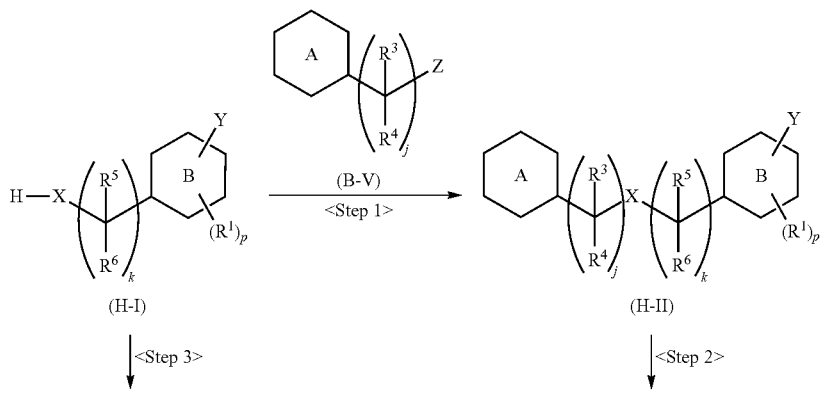

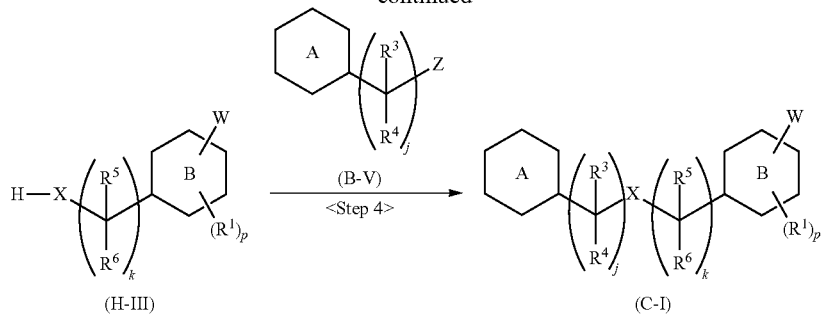

<Step 1>
A compound of Formula (H-I) is subjected to substitution reaction with a compound of Formula (B-V). A compound of Formula (H-II) can be produced by reacting the compound of Formula (H-I), which is known in the art or can be easily produced from a known compound, with the compound of Formula (B-V) in a similar manner to that in
<Step 4> in (Production Method B).
<Step 2>
The compound of Formula (H-II) is subjected to boration reaction. The compound of Formula (C-I) can be produced by reacting the compound of Formula (H-II) in a similar manner to that in <Step 1> in (Production Method G).
<Step 3>
The compound of Formula (H-I) is subjected to boration reaction. A compound of Formula (H-III) can be produced by reacting the compound of Formula (H-I) in a similar manner to that in <Step 1> in (Production Method G).
<Step 4>
The compound of Formula (H-III) is subjected to substitution reaction with the compound of Formula (B-V). The compound of Formula (C-I) can be produced by reacting the compound of Formula (H-III) with the compound of Formula (B-V) in a similar manner to that in <Step 4> in (Production Method B).

(4) Next, a method for producing the compound of Formula (C-II) will be described.
<Production Method I>
<When n is 1 or 2 in Formula (C-II) Above>

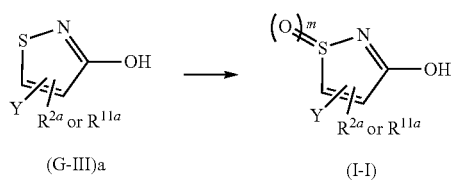

The sulfur atom in a compound of Formula (G-III)a is oxidized. A compound of Formula (I-I) (m=1 or 2) can be produced by reacting the compound of Formula (G-III)a, which is known in the art or can be easily produced from a known compound, in a similar manner to that in <Step 2> in (Production Method A).

The compounds of Formula (G-III)a and Formula (I-I) are included in the compound of Formula (C-II).

When m is 1 in Formula (I-I) above, the compound of Formula (I-I) includes optically active isomers. The isomers can be separated through optical resolution using column chromatography or asymmetric synthesis by a person skilled in the art based on conventional techniques. For example, each enantiomer can be obtained using preparative chromatography as in Step 5 in Example 1 described later.

(5) Hereinafter, the method for producing the compound of Formula (B-V) of the present invention will be described in further detail. As typical examples, methods for producing a compound of Formula (B-V)-II having Partial Structural Formula (A) above and a compound of Formula (B-V)-III having Partial Structural Formula (AA)-1 above will be described.
<Production Method J>

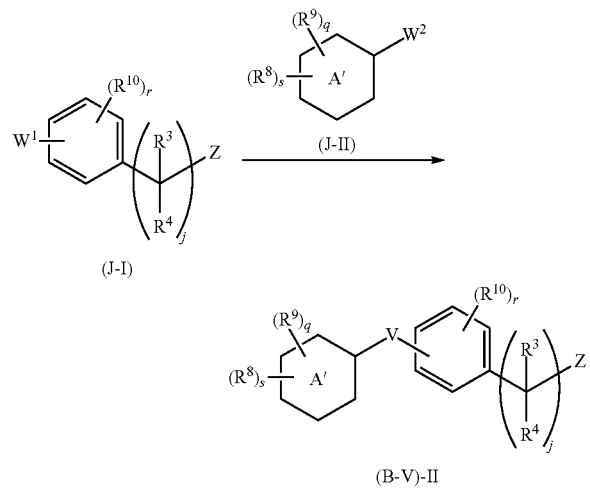

A compound of Formula (J-I) is subjected to substitution reaction on the ring.
<When V=Single Bond>
A compound of Formula (B-V)-II can be produced by reacting the compound of Formula (J-I), which is known in the art or can be easily produced from a known compound, with a compound of Formula (J-II) ($W^2$ is boronic acid, a boronic ester, or a trifluoroborate salt when $W^1$ is a halogen atom or a trifluoromethanesulfonyloxy group, and vice versa) in a similar manner to that in <Step 1> in (Production Method C).
<When V=Oxygen Atom>
In accordance with methods known in literatures, for example, the method described in [Tetrahedron Letters, vol. 44, pp. 3863-3865 (2003)], the compound of Formula (B-V)-II can be produced by reacting the compound of Formula (J-I) in the presence of a compound of Formula (J-II) ($W^2$ is boronic acid, a boronic ester, or a trifluoroborate salt when $W^1$ is a hydroxy group, and vice versa) in the presence of a copper catalyst such as copper(II) acetate and copper(II) trifluoroacetate and a base such as triethylamine, N,N-diisopropylethylamine, and pyridine using a reaction inert solvent such as dichloromethane, 1,4-dioxane, tetrahydrofuran, and N,N-dimethylformamide or a mixed solvent of them at a temperature from 0° C. to a reflux temperature of the solvent.

When $R^8$ or $R^9$ is an electron withdrawing group or the ring A' is heteroaryl, the compound of Formula (B-V)-II can also be produced by reacting a compound of Formula (J-I) ($W^1$=hydroxy group) with a compound of Formula (J-II) ($W^2$=halogen atom) in a similar manner to that in <Step 4> in (Production Method B).

The compound of Formula (MI) used in this step is known in the art or can be easily produced from a known compound. Specifically, a halogenated derivative can be produced from a corresponding compound in accordance with methods known in literatures, for example, the methods described in [WO 2005/063729 pamphlet, Reference Example 1 and the like], [WO 2008/001931 pamphlet, <Step 4A> in Reaction Scheme 2, Reference Examples 1, 54, and the like], and [WO 2009/054423 pamphlet, Production Example 37 and the like]. Furthermore, a boronic acid derivative can be produced by boration reaction of the halogenated derivative in a similar manner to that in <Step 1> in (Production Method G).

<Production Method J-1>

<When j=1, $R^3$, $R^4$=H, and Z=OH in Formula (B-V)-II Above>

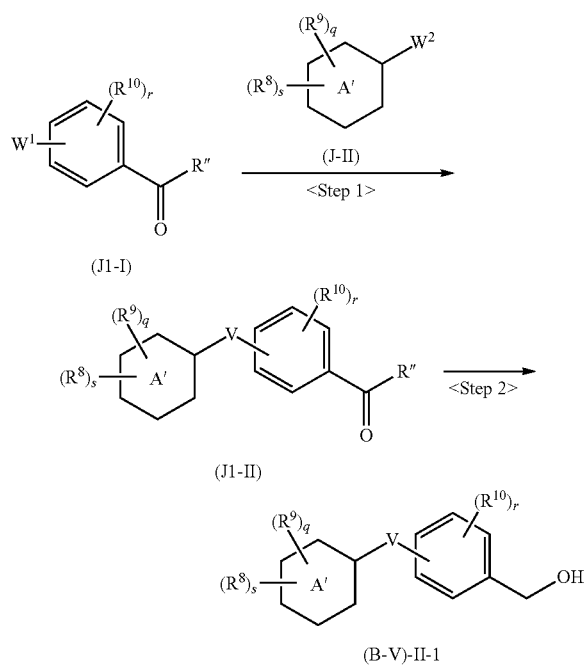

(J1-I)

(J1-II)

(B-V)-II-1

<Step 1>

A compound of Formula (J1-I) is subjected to substitution reaction on the ring.

<When V=Single Bond>

A compound of Formula (J1-II) can be produced by reacting the compound of Formula (J1-I), which is known in the art or can be easily produced from a known compound, with a compound of Formula (J-II) in a similar manner to that in <When V=single bond> in (Production Method J).

<When V=Oxygen Atom>

A compound of Formula (J1-II) can be produced by reacting the compound of

Formula (J1-I) with a compound of Formula (MI) in a similar manner to that in <When V=oxygen atom> in (Production Method J).

<Step 2>

The compound of Formula (J1-II) is subjected to reduction. In accordance with methods known in literatures, for example, the method described in [*Jikken Kagaku Koza* (Experimental Chemistry Course), the fourth edition, vol. 26, Organic Synthesis VIII, Asymmetric Synthesis, Reduction, Sugar, and Labelled Compound, pp. 234-245 (1992), Maruzen Co., Ltd.], the compound of Formula (B-V)-II-1 can be produced by reacting the compound of Formula (J1-II) in the presence of sodium borohydride (when R"=H), diisobutyl aluminum hydride (DIBAH), lithium aluminum hydride (LAH), lithium triethoxyaluminum hydride (when R"=$C_{1-6}$ alkoxy group), borane-tetrahydrofuran ($BH_3$-THF), borane-dimethyl sulfide ($BH_3$-$Me_2S$) (when R"=OH), or the like using a reaction inert solvent including an ether solvent such as diethyl ether, tetrahydrofuran, 1,2-dimethoxyethane, and 1,4-dioxane, a halogenated solvent such as dichloromethane, chloroform, and 1,2-dichloroethane, or an alcoholic solvent such as methanol and ethanol or a mixed solvent of them at a temperature from 0° C. to a reflux temperature of the solvent.

The compound of Formula (B-V)-II-1 can also be produced from a corresponding compound in accordance with methods known in literatures, for example, the methods described in [WO 2005/063729 pamphlet, Reference Examples 2, 3 and the like], [WO 2008/001931 pamphlet, Reaction Scheme 2, Reference Examples 15-19, and the like], [WO 2008/130514 pamphlet, Method A, Method C, and the like], [WO 2009/048527 pamphlet, Reaction Formulae 5 and 6, Example 66.6, and the like], and [WO 2009/054423 pamphlet, Production Examples 12, 24, 37, and the like].

<Production Method J-2>

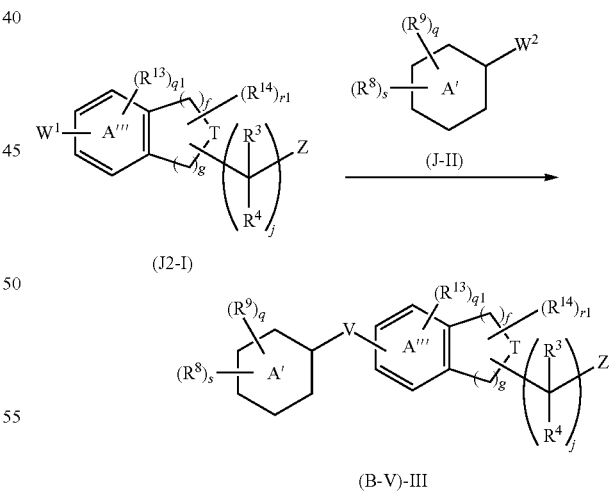

(J2-I)

(B-V)-III

A compound of Formula (J2-I) is subjected to substitution reaction on the ring.

<When V=Single Bond>

The compound of Formula (B-V)-III can be produced by reacting the compound of Formula (J2-I), which is known in the art or can be easily produced from a known compound, with a compound of Formula (J-II) in a similar manner to that in <When V=single bond> in (Production Method J).

<When V=Oxygen Atom>

The compound of Formula (B-V)-III can be produced by reacting the compound of Formula (J2-I) with a compound of Formula (J-II) in a similar manner to that in <When V=Oxygen Atom> in (Production Method J).

The compound of Formula (J2-I) includes optical isomers because a carbon atom in the ring is an asymmetric carbon by bonding the carbon atom to the linker moiety including Z. Such isomers are known in the art or can be easily produced from a known compound. Each enantiomer can be obtained through optical resolution using column chromatography or asymmetric synthesis by a person skilled in the art based on conventional techniques. For example, the isomers are separated with an optical resolution column, and each absolute configuration can be determined in accordance with [Agric. Biol. Chem., vol. 46 (10), pp. 2579-2585 (1982)]. Furthermore, the enantiomers can be obtained in accordance with the method described in [WO 2009/157418 pamphlet, Example 51 and Example 52]. Each enantiomer of Formula (B-V)-III (for example, compounds in Example 25-5 described later) can be produced using such an enantiomer.

<Production Method J-3>
<When j=0 and Z=OH in Formula (B-V)-III Above>

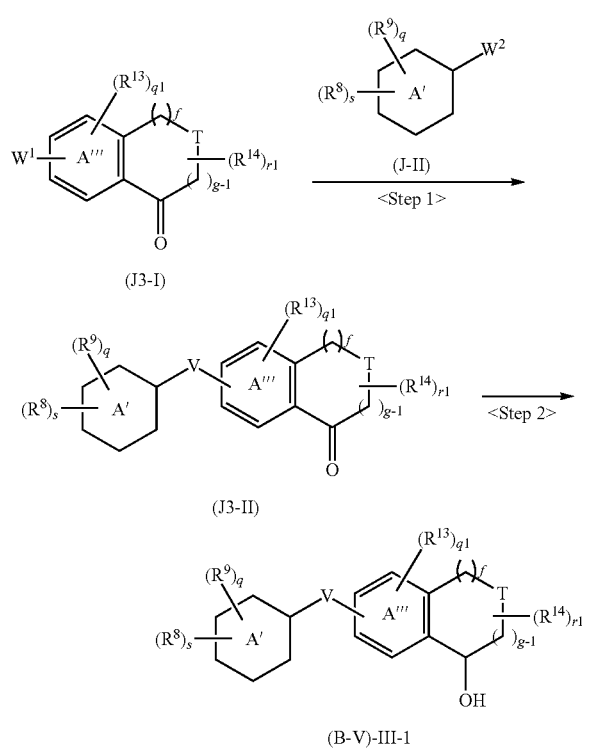

<Step 1>

A compound of Formula (J3-I) is subjected to substitution reaction on the ring.

<When V=Single Bond>

A compound of Formula (J3-II) can be produced by reacting the compound of Formula (J3-I), which is known in the art or can be easily produced from a known compound, with a compound of Formula (J-II) in a similar manner to that in <When V=single bond> in (Production Method J).

<When V=Oxygen Atom>

A compound of Formula (J3-II) can be produced by reacting the compound of Formula (J3-I) with a compound of Formula (J-II) in a similar manner to that in <When V=oxygen atom> in (Production Method J).

<Step 2>

The compound of Formula (J3-II) is subjected to reduction. The compound of Formula (B-V)-III-1 can be produced by reacting the compound of Formula (J3-II) with sodium borohydride, diisobutyl aluminum hydride (DIBAH), or lithium aluminum hydride (LAH) in a similar manner to that in <Step 2> in (Production Method J-1).

The compound of Formula (B-V)-III-1 can also be produced from a corresponding compound in accordance with methods known in literatures, for example, the methods described in [WO 2005/063729 pamphlet, Reference Examples 2, 3 and the like], [WO 2008/001931 pamphlet, Reaction Scheme 2, Reference Examples 15-19, and the like], and [WO 2009/054423 pamphlet, Production Examples 12, 24, 37, and the like].

(5-1) As another typical example of the compound of Formula (B-V), a method for producing a compound of Formula (B-V)-IV having Partial Structural Formula (A1)-IV:

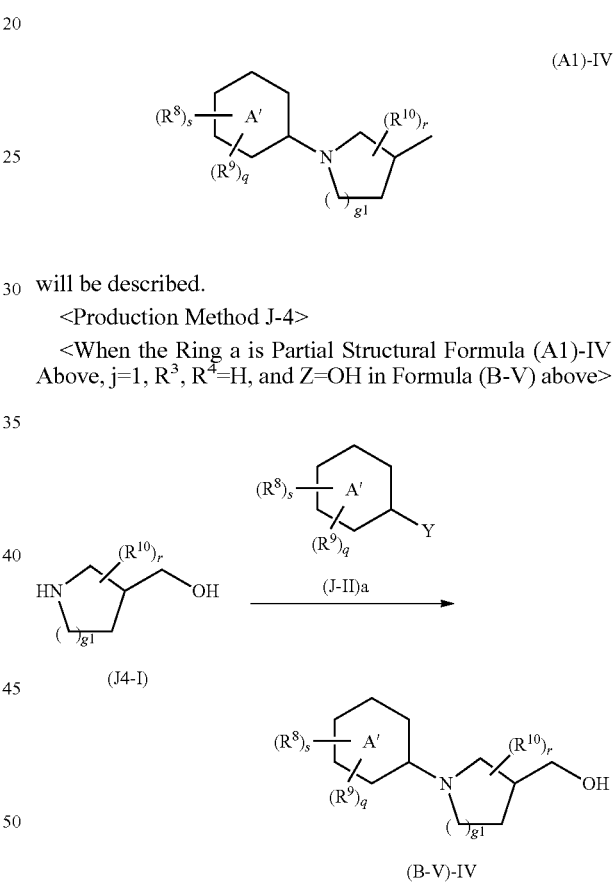

will be described.

<Production Method J-4>
<When the Ring a is Partial Structural Formula (A1)-IV Above, j=1, $R^3$, $R^4$=H, and Z=OH in Formula (B-V) above>

An amino alcohol of Formula (J4-I) is subjected to substitution reaction. In accordance with methods known in literatures, for example, the method described in [WO 2006/021401 pamphlet], the compound of Formula (B-V)-IV can be produced by reacting the compound of Formula (J4-I), which is known in the art or can be easily produced from a known compound, with a compound of Formula (J-II)a in the presence of potassium phosphate and copper iodide using a reaction inert solvent including a polar solvent such as dimethylaminoethanol and N,N-dimethylformamide, an ether solvent such as diethyl ether, tetrahydrofuran, 1,2-dimethoxyethane, and 1,4-dioxane, or an alcoholic solvent such as methanol and ethanol or a mixed solvent of them at a temperature from 0° C. to a reflux temperature of the solvent.

(5-2) As another typical example of the compound of Formula (B-V), a method for producing a compound of Formula (B-V)-V having Partial Structural Formula (AA1)-V:

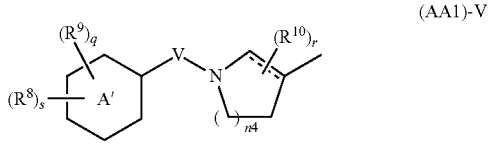

will be described.

<Production Method J-5>
<When the Ring a is Partial Structural Formula (AA1)-V Above (when V=an Oxygen Atom), j=1, $R^3$, $R^4$=H, and Z=OH in Formula (B-V) Above>

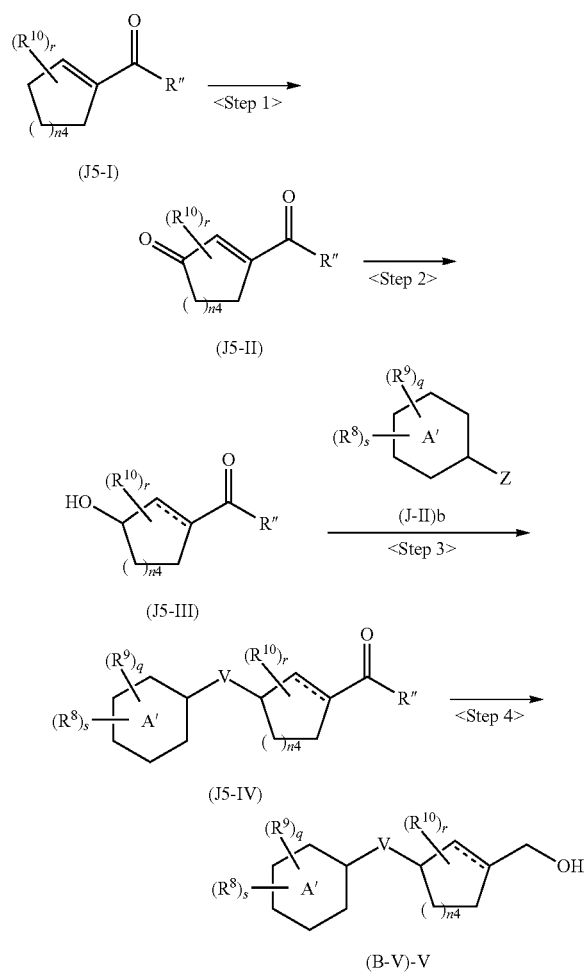

<Step 1>

A compound of Formula (J5-I) [in Formula, R″ is a $C_{1-6}$ alkoxy group] is oxidized. In accordance with methods known in literatures, for example, the method described in [Journal of Organic Chemistry, vol. 43, pp. 2057 (1978)], a compound of Formula (J5-II) can be produced by reacting the compound of Formula (J5-I), which is known in the art or can be easily produced from a known compound, with chromium trioxide ($CrO_3$) in the presence of 3,5-dimethylpyrazole using a reaction inert solvent such as methylene chloride, 1,2-dichloroethane, acetonitrile, and benzene or a mixed solvent of them at a temperature from 0° C. to a reflux temperature of the solvent.

<Step 2>

[When the Ring Structure in Formula (J5-III) has a Double Bond (γ-hydroxy-α,β-Unsaturated Ester)]

The compound of Formula (J5-II) is subjected to reduction. A compound of Formula (J5-III) can be produced by reacting the compound of Formula (J5-II) with sodium borohydride and cerium chloride in a similar manner to that in <Step 2> in (Production Method J-1).

[When the Ring Structure in Formula (J5-III) is Saturated (γ-Hydroxy-α,β-Saturated ester)]

The compound of Formula (J5-II) is subjected to reduction. A compound of Formula (J5-III) can be produced by reacting the compound of Formula (J5-II) with sodium borohydride in a similar manner to that in <Step 2> in (Production Method J-1).

<Step 3>

The compound of Formula (J5-III) is subjected to substitution reaction with a compound of Formula (J-II)b. A compound of Formula (J5-IV) can be produced by reacting the compound of Formula (J-II)b, which is known in the art or can be easily produced from a known compound, with the compound of Formula (J5-III) in a similar manner to that in <Step 4> in (Production Method B).

<Step 4>

[When the Aliphatic Ring Structure has a Double Bond (γ-Hydroxy-α,β-Unsaturated ester)]

The compound of Formula (J5-IV) is subjected to reduction. The compound of Formula (B-V)-V can be produced by reacting the compound of Formula (J5-IV) with diisobutyl aluminum hydride (DIBAH) in a similar manner to that in <Step 2> in (Production Method J-1).

[When the Aliphatic Ring Structure is Saturated (γ-Hydroxy-α,β-Saturated Ester)]

The compound of Formula (J5-IV) is subjected to reduction. The compound of Formula (B-V)-V can be produced by reacting the compound of Formula (J5-IV) with lithium aluminum hydride (LAH) or diisobutyl aluminum hydride (DIBAH) in a similar manner to that in <Step 2> in (Production Method J-1).

(5-3) As another typical example of the compound of Formula (B-V), a method for producing a compound of Formula (B-V)-VI having Partial Structural Formula (AA)-VI:

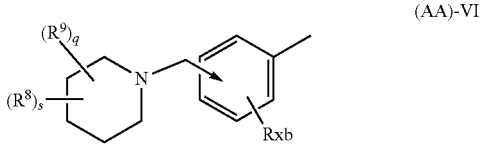

will be described.

<Production Method J-6>

<When the Ring A Is Partial Structural Formula (AA)-VI Above, j=1, $R^3$, $R^4$=H, and Z=OH in Formula (B-V) Above>

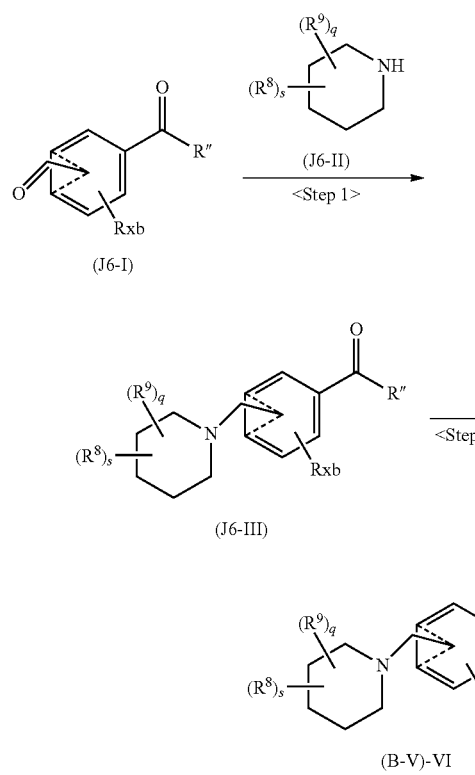

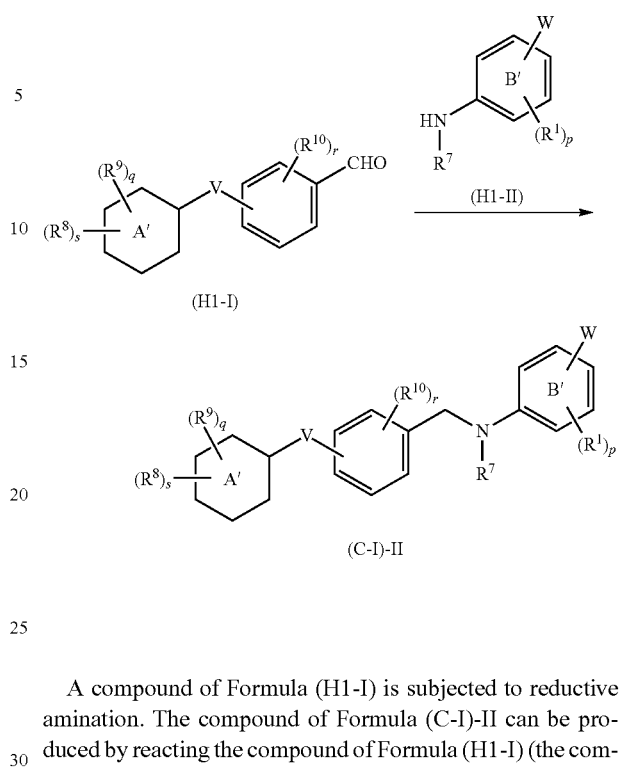

\<Step 1\>

A compound of Formula (J64) [in Formula, R" is a $C_{1-6}$ alkoxy group] is subjected to reductive amination. In accordance with methods known in literatures, for example, the method described in [The Journal of Organic Chemistry, vol. 61, pp. 3849-3862 (1996)], a compound of Formula (J6-III) can be produced by reacting the compound of Formula (J64), which is known in the art or can be easily produced from a known compound, with a compound of Formula (J6-II) in the presence of a reducing agent such as sodium triacetoxyborohydride and sodium cyanoborohydride in the presence or absence of a catalytic amount of acetic acid using a reaction inert solvent such as dichloromethane, 1,2-dichloroethane, tetrahydrofuran, acetonitrile, and toluene or a mixed solvent of them at a temperature from 0° C. to a reflux temperature of the solvent.

\<Step 2\>

The compound of Formula (J6-III) is subjected to reduction. The compound of Formula (B-V)-VI can be produced by reacting the compound of Formula (J6-III) in a similar manner to that in \<Step 2\> in (Production Method J-1).

(3-1) The compound of Formula (C-I) can also be produced by the methods below.

\<Production Method H-1\>

\<When the ring A is Partial Structural Formula (A) above, the ring B is the ring B', j=1, k=0, $R^3$, $R^4$=H, and X=$NR^7$ in Formula (C-I) above\>

A compound of Formula (H1-I) is subjected to reductive amination. The compound of Formula (C-I)-II can be produced by reacting the compound of Formula (H1-I) (the compound of Formula (H1-I) is included in the compound of Formula (J1-II) and can be easily produced from a known compound as shown in \<Step 1\> in (Production Method J-1) above) with a compound of Formula (H1-II) (it is known in the art or can be easily produced from a known compound) in a similar manner to that in \<Step 1\> in (Production Method J-6).

\<Production Method H-2\>

\<When the Ring A is Partial Structural Formula (AA1):

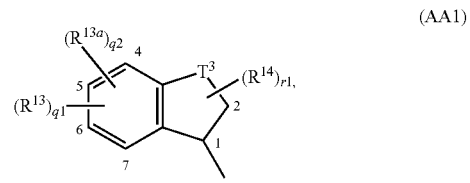

the ring B is the ring B', j, k=0, and X=NH in Formula (C-I) above\>

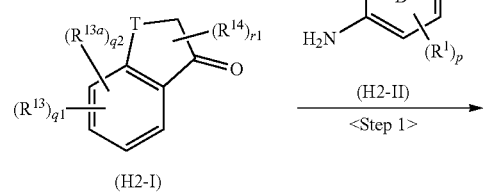

-continued

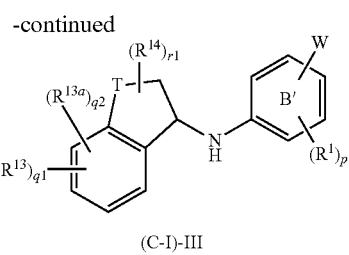

(C-I)-III

A compound of Formula (H2-I) is subjected to reductive amination. In accordance with methods known in literatures, for example, the method described in [WO 2006/128670 pamphlet], the compound of Formula (C-I)-III can be produced by reacting the compound of Formula (H2-I) (it is known in the art or can be easily produced from a known compound as shown in <Step 1> in (Production Method J-3) above and the like) with a compound of Formula (H2-II) (it is known in the art or can be easily produced from a known compound) (<Step 1>).

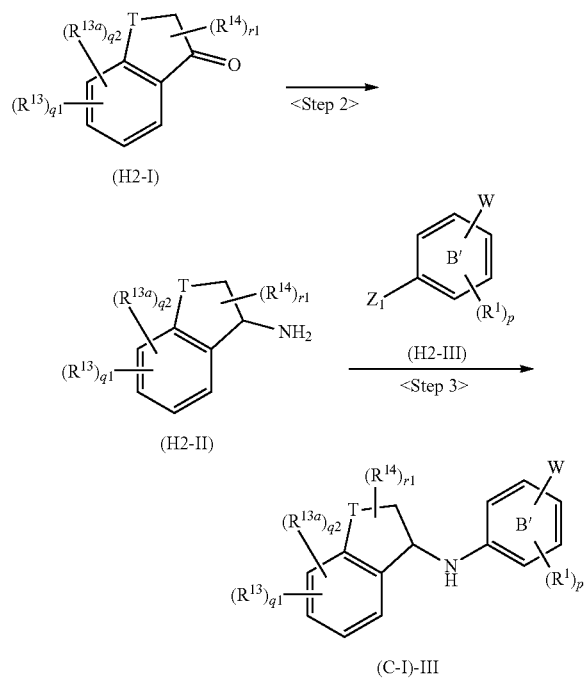

The compound of Formula (C-I)-III can also be produced by reacting, in accordance with methods known in literatures, for example, the method described in [WO 2006/085149 pamphlet], the compound of Formula (H2-I) with hydroxylamine hydrochloride to afford an oxime, then by hydrogenating the oxime using hydrogen and Pd—C to produce a compound of Formula (H2-II) (<Step 2>), and by reacting the obtained compound of Formula (H2-II) with a compound of Formula (H2-III) in accordance with methods known in literatures, for example, the method described in [WO 2005/682859 pamphlet or Journal of the American Chemical Society, vol. 128 (29), pp. 9306-9307 (2006)] (<Step 3>). $Z_1$ in Formula (H2-III) above is halogen, a methanesulfonyloxy group, or a p-toluenesulfonyloxy group in Z above.

<Step 2> above can be carried out with reference to known reaction conditions for reductive amination, for example, in [WO 2006/083454 pamphlet, p. 62, Steps A and B in Preliminary Example] and [WO 2010/143733 pamphlet, Reference Example 68]. <Step 3> above can be carried out in accordance with known reaction conditions for substitution, for example, in [WO 2010/143733 pamphlet, [0184], Step 7].

<Production Method H-3>

<When the Ring A is Partial Structural Formula (A)-V:

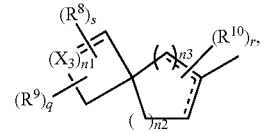

the ring B is the ring B', j=1, k=0, $R^3$, $R^4$=H, and X=oxygen atom in Formula (C-I) above>

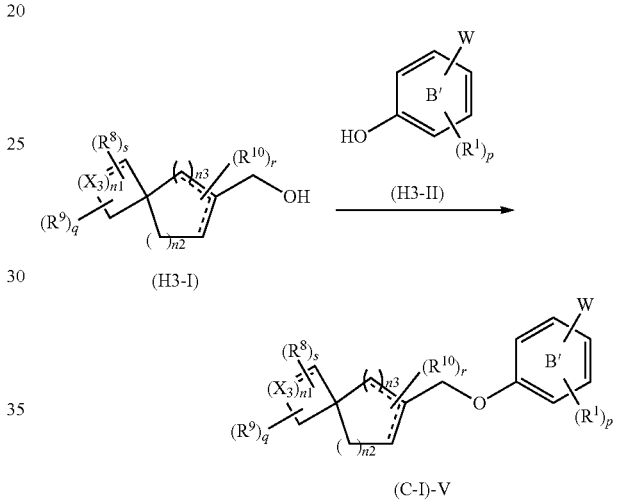

A compound of Formula (H3-I) is subjected to substitution reaction with a compound of Formula (H3-II). The compound of Formula (C-I)-V can be produced by reacting the compound of Formula (H3-II), which is known in the art or can be easily produced from a known compound, with the compound of Formula (H3-I) in a similar manner to that in <Step 4> in (Production Method B) or in accordance with the method described in [WO 2009/054479 pamphlet, Step 1 or Step 1' in Production Method A1 (for example, Step 6 in Example 41)]. For example, condensation is carried out in a solvent at room temperature or under heating. Examples of the reagent include 1,1'-(diazocarbonyl)dipiperidine and triphenylphosphine. Examples of the solvent include an ether solvent such as tetrahydrofuran.

The compound of Formula (H3-I) above is known in the art or can be easily produced from a known compound with reference to, for example, [WO 2009/054479 pamphlet, Production Method B, C, D, or the like (paragraphs [0185] to [0264])].

Hereinafter, the methods for producing the compound of Formula (H3-I) of the present invention will be described in further detail.

<Production Method H-4>

<When n3=1, the broken line adjacent to the carbon atom in the n3 moiety is a double bond, and the other broken lines are single bonds in Formula (H3I) above>

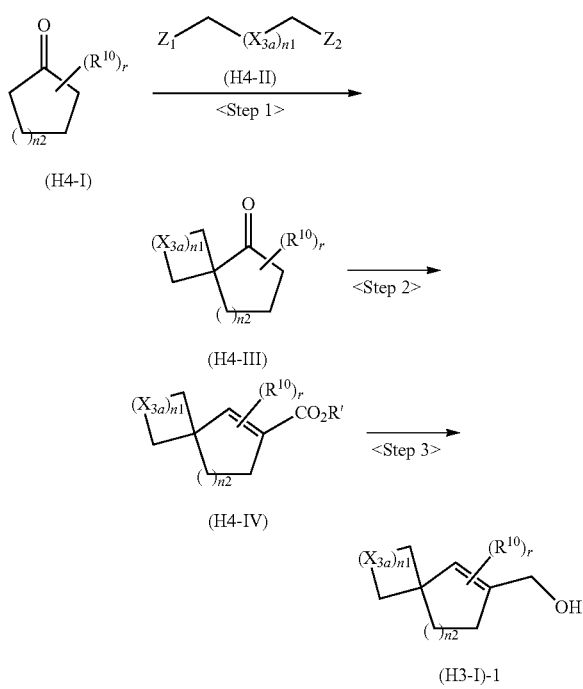

(H4-I)

(H4-II) <Step 1>

(H4-III)

<Step 2>

(H4-IV)

<Step 3>

(H3-I)-1

<Step 1>
A compound of Formula (H4-I) is subjected to substitution reaction with a compound of Formula (H4-II) (each $X_3a$ in Formula (H4-II) is independently —$CR_{V1a}R_{V2a}$— or —$NR_{V3a}$—, each of $R_{V1a}$, $R_{V2a}$, and $R_{V3a}$ is independently a hydrogen atom, —OH, or —$NH_2$, each definition of $Z_1$ and $Z_2$ is the same as that of Z above, and $Z_1$ and $Z_2$ are preferably a halogen atom). A compound of Formula (H4-III) can be produced by reacting the compound of Formula (H4-I), which is known in the art or can be easily produced from a known compound, with the compound of Formula (H4-II) in accordance with the method described in [WO 2009/054479 pamphlet, Production Method D1-1 (for example, Step 1 in Example 41 and Step 4 in Example 104)]. For example, the condensation is carried out in a solvent at room temperature or under heating in the presence of a base. Examples of the base include potassium tert-butoxide and sodium hydride. Examples of the solvent include an aromatic hydrocarbon solvent such as toluene.

<Step 2>
A compound of Formula (H4-IV) can be produced from the compound of Formula (H4-III) in accordance with the method described in [WO 2009/054479 pamphlet, Steps 1 to 4 in Production Method C1-1 (for example, Steps 2 to 4 in Example 41)].

<Step 3>
The compound of Formula (H3-I)-1 can be produced from the compound of Formula (H4-IV) in accordance with the method described in [WO 2009/054479 pamphlet, Step 5 in Production Method C1-1 (for example, Step 5 in Example 41)].

<Production Method H-5>
<When the Ring A is Partial Structural Formula (A)-VI:

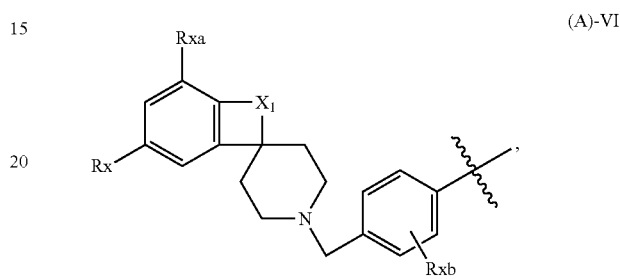

(A)-VI the ring B is a benzene ring, a linker moiety including an isothiazolyl group and X is placed at the p-position, j=1, k=0, and $R^3$, $R^4$=H in Formula (C-I) above>

As shown in the scheme below, in accordance with Scheme I in WO 2011/046851 pamphlet, pp. 8-9, a substituted benzyl bromide of Formula (1) is reacted with a suitable substituted spiropiperidine of Formula (SP) or its hydrochloric acid salt or trifluoroacetic acid salt in the presence of a suitable base such as diisopropylethylamine and cesium carbonate to give a compound of Formula (4) in step 1a. The ester is properly reduced in step 2 with diisobutylaluminum hydride, lithium aluminum hydride, sodium borohydride, or the like to give a substituted benzyl alcohol of Formula (B-V). The compound of Formula (B-V) can be properly used in, for example, (Production Method B), (Production Method E), (Production Method F), and (Production Method H) above and (Production Method L) below. The compound of Formula (B-V) can also be obtained by reduction in step 1b instead of step 1a to give a compound of Formula (2), followed by reaction with the compound of Formula (SP) in step 1c in the same manner as in the above.

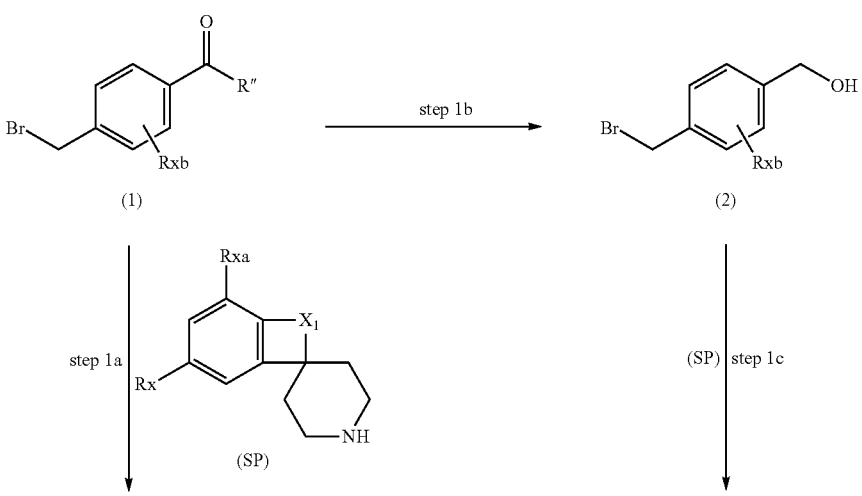

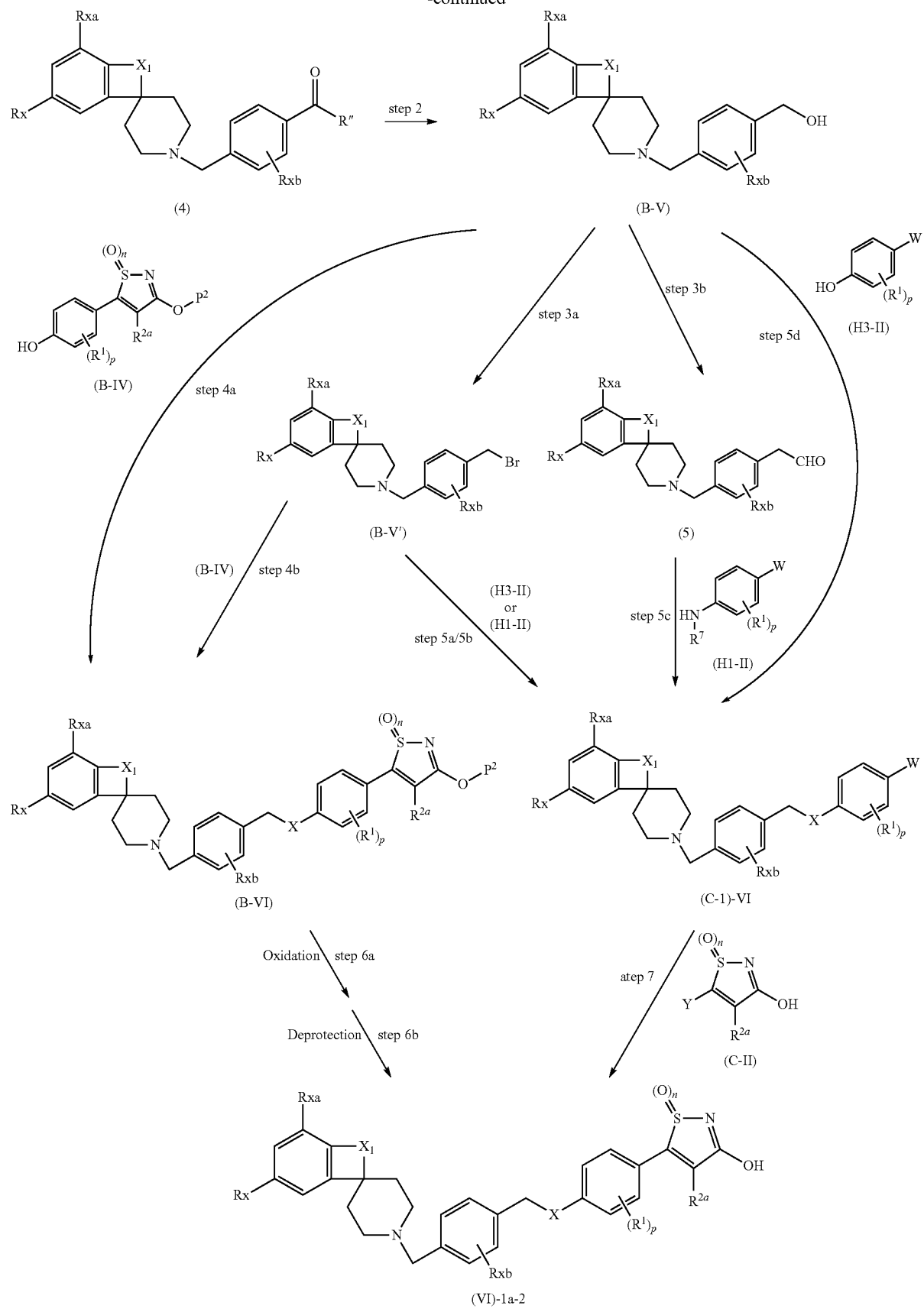

Here, the compound of Formula (B-V) is further reacted with a phenol derivative of Formula (B-IV) by Mitsunobu reaction in step 4a in the presence of a suitable phosphine such as triphenylphosphine and triethylphosphine and an azodicarbonyl such as ADDP or an azodicarboxylate such as DEAD, and then the product is properly oxidized and deprotected in steps 6a and 6b to give a compound of Formula (VI)-1a-2 (X=oxygen atom).

Another pathway may be employed. That is, the compound of Formula (B-V) is derived to a benzyl bromide of Formula (B-V') in step 3a with a suitable brominating agent such as phosphorus tribromide, and then the benzyl bromide is reacted with the phenol derivative of Formula (B-IV) above in step 4b to give the compound of Formula (B-VI).

The compound of Formula (B-V') is also reacted with a compound of Formula (H3-II) or a compound of Formula (H1-II) in step 5a/b to give a corresponding compound of Formula (C-I)-VI (X=oxygen atom or —$NR_7$—). Alternatively, the compound of Formula (C-I)-VI can be derived from the compound of Formula (B-V) by oxidation with a suitable oxidizing agent such as Dess-Martin reagent to give an aldehyde of Formula (5) in step 3b, followed by oxidative amination with a compound of Formula (H1-II) in step 5c. The compound of Formula (C-I)-VI (X=oxygen atom or —$NR_7$—) can also be derived from the compound of Formula (B-V) by direct Mitsunobu reaction with a compound of Formula (H3-II) in step 5d.

The compound of Formula (C-I)-VI is reacted with a compound of Formula (C-II) in step 7 to give a compound of Formula (VI)-1a-2 (X=oxygen atom or —$NR_7$—).

A final compound of Formula (VI)-1a can be produced by reduction of the obtained compound of Formula (VI)-1a-2 in a similar manner to that in <Step 3> in (Production Method A).

Through the synthetic route shown below, the compound of Formula (B-VI) can also be obtained using a known or suitable benzyl bromide derivative to give an intermediate, followed by reaction with a substituted spiropiperidine of Formula (SP). Each definition of substituents and reference signs is the same as in the above.

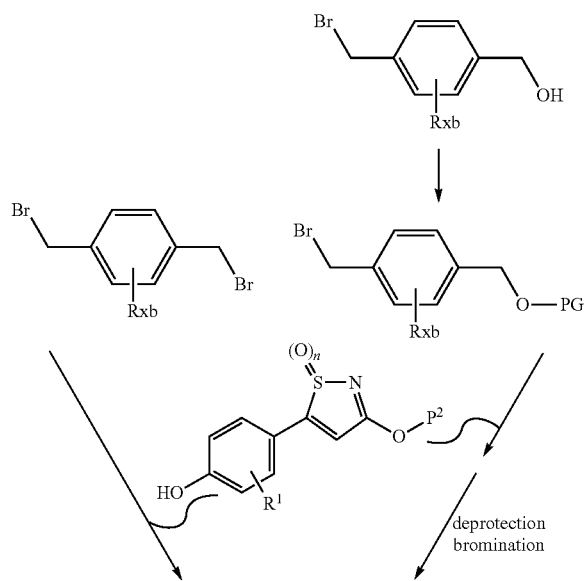

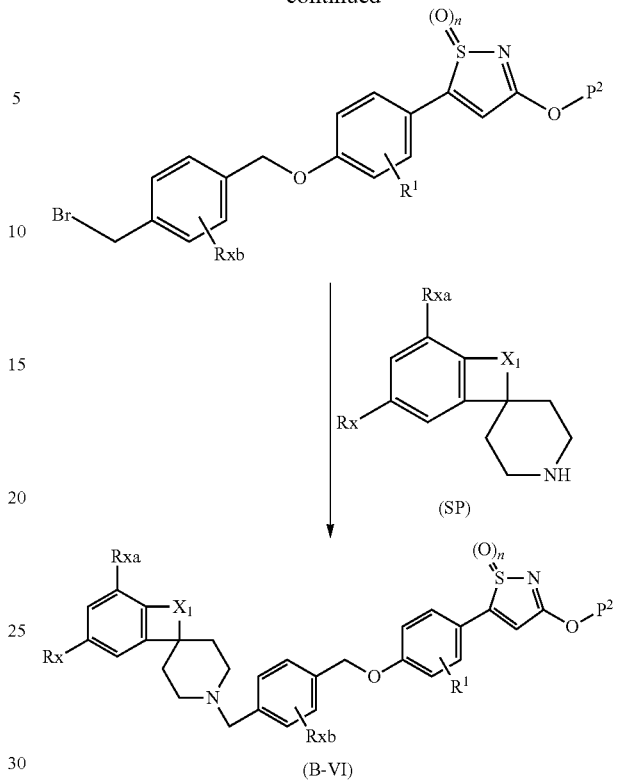

(B-VI)

In particular, a method for producing a compound of Formula (B-V) where $X_1$ is —$N(Rz)CH_2$— can be with reference to WO 2011/064851 pamphlet, pp. 10-11. In accordance with Scheme II in the literature, a protected piperidine-4-carboaldehyde is reacted with a phenylhydrazine that may be substituted at the 2-position and/or 4-position to give a substituted spiro[indoline-3,4'-piperidine]. The product is, as necessary, further alkylated, and then is deprotected to give the compound of Formula (SP) suited for the present invention.

WO 2011/046851 pamphlet discloses in pp. 29-31, as specific known compounds of Formula (B-V) suitably used for Production Method U of the present invention, (4-(spiro[inden-1,4'-piperidin]-1'-ylmethyl)phenyl)methanol as well as [3-chloro-4-(spiro[inden-1,4'-piperidin]-1'-ylmethyl)phenyl]methanol, [2-methoxy-4-(spiro[inden-1,4'-piperidin]-1'-ylmethyl)phenyl]methanol, [3-fluoro-4-(spiro[inden-1,4'-piperidin]-1'-ylmethyl)phenyl]methanol, [4-(spiro[inden-1,4'-piperidin]-1'-ylmethyl)-3-(trifluoromethyl)phenyl]methanol, [3-chloro-4-[(1-methylspiro[indolin-3,4'-piperidin]-1'-yl)methyl]phenyl]methanol, [4-(spiro[indan-1,4'-piperidin]-1'-ylmethyl)-3-(trifluoromethyl)phenyl]methanol, and [4-(spiro[indan-1,4'-piperidin]-1'-ylmethyl)phenyl]methanol.

As other usable compounds of Formula (B-V'), WO 2011/046851 pamphlet also discloses, in pp. 31-32, corresponding bromomethyl derivatives as Prep No. 56-61.

Hereinbefore, the method for producing a compound substituted with an isothiazole ring at the p position with respect to the hetero atom X has been described. Furthermore, an m-isomer that can be properly obtained or synthesized is used in place of the starting material of Formula (1) or Formula (2) to produce a corresponding compound substituted with the isothiazole ring at the m position with respect to the hetero atom X in a similar manner.

<Production Method H-5a>

It can be understood that another substituted spiropiperidine of Formula (SP') is used in place of the substituted spiropiperidine of Formula (SP) in each production route in (Production Method H-5) to give each compound of Formula (B-Va), Formula (B-Va'), Formula (C-1)-VIa, Formula (B-VIa), and Formula (VIa)-1a-2 having the moiety of Formula (SP') that replaces the moiety of Formula (SP) in each compound of Formula (B-V), Formula (B-V'), Formula (C-1)-VI, Formula (B-VI), and Formula (VI)-1a-2.

Furthermore, each compound of Formula (B-V), Formula (B-V'), Formula (B-Va), and Formula (B-Va') described in (Production Method H-5) and (Production Method H-5a) can be used as the compound of Formula (B-V) in (Production Method B), (Production Method E), (Production Method F), or (Production Method H) above, (Production Method L) below, or the like in each step (for example, in <Step 4> in (Production Method B)).

<Production Method H-5b>

In place of the starting material of Formula (1) or Formula (2) used in steps 1a, 1b, and 1c in (Production Method H-5) or (Production Method H-5a), in accordance with the description of scheme I or scheme III in pp. 5 to 10 in WO 2011/066183 pamphlet, a corresponding bromomethyl-heteroaryl-carboxylic acid derivative of Formula (1) or a methyl alcohol of bromomethyl-heteroaryl of Formula (2):

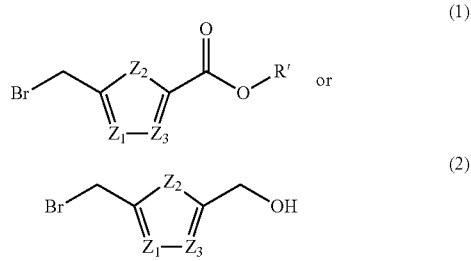

(where each definition of $Z_1$, $Z_2$, and $Z_3$ is the same as that in Formula (A2) IV described in the aspect [1-13-e-3]) is used to produce the compound in the aspect [1-13-e-8] or [1-13-e-8a] having a 5-membered heteroaryl in the molecule.

(6) The compound of Formula (I)-1a can also be produced by the methods below.

<Production Method K>

<When the ring A is Partial Structural Formula (AA)-1 above (that is Formula (III)-1a1), X=oxygen atom, $R^{2b}$=H, and $R^{11a}$=H in Formula (I)-1a above>

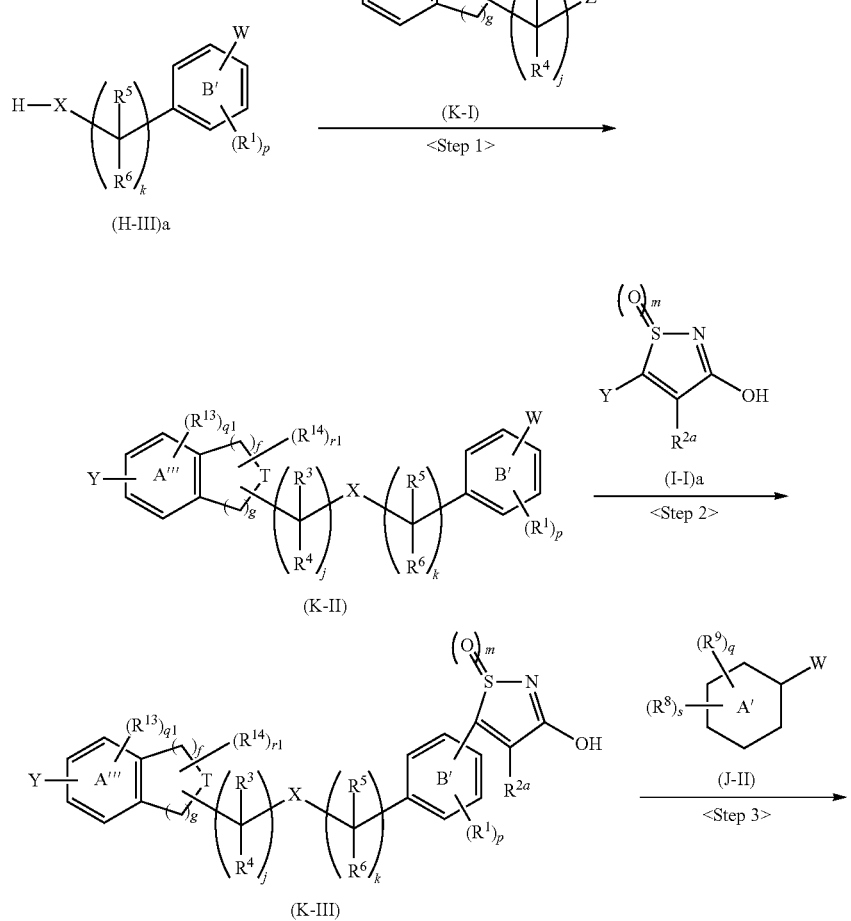

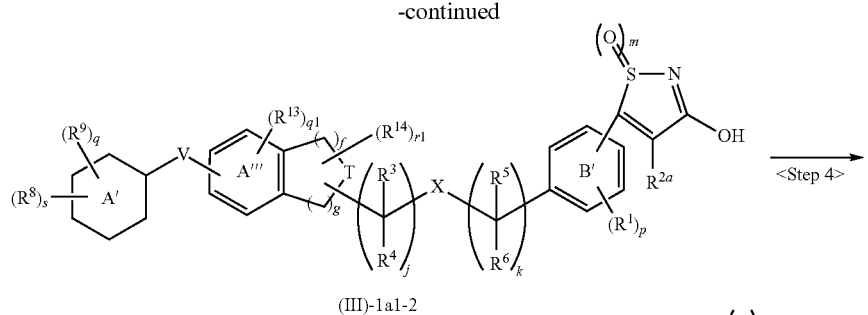

(III)-1a1-2

(III)-1a1

<Step 1>

A compound of Formula (H-III)a is subjected to substitution reaction with a compound of Formula (K-I). A compound of Formula (K-II) can be produced by reacting the compound of Formula (H-III)a obtained in <Step 3> in (Production Method H) above with the compound of Formula (K-I), which is known in the art or can be easily produced from a known compound, in a similar manner to that in <Step 4> in (Production Method B).

<Step 2>

The compound of Formula (K-II) is subjected to substitution reaction with a compound of Formula (I-I)a. A compound of Formula (K-III) can be produced by reacting the compound of Formula (K-II) with the compound of Formula (I-I)a in a similar manner to that in <Step 1> in (Production Method C).

<Step 3>

The compound of Formula (K-III) is subjected to substitution reaction with a compound of Formula (J-II).

<When V=Single Bond>

A compound of Formula (III)-1a1-2 can be produced by reacting the compound of Formula (K-III) with the compound of Formula (J-II) in a similar manner to that in <Step 1> in (Production Method C).

<When V=Oxygen Atom>

In accordance with methods known in literatures, for example, the method described in [Tetrahedron Letters, vol. 49, pp. 1851-1855 (2008)], a compound of Formula (III)-1a1-2 can be produced by reacting the compound of Formula (K-III) in the presence of the compound of Formula (J-II) in the presence of a copper catalyst such as copper(I) iodide, copper(I) bromide, copper(I) chloride, and copper(I) oxide, a base such as potassium phosphate, potassium carbonate, and sodium tert-butoxide, and an additive such as 1-butylimidazole, 1-methylimidazole, and 2,2'-bipyridine using a reaction inert solvent such as toluene, xylene, 1,4-dioxane, and N-methylpyrrolidone or a mixed solvent of them at a temperature from 0° C. to a reflux temperature of the solvent.

In accordance with other methods known in literatures, for example, the method described in [Journal of the American Chemical Society, vol. 121, pp. 4369-4378 (1999)], the compound of Formula (III)-1a1-2 can also be produced by reacting the compounds of Formula (K-III) and Formula (J-II) in the presence of a palladium catalyst such as palladium(II) acetate, tetrakis triphenylphosphine palladium, tris(dibenzylideneacetone)dipalladium, bis(dibenzylideneacetone)palladium, and [1,1'-bis(diphenylphosphino)ferrocene]dichloropalladium(II), a phosphine reagent such as (2-biphenyl)di-(tert-butyl)phosphine, 2-di-(tert-butyl)-2'-(N,N-dimethylamino)biphenyl, and 2-dicyclohexyl-2'-(N,N-dimethylamino)biphenyl, and a base such as potassium phosphate, sodium hydride, and sodium tert-butoxide using a reaction inert solvent such as dichloromethane, 1,4-dioxane, tetrahydrofuran, toluene, and N,N-dimethylformamide or a mixed solvent of them at a temperature from 0° C. to a reflux temperature of the solvent.

<Step 4>

The compound of Formula (III)-1a1-2 is subjected to reduction. The compound of Formula (III)-1a1 can be produced by reacting the compound of Formula (III)-1a1-2 in a similar manner to that in <Step 3> in (Production Method A).

The compound of Formula (K-I) includes optical isomers because a carbon atom is an asymmetric carbon by bonding the carbon atom to Z. As with Formula (J2-I) above, such isomers are known in the art or can be easily produced from a known compound. Each enantiomer can be obtained through optical resolution using column chromatography or asymmetric synthesis by a person skilled in the art based on conventional techniques (for example, (1S)-4-bromo-2,3-dihydro-1H-inden-1-ol). Each enantiomer of Formula (K-II), Formula (K-III), Formula (III)-1a1-2, and Formula (III)-1a1 (for example, compounds in Example 23-3, Example 23-4, Example 23-5, and Example 23 described later) can be produced using such an enantiomer.

<Production Method L>

<When $R^{2b}$=H and $R^{11a}$=H in Formula (I)-1a>

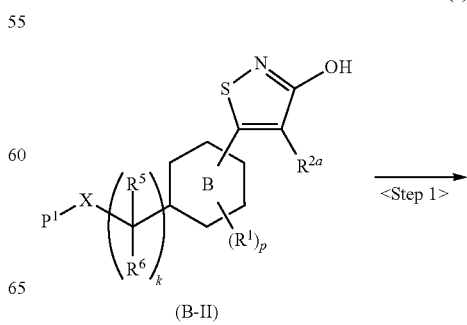

(B-II)

-continued

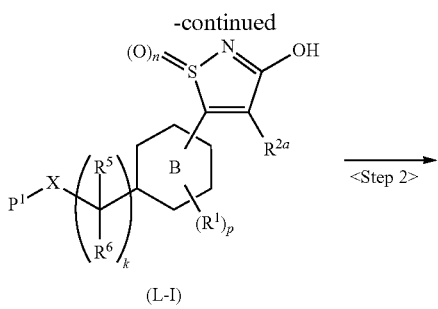

(L-I)

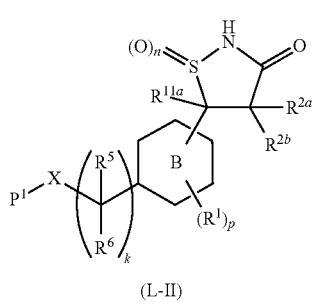

(L-II)

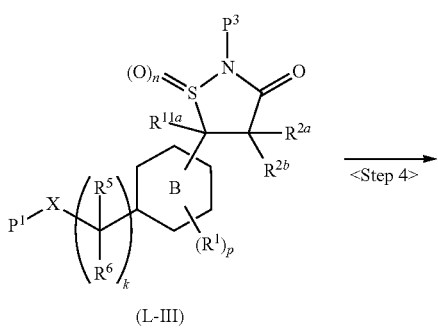

(L-III)

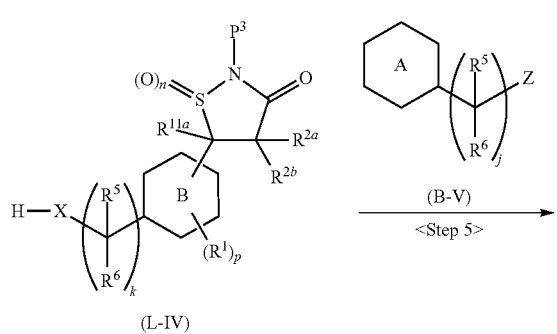

(L-IV)

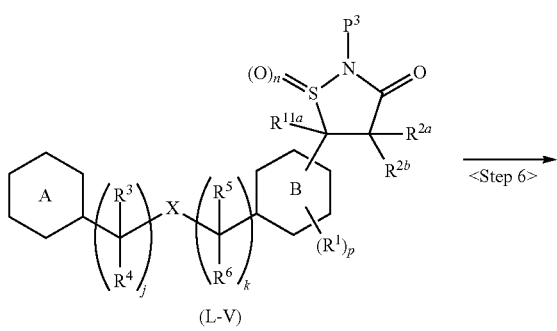

(L-V)

-continued

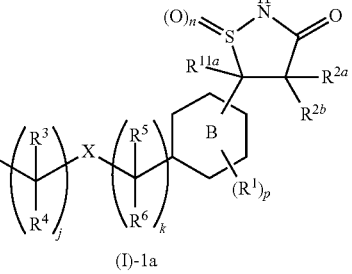

(I)-1a

<Step 1>
The sulfur atom of a compound of Formula (B-II) is oxidized. A compound of Formula (L-I) can be produced by reacting the compound of Formula (B-II) in a similar manner to that in <Step 2> in (Production Method A).

<Step 2>
The compound of Formula (L-I) is subjected to reduction. A compound of Formula (L-II) can be produced by reacting the compound of Formula (L-I) in a similar manner to that in <Step 3> in (Production Method A).

<Step 3>
The compound of Formula (L-III) is protected with a protective group $P^3$. A compound of Formula (L-III) can be produced by reacting the compound of Formula (L-II) in a similar manner to that in <Step 2> in (Production Method B).

<Step 4>
The protective group $P^1$ in the compound of Formula (L-III) is deprotected. A compound of Formula (L-IV) can be produced by reacting the compound of Formula (L-III) in a similar manner to that in <Step 3> in (Production Method B).

<Step 5>
The compound of Formula (L-IV) is subjected to substitution reaction with a compound of Formula (B-V). A compound of Formula (L-V) can be produced by reacting the compound of Formula (L-IV) in a similar manner to that in <Step 4> in (Production Method B).

<Step 6>
The protective group $P^3$ in the compound of Formula (L-V) is deprotected. The compound of Formula (I)-1a can be produced by reacting the compound of Formula (L-V) in a similar manner to that in <Step 3> in (Production Method B).

<Production Method L-1>
<When X=oxygen atom in Formula (I) above>

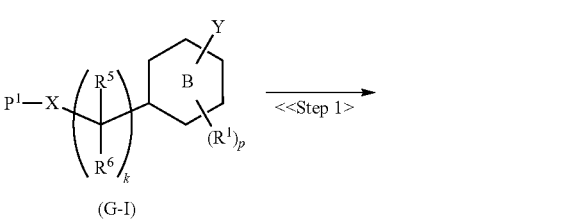

(G-I)

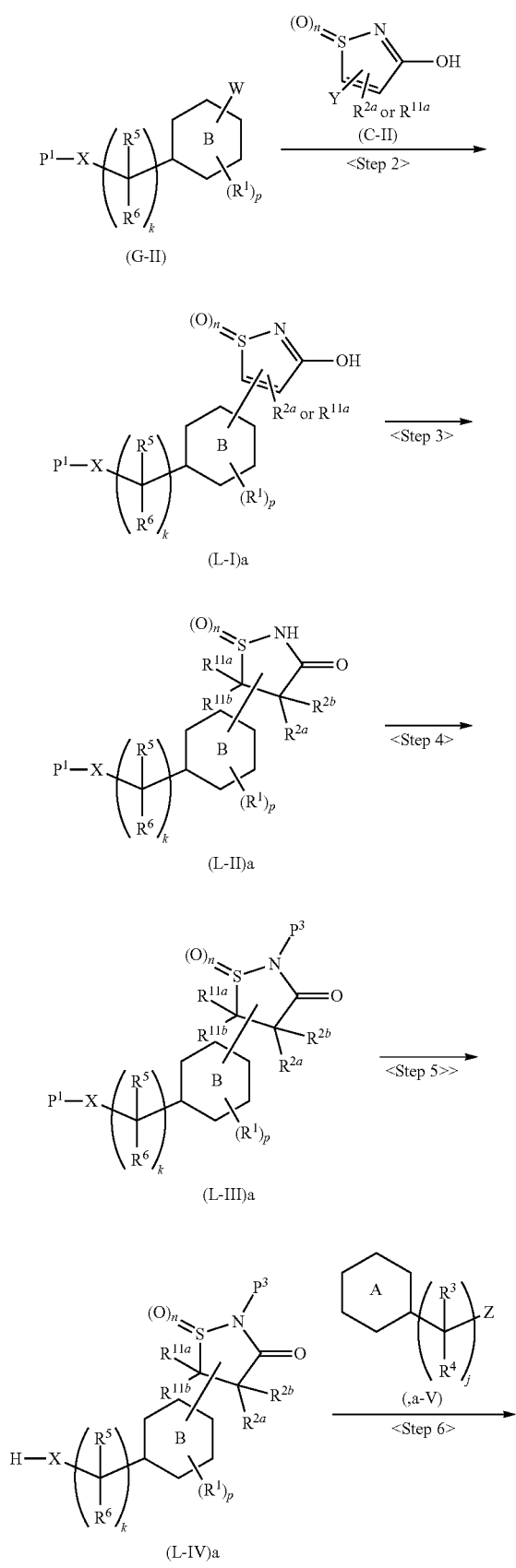

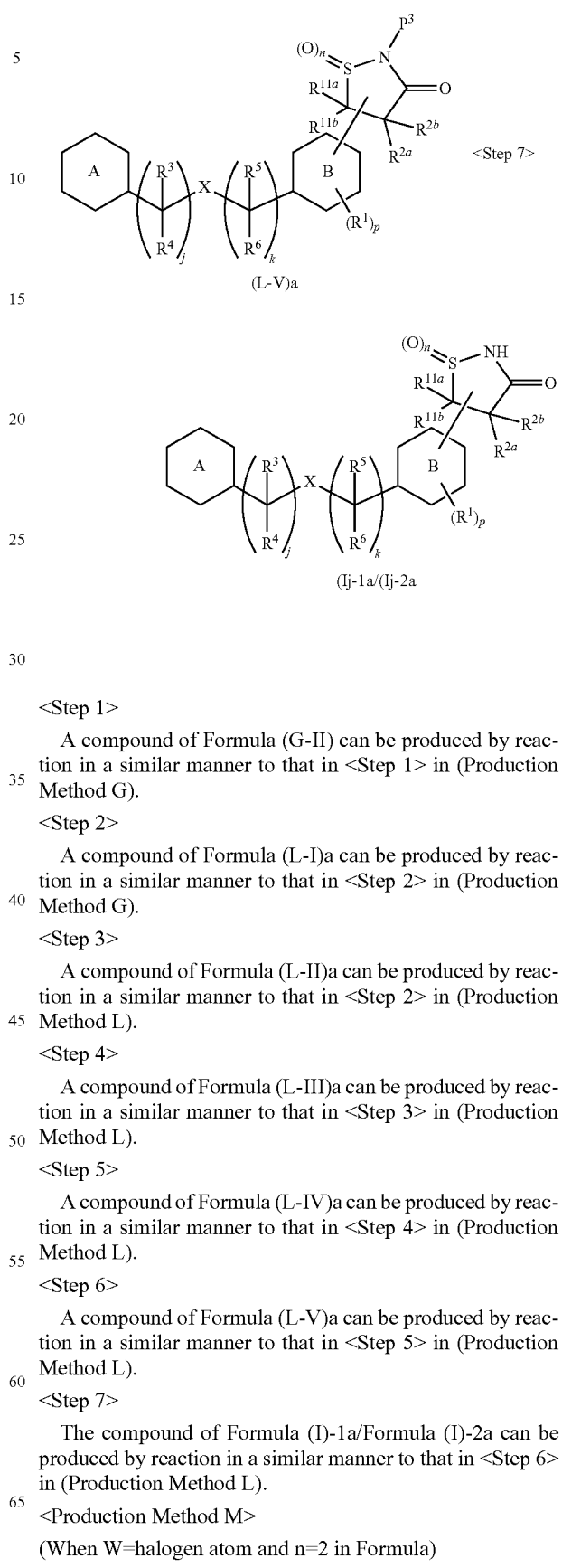

<Step 1>
A compound of Formula (G-II) can be produced by reaction in a similar manner to that in <Step 1> in (Production Method G).

<Step 2>
A compound of Formula (L-I)a can be produced by reaction in a similar manner to that in <Step 2> in (Production Method G).

<Step 3>
A compound of Formula (L-II)a can be produced by reaction in a similar manner to that in <Step 2> in (Production Method L).

<Step 4>
A compound of Formula (L-III)a can be produced by reaction in a similar manner to that in <Step 3> in (Production Method L).

<Step 5>
A compound of Formula (L-IV)a can be produced by reaction in a similar manner to that in <Step 4> in (Production Method L).

<Step 6>
A compound of Formula (L-V)a can be produced by reaction in a similar manner to that in <Step 5> in (Production Method L).

<Step 7>
The compound of Formula (I)-1a/Formula (I)-2a can be produced by reaction in a similar manner to that in <Step 6> in (Production Method L).

<Production Method M>

(When W=halogen atom and n=2 in Formula)

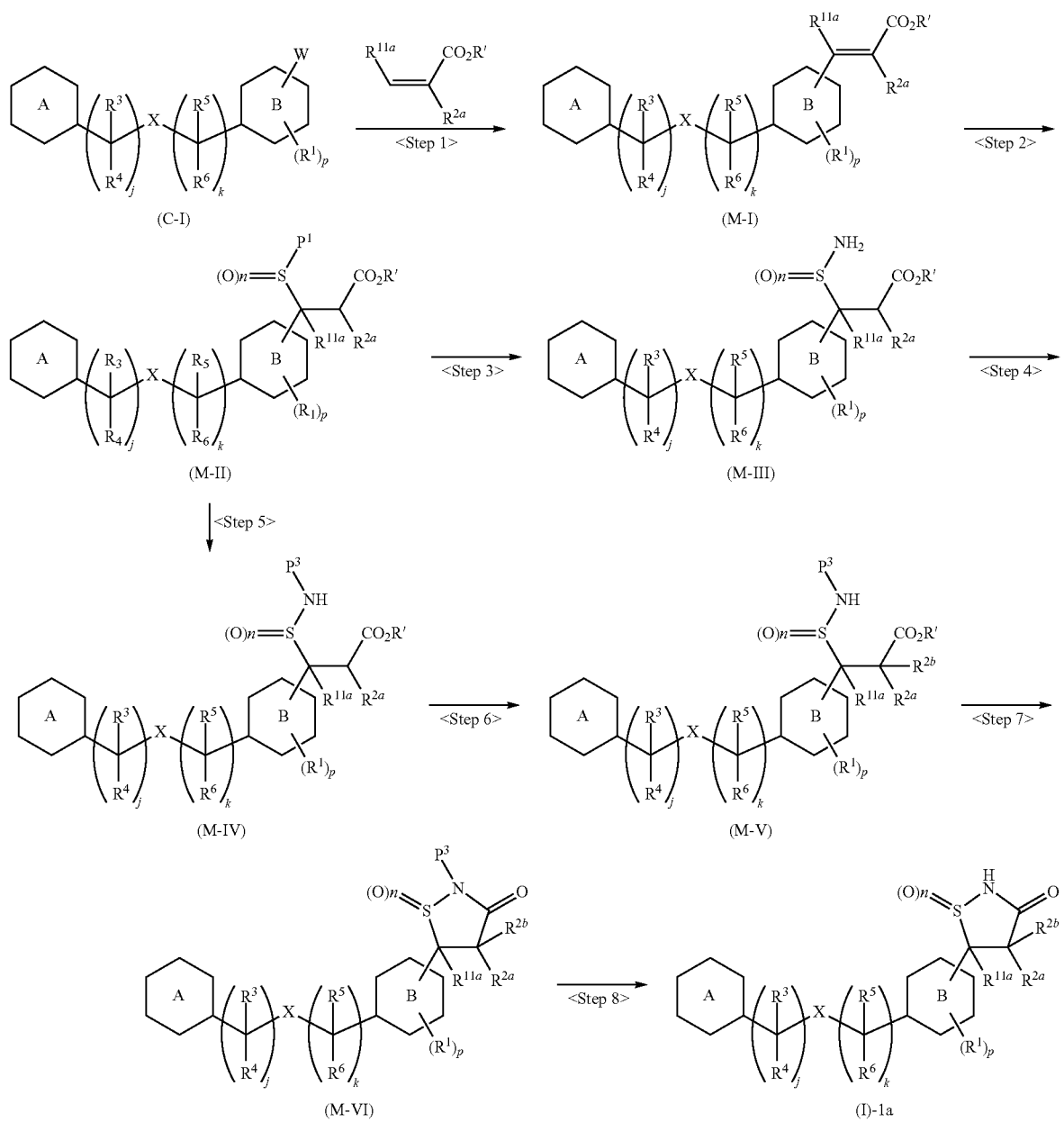

<Step 1>

A compound of Formula (C-I) is reacted. In accordance with methods known in literatures, for example, the method described in [Tetrahedron Letters, vol. 26 (22), pp. 2667-2670 (1985)], a compound of Formula (M-I) can be produced by reacting the compound of Formula (C-I) above in the presence of a palladium catalyst such as palladium diacetate, tetrakis triphenylphosphine palladium, and tris dibenzylideneacetone dipalladium and a base such as potassium carbonate, silver carbonate, and tributylamine using a reaction inert solvent such as acetonitrile, dioxane, tetrahydrofuran, benzene, toluene, dimethyl sulfoxide, and N,N-dimethylformamide or a mixed solvent of them at a temperature from room temperature to a reflux temperature of the solvent.

<Step 2>

The compound of Formula (M-I) is reacted. In accordance with methods known in literatures, for example, the method described in [Organic Letters, vol. 7 (22), pp. 5067-5069 (2005)], a compound of Formula (M-II) can be produced by reacting the compound of Formula (M-I) in the presence of a sulfur reagent such as sodium sulfite using a reaction inert solvent such as ethanol and water or a mixed solvent of them at a temperature from room temperature to a reflux temperature of the solvent or at high temperature and high pressure using a microwave reaction apparatus.

<Step 3>

The compound of Formula (M-II) is reacted. In accordance with methods known in literatures, for example, the method described in [Organic Letters, vol. 7 (22), pp. 5067-5069 (2005)], a compound of Formula (M-III) can be produced by reacting the compound of Formula (M-II) in the presence of a chlorinating reagent such as phosphorus pentachloride using a reaction inert solvent such as methylene chloride and DMF or a mixed solvent of them at a temperature from room temperature to a reflux temperature of the solvent and then by stopping the reaction with aqueous ammonia.

<Step 4>

The compound of Formula (M-III) is protected with a protective group $P^3$. A compound of Formula (M-IV) can be produced by reacting the compound of Formula (M-III) in a similar manner to that in <Step 2> in (Production Method B).

<Step 5>

The compound of Formula (M-II) is reacted. In accordance with methods known in literatures, for example, the method described in [Organic Letters, vol. 7 (22), pp. 5067-5069 (2005)], a compound of Formula (M-IV) can be produced by reacting the compound of Formula (M-II) in the presence of a chlorinating reagent such as phosphorus pentachloride using a reaction inert solvent such as methylene chloride and DMF or a mixed solvent of them at a temperature from room temperature to a reflux temperature of the solvent and then by stopping the reaction with a protected secondary amine such as benzylamine and tosylamine.

<Step 6>

<When $R^{2b} \neq$ hydrogen atom>

The compound of Formula (M-IV) is subjected to substitution reaction. In accordance with methods known in literatures, for example, the method described in [Jikken Kagaku Koza (Experimental Chemistry Course), the fifth edition, vol. 16, Synthesis of Organic Compound IV, Carboxylic acid, Amino acid, and Peptide, pp. 1-70 (2005), Maruzen Co., Ltd.], a compound of Formula (M-V) can be produced by reacting the compound of Formula (M-IV) with, for example, a halogenated alkyl of $R^{2b}X$ in the presence of a base such as sodium ethoxide, sodium methoxide, sodium hydride, lithium hydride, lithium hydroxide, sodium hydroxide, potassium hydroxide, lithium carbonate, sodium carbonate, and potassium carbonate using a reaction inert solvent such as ethanol, water, N,N-dimethylformamide, 1,4-dioxane, and tetrahydrofuran or a mixed solvent of them at a temperature from 0° C. to a reflux temperature of the solvent.

<Step 7>

The compound of Formula (M-V) is subjected to ring formation reaction. In accordance with methods known in literatures, for example, the method described in [Organic Letters, vol. 7 (22), pp. 5067-5069 (2005)], a compound of Formula (M-VI) can be produced by reacting the compound of Formula (M-V) in the presence of sodium methoxide, sodium ethoxide, or the like using a reaction inert solvent such as methanol and ethanol or a mixed solvent of them at a temperature from room temperature to a reflux temperature of the solvent.

<Step 8>

The protective group $P^3$ in the compound of Formula (M-VI) is deprotected. The compound of Formula (I)-1a can be produced by reaction in a similar manner to that in <Step 3> in (Production Method B).

(7) The methods for producing the compound of Formula (I)-1b of the present invention will be described below.

<Production Method N>

(When n=2 in Formula)

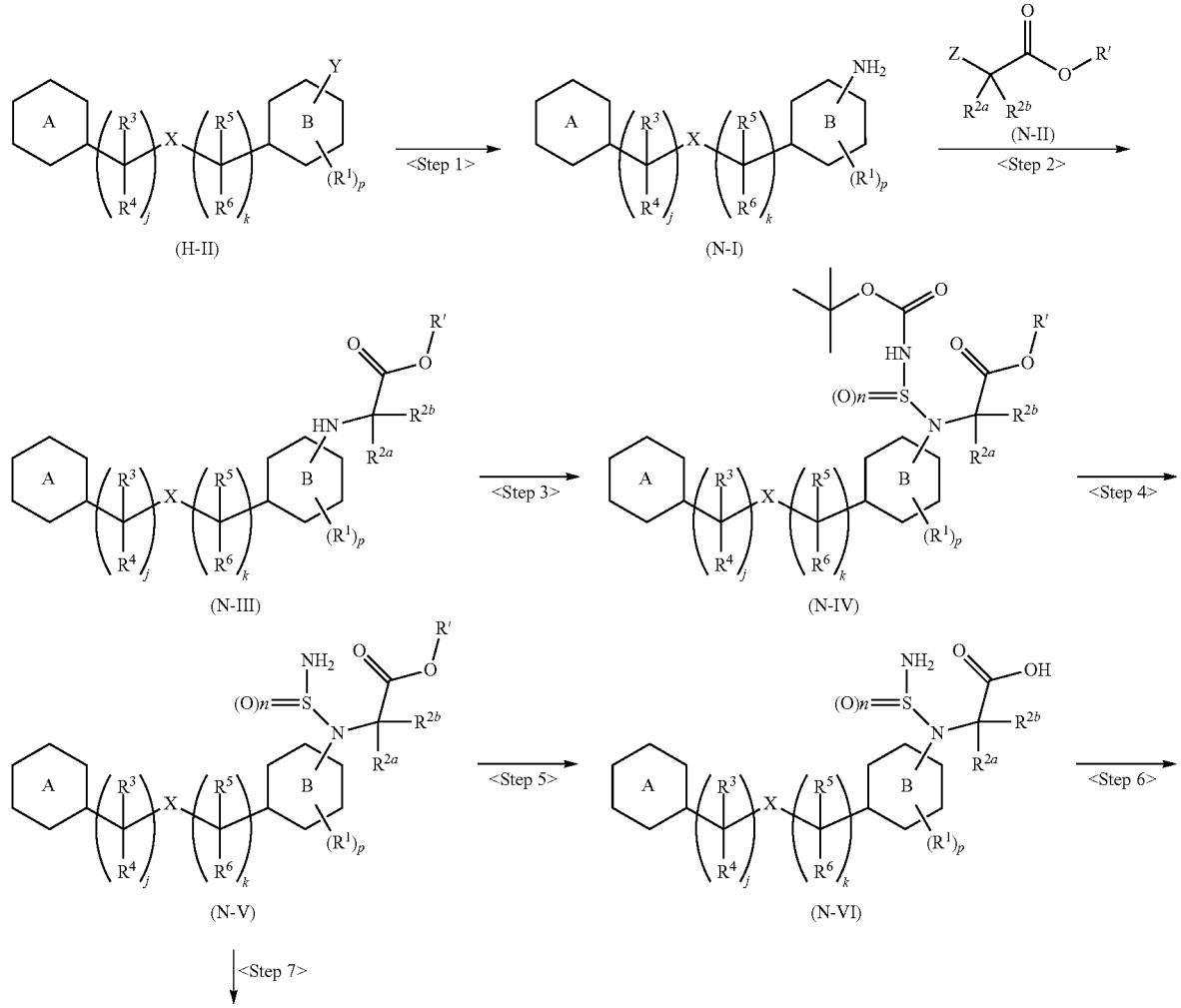

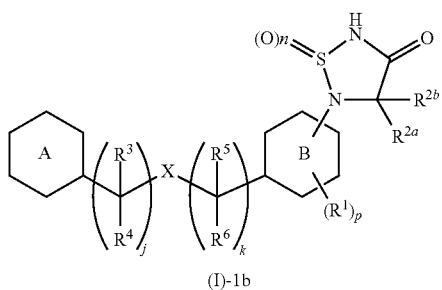

(I)-1b

<Step 1>
A compound of Formula (N-I) can be produced by reacting the compound of Formula (H-II) above (Y=protected imino group (—NP$^1_2$)) in a similar manner to that in <Step 3> in (Production Method B).
<Step 2>
The compound of Formula (N-I) is reacted. In accordance with methods known in literatures, for example, the method described in [Chemical & Pharmaceutical Bulletin, vol. 43 (5), pp. 820-841 (1995)], a compound of Formula (N-III) can be produced by substitution reaction of the compound of Formula (N-I) in the presence of a compound of Formula (N-II), which is known in the art or can be easily produced from a known compound, in the presence or absence of a base such as diisopropylethylamine, triethylamine, pyridine, sodium hydride, sodium hydroxide, potassium carbonate, and cesium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.
<Step 3>
The compound of Formula (N-III) is reacted. In accordance with methods known in literatures, for example, the method described in [WO 2007/110337 pamphlet], each compound of Formula (N-IV) (n=0, 1, or 2) can be produced by reacting the compound of Formula (N-III), for example, in the presence of a sulfur reagent such as carbamic acid n-(chlorosulfonyl)-1,1-dimethylethyl ester and in the presence or absence of a base such as diisopropylethylamine, triethylamine, pyridine, sodium hydride, sodium hydroxide, potassium carbonate, and cesium carbonate in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.
<Step 4>
The compound of Formula (N-IV) is deprotected. A compound of Formula (N-V) can be produced by reaction in a similar manner to that in <Step 3> in (Production Method B).
<Step 5>
The compound of Formula (N-V) is hydrolyzed. A compound of Formula (N-VI) can be produced by reaction in a similar manner to that in <Step 2> in (Production Method E).
<Step 6>
The compound of Formula (N-VI) is subjected to ring formation reaction. The compound of Formula (I)-1b can be produced by reaction in a similar manner to that in <Step 3> in (Production Method E) (in the absence of ammonia).
<Step 7>
The compound of Formula (N-V) is subjected to ring formation reaction. The compound of Formula (I)-1b can be produced by reaction in a similar manner to that in <Step 7> in (Production Method M).

The compounds of Formula (II)-1b and Formula (III)-1b above are included in the compound of Formula (I)-1b in (Production Method N) and can be produced by a similar production method, and these compounds of Formula (I)-1b are included in the compound of Formula (I).

<Production Method O>
(When n=2 in Formula)

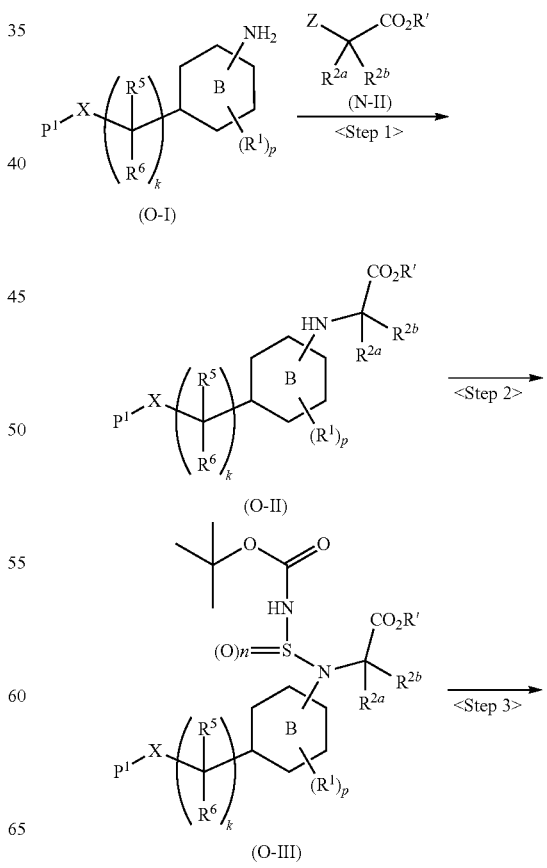

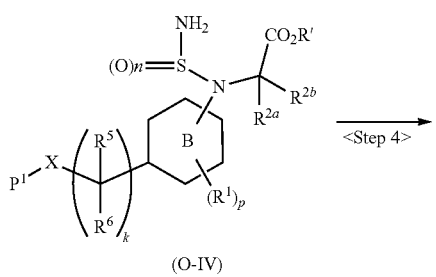

(O-IV)

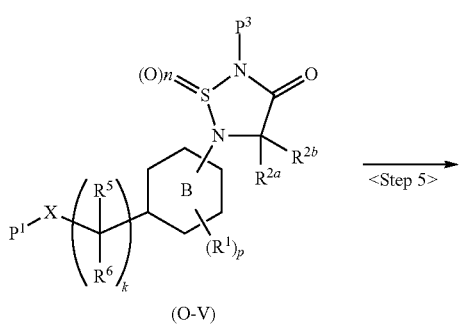

(O-V)

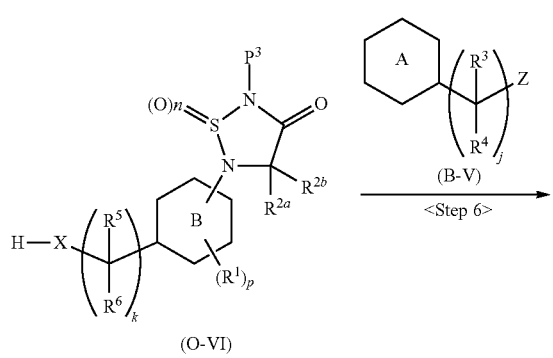

(O-VI)

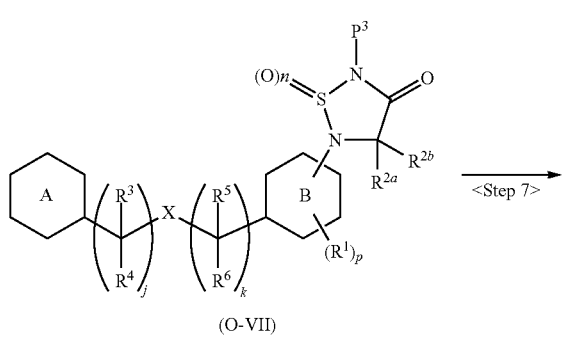

(O-VII)

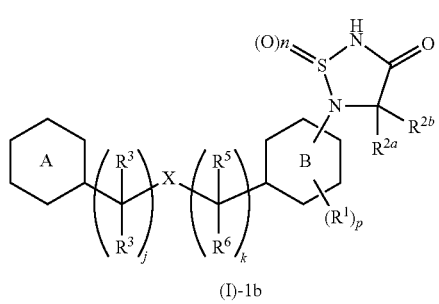

(I)-1b

<Step 1>

A compound of Formula (O-I) is reacted. A compound of Formula (O-II) can be produced by reacting the compound of Formula (O-I), which is known in the art or can be easily produced from a known compound, with a compound of Formula (N-II) in a similar manner to that in <Step 2> in (Production Method N).

<Step 2>

The compound of Formula (O-II) is reacted. A compound of Formula (O-III) can be produced by reaction in a similar manner to that in <Step 3> in (Production Method N).

<Step 3>

The compound of Formula (O-III) is deprotected. A compound of Formula (O-VI) can be produced by reaction in a similar manner to that in <Step 3> in (Production Method B).

<Step 4>

The compound of Formula (O-VI) is subjected to ring formation reaction. A compound of Formula (O-V) can be produced by reaction in a similar manner to that in <Step 7> in (Production Method M).

<Step 5>

The protective group $P^1$ in the compound of Formula (O-V) is deprotected. A compound of Formula (O-VI) can be produced by reaction in a similar manner to that in <Step 3> in (Production Method B).

<Step 6>

The compound of Formula (O-VI) is subjected to substitution reaction with a compound of Formula (B-V). A compound of Formula (O-VII) can be produced by reaction in a similar manner to that in <Step 4> in (Production Method B).

<Step 7>

The protective group $P^3$ in the compound of Formula (O-VII) is deprotected. The compound of Formula (I)-1b can be produced by reaction in a similar manner to that in <Step 3> in (Production Method B).

The compounds of Formula (II)-1b and Formula (III)-1b above are included in the compound of Formula (I)-1b in (Production Method O) and can be produced by a similar production method, and these compounds of Formula (I)-1b are included in the compound of Formula (I).

(7-1) The compounds of Formula (O-V) and Formula (O-VI) can also be produced by the method below.

<Production Method P>

(When n=2 in Formula)

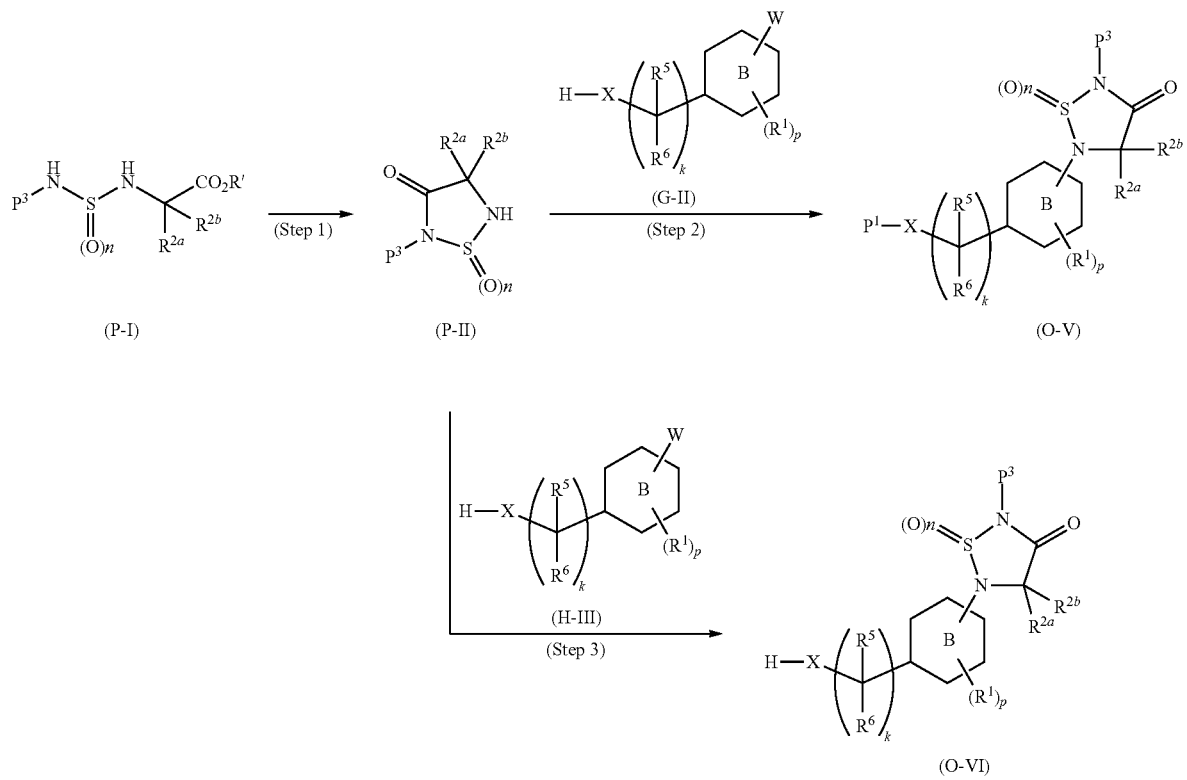

<Step 1>

A compound of Formula (P-I) is subjected to ring formation reaction. A compound of Formula (P-II) can be produced by reacting the compound of Formula (P-I) that can be produced in accordance with methods known in literatures, for example, the method described in [Bioorganic & Medicinal Chemistry, vol. 16 (7), pp. 3550-3556 (2008)] in a similar manner to that in <Step 7> in (Production Method M).

<Step 2>

The compound of Formula (P-II) is subjected to substitution reaction with a compound of Formula (G-II). [When W=halogen in Formula] The compound of Formula (O-V) can be produced by using the compound of Formula (P-II) and the compound of Formula (G-II) above in accordance with methods known in literatures, for example, the method described in [WO 2007/067615 pamphlet]. [When W=boronic acid or boronic ester in Formula] The compound of Formula (O-V) can be produced by using the compound of Formula (P-II) and the compound of Formula (G-II) above in accordance with methods known in literatures, for example, the method described in [Bioorganic & Medicinal Chemistry, vol. 14 (17), pp. 5833-5849 (2006)].

<Step 3>

The compound of Formula (P-II) is subjected to substitution reaction with a compound of Formula (H-III). The compound of Formula (O-VI) can be produced by reacting the compound of Formula (P-II) with the compound of Formula (H-III) above in a similar manner to that in <Step 2> in (Production Method P).

(7-2) The compound of Formula (O-VII) can also be produced by the method below.

<Production Method Q>

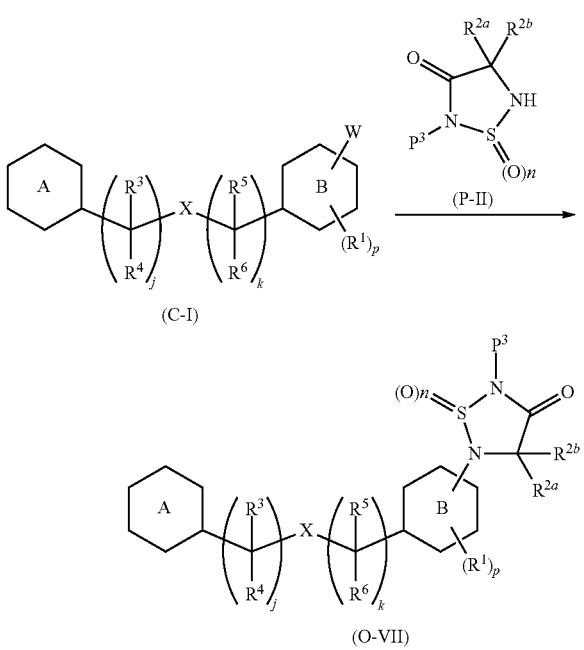

A compound of Formula (C-I) that is easily obtained from a known compound by the method in (Production Method H) is subjected to substitution reaction with a compound of Formula (P-II). The compound of Formula (O-VII) can be produced by reaction in a similar manner to that in <Step 2> in (Production Method P).

(8) The method for producing the compound of Formula (I)-1c of the present invention will be described below.

<Production Method R>

<When $R^{2a}=R^{2b}=H$, $R^{12b}=H$, alkyl, alkenyl, or alkynyl in Formula (I)-c above>

(In Formula, n=2 and Y=formyl group or $COR^{11a}$ group)

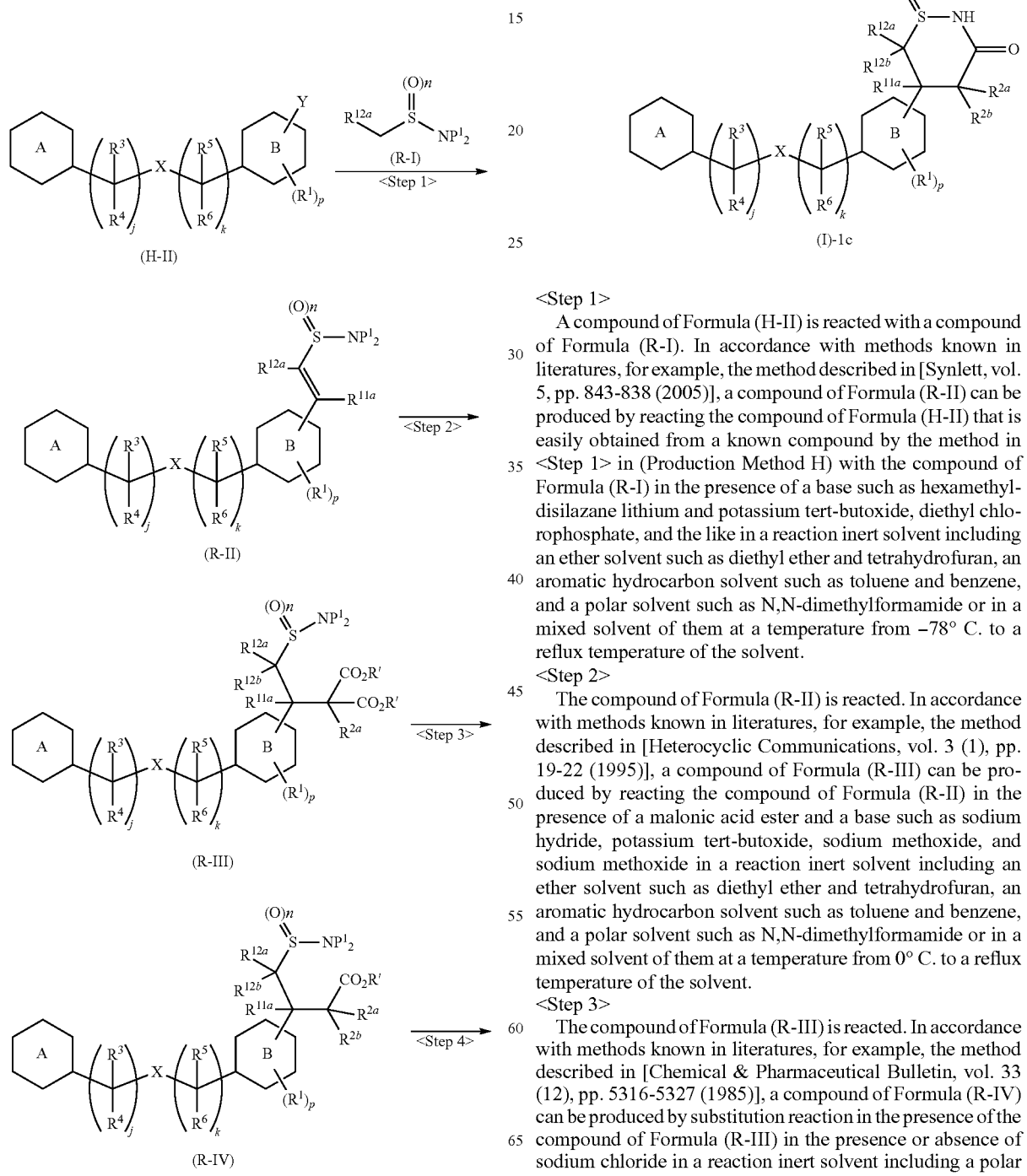

<Step 1>

A compound of Formula (H-II) is reacted with a compound of Formula (R-I). In accordance with methods known in literatures, for example, the method described in [Synlett, vol. 5, pp. 843-838 (2005)], a compound of Formula (R-II) can be produced by reacting the compound of Formula (H-II) that is easily obtained from a known compound by the method in <Step 1> in (Production Method H) with the compound of Formula (R-I) in the presence of a base such as hexamethyldisilazane lithium and potassium tert-butoxide, diethyl chlorophosphate, and the like in a reaction inert solvent including an ether solvent such as diethyl ether and tetrahydrofuran, an aromatic hydrocarbon solvent such as toluene and benzene, and a polar solvent such as N,N-dimethylformamide or in a mixed solvent of them at a temperature from −78° C. to a reflux temperature of the solvent.

<Step 2>

The compound of Formula (R-II) is reacted. In accordance with methods known in literatures, for example, the method described in [Heterocyclic Communications, vol. 3 (1), pp. 19-22 (1995)], a compound of Formula (R-III) can be produced by reacting the compound of Formula (R-II) in the presence of a malonic acid ester and a base such as sodium hydride, potassium tert-butoxide, sodium methoxide, and sodium methoxide in a reaction inert solvent including an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<Step 3>

The compound of Formula (R-III) is reacted. In accordance with methods known in literatures, for example, the method described in [Chemical & Pharmaceutical Bulletin, vol. 33 (12), pp. 5316-5327 (1985)], a compound of Formula (R-IV) can be produced by substitution reaction in the presence of the compound of Formula (R-III) in the presence or absence of sodium chloride in a reaction inert solvent including a polar solvent such as dimethyl sulfoxide and N,N-dimethylformamide or in a mixed solvent of them at a temperature from 0° C. to a reflux temperature of the solvent.

<Step 4>

The protective group $P^1$ in the compound of Formula (R-IV) is deprotected. A compound of Formula (R-V) can be produced by reaction in a similar manner to that in <Step 3> in (Production Method B).

<Step 5>

The compound of Formula (R-V) is subjected to ring formation reaction. The compound of Formula (I)-1c can be produced by reaction in a similar manner to that in <Step 7> in (Production Method M).

The compounds of Formula (II)-1c and Formula (III)-1c above are included in the compound of Formula (I)-1c in (Production Method R) and can be produced by a similar production method, and these compounds of Formula (I)-1c are included in the compound of Formula (I). Similarly, in the production methods in (Production Method S) or later, the compounds of Formula (II)-1c and Formula (III)-1c are included in the compound of Formula (I)-1c and can be produced by a similar production method, and these compounds of Formula (I)-1c are included in the compound of Formula (I).

<Production Method S>

<When $R^{2a}$ and/or $R^{2b} \neq H$ and $R^{12b}=H$ in Formula (I)-1c Above>

(When n=2 in Formula)

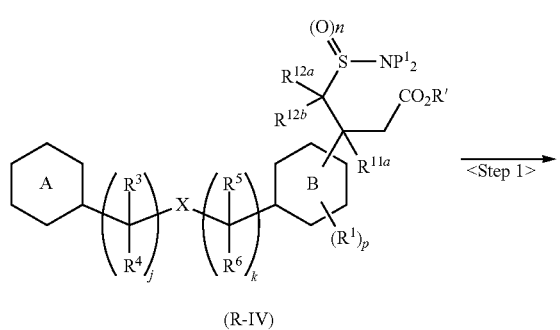

(R-IV)

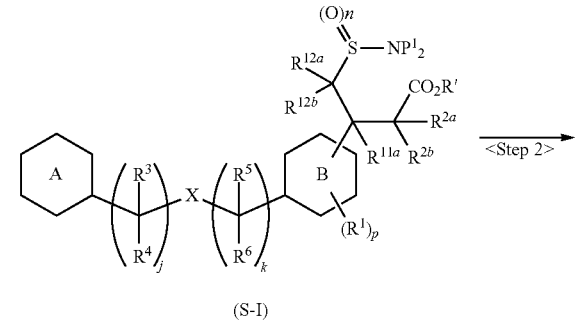

(S-I)

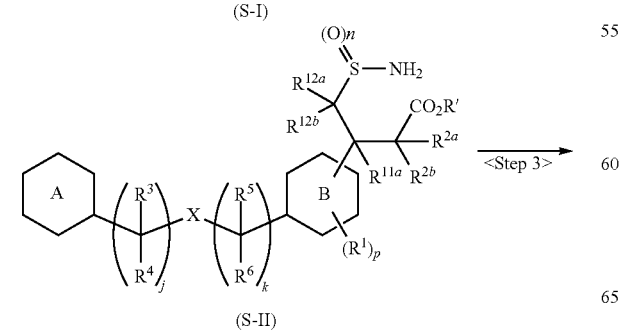

(S-II)

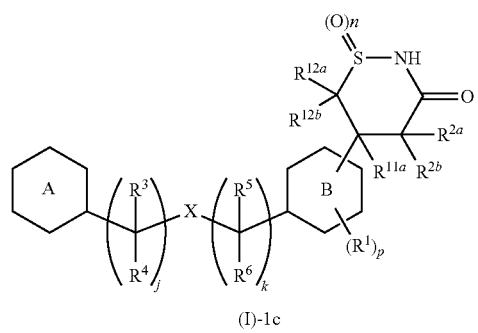

(I)-1c

<Step 1>

A compound of Formula (R-IV) is subjected to substitution reaction. A compound of Formula (S-I) can be produced by reaction in a similar manner to that in <Step 6> in (Production Method M).

<Step 2>

The protective group $P^1$ in the compound of Formula (S-I) is deprotected. A compound of Formula (S-II) can be produced by reaction in a similar manner to that in <Step 3> in (Production Method B).

<Step 3>

The compound of Formula (S-II) is subjected to ring formation reaction. The compound of Formula (I)-1c can be produced by reaction in a similar manner to that in <Step 7> in (Production Method M).

<Production Method T>

<When $R^{12b}$=H, alkyl, alkenyl, or alkynyl in Formula (I)-1c above>

(In Formula, n=2 and Y=formyl group or $COR^{11a}$ group)

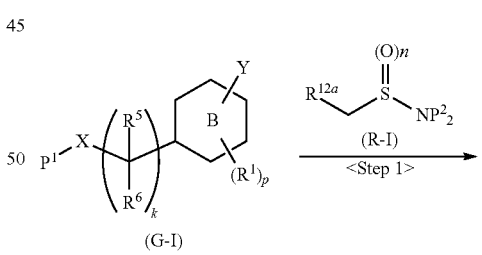

(G-I)

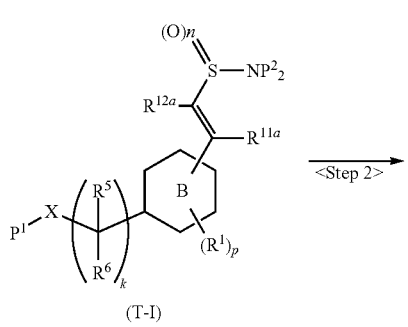

(T-I)

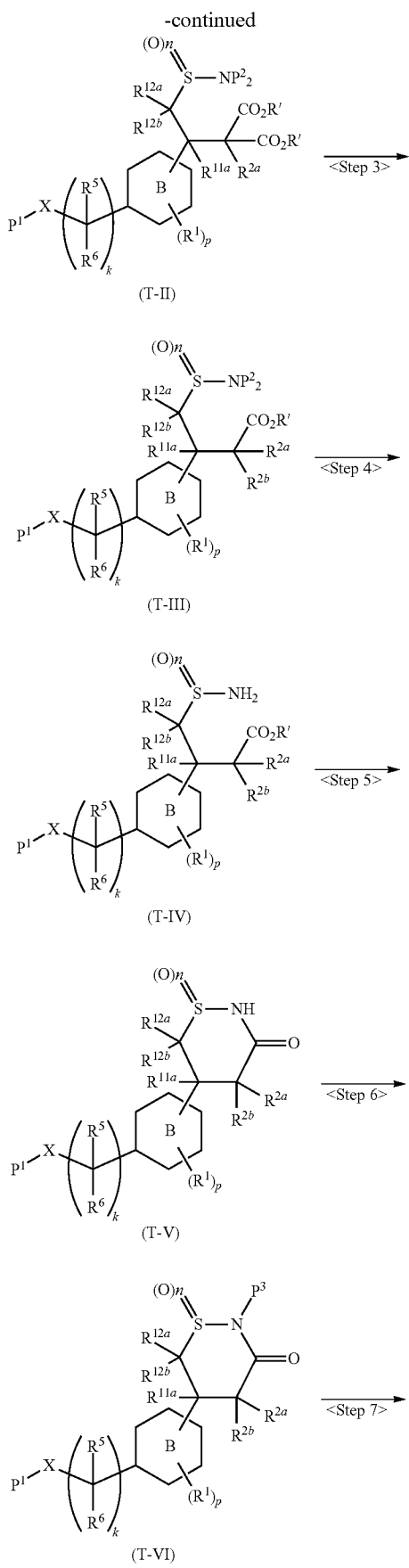
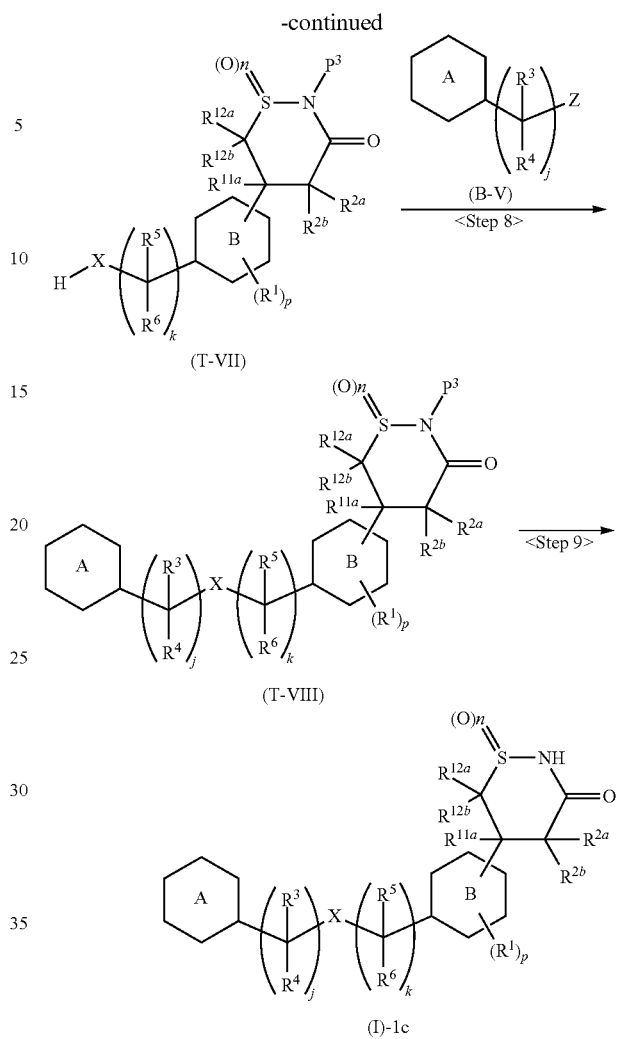

<Step 1>
A compound of Formula (G-I) is reacted. A compound of Formula (T-I) can be produced by reacting a compound of Formula (G-I), which is known in the art or can be easily produced from a known compound, with a compound of Formula (R-I) in a similar manner to that in <Step 1> in (Production Method R).

<Step 2>
The compound of Formula (T-I) is reacted. A compound of Formula (T-II) can be produced by reaction in a similar manner to that in <Step 2> in (Production Method R).

<Step 3>
The compound of Formula (T-II) is reacted. A compound of Formula (T-III) can be produced by reaction in a similar manner to that in <Step 3> in (Production Method R).

<Step 4>
The protective group $P^2$ in the compound of Formula (T-III) is deprotected. A compound of Formula (T-IV) can be produced by reaction in a similar manner to that in <Step 3> in (Production Method B).

<Step 5>
The compound of Formula (T-IV) is subjected to ring formation reaction. A compound of Formula (T-V) can be produced by reaction in a similar manner to that in <Step 7> in (Production Method M).

<Step 6>

The compound of Formula (T-V) is protected with a protective group $P^3$. A compound of Formula (T-VI) can be produced by reacting the compound of Formula (T-V) in a similar manner to that in <Step 2> in (Production Method B).

<Step 7>

The protective group $P^1$ in the compound of Formula (T-VI) is deprotected. A compound of Formula (T-VII) can be produced by reaction in a similar manner to that in <Step 3> in (Production Method B).

<Step 8>

The compound of Formula (T-VII) is subjected to substitution reaction with a compound of Formula (B-V). A compound of Formula (T-VIII) can be produced by reaction in a similar manner to that in <Step 4> in (Production Method B).

<Step 9>

The protective group $P^3$ in the compound of Formula (T-VIII) is deprotected. The compound of Formula (I)-1c can be produced by reaction in a similar manner to that in <Step 3> in (Production Method B).

(8-1) The compound of Formula (I)-1c or Formula (I)-1f can also be produced by the method below.

<Production Method U>

<When $J_1=J_{1a}=CR^{11a}$, $J_2=CR^{12a}R^{12b}$, and h=1 to 3 in Formula (I) Above, that is, In the Case of Formula (I)-1c or Formula (I)-1f>

(In Formula, n=2 and Y=Halogen)

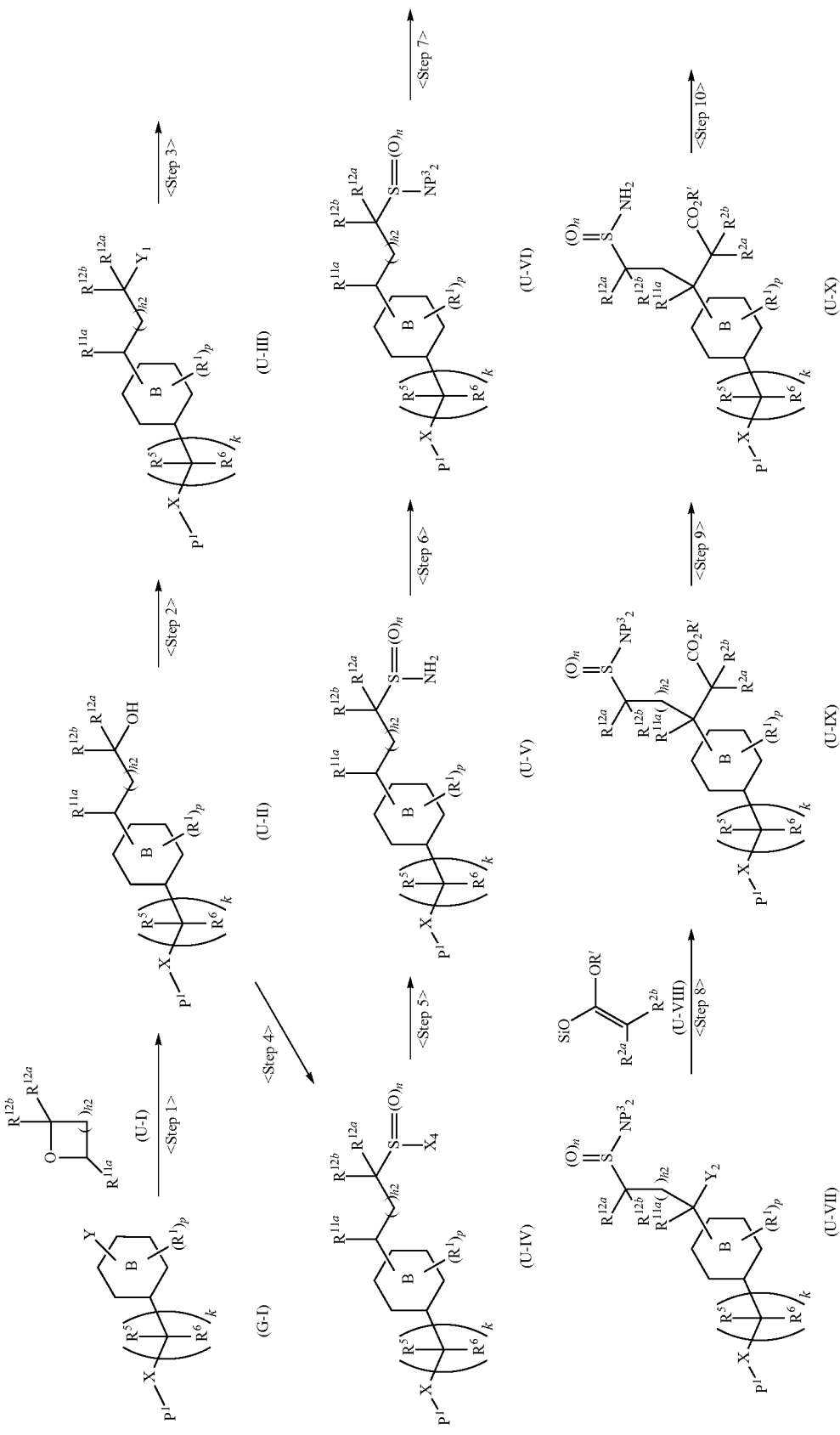

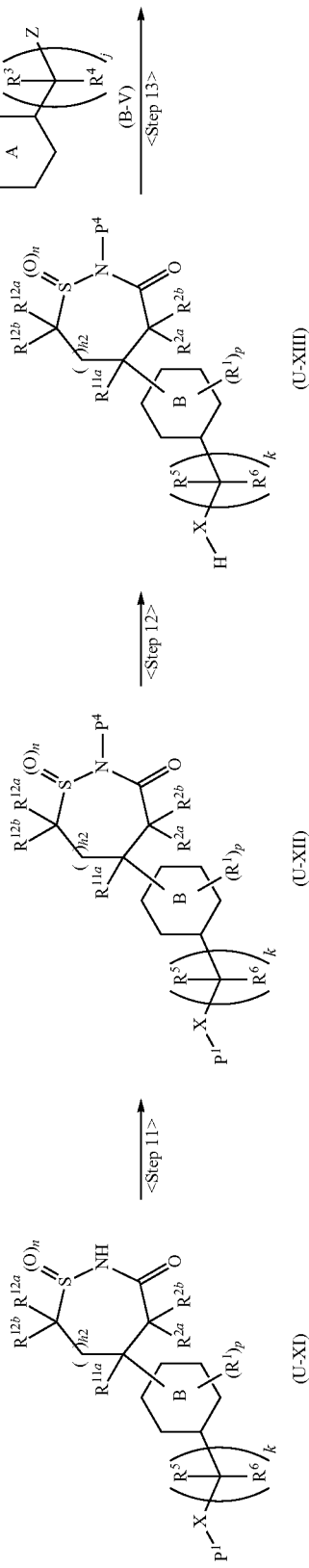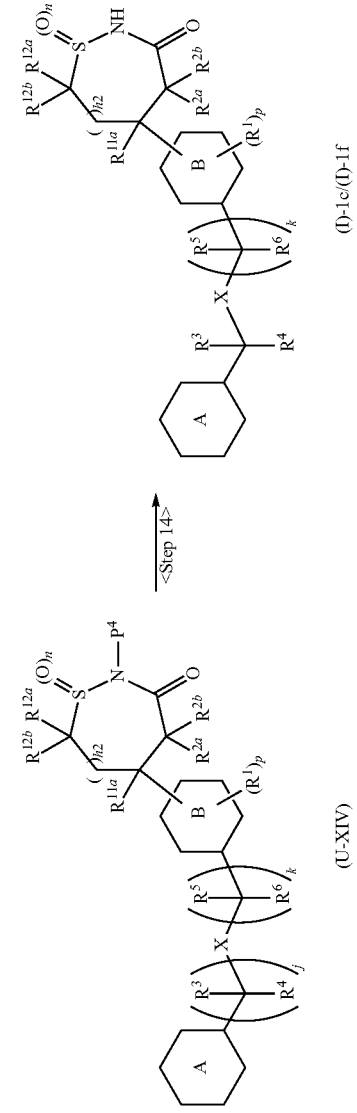

<Step 1>

A compound of Formula (G-II) is reacted. In accordance with methods known in literatures, for example, the method described in [Journal of Organic Chemistry, vol. 49 (16), pp. 2922-2925 (1984)], a compound of Formula (U-II) can be produced by reacting a compound of Formula (G-II), which is known in the art or can be easily produced from a known compound, with various cyclic ethers of Formula (G-I) (for example, ethylene oxide, oxetane, and tetrahydrofuran) in the presence of a base such as n-butyllithium and Grignard reagent, and a Lewis acid such as boron trifluoride diethyl ether complex ($BF_3$-$Et_2O$) in a reaction inert solvent including an ether solvent such as diethyl ether and tetrahydrofuran, an aromatic hydrocarbon solvent such as toluene and benzene, and a polar solvent such as N,N-dimethylformamide or in a mixed solvent of them at a temperature from 0° C. to a reflux temperature of the solvent.

<Step 2>

The compound of Formula (U-II) is reacted. In accordance with methods known in literatures, for example, the method described in [*Jikken Kagaku Koza* (Experimental Chemistry Course), the fifth edition, vol. 13, Synthesis of Organic Compound I, Hydrocarbon and Halide, pp. 374-420 (2004), Maruzen Co., Ltd.], a compound of Formula (U-III) can be produced by reacting the compound of Formula (U-II) in the presence of a halogenating agent such as phosphorus tribromide using a reaction inert solvent such as diethyl ether and 1,4-dioxane or a mixed solvent of them at a temperature from 0° C. to a reflux temperature of the solvent.

<Step 3>

The compound of Formula (U-III) is reacted. In accordance with methods known in literatures, for example, the method described in [Justus Liebigs Annalen der Chemie, vol. 586, pp. 158-164 (1954)], a compound of Formula (U-IV) can be produced by reaction in the presence of the compound of Formula (U-III) in the presence of a sulfur agent such as sodium sulfite, potassium sulfite, sodium disulfite, and thiourea in a reaction inert solvent including an alcoholic solvent such as methanol and ethanol and water or in a mixed solvent of them at a temperature from 0° C. to a reflux temperature of the solvent.

<Step 4>

The compound of Formula (U-II) is reacted. In accordance with, for example, the method described in [Organic Reaction, vol. 42 (1992)], a compound of Formula (U-IV) can be produced by reacting the compound of Formula (U-II) with thioacetic acid in the presence of an organophosphorus compound such as triphenylphosphine and an azo compound such as an azodicarboxylic acid ester and azodicarboxylic amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide and dimethyl sulfoxide or in a mixed solvent of them at a temperature from 0° C. to a reflux temperature of the solvent to afford a compound and by reacting the compound with chlorine in acetic acid as a solvent in accordance with, for example, the method described in [Canadian Journal of Chemistry, vol. 62 (3), pp. 610-614 (1984)].

<Step 5>

[When $X_4$=OH or a salt such as ONa and OK]

The compound of Formula (U-III) is reacted. A compound of Formula (U-IV) can be produced by reaction in a similar manner to that in <Step 3> in (Production Method M).

[When $X_4$=Cl]

The compound of Formula (U-III) is reacted. A compound of Formula (U-IV) can be produced by reaction in a similar manner to that in <Step 3> in (Production Method M) except that the halogenation step is excluded.

<Step 6>

The compound of Formula (U-IV) is protected with a protective group $P^3$. A compound of Formula (U-V) can be produced by reacting the compound of Formula (U-IV) in a similar manner to that in <Step 2> in (Production Method B).

<Step 7>

The compound of Formula (U-V) is reacted. For example, when $R^{11a} \neq H$ and $Y_2$=bromo, in accordance with methods known in literatures, for example, the method described in [Journal of Organic Chemistry, vol. 57 (10), pp. 2967-2970 (1992)], a compound of Formula (U-VI) can be produced by reacting the compound of Formula (U-V) with 2-bromopropanedioic acid-1,3-diethyl ester as a brominating agent at a temperature from 0° C. to a reflux temperature of the solvent. When $R^{11a}$=H and $Y_2$=halogen such as chloro and bromo, in accordance with, for example, the method described in [*Jikken Kagaku Koza* (Experimental Chemistry Course), the fifth edition, vol. 13, Synthesis of Organic Compound I, Hydrocarbon and Halide, pp. 374-420 (2004), Maruzen Co., Ltd.], a compound of Formula (U-VI) can be produced by reaction in the presence of a halogenating agent such as N-chlorosuccinimide and N-bromosuccinimide and $\alpha,\alpha'$-azobisisobutyronitrile (AIBN) using a reaction inert solvent such as carbon tetrachloride and chloroform or a mixed solvent of them at a temperature from 0° C. to a reflux temperature of the solvent.

<Step 8>

The compound of Formula (U-VI) is subjected to substitution reaction with a carboxylic acid methyl ester. In accordance with, for example, the method described in [Tetrahedron, vol. 65 (28), pp. 5462-5471 (2009)], a compound of Formula (U-VIII) can be produced by using the compound of Formula (U-VI), indium bromide ($InBr_3$), and a silyl enolate of Formula (U-VIII).

<Step 9>

The protective group $P^3$ in the compound of Formula (U-IX) is deprotected. A compound of Formula (U-X) can be produced by reaction in a similar manner to that in <Step 3> in (Production Method B).

<Step 10>

The compound of Formula (U-X) is subjected to ring formation reaction. A compound of Formula (U-XI) can be produced by reaction in a similar manner to that in <Step 7> in (Production Method M).

<Step 11>

The compound of Formula (U-XI) is protected with a protective group $P^4$. A compound of Formula (U-XII) can be produced by reacting the compound of Formula (U-XI) in a similar manner to that in <Step 2> in (Production Method B).

<Step 12>

The protective group $P^1$ in the compound of Formula (U-XII) is deprotected. A compound of Formula (U-XIII) can be produced by reaction in a similar manner to that in <Step 3> in (Production Method B).

<Step 13>

The compound of Formula (U-XIII) is subjected to substitution reaction with a compound of Formula (B-V). A compound of Formula (U-XIV) can be produced by reaction in a similar manner to that in <Step 4> in (Production Method B).

<Step 14>

The protective group $P^4$ in the compound of Formula (U-XIV) is deprotected. The compound of Formula (I)-1c (when h2=0) or Formula (I)-1f (when h2=1 or 2) can be produced by reaction in a similar manner to that in <Step 3> in (Production Method B).

The compounds of Formula (II)-1f and Formula (III)-1f above are included in the compound of Formula (I)-1f in (Production Method U) and can be produced by a similar production method, and these compounds of Formula (I)-1f are included in the compound of Formula (I).

In Formula (I) above, Formula (I)-1c and Formula (I)-1f include optical isomers. The isomers can be separated through optical resolution using chiral column chromatography or asymmetric synthesis by a person skilled in the art based on conventional techniques.

(9) The methods for producing the compound of Formula (I)-1d of the present invention will be described below.

<Production Method V>
<When n=1 to 2, $R^{2a}=R^{2b}$=H, Y=CH=CH—COOR', and n=2 in Formula (I)-1d above>

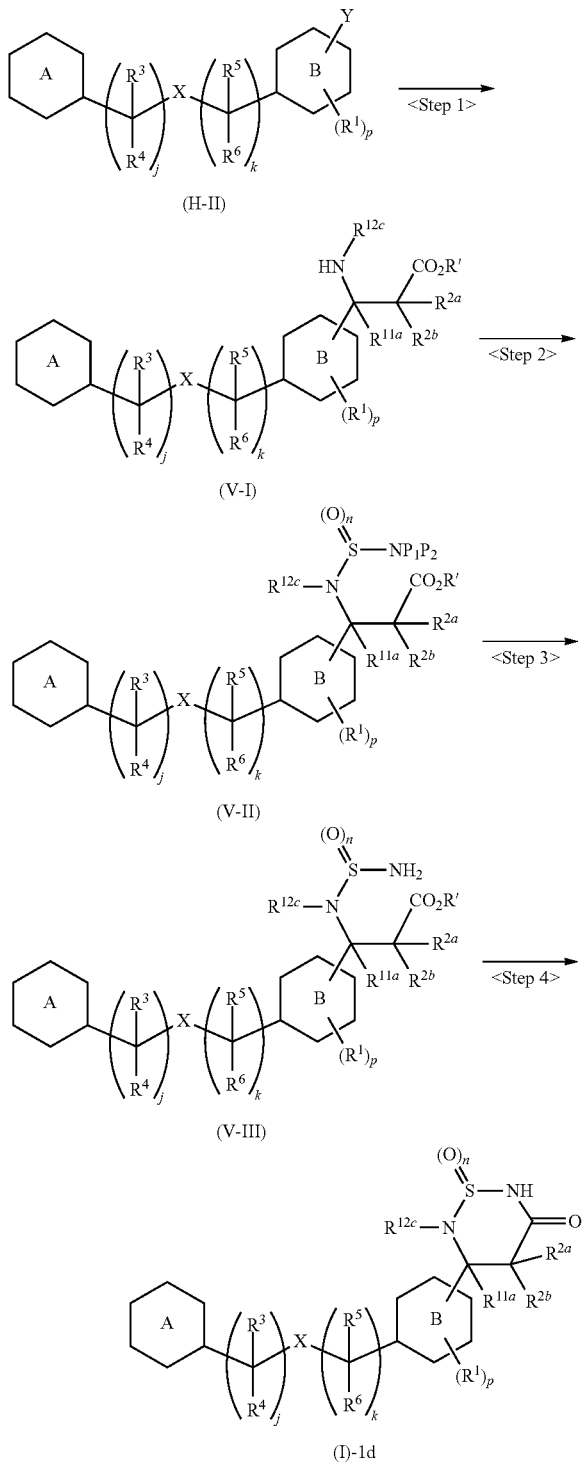

<Step 1>
A compound of Formula (H-II) is reacted. In accordance with methods known in literatures, for example, the method described in [Journal of Organic Chemistry, vol. 50 (13), pp. 2259-2263 (1985)], a compound of Formula (V-I) can be produced by reacting the compound of Formula (H-II) that is easily obtained from a known compound by the method in <Step 1> in (Production Method H) in the presence of an amine such as ammonium acetate, an alkyl ammonium, and aqueous ammonia, malonic acid, and the like in a reaction inert solvent including a polar solvent such as ethanol, butanol, and water or in a mixed solvent of them at a temperature from 0° C. to a reflux temperature of the solvent.

<Step 2>
The compound of Formula (V-I) is reacted. In accordance with methods known in literatures, for example, the method described in [Synlett, vol. 5, pp. 843-838 (2005)], a compound of Formula (VII) can be produced by reacting the compound of Formula (V-I) with a sulfur agent such as an N-chlorosulfonylcarbamic acid ester in the presence of a base such as sodium hydride, sodium hydroxide, triethylamine, and pyridine in a reaction inert solvent including an ether solvent such as diethyl ether and tetrahydrofuran, an aromatic hydrocarbon solvent such as toluene and benzene, and a polar solvent such as methanol, ethanol, and N,N-dimethylformamide or in a mixed solvent of them at a temperature from −78° C. to a reflux temperature of the solvent.

<Step 3>
The protective groups $P^1$ and $P^2$ in the compound of Formula (V-II) are deprotected. A compound of Formula (V-III) can be produced by reaction in a similar manner to that in <Step 3> in (Production Method B).

<Step 4>
The compound of Formula (V-V) is subjected to ring formation reaction. The compound of Formula (I)-1d can be produced by reaction in a similar manner to that in <Step 7> in (Production Method M).

The compounds of Formula (II)-1d and Formula (III)-1d above are included in the compound of Formula (I)-1d in (Production Method V) and can be produced by a similar production method, and these compounds of Formula (I)-1d are included in the compound of Formula (I).

Similarly, in the production methods in (Production Method W) or later, the compounds of Formula (II)-1d and Formula (III)-1d above are included in the compound of Formula (I)-1d and can be produced by a similar production method, and these compounds of Formula (I)-1d are included in the compound of Formula (I).

<Production Method W>
<When n=2 and $R^{11a}$=H>

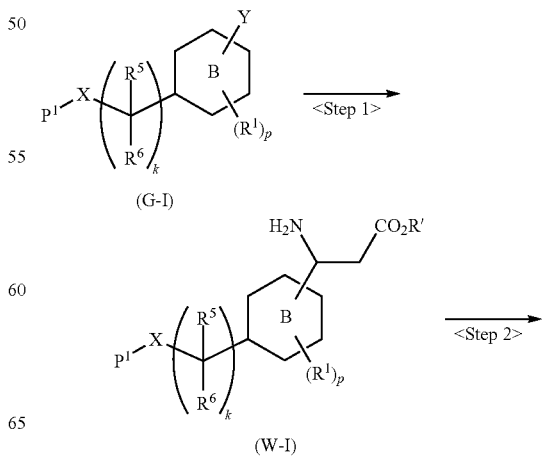

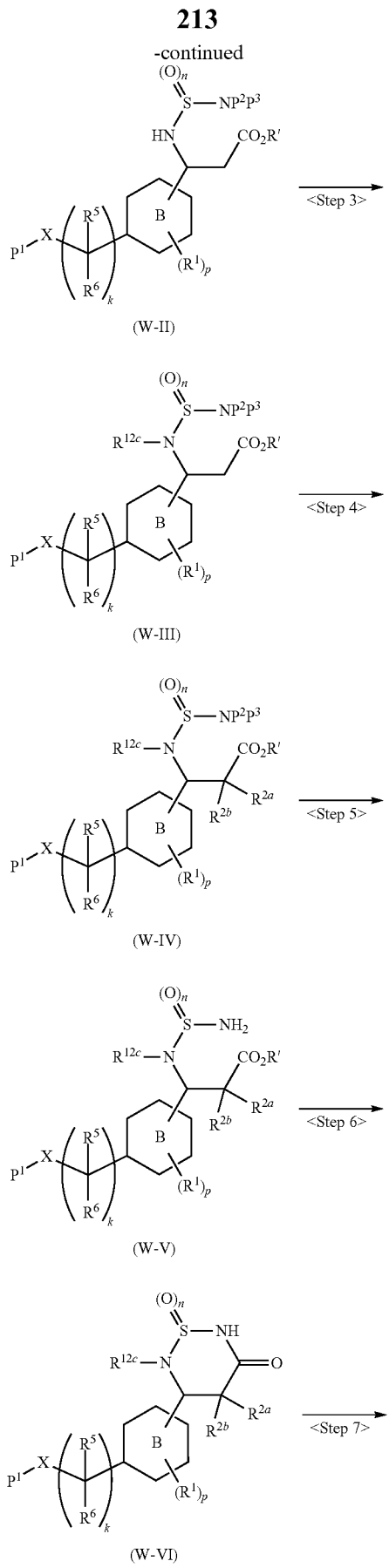
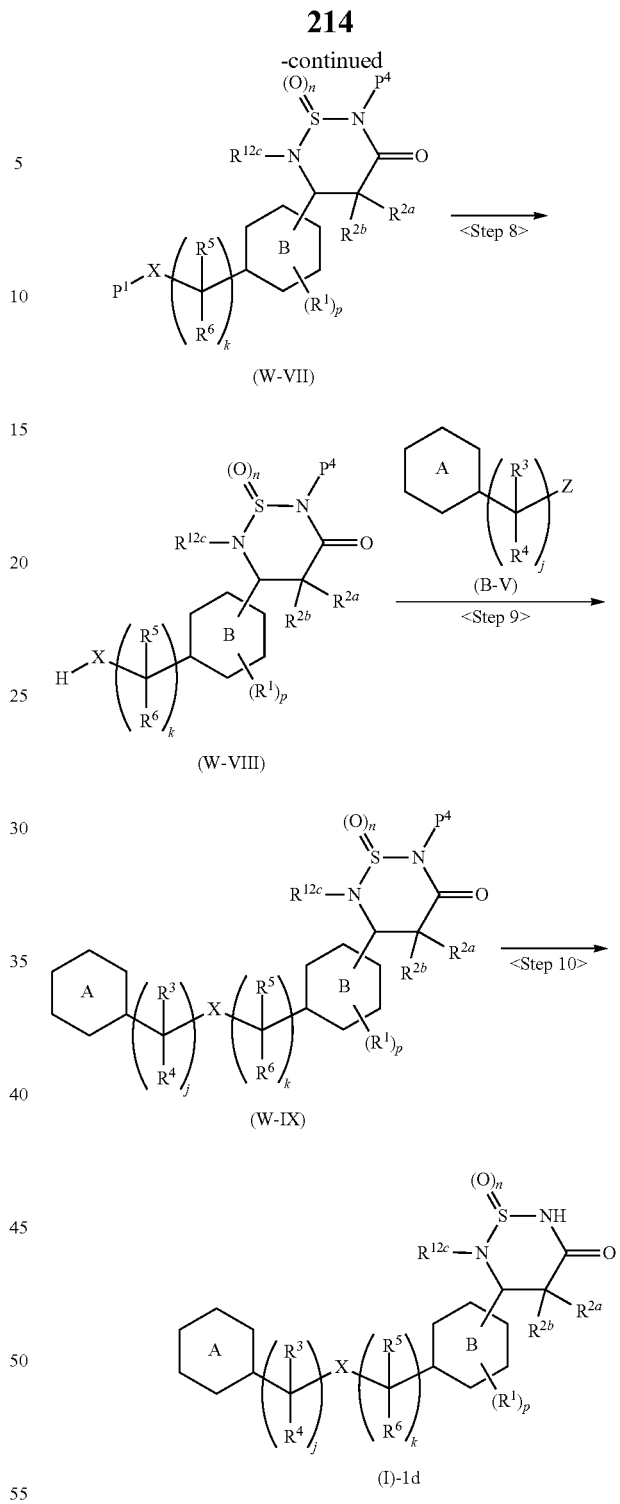

<Step 1>

A compound of Formula (G-I) is reacted. A compound of Formula (W-I) can be produced by reacting the compound of Formula (G-I), which is known in the art or can be easily produced from a known compound, in a similar manner to that in <Step 1> in (Production Method V).

<Step 2>

The compound of Formula (G-I) is reacted. A compound of Formula (W-II) can be produced by reaction in a similar manner to that in <Step 4> in (Production Method V).

<Step 3>

<When $R^{12c}$≠Hydrogen Atom>

The compound of Formula (W-II) is reacted. In accordance with methods known in literatures, for example, the method described in [Synlett, vol. 5, pp. 697-699 (2002)], a compound of Formula (W-III) can be produced by reacting the compound of Formula (W-II) with a compound of $R^{12C}$OH in the presence of an organophosphorus compound such as triphenylphosphine and an azo compound such as an azodicarboxylic acid ester and azodicarboxylic amide in a reaction inert solvent including a halogenated solvent such as dichloromethane and chloroform, an ether solvent such as diethyl ether and tetrahydrofuran, an aromatic hydrocarbon solvent such as toluene and benzene, and a polar solvent such as N,N-dimethylformamide and dimethyl sulfoxide or in a mixed solvent of them at a temperature from 0° C. to a reflux temperature of the solvent.

<Step 4>

<When $R^{2a}$ and/or $R^{2b}$≠Hydrogen Atom>

The compound of Formula (W-III) is subjected to substitution reaction. A compound of Formula (W-IV) can be produced by reaction in a similar manner to that in <Step 6> in (Production Method M).

<Step 5>

The protective groups $P^2$ and $P^3$ in the compound of Formula (W-IV) are deprotected. A compound of Formula (W-V) can be produced by reacting the compound of Formula (W-IV) in a similar manner to that in <Step 3> in (Production Method B).

<Step 6>

The compound of Formula (W-V) is subjected to ring formation reaction. A compound of Formula (W-VI) can be produced by reacting the compound of Formula (W-V) in a similar manner to that in <Step 7> in (Production Method M).

<Step 7>

The compound of Formula (W-VI) is protected with a protective group $P^4$. A compound of Formula (W VII) can be produced by reacting the compound of Formula (W-VI) in a similar manner to that in <Step 2> in (Production Method B).

<Step 8>

The protective group $P^1$ in the compound of Formula (W-VII) is deprotected. A compound of Formula (W-VIII) can be produced by reaction in a similar manner to that in <Step 3> in (Production Method B).

<Step 9>

The compound of Formula (W-VIII) is subjected to substitution reaction with a compound of Formula (B-V). A compound of Formula (W-IX) can be produced by reaction in a similar manner to that in <Step 4> in (Production Method B).

<Step 10>

The protective group $P^4$ in the compound of Formula (W-IX) is deprotected. The compound of Formula (I)-1d can be produced by reaction in a similar manner to that in <Step 3> in (Production Method B).

(9-1) The compound of Formula (I)-1d or Formula (I)-1e can also be produced by the method below.

<Production Method X>

<When $J_1=J_{1a}=CR^{11a}$, $J_2=NR^{12c}$, and h=1 to 3 in Formula (I) above, that is, in the case of Formula (I)-1d or Formula (I)-1e and when n=2 and $R^{11a}$=H>

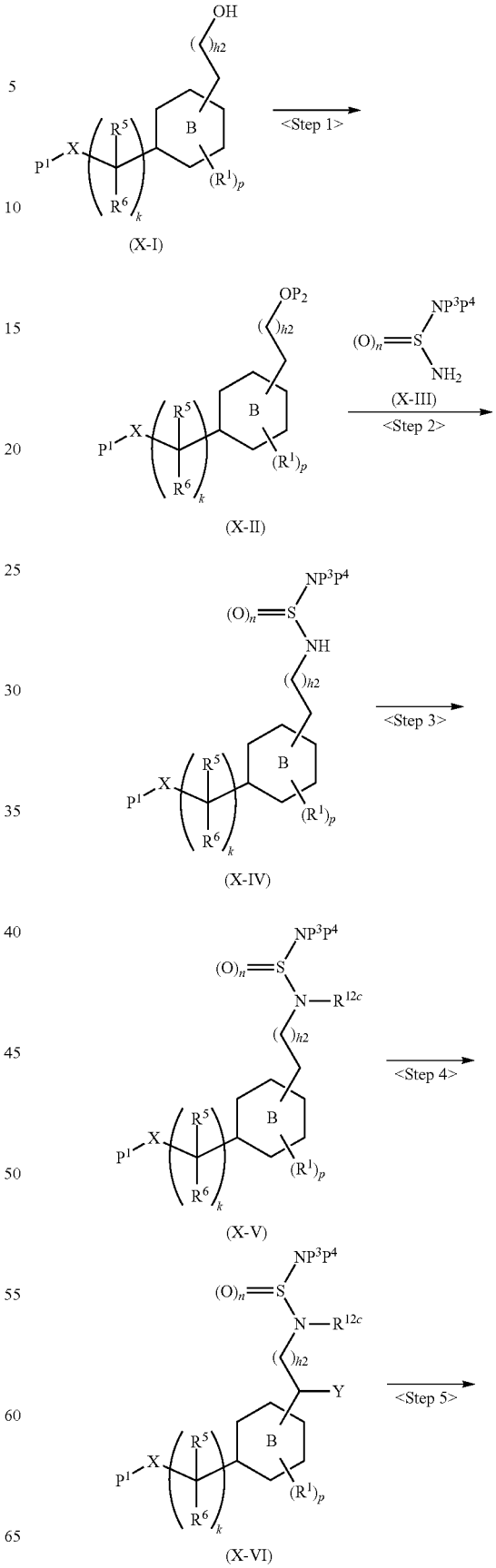

-continued

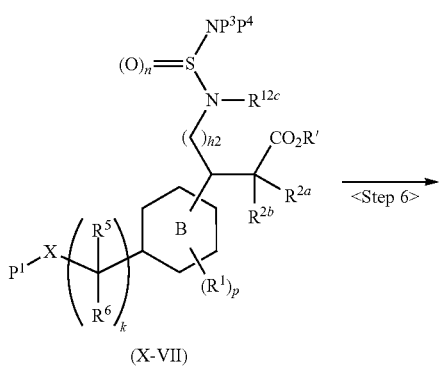

(X-VII)

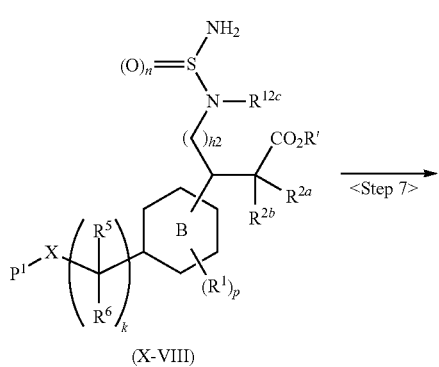

(X-VIII)

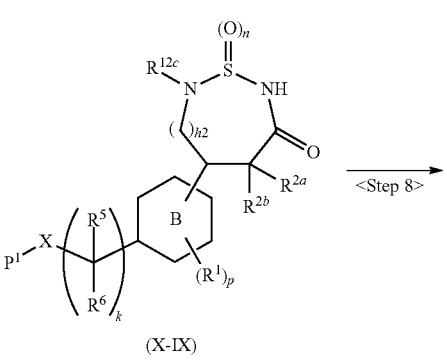

(X-IX)

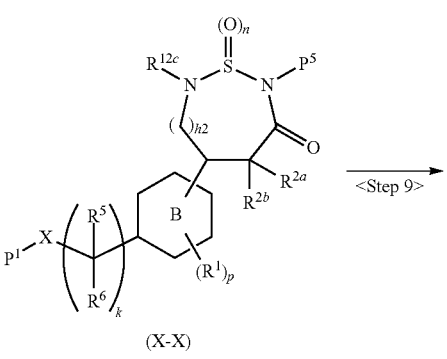

(X-X)

-continued

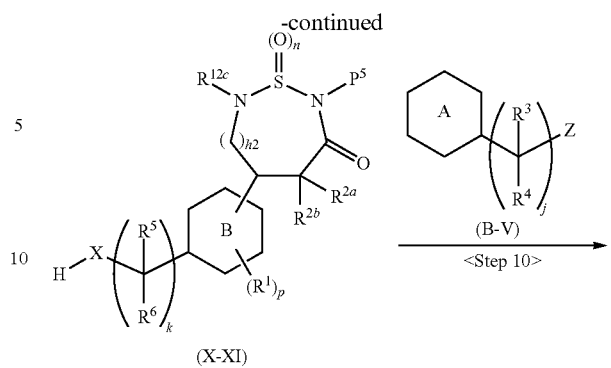

(X-XI)

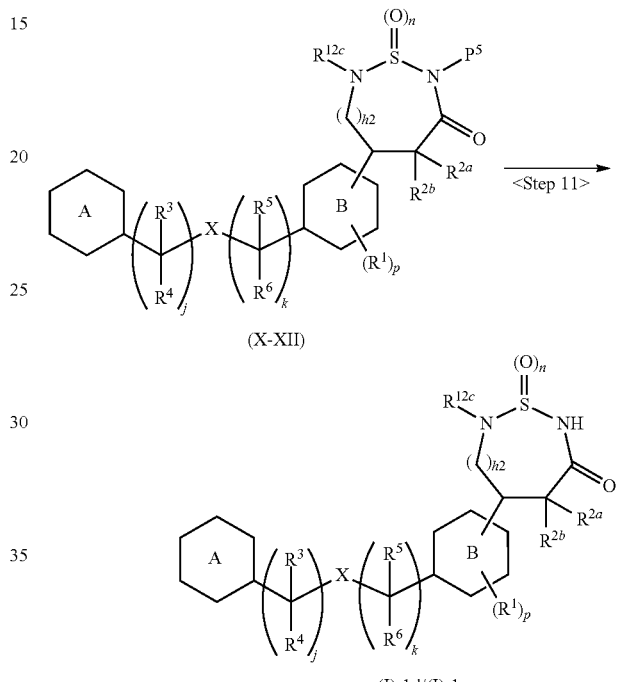

(X-XII)

(I)-1d/(I)-1e

<Step 1>

A compound of Formula (X-I) is protected with a protective group $P^2$. A compound of Formula (X-II) can be produced by reacting the compound of Formula (X-I) that is obtained in (Production Method Y) or (Production Method Z) described later in a similar manner to that in <Step 2> in (Production Method B).

<Step 2>

The compound of Formula (X-II) is reacted. A compound of Formula (X-IV) can be produced from the compound of Formula (X-II) and a compound of Formula (X-III) in accordance with, for example, the method described in [Synlett, vol. 6, pp. 833-836 (2006)].

<Step 3>

<When $R^{12c}$≠Hydrogen Atom>

The compound of Formula (X-IV) is reacted. A compound of Formula (X-V) can be produced by reaction in a similar manner to that in <Step 3> in (Production Method W).

<Step 4>

The compound of Formula (X-V) is subjected to substitution reaction. A compound of Formula (X-VI) can be produced by reaction in a similar manner to that in <Step 2> in (Production Method U).

<Step 5>

The compound of Formula (X-VI) is subjected to substitution reaction. A compound of Formula (X-VII) can be produced from the compound of Formula (X-VI) in accordance with, for example, the method described in [Journal of the American Chemical Society, vol. 73, pp. 3987-3993 (1953)].

<Step 6>

The protective groups $P^3$ and $P^4$ in the compound of Formula (X-VII) are deprotected. A compound of Formula (X-VIII) can be produced by reacting the compound of Formula (X-VII) in a similar manner to that in <Step 3> in (Production Method B).

<Step 7>

The compound of Formula (X-VIII) is subjected to ring formation reaction. A compound of Formula (X-IX) can be produced by reacting the compound of Formula (X-VIII) in a similar manner to that in <Step 7> in (Production Method M).

<Step 8>

The compound of Formula (X-IX) is protected with a protective group $P^5$. A compound of Formula(X-X) can be produced by reacting the compound of Formula (X-IX) in a similar manner to that in <Step 2> in (Production Method B).

<Step 9>

The protective group $P^1$ in the compound of Formula (X-X) is deprotected. A compound of Formula (X-XI) can be produced by reaction in a similar manner to that in <Step 3> in (Production Method B).

<Step 10>

The compound of Formula (X-XI) is subjected to substitution reaction with a compound of Formula (B-V). A compound of Formula (X-XII) can be produced by reaction in a similar manner to that in <Step 4> in (Production Method B).

<Step 11>

The protective group $P^5$ in the compound of Formula (X-XII) is deprotected. The compound of Formula (I)-1d (when h2=0) or Formula (I)-1e (when h2=1 or 2) can be produced by reaction in a similar manner to that in <Step 3> in (Production Method B).

The compounds of Formula (II)-1e and Formula (III)-1e above are included in the compound of Formula (I)-1e in (Production Method X) and can be produced by a similar production method, and these compounds of Formula (I)-1e are included in the compound of Formula (I).

(9-2) Next, methods for producing the compound of Formula (X-I) will be described.

<Production Method Y>

<When h2=0 and Y=halogen atom in Formula (X-I) above>

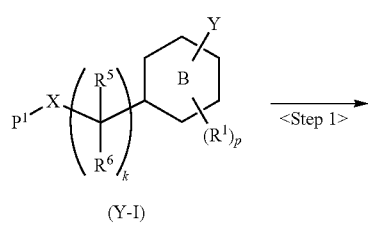

(Y-I)

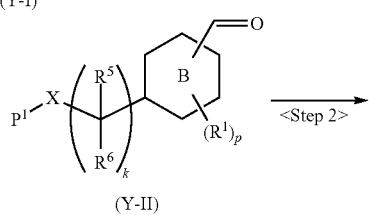

(Y-II)

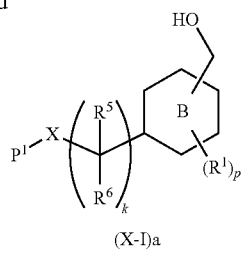

(X-I)a

<Step 1>

A compound of Formula (Y-I) is reacted. In accordance with methods known in literatures, for example, the method described in [Tetrahedron, vol. 57 (24), pp. 5243-5253 (2001)], a compound of Formula (Y-II) can be produced by reacting the compound of Formula (Y-I) in the presence of a base such as n-butyllithium and dimethylformamide in a reaction inert solvent including an ether solvent such as diethyl ether and tetrahydrofuran and an aromatic hydrocarbon solvent such as hexane, toluene, and benzene or in a mixed solvent of them at a temperature from 0° C. to a reflux temperature of the solvent.

<Step 2>

The compound of Formula (Y-II) is subjected to reduction. The compound of Formula (X-I)a can be produced by reacting the compound of Formula (Y-II) in a similar manner to that in <Step 2> in (Production Method J-1).

<Production Method Y-1>

<When h2=1 to 2 in Formula (X-I) above>

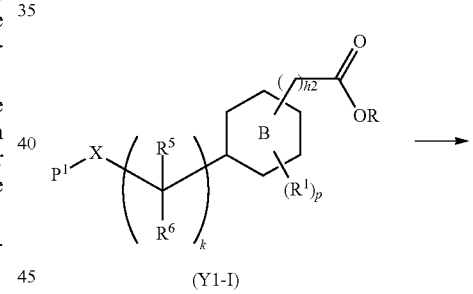

(Y1-I)

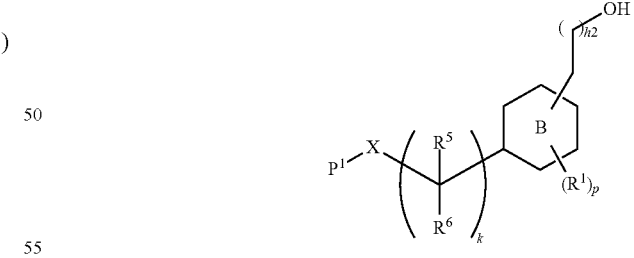

(X-I)b

A compound of Formula (Y1-I) is subjected to reduction. The compound of Formula (X-I)b can be produced by reacting the compound of Formula (Y-I) in a similar manner to that in <Step 2> in (Production Method J-1).

(9-3) The compound of Formula (V-II) can also be produced by the method below.

<Production Method Z>

<Y=—CH=CH—COOR' in Formula>

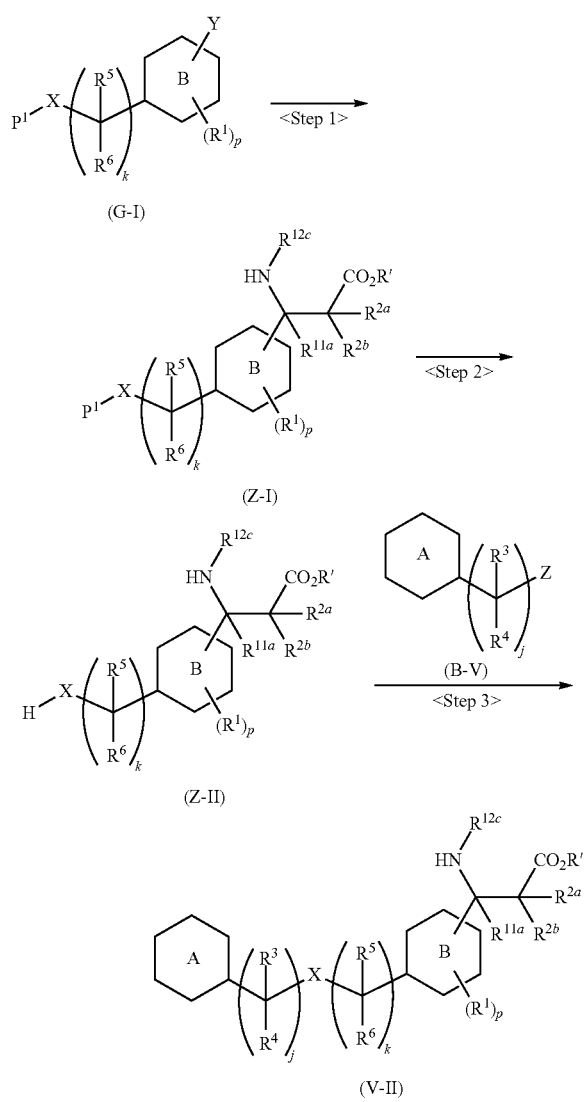

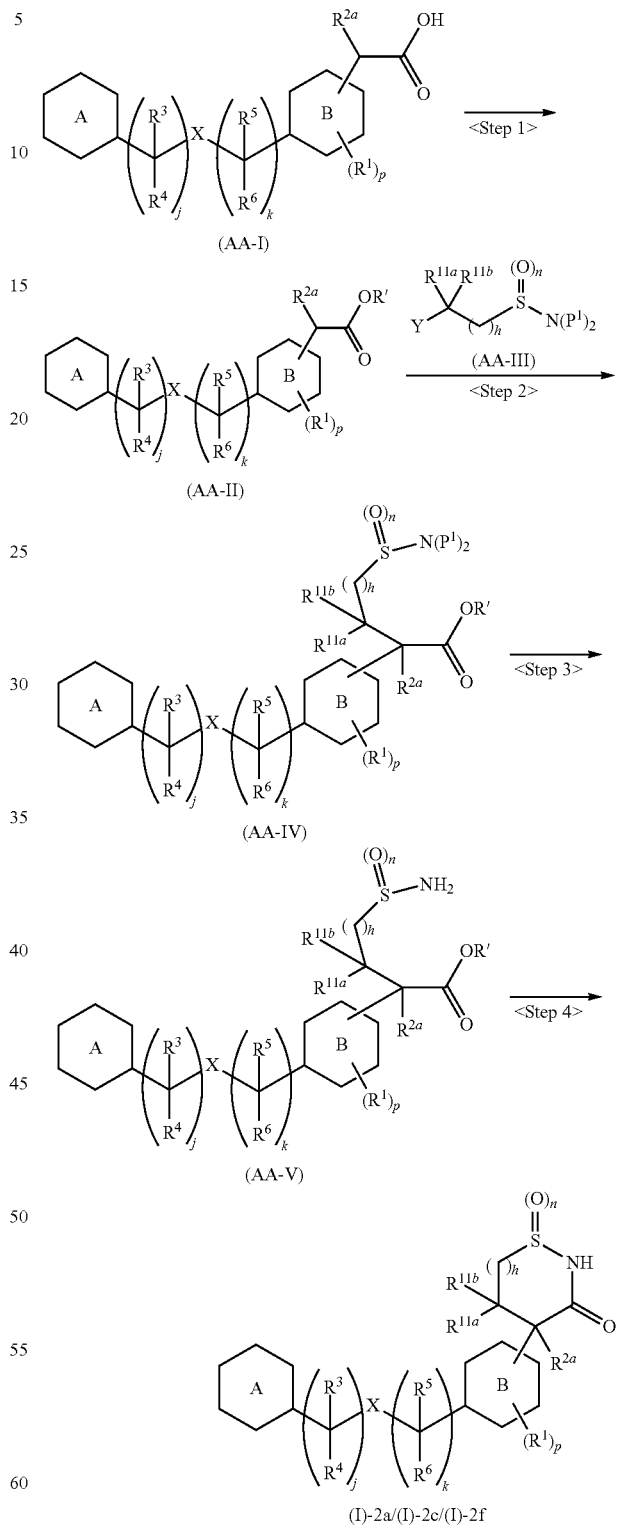

<Production Method AA>
<When n=1, 2>

<Step 1>

A compound of Formula (Z-I) can be produced by using a compound of Formula (G-I), which is known in the art or can be easily produced from a known compound, by the method in <Step 1> and <Step 2> or <Step 3> in (Production Method V).

<Step 2>

The protective group $P^1$ in the compound of Formula (Z-I) is deprotected. A compound of Formula (Z-II) can be produced by reaction in a similar manner to that in <Step 3> in (Production Method B).

<Step 3>

The compound of Formula (Z-II) is subjected to substitution reaction with a compound of Formula (B-V). The compound of Formula (V-II) can be produced by reaction in a similar manner to that in <Step 4> in (Production Method B).

In Formula (I) above, Formulae (I)-1b, (I)-1c, (I)-1d, (I)-1e, and (I)-1f include optical isomers. The isomers can be separated through optical resolution using chiral column chromatography, preferential crystallization using an optically active salt, or asymmetric synthesis by a person skilled in the art based on conventional techniques.

<Step 1>

A compound of Formula (AA-II) can be produced in a similar manner to that in <Step 2> in (Production Method B) by reacting a compound of Formula (AA-I), which is known in the art or can be easily produced from a known compound (for example, a phenylacetic acid derivative such as 4-hydroxy-a-methylphenylacetic acid (manufactured by Tokyo Chemical Industry Co., Ltd.) when the ring B is a benzene ring, or 2,3-dihydro-6-hydroxy-3-benzofuran acetic acid, 3,4-dihydro-7-hydroxy-2H-1-benzopyran-4-acetic acid, 2,3-dihydro-6-hydroxy-benzo[b]thiophene-3-acetic acid, and the like that can be produced in accordance with, for example, the method described in WO 2006/083781 pamphlet when the ring B is a bicyclic hetero ring such as a 2,3-dihydrobenzofuran ring, a 3,4-dihydro-2H-1-benzopyran ring, and a 2,3-dihydrobenzo[b]thiophene ring).

<Step 2>

The compound of Formula (AA-II) is subjected to substitution reaction. A compound of Formula (AA-IV) can be produced by reacting the compound of Formula (AA-II) with a compound of Formula (AA-III) in a similar manner to that in <Step 5> in (Production Method X).

<Step 3>

The protective group $P^1$ in the compound of Formula (AA-IV) is deprotected. A compound of Formula (AA-V) can be produced by reacting the compound of Formula (A-IV) in a similar manner to that in <Step 3> in (Production Method B).

<Step 4>

The compound of Formula (AA-V) is subjected to ring formation reaction. A compound of Formula (I)-2a/Formula (I)-2c/Formula (I)-2f can be produced by reacting the compound of Formula (AA-V) in a similar manner to that in <Step 7> in (Production Method M).

<Production Method BB>

<When n=2>

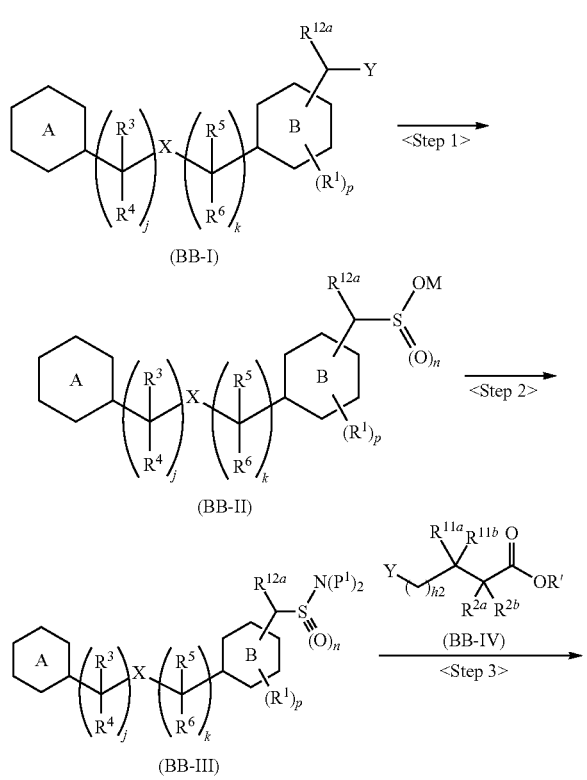

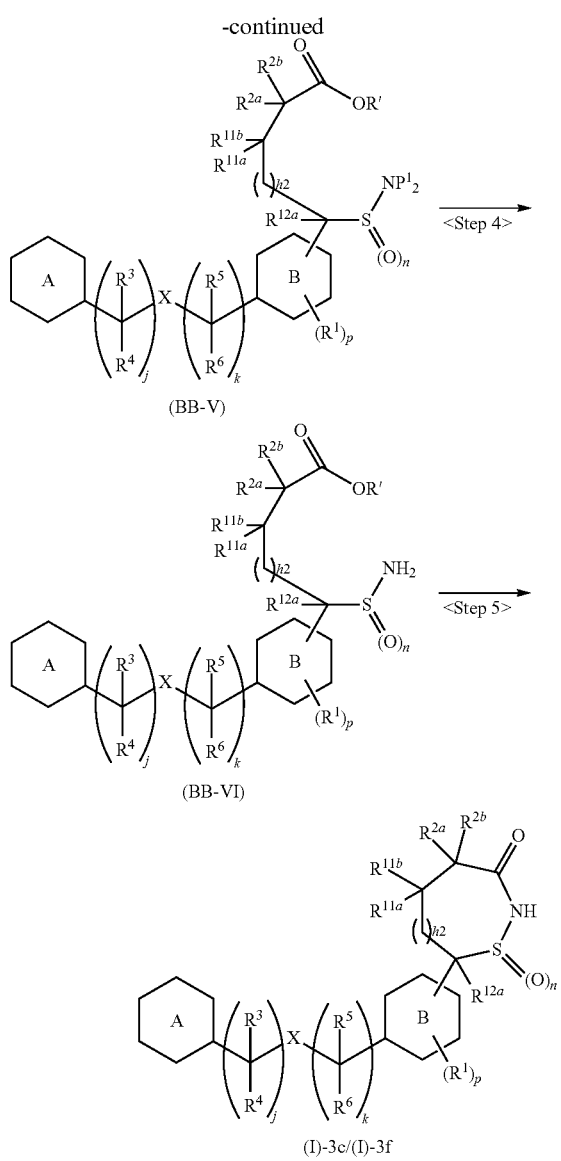

<Step 1>

A compound of Formula (BB-II) can be produced by reacting a compound of Formula (BB-I), which is known in the art or can be easily produced from a known compound (for example, a benzyl bromide derivative such as 4-(1-bromoethyl)-phenol when the ring B is a benzene ring, and 3-(bromomethyl)-6-hydroxy-2,3-dihydrobenzofuran that can be derived from 6-hydroxy-3 (2H)-benzofuran in accordance with a method known in a literature when the ring B is a bicyclic compound such as 2,3-dihydro-6-hydroxy-3-benzofuran ring), with a sulfur source such as sodium sulfite and potassium sulfite in a similar manner to that in <Step 3> in (Production Method U) (M is a metal such as Na and K in Formula (BB-II)).

<Step 2>

The compound of Formula (BB-II) is subjected to halogenation and sulfonylation, followed by sulfonamidation. A compound of Formula (BB-III) can be produced by reacting the compound of Formula (BB-II) in a similar manner to that in <Step 5> in (Production Method M).

<Step 3>

The compound of Formula (BB-III) is subjected to substitution reaction. A compound of Formula (BB-V) can be produced by reacting the compound of Formula (BB-III) with a compound of Formula (BB-IV) in a similar manner to that in <Step 5> in (Production Method X).

<Step 4>

The protective group $P^1$ in the compound of Formula (BB-V) is deprotected. A compound of Formula (BB-VI) can be produced by reacting the compound of Formula (BB-V) in a similar manner to that in <Step 3> in (Production Method B).

<Step 5>

The compound of Formula (BB-VI) is subjected to ring formation reaction. A compound of Formula (I)-3c/Formula (I)-3f can be produced by reacting the compound of Formula (BB-VI) in a similar manner to that in <Step 7> in (Production Method M).

[Concomitant Drug Containing Compound of the Present Invention]

The compound and pharmaceutical composition of the present invention can be used in combination with other drugs or medicines by a general method performed in medical practice. Particularly, such combination is used for the prevention, progress delay, and therapies of the mediating state of the GPR40 agonist, and is further particularly used against at least one disease selected from the group consisting of diabetes (Type 1 diabetes, Type 2 diabetes, and boederline type diabetes (impaired glucose tolerance (IGT) and/or impaired fasting glycemia (IFG))), insulin resistance, hyperinsulinemia, obesity, adiposity, and various diseases derived from or related to these diseases.

Examples of an insulin sensitizer and an anti-diabetic drug include 1) PPAR gamma agonists (specifically, pioglitazone, rosiglitazone, troglitazone, ciglitazone, darglitazone, englitazone, netoglitazone, etc.), 2) biguanide agents (specifically, metformin, buformin, phenformin, etc.), 3) sulfonylureas (specifically, tolbutamide, acetohexamide, chlorpropamide, glibenclamide, gliclazide, glipizide, glimepiride, glipentide, gliquidone, glisolamide, tolazamide, etc.), 4) rapid-acting insulin secretagogues (specifically, nateglinide, mitiglinide, repaglinide, etc.), 5) alpha-glucosidase inhibitors (specifically, acarbose, voglibose, miglitol, camiglibose, adiposin, emiglitate, pradimicin Q, salbostatin, etc.), 6) insulin or insulin derivatives (specifically, insulin zinc suspensions, insulin lispro, insulin aspart, regular insulin, NPH insulin, insulin glargine, insulin detemir, mixed insulin, etc.), 7) GLP-1 and GLP-1 agonists (specifically, exenatide, liraglutide, etc.), 8) DPP-IV inhibitors (specifically, sitagliptin, vildagliptin, alogliptin, saxagliptin, NVP-DPP-728, etc.), and 9) alpha-2 antagonists (specifically, midaglizole, isaglidole, deriglidole, idazoxan, efaroxan, etc.).

Examples of the insulin sensitizer and the anti-diabetic drug also include a hypolipidemic agent and a dyslipidemia therapeutic agent. Examples of the hypolipidemic agent and the dyslipidemia therapeutic agent include 1) omega-3 fatty acids (specifically, ethyl icosapentate (EPA-E preparation), docosahexaenoic acid (DHA), etc.), 2) HMG-CoA reductase inhibitors (specifically, atorvastatin, simvastatin, pitavastatin, itavastatin, fluvastatin, lovastatin, pravastatin, rivastatin, rosuvastatin, etc.), 3) HMG-CoA synthase inhibitors, 4) cholesterol absorption inhibitors (specifically, ezetimibe), 5) acyl-CoA-cholesterol acyltransferase (ACAT) inhibitors, 6) CETP inhibitors, 7) squalene synthase inhibitors, 8) antioxidants (specifically, probucol, etc.), 9) PPAR alpha agonists (specifically, clofibrate, etofibrate, fenofibrate, bezafibrate, ciprofibrate, gemfibrozil, KRP-101, etc.), 10) PPAR delta agonists, 11) LXR agonists, 12) FXR agonists (specifically, INT-747, etc.), 13) MTTP inhibitors, 14) squalene epoxidase inhibitors, and 15) bile acid absorption inhibitors (specifically, cholestyramine, colestipol, etc).

In addition, examples of the insulin sensitizer and the anti-diabetic drug also include an anti-obesity agent. Specific examples of the anti-obesity agent include 1) CB-1 receptor antagonists (specifically, rimonabant, SR-147778, BAY-65-2520, etc.), 2) monoamine reuptake inhibitors (specifically, sibutramine, mazindol, etc.), 3) serotonin reuptake inhibitors (specifically, fluoxetine, paroxetine, etc.), 4) lipase inhibitors (specifically, orlistat, cetilistat, etc.), 5) neuropeptide Y (NPY) receptor antagonists (specifically, S-2367, etc.), 6) peptide YY (PYY) receptor antagonists, and 7) adrenergic beta-3 receptor agonists (specifically, KRP-204, TRK-380/TAC-301, etc).

The therapies can be performed in combination with not only other drugs, but also other therapies. Examples of the therapies include the improvement of lifestyle through weight control, exercise therapy, and diet therapy, and radiotherapy.

Against GPR40-involving diseases except for diabetes and obesity, the therapies can be performed in combination with drugs used in the respective fields.

The combined use of the concomitant drug and conventional drugs against the diseases described above enables the dosage of the conventional drugs to be reduced, which can reduce the side effects of the conventional drugs. It is needless to say the combining method using the drugs is not limited to the diseases, and the drugs to be used in combination are not limited to the compounds exemplified above.

To use the compound of the present invention in combination with the drug to be used in combination, they may be individual preparations or be a drug combination. In the form of individual preparations, the compound and the drug can be taken at the same time or can be administered at different times.

[Producing preparations of prophylactic or therapeutic agents of the present invention]

The medicines of the present invention are administered in the form of pharmaceutical compositions.

The pharmaceutical compositions of the present invention may include at least the compound of Formula (I) or Formula (II) of the present invention and are produced in combination with pharmaceutically acceptable additives. More in detail, various dosage forms can be prepared by appropriately combining the compound of the present invention and, for example, excipients (for example, lactose, white soft sugar, mannitol, microcrystalline cellulose, silicic acid, corn starch, and potato starch), bonding agents (for example, celluloses (hydroxypropylcellulose (HPC), hydroxypropylmethylcellulose (HPMC), microcrystalline cellulose, saccharide (lactose, mannitol, white soft sugar, sorbitol, erythritol, and xylitol), starches (corn starch and potato starch), gelatinized starch, dextrin, polyvinylpyrrolidone (PVP), macrogol, polyvinyl alcohol (PVA)), lubricants (for example, magnesium stearate, calcium stearate, talc, and carboxymethylcellulose), disintegrants (for example, starches (corn starch and potato starch), sodium carboxymethyl starch, carmellose, carmellose calcium, croscarmellose sodium, and crospovidone), coating agents (for example, celluloses (hydroxypropylcellulose (HPC), hydroxypropylmethylcellulose (HPMC), aminoalkylmethacrylate copolymers E, and methacrylic copolymers LD), plasticizers (for example, triethyl citrate and macrogol), masking agents (for example, titanium oxide), colorants, flavoring agents, antiseptics (for example, benzalkonium chloride and p-hydroxybenzoate esters), tonicity agents (for example, glycerin, sodium chloride, calcium chloride, mannitol, and dextrose), pH regulators (for example, sodium hydroxide, potassium hydroxide, sodium carbonate, hydrochloric acid, sulfuric acid, and buffer solutions such as phosphate buffer solutions), stabilizing agents (for example, sugar, sugar alcohol, and xanthan gum), dispersants, antioxidants (for example, ascorbic acid, butylated hydroxyanisole (BHA), propyl gallate, and dl-alpha-tocopherol), buffer agents, preservatives (for example, paraben, benzyl alcohol, and benzalkonium chloride), perfumes (for example, vanillin, l-menthol, and rose oil), solubilizing agents (for example, polyoxyethylene hydrogenated castor oil, polysorbate 80, polyethylene glycol, phospholipid cholesterol, and triethanolamine), absorbefacients (for example, sodium glycolate, sodium edetate, sodium caprate, acylcarnitines, and limonene), gelators, suspending agents, emulsifiers, and generally used suitable additives and solvents.

Examples of the various dosage forms include tablets, capsules, granules, powderes, pills, aerosols, inhalants, ointments, adhesive patches, suppositories, injections, troches, liquids, spirits, suspensions, extracts, and elixirs. The dosage forms can be administered to patients through oral administration, subcutaneous injection, intramuscular injection, intranasal administration, transdermal administration, intravenous injection, intraarterial injection, perineural administration, epidural administration, administration in subdural cavity, intraventricular administration, rectal administration, inhalation, or the like.

The dosage of the compound of the present invention is generally, 0.005 mg to 3.0 g, preferably, 0.05 mg to 2.5 g, and more preferably, 0.1 mg to 1.5 g per day for adults, but can be reduced or increased as needed depending on symptoms or administration routes.

The compound can be administered as a whole at once or be separately administered by being divided into two to six doses through oral administration or parenteral administration, or can be administered through repeated administration such as intravenous infusion.

The present specification incorporates, as references, the whole publications cited in the present specification, for example, related-art documents, publications of unexamined applications, patent publications, and other patent documents.

PHARMACOLOGICAL TEST EXAMPLES

The present invention is specifically described below with reference to test examples but is not limited to them.

The following pharmacological test examples 1 to 7 provide methods for investigating the efficacy of the compound of the present invention.

Pharmacological Test Example 1

Agonist Action on GPR40 of Human Origin

A CHO cell strain stably expressing GPR40 of human origin was used to determine the agonist action of a title compound. This cell strain was seeded in a clear bottom 96 well plate at $2\times10^4$ cells/100 μL/well. The cell strain was cultured in a $CO_2$ incubator overnight using a Ham's F-12 medium containing a 10% fetal bovine serum, 100 U/mL penicillin, 0.1 mg/mL streptomycin, and 400 μg/mL. Geneticin. Calcium 4 Assay Kit (Molecular Devices) was used as a fluorescent calcium indicator. One mL of 77 mg/mL probenecid (Invitrogen) was added to 100 mL of a calcium indicator solution to prepare a solution (loading solution) mixed with a 20 mM HEPES-containing Hanks' balanced salt solution (HBSS) in equal proportions. To the cells from which the culture solution was removed, 200 μL of the loading solution was added, and the cells were cultured in a $CO_2$ incubator for 1 hour. The title compound was diluted with a 20 mM HEPES-containing HBSS and was added to the cells by 50 μL, and the fluctuation of the $Ca^{2+}$ concentration was measured by an intracellular ion analyzer. The $EC_{50}$ value of the title compound was calculated using the dose-response curve of fluorescence intensity variation. Table 1 indicates the compound of the present invention having an $EC_{50}$ value of less than 0.3 μM as A and the compound of the present invention having an $EC_{50}$ value of 0.3 μM or more and less than 3 μM as B.

TABLE 1

| Compound of Examples | $EC_{50}$ values |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | B |
| 16 | A |
| 17 | A |
| 18 | B |
| 19 | A |
| 20 | B |
| 21 | A |
| 22 | A |
| 23(A)-b | B |
| 24(A)-a | A |
| 25(A)-a | A |
| 26 | A |
| 27 | A |
| 28 | B |
| 29 | A |
| 30 | A |
| 31 | A |
| 32 | A |
| 33 | A |
| 34 | A |
| 35 | A |

Pharmacological Test Example 2

Oral Glucose Tolerance Test

A reduction of blood glucose excursion of a subject compound after glucose load is examined using male C57BL/6J mice or SD rats fasted overnight. The subject compound is suspended with a solvent (for example, 0.5% carboxymethylcellulose) and is orally administered before glucose load. The solvent is singly administered to the control group. Blood specimen collection is performed before compound administration (pre-administration blood collection), after compound administration and immediately before glucose load, during glucose load, after 15, 30, 60, and 120 minutes, and the blood glucose level of the collected blood is measured. The reduction of blood glucose excursion is obtained by orally administering a dosage of 0.3 to 10 mg/kg of the preferable compound of the compound of the present invention.

Pharmacological Test Example 3

Solubility Test (1) DMSO precipitation solubility (Kinetic Solubility)

A 10 mM DMSO solution of the compound of the present invention is added to a 50 mM phosphate buffer solution (pH 7.4) to the final concentration of 100 μM. The resultant solution is incubated with stirring at 600 rpm for 1.5 hours at room temperature, and then is filtered through a filter plate (4 μm, MultiScreen Solubility Filter Plate, Millipore). The absorbance of the obtained filtrate is measured at the maximum absorption wavelength using a plate reader (Powerscan HT, (Dainippon Pharmaceutical)). In this process, DMSO solutions of known concentration of the test compound (1, 3, 10, 30, and 100 μM) are prepared as standard solutions for a calibration curve. The absorbance of each of the standard solutions is measured to generate a calibration curve. The solubility (μM) of the compound is calculated using the absorbance values of the filtrate and the standard solutions.

(2) Crystal Solubility (Thermodynamic Solubility)

The compound of the present invention is added to water so as to be 1 mg/mL

The resultant solution is incubated at 37° C. for 24 hours, and then is centrifuged. The obtained supernatant is analyzed by HPLC to detect the peak at the maximum absorption wavelength, and thus, the peak area is calculated. Similarly, DMSO solutions of known concentration of the test compound (0.03, 0.1, 0.3, 1, 3, and 10 μg/mL) are added as standard solutions for a calibration curve. The peak area of each of the standard solutions is measured. The solubility (μg/mL) of the compound is calculated using the peak areas of the obtained calibration curve.

Pharmacological Test Example 4

Metabolic Stability Test

The 10 mM DMSO solution of the compound of the present invention is added to a solution containing liver microsome (human, mouse, or rat; XenoTech) and a NADPH generating systems (water containing beta-NADP, Glucose-6-Phosphate, G-6-PDH(Y), and $MgCl_2$) to the final concentration of 1 μM. The resultant solution is incubated at 37° C. for 20 minutes, and then the reaction is terminated by adding acetonitrile. Similarly, samples are collected at predetermined times during the incubation, and then the reaction is terminated. Each reaction solution is filtrated by centrifugation using a filter plate (MultiScreen HTS-HV plate, Millipore). The test compound in the filtrate is measured by high performance liquid chromatogram/mass spectrometry. Similarly, a sample with a reaction time of 0 is measured as a control. The compound concentration of the control is regarded as 100%, and the residual ratio of the compound in each reaction solution is calculated. These residual ratios are plotted with respect to the time, and the metabolic clearance (μL/mg/min) is calculated from the slope of the obtained regression line.

Pharmacological Test Example 5 hERG Inhibition Test By Patch-clamp technique

An effect against a human ether-a-go-go related gene (hERG) channel is measured using a fully automatic patch-clamp system (Patchliner (Nanion)). To confirm the hERG $I_{Kr}$ current of a cell (hERG-HEK (Upstate)), the membrane potential is kept at −80 mV, and a depolarizing pulse is applied to the cell on a regular basis. After the generated current became stable, a test compound is added. The effect of the test compound against the hERG channel is confirmed from the change in tail current induced by a repolarizing pulse at −40 mV for 0.5 second subsequent to a depolarizing pulse at 40 mV for 0.5 second. The stimulation is performed at a frequency of once every 10 seconds. The measurement is performed at room temperature. The hERG channel inhibition rate is calculated as the reduction rate (suppression rate) of a tail current two minutes after the application of the test compound relative to the maximum tail current before the application.

The calculated suppression rate shows the possibility that drug-induced QT prolongation followed by fatal side effects (such as ventricular tachycardia and sudden death).

Pharmacological Test Example 6

Pharmacokinetics Study (Cassette Dosing PK)

The compound of the present invention is orally administrated in a single dose to T- or 8-week-old male C57BL/6J Jcl mice or SD rats at 1 mg/kg (the vehicle is DMSO: Tween 80: ultrapure water=1:1:8 and 10 mL/kg). After the administration, the blood of the mouse is collected from the abdominal aorta after 0.25, 0.5, 1, and 2 hours, and the blood of the rat is collected from the jugular vein after 0.5, 1, 2, and 4 hours. The blood is centrifuged (3000 rpm, 15 minutes, and 4° C.) to obtain plasma, and the test compound in the plasma is measured by high performance liquid chromatogram/mass spectrometry.

Similarly, standard solutions of known concentration of the test compound (0.01, 0.02, 0.05, 0.1, 0.2, 0.5, and 1 μg/mL) are measured to generate a calibration curve. The concentration (μg/mL) of the compound in the plasma is calculated using the calibration curve, and the maximum concentration in the plasma is indicated by Cmax (μg/mL)

Pharmacological Test Example 7

Safety Assessment Study

The compound of the present invention is orally administrated in a single dose to mice or rats. No death is confirmed and no noticeable behavior disorder is observed, and therefore the safety of the compound of the present invention is shown.

As a result, the compound of the present invention showed an excellent GPR40 agonist action and reduced blood glucose excursion in the single oral dose glucose tolerance test using normal mice or rats. In the safety assessment study, no abnormality to indicates low toxicity of the compound of the present invention.

By performing the tests described above, the compound of the present invention is confirmed to have favorable properties in one regard, such as solubility, metabolic stability, pharmacokinetics, and the avoidance of an hERG channel inhibition action.

Accordingly, the compound of the present invention is expected to be used as a GPR40 agonist for insulin secretagogues and prophylactic and/or therapeutic agents against diabetes (particularly, Type 2 diabetes or boederline type diabetes), obesity, and adiposity.

PREPARATION EXAMPLE

Hereinafter, Examples of the pharmaceutical compositions of the present invention are described.

Preparation Example 1

Tablet

| | |
|---|---|
| Compound of Example 2 | 100 g |
| Lactose | 137 g |
| Crystalline cellulose | 30 g |
| Hydroxypropylcellulose | 15 g |
| Sodium carboxymethyl starch | 15 g |
| Magnesium stearate | 3 g |

The above components are weighed and then are uniformly mixed. The mixture is formed into tablets having a weight of 150 mg.

Preparation Example 2

Film Coating

| | |
|---|---|
| Hydroxypropylmethylcellulose | 9 g |
| Macrogol 6000 | 1 g |
| Titanium oxide | 2 g |

The above components are weighed. Subsequently, hydroxypropylmethylcellulose and macrogol 6000 are dissolved into water to disperse titanium oxide. The resultant liquid is film-coated on 300 g of the tablets of Preparation Example 1 to obtain film-coated tablets.

Preparation Example 3

Capsules

| | |
|---|---|
| Compound of Example 6 | 50 g |
| Lactose | 435 g |
| Magnesium stearate | 15 g |

The above components are weighed and then are uniformly mixed. Adequate hard capsules are each filled with 300 mg of the mixture by weight with a capsule inserter to produce capsules.

Preparation Example 4

Capsules

| | |
|---|---|
| Compound of Example 8 | 100 g |
| Lactose | 63 g |
| Corn starch | 25 g |
| Hydroxypropylcellulose | 10 g |
| Talc | 2 g |

The above components are weighed, and then the compound of Example 8, lactose, and corn starch are uniformly mixed. A hydroxypropylcellulose aqueous solution is added to the resultant mixture to produce granules by wet granulation. Talc is uniformly mixed with the granules, and adequate hard capsules are each filled with 200 mg of the mixture by weight to produce capsules.

Preparation Example 5

Powders

| | |
|---|---|
| Compound of Example 11 | 200 g |
| Lactose | 790 g |
| Magnesium stearate | 10 g |

The above components are weighed and then are uniformly mixed to produce 20% powdered drugs.

Preparation Example 6

Granules and Fine Granules

| | |
|---|---|
| Compound of Example 13 | 100 g |
| Lactose | 200 g |
| Crystalline cellulose | 100 g |
| Partially gelatinized starch | 50 g |
| Hydroxypropylcellulose | 50 g |

The above components are weighed, and the compound of Example 13, lactose, crystalline cellulose, and partially pregelatinized starch are uniformly mixed. A hydroxypropylcellulose (HPC) aqueous solution is added to the resultant mixture to produce granules or fine granules by wet granulation. The granules or fine granules are dried to be formulation of granules or fine granules.

EXAMPLES

Next, in order to describe the present invention further in detail, there are described Examples which should not be construed as limiting the scope of the present invention.

For the measurement of the nuclear magnetic resonance spectrum (NMR), JEOL JNM-ECX400 FT-NMR (manufactured by JEOL Ltd.) and JEOL JNM-ECX300 FT-NMR (manufactured by JEOL Ltd.) were used. As the LC-MS, a Waters Fraction Lynx MS system (manufactured by Waters Corporation) was used and as the column, a Sun Fire column (4.6 mm×5 cm, 5 µm) (manufactured by Waters Corporation) was used. As a mobile phase, methanol:0.05% acetic acid aqueous solution=1:9 (0 min) to 10:0 (5 min) to 10:0 (7 min) (gradient condition) or methanol:0.05% trifluoroacetic acid aqueous solution=1:9 (0 min) to 10:0 (5 min) to 10:0 (7 min) (gradient condition) was used. For the preparative isolation system, gradient conditions appropriately changed depending on the type of the compound were used. In the present invention, in the preparative chromatography of a mixture of optical isomers, an enantiomer having a shorter elution time is expressed as A and an enantiomer having a longer elution time is expressed as B as well as a diastereomer having a shorter elution time is expressed as a and a diastereomer having a longer elution time is expressed as b.

Reference Example 1

Synthesis of 4-Hydroxyphenylboronic Acid N-Methyliminodiacetic Acid Ester

A suspension of 4-hydroxyphenylboronic acid (10.3 g) and N-methyliminodiacetic acid (11.0 g) in dimethyl sulfoxide (37 mL)- toluene (333 mL) was heated and refluxed for 1.5 hours. From the resultant reaction mixture, toluene was removed by evaporation under reduced pressure and the reaction mixture was poured into water (400 mL). The resultant reaction mixture was stirred for 1.5 hours. The precipitate was filtered, washed with water, and then dried under reduced pressure to give the title compound (16.4 g) as a gray white solid.

Reference Example 2

Synthesis of 3'-(Bromomethyl)-2,6-Dimethyl-4-(3-(Methylsulfonyl)Propoxy)-1,1'-Biphenyl Concentrated sulfuric acid (1.4 g) was added dropwise to 48% hydrobromic acid (15 ml) at room temperature and [2',6'-dimethyl-4'-[3-(methylsulfonyl)propoxy]-[1,1'-biphenyl]-3-yl]methanol (25 g) synthesized in accordance with the method described in [WO 2008/001931 pamphlet] was divided into five portions and added to the mixture. The reaction mixture was stirred at 60° C. for 2.5 hours and 48% hydrobromic acid (3.3 ml) was added to the mixture. The mixture was further stirred for 1 hour at the same temperature. After the reaction mixture was allowed to cool, water was added to the reaction mixture. The mixture was extracted with ethyl acetate. The obtained organic phase was washed with water, then washed with brine, and dried over anhydrous sodium sulfate. From the organic phase, the solvent was removed by evaporation under reduced pressure to give the title compound (27 g) as a pale yellow solid.

Example 1

Synthesis of 5-[4-[[3-[4-(2-ethoxyethoxy)-2,6-dimethylphenyl]phenyl]methoxy]phenyl]-1-oxo-1,2-thiazolidin-3-one <Step 1> Synthesis of 1-bromo-2,6-dimethyl-4-(2-ethoxyethoxy)benzene In accordance with the method described in [WO 2005/063729 pamphlet, Reference Example 31], the title compound (12.8 g) was obtained as a colorless oil from 4-bromo-3,5-dimethylphenol (10.0 g) and 2-chloroethyl ethyl ether (5.94 mL).

<Step 2> Synthesis of (3-(2,6-dimethyl-4-(2-ethoxyethoxy)phenyl)phenyl)methanol

To a mixed solution of the compound (6.40 g) obtained in (Example 1)<Step 1> and 3-(hydroxymethyl)phenylboronic acid (3.56 g) in 1,4-dioxane (70 mL)- water (7 mL), bis(dibenzylideneacetone)palladium (1.35 g), 2-dicyclohexylphosphino-2',6'-dimethoxybiphenyl (SPhos: 1.92 g), and potassium phosphate monohydrate (10.8 g) were sequentially added and the resultant reaction mixture was heated and stirred at 100° C. for 4 hours. To the reaction mixture, water was added and the mixture was extracted with ethyl acetate. The organic phase was washed with brine and then dried over anhydrous sodium sulfate. From the organic phase, the solvent was removed by evaporation under reduced pressure. The resultant residue was purified by silica gel column chromatography (eluent; n-hexane:ethyl acetate=80:20 to 75:25) to give the title compound (4.13 g) as a colorless oil.

<Step 3> Synthesis of 4-((3-(2,6-dimethyl-4-(2-ethoxyethoxy)phenyl)phenypmethoxy)phenylboronic acid N-methyliminodiacetic acid ester To a solution of the compound (1.50 g) obtained in (Example 1)<Step 2>, the compound (1.49 g) obtained in (Reference Example 1), and tri-n-butylphosphine (1.48 mL) in tetrahydrofuran (50 mL), 1,1'-azobis(N,N-dimethylformamide) (1.03 g) was added under ice-cooling and the resultant reaction mixture was stirred at room temperature for 2 hours. From the reaction mixture, the solvent was removed by evaporation under reduced pressure and the resultant residue was purified by silica gel column chromatography (eluent; n-hexane:ethyl acetate) to give the title compound (2.37 g) as a white amorphous solid.

<Step 4> Synthesis of 5-chloro-isothiazol-3-ol 1-oxide

To a suspension of 5-chloro-isothiazol-3-ol (31.8 g) in dichloromethane (640 mL), m-chloroperbenzoic acid (content 65%) (60.7 g) was added under ice-cooling and the resultant reaction mixture was stirred at room temperature for 15 hours. The reaction mixture was filtered and then the filtrate was concentrated under reduced pressure. To the residue, dichloromethane was added and the precipitate was filtered off. The filtrate was concentrated under reduced pressure and the resultant residue was purified by silica gel chromatography (eluent; n-hexane:ethyl acetate=67:33 to 60:40) to give the title compound (26.0 g) as a white solid.

<Step 5> Optical resolution of (Rac)-5-chloro-isothiazol-3-ol 1-oxide

Optical resolution of the compound (30.5 g) obtained in (Example 1)<Step 4> was conducted by preparative chromatography (column: CHIRALPAK AS-H (5 cm×25 cm) manufactured by Daicel Chemical Industries, Ltd., eluent; carbon dioxide:methanol=86:14 (V/V), flow rate: 200 g/second, detection: UV 238 nm) to give each enantiomer of the title compound.

Primary fraction (14.7 g, white solid, >99% ee, retention time 4.8 minutes (enantiomer A: Example 1-5 (A)))

Secondary fraction (14.1 g, white solid, >98% ee, retention time 5 3 minutes (enantiomer B: Example 1-5 (B)))

The optical purity and the retention time were determined under the following conditions.

Column: CHIRALPAK AD-H (0.46 cm×25 cm) (manufactured by Daicel Chemical Industries, Ltd.),
Eluent: methanol:acetic acid=100:0.1 (v/v),
Flow rate: 1.0 mL/min,
Detection: UV 282 nm,
Column temperature: 40° C.

Hereinafter, the compounds and derivatives of them synthesized using the enantiomer A (Example 1-5 (A)) obtained in (Example 1)<Step 5> is expressed as "name of the compound+(A)" and the compounds and derivatives of them synthesized using the enantiomer B (Example 1-5 (B)) obtained in (Example 1)<Step 5> is expressed as "name of the compound+(B)".

<Step 6> Synthesis of 5-(4-((3-(2,6-dimethyl4-(2-ethoxyethoxy)phenyl)phenyl)methoxy)phenyl) isothiazol-3-ol 1-oxide (A)

To a solution of the compound (0.20 g) obtained in (Example 1)<Step 3> in 1,4-dioxane (3 7 mL), a 1M sodium hydroxide aqueous solution (1.1 mL) was added and the resultant reaction mixture was stirred at room temperature for 1.5 hours. To the reaction mixture, the enantiomer A (Example 1-5 (A)) (74 mg) obtained in (Example 1)<Step 5>, 2-dicyclohexylphosphino-2',6'-dimethoxybiphenyl (SPhos: 31 mg), and palladium acetate (8.4 mg) were sequentially added and the resultant reaction mixture was heated and stirred at 90° C. for 3 hours. To the reaction mixture, a saturated aqueous ammonium chloride solution was added and the mixture was extracted with ethyl acetate. The organic phase was washed with brine and then dried over anhydrous sodium sulfate. From the organic phase, the solvent was removed by evaporation under reduced pressure and the resultant residue was purified by LC/MS to give the title compound (9.2 mg) as a pale yellow amorphous solid.

<Step 7> Synthesis of 5-[4-[[3-[[4-(2-ethoxyethoxy)-2,6-dimethylphenyl]phenyl]methoxy]phenyl]-1-oxo-1,2-thiazolidin-3-one (A)

To a solution of the compound (50 mg) obtained in (Example 1)<Step 6> in absolute THF (1 mL), a solution of 1M L-Selectride in tetrahydrofuran (0.31 mL) was added at 0° C. and the resultant reaction mixture was stirred at the same temperature for 1.5 hours. To the reaction mixture, 1M hydrochloric acid was added and the mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate) to give the title compound (4.6 mg) as a white solid. The obtained compound by the reduction in this step is a mixture of diastereomers having a new asymmetric center.

The compounds of Examples 2 to Example 4 below were synthesized by the same method or a similar method in Example 1 from each corresponding raw material through a corresponding substituted phenylboronic acid ester and further through a corresponding substituted isothiazole.

Example 2

5-[4-[[3-[4-(2-ethoxyethoxy)-3-fluoro-2,6-dimethylphenyl]phenyl]methoxy]phenyl]-1-oxo-1,2-thiazolidin-3-one (A)

Example 3

5-[4-[[3-[3-fluoro-4-(3-hydroxy-3-methylbutoxy)-2,6-dimethylphenyl]phenyl]methoxy]phenyl]-1-oxo-1,2-thiazolidin-3-one (A)

Example 4

5-[4-[[3-[4-(3-hydroxy-3-methylbutoxy)-2,6-dimethylphenyl]phenyl]methoxy]phenyl]-1-oxo-1,2-thiazolidin-3-one (A)

Example 5

Synthesis of optically active 5-[4-[[3-[2,4-dimethyl-6-(3-methylsulfonylpropoxy)pyridin-3-yl]phenyl]methoxy]phenyl]-1-oxo-1,2-thiazolidin-3-one (A)-a and (A)-b <Step 1> Synthesis of 5-(4((3-(2,4-dimethyl-6-(3-(methylsulfonyl)propoxy)pyridin-3-yl)phenyl)methoxy)phenyl)isothiazol-3-ol 1-oxide (A)

The title compound was synthesized by the same method or a similar method in <Step 1> to <Step 6> in (Example 1) from a corresponding raw material through a corresponding substituted phenylboronic acid ester.

<Step 2> Synthesis of 5-[4-[[3-[2,4-dimethyl-6-(3-methylsulfonylpropoxy)pyridin-3-yl]phenyl]methoxy]phenyl]-1-oxo-1,2-thiazolidin-3-one (A)-a and (A)-b To a solution of the compound (200 mg) obtained in (Example 5)<Step 1> in absolute THF (6 mL), a solution of 1M L-Selectride in tetrahydrofuran (1.5 mL) was added at 0° C. and the resultant reaction mixture was stirred at the same temperature for 1 hour. To the reaction mixture, 1M hydrochloric acid was added and the mixture was extracted with ethyl acetate. The organic phase was washed with brine and then dried over anhydrous sodium sulfate. From the organic phase, the solvent was removed by evaporation under reduced pressure and the resultant residue was purified by LC/MS to give each diastereomer of the title compound.

Primary fraction (1.6 mg, pale yellow solid, retention time 5.25 minutes, diastereomer a: Example 5 (A)-a)

Secondary fraction (3.4 mg, pale yellow solid, retention time 5.32 minutes, diastereomer b: Example 5 (A)-b)

Hereinafter, for example, the mixture of diastereomers that are obtained by the reduction in Example 5<Step 2> using the enantiomer A (Example 5-1 (A)) obtained in Example 5 <Step 1> can be separated into optically active diastereomers as shown in Example 5 <Step 2>. For example, when a resolution column is used, the primary fraction that is firstly eluted in the separation condition is expressed as "name of the compound+a" as a diastereomer a (Example 5 (A)-a) and the secondary fraction that is eluted later is expressed as "name of the compound+b" as a diastereomer b (Example 5 (A)-b).

For example, Example 5-1 (B), Example 5 (B)-a, and Example 5 (B)-b can similarly be obtained when the enantiomer B obtained in Example 1 <Step 5> is used in Example 5 <Step 1>.

The compound of Example 6 below was synthesized by the same method or a similar method in Example 5 form each corresponding raw material through a corresponding substituted phenylboronic acid ester and further through a corresponding substituted isothiazole.

Example 6

5-[4-[[3-[6-(3-hydroxy-3-methylbutoxy)-2,4-dimethylpyridin-3-yl]phenyl]methoxy]phenyl]-1-oxo-1,2-thiazolidin-3-one (A)-a trifluoroacetic acid salt and (A)-b trifluoroacetic acid salt Primary fraction (6.4 mg, colorless amorphous solid, retention time 5.72 minutes, diastereomer a: Example 6 (A)-a)

Secondary fraction (8.1 mg, colorless oil, retention time 5.77 minutes, diastereomer b: Example 6 (A)-b)

Example 7

Synthesis of 5-[4-[[3-[4-(3-hydroxy-3-methylbutoxy)-2,5-dimethylphenyl]phenyl]methoxy]phenyl]-1-oxo-1,2-thiazolidin-3-one (A)-a and (A)-b <Step 1> Synthesis of 3-hydroxy-5-(4-((4'(3-hydroxy-3-methylbutoxy)-2',5'-dimethyl-[1,1'-biphenyl]-3-yl)methoxy)phenyl)isothiazole1-oxide (A)

The title compound was synthesized by the same method or a similar method in <Step 1> to <Step 6> in (Example 1) from a corresponding raw material through a corresponding substituted phenylboronic acid ester.

<Step 2> Synthesis of 5-[4-[[3-[4-(3-hydroxy-3-methylbutoxy)-2,5-dimethylphenyl]phenyl]methoxy] phenyl]-1-oxo-1,2-thiazolidin-3-one (A)-a and (A)-b To a solution of the compound (100 mg) obtained in (Example 7)<Step 1> in absolute THF (3 mL), a solution of 1M L-Selectride in tetrahydrofuran (0 79 mL) was added at 0° C. and the resultant reaction mixture was stirred at the same temperature for 1.5 hours. To the reaction mixture, 1M hydrochloric acid was added and the mixture was extracted with ethyl acetate. The organic phase was washed with brine and then dried over anhydrous sodium sulfate. From the organic phase, the solvent was removed by evaporation under reduced pressure and the resultant residue was separated and purified by LC/MS. Optical resolution of the resultant solid was conducted by preparative chromatography (column: CHIRALPAK IB (2 cm×25 cm) manufactured by Daicel Chemical Industries, Ltd., eluent; hexane:ethanol:trifluoroacetic acid=70:30:0.1 (V/V), flow rate: 17 mL/min) to give each diastereomer of the title compound. The retention times were determined by LC/MS.

Primary fraction (10 mg, colorless amorphous solid, retention time 6.20 minutes, diastereomer a: Example 7 (A)-a)

Secondary fraction (21 mg, colorless amorphous solid, retention time 6.10 minutes, diastereomer b: Example 7 (A)-b)

Example 8

Synthesis of 5-[4-[[3-[4-(3-hydroxypropoxy)-2,6-dimethylphenyl]phenyl]methoxy]phenyl]-1-oxo-1,2-thiazolidin-3-one (A)<

<Step 1> Synthesis of 1-bromo-4-(3-((tert-butyldimethylsilyl)oxy)propoxy)-2,6-dimethylbenzene In accordance with the method in (Example 1)<Step 1>, the title compound (7.60 g) was obtained as a colorless oil from 4-bromo-3,5-dimethylphenol (4.00 g) and 3-((tert-butyldimethylsilyl)oxy)propyl bromide (5.55 g).

<Step 2> Synthesis of (3-(2,6-dimethyl-4-(3-(tert-butyldimethylsilypoxy)propoxyphenyl)phenyl) methanol In accordance with the method in (Example 1)<Step 2>, the title compound (1.34 g) was obtained as a brown oil from the compound (3.60 g) obtained in (Example 8)<Step 1>.

<Step 3> Synthesis of 4-((3-(4-(3-((tert-butyldimethylsilypoxy)propoxy)-2,6-dimethylphenyl)phenyl) methoxy) phenylboronic acid N-methyliminodiacetic acid ester In accordance with the method in (Example 1)<Step 3>, the title compound (1.21 g) was obtained as a pale yellow amorphous solid from the compound (1.20 g) obtained in (Example 8)<Step 2>.

<Step 4> Synthesis of 5-(4-((3-(2,6-dimethyl-4-(3-hydroxypropoxy)phenyl)phenyl)methoxy)phenyl) isothiazol-3-ol 1-oxide (A)

To a solution of the compound (0.20 g) obtained in (Example 8)<Step 3> in 1,4-dioxane (3 2 mL), a 1M sodium hydroxide aqueous solution (0.9 mL) was added and the resultant reaction mixture was stirred at room temperature for 1.5 hours. To the reaction mixture, the enantiomer A (62 mg) obtained in (Example 1)<Step 5>, 2-dicyclohexylphosphino-2',6'-dimethoxybiphenyl (SPhos: 26 mg), and palladium acetate (7.1 mg) were sequentially added and the resultant reaction mixture was heated and stirred at 100° C. for 2 hours. To the reaction mixture, a saturated aqueous ammonium chloride solution was added and the mixture was extracted with ethyl acetate. The organic phase was washed with brine and then dried over anhydrous sodium sulfate. From the organic phase, the solvent was removed by evaporation under reduced pressure and the resultant residue was dissolved in ethanol (5.0 mL) and tetrahydrofuran (5.0 mL). To the solution, concentrated hydrochloric acid (4.1 mL) was added and the resultant reaction mixture was stirred at room temperature for 8 hours. To the reaction mixture, a saturated aqueous sodium hydrogen carbonate was added to make the mixture weak acidic and the mixture was extracted with ethyl acetate. The organic phase was washed with brine and then dried over anhydrous sodium sulfate. From the organic phase, the solvent was removed by evaporation under reduced pressure and the resultant residue was purified by LC/MS to give the title compound (23 mg) as a pale yellow amorphous solid.

<Step 5> Synthesis of 5-[4-[[3-[4-(3-hydroxypropoxy)-2,6-dimethylphenyl]phenyl]methoxy]phenyl]-1-oxo-1,2-thiazolidin-3-one (A)

In accordance with the method in (Example 1)<Step 7>, the title compound (4.2 mg) was obtained as a pale yellow amorphous solid from the compound (11 mg) obtained in (Example 8)<Step 4>. The title compound is a mixture of diastereomers.

The compounds of Example 9 to Example 10 below were synthesized by the same method or a similar method in Example 8 form each corresponding raw material through a corresponding substituted phenylboronic acid ester and further through a corresponding substituted isothiazole.

Example 9

5-[4-[[3-[4-[(2R)-2,3-dihydroxypropoxy]-2,6-dimethylphenyl]phenyl]methoxy]phenyl]-1-oxo-1,2-thiazolidin-3-one (A)

Example 10

5-[4-[[3-[4-[3-hydroxy-2-(hydroxymethyl)propoxy]-2,6-dimethylphenyl]phenyl]methoxy] phenyl]-1-oxo-1,2-thiazolidin-3-one (A)

Example 11

Synthesis of 5-[4-[[3-[4-(3-aminopropoxy)-2,6-dimethylphenyl]phenyl]methoxy]phenyl]-1-oxo-1,2-thiazolidin-3-one trifluoroacetic acid salt <Step 1> Synthesis of 3-(4-bromo-3,5-dimethylphenoxy)propyl)carbamic acid tert-butyl ester In accordance with the method in (Example 1)<Step 3>, the title compound (6.6 g) was obtained as a white solid from 4-bromo-3,5-dimethylphenol (5.00 g) and (3-hydroxypropyl)carbamic acid tert-butyl ester (5.2 g).

<Step 2> Synthesis of (3-((3'-formyl-2,6-dimethyl-[1,1'-biphenyl]-4-yl)oxy)propyl)carbamic acid tert-butyl ester In accordance with the method in (Example 1)<Step 2>, the title compound (1.95 g) was obtained as a red oil from the compound (2.3 g) obtained in (Example 11)<Step 1> and 3-formylphenylboronic acid (0.95 g).

<Step 3> Synthesis of 3-((3'-hydroxymethyl-2,6-dimethyl-[1,1'-biphenyl]-4-yl)oxy)propyl)carbamic acid tert-butyl ester The compound (1.84 g) obtained in (Example 11)<Step 2> was dissolved in a solution of tetrahydrofuran (12.0 mL) and methanol (6.0 mL). To the solution, sodium borohydride (0.18 g) was gradually added under ice-cooling. The reaction mixture was allowed to reach room temperature and stirred for 2 hours. To the reaction mixture, a saturated aqueous ammonium chloride solution was added to make the mixture pH 7 and the mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate=75:25 to 70:30) to give the title compound (1.73 g) as an amorphous solid.

<Step 4> Synthesis of (3-((2,6-dimethyl-3'-(4-(6-methyl-4,8-dioxo-1,3,6,2-dioxazaborocan-2-yl)phenoxy)methyl-[1,1'-biphenyl]-4-yl)oxy)propyl)carbamic acid tert-butyl ester In accordance with the method in Example 1 <Step 3>, the title compound (2.09 g) was obtained as a white amorphous solid from the compound (1.70 g) obtained in (Example 11)<Step 3>.

<Step 5> Synthesis of (3-((2,6-dimethyl-3'-((4(4-(1-oxide -3-oxo-2,3-dihydroisothiazol-5-yl)phenoxy)methyl-[1,1'-biphenyl]-4-yl)oxy)propyl)carbamic acid tert-butyl ester (A)

In accordance with the method in Example 1 <Step 6>, the title compound (45.6 mg) was obtained as a white amorphous solid from the compound (100 mg) obtained in (Example 11)<Step 4> using the enantiomer A (Example 1-5 (A)) obtained in (Example 1)<Step 5>.

<Step 6> Synthesis of 5-(4-((4'-(3-aminopropoxy)-2',6'-dimethyl-[1,1'-biphenyl]-3-yl)methoxy)phenyl) isothiazol-3(2H)-one 1-oxide (A)

The compound (45 mg) obtained in (Example 11)<Step 5> was dissolved in ethyl acetate (1.0 mL). To the solution, a solution of 4M hydrogen chloride in ethyl acetate (1.0 mL) was added and the resultant reaction mixture was stirred at room temperature over night. The reaction mixture was concentrated under reduced pressure and dried to give the title compound (49 mg) as a yellow solid.

<Step 7> Synthesis of 5-[4-[[3-[4-[(3R)-3-hydroxybutoxy]-2,6-dimethylphenyl]phenyl]methoxy]phenyl]-1-oxo-1,2-thiazolidin-3-one (A)

In accordance with the method in (Example 1)<Step 7>, the title compound (26 mg) was obtained as a colorless amorphous solid from the compound (50 mg) obtained in (Example 11)<Step 6>. The obtained compound is a mixture of diastereomers.

Example 12

Synthesis of 5-[4-[[3-[4-[(3R)-3-hydroxybutoxy]-2,6-dimethylphenyl]phenyl]methoxy]phenyl]-1-oxo-1,2-thiazolidin-3-one (A)

<Step 1> Synthesis of (3R)-3-acetoxybutoxy 4-methylbenzenesulfonate

The hydroxy group in (3R)-3-hydroxybutoxy 4-methylbenzenesulfonate (35.0 g) that was synthesized in accordance with the method in [Tetrahedron: Asymmetry, vol. 5 (1), pp. 117-118 (1994)] was acetylated in a common procedure to give the title compound (15.6 g) as a yellow oil.

<Step 2> Synthesis of 4-((3R)-3-acetoxybutoxy)-1-bromo-2,6-dimethylbenzene

In accordance with the method in (Example 1)<Step 1>, the title compound (4.09 g) was obtained as a colorless oil from 4-bromo-3,5-dimethylphenol (5.00 g) and the compound (7.83 g) obtained in (Example 12)<Step 1>.

<Step 3> Synthesis of (3-(4-((3R)-3-acetoxybutoxy)-2,6-dimethylphenyl)phenyl)methanol In accordance with the method in (Example 1)<Step 2>, the title compound (1.36 g) was obtained as a brown oil from the compound (2.00 g) obtained in (Example 12)<Step 2>.

<Step 4> Synthesis of 4-((3-(4-((3R)-3-acetoxybutoxy)-2,6-dimethylphenyl)phenyl)methoxy)phenylboronic acid N-methyliminodiacetic acid ester In accordance with the method in (Example 1)<Step 3>, the title compound (1.83 g) was obtained as a white solid from the compound (1.20 g) obtained in (Example 12)<Step 3>.

<Step 5> Synthesis of 5-(4-((3-(2,6-dimethyl-4-((3R)-3-hydroxybutoxy)phenyl)phenyl)methoxy) phenyl)isothiazol-3-ol 1-oxide (A)

To a solution of the compound (0.40 g) obtained in (Example 12)<Step 4> in 1,4-dioxane (7.0 mL), a 1M sodium hydroxide aqueous solution (2.1 mL) was added and the resultant reaction mixture was stirred at room temperature for 1.5 hours. To the reaction mixture, the enantiomer A (137 mg) obtained in (Example 1)<Step 5>, 2-dicyclohexylphosphino-2',6'-dimethoxybiphenyl (SPhos: 57 mg), and palladium acetate (39 mg) were sequentially added and the resultant reaction mixture was heated and stirred at 100° C. for 2 hours. To the reaction mixture, a saturated aqueous ammonium chloride solution was added and the mixture was extracted with ethyl acetate. The organic phase was washed with brine and then dried over anhydrous sodium sulfate. From the organic phase, the solvent was removed by evaporation under reduced pressure and the resultant residue was dissolved in ethanol (5.0 mL). To the solution, a 1M sodium hydroxide aqueous solution (4.9 mL) was added and the resultant reaction mixture was stirred at room temperature for 8 hours. To the reaction mixture, a saturated aqueous ammonium chloride solution was added to make the mixture weak acidic and the mixture was extracted with ethyl acetate. The organic phase was washed with brine and then dried over anhydrous sodium sulfate. From the organic phase, the solvent was removed by evaporation under reduced pressure and the resultant residue was purified by LC/MS to give the title compound (29 mg) as a pale yellow amorphous solid.

<Step 6> Synthesis of 5-[4-[[3-[4-[(3R)-3-hydroxybutoxy]-2,6-dimethylphenyl]phenyl]-methoxy]phenyl]-1-oxo-1,2-thiazolidin-3-one (A)

In accordance with the method in (Example 1)<Step 7>, the title compound (5.2 mg) was obtained as a pale yellow amorphous solid from the compound (11 mg) obtained in (Example 12)<Step 5>. The obtained compound is a mixture of diastereomers.

Example 13

Synthesis of 5-[4-[[3-[2,6-dimethyl 4-(3-methylsulfonylpropoxy)phenyl]phenyl]methoxy]phenyl]-1-oxo-1,2-thiazolidin-3-one (A)

<Step 1> Synthesis of (3-(2,6-dimethyl 4-((tert-butyldimethylsilyl)oxy)phenyl)phenyl)methanol In accordance with the method in (Example 1)<Step 2>, the title compound (10.4 g) was obtained as an orange solid from 1-bromo-4-((tert-butyldimethylsilyl)oxy)-2,6-dimethylbenzene (15.0 g) that was synthesized in accordance with the method described in [WO 2005/063729 pamphlet].

<Step 2> Synthesis of 4-((3-(2,6-dimethyl-4-((tert-butyldimethylsilypoxy)phenyl)phenypmethoxy)phenylboronic acid N-methyliminodiacetic acid ester In accordance with the method in (Example 1)<Step 3>, the title compound (0.24 g) was obtained as a pale yellow amorphous solid from the compound (0.20 g) obtained in (Example 13)<Step 1>.

<Step 3> Synthesis of 4-((3-(2,6-dimethyl-4-hydroxyphenyl)phenyl)methoxy)phenylboronic acid N-methyliminodiacetic acid ester To a solution of the compound (4.18 g) obtained in (Example 13)<Step 2> in tetrahydrofuran (70 mL), a solution of 1M tetrabutylammonium fluoride in tetrahydrofuran (14.6 mL) was added under ice-cooling and the mixture was stirred under ice-cooling for 30 minutes. Water was added to the reaction mixture and the mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate=33:67 to 20:80) to give the title compound (1.06 g) as a beige amorphous solid.

<Step 4> Synthesis of 4-((3-(2,6-dimethyl-4-(3-(methylsulfonyl)propoxy)phenyl)phenyl)methoxy)phenylboronic acid N-methyliminodiacetic acid ester In accordance with the method in (Example 1)<Step 1>, the title compound (79 mg) was obtained as a white solid from the compound (0.20 g) obtained in (Example 13)<Step 3> and 3-(methylsulfonyl)propyl 4-methylbenzenesulfonate (0.14 g) synthesized in accordance with the method described in [WO 2007/018314 pamphlet].

<Step 5> Synthesis of 5-(4-((3-(2,6-dimethyl 4-(3-(methylsulfonyl)propoxy)phenyl)phenyl)methoxy)phenyl)isothiazol-3-ol 1-oxide (A)

In accordance with the method in (Example 1)<Step 6>, the title compound (15 mg) was obtained as a beige solid from the compound (76 mg) obtained in (Example 13)<Step 4> using the enantiomer A (Example 1-5 (A)) obtained in (Example 1)<Step 5>.

<Step 6> Synthesis of 5-[4-[[3-[2,6-dimethyl 4-(3-methylsulfonylpropoxy)phenyl]phenyl]methoxy]phenyl]-1-oxo-1,2-thiazolidin-3-one (A)-a and (A)-b In accordance with the method in (Example 7)<Step 2>, each diastereomer of the title compound was obtained from the compound (100 mg) obtained in (Example 13)<Step 5>. The separation condition was as follows. Preparative chromatography (column: CHIRALPAK IB (2 cm×25 cm) manufactured by Daicel Chemical Industries, Ltd., eluent; hexane:ethanol:trifluoroacetic acid=50:50:0.1 (V/V), flow rate: 17 mL/min). The retention times were determined by LC/MS.

Primary fraction (7.8 mg, colorless amorphous solid, retention time 5.62 minutes, diastereomer a: Example 13 (A)-a)

Secondary fraction (6.0 mg, colorless amorphous solid, retention time 5.53 minutes, diastereomer b: Example 13 (A)-b)

Example 14

Synthesis of 5-[4-[[3-(2,6-dimethylphenyl)phenyl]methoxy]phenyl]-1,1-dioxo-1,2,5-thiadiazolidin-3-one <Step 1> Synthesis of (4-((2',6'-dimethyl-[1,1'-biphenyl]-3-yl)methoxy)phenyl)carbamic acid tert-butyl ester To a solution of (2',6'-dimethyl-[1,1'-biphenyl]-3-yl)methanol (4.0 g), 4-hydroxycarbamic acid tert-butyl ester (5.91 g), and tri-n-butylphosphine (6.97 mL) in tetrahydrofuran (80 mL), 1,1'-azobis(N,N-dimethylformamide) (4.87 g) was added under ice-cooling and the resultant reaction mixture was stirred at room temperature for 62 hours. The precipitated solid was filtered off and the solvent in the filtrate was removed by evaporation under reduced pressure. To the resultant residue, water was added and the mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate=95:5) twice to give the title compound (6.17 g) as a colorless amorphous solid.

<Step 2> Synthesis of 4-((2',6'-dimethyl-[1,1'-biphenyl]-3-yl)methoxy)aniline

The compound (6.15 g) obtained in (Example 14)<Step 1> was dissolved in ethyl acetate (27 mL). To the solution, a solution of 4M hydrogen chloride in ethyl acetate (19 mL) was added and the resultant reaction mixture was stirred at room temperature over night. The reaction mixture was diluted with ethyl acetate. To the mixture, a saturated aqueous sodium hydrogen carbonate solution was added to make the mixture basic and the mixture was extracted with ethyl acetate. The obtained organic phase was washed with brine and then dried over anhydrous sodium sulfate. The organic phase was concentrated under reduced pressure to give the title compound (4.58 g) as a pale brown oil.

<Step 3> Synthesis of tert-butyl 2-((4-((2',6'-dimethyl-[1,1'-biphenyl]-3-yl)methoxy)phenyl)amino) acetate To a solution of the compound (0.50 g) obtained in (Example 14)<Step 2> in N,N'-dimethylformamide (3.3 mL), diisopropylethylamine (0.57 mL) and tert-butyl 2-bromoacetate (0.23 mL) were sequentially added and the resultant reaction mixture was stirred at 60° C. for 4 hours. The reaction mixture was allowed to reach room temperature, then diluted with water, and extracted with ethyl acetate. The obtained organic phase was washed with brine and then dried over anhydrous sodium sulfate. From the organic phase, the solvent was removed by evaporation under reduced pressure. The resultant residue was purified by silica gel column chromatography (eluent; n-hexane:ethyl acetate=90:10) to give the title compound (0.60 g) as a pale yellow oil.

<Step 4> Synthesis of tert-butyl 2((N-(tert-butoxycarbonypsulfamoyl)(4-((2',6'-dimethyl-[1,1'-biphenyl]-3-yl)methoxy)phenyl)amino)acetate To a solution of tert-butanol (0.14 mL) in methylene chloride (0.70 mL), chlorosulfonyl isocyanate (0.13 mL) was added under ice-cooling. The resultant reaction mixture was stirred at room temperature for 30 minutes to prepare a solution of chlorosulfonyl carbamic acid tert-butyl ester in methylene chloride. The mixed solution was added to a solution of the compound (0.30 g) obtained in (Example 14)<Step 3> and diisopropylethylamine (0.38 mL) in methylene chloride (0.70 mL) under ice-cooling and the resultant reaction mixture was stirred at room temperature for 4 hours. The reaction solution was diluted with water and extracted with methylene chloride. The obtained organic phase was washed with brine and then dried over anhydrous sodium sulfate. From the organic phase, the solvent was removed by evaporation under reduced pressure to give a mixture (0.48 g) containing the title compound as a colorless amorphous solid.

<Step 5> Synthesis of 2-((4-((2',6'-dimethyl-[1,1'-biphenyl]-3-yl)methoxy)phenyl)(sulfamoyl)amino) acetic acid To a solution of the compound (0.30 g) obtained in (Example 14)<Step 4> in methylene chloride (3.0 mL), trifluoroacetic acid (0.8 mL) was added under ice-cooling and the resultant reaction mixture was stirred at room temperature for 21 hours. To the reaction solution, water was added and the mixture was extracted with methylene chloride. The obtained organic phase was washed with brine and then dried over anhydrous sodium sulfate. From the organic phase, the solvent was removed by evaporation under reduced pressure to give the title compound (0.20 g) as a brown amorphous solid.

<Step 6> Synthesis of 5-[4-[[3-(2,6-dimethylphenyl) phenyl]methoxy]phenyl]-1,1-dioxo-1,2,5-thiadiazolidin-3-one To a solution of the compound (80.0 mg) obtained in (Example 14)<Step 5> in tetrahydrofuran (1.2 mL), 1-hydroxybenzotriazole monohydrate (27.8 mg) and 1-ethyl-3-(3'-dimethylaminopropyl)carbodiimide hydrochloride (WSC—HCl: 34.8 mg) were sequentially added and the resultant reaction mixture was stirred at room temperature for 10 minutes. Subsequently, triethylamine (27.84 µl) was added and the resultant reaction mixture was stirred at room temperature for 15 hours. From the reaction mixture, the solvent was removed by evaporation under reduced pressure. To the residue, ethyl acetate was added. The mixture was sequentially washed with 1M hydrochloric acid and brine and then dried over anhydrous sodium sulfate. From the organic phase, the solvent was removed by evaporation under reduced pressure. The resultant residue was purified by preparative TLC (eluent; methylene chloride:methanol=20:1, 1% acetic acid). The obtained compound was triturated with ether to give the title compound (10.2 mg) as a brown solid.

Example 15

Synthesis of 5-[4-[[3-[2,6-dimethyl-4-(3-methylsulfonylpropoxy)phenyl]phenyl]methoxy]phenyl]-1,1-dioxo-1,2,5-thiadiazolidin-3-one <Step 1> Synthesis of (4-((2',6'-dimethyl-4'-(3-methylsulfonyl)propoxy-[1,1'-biphenyl]-3-yl)methoxy) phenyl)carbamic acid tert-butyl ester In accordance with the method in (Example 14)<Step 1>, the title compound (1.54 g) was obtained as a white amorphous solid from {2',6'-dimethyl-4'-[3-(methylsulfonyl)propoxy]-[1,1'-biphenyl]-3-yl}methanol (1.0 g) that was synthesized in accordance with the method described in [WO 2008/001931 pamphlet].

<Step 2> Synthesis of 4((2',6'-dimethyl-4'-(3-methylsulfonyl)propoxy-[1,1'-biphenyl]-3-yl)methoxy) aniline In accordance with the method in (Example 14)<Step 2>, the title compound (1.18 g) was obtained as a pale yellow oil from the compound (1.53 g) synthesized in (Example 15)<Step 1>.

<Step 3> Synthesis of ethyl 2-((4((2',6'-dimethyl-4'-[3-(methylsulfonyl)propoxy]-[1,1'-biphenyl]-3-yl)methoxy)phenyl)amino)acetate In accordance with the method in (Example 14)<Step 3>, the title compound (0.40 g) was obtained as a pale yellow oil from the compound (0.40 g) obtained in (Example 15)<Step 2> and ethyl 2-bromoacetate (95.6 µl).

<Step 4> Synthesis of ethyl 2((N-(tert-butoxycarbonyl)sulfamoyl)(4-((2',6'-dimethyl-4'-(3-(methylsulfonyl)propoxy)-[1,1'-biphenyl]-3-yl)methoxy)phenyl)amino)acetate In accordance with the method in (Example 14)<Step 4>, the title compound (0.55 g) was obtained as a brown amorphous solid from the compound (0.38 g) obtained in (Example 15)<Step 3>.

<Step 5> Synthesis of ethyl 2-((4-((2',6'-dimethyl-4'-[3-(methylsulfonyl)propoxy]-[1,1'-biphenyl]-3-yl)methoxy)phenyl)(sulfamoyl)amino)acetate In accordance with the method in (Example 14)<Step 5>, the title compound (0.47 g) was obtained as a brown amorphous solid from the compound (0.53 g) obtained in (Example 15)<Step 4>.

<Step 6> Synthesis of 5-[4-[[3-[2,6-dimethyl-4-(3-methylsulfonylpropoxy)phenyl]phenyl]methoxy]phenyl]-1,1-dioxo-1,2,5-thiadiazolidin-3-one To a solution of the compound (0.20 g) obtained in (Example 15)<Step 5> in ethanol (0.80 mL), a 2M sodium hydroxide aqueous solution (0.33 mL) was added under ice-cooling and the resultant reaction mixture was stirred for 30 minutes. To the reaction solution, ethyl acetate and 1M hydrochloric acid were added and the mixture was extracted with ethyl acetate. The organic phase was dried over anhydrous sodium sulfate. From the organic phase, the solvent was removed by evaporation under reduced pressure and the resultant residue was purified by LC/MS to give the title compound (17 mg) as a pale beige solid.

Example 16

Synthesis of 5-[2-chloro-4-[[3-(2,6-dimethylphenyl)phenyl]methoxy]phenyl]-1,1-dioxo-1,2,5-thiadiazolidin-3-one <Step 1> Synthesis of (2-chloro-4-hydroxyphenyl)carbamic acid tert-butyl ester To a solution of 4-amino-3-chlorophenol hydrochloride (1.0 g) and triethylamine (0.77 mL) in tetrahydrofuran (4.6 mL), di-tert-butyl carbonate (1.39 mL) was slowly added dropwise and the resultant reaction mixture was heated and refluxed for 8 hours. The reaction mixture was allowed to reach room temperature and added to a saturated aqueous ammonium chloride. The mixture was extracted with ethyl acetate and the organic phase was dried over anhydrous sodium sulfate. From the organic phase, the solvent was removed by evaporation under reduced pressure to give a mixture (1.42 g) containing the title compound as a pale brown solid.

<Step 2> Synthesis of (2-chloro-4-((2',6'-dimethyl-[1,1'-biphenyl]-3-yl)methoxy)phenyl)carbamic acid tert-butyl ester In accordance with the method in (Example 14)<Step 1>, a mixture (0.83 g) containing the title compound was obtained as a colorless oil using the compound (0.69 g) obtained in (Example 16)<Step 1>.

<Step 3> Synthesis of 2-chloro-4-((2',6'-dimethyl-[1,1'-biphenyl]-3-yl)methoxy)aniline hydrochloride To a solution of the compound (0.78 g) obtained in (Example 16)<Step 2> in ethyl acetate (3.0 mL), a solution of 4M hydrogen chloride in ethyl acetate (2.23 mL) was added and the resultant reaction mixture was stirred at room temperature for 3 hours. The precipitate was collected by filtration and dried under reduced pressure to give the title compound (0.47 g) as a white solid.

<Step 4> Synthesis of ethyl 2-((2-chloro-4-((2',6'-dimethyl-[1,1'-biphenyl]-3-yl)methoxy)phenyl)amino)acetate In accordance with the method in (Example 14)<Step 3>, the title compound (357 mg) was obtained as a pale yellow oil using the compound (0.40 g) obtained in (Example 16)<Step 3> and ethyl 2-bromoacetate (0.24 mL)<

Step 5> Synthesis of ethyl 2-((2-chloro-4-((2',6'-dimethyl-[1,1'-biphenyl]-3-yl)methoxy)phenyl)(sulfamoyl)amino)acetate In accordance with the methods in (Example 14)<Step 4> and (Example 14)<Step 5>, a mixture (839 mg) containing the title compound was obtained as a brown oil using the compound (0.34 g) obtained in (Example 16)<Step 4>.

<Step 6> Synthesis of 5-[2-chloro-4-[[3-(2,6-dimethylphenyl)phenyl]methoxy]phenyl]-1,1-dioxo-1,2,5-thiadiazolidin-3-one In accordance with the method in (Example 15)<Step 6>, the title compound (46 mg) was obtained as a pale brown amorphous solid using the compound (0.80 g) obtained in (Example 16)<Step 5>.

Example 17

Synthesis of 5-[4-[[3-(2,6-dimethylphenyl)phenyl]methoxy]-2-methylphenyl]-1,1-dioxo-1,2,5-thiadiazolidin-3-one <Step 1> Synthesis of (4-hydroxy-2-methylphenyl)carbamic acid tert-butyl ester In accordance with the method in (Example 16)<Step 1>, the title compound (1.71 g) was obtained as a pale brown amorphous solid using 4-amino-3-methylphenol (1.0 g).

<Step 2> Synthesis of (4-((2',6'-dimethyl-[1,1'-biphenyl]-3-yl)methoxy)-2-methylphenyl)carbamic acid tert-butyl ester In accordance with the method in (Example 16)<Step 2>, the title compound (0.70 g) was obtained as a colorless amorphous solid using the compound (0.40 g) obtained in (Example 17)<Step 1>.

<Step 3> Synthesis of 4-((2',6'-dimethyl-[1,1'-biphenyl]-3-yl)methoxy)-2-methylaniline hydrochloride In accordance with the method in (Example 16)<Step 3>, the title compound (0.47 g) was obtained as a white solid using the compound (0.65 g) obtained in (Example 17) <Step 2>.

<Step 4> Synthesis of ethyl 2-((4-((2',6'-dimethyl-[1',1'-biphenyl]-3-yl)methoxy)-2-methylphenyl)amino)acetate In accordance with the method in (Example 16)<Step 4>, the title compound (0.31 g) was obtained as a brown oil using the compound (0.40 g) obtained in (Example 17) <Step 3>.

<Step 5> Synthesis of ethyl 2-((4-((2',6'-dimethyl-[1,1'-biphenyl]-3-yl)methoxy)-2-methylphenyl)(sulfamoyl)amino)acetate In accordance with the method in (Example 16)<Step 5>, a mixture (895 mg) containing the title compound was obtained as a brown oil using the compound (0.30 g) obtained in (Example 17)<Step 4>.

<Step 6> Synthesis of 5-[4-[[3-(2,6-dimethylphenyl)phenyl]methoxy]-2-methylphenyl]-1,1-dioxo-1,2,5-thiadiazolidin-3-one In accordance with the method in (Example 15)<Step 6>, the title compound (27 mg) was obtained as a brown amorphous solid using the compound (0.85 g) obtained in (Example 17)<Step 5>.

Example 18

Synthesis of 5-[4-[[3-(2,6-dimethylphenyl)phenyl]methoxy]phenyl]-4-methyl-1,1-dioxo-1,2,5-thiadiazolidin-3-one <Step 1> Synthesis of ethyl 2-((4-((2',6'-dimethyl-[1,1'-biphenyl]-3-yl)methoxy)phenyl)amino)propionate In accordance with the method in (Example 14)<Step 3>, the title compound (0.56 g) was obtained as an orange oil from a hydrochloride (0.50 g) of the compound obtained in (Example 14)<Step 2> and ethyl 2-bromopropionate (0.39 mL).

<Step 2> Synthesis of ethyl 2-(((N-(tert-butoxycarbonyl)sulfamoyl) (4-((2',6'-dimethyl-[1,1'-biphenyl]-3-yl)methoxy)phenyl)amino)propionate In accordance with the method in (Example 14)<Step 4>, a mixture (753 mg) containing the title compound was obtained as a brown amorphous solid using the compound (0.55 g) obtained in (Example 18)<Step 1>.

<Step 3> Synthesis of ethyl 2-((4-((2',6'-dimethyl-[1,1'-biphenyl]-3-yl)methoxy)phenyl)(sulfamoyl)amino)propionate In accordance with the method in (Example 14)<Step 5>, a mixture (0.70 g) containing the title compound was obtained as a brown amorphous solid using the compound (0.74 g) obtained in (Example 18)<Step 2>.

<Step 4> Synthesis of 5-[4-[[3-(2,6-dimethylphenyl)phenyl]methoxy]phenyl]-4-methyl-1,1-dioxo-1,2,5-thiadiazolidin-3-one In accordance with the method in (Example 15)<Step 6>, the title compound (5 mg) was obtained as a pale yellow solid using the compound (0.30 g) obtained in (Example 18)<Step 3>.

Example 19

Synthesis of 5-[4-[[3-[2,6-dimethyl 4-(3-methylsulfonylpropoxy)phenyl]phenyl]methoxy]phenyl]-1,1-dioxo-1,2-thiazolidin-3-one <Step 1> Synthesis of 5-(4-((2',6'-dimethyl-4'-(3-(methylsulfonyl)propoxy)-[1,1'-biphenyl]-3-yl)methoxy)phenyl)isothiazol-3(2H)-one 1,1-dioxide To a solution of the compound (50 mg) obtained in (Example 13)<Step 5> in methanol (5.0 mL), water (0.5 mL) and OXONE (registered trademark) (117 mg) were added and the resultant reaction mixture was stirred at 40° C. for 18 hours. Subsequently, the mixture was stirred at 100° C. for 23 hours. The reaction mixture was allowed to reach room temperature and water was added. The mixture was extracted with ethyl acetate. The organic phase was washed with brine and dried over anhydrous sodium sulfate. From the organic phase, the solvent was removed by evaporation under reduced pressure to give a mixture (50.0 mg) containing the title compound as a colorless solid.

<Step 2> Synthesis of 5-[4-[[3-[2,6-dimethyl-4-(3-methylsulfonylpropoxy)phenyl]phenyl]methoxy]phenyl]-1,1-dioxo-1,2-thiazolidin-3-one In accordance with the method in (Example 1)<Step 7>, the title compound (6.0 mg) was obtained as a colorless solid using the compound (50 mg) obtained in (Example 19)<Step 1>. The obtained compound is a racemic mixture.

Example 20

Synthesis of 5-[4-[[3-[6-(3-hydroxy-3-methylbutoxy)-2,4-dimethylpyridin-3-yl]phenyl]methoxy]phenyl]-1,1-dioxo-1,2-thiazolidin-3-one To a solution of the compound (50 mg) obtained in (Example 6) in acetone (5 mL), water (0.5 mL) and OXONE (registered trademark) (363 mg) were added and the resultant reaction mixture was stirred at 90° C. for 16 hours. The reaction mixture was allowed to reach room temperature and water was added. The mixture was extracted with ethyl acetate. The organic phase was washed with brine and dried over anhydrous sodium sulfate. From the organic phase, the solvent was removed by evaporation under reduced pressure and the resultant residue was purified by silica gel column chromatography (eluent; methylene chloride:methanol=20:1) to give the title compound (11 mg) as a colorless amorphous solid. The obtained compound is a racemic mixture.

Example 21

Synthesis of 5-[4-[[3-(2,6-dimethylphenyl)phenyl]methoxy]phenyl]-1,1-dioxo-1,2,6-thiadiazinan-3-one <Step 1> Synthesis of 4((2',6'-dimethyl-[1,1'-biphenyl]-3-yl)methoxy)benzaldehyde To a solution of (2',6'-dimethyl-[1,1'-biphenyl]-3-yl)methanol (1.0 g), 4-hydroxybenzaldehyde (0.58 g), and triphenylphosphine (1.48 g) in tetrahydrofuran (10 mL), a solution of 40% diisopropylazodicarboxylic acid diisopropyl in toluene (1.09 mL) was added under ice-cooling and the resultant reaction mixture was stirred under ice-cooling for 3 hours. A solution of diisopropyl azodicarboxylate in toluene (0.6 mL) was further added and the resultant reaction mixture was stirred at room temperature for 12 hours. From the reaction mixture, the solvent was removed by evaporation under reduced pressure to give a residue and water was added to the resultant residue. The mixture was extracted with an organic solvent and the resultant organic phase was dried over anhydrous sodium sulfate. From the organic phase, the solvent was removed by evaporation under reduced pressure and the resultant residue was purified by silica gel column chromatography (eluent; n-heptane:ethyl acetate=100:0 to 100:20) to give the title compound (1.2 g) as a colorless oil.

<Step 2> Synthesis of ethyl 3-amino-3-(4-((2',6'-dimethyl-[1,1'-biphenyl]-3-yl)methoxy)phenyl)propionate A mixed solution of the compound (1 g) obtained in (Example 21)<Step 1>, ammonium acetate (0.73 g), and monoethyl malonate (0.44 g) in ethanol (15 mL) was heated and refluxed for 20 hours. The reaction mixture was allowed to reach room temperature and a 2M sodium hydroxide aqueous solution was added. The mixture was extracted with ethyl acetate. The obtained organic phase was dried over anhydrous sodium sulfate. From the organic phase, the solvent was removed by evaporation under reduced pressure and the resultant residue was purified by silica gel column chromatography (eluent; n-heptane:ethyl acetate=100:0 to 100:20) to give the title compound (0.28 g) as a yellow oil.

<Step 3> Synthesis of ethyl 3-(4-((2',6'-dimethyl-[1,1'-biphenyl]-3-yl)methoxy)phenyl)-3-(sulfamoyl)propionate In accordance with the method in (Example 14)<Step 4>, a mixture (8 mg) containing the title compound was obtained as a pale yellow amorphous solid using the compound (200 mg) obtained in (Example 21)<Step 2>.

<Step 4> Synthesis of 5-[4-[[3-(2,6-dimethylphenyl)phenyl]methoxy]phenyl]-1,1-dioxo-1,2,6-thiadiazinan-3-one In accordance with the method in (Example 15)<Step 6>, the title compound (3.2 mg) was obtained as a pale yellow solid using the compound (7.0 mg) obtained in (Example 21)<Step 3>. The title compound is a racemic mixture.

Example 22

Synthesis of 5-[4-[[3-(2,6-dimethylphenyl)phenyl]methoxy]phenyl]-1,1-dioxo-1,2-thiazinan-3-one <Step 1> Synthesis of N,N-bis(4-methoxybenzyl)methanesulfonamide To a solution of methanesulfonamide (5 g) in N,N-dimethylformamide (75 mL), potassium carbonate (29.1 g) was added and the resultant reaction mixture was stirred at room temperature for 5 hours. To the solution, p-methoxybenzyl chloride (18.1 g) was added and the resultant reaction mixture was stirred at room temperature for 19 hours. To the reaction solution, water was added and the mixture was extracted with ethyl acetate. The obtained organic phase was dried over anhydrous sodium sulfate. From the organic phase, the solvent was removed by evaporation under reduced pressure to give the title compound (17.1 g) as a white solid.

<Step 2> Synthesis of 2-(4-((2',6'-dimethyl-[1,1'-biphenyl]-3-yl)methoxy)phenyl)-N,N-bis(4-methoxybenzyl)ethenesulfonamide To a solution of the compound (1.19 g) obtained in (Example 22)<Step 1> in tetrahydrofuran (5.5 mL), a solution of 1M lithium hexamethyldisilazide in tetrahydrofuran (8.29 mL) was added dropwise at −20° C. After stirring the mixture at −20° C. for 1 hour, a solution of diethyl chlorophosphate (0.51 mL) in tetrahydrofuran (3 mL) was added dropwise. After stirring the mixture at −20° C. for 1 hour, a solution of the compound (0.75 g) obtained in (Example 21)<Step 1> in tetrahydrofuran (3 mL) was added dropwise. After stirring the mixture at room temperature for 19 hours, 1M hydrochloric acid and water were sequentially added to the reaction solution and the mixture was extracted with ethyl acetate. The obtained organic phase was washed with brine and dried over anhydrous sodium sulfate. From the organic phase, the solvent was removed by evaporation under reduced pressure and the resultant residue was purified by silica gel column chromatography (eluent; n-hexane:ethyl acetate=90:10 to 80:20) to give the title compound (890 mg) as a colorless oil.

<Step 3> Synthesis of dimethyl 2-(2-(N,N-bis(4-methoxybenzyl)sulfamoyl)-1-(4-((2',6'-dimethyl-[1,1'-biphenyl]-3-yl)methoxy)phenyl)ethyl)malonate To a solution of dimethyl malonate (0.54 g) in tetrahydrofuran (6 mL), a solution of 28% sodium methoxide in methanol (0.81 g) was added and the resultant reaction mixture was stirred for 1 hour. Subsequently, a solution of the compound (0.87 g) obtained in (Example 22)<Step 2> in tetrahydrofuran (4 mL) was added and the resultant reaction mixture was heated and refluxed for 17 hours. The reaction mixture was allowed to reach room temperature and a 10% citric acid aqueous solution was added. The mixture was extracted with ethyl acetate. The organic phase was washed with brine and the resultant organic phase was dried over anhydrous sodium sulfate. From the organic phase, the solvent was removed by evaporation under reduced pressure and the resultant residue was purified by silica gel column chromatography (eluent; n-hexane:ethyl acetate=85:15 to 70:30) to give the title compound (730 mg) as a white amorphous solid.

<Step 4> Synthesis of methyl 4-(N,N-bis(4-methoxybenzyl)sulfamoyl)-3-(4-((2',6'-dimethyl-[1,1'-biphenyl]-3-yl)methoxy)phenyl)butanoate To a solution of the compound (0.72 g) obtained in (Example 22)<Step 3> in N,N-dimethylformamide (6.0 mL), water (33.8 mg) and sodium chloride (54.92 mg) were added and the resultant reaction mixture was heated and refluxed for 2.5 hours. The reaction mixture was allowed to reach room temperature and water was added. The mixture was extracted with ethyl acetate. The organic phase was washed with brine and the resultant organic phase was dried over anhydrous sodium sulfate. From the organic phase, the solvent was removed by evaporation under reduced pressure and the resultant residue was purified by silica gel column chromatography (eluent; n-hexane:ethyl acetate=85:15 to 70:30) to give the title compound (358 mg) as a colorless oil.

<Step 5> Synthesis of methyl 3-(4((2',6'-dimethyl-[1,1'-biphenyl]-3-yl)methoxy)phenyl)-4-sulfamoylbutanoate To a solution of the compound (0.32 g) obtained in (Example 22)<Step 4> in methylene chloride (3.0 mL), trifluoroacetic acid (0.60 mL) was added and the resultant reaction mixture was stirred at room temperature for 15 hours. The reaction solution was poured into a mixed solution of a 10% potassium carbonate aqueous solution and ethyl acetate and the mixture was extracted with ethyl acetate. The obtained organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate=75:25 to 65:35) to give the title compound (150 mg) as a colorless oil.

<Step 6> Synthesis of 5-[4-[[3-(2,6-dimethylphenyl)phenyl]methoxy]phenyl]-1,1-dioxo-1,2-thiazinan-3-one To a mixed solution of the compound (140 mg) obtained in (Example 22)<Step 5> in methanol (2 0 mL) and tetrahydrofuran (1.0 mL), a solution of 28% sodium methoxide in methanol (57.7 mg) was added and the resultant reaction mixture was stirred for 1 hour. To the reaction solution, 1M hydrochloric acid was added and the mixture was extracted with ethyl acetate. The obtained organic phase was washed with brine and dried over anhydrous sodium sulfate. From the organic phase, the solvent was removed by evaporation under reduced pressure and the resultant residue was triturated with a mixed solution of n-hexane:ethyl acetate=2:1 to give the title compound (93 mg) as a white solid. The title compound is a racemic mixture.

Example 23

Synthesis of 5-(4-(((R)-4-(6-(3-hydroxy-3-methylbutoxy)-2-methylpyridin-3-yl)-2,3-dihydro-1H-inden-1-yl)oxy)phenyl)-1-oxo-1,2-thiazolidin-3-one (A)

<Step 1> Synthesis of 4-(5-bromo-6-methylpyridin-2-yloxy)-2-methylbutan-2-ol To a suspension of sodium hydride (containing about 40% of a mineral oil, 0.38 g) in N,N-dimethylformamide (10 mL), 5-bromo-2-hydroxy-6-methylpyridine (1.00 g) and 3-hydroxy-3-methylbutyl 4-methylbenzenesulfonate (1.51 g) were added under ice-cooling and the resultant reaction mixture was stirred at 60° C. for 2.5 hours. To the mixture, 3-hydroxy-3-methylbutyl 4-methylbenzenesulfonate (0.50 g) was further added and the resultant reaction mixture was stirred at 60° C. for 1.5 hours. Sodium hydride (containing about 40% of a mineral oil, 40 mg) was further added. To the reaction mixture, a saturated aqueous ammonium chloride solution was added and the mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate=50:50 to 33:67) to give the title compound (1.3 g) as a pale yellow oil.

<Step 2> Synthesis of 4-[5-(5,5-dimethyl-1,3,2-dioxaborinan-2-yl)-6-methylpyridin-2-yl]oxy-2-methylbutan-2-ol To a solution of the compound (2.85 g) obtained in (Example 23)<Step 1> and bis(neopentyl glycolate)diboron (2.82 g) in 1,4-dioxane (45 mL), potassium acetate (3.06 g) and a [1,1'-bis(diphenylphosphino)ferrocene]dichloropalladium (II) — dichloromethane adduct (0.42 g) were added. The mixture was degassed and then heated and refluxed for 16 hours. To the reaction mixture, water (200 mL) was added and the mixture was extracted with ethyl acetate (200 mL). The organic phase was washed with brine (80 mL) and then dried over anhydrous sodium sulfate. From the organic phase, the solvent was removed by evaporation under reduced pressure and the resultant residue was purified by silica gel column chromatography (eluent; n-hexane:ethyl acetate=95:5 to 80:20) to give the title compound (2.2 g).

<Step 3> Synthesis of 4-(((1R)-4-bromo-2,3-dihydro-1H-inden-1-yloxy)phenylboronic acid N-methyliminodiacetic acid ester To a mixed solution of the compound (0.20 g) obtained in (Reference Example 1), (1S)-4-bromo-2,3-dihydro-1H-inden-1-ol (153 mg) that was commercially available or could be obtained by a known method, and tri-n-butylphosphine (0.50 mL) in tetrahydrofuran (3 mL), 1,1'-azobis(N,N-dimethylformamide) (0.35 g) was added under ice-cooling. The resultant reaction mixture was stirred at room temperature for 1.5 hours. From the reaction mixture, the solvent was removed by evaporation under reduced pressure and the resultant residue was purified by silica gel column chromatography (eluent; n-hexane:ethyl acetate=50:50 to 0:100). From the eluted solution, the solvent was removed by evaporation under reduced pressure to give a crude product containing the title compound.

<Step 4> Synthesis of 5-(4-((1R)-4-bromo-2,3-dihydro-1H-inden-1-yloxy)phenyisothiazol-3-ol 1-oxide (A)

In accordance with the method in (Example 1)<Step 6>, the title compound (24.6 mg) was obtained from the crude product (178 mg) obtained in (Example 23)<Step 3>.

<Step 5> Synthesis of 3-hydroxy-5-(4-(((R)-4-(6-(3-hydroxy-3-methylbutoxy)-2-methylpyridin-3-yl)-2,3-dihydro-1H-inden-1-yl)oxy)phenyl)isothiazole 1-oxide (A)

A mixed solvent of the compound (50 mg) obtained in (Example 23)<Step 4>, the compound (49.4 mg) obtained in (Example 23)<Step 2>, bis(dibenzylideneacetone)palladium (7.1 mg), 2-dicyclohexylphosphino-2',4',6'=triisopropylbiphenyl (XPhos: 11.8 mg), potassium carbonate (34.2 mg), 1,4-dioxane (1.0 mL), and water (0.5 mL) was heated and refluxed for 4 hours. The reaction solution was extracted with ethyl acetate and the organic phase was dried over anhydrous sodium sulfate. From the organic phase, the solvent was removed by evaporation under reduced pressure and the resultant residue was purified by silica gel column chromatography (eluent; ethyl acetate:methanol=100:0 to 80:20). From the eluted solution, the solvent was removed by evaporation under reduced pressure to give the title compound (12 mg) as a colorless amorphous solid.

<Step 6> Synthesis of 5-(4-(((R)-4-(6-(3-hydroxy-3-methylbutoxy)-2-methylpyridin-3-yl)-2,3-dihydro-1H-inden-1-yl)oxy)phenyl)-1-oxo-1,2-thiazolidin-3-one (A)

In accordance with the method in (Example 7)<Step 2>, each diastereomer of the title compound was obtained from the compound (0.13 g) obtained in (Example 23)<Step 5>.

Primary fraction (10.3 mg, white amorphous solid, retention time 5.85 minutes (LC/MS), diastereomer a: Example 23 (A)-a)

Secondary fraction (3.3 mg, white amorphous solid, retention time 5.77 minutes (LC/MS), diastereomer b: Example 23 (A)-b)

Example 24

Synthesis of 5-[4-[[(1R)-4-[6-(3-hydroxy-3-methylbutoxy)-2,6-dimethylphenyl]-2,3-dihydro-1H-inden-1-yl]oxy]phenyl]-1-oxo-1,2-thiazolidin-3-one (A)

<Step 1> Synthesis of 4-(4-bromo-3,5-dimethylphenoxy)-2-methylbutan-2-ol

A mixed solution of 3-hydroxy-3-methylbutyl 4-methylbenzenesulfonate (4.24 g) synthesized in accordance with the method described in [WO 2009/067613 pamphlet, Example 308], 4-bromo-3,5-dimethylphenol (3.0 g), and potassium carbonate (3.09 g) in N,N-dimethylformamide (15 mL) was stirred at 80° C. for 3 hours. To the reaction mixture, ethyl acetate (200 mL) and water (100 mL) were added and the mixture was extracted with ethyl acetate. The organic phase was successively washed with water (50 mL) and brine (50 mL) and then dried over anhydrous sodium sulfate. From the organic phase, the solvent was removed by evaporation under reduced pressure and the resultant residue was purified by silica gel column chromatography (eluent; n-hexane:ethyl acetate=80:20 to 70:30). From the eluted solution, the solvent was removed by evaporation under reduced pressure to give the title compound (3.9 g).

<Step 2> Synthesis of 4-(4-(5,5-dimethyl-1,3,2-dioxaborinan-2-yl)-3,5-dimethylphenoxy)-2-methylbutan-2-ol In accordance with the method in (Example 23)<Step 2>, the title compound (2.65 g) was obtained using the compound (3.90 g) obtained in (Example 24)<Step 1>.

<Step 3> Synthesis of 5-[4-[[(1R)-4-[6-(3-hydroxy-3-methylbutoxy)-2,6-dimethylphenyl]-2,3-dihydro-1H-inden-1-yl]oxy]phenyl]isothiazol-3-ol 1-oxide (A)

In accordance with the method in (Example 23)<Step 5>, the title compound (8 mg) was obtained as a pale yellow solid using the compound (50 mg) obtained in (Example 23)<Step 4> and the compound (0.12 g) obtained in (Example 24)<Step 2>.

<Step 4> Synthesis of 5-[4-[[(1R)-4-[6-(3-hydroxy-3-methylbutoxy)-2,6-dimethylphenyl]-2,3-dihydro-1H-inden-1-yl]oxy]phenyl]-1-oxo-1,2-thiazolidin-3-one (A)

In accordance with the method in (Example 7)<Step 2>, each diastereomer of the title compound was obtained from the compound (0.17 g) obtained in (Example 24)<Step 3>.

Primary fraction (34.3 mg, white amorphous solid, retention time 6.17 minutes (LC/MS), diastereomer a: Example 24 (A)-a)

Secondary fraction (40.5 mg, white amorphous solid, retention time 6.08 minutes (LC/MS), diastereomer b: Example 24 (A)-b)

Example 25

Synthesis of 4-(((1R)-1-(4-(1-oxo-1,2-thiazolidin-3-on-5-yl)phenoxy)-2,3-dihydro-1H-inden-4-yl)oxy)benzonitrile (A)

<Step 1> Synthesis of 2-(((S)-4-bromo-2,3-dihydro-1H-inden-1-yl)oxy)tetrahydro-2H-pyran In methylene chloride (16.2 mL), 3,4-dihydro-2H-pyran (10.6 mL) was dissolved. To the solution, a solution of 4M hydrogen chloride in 1,4-dioxane (31.1 μL) was added and (1S)-4-bromo-2,3-dihydro-1H-inden-1-ol (10.0 g) that was commercially available or could be obtained by a known method was added. The resultant reaction mixture was stirred at room temperature for 3 hours. To the reaction mixture, a saturated aqueous sodium hydrogen carbonate solution (60 mL) was added and extracted with methylene chloride (60 mL). The organic phase was washed with brine (60 mL) and dried over anhydrous sodium sulfate. From the organic phase, the solvent was removed by evaporation under reduced pressure and the resultant residue was purified by silica gel column chromatography (eluent; n-hexane:ethyl acetate=95:5). From the eluted solution, the solvent was removed by evaporation under reduced pressure to give the title compound (15 g).

<Step 2> Synthesis of 5,5-dimethyl-2((1S)-1-((tetrahydro-2H-pyran-2-yl)oxy-2,3-dihydro-1H-inden-4-yl)-1,3,2-dioxaborinane To a solution of the compound (14.0 g) obtained in (Example 25)<Step 1> in 1,4-dioxane (213 mL), 5,5,5',5'-tetramethyl-2,2'-di(1,3,2-dioxaborinane) (17.3 g), potassium acetate (18.8 g), and a 1,1'-bis(diphenylphosphino)ferrocene-palladium(II) dichloride—dichloromethane complex (2.61 g) were sequentially added and the resultant reaction mixture was heated and refluxed for 3 hours. To the reaction mixture, water (300 mL) was added and the mixture was filtered with Celite while washing the mixture with ethyl acetate (250 mL). To the filtrate, brine (200 mL) was added and the mixture was extracted with ethyl acetate (200 mL). The organic phase was dried over anhydrous sodium sulfate. From the organic phase, the solvent was removed by evaporation under reduced pressure and the resultant residue was purified by silica gel column chromatography (eluent; n-hexane:ethyl acetate=70:30). From the eluted solution, the solvent was removed by evaporation under reduced pressure to give the title compound (15.3 g) as an orange oil.

<Step 3> Synthesis of ((1S)-1-((tetrahydro-2H-pyran-2-yl)oxy-2,3-dihydro-1H-inden-4-yl)boronic acid To a solution of the compound (8.20 g) obtained in (Example 25)<Step 2> in ethyl acetate (370 mL), water (1.10 L) was added and the resultant reaction mixture was stirred at room temperature for 16 hours. Liquid separation of the reaction mixture was conducted and the organic phase was washed with brine (200 mL) and dried over anhydrous sodium sulfate. From the organic phase, the solvent was removed by evaporation under reduced pressure and the resultant residue was purified by silica gel column chromatography (eluent; n-hexane:ethyl acetate=90:10 to 50:50). From the eluted solution, the solvent was removed by evaporation under reduced pressure to give the title compound (3.00 g) as a yellowish white solid.

<Step 4> Synthesis of 4-(((1S)-1-((tetrahydro-2H-pyran-2-yl)oxy)-2,3-dihydro-1H-inden-4-yl)oxy)benzonitrile To a solution of the compound (0.50 g) obtained in (Example 25)<Step 3> in methylene chloride (16 mL), 4-hydroxybenzonitrile (0.19 g), copper(II) acetate (0.32 g), and triethylamine (1.16 mL) were added and the resultant reaction mixture was stirred in an oxygen atmosphere at room temperature for 3 days. The reaction mixture was filtered with Celite. From the filtrate, the solvent was removed by evaporation under reduced pressure and the resultant residue was purified by silica gel column chromatography. From the eluted solution, the solvent was removed by evaporation under reduced pressure to give the title compound (0.42 g) as a colorless oil.

<Step 5> Synthesis of (S)-4-((1-hydroxy-2,3-dihydro-1H-inden-4-yl)oxy)benzonitrile The compound (0.40 g) obtained in (Example 25)<Step 4> was dissolved in a 1:1 mixed solvent (8.0 mL) of methanol and tetrahydrofuran. To the solution, 1M hydrochloric acid (4.0 mL) was added and the resultant reaction mixture was stirred at room temperature for 18 hours. From the reaction mixture, the solvent was removed by evaporation under reduced pressure. To the residue, a 1M sodium hydroxide aqueous solution was added to make the mixture basic. The mixture was extracted with ethyl acetate. The organic phase was washed with brine and then dried over anhydrous sodium sulfate. From the organic phase, the solvent was removed by evaporation under reduced pressure to give the title compound (0.29 g) as a colorless oil.

<Step 6> Synthesis of (R)-4-((4-(4-cyanophenoxy)-2,3-dihydro-1H-inden-1-yl)oxy)phenylboronic acid N-methyliminodiacetic acid ester In accordance with the method in (Example 1)<Step 3>, a mixture (330 mg) containing the title compound was obtained as a white solid from the compound (0.3 g) obtained in (Example 25)<Step 5>.

<Step 7> Synthesis of 4-(((1R)-1-(4-(3-hydroxy-1-oxidoisothiazol-5-yl)phenoxy)-2,3-dihydro-1H-inden-4-yl)oxy)benzonitrile (A)

In accordance with the method in (Example 1)<Step 6>, the title compound (92 mg) was obtained as a pale yellow solid from the compound (0.2 g) obtained in (Example 25)<Step 6>.

<Step 8> Synthesis of 4-(((1R)-1-(4-(1-oxo-1,2-thiazolidin-3-on-5-yl)phenoxy)-2,3-dihydro-1H-inden-4-yl)oxy) benzonitrile (A)

In accordance with the method in (Example 7)<Step 2>, each diastereomer of the title compound was obtained from the compound (130 mg) obtained in (Example 25)<Step 7>.

Primary fraction (25.3 mg, white solid, retention time 5.65 minutes (LC/MS),
diastereomer a: Example 25 (A)-a)
Secondary fraction (31.4 mg, white solid, retention time 5.60 minutes (LC/MS), diastereomer b: Example 25 (A)-b)

Example 26

Synthesis of 4-(((1R)-1-(4-(1,1-dioxo-1,2,6-thiadiazinan-3-on-5-yl)phenoxy)-2,3-dihydro-1H-inden-4-yl)oxy)benzonitrile <Step 1> Synthesis of ethyl 3-(4-hydroxyphenyl)-3-(2, 2, 2-trifluoroacetamide) propionate To a solution of ethyl 3-amino-3-(4-hydroxyphenyl)propionate (1.0 g) that was commercially available or could be obtained by a known method in methylene chloride (0.41 mL), trifluoroacetic anhydride (0.70 mL) was added under 10° C. and the resultant reaction mixture was stirred at room temperature for 5 hours. To the reaction mixture, pyridine (0.41 mL) was added at under 10° C. and the resultant reaction mixture was stirred at room temperature for 1 hour. To the reaction mixture, trifluoroacetic anhydride (0.70 mL) and pyridine (0.41 mL) were further added and the resultant reaction mixture was stirred at room temperature for 15 hours. From the reaction mixture, the solvent was removed by evaporation under reduced pressure. The residue was diluted with ethyl acetate (50 mL), then successively washed with 0.5M hydrochloric acid (50 ml) and water (50 mL), and dried over anhydrous sodium sulfate. From the organic phase, the solvent was removed by evaporation under reduced pressure and the resultant residue was washed with hexane to give the title compound (900 mg) as a yellow solid.

<Step 2> Synthesis of ethyl 3-(4-(((R)-4-(4-cyanophenoxy)-2,3-dihydro-1H-inden-1-yl)oxy)phenyl)-3-(2,2,2-trifluoroacetamide)propionate In accordance with the method in (Example 23)<Step 3>, the title compound (680 mg) was obtained as a yellow oil using the compound (0.40 g) obtained in (Example 26)<Step 1> and the compound (0.33 g) obtained in (Example 25)<Step 5>.

<Step 3> Synthesis of ethyl 3-amino-3-(4-(((R)-4-(4-cyanophenoxy)-2,3-dihydro-1H-inden-1-yl)oxy) phenyl)propionate The compound (0.45 g) obtained in (Example 26)<Step 2> was dissolved in ethanol (10 mL). To the solution, sodium borohydride (63.2 mg) was added and the resultant reaction mixture was stirred at room temperature for 16 hours. The reaction mixture was diluted with water (50 mL) and extracted with ethyl acetate (50 mL). The obtained organic phase was dried over anhydrous sodium sulfate. From the organic phase, the solvent was removed by evaporation under reduced pressure and the resultant residue was purified by silica gel column chromatography (eluent; n-hexane:ethyl acetate=0:100). From the eluted solution, the solvent was removed by evaporation under reduced pressure to give a mixture (290 mg) containing the title compound as a colorless solid.

\<Step 4\> Synthesis of ethyl 3-(4-(((R)-4-(4-cyanophenoxy)-2,3-dihydro-1H-inden-1-yl)oxy)phenyl)-3-(sulfamoylamino)propionate To a solution of chlorosulfonyl isocyanate in tetrahydrofuran, aqueous tetrahydrofuran was added under 10° C. The reaction mixture was stirred at room temperature for 30 minutes to prepare a solution of sulfamoyl chloride in tetrahydrofuran. A solution of the compound obtained in (Example 26)\<Step 3\> in tetrahydrofuran was prepared in another container. To the container, pyridine (0.10 ml) was added and the solution of sulfamoyl chloride in tetrahydrofuran was added dropwise under 10° C. The resultant reaction mixture was stirred at room temperature for 19 hours. To the reaction mixture, water (30 mL) was added. The mixture was extracted with ethyl acetate (20 mL) twice. The obtained organic phase was washed with water (20 mL) and dried over anhydrous sodium sulfate. From the organic phase, the solvent was removed by evaporation under reduced pressure and the resultant residue was purified by silica gel column chromatography. From the eluted solution, the solvent was removed by evaporation under reduced pressure to give the title compound.

\<Step 5\> Synthesis of 4-(((1R)-1-(4-(1,1-dioxo-1,2,6-thiadiazinan-3-on-5-yl)phenoxy)-2,3-dihydro-1H-inden-4-yl)oxy)benzonitrile The compound (15 mg) obtained in (Example 26)\<Step 4\> was dissolved in ethanol (1.5 mL) and a 1M sodium hydroxide aqueous solution (0.15 mL) was added to the solution. The resultant reaction mixture was stirred at room temperature for 2 hours. To the reaction mixture, a saturated aqueous ammonium chloride solution (1 mL) and water (1 mL) were added. The mixture was extracted with ethyl acetate (10 mL) and the organic phase was dried over anhydrous sodium sulfate. From the organic phase, the solvent was removed by evaporation under reduced pressure and the resultant residue was purified by silica gel column chromatography (eluent; n-hexane:ethyl acetate=0:100). From the eluted solution, the solvent was removed by evaporation under reduced pressure to give the title compound (7.5 mg) as a colorless amorphous solid.

Each compound of (Example 27) to (Example 28) below was synthesized by the same method or a similar method in (Example 1) or (Example 26).

Example 27

5-(4-(((R)-4-phenoxy-2,3-dihydro-1H-inden-1-yl)oxy)phenyl)-1-oxo-1,2-thiazolidin-3-one Example 28

5-(44(7-(trifluoromethyl)-2,3-dihydrobenzofuran-3-yl)oxy)phenyl)-1-oxo-1,2-thiazolidin-3-one Example 29

Synthesis of 5-(4-(((R)-4-bromo-2,3-dihydro-1H-inden-1-yl)oxy)phenyl)-1-oxo-1,2-thiazolidin-3-one To a solution of 1N L-Selectride in tetrahydrofuran (14.8 mL), tetrabutylammonium chloride (4.1 g) was added under ice-cooling and a solution of the compound (1 g) obtained in (Example 23)\<Step 4\> in anhydrous THF (5 mL) was added dropwise under 3° C. The reaction mixture was allowed to reach room temperature and stirred for 2 days. To the reaction mixture, 1M hydrochloric acid was added. The mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate) to give the title compound (0.44 g) as a yellow solid. The reduced title compound in this step is a mixture of diastereomers because the compound has a new asymmetric center (carbon atom).

Example 30

Synthesis of 5-(4-(((R)-4-(2,6-dimethyl 4-(3-(methylsulfonyl)propoxy)phenyl)-2,3-dihydro-1H-inden-1-yl)oxy)phenyl)-1-oxo-1,2-thiazolidin-3-one \<Step 1\> Synthesis of 2-bromo-1,3-dimethyl-5-(3-(methylsulfonyl)propoxy)benzene In accordance with the method in (Example 23)\<Step 1\>, the title compound (289 g) was obtained as a white solid from 4-bromo-3,5-dimethylphenol (217 g) and 3-(methylsulfonyl)propyl 4-methylbenzenesulfonate (300 g).

\<Step 2\> Synthesis of 2-(2,6-dimethyl-4-(3-(methylsulfonyl)propoxy)phenyl)-5,5-dimethyl-1,3,2-dioxaborinane In accordance with the method in (Example 23)\<Step 2\>, the title compound (0.70 g) was obtained as a beige solid from the compound (1.0 g) obtained in (Example 30)\<Step 1\>.

\<Step 3\> Synthesis of 5-(4-(((R)-4-(2,6-dimethyl 4-(3-(methylsulfonyl)propoxy)phenyl)-2,3-dihydro-1H-inden-1-yl)oxy)phenyl)-1-oxo-1,2-thiazolidin-3-one To a solution of the compound (0.10 g) in (Example 29), the compound (0.13 g) obtained in (Example 30)\<Step 2\>, potassium carbonate (34 mg), 2-dicyclohexylphosphino-T,4', 6'-triisopropylbiphenyl (XPhos: 23 mg), and bis(dibenzylideneacetone)palladium (14 mg) in 1,4-dioxane (4 mL), water (2 mL) was added. The inside of the reaction system was purged with nitrogen and the resultant reaction mixture was heated and refluxed for 2 hours. To the reaction mixture, a saturated aqueous ammonium chloride solution was added. The mixture was extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate) to give the title compound (55 mg) as a pale yellow solid. The title compound is a mixture of diastereomers because it has the asymmetric center as with the compound in Example 29.

Example 31

Synthesis of 5-[4-[[3-[2,6-dimethyl 4-(3-methylsulfonylpropoxy)phenyl]phenyl]methoxy]phenyl]-1,1-dioxo-1,2-thiazinan-3-one \<Step 1\> Synthesis of N,N-bis((2-(trimethylsilyl)ethoxy)methyl)methanesulfonamide Sodium hydride (4.6 g) was added to DMF (35 ml). To the solution, a solution of methanesulfonamide (5.0 g) in DMF (15 ml) was added dropwise. (2-(chlorotrimethoxy)ethyl)trimethylsilane (18.6 ml) was added to the solution and the resultant reaction mixture was stirred at room temperature for 2 hours. The reaction mixture was poured into ice water and extracted with ethyl acetate. The organic phase was washed with brine and then dried over anhydrous sodium sulfate. From the organic phase, the solvent was removed by evaporation under reduced pressure and the resultant residue was purified by silica gel column chromatography (eluent; n-hexane:ethyl acetate) to give the title compound (7.4 g) as a colorless oil.

<Step 2> Synthesis of 4-((2',6'-dimethyl-4'-(3-(methylsulfonyl)propoxy)-[1,1'-biphenyl]-3-yl)methoxy)benzaldehyde To a solution of the compound (3.0 g) in (Reference Example 2) in DMF (40 ml), potassium carbonate (1.2 g) and 4-hydroxybenzaldehyde (0.94 g) were added at room temperature. The inside of the reaction system was purged with nitrogen and the mixture was heated and stirred at 80° C. for 2 hours. After the reaction mixture was allowed to cool to room temperature, water was added to the reaction mixture. The mixture was extracted with ethyl acetate. The organic phase was washed with brine and then dried over anhydrous sodium sulfate. From the organic phase, the solvent was removed by evaporation under reduced pressure to give the title compound (3.3 g) as a pale yellow oil.

<Step 3> Synthesis of (E)-2-(4-((2',6'-dimethyl-4'-(3-(methylsulfonyl)propoxy)-[1,1'-biphenyl]-3-yl)methoxy)phenyl)-N,N-bis((2-(trimethylsilyl)ethoxy)methyl)ethenesulfonamide A solution of the compound (2.4 g) in (Example 31)<Step 1> in THF (7 ml) was cooled in an acetonitrile—dry ice bath. To the solution, a solution of 1M lithium hexamethyldisilazane in THF (14.6 ml) was added dropwise and the resultant reaction mixture was stirred at the same temperature for 50 minutes. Next, diethyl chlorophosphonate (1.1 ml) was added dropwise and the resultant reaction mixture was further stirred for 90 minutes. Then, a solution of the compound (3.0 g) in (Example 31)<Step 2> in THF (10 ml) was added dropwise. The resultant reaction mixture was sitrred at the same temperature for 30 minutes, next stirred under ice-cooling for 1 hour, then allowed to reach room temperature, and stirred for 1 hour. To the reaction mixture, 1M hydrochloric acid was added. The mixture was extracted with ethyl acetate. The organic phase was washed with saturated aqueous sodium hydrogen carbonate, then washed with a half saturated salt solution, and dried over anhydrous sodium sulfate. From the organic phase, the solvent was removed by evaporation under reduced pressure and the resultant residue was purified by silica gel column chromatography (eluent; n-hexane:ethyl acetate) to give the title compound (6.0 g) as a pale yellow oil.

<Step 4> Synthesis of dimethyl 2-(2-(N,N-bis(2-(trimethylsilyl)ethoxymethyl)sulfamoyl)-1-(4-((2',6'-dimethyl-4'-(3(methylsulfonyl)propoxy)-[1,1'-biphenyl]-3-yl)methoxy)phenyl)ethyl)malonate To a solution of dimethyl malonate (1.5 ml) in THF (10 ml), a solution of 28% sodium methoxide in methanol (2.6 g) was added at room temperature. The mixture was stirred for 10 minutes. To the reaction mixture, a solution of the compound (3.5 g) in (Example 31)<Step 3> in THF (30 ml) was added and the resultant reaction mixture was heated and refluxed for 65 hours. To the reaction mixture, a saturated aqueous ammonium chloride solution was added. The mixture was extracted with ethyl acetate. The organic phase was washed with saturated aqueous sodium hydrogen carbonate, then washed with brine, and dried over anhydrous sodium sulfate. From the organic phase, the solvent was removed by evaporation under reduced pressure and the resultant residue was purified by silica gel column chromatography (eluent; n-hexane:ethyl acetate) to give the title compound (3.5 g) as a colorless oil.

<Step 5> Synthesis of methyl 4-(N,N-bis(2-(trimethylsilyl)-ethoxymethyl)sulfamoyl)-3-(4((2',6'-dimethyl-4'-(3-(methylsulfonyl)propoxy)-[1,1'-biphenyl]-3-yl)methoxy)phenyl)butanoate To a solution of the compound (3.5 g) in (Example 31)<Step 4> in DMF (35 ml), sodium chloride (0.22 g) and water (0.14 ml) were added and the resultant reaction mixture was heated and refluxed for 17 hours. To the reaction mixture, water was added and the mixture was extracted with ethyl acetate. The organic phase was washed with water, then washed with brine, and dried over anhydrous sodium sulfate. From the organic phase, the solvent was removed by evaporation under reduced pressure to give the title compound (3.0 g) as a colorless oil.

<Step 6> Synthesis of methyl 3-(4-((2',6'-dimethyl-4'-(3-(methylsulfonyl)propoxy)-[1,1'-biphenyl]-3-yl)methoxy)phenyl)-4-sulfamoylbutanoate To a solution of the compound (1.5 g) in (Example 31)<Step 5> in acetic acid (15 ml), water (7.5 ml) was added and the resultant reaction mixture was heated and stirred at 80° C. for 3 hours. To the reaction mixture, water was added and the mixture was extracted with ethyl acetate. The organic phase was washed with water, then washed with brine, and dried over anhydrous sodium sulfate. From the organic phase, the solvent was removed by evaporation under reduced pressure and the resultant residue was purified by silica gel column chromatography (eluent; n-hexane:ethyl acetate) to give the title compound (0.34 g) as a colorless oil.

<Step 7> Synthesis of 5-[4-[[3-[2,6-dimethyl-4-(3-methylsulfonylpropoxy)phenyl]phenyl]methoxy]phenyl]-1,1-dioxo-1,2-thiazinan-3-one To a solution of the compound (20 mg) in (Example 31)<Step 6> in methanol (0.40 ml), a solution of 28% sodium methoxide in methanol (8.3 mg) was added at room temperature and the resultant reaction mixture was stirred for 1 hour. To the reaction mixture, 1M hydrochloric acid was added and the mixture was extracted with ethyl acetate. The organic phase was washed with saturated aqueous sodium hydrogen carbonate, then washed with brine, and dried over anhydrous sodium sulfate. From the organic phase, the solvent was removed by evaporation under reduced pressure to give the title compound (15 mg) as a colorless solid.

Example 32

Synthesis of 4-(((1R)-1-(4-(1,1-dioxo-3-oxo-1,2-thiazinan-5-yl)phenoxy)-2,3-dihydro-1H-inden-4-yl)oxy)benzonitrile <Step 1> Synthesis of (E)-2-(4-(benzyloxy)phenyl)-N,N-bis((2-(trimethylsilyl)ethoxy)methyl)ethenesulfonamide In accordance with the method in (Example 31)<Step 3>, the title compound (6.1 g) was obtained as a colorless solid from the compound (7.5 g) obtained in (Example 31)<Step 1> and 4-benzyloxybenzaldehyde (4.5 g).

<Step 2> Synthesis of dimethyl 2-(1-(4-(benzyloxy) phenyl)-2-(N,N-bis(2-(trimethylsilyl)-ethoxymethyl) sulfamoyl)ethyl)malonate In accordance with the method in (Example 31)<Step 4>, the title compound (2.5 g) was obtained as a colorless oil from the compound (3.0 g) obtained in (Example 32)<Step 1>.

<Step 3> Synthesis of methyl 3-(4-(benzyloxy)phenyl)-4-(N,N-bis(2-(trimethylsilyl)-ethoxymethyl) sulfamoyl)butanoate In accordance with the method in (Example 31)<Step 5>, the title compound (1.3 g) was obtained as a colorless oil from the compound (2.4 g) obtained in (Example 32) <Step 2>.

<Step 4> Synthesis of methyl 4-(N,N-bis(2-(trimethylsilyl)-ethoxymethyl)sulfamoyl)-3-(4-hydroxyphenyl)butanoate To a solution of the compound (20 mg) in (Example 32)<Step 3> in methanol (1.0 ml), 10% palladium—carbon (2.0 mg) was added and the resultant reaction mixture was stirred in a hydrogen atmosphere for 16 hours. The inside of the reaction system was purged with nitrogen. Then, the reaction mixture was filtered with Celite. From the filtrate, the solvent was removed by evaporation under reduced pressure to give the title compound (17 mg).

<Step 5> Synthesis of methyl 4-(N,N-bis(2-(trimethylsilyl)-ethoxymethyl)sulfamoyl)-3-(4-(((R)-4-(4-cyanophenoxy)-2,3-dihydro-1H-inden-1-yl)oxy) phenyl)butanoate A mixture of the compound (0.23 g) in (Example 25)<Step 5>, the compound (0.48 g) in (Example 32)<Step 4>, molecular sieves 3A (0.50 g), and toluene (9.0 ml) was heated and refluxed. To the mixture, cyanomethylenetributylphosphorane (1.2 ml) was added dropwise and the resultant reaction mixture was heated and refluxed for 2.5 hours. After the reaction mixture was allowed to cool to room temperature, the solvent was removed by evaporation under reduced pressure and the resultant residue was purified by silica gel column chromatography (eluent; n-hexane:ethyl acetate) to give the title compound (0.25 g) as a pale yellow viscous oil.

<Step 6> Synthesis of 4-(((1R)-1-(4-(1,1-dioxo-3-oxo-1,2-thiazinan-5-yl)phenoxy)-2,3-dihydro-1H-inden-4-yl)oxy)benzonitrile To a solution of the compound (30 mg) in (Example 32)<Step 5> in THF (0.6 ml), a solution of 1M tetrabutylammonium fluoride in THF (0.15 ml) was added at room temperature. The resultant reaction mixture was stirred at room temperature for 30 minutes, then heated and refluxed for 1 hour, and stirred at room temperature for 16 hours. The reaction mixture was filtered and washed with ethyl acetate. To the obtained organic phase, 1M hydrochloric acid was added and the mixture was extracted with ethyl acetate. The organic phase was washed with water, then washed with brine, and dried over anhydrous sodium sulfate. From the organic phase, the solvent was removed by evaporation under reduced pressure and the resultant residue was purified by silica gel column chromatography (eluent; methylene chloride:methanol) to give the title compound (3.2 mg) as a pale brown solid.

Example 33

Synthesis of 5-(4-(((R)-4-bromo-2,3-dihydro-1H-inden-1-yl)oxy)phenyl)-1,1-dioxo-1,2-thiazinan-3-one <Step 1> Synthesis of (R)-4-((4-bromo-2,3-dihydro-1H-inden-1-yl)oxy)benzaldehyde In accordance with the method in (Example 1)<Step 3>, the title compound (5.5 g) was obtained as a colorless solid from (S)-4-bromo-2,3-dihydro-1H-inden-1-ol (6.0 g) and 4-hydroxybenzaldehyde (3.5 g).

<Step 2> Synthesis of (R,E)-2-(4-((4-bromo-2,3-dihydro-1H-inden-1-yl)oxy)phenyl)-N,N-bis((2-(trimethylsilyl)ethoxy)methyl)ethenesulfonamide In accordance with the method in (Example 31)<Step 3>, the title compound (8.2 g) was obtained as a yellow oil from the compound (6.0 g) obtained in (Example 31)<Step 1> and the compound (5.4 g) obtained in (Example 33)<Step 1>.

<Step 3> Dimethyl 2-(2-(N,N-bis(2-(trimethylsilyl) ethoxymethyl)sulfamoyl)-1-(4-(((R)-4-bromo-2,3-dihydro-1H-inden-1-yl)oxy)phenyl)ethyl)malonate In accordance with the method in (Example 31)<Step 4>, the title compound (9.6 g) was obtained as a yellow oil from the compound (8.2 g) obtained in (Example 33)<Step 2>.

<Step 4> Synthesis of methyl 4-(N,N-bis(2-(trimethylsilyl)ethoxymethyl)sulfamoyl)-3-(4-(((R)-4-bromo-2,3-dihydro-1 H-inden-1-yl)oxy)phenyl)butanoate In accordance with the method in (Example 31)<Step 5>, the title compound (5.9 g) was obtained as a colorless oil from the compound (9.6 g) obtained in (Example 33) <Step 3>.

<Step 5> Synthesis of 5-(4-(((R)-4-bromo-2,3-dihydro-1 1-1-inden-1-yl)oxy)phenyl)-1,1-dioxo-1,2-thiazinan-3-one In accordance with the method in (Example 32)<Step 6>, the title compound (5.1 mg) was obtained as a pale brown solid from the compound (30 mg) obtained in (Example 33)<Step 4>.

Example 34

Synthesis of 5-(4-(((R)-4-(4-(3-hydroxy-3-methylbutoxy)-2,6-dimethylphenyl)-2,3-dihydro-1H-inden-1-yl)oxy)phenyl)-1,1-dioxo-1,2-thiazinan-3-one In accordance with the method in (Example 30)<Step 3>, the title compound (6.0 mg) was obtained as a white solid from the compound (17 mg) obtained in (Example 33) and the compound (16 mg) obtained in (Example 24)<Step 2>.

Example 35

Synthesis of 5-[4-[[3-[6-(3-hydroxy-3-methylbutoxy)-2,4-dimethylpyridin-3-yl]phenyl]methoxy] phenyl]-1,1-dioxo-1,2-thiazinan-3-one <Step 1> Synthesis of (E)-2-(4-((3-bromobenzyl) oxy)phenyl)-N,N-bis((2-(trimethylsilyl)ethoxy)methyl)ethenesulfonamide In accordance with the method in (Example 31)<Step 3>, the title compound (18 g) was obtained as a white solid from 4-[(3-bromobenzyl)oxy]benzaldehyde (11 g) and the compound (13.4 g) obtained in (Example 31)<Step 1>.

<Step 2> Synthesis of dimethyl 2-(2-(N,N-bis((2-(trimethylsilyl)ethoxymethyl)sulfamoyl)-1-(4-((3-bromobenzyl)oxy)phenyl)ethyl)malonate In accordance with the method in (Example 31)<Step 4>, the title compound (23 g) was obtained as a colorless oil from the compound (18 g) obtained in (Example 35)<Step 1>.

<Step 3> Synthesis of methyl 4-(N,N-bis(2-(trimethyl silyl)ethoxymethyl)sulfamoyl)-3-(4-((3-bromobenzyl)oxy)phenyl)butanoate In accordance with the method in (Example 31)<Step 5>, the title compound (21 g) was obtained as a colorless oil from the compound (23 g) obtained in (Example 35)<Step 2>.

<Step 4> Synthesis of methyl 3-(4-((3-bromobenzyl)oxy)phenyl)-4-sulfamoylbutanoate In accordance with the method in (Example 31)<Step 6>, the title compound (0.32 g) was obtained as a colorless oil from the compound (1.0 g) obtained in (Example 35) <Step 3>.

<Step 5> Synthesis of 5-(4-((3-bromobenzyl)oxy)phenyl)-1,2-thiazinan-3-one 1,1-dioxide In accordance with the method in (Example 31)<Step 7>, the title compound (0.12 g) was obtained as a white solid from the compound (0.16 g) obtained in (Example 35) <Step 4>.

<Step 6> Synthesis of 5-[4-[[3-[6-(3-hydroxy-3-methylbutoxy)-2,4-dimethylpyridin-3-yl]phenyl]methoxy]phenyl]-1,1-dioxo-1,2-thiazinan-3-one In accordance with the method in (Example 30)<Step 3>, the title compound (29 mg) was obtained as a white solid from the compound (0.10 g) obtained in (Example 35) <Step 5> and 4-((5-(5,5-dimethyl-1,3,2-dioxaborinan-2-yl)-4,6-dimethylpyridin-2-yl)oxy)-2-methylbutan-2-ol (86 mg) synthesized by a similar method of (Example 23)<Step 2>.

The compounds shown below, the compounds of Formulae 9 to 12 ((Example 1P) to (Example 157P)), compounds that can be obtained in combination of Partial Structural Formulae shown in the aspect [1-19-1] to the aspect [1-19-2], salts of them, solvates of them, and optical isomers of them can also be easily synthesized by using Production Methods above, the methods described in Examples, methods known by a person skilled in the art, or modified methods of them.

5-[4-[[3-[2,4-dimethyl-6-(3-methylsulfonylpropoxy)pyridin-3-yl] phenyl]methoxy]phenyl]-1,1-dioxo-1,2-thiazolidin-3-one;
5-[4-[[3-[2,4-dimethyl-6-(3-methylsulfonylpropoxy)pyridin-3-yl]phenyl]methoxy]phenyl]-1,1-dioxo-1,2,5-thiadiazolidin-3-one;
5-[4-[[3-[6-(3-hydroxy-3-methylbutoxy)-2,4-dimethylpyridin-3-yl]phenyl]methoxy]phenyl]-1,1-dioxo-1,2,5-thiadiazolidin-3-one;
5-[2-chloro-4-[[3-[2,6-dimethyl-4-(3-methylsulfonylpropoxy)phenyl]phenyl]methoxy]phenyl]-1,1-dioxo-1,2,5-thiadiazolidin-3-one;
5-[2-chloro-4-[[3-[2,4-dimethyl-6-(3-methylsulfonylpropoxy)pyridin-3-yl] phenyl]methoxy]phenyl]-1,1-dioxo-1,2,5-thiadiazolidin-3-one;
5-[2-chloro-4-[[3-[6-(3-hydroxy-3-methylbutoxy)-2,4-dimethylpyridin-3-yl] phenyl]methoxy]phenyl]-1,1-dioxo-1,2,5-thiadiazolidin-3-one;
5-[4-[[3-[2,6-dimethyl-4-(3-methylsulfonylpropoxy)phenyl]phenyl]methoxy]phenyl]-1,1-dioxo-1,2,6-thiadiazinan-3-one;
5-[4-[[3-[2,4-dimethyl-6-(3-methylsulfonylpropoxy)pyridin-3-yl] phenyl]methoxy] phenyl]-1,1-dioxo-1,2,6-thiadiazinan-3-one;
5-[4-[[3-[6-(3-hydroxy-3-methylbutoxy)-2,4-dimethylpyridin-3-yl]phenyl]methoxy]phenyl]-1,1-dioxo-1,2,6-thiadiazinan-3-one (Example 14P);
5-[4-[[3-[2,4-dimethyl-6-(3-methylsulfonylpropoxy)pyridin-3-yl]phenyl]methoxy]phenyl]-1,1-dioxo-1,2-thiazinan-3-one; and
5-(4-((3-(2,6-dimethylphenyl)phenyl)methoxy)phenyl)-1,1-dioxo-1,2-thiazolidin-3-one (Example 37P).

The structures of the final compounds synthesized in (Example 1) to (Example 35) above and the structures of the compounds in (Example 1P) to (Example 157P) are shown in the figures below (Structural Formulae 1 to 12). LC/MS data and NMR data (no mark: 400 MHz NMR, *: 300 MHz NMR) of these final compounds of Examples are also shown in Tables below (Tables 2, 3, 7, and 8). The structures of the intermediate compounds synthesized in Examples and the compounds of Reference Examples are shown in the figures below (Structural Formulae 13 to 19) and LC/MS data of these intermediate compounds and the compounds of Reference Examples and NMR data (no mark: 400 MHz NMR, *: 300 MHz NMR) of these intermediate compounds and the compounds of Reference Examples are also shown in Tables below (Tables 4, 5, 6, 9, 10, 11, and 12). Here, with respect to the intermediate compound, for example, the compound obtained in Example 1 <Step 1> is expressed as "1-1".

Structural Formula 1

| Example No. | Structure |
|---|---|
| 1 | 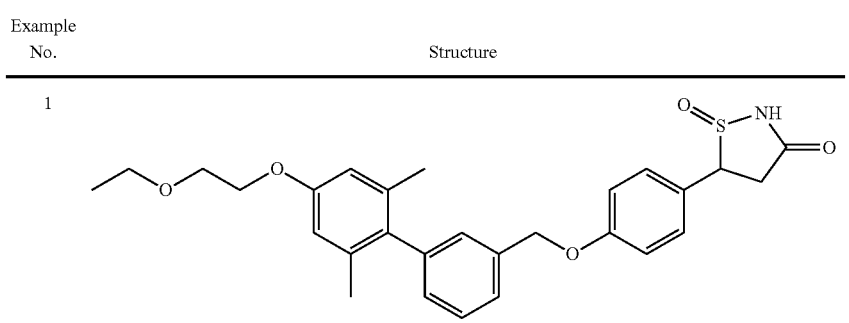 |

| Example No. | Structure |
|---|---|
| 2 | 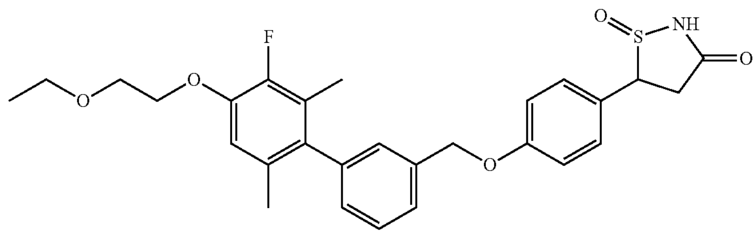 [SMILES: CCOCCOc1cc(C)c(-c2cccc(COc3ccc(C4CC(=O)NS4=O)cc3)c2)c(C)c1F] |
| 3 | 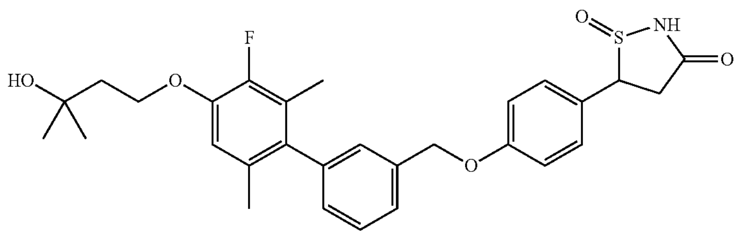 [SMILES: Cc1cc(OCCC(C)(C)O)c(F)c(C)c1-c1cccc(COc2ccc(C3CC(=O)NS3=O)cc2)c1] |
| 4 | 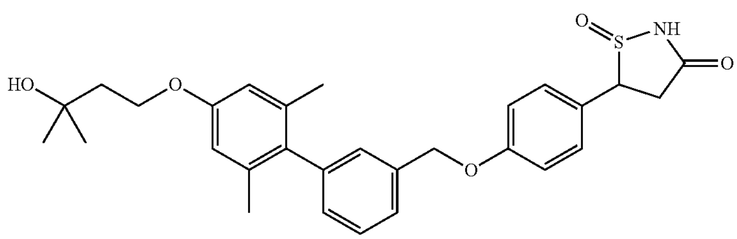 [SMILES: Cc1cc(OCCC(C)(C)O)cc(C)c1-c1cccc(COc2ccc(C3CC(=O)NS3=O)cc2)c1] |
| 5 | 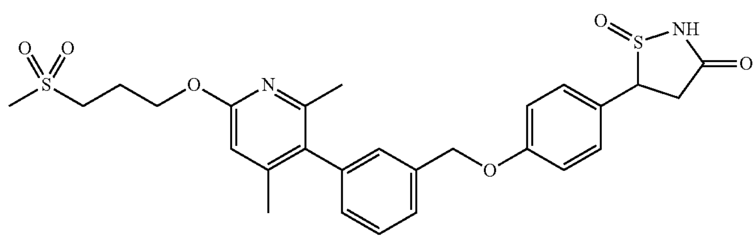 [SMILES: Cc1cc(OCCCS(C)(=O)=O)nc(C)c1-c1cccc(COc2ccc(C3CC(=O)NS3=O)cc2)c1] |
| 6 | 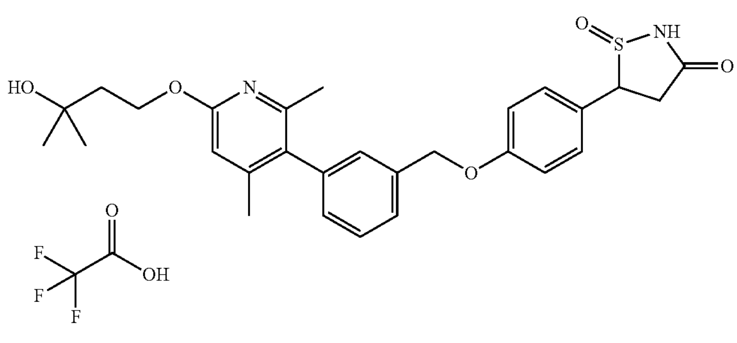 [SMILES: Cc1cc(OCCC(C)(C)O)nc(C)c1-c1cccc(COc2ccc(C3CC(=O)NS3=O)cc2)c1 ; O=C(O)C(F)(F)F] |
| 7 | 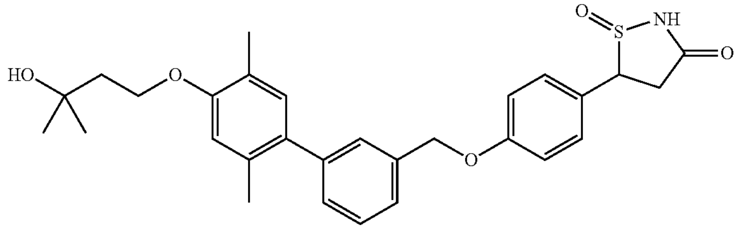 [SMILES: Cc1cc(-c2cccc(COc3ccc(C4CC(=O)NS4=O)cc3)c2)c(C)cc1OCCC(C)(C)O] |

-continued
| Example No. | Structure |
|---|---|
| 8 | 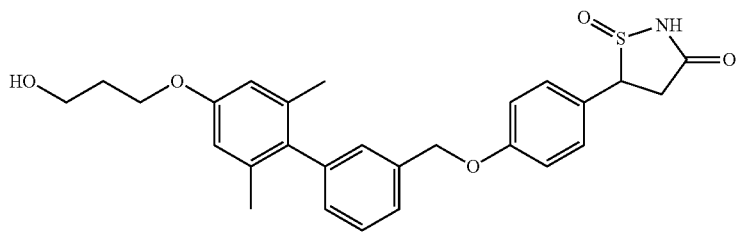 [SMILES: Cc1cc(OCCCO)cc(C)c1-c1cccc(COc2ccc(C3CC(=O)NS3=O)cc2)c1] |
| 9 | 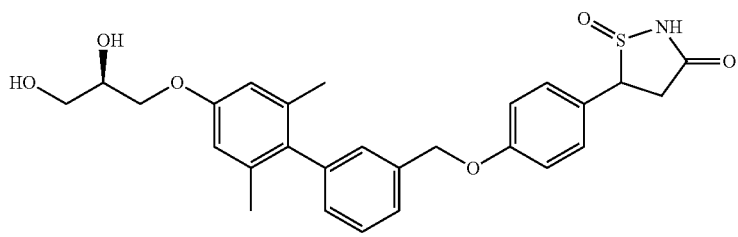 [SMILES: Cc1cc(OC[C@H](O)CO)cc(C)c1-c1cccc(COc2ccc(C3CC(=O)NS3=O)cc2)c1] |
| 10 | 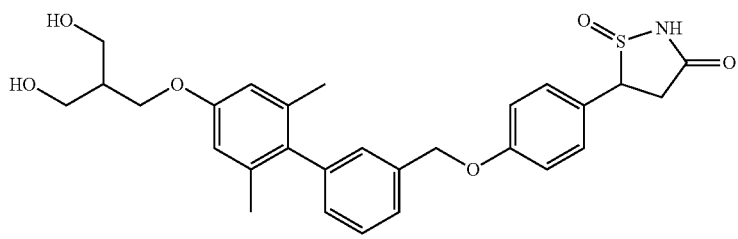 [SMILES: Cc1cc(OCC(CO)CO)cc(C)c1-c1cccc(COc2ccc(C3CC(=O)NS3=O)cc2)c1] |
| 11 | 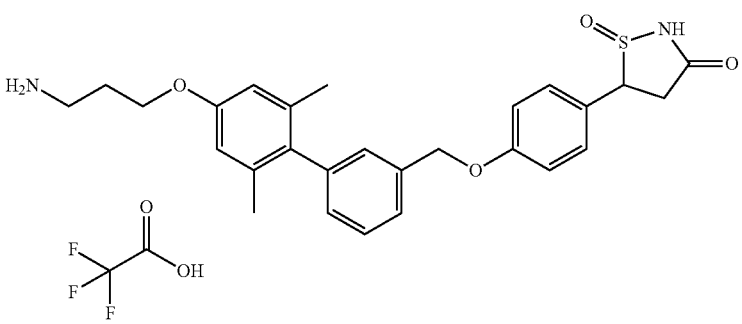 [SMILES: Cc1cc(OCCCN)cc(C)c1-c1cccc(COc2ccc(C3CC(=O)NS3=O)cc2)c1 ; O=C(O)C(F)(F)F] |
| 12 | 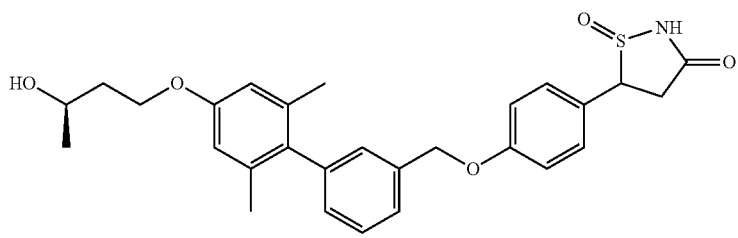 [SMILES: Cc1cc(OCC[C@@H](C)O)cc(C)c1-c1cccc(COc2ccc(C3CC(=O)NS3=O)cc2)c1] |
| 13 | 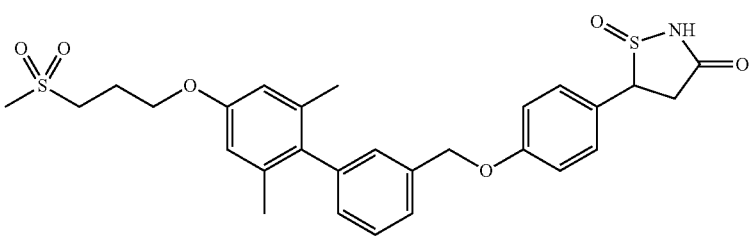 [SMILES: Cc1cc(OCCCS(C)(=O)=O)cc(C)c1-c1cccc(COc2ccc(C3CC(=O)NS3=O)cc2)c1] |

-continued
| Example No. | Structure |
|---|---|
| 14 | 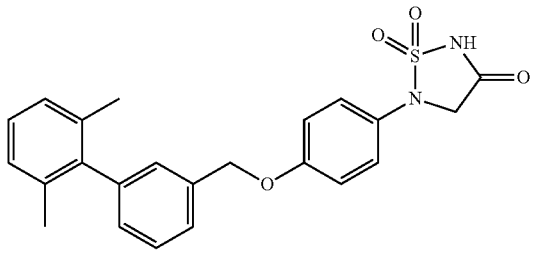 [SMILES: Cc1cccc(C)c1-c1cccc(COc2ccc(N3CC(=O)NS3(=O)=O)cc2)c1] |
| 15 | 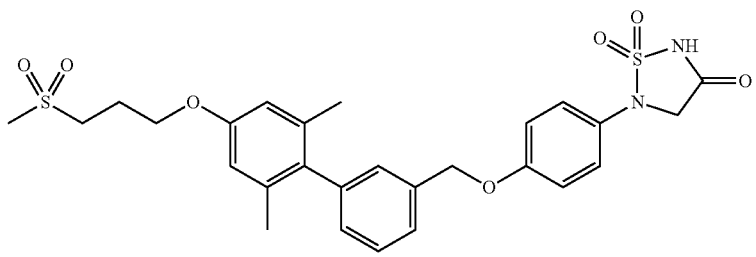 [SMILES: Cc1cc(OCCCS(C)(=O)=O)cc(C)c1-c1cccc(COc2ccc(N3CC(=O)NS3(=O)=O)cc2)c1] |
| 16 | 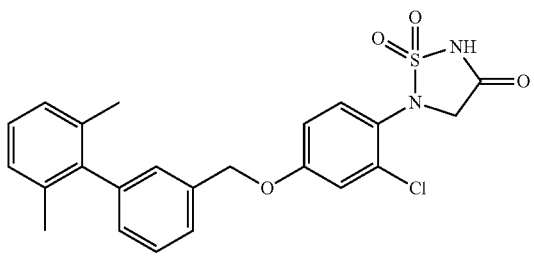 [SMILES: Cc1cccc(C)c1-c1cccc(COc2ccc(N3CC(=O)NS3(=O)=O)c(Cl)c2)c1] |
| 17 | 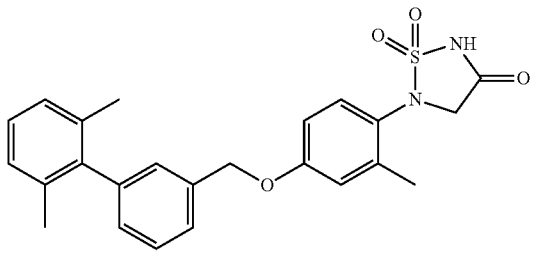 [SMILES: Cc1cc(OCc2cccc(-c3c(C)cccc3C)c2)ccc1N1CC(=O)NS1(=O)=O] |
| 18 | 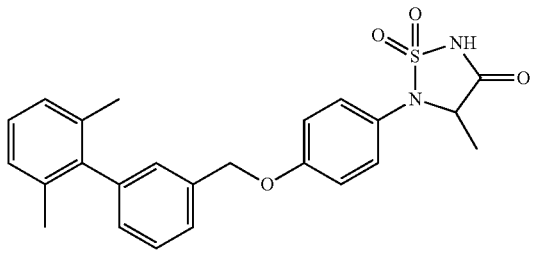 [SMILES: Cc1cccc(C)c1-c1cccc(COc2ccc(N3C(C)C(=O)NS3(=O)=O)cc2)c1] |
| 19 | 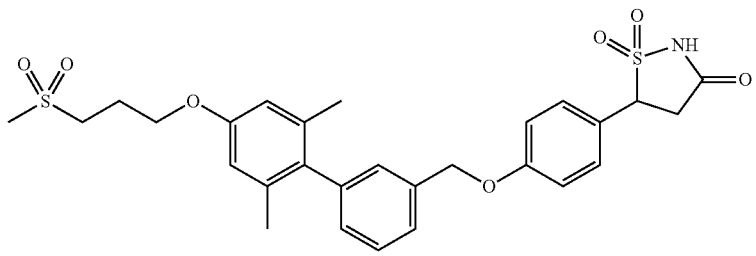 |

-continued
| Example No. | Structure |
|---|---|
| 20 | 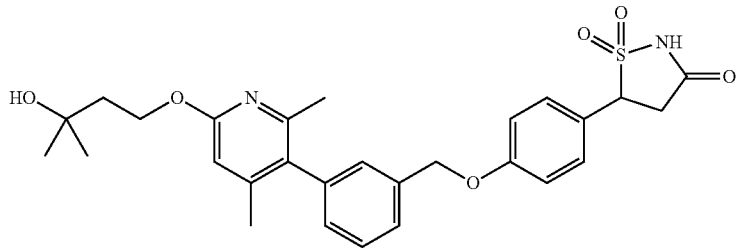 [SMILES: Cc1cc(OCCC(C)(C)O)nc(C)c1-c1cccc(COc2ccc(C3CC(=O)NS3(=O)=O)cc2)c1] |
| 21 | 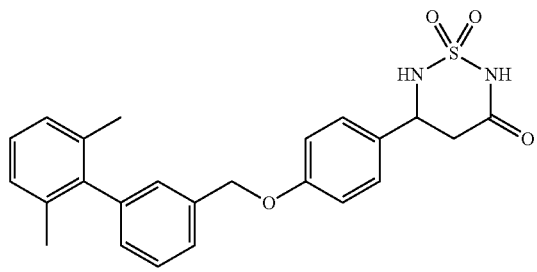 [SMILES: Cc1cccc(C)c1-c1cccc(COc2ccc(C3CC(=O)NS(=O)(=O)N3)cc2)c1] |
| 22 | 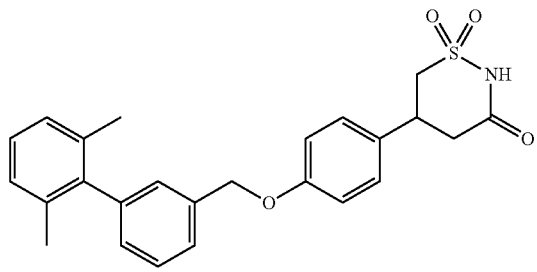 [SMILES: Cc1cccc(C)c1-c1cccc(COc2ccc(C3CC(=O)NS(=O)(=O)C3)cc2)c1] |
Structural Formula 2
Example 23
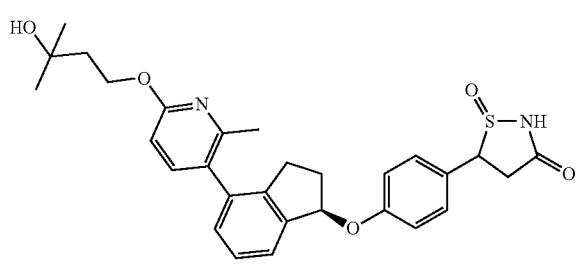
Example 24
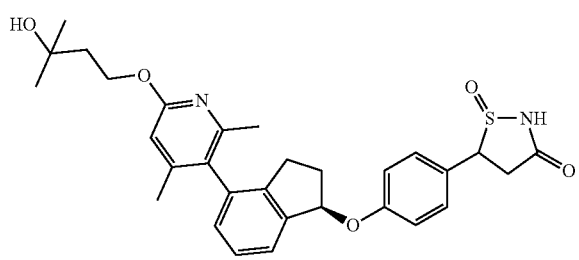
-continued
Example 25
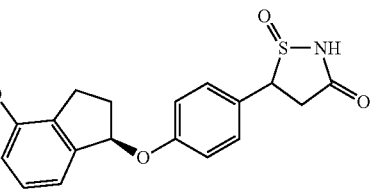
Example 26
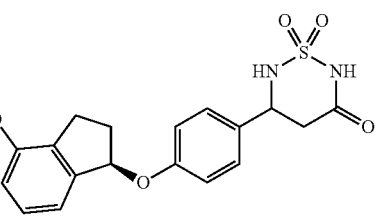

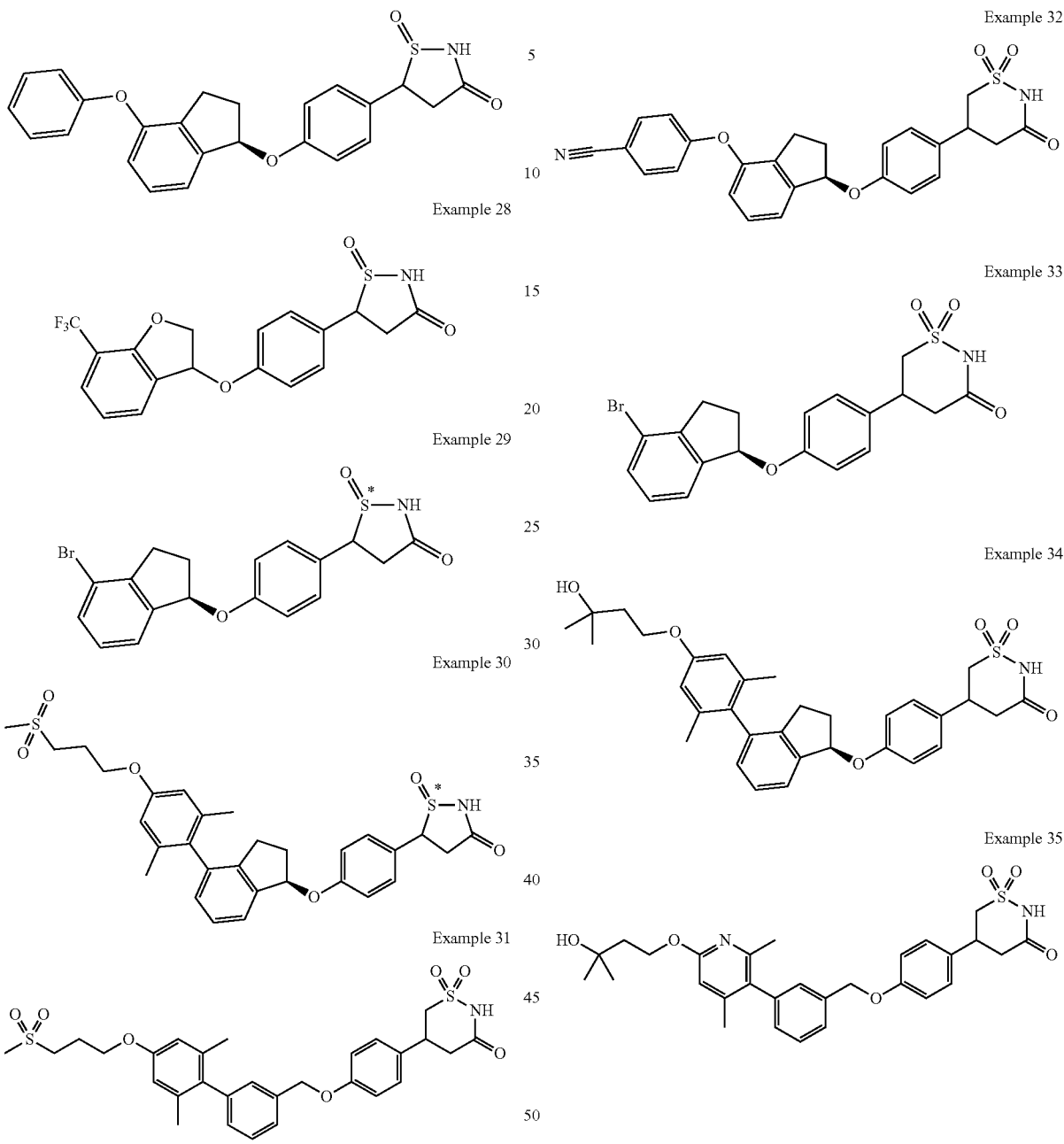
Example 27, Example 28, Example 29, Example 30, Example 31, Example 32, Example 33, Example 34, Example 35
Structural Formula 3
Example 1P
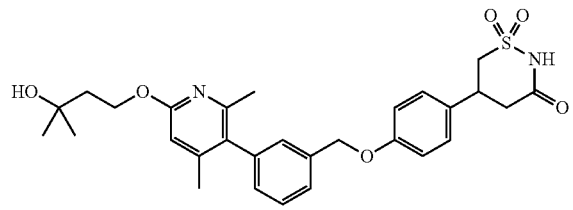
Example 2P
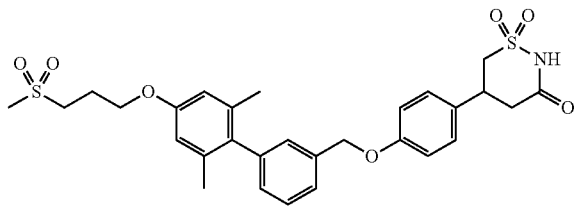

-continued
Example 3P
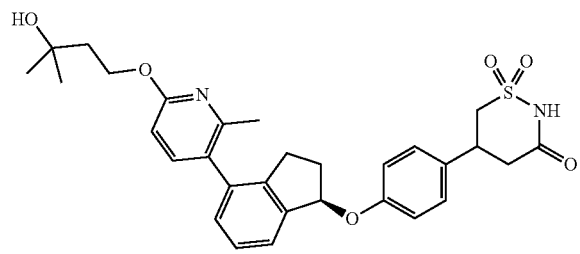
Example 4P
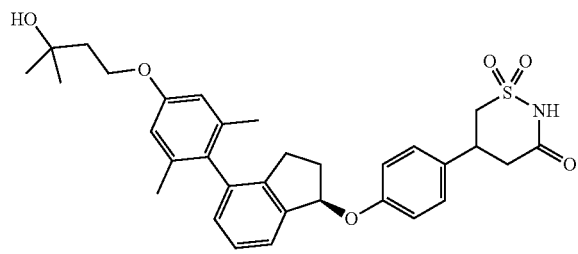
Example 5P
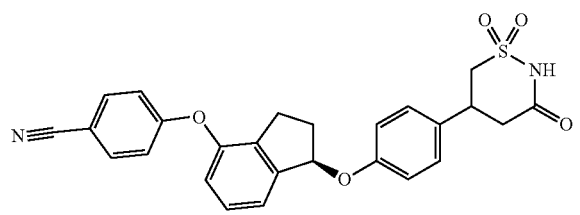
Example 6P
Example 7P
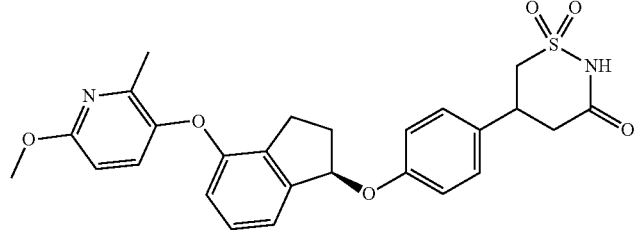
Example 8P
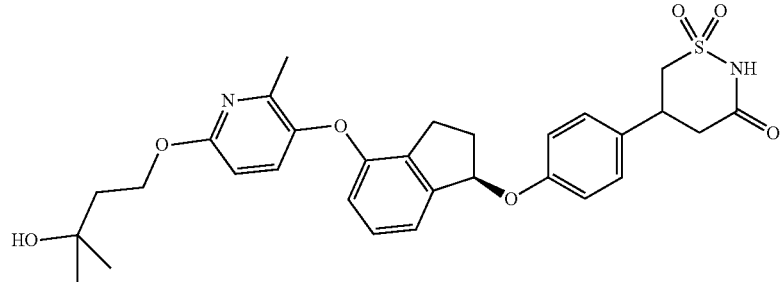
Example 9P
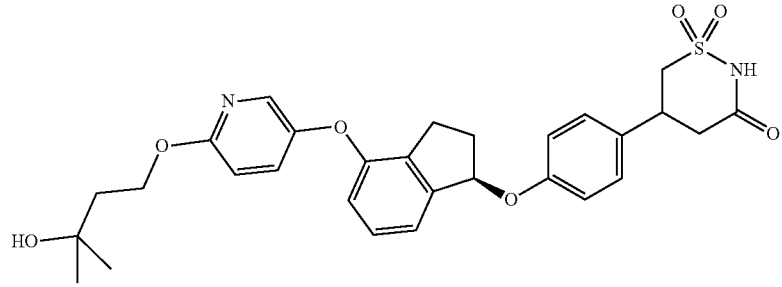
Example 10P
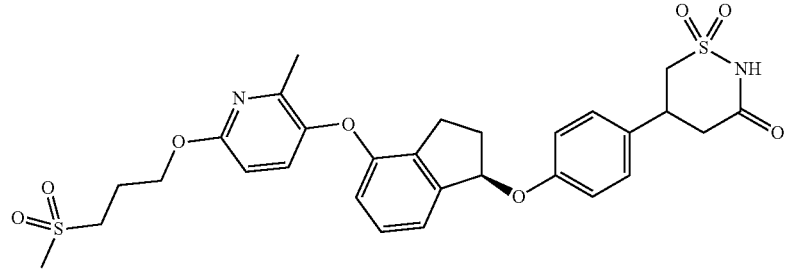

-continued
Example 11P
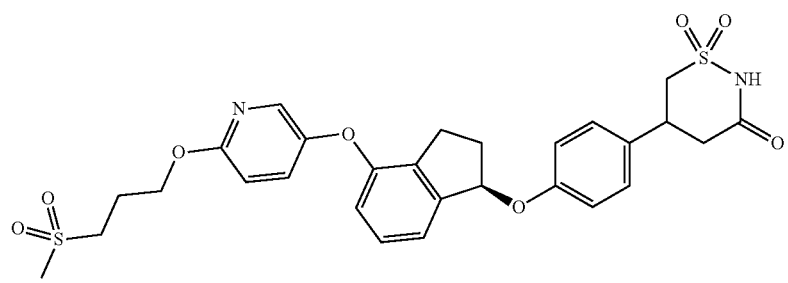
Example 12P
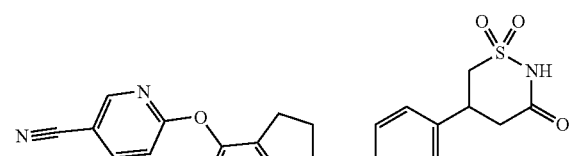
Example 13P
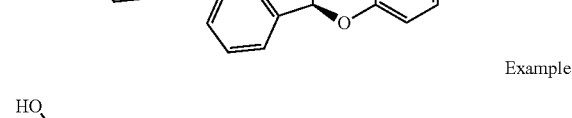
Example 14P
Example 15P
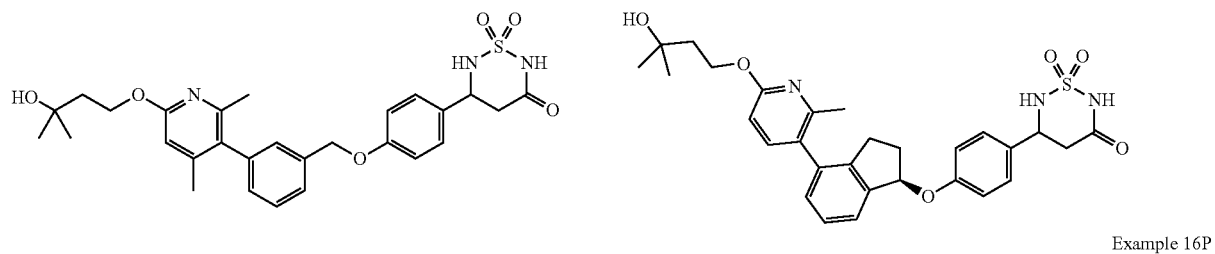
Example 16P
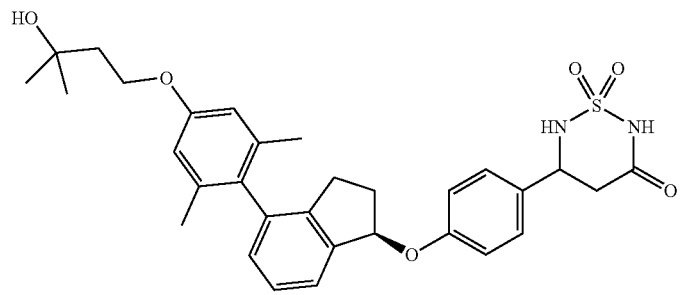
Structural Formula 4
Example 17P
Example 18P
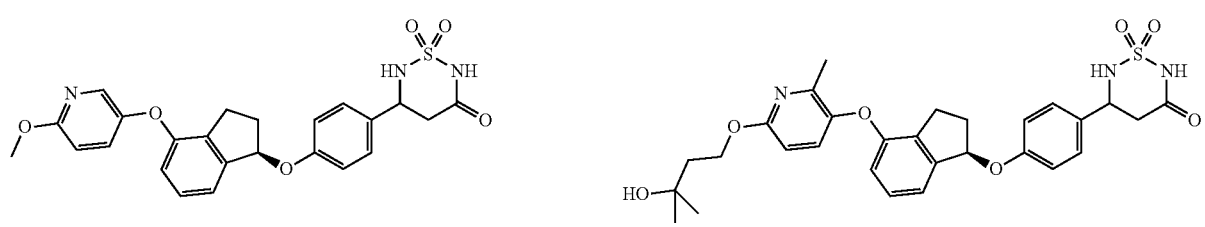
Example 19P
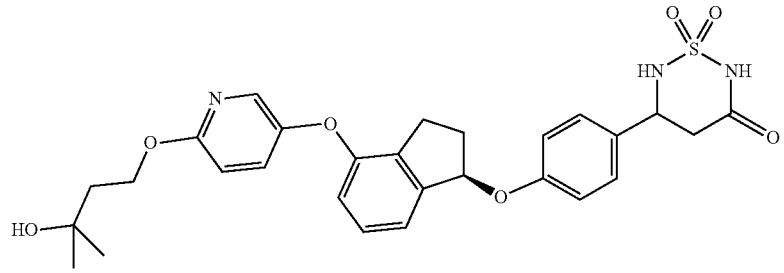

-continued
Example 20P
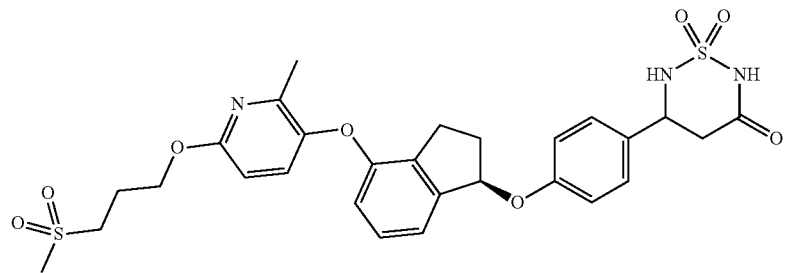
Example 21P
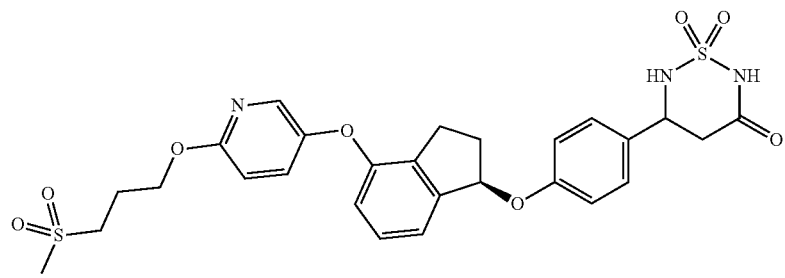
Example 22P
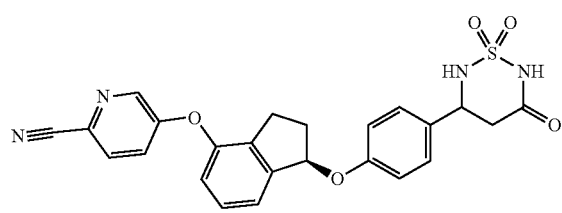
Example 23P
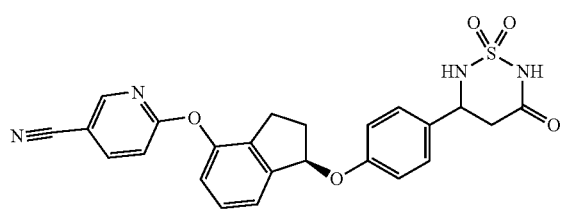
Example 24P
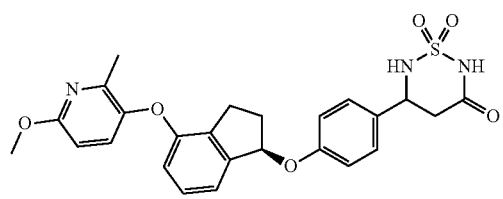
Example 25P
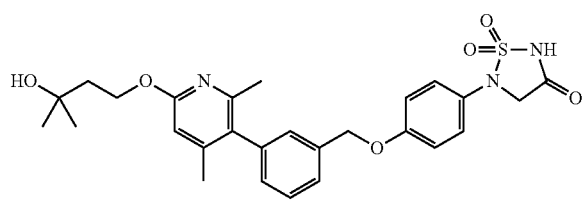
Example 26P
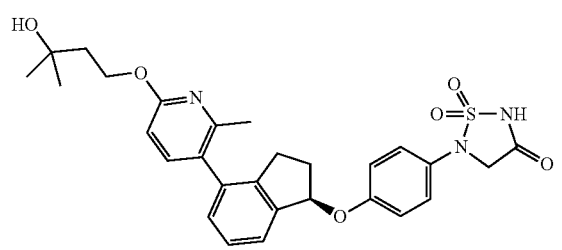
Example 27P
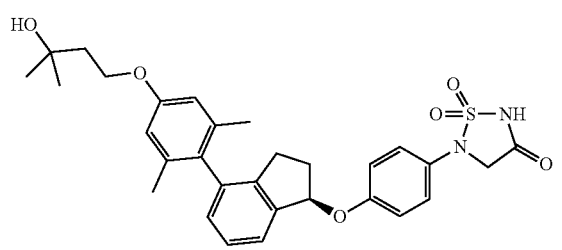
Example 28P
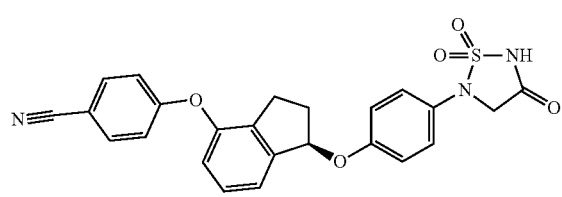
Example 29P
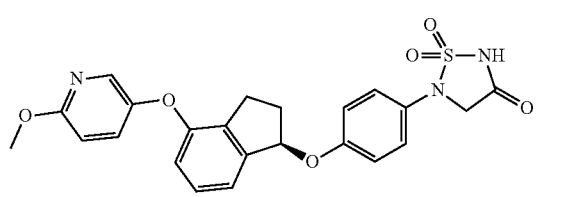

-continued
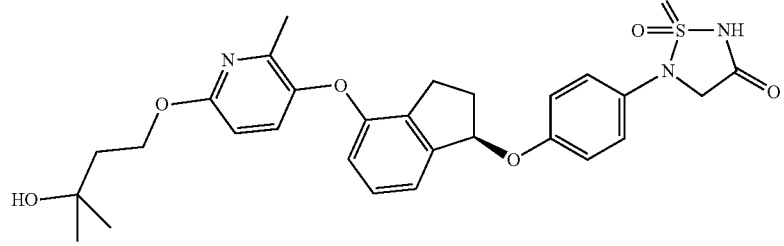
Example 30P
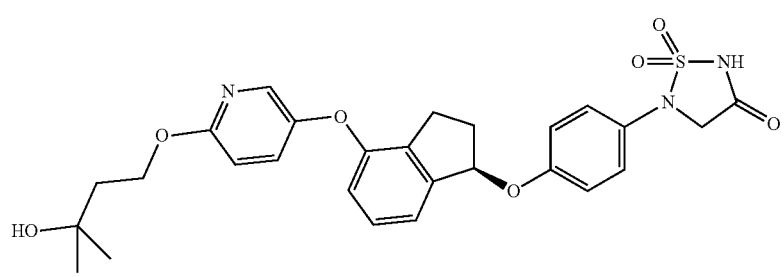
Example 31P
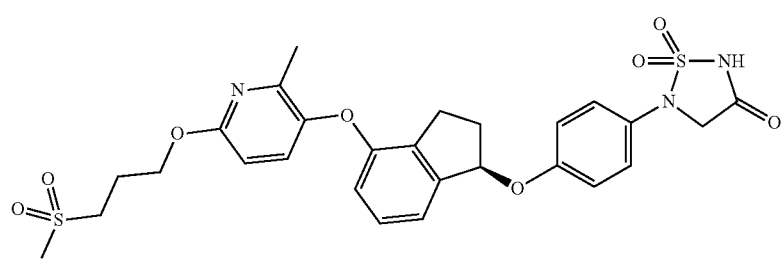
Example 32P
Structural Formula 5
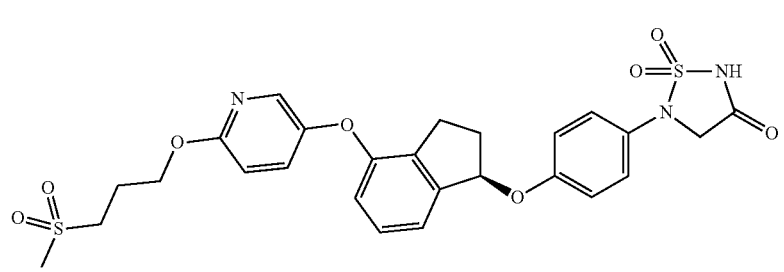
Example 33P
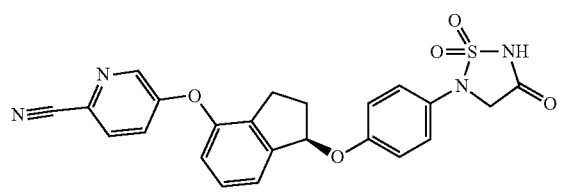
Example 34P
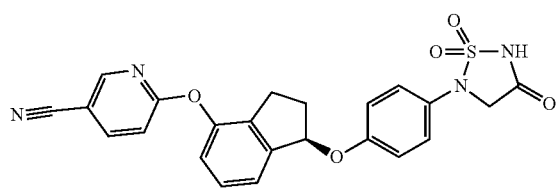
Example 35P
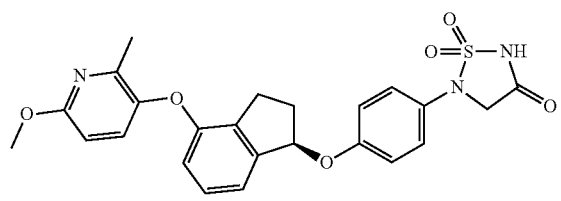
Example 36P
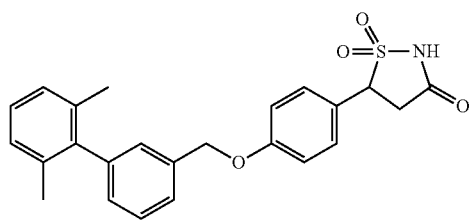
Example 37P -continued
Example 38P
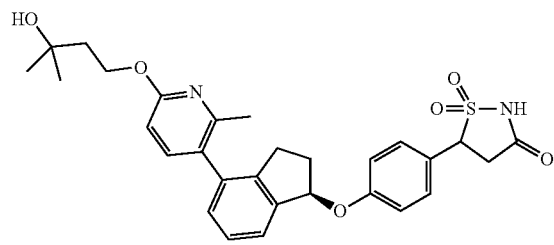
Example 39P
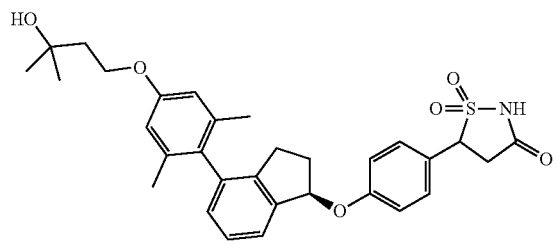
Example 40P
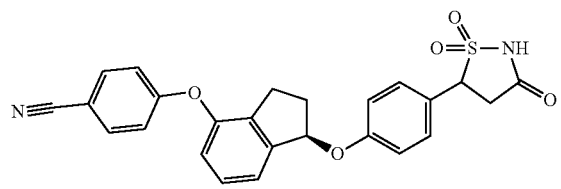
Example 41P
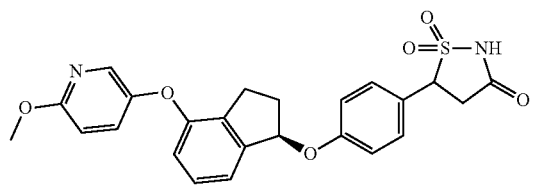
Example 42P
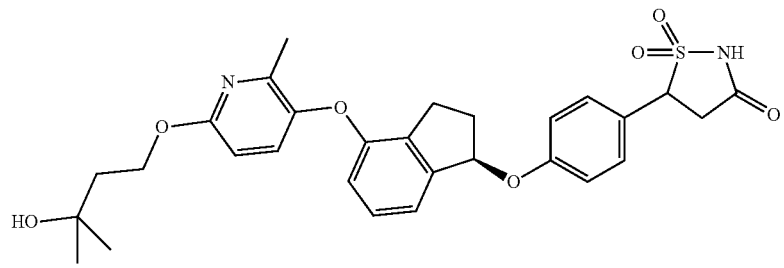
Example 43P
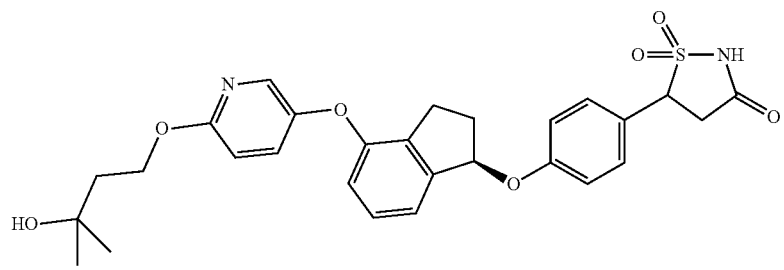
Example 44P
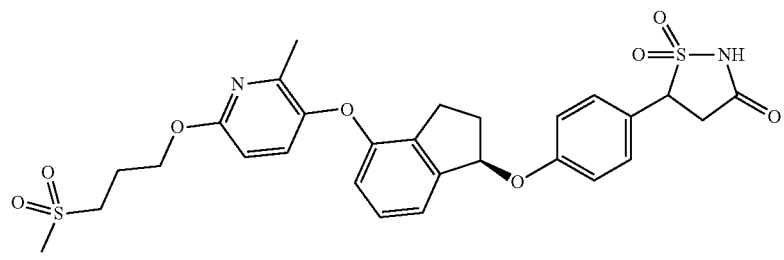
Example 45P
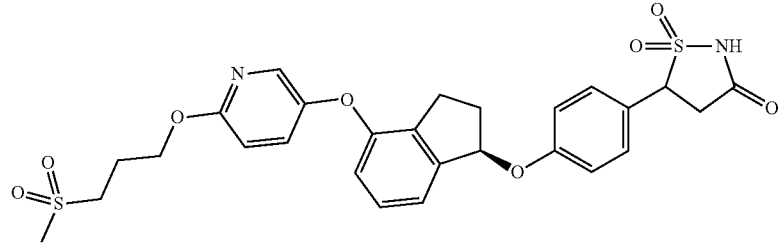

Example 46P
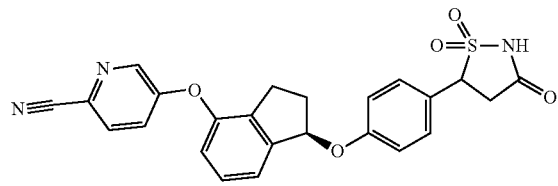
Example 47P
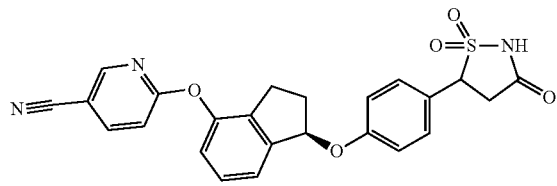
Example 48P
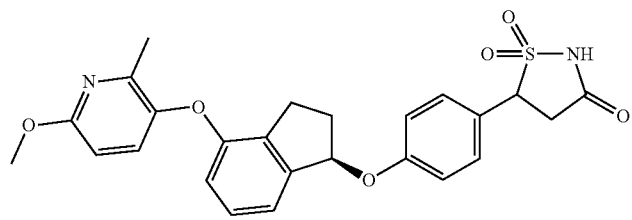
Structural Formula 6
Example 49P
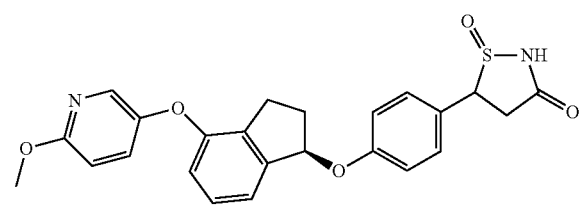
Example 53P
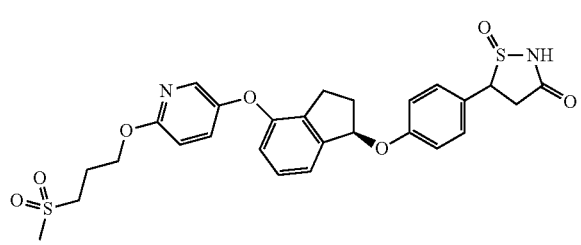
Example 50P
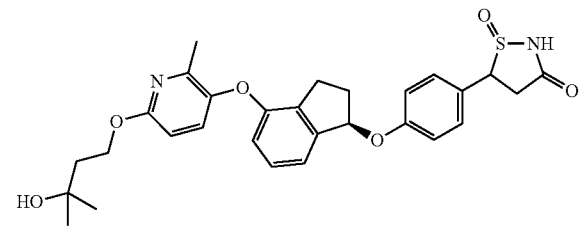
Example 54P
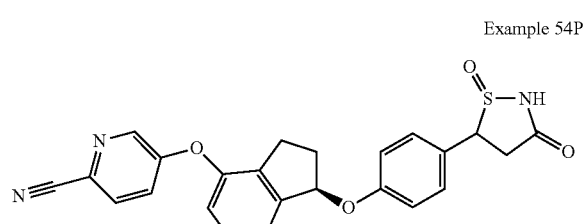
Example 51P
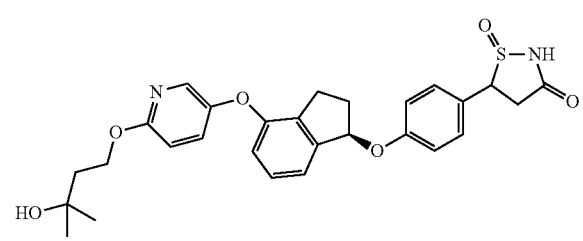
Example 55P
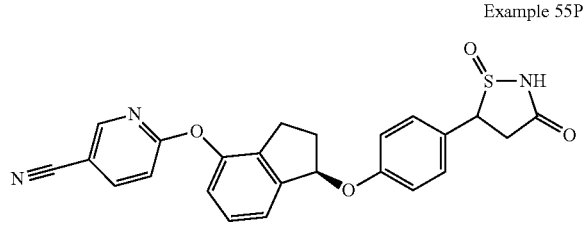
Example 52P
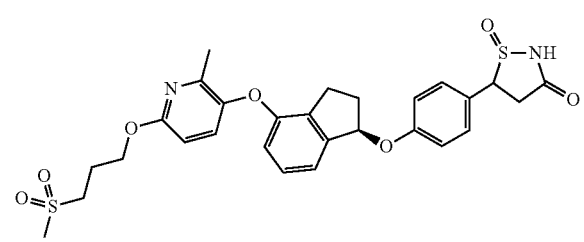
Example 56P
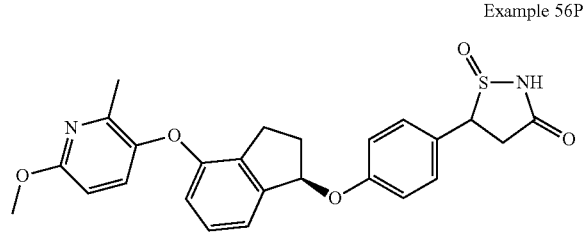

-continued
Example 57P
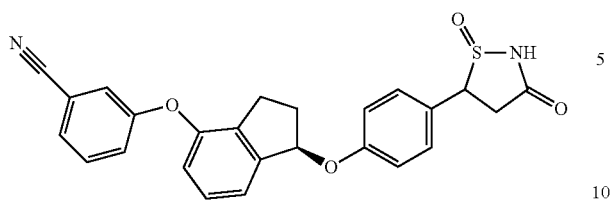
Structural Formula 7
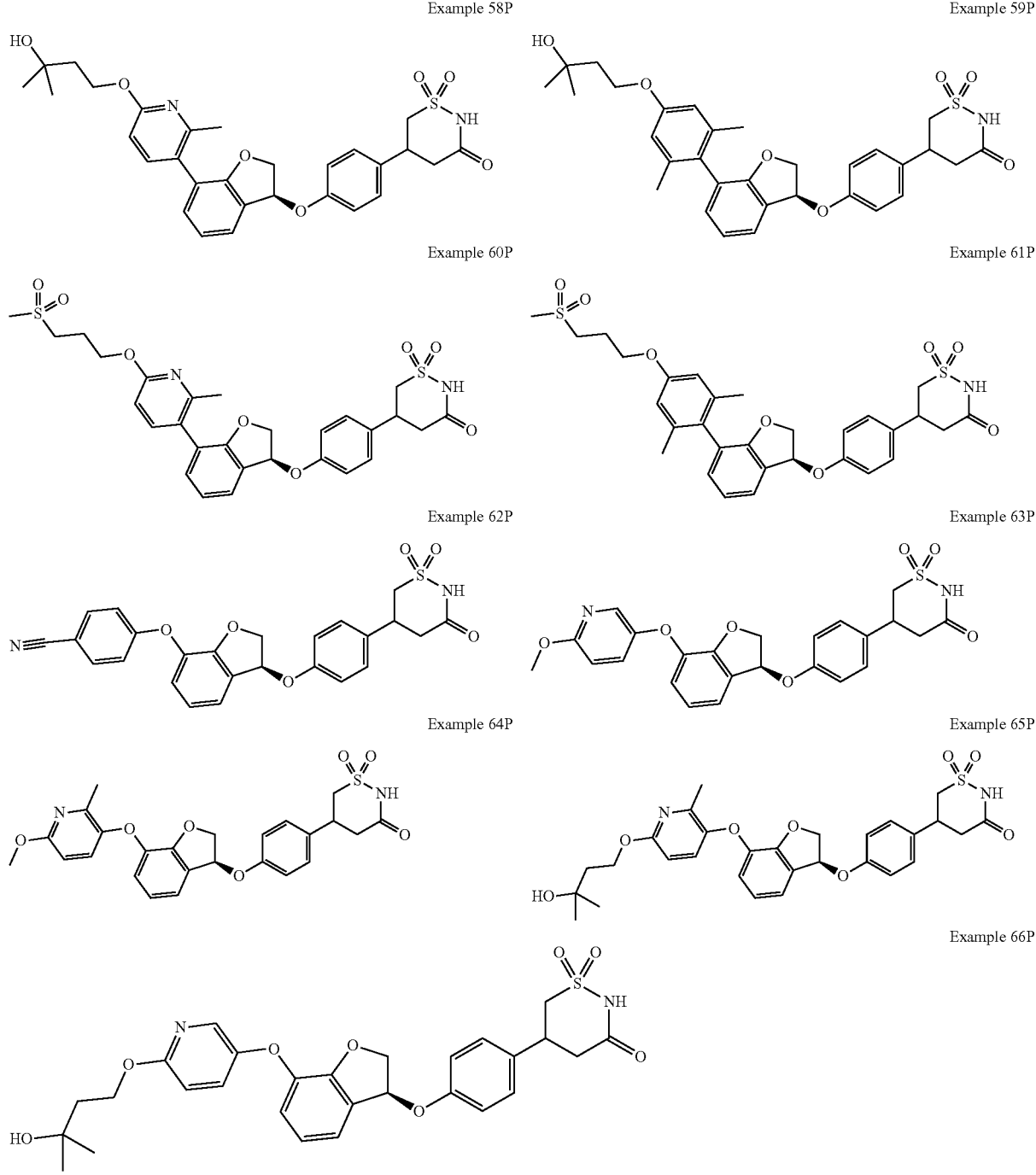

Example 67P
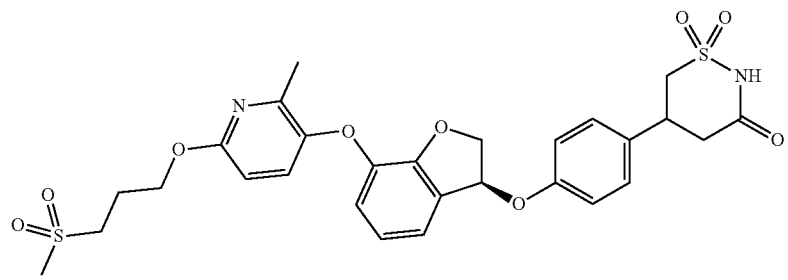
Example 68P
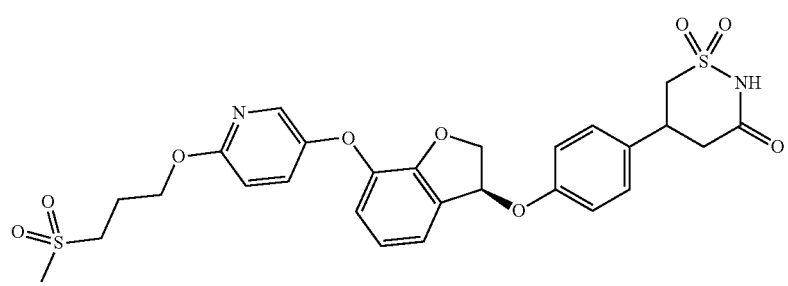
Example 69P
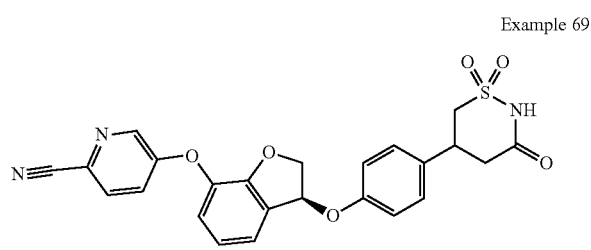
Example 70P
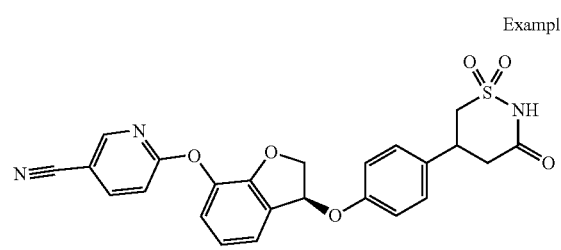
Example 71P
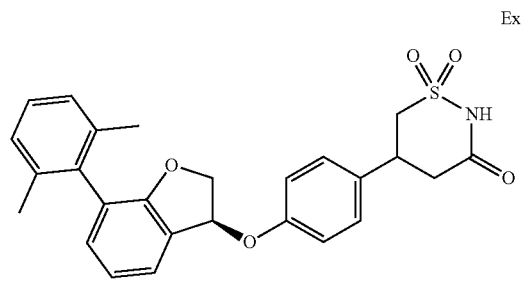
Example 72P
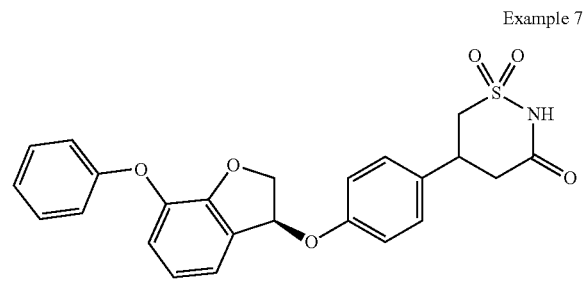
Structural Formula 8
Example 73P
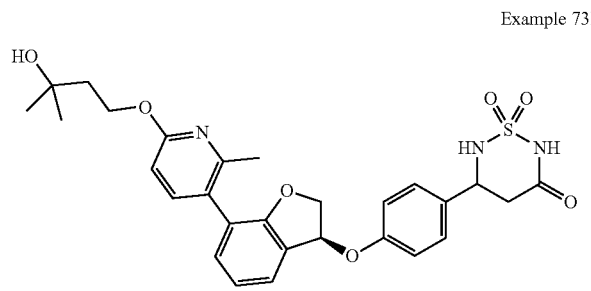
Example 74P
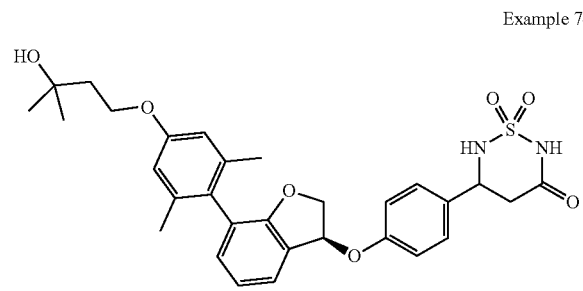

-continued
Example 75P
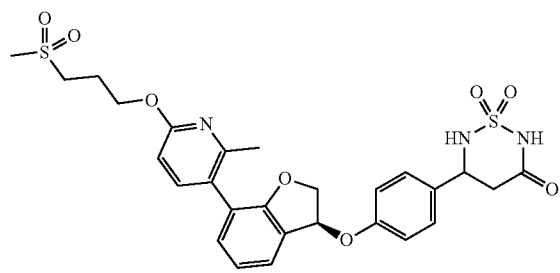
Example 76P
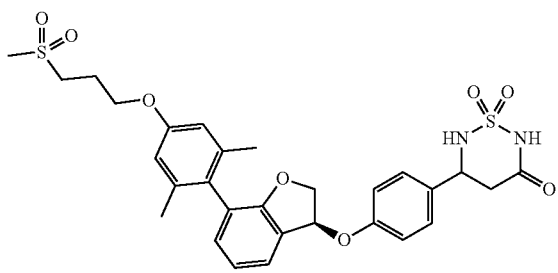
Example 77P
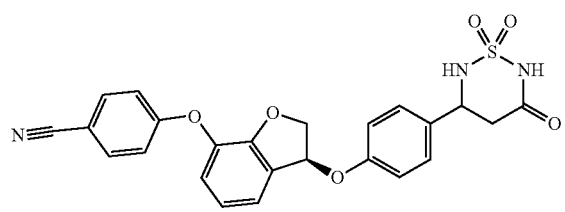
Example 78P
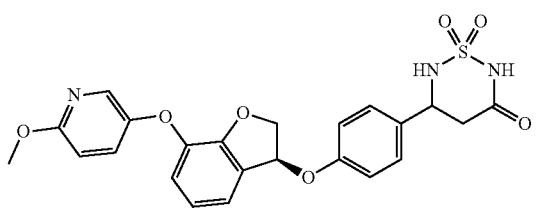
Example 79P
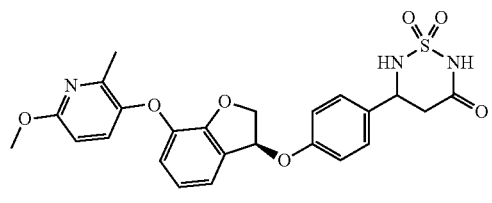
Example 80P
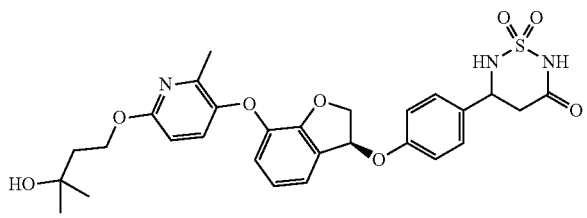
Example 81P
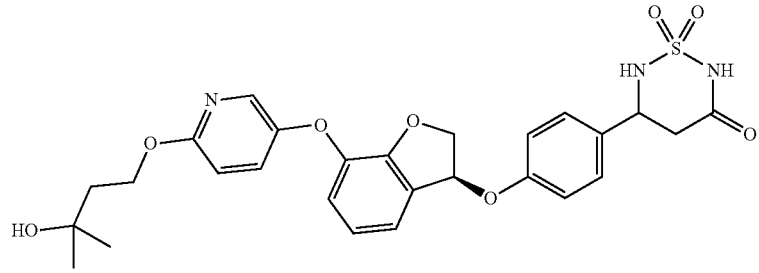
Example 82P
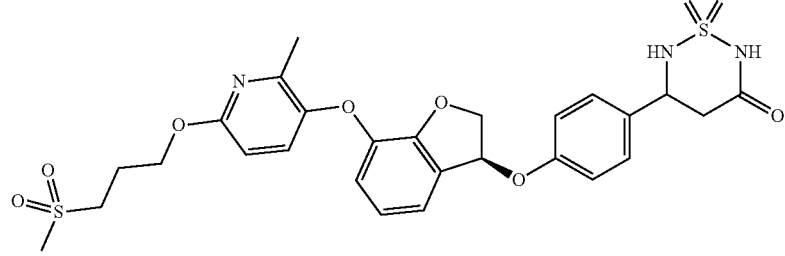
Example 83P
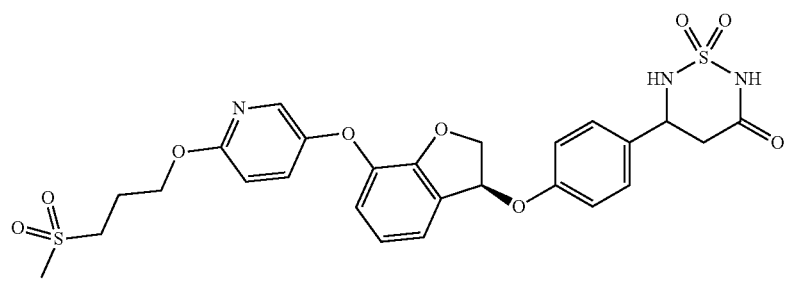

-continued
Example 84P
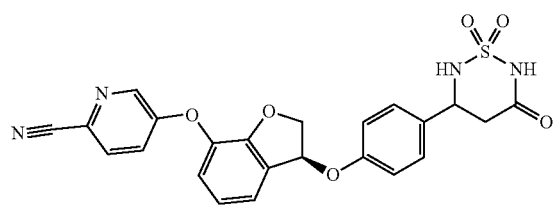
Example 85P
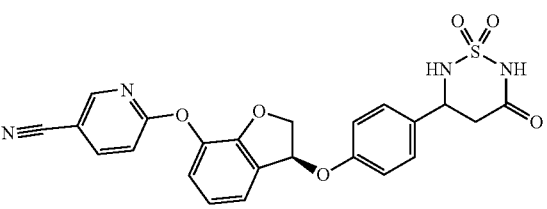
Example 86P
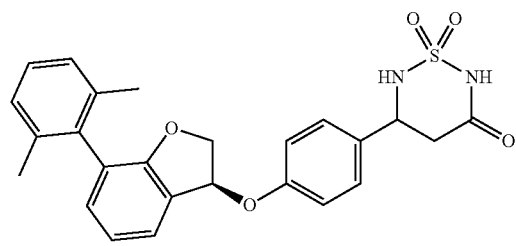
Example 87P
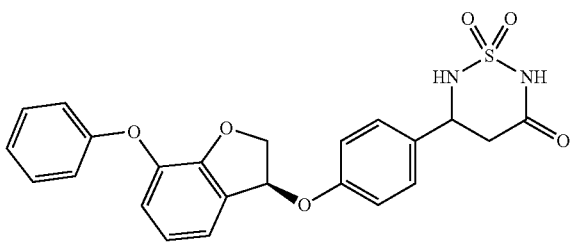
Structural Formula 9
Example 88P
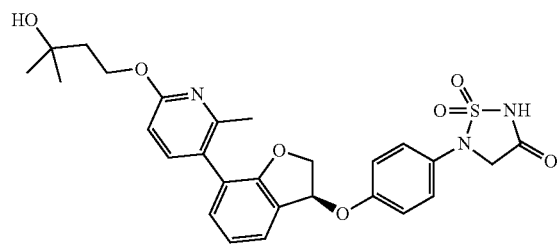
Example 89P
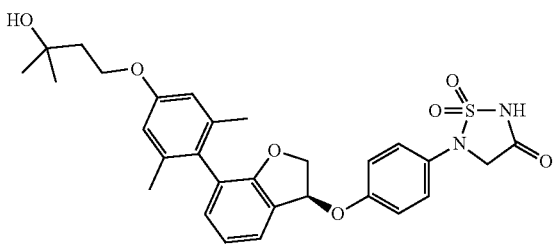
Example 90P
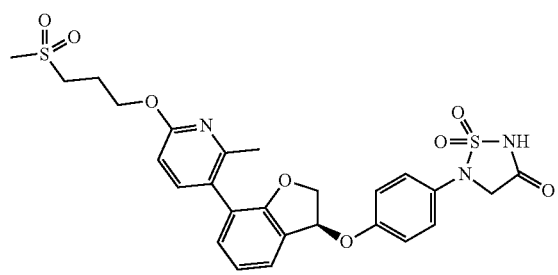
Example 91P
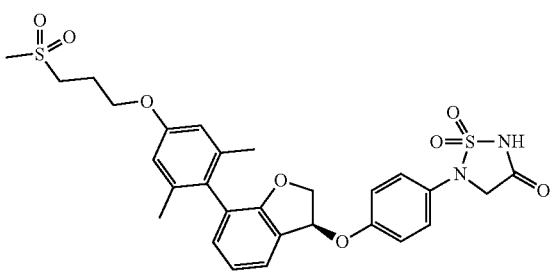
Example 92P
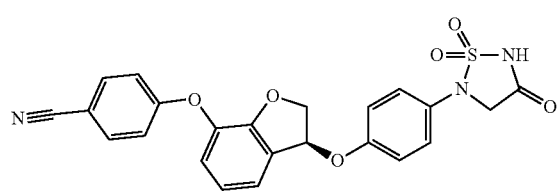
Example 93P
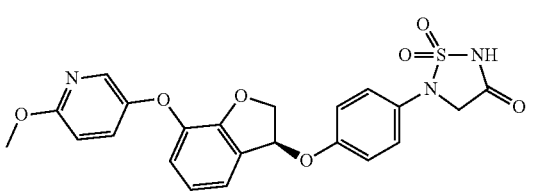
Example 94P
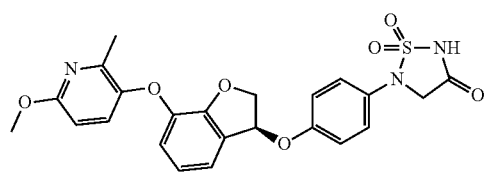
Example 95P
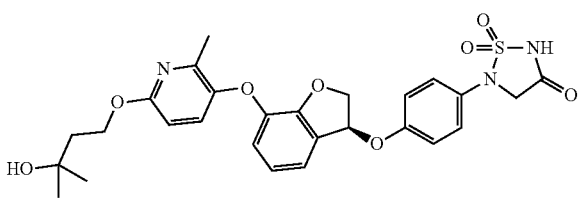

-continued
Example 96P
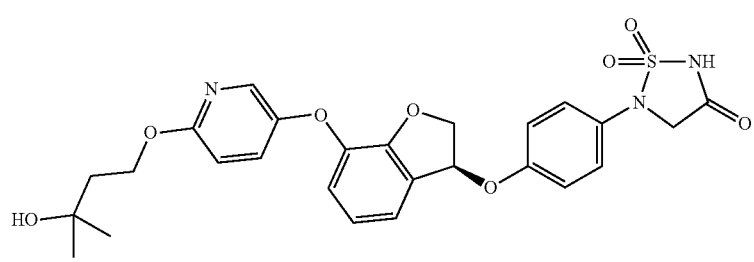
Example 97P
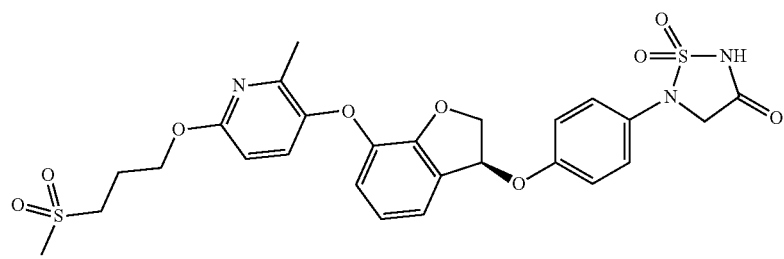
Example 98P
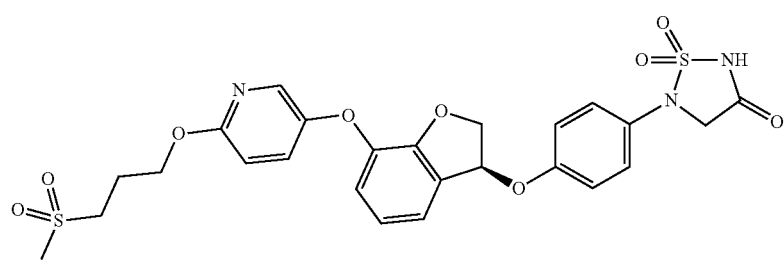
Example 99P
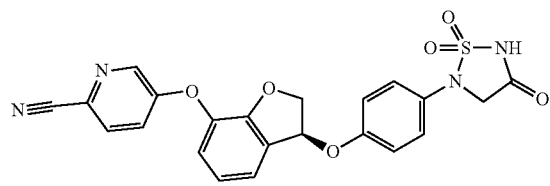
Example 100P
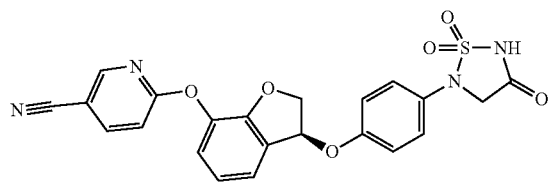
Example 101P
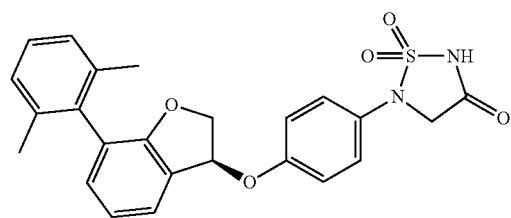
Example 102P
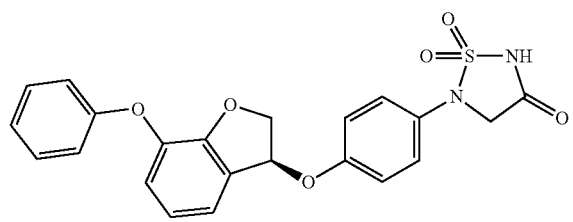
Structural Formula 10
Example 118P
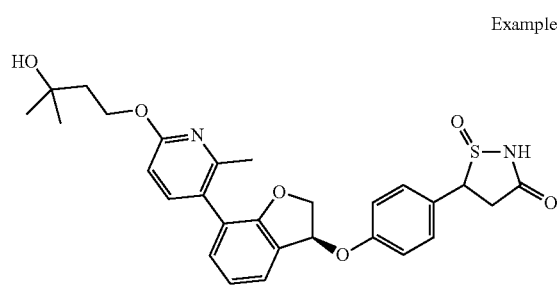
Example 119P
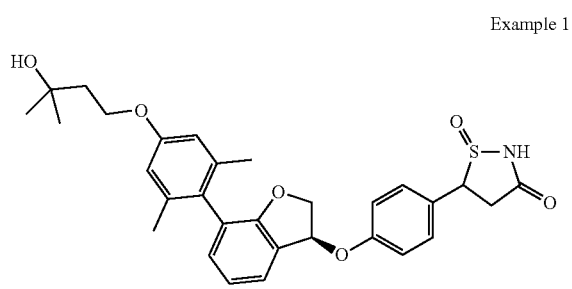

-continued
Example 120P
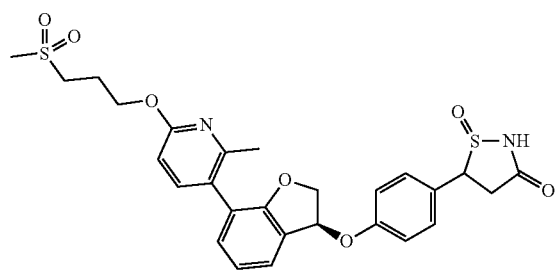
Example 121P
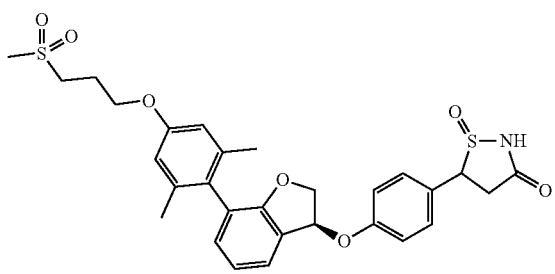
Example 122P
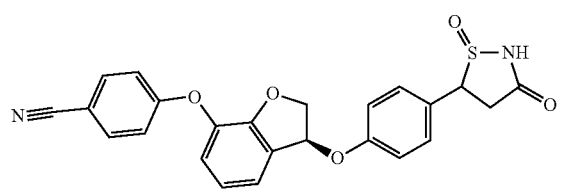
Example 123P
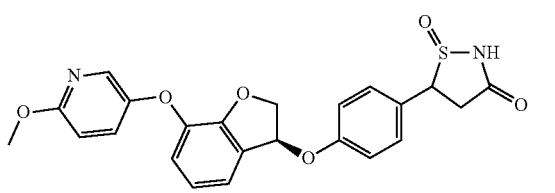
Example 124P
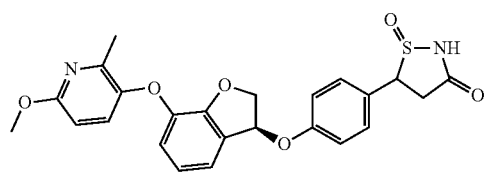
Example 125P
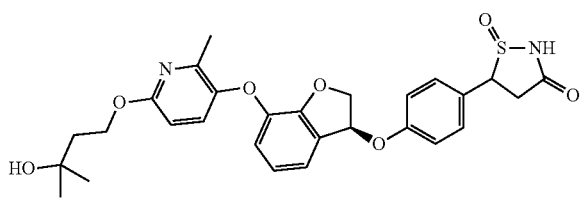
Example 126P
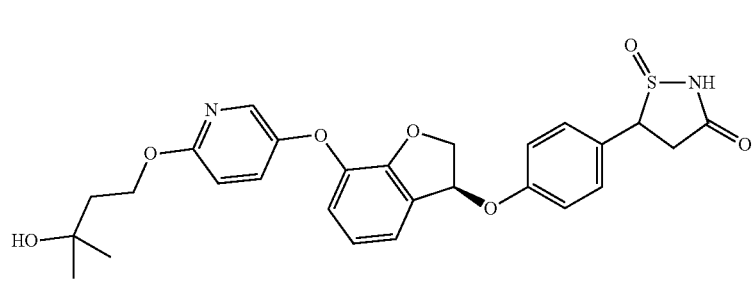
Example 127P
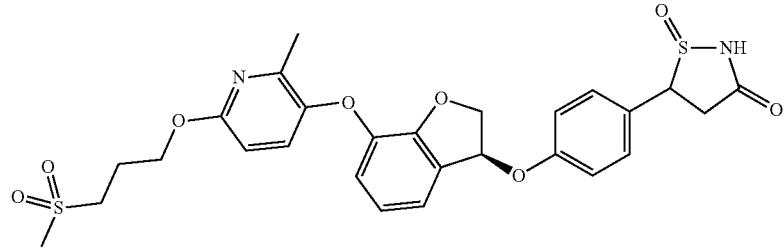
Example 128P
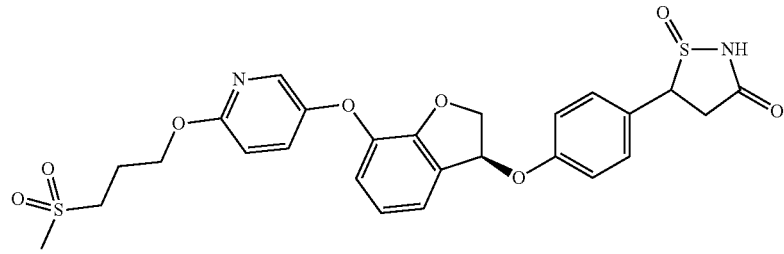

Example 129P
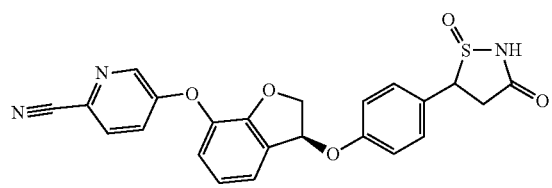
Example 130P
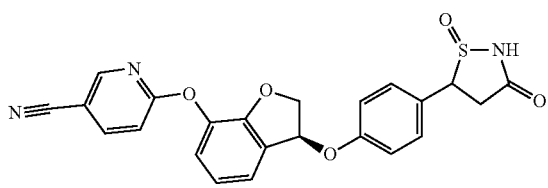
Example 131P
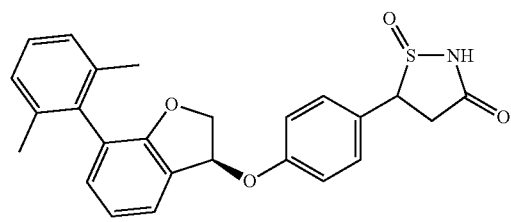
Example 132P
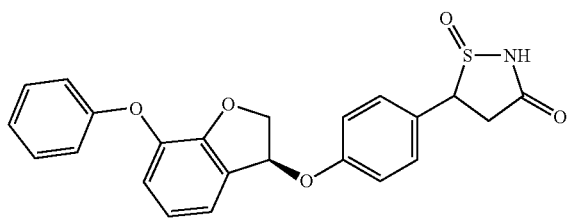
Structural Formula 11
Example 133P
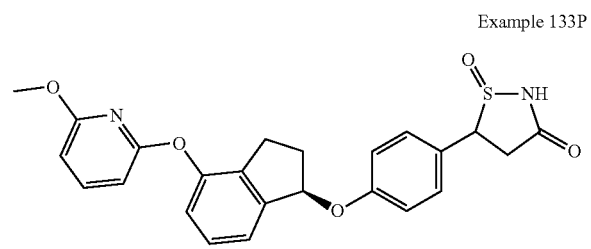
-continued
Example 137P
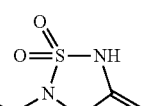
Example 134P
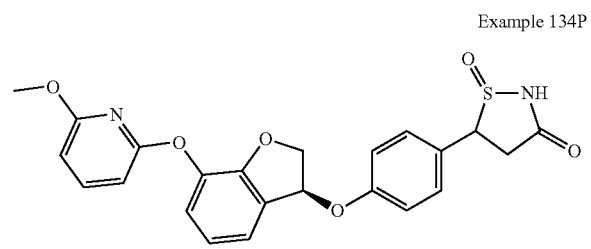
Example 138P
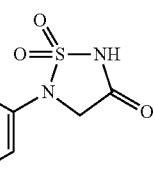
Example 135P
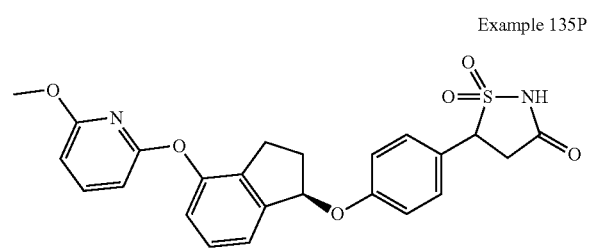
Example 139P
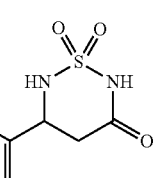
Example 136P
Example 140P
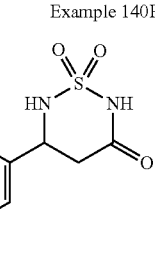

-continued
Example 141P
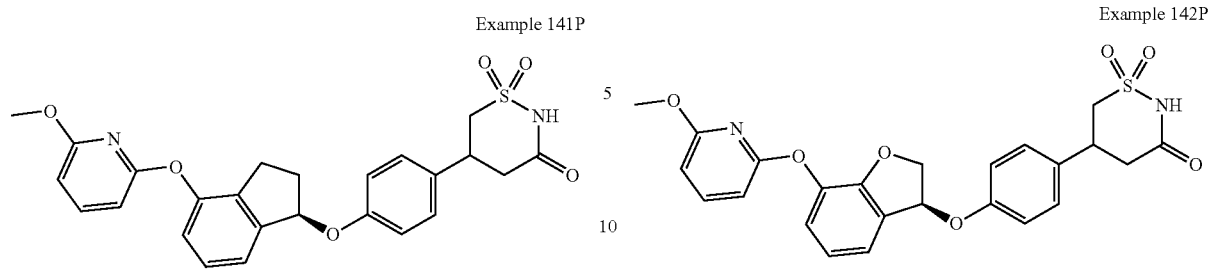
Example 143P
Example 145P
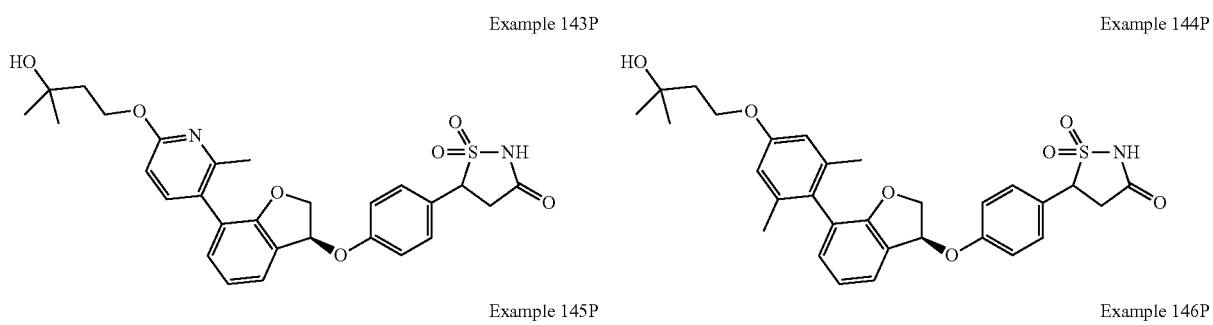
Example 147P
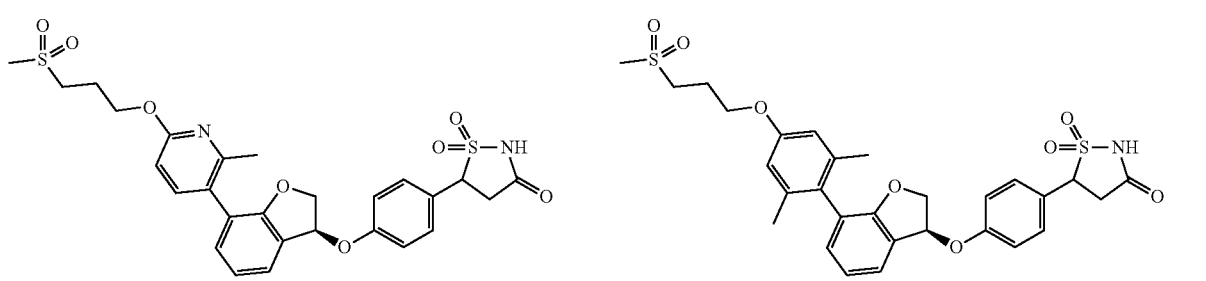
Example 149P
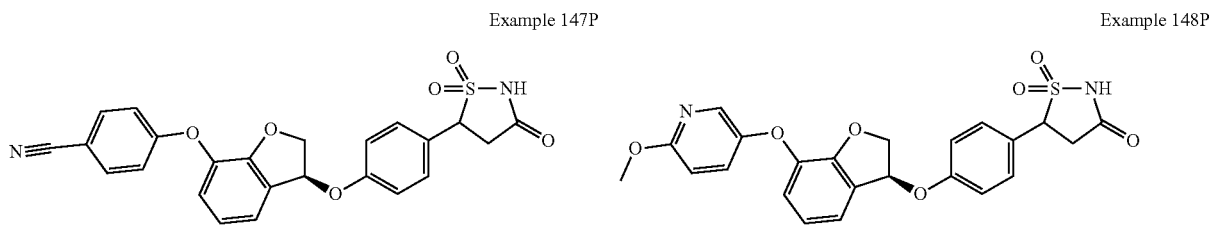
Example 151P
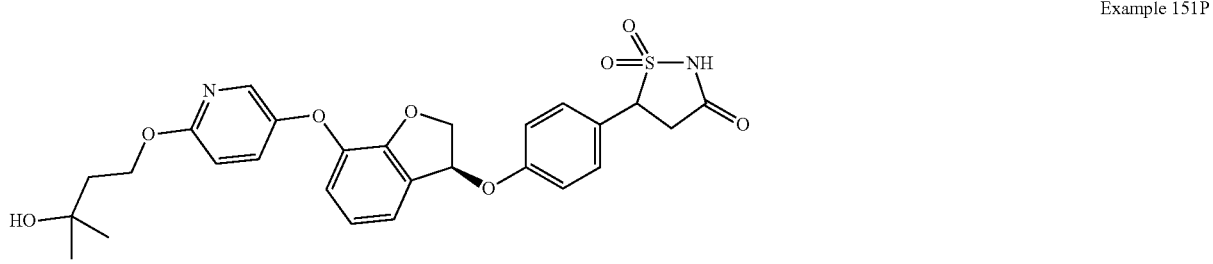
-continued
Example 142P
Structural Formula 12
Example 144P
Example 146P
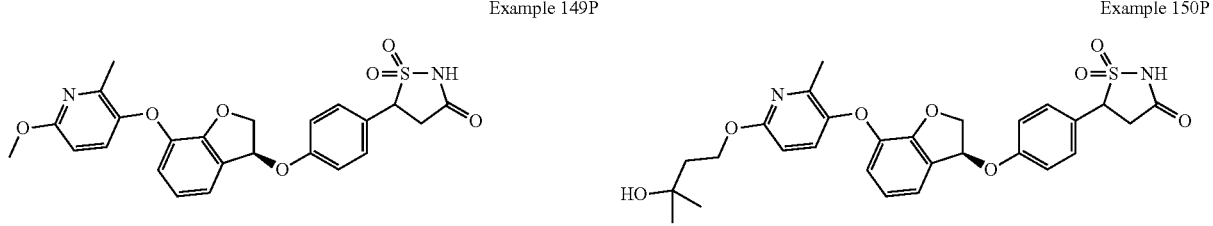
Example 148P
Example 150P -continued
Example 152P
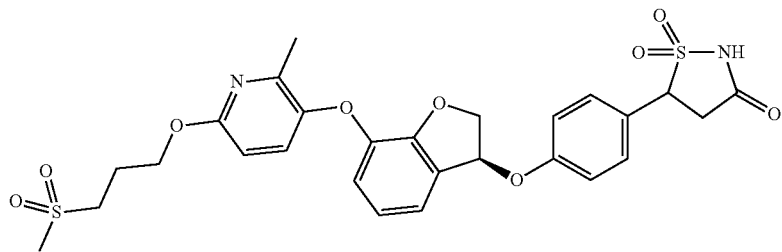
Example 153P
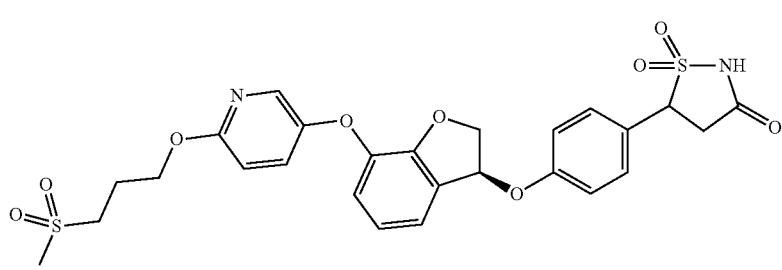
Example 154P
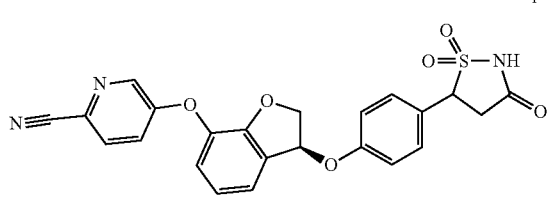
Example 155P
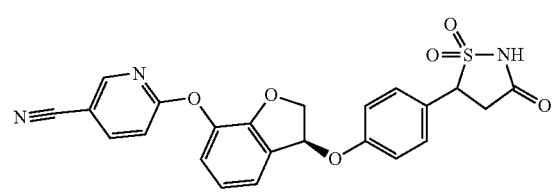
Example 156P
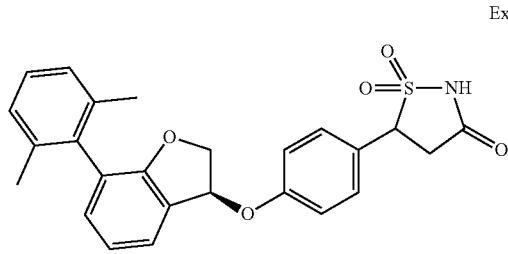
Example 157P
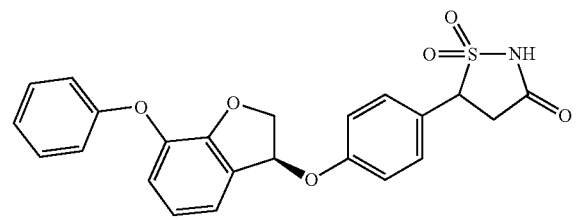
Structural Formula 13
| Example No. | Substituted Phenylboronic Ester |
|---|---|
| 1 | 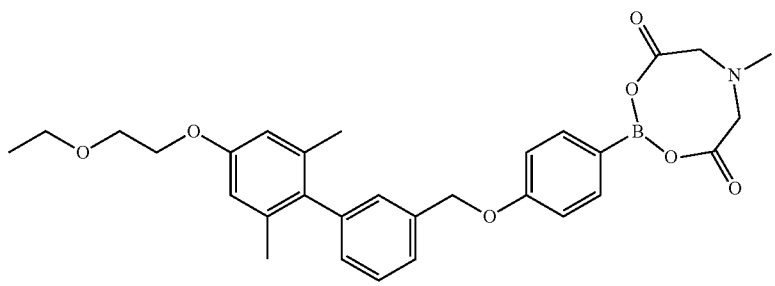 [SMILES: CCOCCOc1cc(C)c(-c2cccc(COc3ccc(B4OC(=O)CN(C)CC(=O)O4)cc3)c2)c(C)c1] |

-continued
2 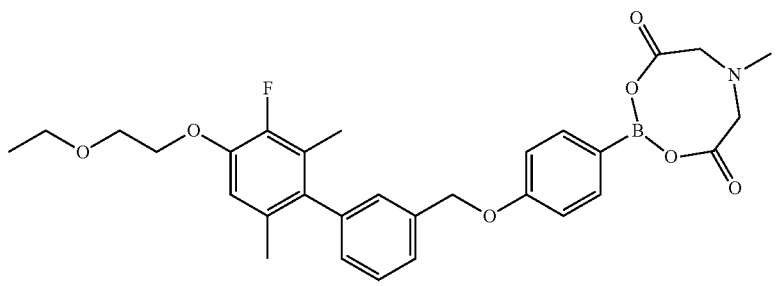 [SMILES: CCOCCOc1cc(C)c(-c2cccc(COc3ccc(B4OC(=O)CN(C)CC(=O)O4)cc3)c2)c(C)c1F]
3 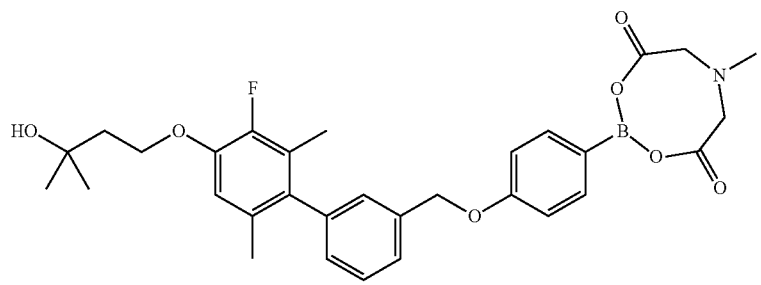 [SMILES: Cc1cc(OCCC(C)(C)O)c(F)c(C)c1-c1cccc(COc2ccc(B3OC(=O)CN(C)CC(=O)O3)cc2)c1]
4 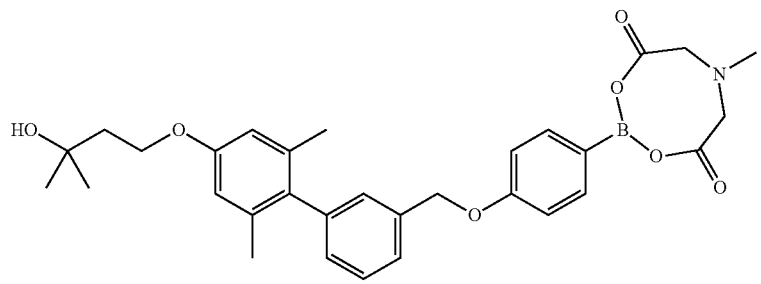 [SMILES: Cc1cc(OCCC(C)(C)O)cc(C)c1-c1cccc(COc2ccc(B3OC(=O)CN(C)CC(=O)O3)cc2)c1]
5 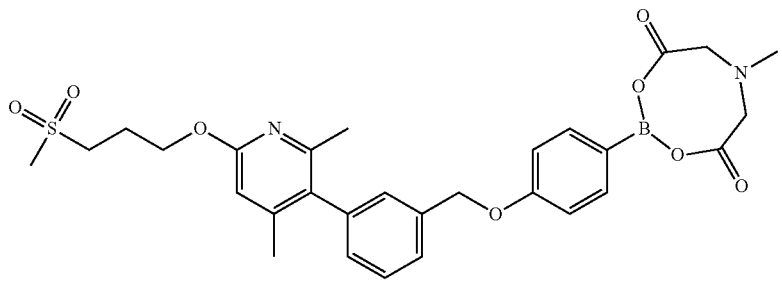 [SMILES: Cc1cc(OCCCS(C)(=O)=O)nc(C)c1-c1cccc(COc2ccc(B3OC(=O)CN(C)CC(=O)O3)cc2)c1]
6 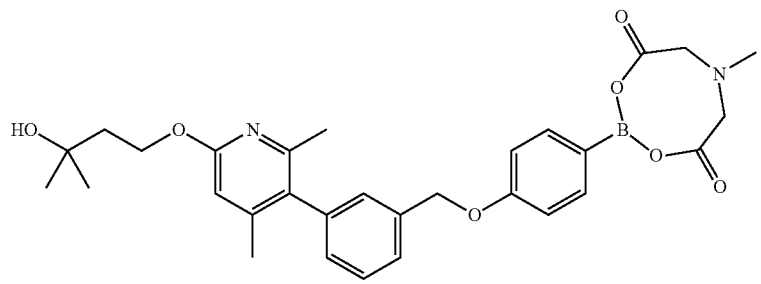 [SMILES: Cc1cc(OCCC(C)(C)O)nc(C)c1-c1cccc(COc2ccc(B3OC(=O)CN(C)CC(=O)O3)cc2)c1]

| | |
|---|---|
| 7 | 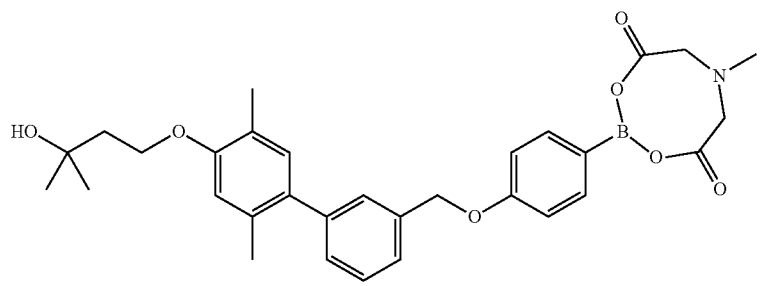 [SMILES: Cc1cc(-c2cccc(COc3ccc(B4OC(=O)CN(C)CC(=O)O4)cc3)c2)c(C)cc1OCCC(C)(C)O] |
| 8 | 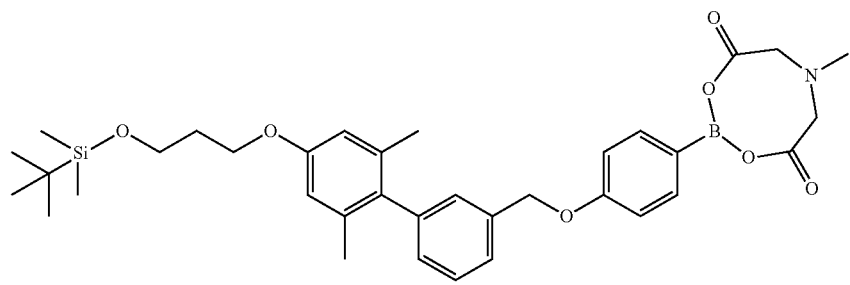 [SMILES: Cc1cc(OCCCO[Si](C)(C)C(C)(C)C)cc(C)c1-c1cccc(COc2ccc(B3OC(=O)CN(C)CC(=O)O3)cc2)c1] |
| 9 | 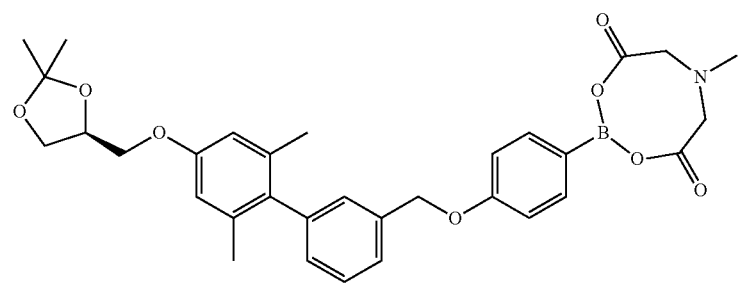 [SMILES: Cc1cc(OC[C@H]2COC(C)(C)O2)cc(C)c1-c1cccc(COc2ccc(B3OC(=O)CN(C)CC(=O)O3)cc2)c1] |
| Example No. | Substituted Isothiazole |
|---|---|
| 1 | 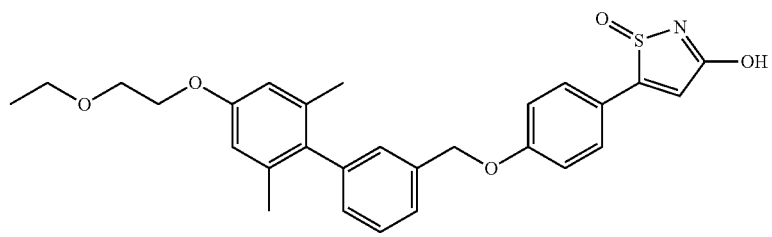 [SMILES: CCOCCOc1cc(C)c(-c2cccc(COc3ccc(C4=CC(O)=NS4=O)cc3)c2)c(C)c1] |
| 2 | 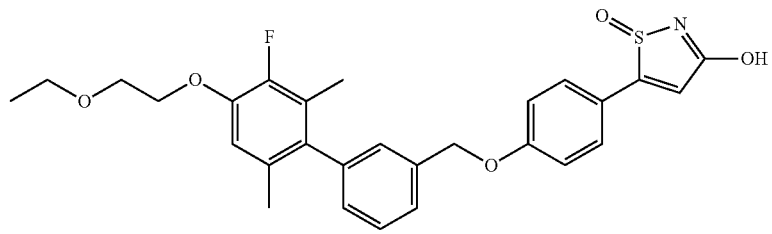 [SMILES: CCOCCOc1cc(C)c(-c2cccc(COc3ccc(C4=CC(O)=NS4=O)cc3)c2)c(C)c1F] |
| 3 | 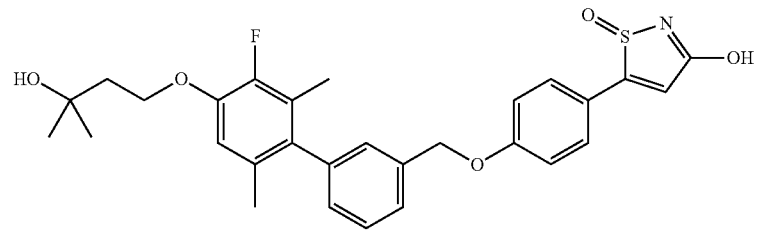 [SMILES: Cc1cc(OCCC(C)(C)O)c(F)c(C)c1-c1cccc(COc2ccc(C3=CC(O)=NS3=O)cc2)c1] |

4 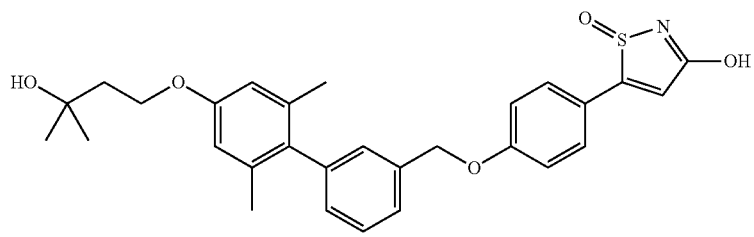 [SMILES: Cc1cc(OCCC(C)(C)O)cc(C)c1-c1cccc(COc2ccc(C3=CC(O)=NS3=O)cc2)c1]
5 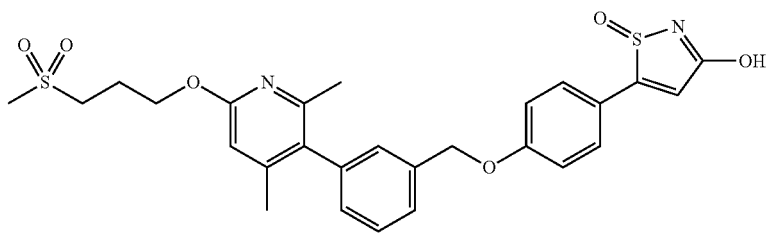 [SMILES: Cc1cc(OCCCS(C)(=O)=O)nc(C)c1-c1cccc(COc2ccc(C3=CC(O)=NS3=O)cc2)c1]
6 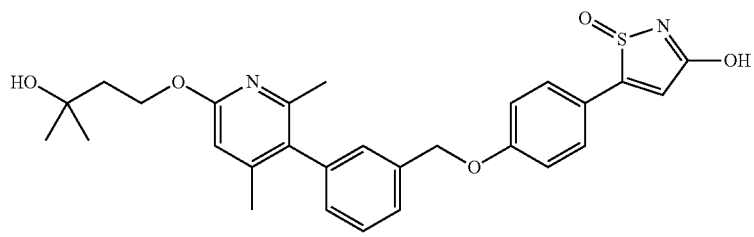 [SMILES: Cc1cc(OCCC(C)(C)O)nc(C)c1-c1cccc(COc2ccc(C3=CC(O)=NS3=O)cc2)c1]
7 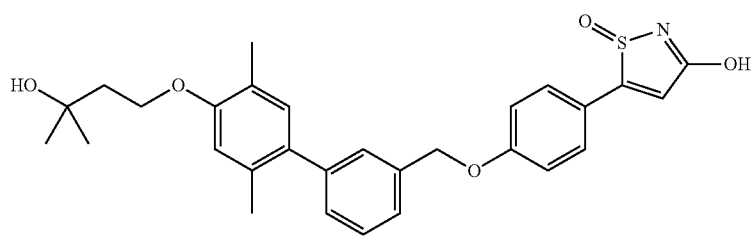 [SMILES: Cc1cc(-c2cccc(COc3ccc(C4=CC(O)=NS4=O)cc3)c2)c(C)cc1OCCC(C)(C)O]
8 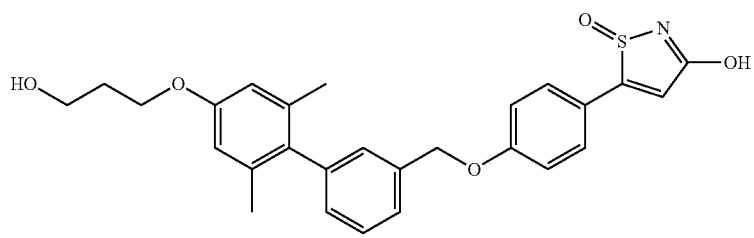 [SMILES: Cc1cc(OCCCO)cc(C)c1-c1cccc(COc2ccc(C3=CC(O)=NS3=O)cc2)c1]
9 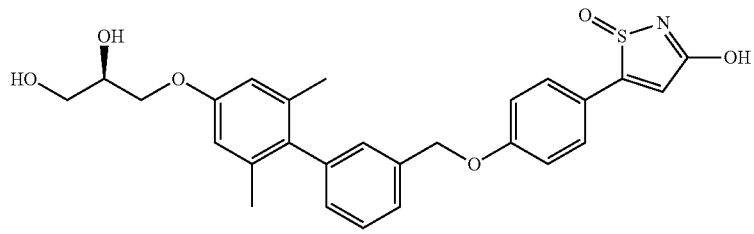 [SMILES: Cc1cc(OC[C@H](O)CO)cc(C)c1-c1cccc(COc2ccc(C3=CC(O)=NS3=O)cc2)c1]

Structural Formula 14
| Example No. | Substituted Phenylboronic Ester |
|---|---|
| 10 | 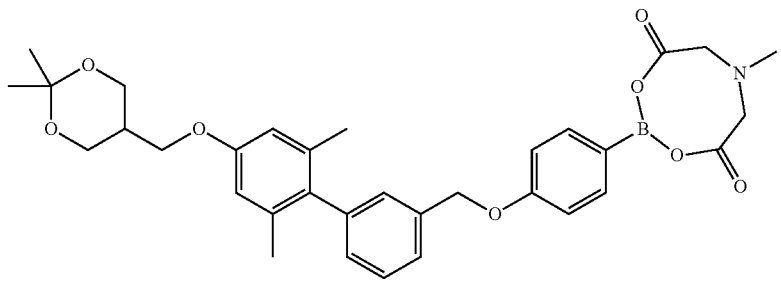 |
| 11 | 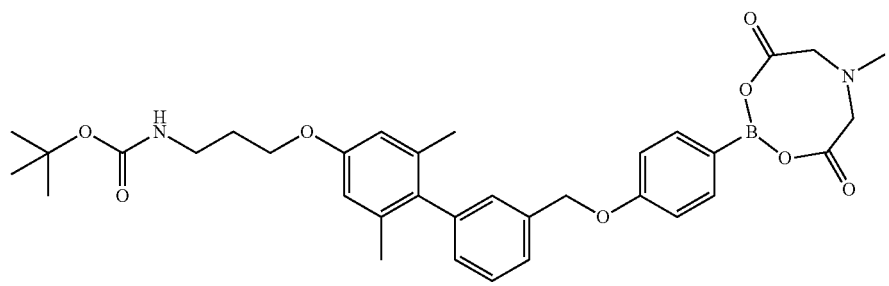 [SMILES: Cc1cc(OCCCNC(=O)OC(C)(C)C)cc(C)c1-c1cccc(COc2ccc(B3OC(=O)CN(C)CC(=O)O3)cc2)c1] |
| 12 | 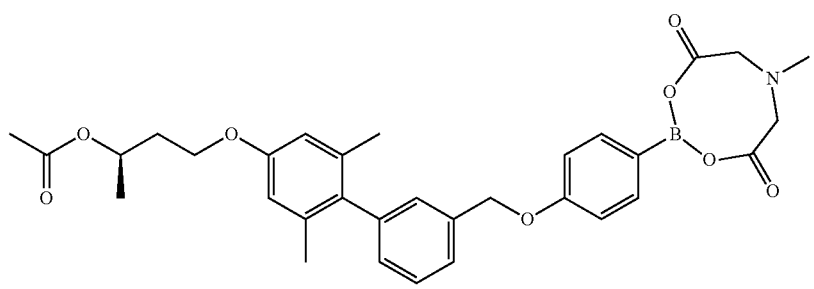 [SMILES: CC(=O)O[C@H](C)CCOc1cc(C)c(-c2cccc(COc3ccc(B4OC(=O)CN(C)CC(=O)O4)cc3)c2)c(C)c1] |
| 13 | 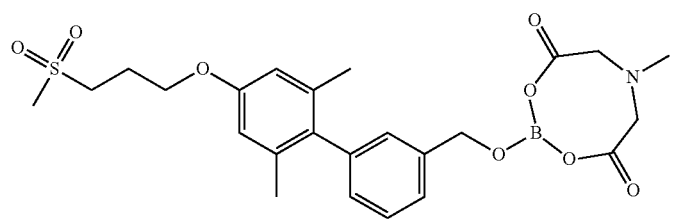 [SMILES: Cc1cc(OCCCS(C)(=O)=O)cc(C)c1-c1cccc(COB2OC(=O)CN(C)CC(=O)O2)c1] |
| Example No. | Substituted Isothiazole |
|---|---|
| 10 | 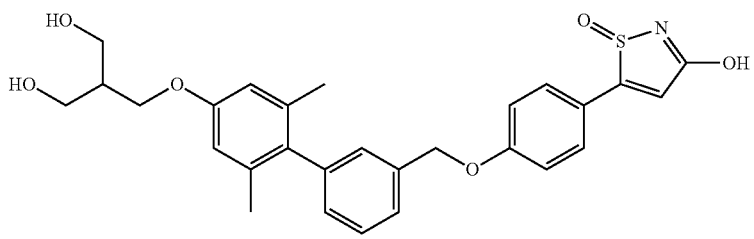 [SMILES: Cc1cc(OCC(CO)CO)cc(C)c1-c1cccc(COc2ccc(C3=CC(O)=NS3=O)cc2)c1] |

-continued
11 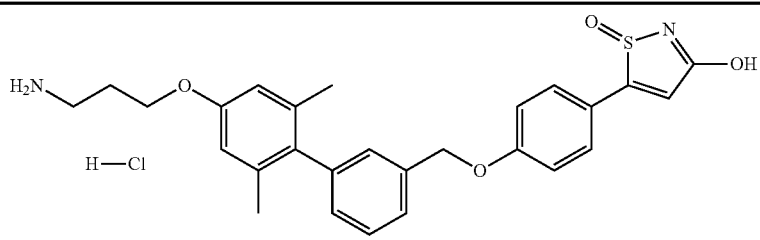
12 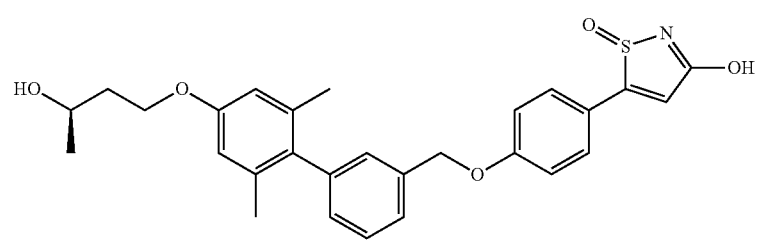 [SMILES: Cc1cc(OCC[C@@H](C)O)cc(C)c1-c1cccc(COc2ccc(C3=CC(O)=NS3=O)cc2)c1]
13 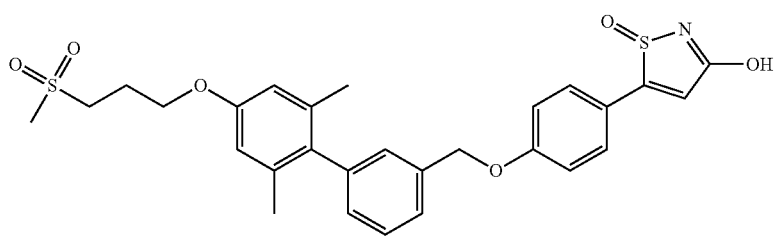 [SMILES: Cc1cc(OCCCS(C)(=O)=O)cc(C)c1-c1cccc(COc2ccc(C3=CC(O)=NS3=O)cc2)c1]
Structural Formula 15
| No. | Structure |
|---|---|
| 14-1 | 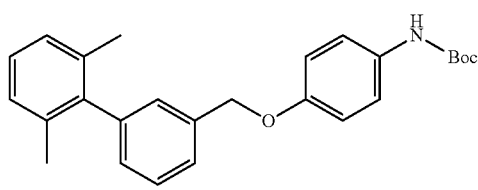 [SMILES: Cc1cccc(C)c1-c1cccc(COc2ccc(NC(=O)OC(C)(C)C)cc2)c1] |
| 14-2 | 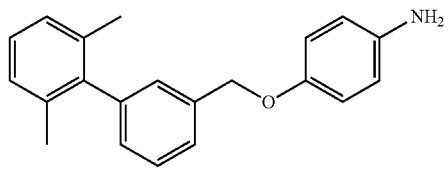 [SMILES: Cc1cccc(C)c1-c1cccc(COc2ccc(N)cc2)c1] |
| 14-3 | 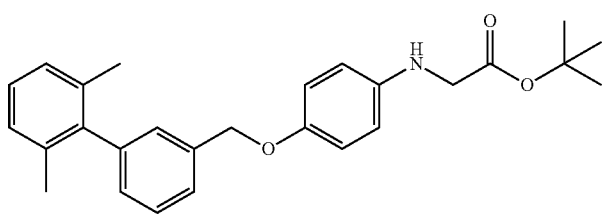 [SMILES: Cc1cccc(C)c1-c1cccc(COc2ccc(NCC(=O)OC(C)(C)C)cc2)c1] |

-continued
| No. | Structure |
|---|---|
| 14-4 | 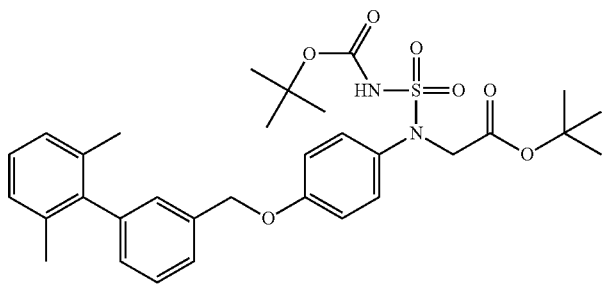 [SMILES: Cc1cccc(C)c1-c1cccc(COc2ccc(N(CC(=O)OC(C)(C)C)S(=O)(=O)NC(=O)OC(C)(C)C)cc2)c1] |
| 14-5 | 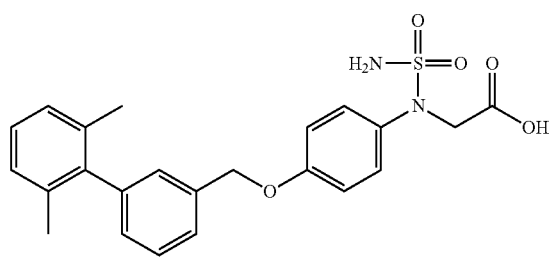 [SMILES: Cc1cccc(C)c1-c1cccc(COc2ccc(N(CC(=O)O)S(N)(=O)=O)cc2)c1] |
| 15-1 | 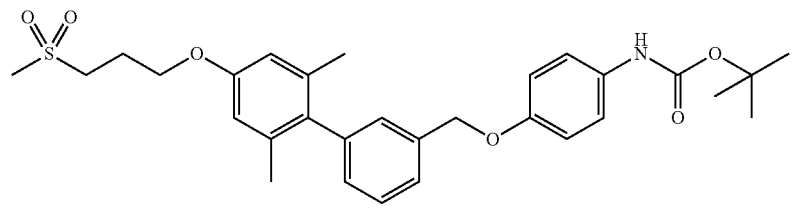 [SMILES: Cc1cc(OCCCS(C)(=O)=O)cc(C)c1-c1cccc(COc2ccc(NC(=O)OC(C)(C)C)cc2)c1] |
| 15-2 | 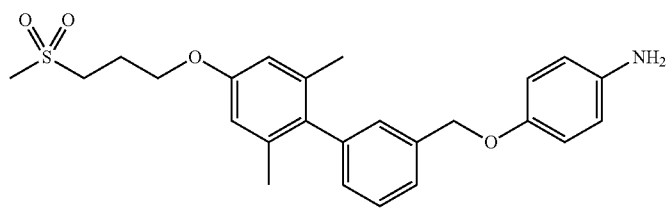 [SMILES: Cc1cc(OCCCS(C)(=O)=O)cc(C)c1-c1cccc(COc2ccc(N)cc2)c1] |
| 15-3 | 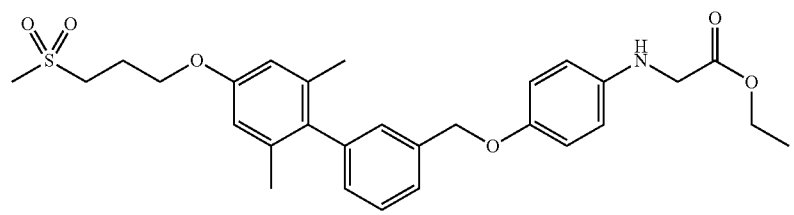 [SMILES: CCOC(=O)CNc1ccc(OCc2cccc(-c3c(C)cc(OCCCS(C)(=O)=O)cc3C)c2)cc1] |
| 15-4 | 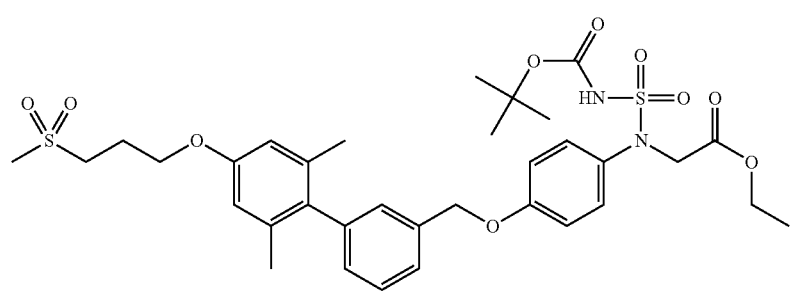 [SMILES: CCOC(=O)CN(c1ccc(OCc2cccc(-c3c(C)cc(OCCCS(C)(=O)=O)cc3C)c2)cc1)S(=O)(=O)NC(=O)OC(C)(C)C] |

-continued

| No. | Structure |
|---|---|
| 15-5 | 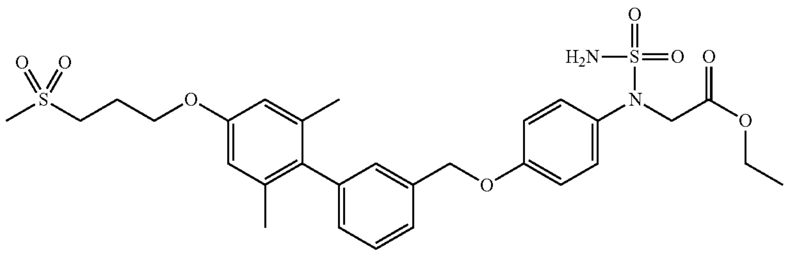 [SMILES: CCOC(=O)CN(c1ccc(OCc2cccc(-c3c(C)cc(OCCCS(C)(=O)=O)cc3C)c2)cc1)S(N)(=O)=O] |
| 16-1 | 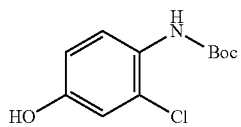 [SMILES: CC(C)(C)OC(=O)Nc1ccc(O)cc1Cl] |
| 16-2 | 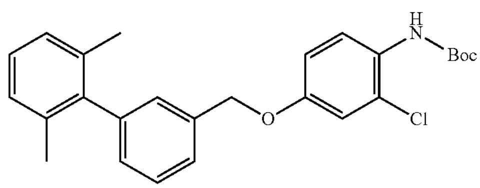 [SMILES: Cc1cccc(C)c1-c1cccc(COc2ccc(NC(=O)OC(C)(C)C)c(Cl)c2)c1] |
| 16-3 | 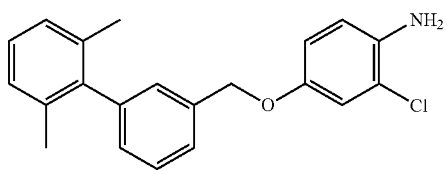 [SMILES: Cc1cccc(C)c1-c1cccc(COc2ccc(N)c(Cl)c2)c1] |
| 16-4 | 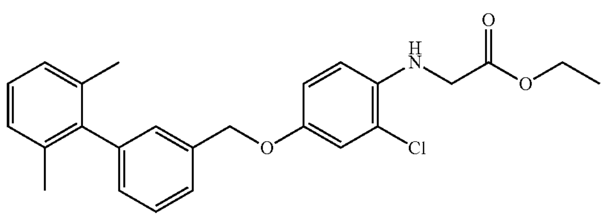 [SMILES: CCOC(=O)CNc1ccc(OCc2cccc(-c3c(C)cccc3C)c2)cc1Cl] |
| 16-5 | 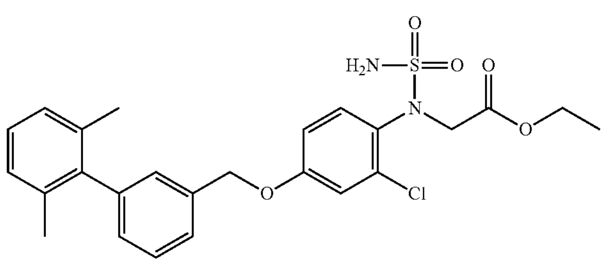 |
| 17-1 | 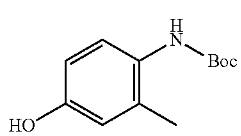 [SMILES: Cc1cc(O)ccc1NC(=O)OC(C)(C)C] |
| 17-2 | 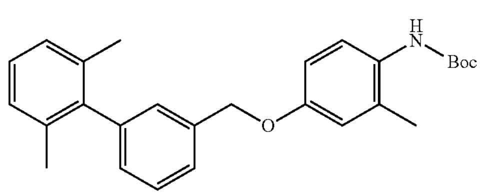 [SMILES: Cc1cc(OCc2cccc(-c3c(C)cccc3C)c2)ccc1NC(=O)OC(C)(C)C] |

-continued

| No. | Structure |
|---|---|
| 17-3 | 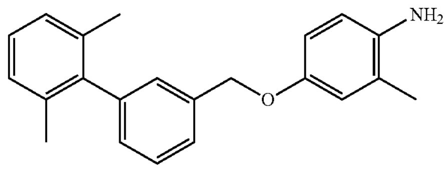 [SMILES: Cc1cc(OCc2cccc(-c3c(C)cccc3C)c2)ccc1N] |
| 17-4 | 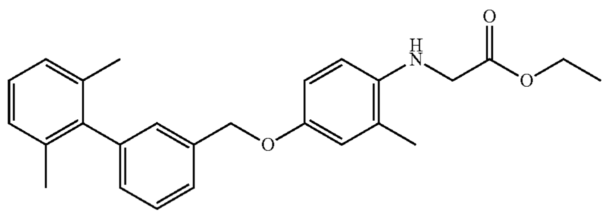 [SMILES: CCOC(=O)CNc1ccc(OCc2cccc(-c3c(C)cccc3C)c2)cc1C] |
| 17-5 | 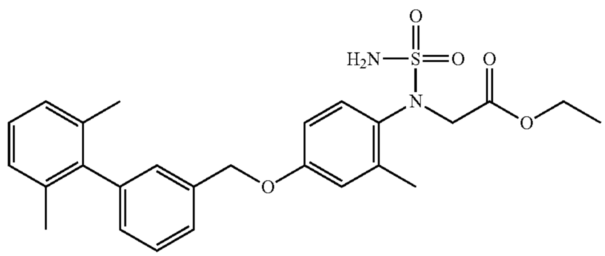 [SMILES: CCOC(=O)CN(c1ccc(OCc2cccc(-c3c(C)cccc3C)c2)cc1C)S(N)(=O)=O] |
| 18-1 | 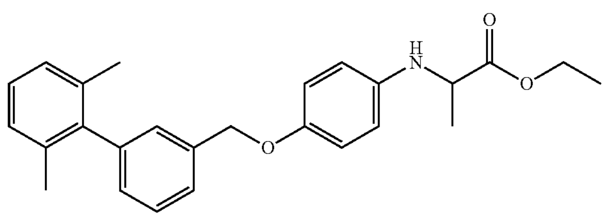 [SMILES: CCOC(=O)C(C)Nc1ccc(OCc2cccc(-c3c(C)cccc3C)c2)cc1] |
| 18-2 | 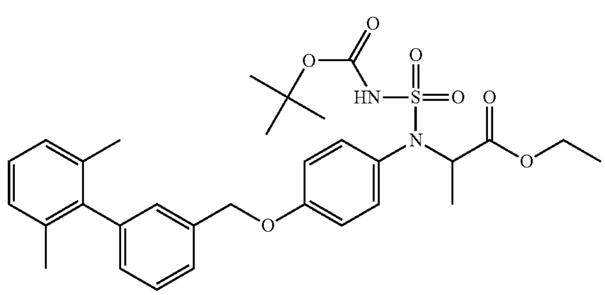 [SMILES: CCOC(=O)C(C)N(c1ccc(OCc2cccc(-c3c(C)cccc3C)c2)cc1)S(=O)(=O)NC(=O)OC(C)(C)C] |

Structural Formula 16

| No. | Structure |
|---|---|
| 18-3 | 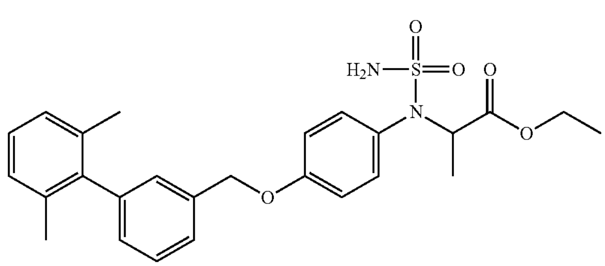 [SMILES: CCOC(=O)C(C)N(c1ccc(OCc2cccc(-c3c(C)cccc3C)c2)cc1)S(N)(=O)=O] |

| No. | Structure |
|---|---|
| 19-1 | 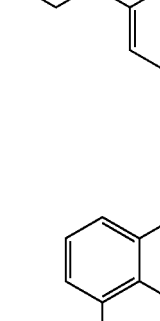 |
| 21-1 | 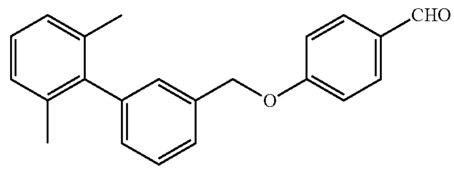 [SMILES: Cc1cccc(C)c1-c1cccc(COc2ccc(C=O)cc2)c1] |
| 21-2 | 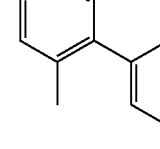 |
| 21-3 | 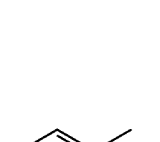 |
| 22-1 | 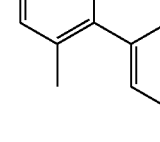 |
| 22-2 | 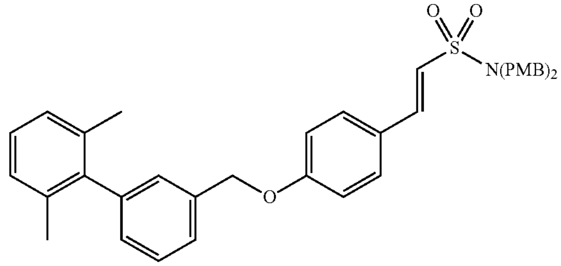 |

-continued
| No. | Structure |
|---|---|
| 22-3 | 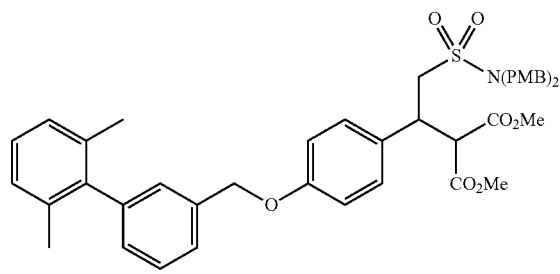 |
| 22-4 | 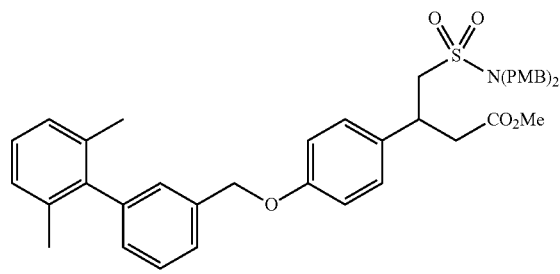 |
| 22-5 | 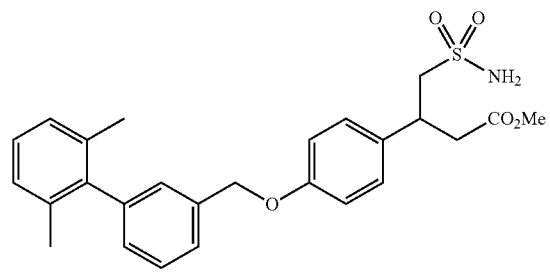 [SMILES: COC(=O)CC(CS(N)(=O)=O)c1ccc(OCc2cccc(-c3c(C)cccc3C)c2)cc1] |
Structural Formula 17
Example 23-1
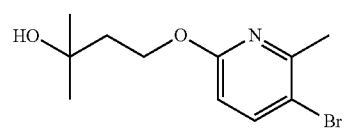
Example 23-2
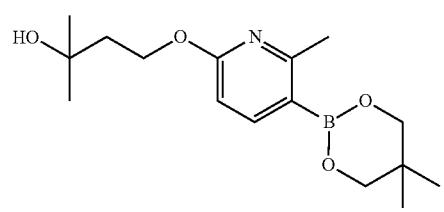
Example 23-3
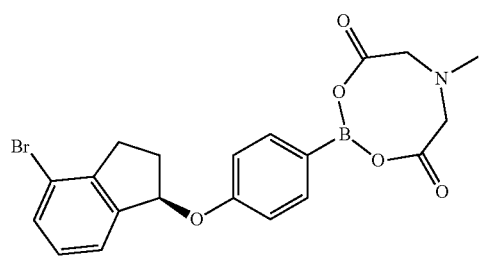
-continued
Example 23-4
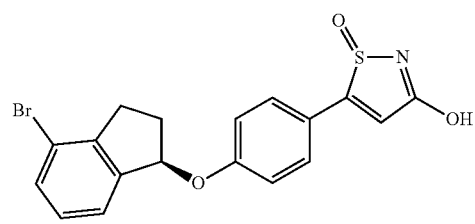
Example 23-5
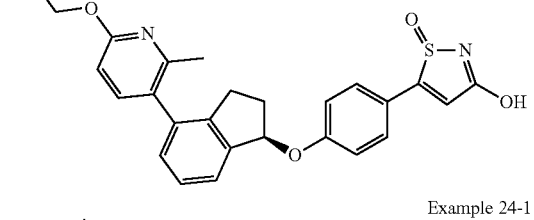
Example 24-1
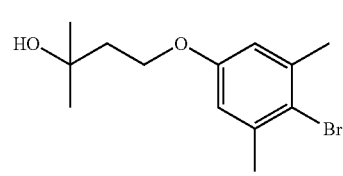

Example 24-2
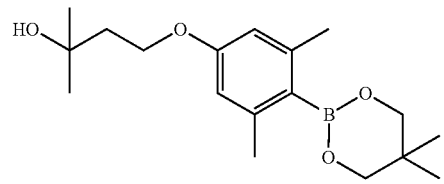
Example 25-5
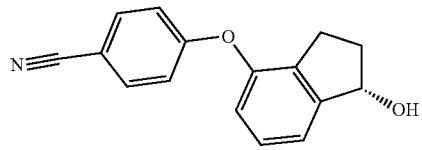
Example 24-3
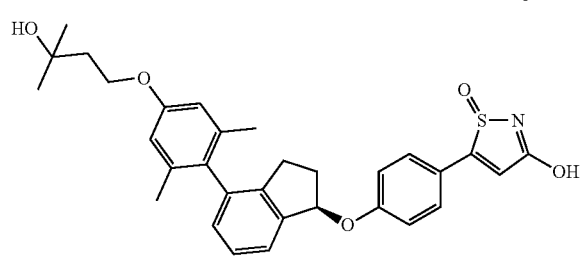
Example 25-6
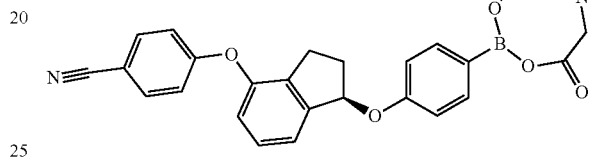
Example 25-1
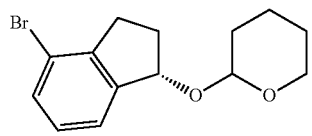
Example 25-7
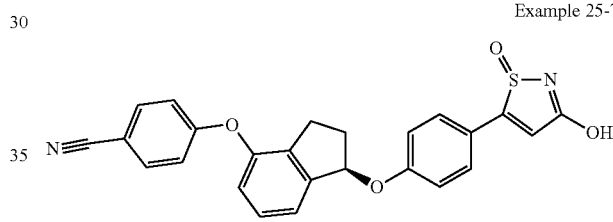
Example 25-2
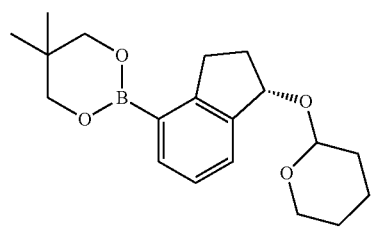
Example 26-1
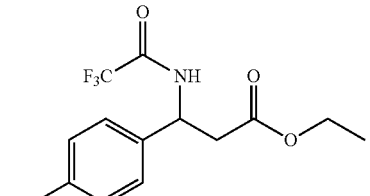
Example 25-3
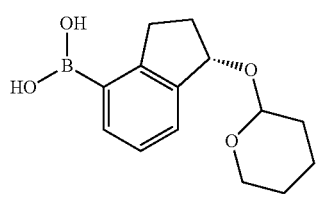
Example 25-4
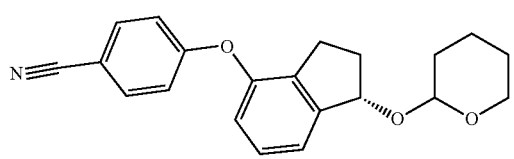
Example 26-2
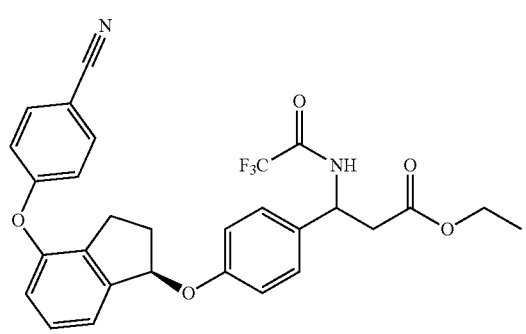

Example 26-3
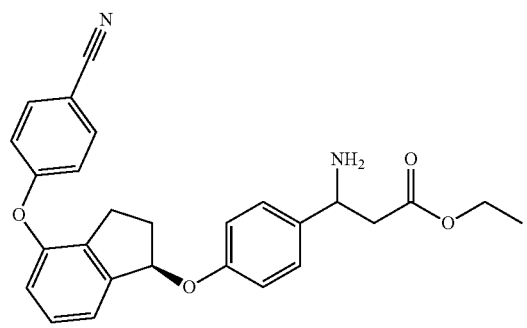
Example 26-4
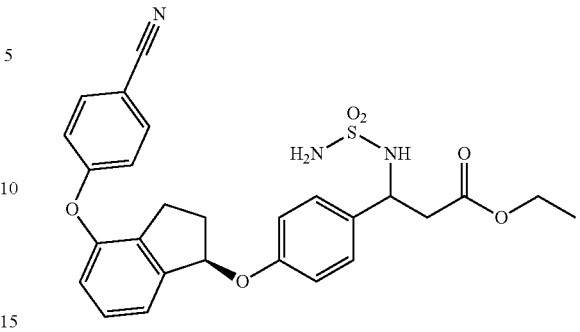
Structural Formula 18
Example 30-1
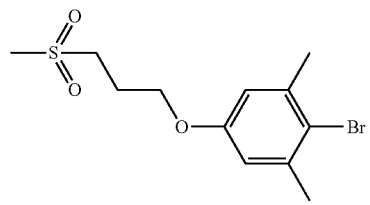
Example 30-2
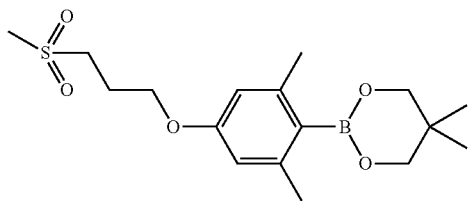
Example 31-1
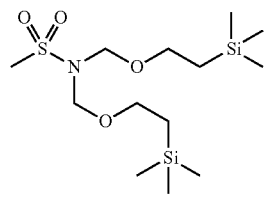
Example 31-2
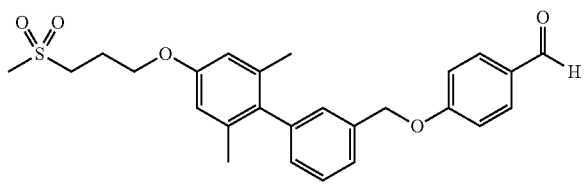
Example 31-3
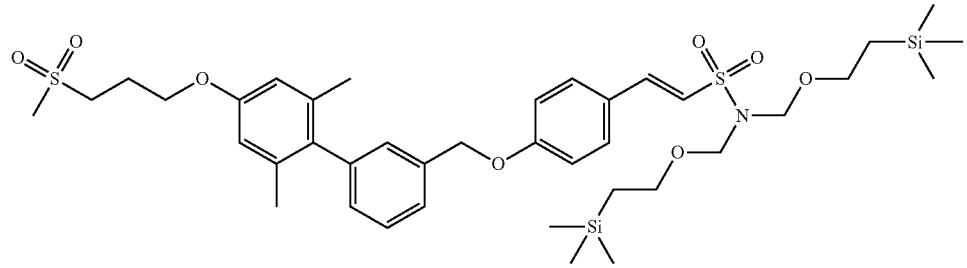
Example 31-4
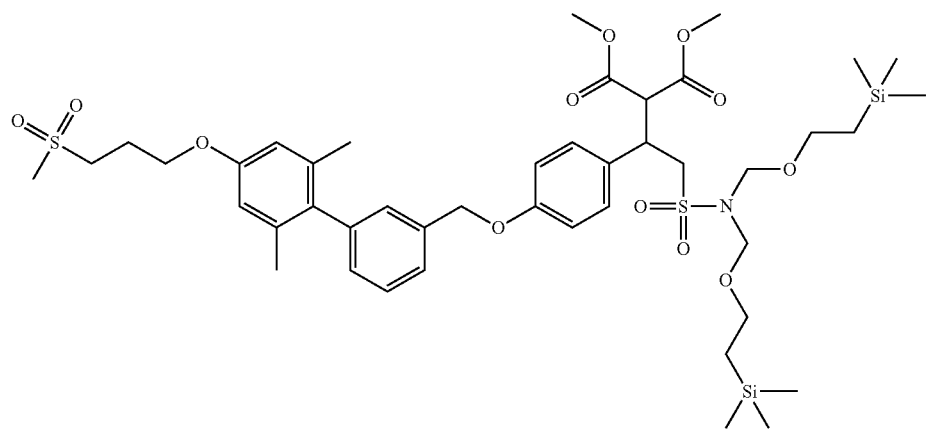

-continued
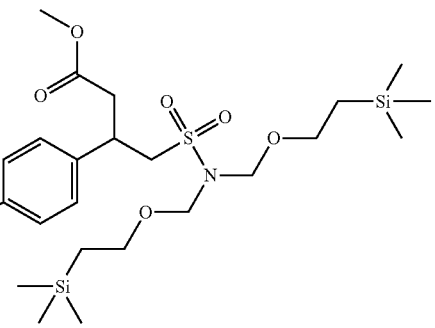
Example 31-5
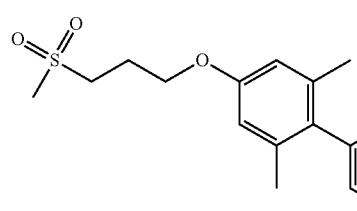
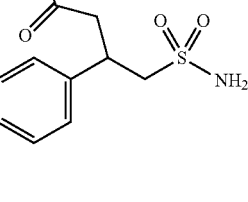
Example 31-6
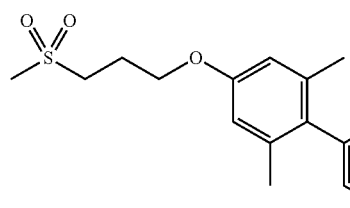
Example 32-1
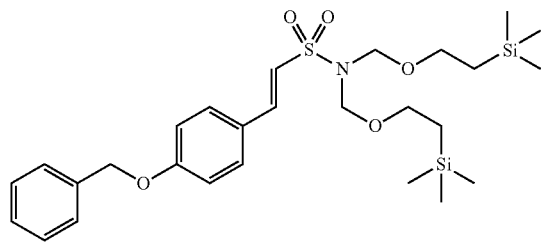
Example 32-2
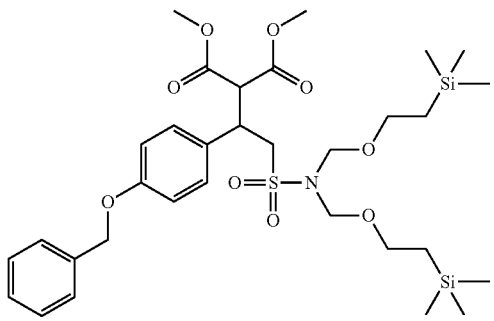
Example 32-3
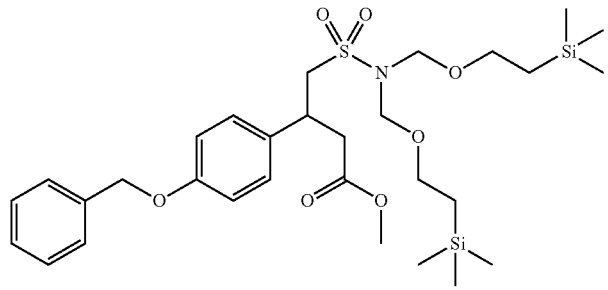
Structural Formula 19
Example 32-4
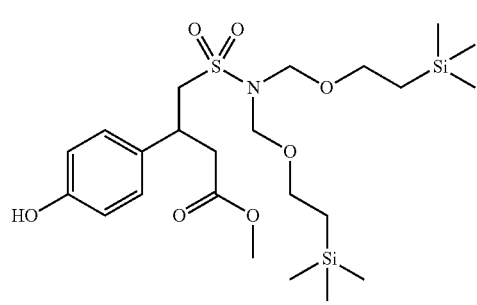

Example 32-5
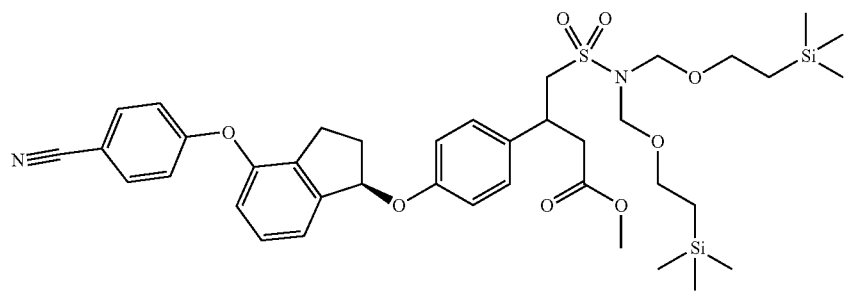
Example 33-1
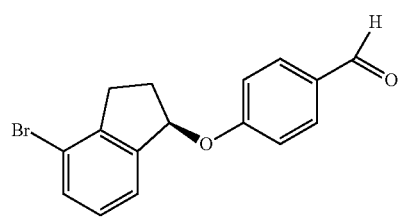
Example 33-2
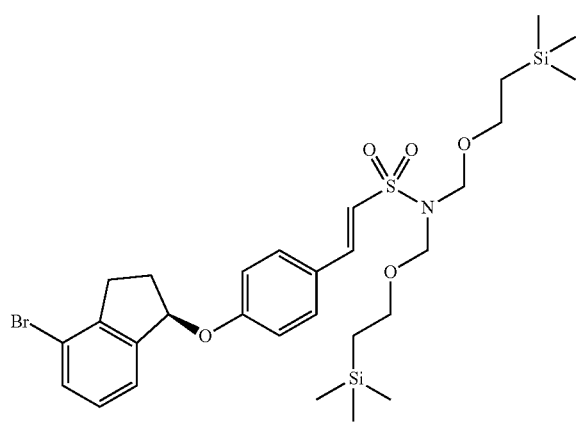
Example 33-3
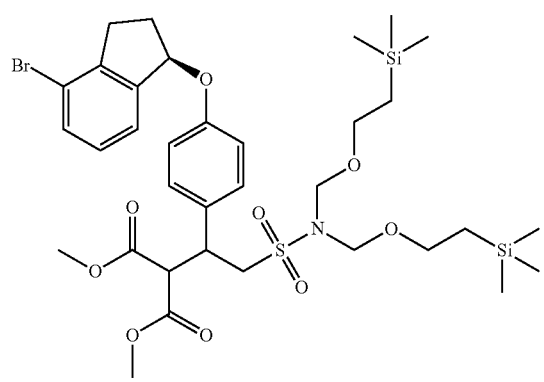
Example 33-4
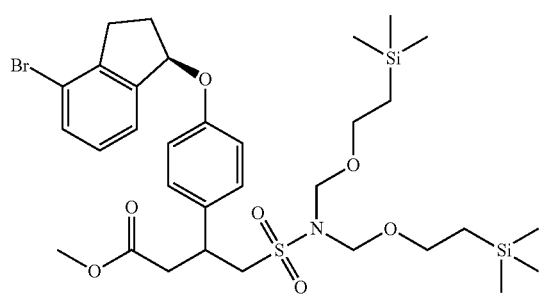
Example 35-1
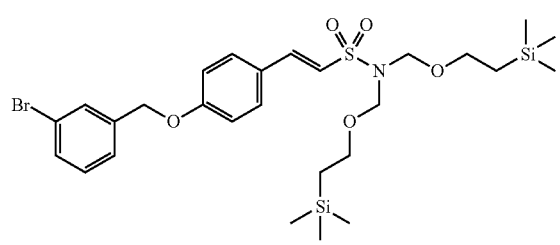
Example 35-2
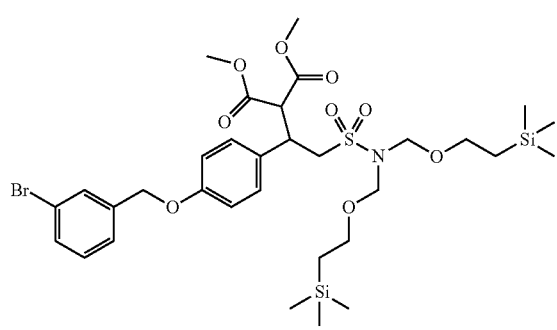

Example 35-3

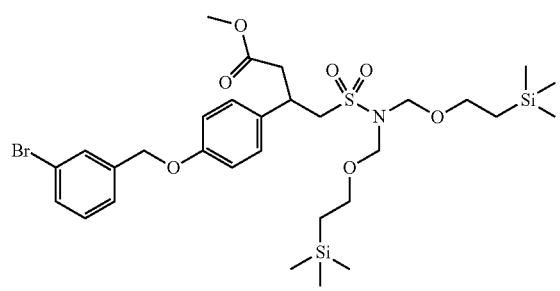

Example 35-4

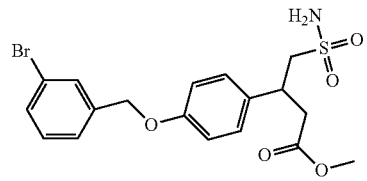

Example 35-5

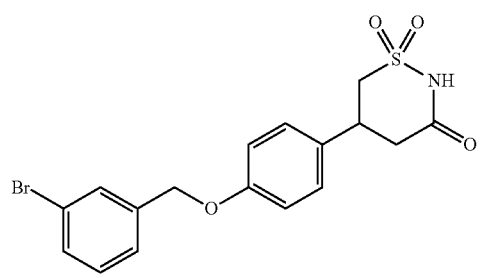

Reference Example 2

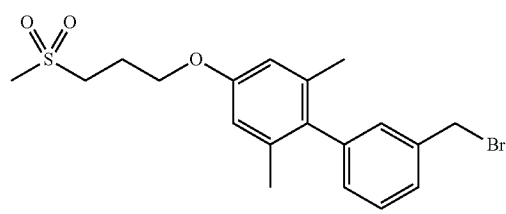

TABLE 2

| Example No. | ESI-MS (M + 1)+ | Retention Time (Minute) |
|---|---|---|
| 1 | 494 | 6.10 |
| 2 | 512 | 6.03 |
| 3 | 526 | 6.00 |
| 4 | 530* | 5.98 |
| 5(A)-b | 543 | 5.32 |
| 6(A)-b | 509 | 5.77 |
| 7(A)-a | 530* | 6.20 |
| 8 | 480 | 5.79 |
| 9 | 496 | 5.33 |
| 10 | 510 | 5.42 |
| 11 | 479 | 3.90 |
| 12 | 494 | 5.97 |
| 13(A)-a | 542 | 5.62 |
| 14 | 445* | 5.72# |
| 15 | 559 | 6.50 |
| 16 | 456& | — |
| 17 | 436& | — |
| 18 | 459* | 5.65 |
| 19 | 558 | 5.82# |
| 20 | 525 | 4.73# |
| 21 | 437 | 6.20# |
| 22 | 436 | 6.30 |

*(M + Na)+, #TFA system, &EI-MS(M+)

TABLE 3

| Example | MS-ESI (m/z) [M + H]+ | Retention Time (Minute) |
|---|---|---|
| 23-(A)-a | 521 | 5.85 |
| 23-(A)-b | 521 | 5.77 |
| 24-(A)-a | 534 | 6.17 |
| 24-(A)-b | 534 | 6.08 |
| 25-(A)-a | 445 | 5.65 |
| 25-(A)-b | 445 | 5.60 |
| 26 | 477# | 5.72 |
| 27 | 442** | 5.98 |
| 28 | 420**, # | 5.30 |
| 29 | 428, 430** | 5.80, 5.92 |
| 30 | 590** | 5.60# |

TABLE 3-continued

| Example | MS-ESI (m/z) [M + H]+ | Retention Time (Minute) |
|---|---|---|
| 31 | 572 | 5.82# |
| 32 | 497 | 5.82# |
| 33 | 436, 438 | 6.05# |
| 34 | 586** | 6.31# |
| 35 | 539 | 5.02# |

*[M + H]−

**[M + Na]+

TFA system

TABLE 4

| Example No. | Substituted Phenylboronic Ester | | Substituted Isothiazole | |
|---|---|---|---|---|
| | ESI-MS (M + 1)+ | Retention Time (Minute) | ESI-MS (M + 1)+ | Retention Time (Minute) |
| 1 | 532 | 5.87 | 492 | 6.08# |
| 2 | 550 | 6.03 | 510 | 6.07# |
| 3 | 586* | 5.98 | 524 | 6.02# |
| 4 | 546 | 5.95# | 528* | 6.05 |
| 5 | 581 | 4.32# | 541 | 4.54# |
| 6 | 547 | 5.62 | 507 | 4.83 |
| 7 | 568* | 6.02 | 528* | 6.53 |
| 8 | 632 | 6.97# | 478 | 5.77# |
| 9 | 668* | 6.97# | 494 | 5.45# |
| 10 | 588 | 6.07# | 508 | 5.75 |
| 11 | 617 | 6.12 | 577 | 6.57 |
| 12 | 574 | 6.15 | 492 | 6.01# |
| 13 | 580 | 5.49 | 540 | 5.78 |

*(M + Na)+

TFA system

TABLE 5

| No. | ESI-MS (M + 1)+ | Retention Time (Minute) | No. | ESI-MS (M + 1)+ | Retention Time (Minute) | No. | ESI-MS (M + 1)+ | Retention Time (Minute) |
|---|---|---|---|---|---|---|---|---|
| 14-1 | 426* | 6.72 | 14-2 | 304 | 5.57 | 14-3 | 418 | 6.72 |
| 14-4 | 619* | 6.84 | 14-5 | 441 | 5.98 | | | |
| 15-1 | 562* | 6.18 | 15-2 | 440 | 4.82 | 15-3 | 526 | 5.95 |
| 15-4 | 727* | 6.18 | 15-5 | 605 | 5.70 | | | |
| 16-1 | 266* | 5.05 | 16-2 | 460* | 6.92 | 16-3 | 338 | 6.45 |
| 16-4 | 424 | 6.82 | 16-5 | 503 | 6.38 | | | |
| 17-1 | 246* | 4.53 | 17-2 | 440* | 6.65 | 17-3 | 318 | 5.95 |
| 17-4 | 404 | 6.68 | 17-5 | 505* | 6.37 | | | |
| 18-1 | 404 | 6.56 | 18-2 | 605* | 6.72 | 18-3 | 483 | 6.35 |
| 19-1 | 556 | 6.22# | | | | | | |
| 21-1 | 339 | 6.45 | 21-2 | 404 | 4.42 | 21-3 | 505* | 6.17 |
| 22-1 | 358* | 5.40 | 22-2 | 634 | 7.06 | 22-3 | 788* | 6.80 |
| 22-4 | 730* | 6.92 | 22-5 | 468 | 6.13 | | | |

TABLE 6

| Example | MS-ESI (m/z) [M + H]+ | Retention Time (Minute) |
|---|---|---|
| 23-1 | 296** | 5.78 |
| 23-3 | 443*, # | 5.75 |
| 23-5 | 519 | 6.08 |
| 24-1 | 309** | 6.22 |
| 24-2 | 343** | 5.94 |
| 24-3 | 532 | 6.46 |
| 25-3 | 285** | 5.18 |
| 25-4 | 358** | 6.15 |
| 25-5 | 234# | 5.18 |
| 25-6 | 481* | 5.57 |
| 25-7 | 443# | 5.70 |
| 30-1 | 343, 345** | 5.63 |
| 31-1 | 378** | 6.52 |
| 31-2 | 475** | 6.20 |
| 31-3 | 813** | 7.03 |
| 31-4 | 944** | 6.85 |
| 31-5 | 886** | 6.87 |
| 31-6 | 626** | 5.63 |
| 32-1 | 572** | 7.06 |
| 32-2 | 704** | 6.92 |
| 32-3 | 646** | 7.03 |
| 32-4 | 556** | 6.50 |
| 32-5 | 789** | 7.05 |
| 33-1 | — | 6.13 |
| 33-2 | 678, 680** | 7.37 |
| 33-3 | 808, 810** | 7.24 |
| 33-4 | 750, 752** | 7.26 |
| 35-1 | 650, 652** | 7.23 |
| 35-2 | 782, 784** | 7.03 |
| 35-3 | 724, 726** | 7.10 |
| 35-4 | 464, 466** | 5.55 |
| 35-5 | 432, 434** | 5.78# |
| Reference Example 2 | 433, 435** | 5.93 |

*[M + H]−
**[M + Na]+
TFA system

TABLE 7

| Example | NMR data (,: ppm) <400 MHz (*: 300 MHz)> |
|---|---|
| 1 | (CDCl$_3$) δ: 7.42 (1H, t, J = 8 Hz), 7.40-7.32 (1H, m), 7.20-7.13 (1H, m), 7.17 (2H, d, J = 9 Hz), 7.12-7.07 (1H, m), 6.98 (2H, d, J = 9 Hz), 6.68 (2H, s), 5.10 (2H, s), 4.41 (1H, d, J = 7 Hz), 4.13 (2H, t, J = 5 Hz), 3.80 (2H, t, J = 5 Hz), 3.62 (2H, q, J = 7 Hz), 3.55 (1H, d, J = 8 Hz), 2.91-2.84 (1H, m), 1.97 (6H, s), 1.25 (3H, t, J = 7 Hz). |
| 12* | (CDCl$_3$) δ: 7.50-7.33 (4H, m), 7.21-6.96 (4H, m), 6.68 (2H, s), 5.16-5.10 (2H, m), 4.53-4.39 (1H, m), 4.26-4.07 (3H, m), 3.70-3.52 (0.25H, m, isomer-1), 3.35-3.21 (0.75H, m, isomer-2), 3.02-2.83 (1H, m), 2.03-1.90 (2H, m), 2.00 (6H, s), 1.30 (3H, d, J = 6 Hz). |
| 13 | (DMSO-D$_6$) δ: 11.00 (1H, s), 7.48-7.35 (2H, m), 7.22 (2H, d, J = 9 Hz), 7.14 (1H, s), 7.09-7.00 (3H, m), 6.70 (2H, s), 5.16 (2H, s), 4.51 (1H, d, J = 8 Hz), 4.08 (2H, t, J = 6 Hz), 3.52-3.39 (1H, m), 3.27 (2H, t, J = 8 Hz), 3.02 (3H, s), 2.80 (1H, d, J = 17 Hz), 2.19-2.08 (2H, m), 1.90 (6H, s). |
| 14* | (DMSO-D$_6$) δ: 7.50-7.37 (2H, m), 7.22-6.88 (9H, m), 5.10 (2H, s), 3.90 (2H, s), 1.95 (6H, s). |
| 16* | (CDCl$_3$) δ: 7.57-7.28 (3H, m), 7.20-6.95 (6H, m), 6.95-6.80 (1H, m), 5.07 (2H, s), 4.40 (2H, br s), 1.99 (6H, s). |
| 17* | (CDCl$_3$) δ: 7.48-7.28 (3H, m), 7.20-7.01 (5H, m), 6.89-6.77 (2H, m), 5.08 (2H, s), 4.29 (2H, br s), 2.36 (3H, s), 2.00 (6H, s). |
| 18* | (CDCl$_3$) δ: 7.50-7.31 (4H, m), 7.21-7.00 (7H, m), 5.14 (2H, s), 4.51 (1H, q, J = 7 Hz), 2.01 (6H, s), 1.45 (3H, d, J = 7 Hz). |
| 19 | (DMSO-D$_6$) δ: 7.47-7.38 (2H, m), 7.20 (2H, d, J = 9Hz), 7.16 (1H, s), 7.05 (1H, dt, J = 7, 2 Hz), 6.96 (2H, d, J = 9 Hz), 6.70 (2H, s), 5.14 (2H, s), 4.33 (1H, t, J = 8 Hz), 4.08 (2H, t, J = 6 Hz), 3.30-3.24 (1H, m), 3.02 (3H, s), 2.84 (1H, dd, J = 16, 8 Hz), 2.63 (2H, dd, J = 16, 8 Hz), 2.17-2.10 (2H, m), 1.92 (6H, s). |
| 21 | (DMSO-D$_6$) δ: 11.97 (1H, br s), 7.93 (1H, br s), 7.52-7.41 (2H, m), 7.37 (2H, d, J = 9 Hz), 7.20 (1H, s), 7.18-7.08 (4H, m), 7.03 (2H, d, J = 9 Hz), 5.19 (2H, s), 4.76-4.66 (1H, m), 2.80-2.66 (1H, m), 2.64-2.54 (1H, m), 1.95 (6H, s). |
| 22 | (CDCl$_3$) δ: 7.46 (1H, t, J = 8 Hz), 7.40 (1H, d, J = 8 Hz), 7.22-7.08 (7H, m), 6.99 (2H, d, J = 9 Hz), 5.13 (2H, s), 3.81-3.69 (1H, m), 3.66-3.59 (1H, m), 3.45 (1H, dd, J = 14, 12 Hz), 3.03-2.92 (1H, m), 2.82 (1H, dd, J = 17, 12 Hz), 2.01 (6H, s). |

TABLE 8

| Example | NMR data (δ: ppm) <400MHz (*: 300 MHz)> |
|---|---|
| 23 (A)-a | 1H-NMR (CDCl$_3$) δ: 7.47-7.27 (4H, m), 7.22 (2H, d, J = 9 Hz), 7.16 (1H, d, J = 6 Hz), 7.04 (2H, d, J = 9 Hz), 6.61 (1H, d, J = 8 Hz), 5.84-5.79 (1H, m), 4.56 (2H, t, J = 6 Hz), 4.44 (1H, d, J = 8 Hz), 3.60 (1H, dd, J = 17, 8 Hz), 2.92-2.80 (1H, m), 2.91 (1H, d, 17 Hz), 2.71-2.60 (1H, m), 2.60-2.49 (1H, m), 2.27 (3H, s), 2.19-2.09 (1H, m), 2.02 (2H, t, J = 6 Hz), 1.32 (6H, s). |
| 23 (A)-b | 1H-NMR (CDCl$_3$) δ: 7.62 (1H, s), 7.45-7.29 (5H, m), 7.16 (1H, d, J = 6 Hz), 7.09 (2H, d, J = 9 Hz), 6.61 (1H, d, J = 8 Hz), 5.86-5.82 (1H, m), 4.56 (2H, t, J = 6 Hz), 4.51 (1H, dd, J = 12, 7 Hz), 3.30 (1H, dd, J = 17, 12 Hz), 2.98 (1H, dd, J = 17, 7 Hz), 2.94-2.81 (1H, m), 2.73-2.51 (2H, m), 2.28 (3H, s), 2.21-2.11 (1H, m), 2.02 (2H, t, J = 6 Hz), 1.32 (6H, s). |

TABLE 8-continued

| Example | NMR data (δ: ppm) <400MHz (*: 300 MHz)> |
|---|---|
| 26 | 1H-NMR (CDCl3) δ: 7.62 (2H, d, J = 9 Hz), 7.38-7.30 (4H, m), 7.07 (2H, d, J = 9 Hz), 7.02 (1H, dd, J = 4, 4 Hz), 6.99 (2H, d, J = 9 Hz), 5.86-5.79 (1H, m), 5.00-4.91 (1H, m), 4.65 (1H, d, J = 11 Hz), 3.09 (1H, dd, J = 17, 4 Hz), 3.03-2.91 (1H, m), 2.91 (1H, dd, J = 12, 17 Hz), 2.83-2.72 (1H, m), 2.67-2.55 (1H, m), 2.27-2.15 (1H, m). |
| 31 | 1H-NMR (CDCl3) δ: 7.48-7.34 (2H, m), 7.19-7.03 (4H, m), 7.01-6.92 (2H, m), 6.64 (2H, s), 5.10 (2H, s), 4.18-4.06 (2H, m), 3.80-3.56 (2H, m), 3.53-3.37 (1H, m), 3.31-3.22 (2H, m), 3.01-2.90 (1H, m), 2.97 (3H, s), 2.86-2.71 (1H, m), 2.42-2.29 (2H, m), 1.97 (6H, s). |
| 35 | 1H-NMR (DMSO-D6) δ: 7.50-7.40 (2H, m), 7.23-7.16 (3H, m), 7.15-7.10 (1H, m), 6.93 (2H, d, J = 9 Hz), 6.55 (1H, s), 5.13 (2H, s), 4.37 (1H, s), 4.33 (2H, t, J = 7 Hz), 3.26-3.15 (1H, m), 2.94-2.79 (2H, m), 2.28-2.20 (1H, m), 2.19-2.09 (1H, m), 2.06 (3H, s), 1.90 (3H, s), 1.82 (2H, t, J = 7 Hz), 1.16 (6H, s). |

TABLE 9

Substituted Isothiazole

| Example | NMR data (δ: ppm) <400 MHz (*: 300 MHz)> |
|---|---|
| 1-6 | (DMSO-D$_6$) δ: 11.27 (1H, s), 7.80 (2H, d, J = 9 Hz), 7.51-7.40 (2H, m), 7.24-7.16 (3H, m), 7.08 (1H, d, J = 7 Hz), 7.07 (1H, s), 6.71 (2H, s), 5.27 (2H, s), 4.10-4.05 (2H, m), 3.72-3.66 (2H, m), 3.51 (2H, q, J = 7 Hz), 1.92 (6H, s), 1.14 (3H, t, J = 7 Hz) |
| 12-5 | (DMSO-D$_6$) δ: 11.28 (1H, s), 7.83-7.76 (2H, m), 7.50-7.39 (2H, m), 7.24-7.16 (3H, m), 7.08 (1H, d, J = 9 Hz), 6.68 (2H, s), 5.26 (2H, s), 4.58-4.53 (1H, m), 4.09-3.95 (2H, m), 3.87-3.74 (1H, m), 1.91 (6H, s), 1.81-1.68 (2H, m), 1.15-1.08 (3H, m) |
| 13-5 | (DMSO-D$_6$) δ: 7.79 (2H, d, J = 9 Hz), 7.50-7.39 (2H, m), 7.23-7.16 (3H, m), 7.11-7.03 (2H, m), 6.71 (2H, s), 5.26 (2H, s), 4.08 (2H, t, J = 6 Hz), 3.31-3.24 (2H, m), 3.03 (3H, s), 2.19-2.09 (2H, m), 1.92 (6H, s) |

TABLE 10

Substituted Boronic Ester

| Example | NMR data (δ: ppm) <400 MHz (*: 300 MHz)> |
|---|---|
| 1-3 | (CDCl$_3$) δ: 7.45-7.35 (4H, m), 7.18 (1H, s), 7.11-7.06 (1H, m), 6.99 (2H, d, J = 9 Hz), 6.69 (2H, s), 5.11 (2H, s), 4.16-4.12 (2H, m), 3.95 (2H, d, J = 16 Hz), 3.80 (2H, t, J = 5 Hz), 3.75 (2H, d, J = 16 Hz), 3.62 (2H, q, J = 7 Hz), 2.53 (3H, s), 1.98 (6H, s), 1.25 (3H, t, J = 7 Hz) |
| 12-4 | (CDCl$_3$) δ: 7.47-7.35 (4H, m), 7.17 (1H, s), 7.08 (1H, d, J = 7 Hz), 6.99 (2H, d, J = 9 Hz), 6.63 (2H, s), 5.20-5.06 (2H, m), 5.12 (1H, s), 4.01 (2H, t, J = 6 Hz), 3.89 (2H, d, J = 16 Hz), 3.74 (2H, d, J = 16 Hz), 2.54 (3H, s), 2.12-1.99 (2H, m), 2.05 (3H, s), 1.98 (6H, s), 1.32 (3H, d, J = 6 Hz) |
| 13-4* | (DMSO-D$_6$) δ: 7.50-7.37 (2H, m), 7.33 (2H, d, J = 9 Hz), 7.16 (1H, s), 7.10-7.02 (1H, m), 6.99 (2H, d, J = 9 Hz), 6.70 (2H, s), 5.16 (2H, s), 4.30 (2H, d, J = 17 Hz), 4.14-3.97 (4H, m), 3.31-3.22 (2H, m), 3.03 (3H, s), 2.47 (3H, s), 2.20-2.07 (2H, m), 1.91 (6H, s) |

TABLE 11

| Example | NMR data (δ: ppm) <400 MHz (*: 300 MHz)> |
|---|---|
| 14-3 | (CDCl$_3$) δ: 7.46-7.36 (2H, m), 7.21-7.12 (2H, m), 7.12-7.05 (3H, m), 6.84 (2H, d, J = 9 Hz), 6.55 (2H, d, J = 9 Hz), 5.03 (2H, s), 4.01 (1H, br s), 3.75 (2H, s), 2.01 (6H, s), 1.47 (9H, s). |
| 14-5* | (CDCl$_3$) δ: 7.49-7.32 (4H, m), 7.22-7.05 (5H, m), 6.96 (2H, d, J = 9 Hz), 5.11 (2H, s), 5.00 (2H, br s), 4.45 (2H, s), 2.01 (6H, s). |
| 18-3* | (CDCl$_3$) δ: 7.49-7.28 (4H, m), 7.22-7.04 (5H, m), 7.00-6.91 (2H, m), 5.11 (2H, s), 4.95 (1H, q, J = 8 Hz), 4.25 (2H, q, J = 7 Hz), 2.01 (6H, s), 1.31 (3H, t, J = 7 Hz), 1.23 (4H, d, J = 8 Hz). |
| 21-2* | (CDCl$_3$) δ: 7.49-7.36 (2H, m), 7.27 (2H, d, J = 9 Hz), 7.22-7.06 (5H, m), 6.94 (2H, d, J = 9 Hz), 5.10 (2H, s), 4.38 (1H, dd, J = 8, 6 Hz), 4.13 (2H, q, J = 7 Hz), 2.70-2.59 (2H, m), 2.01 (6H, s), 1.23 (3H, t, J = 7 Hz). |
| 22-3* | (CDCl$_3$) δ: 7.49-7.37 (2H, m), 7.24-7.06 (11H, m), 6.90 (2H, d, J = 9Hz), 6.83 (4H, d, J = 9 Hz), 5.08 (2H, s), 4.22 (2H, d, J = 15 Hz), 4.03-3.96 (1H, m), 4.03 (2H, d, J = 15 Hz), 3.85 (1H, d, J = 8 Hz), 3.80 (6H, s), 3.70 (3H, s), 3.62-3.51 (1H, m), 3.55 (3H, s), 3.32 (1H, dd, J = 14, 8 Hz), 2.03 (6H, s). |
| 22-4* | (CDCl$_3$) δ: 7.51-7.37 (2H, m), 7.24-7.14 (6H, m), 7.14-7.08 (3H, m), 7.03 (2H, d, J = 9 Hz), 6.90 (2H, d, J = 9 Hz), 6.85 (4H, d, J = 9 Hz), 5.09 (2H, s), 4.31 (2H, d, J = 15 Hz), 4.11 (2H, d, J = 15 Hz), 3.81 (6H, s), 3.76-3.63 (1H, m), 3.56 (3H, s), 3.25 (1H, dd, J = 14, 8 Hz), 3.10 (1H, t, J = 5 Hz), 3.05 (1H, dd, J = 5, 2 Hz), 2.69 (1H, dd, J = 16, 9 Hz), 2.02 (6H, s). |
| 22-5 | (CDCl$_3$) δ: 7.46 (1H, t, J = 8 Hz), 7.39 (1H, d, J = 8 Hz), 7.23-7.15 (4H, m), 7.15-7.08 (3H, m), 6.96 (2H, d, J = 7 Hz), 5.10 (2H, s), 4.23 (2H, br s), 3.82-3.71 (1H, m), 3.63 (3H, s), 3.54 (1H, dd, J = 14, 7 Hz), 3.39 (1H, dd, J = 14, 8 Hz), 2.94 (1H, dd, J = 16, 7 Hz), 2.73 (1H, dd, J = 16, 7 Hz), 2.02 (6H, s). |

TABLE 12

| Example | NMR data (δ: ppm) <400 MHz (*: 300 MHz)> |
|---|---|
| 23-2* | $^1$H-NMR (CDCl$_3$) δ: 7.92 (1H, d, J = 8 Hz), 6.51 (1H, d, J = 8 Hz), 4.55 (2H, t, J = 6 Hz), 3.77 (4H, s), 2.64 (3H, s), 1.98 (2H, t, J = 6 Hz), 1.29 (6H, s), 1.03 (6H, s). |
| 23-4 | $^1$H-NMR (DMSO-d$_6$) 11.28 (1H, s), 7.83 (2H, d, J = 9 Hz), 7.57 (1H, d, J = 8 Hz), 7.46-7.41 (2H, m), 7.27-7.19 (1H, m), 7.23 (2H, d, J = 9 Hz), 7.11 (1H, s), 6.10 (1H, dd, J = 7, 4 Hz), 3.11-2.97 (1H, m), 2.97-2.83 (1H, m), 2.71-2.58 (1H, m), 2.15-2.00 (1H, m) |
| 25-1 | $^1$H-NMR (CDCl$_3$) δ: 7.42-7.38 (3H, m), 7.28 (1H, d, J = 8 Hz), 7.09 (2H, dt, J = 14, 6 Hz), 5.37 (1H, t, J = 6 Hz), 5.21 (1H, dd, J = 7, 5 Hz), 4.86-4.81 (2H, m), 4.03-3.93 (2H, m), 3.63-3.54 (2H, m), 3.13-3.03 (2H, m), 2.86-2.77 (1H, m), 2.49-2.38 (2H, m), 2.21-2.13 (1H, m), 2.06-1.98 (1H, m), 1.91-1.78 (2H, m), 1.78-1.68 (2H, m), 1.68-1.47 (8H, m). |
| 25-2 | $^1$H-NMR (CDCl$_3$) δ: 7.72-7.68 (2H, m), 7.52 (1H, d, J = 7 Hz), 7.40 (1H, d, J = 8 Hz), 7.24-7.16 (2H, m), 5.29 (1H, t, J = 6 Hz), 5.13 (1H, dd, J = 7, 5 Hz), 4.87 (1H, t, J = 4 Hz), 4.83 (1H, dd, J = 5, 3 Hz), 4.08-3.94 (2H, m), 3.75 (4H, s), 3.75 (4H, s), 3.62-3.54 (2H, m), 3.33-3.22 (2H, m), 3.04-2.94 (2H, m), 2.42-2.32 (2H, m), 2.16-2.07 (1H, m), 1.75-1.52 (13H, m), 1.02 (6H, s), 1.01 (6H, s). |
| 26-1* | 1H-NMR (DMSO-d6) δ: 9.84 (1H, d, J = 9 Hz), 9.42 (1H, s), 7.14 (2H, d, J = 8 Hz), 6.70 (2H, d, J = 8 Hz), 5.17 (1H, ddd, J = 9 Hz, 9 Hz, 6 Hz), 4.09-3.98 (2H, m), 2.92 (1H, dd, J = 16 Hz, 9 Hz), 2.80 (1H, dd, J = 16 Hz, 6 Hz), 1.12 (3H, t, J = 7 Hz). |
| 26-2* | 1H-NMR (CDCl3) δ: 7.71 (1H, d, J = 9 Hz), 7.61 (2H, d, J = 9 Hz), 7.35-7.30 (2H, m), 7.26 (2H, d, J = 9 Hz), 7.04-6.95 (5H, m), 5.79 (1H, dd, J = 7 Hz, 4 Hz), 5.45-5.35 (1H, m), 4.15 (2H, q, J = 7 Hz), 3.04-2.86 (3H, m), 2.83-2.68 (1H, m), 2.66-2.51 (1H, m), 2.29-2.12 (1H, m), 1.23 (3H, t, J = 7 Hz). |
| 26-3* | 1H-NMR (CD3OD) δ: 7.69 (2H, d, J = 9 Hz), 7.35-7.28 (4H, m), 7.06-6.96 (5H, m), 5.85 (1H, dd, J = 7 Hz, 4 Hz), 4.29 (1H, dd, J = 7 Hz, 8 Hz), 4.09 (2H, q, J = 7 Hz), 2.95-2.81 (3H, m), 2.80-2.50 (4H, m), 2.18-2.04 (1H, m), 1.20 (3H, t, J = 7 Hz). |
| 26-4* | 1H-NMR (CDCl3) δ: 7.61 (2H, d, J = 9 Hz), 7.37-7.30 (4H, m), 7.06-6.95 (5H, m), 5.79 (1H, dd, J = 7 Hz, 4 Hz), 5.48 (1H, d, J = 7 Hz), 4.94-4.84 (1H, m), 4.43 (2H, s), 4.13 (2H, q, J = 7 Hz), 3.03-2.84 (3H, m), 2.83-2.68 (1H, m), 2.66-2.50 (1H, m), 2.27-2.12 (1H, m), 1.24 (3H, t, J = 7 Hz). |
| 30-2 | 1H-NMR (CDCl3) δ: 6.48 (2H, s), 4.07 (2H, t, J = 6 Hz), 3.77 (4H, s), 3.28-3.18 (2H, m), 2.93 (3H, s), 2.36 (6H, s), 2.36-2.24 (2H, m), 1.09 (6H, s). |
| 33-1 | 1H-NMR (CDCl3) δ: 9.90 (1H, s), 7.87 (2H, d, J = 9 Hz), 7.50 (1H, d, J = 8 Hz), 7.37 (1H, d, J = 8 Hz), 7.15 (1H, t, J = 8 Hz), 7.09 (2H, d, J = 9 Hz), 5.96-5.89 (1H, m), 3.23-3.12 (1H, m), 3.03-2.92 (1H, m), 2.70-2.59 (1H, m), 2.29-2.18 (1H, m). |

TABLE 12-continued

| Example | NMR data (δ: ppm) <400 MHz (*: 300 MHz)> |
|---|---|
| 35-5 | 1H-NMR (DMSO-D6) δ: 12.15 (1H, s), 7.64 (1H, s), 7.52 (1H, d, J = 8 Hz), 7.44 (1H, d, J = 8 Hz), 7.35 (1H, t, J = 8 Hz), 7.30 (2H, d, J = 9 Hz), 6.98 (2H, d, J = 9 Hz), 5.11 (2H, s), 3.84-3.73 (1H, m), 3.73-3.62 (1H, m), 3.62-3.49 (1H, m), 2.82-2.71 (1H, m), 2.71-2.60 (1H, m). |

The invention claimed is:

1. A compound of Formula (I):

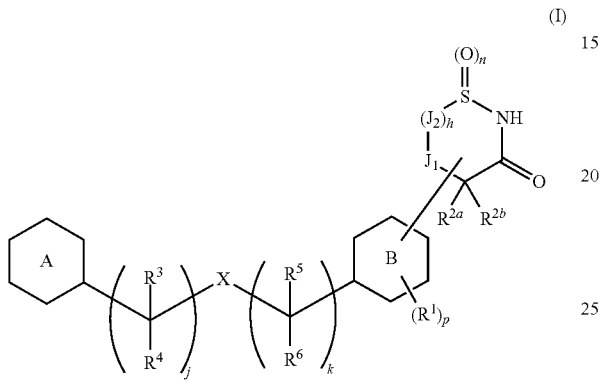

wherein n is an integer of 0 to 2; p is an integer of 0 to 4; h is 1; j is an integer of 0 to 3; k is 0;

a ring A is a $C_{6-14}$ aryl group which is optionally substituted with 1 to 5 L(s), a 3- to 14-membered heterocyclic group which is optionally substituted with 1 to 5 L(s), a $C_{5-7}$ cycloalkyl group which is optionally substituted with 1 to 5 L(s), a $C_{5-7}$ cycloalkenyl group which is optionally substituted with 1 to 5 L(s), a 6- to 14-membered Spiro ring group which is optionally substituted with 1 to 5 L(s), or a 2-phenylamino-2-oxoacetyl group which is optionally substituted with 1 to 5 L(s);

a ring B is benzene ring;

X is an oxygen atom, a sulfur atom, or —$NR^7$—;

$J_1$ is —$CR^{11a}R^{11b}$—; $J_2$ is —$CR^{12a}R^{12b}$—;

$R^1$s are independently a group optionally selected from a halogen atom, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, and a cyano group;

$R^{2a}$ and $R^{2b}$ are independently a group optionally selected from a hydrogen atom, a halogen atom, a $C_{1-6}$ alkyl group, a $C_{2-6}$ alkenyl group, a $C_{2-6}$ alkynyl group, a $C_{1-6}$ alkoxy group, and a cyano group;

$R^3$, $R^4$, $R^5$, $R^6$, and $R^7$ are independently a group optionally selected from a hydrogen atom, a $C_{1-6}$ alkyl group, a halogenated $C_{1-6}$ alkyl group, a $C_{2-6}$ alkenyl group, and a $C_{2-6}$ alkynyl group;

$R^{11a}$ and $R^{11b}$ are independently a group optionally selected from a hydrogen atom, a halogen atom, a $C_{1-6}$ alkyl group, a halogenated $C_{1-6}$ alkyl group, a $C_{2-6}$ alkenyl group, a $C_{2-6}$ alkynyl group, a $C_{1-6}$ alkoxy group, a halogenated $C_{1-6}$ alkoxy group, a $C_{2-7}$ alkanoyl group, and a carboxy group;

$R^{12a}$ and $R^{12b}$ are independently a group optionally selected from a hydrogen atom, a halogen atom, a $C_{1-6}$ alkyl group, a halogenated $C_{1-6}$ alkyl group, a $C_{2-6}$ alkenyl group, a $C_{2-6}$ alkynyl group, a $C_{1-6}$ alkoxy group, a halogenated $C_{1-6}$ alkoxy group, and a cyano group;

with the proviso that in the cyclic amide structure moiety, there is not one of the substituents ($R^{2b}$, $R^{11b}$, or $R^{12b}$) on an atom to which the ring B is bonded;

Ls are independently a group optionally selected from a halogen atom, —OH, an oxo group, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, a $C_{2-10}$ alkynyloxy group which is optionally substituted with 1 to 5 substituent(s) RI, an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, —SH, —$SF_5$, a —$S(O)_iR^a$ (i is an integer of 0 to 2) group, a —$NR^bR^c$ group, and a substituted spiropiperidinylmethyl group;

$R^a$ is a $C_{1-6}$ alkyl group or a halogenated $C_{1-6}$ alkyl group;

$R^b$ and $R^c$ are independently a group optionally selected from a hydrogen atom, a $C_{1-6}$ alkyl group, a halogenated $C_{1-6}$ alkyl group, a $C_{2-6}$ alkenyl group, a $C_{2-6}$ alkynyl group, a $C_{2-7}$ alkanoyl group (the alkanoyl group is optionally substituted with —OH or a $C_{1-6}$ alkoxy group), a $C_{1-6}$ alkylsulfonyl group, an arylcarbonyl group, and a heterocyclic carbonyl group, where $R^b$ and $R^c$ optionally form together with a nitrogen atom to which they are bonded, a 3- to 8-membered cyclic group, where in the cyclic group, one or two carbon atom(s) is(are) optionally substituted with an atom optionally selected from an oxygen atom, a sulfur atom, and a nitrogen atom (the nitrogen atom is optionally substituted with a $C_{1-6}$ alkyl group which is optionally substituted with 1 to 5 substituent(s) RI) or with a carbonyl group, and the cyclic group is optionally further substituted with 1 to 5 substituent(s) RII;

where the substituents RI are the same as or different from each other and are each a group optionally selected from a halogen atom, —OH, a cyano group, a $C_{1-6}$ alkoxy group (the $C_{1-6}$ alkoxy group is optionally substituted with 1 to 5 halogen atom(s), 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —$S(O)_iR^a$ (i is an integer of 0 to 2) group(s), 1 to 5 —$SO_2NR^dR^e$ group(s), 1 to 5 —$CONR^dR^e$ group(s), or 1 to 5 —$NR^{b1}R^{c1}$ group(s)), a —$NR^{b1}R^{c1}$ group, and a heterocyclic oxy group (the heterocyclic oxy group is optionally substituted with 1 to 3 $C_{1-6}$ alkyl group(s) or 1 to 3 oxo group(s));

the substituents RII are the same as or different from each other and are each a group optionally selected from the substituents RI, a $C_{1-6}$ alkyl group (the $C_{1-6}$ alkyl group is optionally substituted with 1 to 5 halogen atom(s), 1 to 5 —OH, 1 to 5 $C_{1-6}$ alkoxy group(s), 1 to 5 —S(O)$_i$R$^a$ (i is an integer of 0 to 2) group(s), 1 to 5 —NR$^{b1}$R$^{c1}$ group(s), 1 to 5 —SO$_2$NR$^d$R$^e$ group(s), or 1 to 5 —CONR$^d$R$^e$ group(s)), a $C_{2-6}$ alkenyl group, a $C_{2-7}$ alkanoyl group, an aralkyloxy group, a heterocyclic group (the heterocyclic group is optionally substituted with 1 to 3 $C_{1-6}$ alkyl group(s) or 1 to 3 oxo group(s)), a heterocyclic carbonyl group (the heterocyclic carbonyl group is optionally substituted with 1 to 3 $C_{1-6}$ alkyl group(s) or 1 to 3 oxo group(s)), a —S(O)$_i$R$^a$ (i is an integer of 0 to 2) group, a —CONR$^d$R$^e$ group, and a —CONR$^d$R$^{e1}$ group;

R$^d$ and R$^e$ are independently a hydrogen atom or a $C_{1-6}$ alkyl group (the $C_{1-6}$ alkyl group is optionally substituted with 1 to 5 halogen atom(s), 1 to 5 —OH, or 1 to 5 $C_{1-6}$ alkoxy group(s));

R$^{e1}$ is a $C_{1-6}$ alkyl group (the $C_{1-6}$ alkyl group is substituted with 1 to 5 —OH, 1 to 5 $C_{1-6}$ alkoxy group(s), 1 to 5 aryl group(s) (the aryl group is optionally substituted with 1 to 3 halogen atom(s)), 1 to 5 heterocyclic group(s) (the heterocyclic group is optionally substituted with 1 to 3 $C_{1-6}$ alkyl group(s) or 1 to 3 oxo group(s)), 1 to 5 —S(O)$_i$ R$^a$ (i is an integer of 0 to 2) group(s), 1 to 5 —SO$_2$NR$^d$R$^e$ group(s), 1 to 5 —CONR$^d$R$^e$ group(s), or 1 to 5 —NR$^{b1}$R$^{c1}$ group(s));

R$^{b1}$ and R$^{c1}$ are independently a group optionally selected from a hydrogen atom, a $C_{1-6}$ alkyl group, a $C_{2-7}$ alkanoyl group, and a $C_{1-6}$ alkylsulfonyl group, where R$^{b1}$ and R$^{c1}$ optionally form together with a nitrogen atom to which they are bonded, a 3 - to 8-membered cyclic group, where in the cyclic group, one or two carbon atom(s) is(are) optionally substituted with an atom optionally selected from an oxygen atom, a sulfur atom, and a nitrogen atom (the nitrogen atom is optionally substituted with a $C_{1-6}$ alkyl group) or with a carbonyl group, or a pharmaceutically acceptable salt of the compound.

2. The compound according to claim 1 of Formula (I)-1:

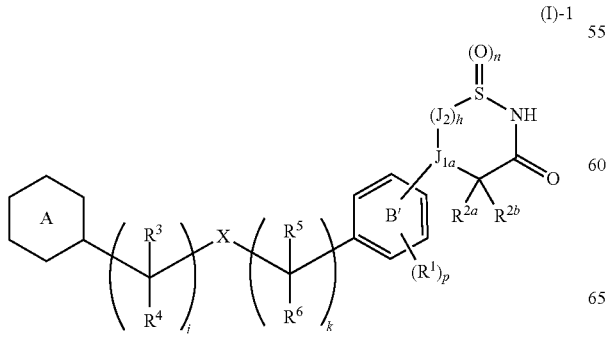

(I)-1 wherein n, p, h, j, k, the ring A, X, J$_2$, R$^1$, R$^{2a}$, R$^{2b}$, R$^3$, R$^4$, R$^5$, and R$^6$ are the same as defined in Formula (I); a ring B' is a benzene ring; and J$_{1a}$ is CR$^{11a}$, or a pharmaceutically acceptable salt of the compound.

3. The compound according to claim 2 of Formula (II):

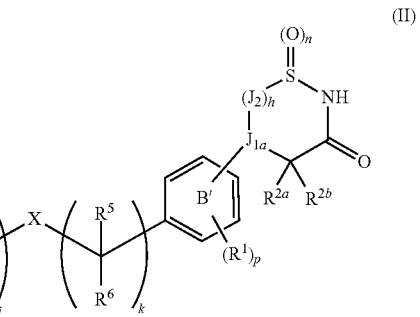

(II)

wherein n, p, h, j, k, X, J$_2$, R$^1$, R$^{2a}$, R$^{2b}$, R$^3$, R$^4$, R$^5$, and R$^6$ are the same as defined in Formula (I); the ring B' and J$_{1a}$ are the same as defined in Formula (I)-1;

q and r are independently an integer of 0 to 4; s is an integer of 0 to 2 (with the proviso that q+s is an integer of 0 to 5);

a ring A' is an aryl group or a heteroaryl group;

V is a single bond or an oxygen atom;

R$^8$s are independently a group optionally selected from a $C_{1-6}$ alkoxy group which is substituted with 1 to 5 substituent(s) M, a $C_{2-6}$ alkenyloxy group which is substituted with 1 to 5 substituent(s) M, a $C_{2-6}$ alkynyloxy group which is substituted with 1 to 5 substituent(s) M, a —CONR$^d$R$^{e1}$ group, an aralkyloxy group, a heterocyclic oxy group (the heterocyclic oxy group is optionally substituted with 1 to 3 $C_{1-6}$ alkyl group(s) or 1 to 3 oxo group(s)), a heterocyclic group (the heterocyclic group is optionally substituted with 1 to 3 $C_{1-6}$ alkyl group(s) or 1 to 3 oxo group(s)), and a heterocyclic carbonyl group (the heterocyclic carbonyl group is optionally substituted with 1 to 3 $C_{1-6}$ alkyl group(s) or 1 to 3 oxo group(s));

the substituents M are independently a group optionally selected from a halogen atom, —OH, a $C_{1-6}$ alkoxy group, an aryl group (the aryl group is optionally substituted with 1 to 3 halogen atom(s)), a heterocyclic group (the heterocyclic group is optionally substituted with 1 to 3 —OH, 1 to 3 $C_{1-6}$ alkyl group(s), or 1 to 3 oxo group(s)), a —S(O)$_i$R$^a$ (i is an integer of 0 to 2) group, a —NR$^{b1}$R$^{c1}$ group, a —SO$_2$NR$^d$R$^e$ group, and a —CONR$^d$R$^e$ group;

R$^9$s and R$^{10}$s are independently a group optionally selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, a $C_{2-7}$ alkanoyl group, —SH, a —S(O)$_i$R$^a$ (i is an integer of 0 to 2) group, a —NR$^{b1}$R$^{c1}$ group, and a —CONR$^d$R$^e$ group;

R$^a$, R$^d$, R$^e$, R$^{b1}$, R$^{c1}$, R$^{e1}$ are the same as defined in Formula (I), or a pharmaceutically acceptable salt of the compound.

4. The compound according to claim 3, wherein X is an oxygen atom and any one of q and s is 1 or more, or a pharmaceutically acceptable salt of the compound.

5. The compound according to claim 3 of Formula (II-1)-1:

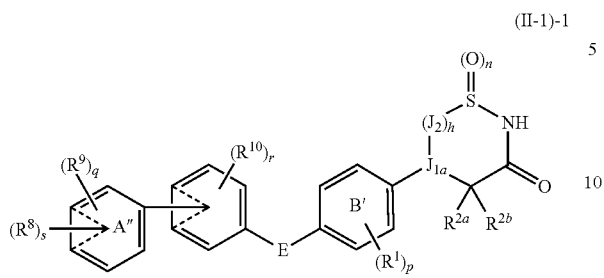

(II-1)-1 wherein n, p, h, $J_2$, $R^1$, $R^{2a}$, and $R^{2b}$ are the same as defined in Formula (I);
the ring B' and $J_{1a}$ are the same as defined in Formula (I)-1;
q, r, s, $R^8$, $R^9$, and $R^{10}$ are the same as defined in Formula (II);
a ring A" is a benzene ring, a pyridine ring, or a pyrimidine ring;
broken lines indicate where the ring A" or $R^8$s are bonded;
E is a group optionally selected from Formula (c1) to Formula (c6):

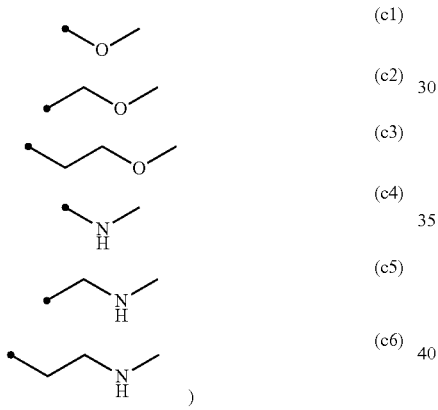

or a pharmaceutically acceptable salt of the compound.

6. The compound according to claim 5, wherein E is Formula (c2), and any one of q and s is 1 or more,
or a pharmaceutically acceptable salt of the compound.

7. The compound according to claim 3 or 5, wherein s is 1,
or a pharmaceutically acceptable salt of the compound.

8. The compound according to claim 2 of Formula (III):

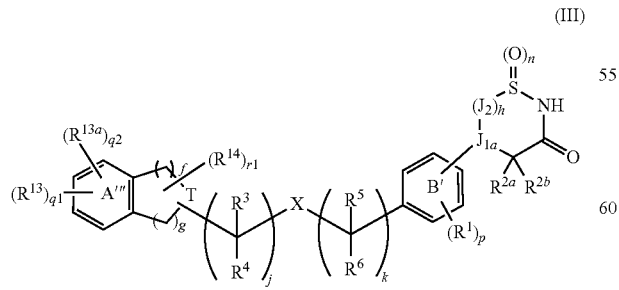

(III)

wherein n, p, h, j, k, $J_2$, X, $R^1$, $R^{2a}$, $R^{2b}$, $R^3$, $R^4$, $R^5$, and $R^6$ are the same as defined in Formula (I); the ring B' and $J_{1a}$ are the same as defined in Formula (I)-1;

f is an integer of 0 to 2; g is an integer of 1 to 4; q1 is an integer of 0 to 3; q2 is 0 or 1; r1 is an integer of 0 to 2 (with the proviso that q1+q2+r1 is an integer of 0 to 5);
a ring A''' is a benzene ring or a pyridine ring;
T is —$CH_2$—, an oxygen atom, —$S(O)_i$— (i is an integer of 0 to 2), or —$NR^7$— ($R^7$ is the same as $R^7$ defined in Formula (I));
$R^{13}$s are independently a group optionally selected from a halogen atom, —OH, a cyano group, a $C_{1-10}$ alkyl group which is optionally substituted with 1 to 5 substituent(s) RI, a $C_{2-10}$ alkenyl group which is optionally substituted with 1 to 5 substituent(s) RI, a $C_{2-10}$ alkynyl group which is optionally substituted with 1 to 5 substituent(s) RI, a $C_{1-10}$ alkoxy group which is optionally substituted with 1 to 5 substituent(s) RI, a $C_{2-10}$ alkenyloxy group which is optionally substituted with 1 to 5 substituent(s) RI, a $C_{2-10}$ alkynyloxy group which is optionally substituted with 1 to 5 substituents(s) RI, —SH, a —$S(O)_iR^a$ (i is an integer of 0 to 2) group, and a —$NR^bR^c$ group;
$R^{13a}$ is a group optionally selected from an aryl group which is optionally substituted with 1 to 5 substituent(s) RII, a heterocyclic group which is optionally substituted with 1 to 5 substituent(s) RII, an aralkyl group which is optionally substituted with 1 to 5 substituent(s) RII, a heteroarylalkyl group which is optionally substituted with 1 to 5 substituent(s) RII, a non-aromatic heterocyclic alkyl group which is optionally substituted with 1 to 5 substituent(s) RII, an aryloxy group which is optionally substituted with 1 to 5 substituent(s) RII, a heteroaryloxy group which is optionally substituted with 1 to 5 substituent(s) RII, a non-aromatic heterocyclic oxy group which is optionally substituted with 1 to 5 substituent(s) RII, an aralkyloxy group which is optionally substituted with 1 to 5 substituent(s) RII, a heteroarylalkyloxy group which is optionally substituted with 1 to 5 substituent(s) RII, and a substituted spiropiperidinylmethyl group;
$R^{14}$s are independently a group optionally selected from a halogen atom, —OH, a cyano group, a $C_{1-6}$ alkyl group which is optionally substituted with 1 to 5 substituent(s) RI, a $C_{2-6}$ alkenyl group which is optionally substituted with 1 to 5 substituent(s) RI, a $C_{2-6}$ alkynyl group which is optionally substituted with 1 to 5 substituent(s) RI, a $C_{1-6}$ alkoxy group which is optionally substituted with 1 to 5 substituent(s) RI, —SH, a —$S(O)_iR^a$ (i is an integer of 0 to 2) group, and a —$NR^bR^c$ group;
$R^a$, $R^b$, $R^c$, the substituent RI, and the substituent RII are the same as defined in Formula (I),
or a pharmaceutically acceptable salt of the compound.

9. The compound according to claim 8 of Formula (III-1)-1:

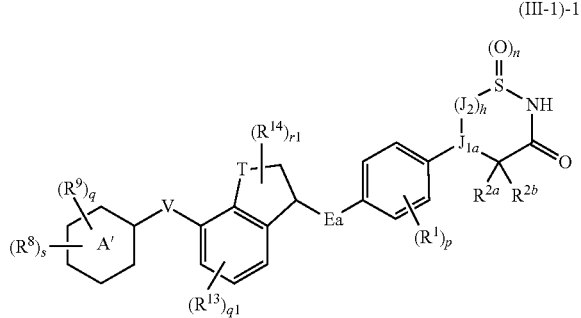

(III-1)-1 wherein n, p, h, $J_2$, $R^1$, $R^{2a}$, and $R^{2b}$ are the same as defined in Formula (I); $J_{1a}$ is the same as defined in Formula (I)-1;

q, s, the ring A', V, $R^8$, and $R^9$ are the same as defined in Formula (II);

q1, r1, T, $R^{13}$, and $R^{14}$ are the same as defined in Formula (III);

Ea is Formula (c1) or Formula (c4) shown as E in Formula (II-1)-1, or a pharmaceutically acceptable salt of the compound.

10. The compound according to claim 9, wherein Ea is Formula (c1), and any one of q and s is 1 or more, or a pharmaceutically acceptable salt of the compound.

11. A pharmaceutical composition comprising a compound of claim 1, or a pharmaceutically acceptable salt of the compound.

12. A pharmaceutical composition comprising a compound of claim 1, or a pharmaceutically acceptable salt of the compound; and a compound selected from the group consisting of a PPAR gamma agonist, a biguanide agent, a sulfonylurea, a rapid-acting insulin secretagogues, an alpha-glucosidase inhibitor, insulin or an insulin derivative, GLP-1 and a GLP-1 agonist, a DPP-IV inhibitor, an alpha-2 antagonist, an SGLT2 inhibitor, omega-3 fatty acids, an HMG-CoA reductase inhibitor, an HMG-CoA synthase inhibitor, a cholesterol absorption inhibitor, an acyl-CoA-cholesterol acyltransferase (ACAT) inhibitor, a CETP inhibitor, a squalene synthase inhibitor, an antioxidant, a PPAR alpha agonist, a PPAR delta agonist, an LXR agonist, an FXR agonist, an MTTP inhibitor, a squalene epoxidase inhibitor, a bile acid absorption inhibitor, a CB-1 receptor antagonist, a monoamine reuptake inhibitor, a serotonin reuptake inhibitor, a lipase inhibitor, a neuropeptide Y (NPY) receptor antagonist, a peptide YY (PYY) receptor antagonist, and an adrenergic beta-3 receptor agonist.

13. The pharmaceutical composition of claim 12 wherein the DPP-IV inhibitor is selected from sitagliptin, vildagliptin, alogliptin, and saxagliptin, or a pharmaceutically acceptable salt thereof.

14. The pharmaceutical composition of claim 12 wherein the DPP-IV inhibitor is sitagliptin, or a pharmaceutically acceptable salt thereof.

15. A method for treating diabetes comprising the administration to a patient of an effective amount of the compound of claim 1, or a pharmaceutically acceptable salt of the compound.

16. A method for treating diabetes comprising the administration to a patient of an effective amount of the compound of claim 1, or a pharmaceutically acceptable salt of the compound, and a compound selected from a group consisting of a PPAR gamma agonist, a biguanide agent, a sulfonylurea, a rapid-acting insulin secretagogue, an alpha-glucosidase inhibitor, insulin or an insulin derivative, GLP-1 and a GLP-1 agonist, a DPP-IVinhibitor, an alpha-2 antagonist, an SGLT2 inhibitor, omega-3 fatty acids, an HMG-CoA reductase inhibitor, an HMG-CoA synthase inhibitor, a cholesterol absorption inhibitor, an acyl-CoA-cholesterol acyltransferase (ACAT) inhibitor, a CETP inhibitor, a squalene synthase inhibitor, an antioxidant, a PPAR alpha agonist, a PPAR delta agonist, an LXR agonist, an FXR agonist, an MTTP inhibitor, a squalene epoxidase inhibitor, a bile acid absorption inhibitor, a CB-1 receptor antagonist, a monoamine reuptake inhibitor, a serotonin reuptake inhibitor, a lipase inhibitor, a neuropeptide Y (NPY) receptor antagonist, a peptide YY (PYY) receptor antagonist, and an adrenergic beta-3 receptor agonist.

17. The method of claim 16 wherein the DPP-IV inhibitor is selected from sitagliptin, vildagliptin, alogliptin, saxagliptin, or a pharmaceutically acceptable salt thereof.

18. The method of claim 16 wherein the DPP-IV inhibitor is sitagliptin, or a pharmaceutically acceptable salt thereof.

* * * * *